US008058016B2

(12) United States Patent
Nordstedt et al.

(10) Patent No.: US 8,058,016 B2
(45) Date of Patent: Nov. 15, 2011

(54) METHODS OF USING AN ANTIBODY THAT BINDS TO APOLIPOPROTEIN E

(75) Inventors: Christer Nordstedt, Södertälje (SE); Tom Goldschmidt, Södertälje (SE); Maria Henderikx, Hasselt (BE); René Hoet, Maastricht (NL); Henricus Hoogenboom, Maastricht (NL); Simon Hufton, Lancashire (GB); Christin V. Andersson, Södertälje (SE); Johanna Lindquist, Södertälje (SE); Dan Sunnemark, Södertälje (SE); Sergy Leonov, Södertälje (SE)

(73) Assignees: Astrazeneca AB, Sodertalje (SE); Dyax Corporation, Cambridge, MA (US)

( * ) Notice: Subject to any disclaimer, the term of this patent is extended or adjusted under 35 U.S.C. 154(b) by 0 days.

(21) Appl. No.: 12/585,180

(22) Filed: Sep. 8, 2009

(65) Prior Publication Data

US 2010/0061993 A1    Mar. 11, 2010

Related U.S. Application Data

(63) Continuation of application No. 10/579,445, filed as application No. PCT/EP2004/013426 on Nov. 26, 2004, now Pat. No. 7,612,179.

(60) Provisional application No. 60/525,174, filed on Nov. 28, 2003.

(51) Int. Cl.
*G01N 33/53* (2006.01)
*G01N 33/567* (2006.01)

(52) U.S. Cl. ........................ 435/7.1; 435/7.21

(58) Field of Classification Search .................. None
See application file for complete search history.

(56) References Cited

U.S. PATENT DOCUMENTS

| | | | |
|---|---|---|---|
| 5,807,978 | A | 9/1998 | Kokolus et al. |
| 6,046,381 | A | 4/2000 | Mucke et al. |
| 6,107,045 | A | 8/2000 | Koren et al. |
| 6,787,519 | B2 | 9/2004 | Huang et al. |
| 2002/0155426 | A1 | 10/2002 | Cordell et al. |
| 2004/0157267 | A1 | 8/2004 | Huang |

FOREIGN PATENT DOCUMENTS

| | | |
|---|---|---|
| EP | 1434053 | 6/2004 |
| WO | 94/09155 | 4/1994 |
| WO | 2004/011943 | 2/2004 |

OTHER PUBLICATIONS

Aizawa et al. "Amino-terminus truncated apolipoprotein E is the major species in amyloid deposits in Alzheimer's disease-affected brians: A possible role for apolipoprotein E in Alzheimer's disease" Brain Res. 768:208-214 (1997).

Bi et al. "Rapid induction of intraneuronal neurofibrillary tangles in apolipoprotein E-deficient mice" Proc. Natl. Acad. Sci. USA 98:8832-8837 (2001).
Biodesign International, "Mouse anti-apolipoprotein E monoclonal antibody" Catalog No. H61529M (2002).
Bury et al. "1. Apoliprotein quantification by ELISA: Technical aspects and clinical applications" Rev. Immuno. Technol. 1:1-25 (1998).
Carlsson et al. "Clinical relevance of the quantification of apolipoprotein E in cerebrospinal fluid" Clin. Chimica Acta 196:167-176 (1991).
Casset et al. "A peptide mimetic of an anti-CD4 monoclonal antibody by rational design" Biochem. Biophys. Res. Comm. 307:198-205 (2003).
Castano et al. "Apolipoprotein E carboxyl-terminal fragments are complexed to amyloids A and L" J. Biol. Chem. 270:17610-17615 (1995).
Chemicon International "Goat anti-apolipoprotein E polyclonal antibody" Catalog No. AB947 (2001).
Chemicon International "Mouse anti-apolipoprotein E monoclonal antibody" Catalog No. MAB1062 (2002).
Chen et al. "Selection and analysis of an optimized anti-VEGF antibody: Crystal structure of an affinity-matured Fab in complex with antigen" J. Mol. Biol. 293:865-881 (1999).
Cho et al. "Quantitation of apoE domains in Alzheimer disease brain suggests a role for apoE in Aβ aggregation" J. Neuropathol. Exp. Neurol. 160:342-349 (2001).
Davies et al. "Affinity improvement of single antibody VH domains: Residues in all three hypervariable regions affect antigen binding" Immunotechnol. 2:169-179 (1996).
De Pascalis et al. " Grafting of abbreviated complementarity-determining regions containing specificity determining residues essential for ligand contact to engineer a less immunogenic humanized monoclonal antibody" J. Immunol. 169:3076-3084 (2002).
Demeester et al. "Characterization and functional studies of lipoproteins, lipid transfer proteins, and lecithin: Cholesterol acyltransferase in CSF of normal individuals and patients with Alzheimer's disease" J. Lipid Res. 41:963-974 (2000).
Fujita et al. "Apolipoprotein E is found in astrocytes but not in microglia in the normal mouse brain" Neurosci. Res. 35:123-133 (1999).
Golabek et al. "Sodium dodecyl sulfate-resistant complexes of Alzheimer's amyloid β-peptide with the N-terminal, receptor binding domain of apolipoprotein E" Biophys. J. 79:1008-1015 (2000).
Harris et al. "Carboxyl-terminal-truncated apolipoprotein E4 causes Alzheimer's disease-like neurodegeneration and behavioral deficits in transgenic mice" Proc. Natl. Acad. Sci. USA 100:10966-10971 (2003).
Hock et al. "Antibodies against β-amyloid slow cognitive decline in Alzheimer's disease" Neuron 38:547-554 (2003).
Holm et al. Functional mapping and single chain construction of the anti-ctytokeratin 8 monoclonal antibody TS1. Mol. Immunol. 44:1075-1084 (2007).
Huang et al. "Apolipoprotein E fragments present in Alzheimer's disease brains induce neurofibrillary tangle-like intracellular inclusions in neurons" Proc. Natl. Acad. Sci. USA 98:8838-8843 (2001).
Klezovitch et al. "Structural determinants in the C-terminal domain of apolipoprotein E mediating binding to the protein core of human aortic biglycan" J. Biol. Chem. 275:18913-18918 (2000).

(Continued)

*Primary Examiner* — Anne M. Gussow
(74) *Attorney, Agent, or Firm* — Nixon & Vanderhye P.C.

(57) ABSTRACT

A human antibody fragment, which antibody or fragment:
(i) binds to a polypeptide having the amino acid sequence shown in SEQ ID NO: 1 of the C-terminal domain of Apolipoprotein E (ApoE-CTD) or the amino acid sequence of a part thereof; and
(ii) binds to human plaques.

19 Claims, 31 Drawing Sheets

OTHER PUBLICATIONS

Labeur et al. "Immunological assays of apolipoproteins in plasma: Methods and instrumentation" Clin. Chem. 36:591-597 (1990).

Lederman et al. "A single amino acid substitution in a common African allele of the CD4 molecule ablates binding of the monoclonal antibody OKT4" Mol. Immunol. 28:1171-1181 (1991).

Lee et al. "Microbial cell-surface display" Trends Biotechnol. 21:45-52 (2003).

Li et al. "B-endorphin omission analogs: Dissociation of immunoreactivity from other biological activities" Proc. Nat. Acad. Sci. 77:3211-3214 (1980).

Lynch et al. "Apolipoprotein E modulates glial activation and the endogenous central nervous system inflammatory response" J. Neuroimmunol. 114:107-113 (2001).

Maccallum et al. "Antibody-antigen interactions: Contact analysis and binding site topography" J. Mol. Biol. 262:732-745 (1996).

Mahley et al. "Apolipoprotein E structure, function, and possible roles in Alzheimer's disease" Ann. N. Y. Acad. Sci. 777:139-145 (1996).

Namba et al. "Apolipoprotein E immunoreactivity in cerebral amyloid deposits and neurofibrillary tangles in Alzheimer's disease and kuru plaque amyloid in Creutzfeldt-Jakob disease" Brain Res. 541:163-166 (1991).

Marcel et al. "Distribution and concentration of cholesteryl ester transfer protein in plasma of normolipemic subjects" J. Clin. Invest. 85:10-17 (1990).

Milne et al. "Characterization of monoclonal antibodies against human apolipoprotein E" J. Clin. Invest. 68:111-117 (1981).

Näslund et al. "Characterization of stable complexes involving apolipoprotein E and the amyloid β peptide in Alzheimer's disease brain" Neuron 15:219-228 (1995).

Nishida et al. "Apolipoproteins J and E co-localise with amyloid in gelatinous drop-like and lattice type I corneal dystrophies" Br. J. Ophthalmol. 83:1178-1182 (1999).

Perugini et al. "Self-association of human apolipoprotein E3 and E4 in the presence and absence of phospholipid" J. Biol. Chem. 275:36758-36765 (2000).

Pillot et al. "β-Amyloid peptide interacts specifically with the carboxy-terminal domain of human apolipoprotein E: Relevance to Alzheimer's disease" J. Neurochem. 72:230-237 (1999).

Rudikoff et al. "Single amino acid substitution altering antigen-binding specificity" Proc. Nat. Acad. Sci. 79:1979-1983 (1982).

Sadowski et al. "Inhibition of apolipoprotein E binding to amyloid—beta decreases fibril formation and deposition in vitro and in vivo" Meeting of the Society for Neuroscience, Abstract No. 666.6 (2003).

Saunders et al. "The role of apolipoprotein E in Alzheimer's disease: Pharmacogenomic target selection" Biochim. Biophys. Acta 1502:85-94 (2000).

Sparrow et al. "Apolipoprotein E: Phospholipid binding studies with synthetic peptides from the carboxyl terminus" Biochem. 31:1065-1068 (1992).

Terai et al. "Apolipoprotein E deposition and astrogliosis are associated with maturation of β-amyloid plaques in βAPPswe transgenic mouse: Implications for the pathogenesis of Alzheimer's disease" Brain Res. 900:48-56 (2001).

Vajdos et al. "Comprehensive functional maps of the antigen-binding site of an anti-ErbB2 antibody obtained with shotgun scanning mutagenesis" J. Mol. Biol. 320:415-428 (2002).

Yamada et al. "Further characterization of a monoclonal antibody recognizing apolipoprotein E peptides in amyloid deposits" Annals Clin. Lab. Sci. 27:276-281 (1997).

Yamada et al. "A monoclonal antibody recognizing apolipoprotein E peptides in systemic amyloid deposit" Annals Clin. Lab. Sci. 24:243-249 (1994).

Weisgraber et al. "Human apolipoprotein E: The Alzheimer's disease connection" FASEB J. 10:1485-1494 (1996).

Wisniewski et al. "Apolipoprotein E: A pathological chaperone protein in patients with cerebral and systemic amyloid" Neurosci. Lett. 135:235-238 (1992).

Wisniewski et al. "Is Alzheimer's disease an apolipoprotein E amyloidosis?" Lancet 345:956-958 (1995).

Wu et al. "Humanization of a murine monoclonal antibody by simultaneous optimization of framework and CDR residues" J. Mol. Biol. 294:151-162 (1999).

International Search Report for PCT/EP2004/013426 dated Jun. 3, 2005.

International Preliminary Report on Patentability for PCT/EP2004/013426 dated Jul. 10, 2007.

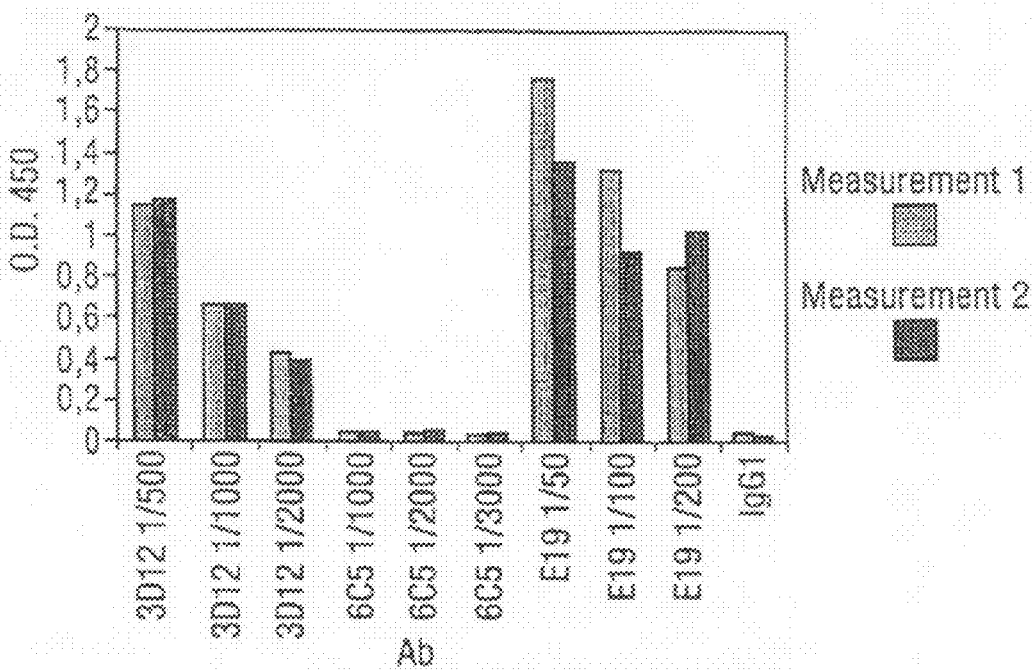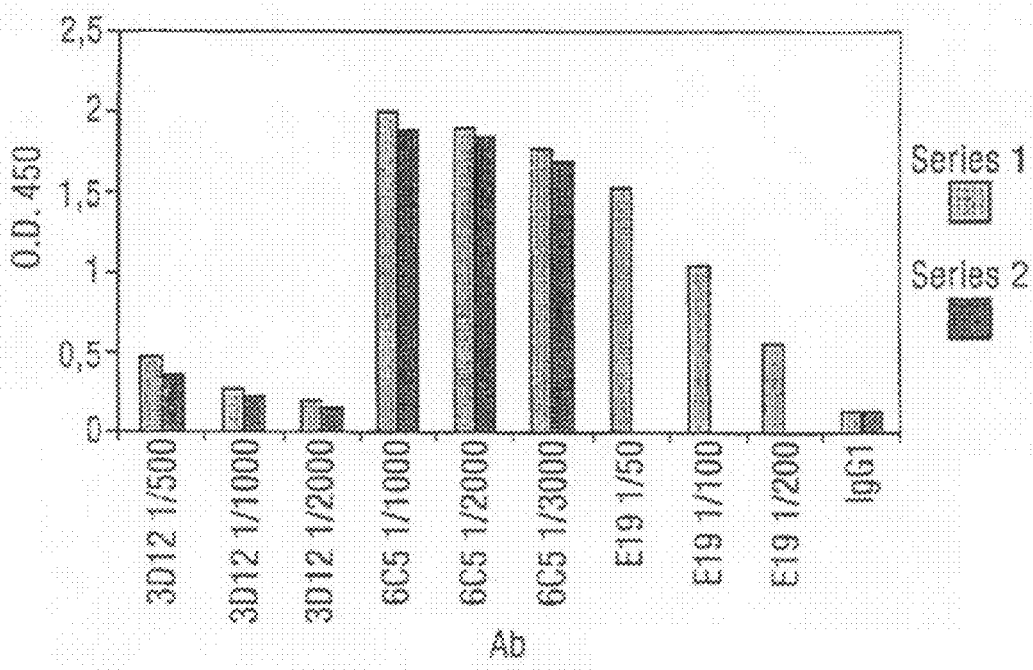

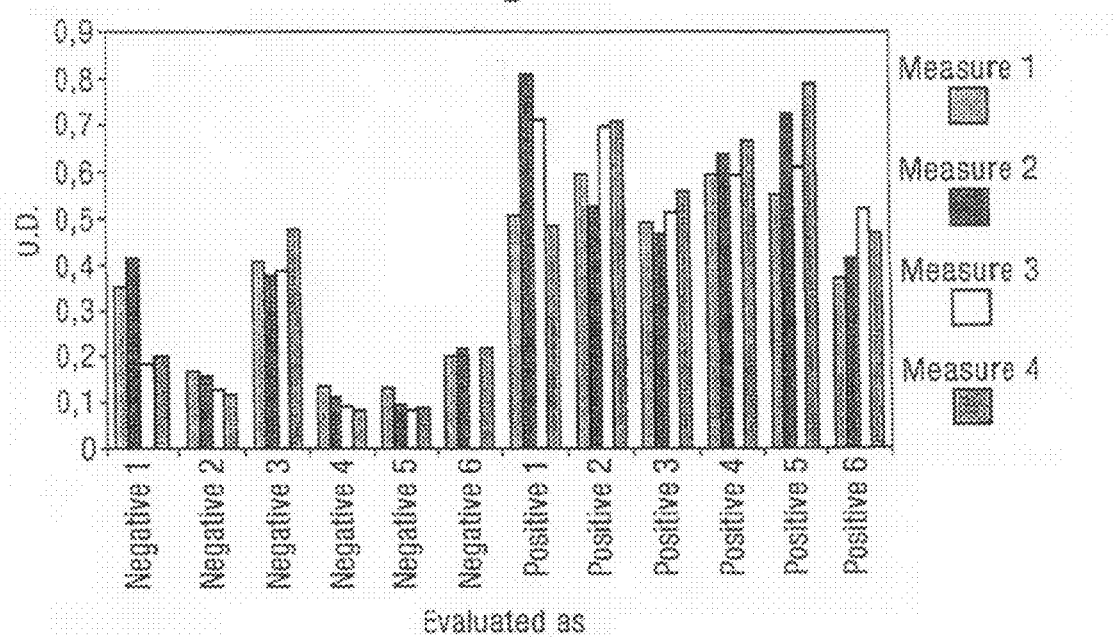
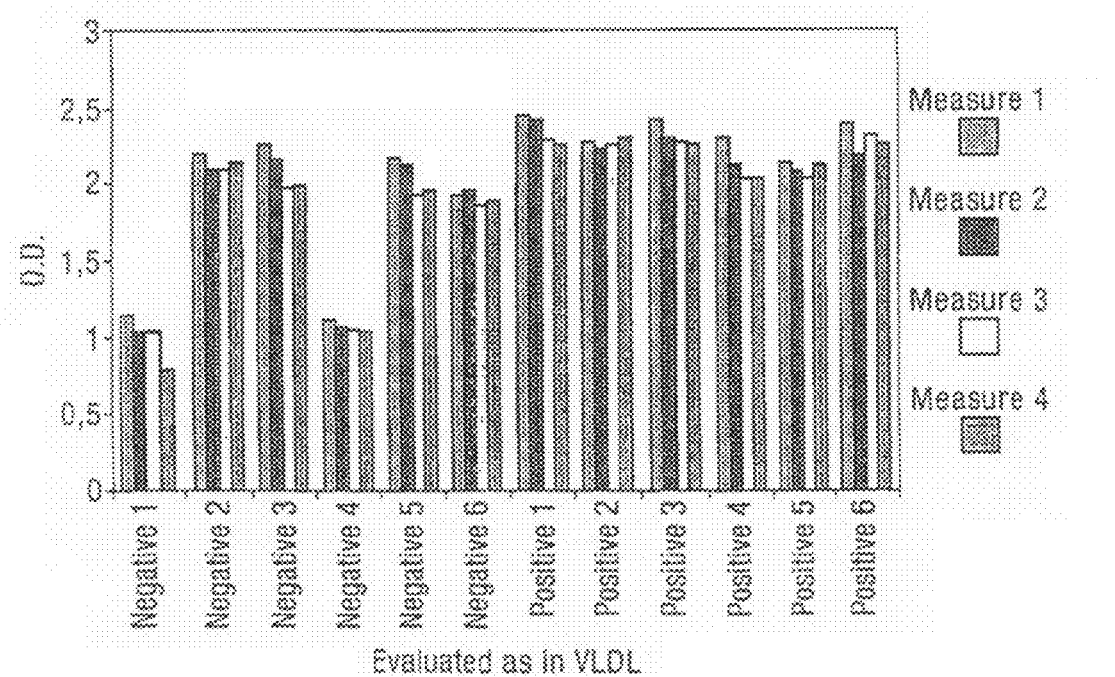
Fig. 2.

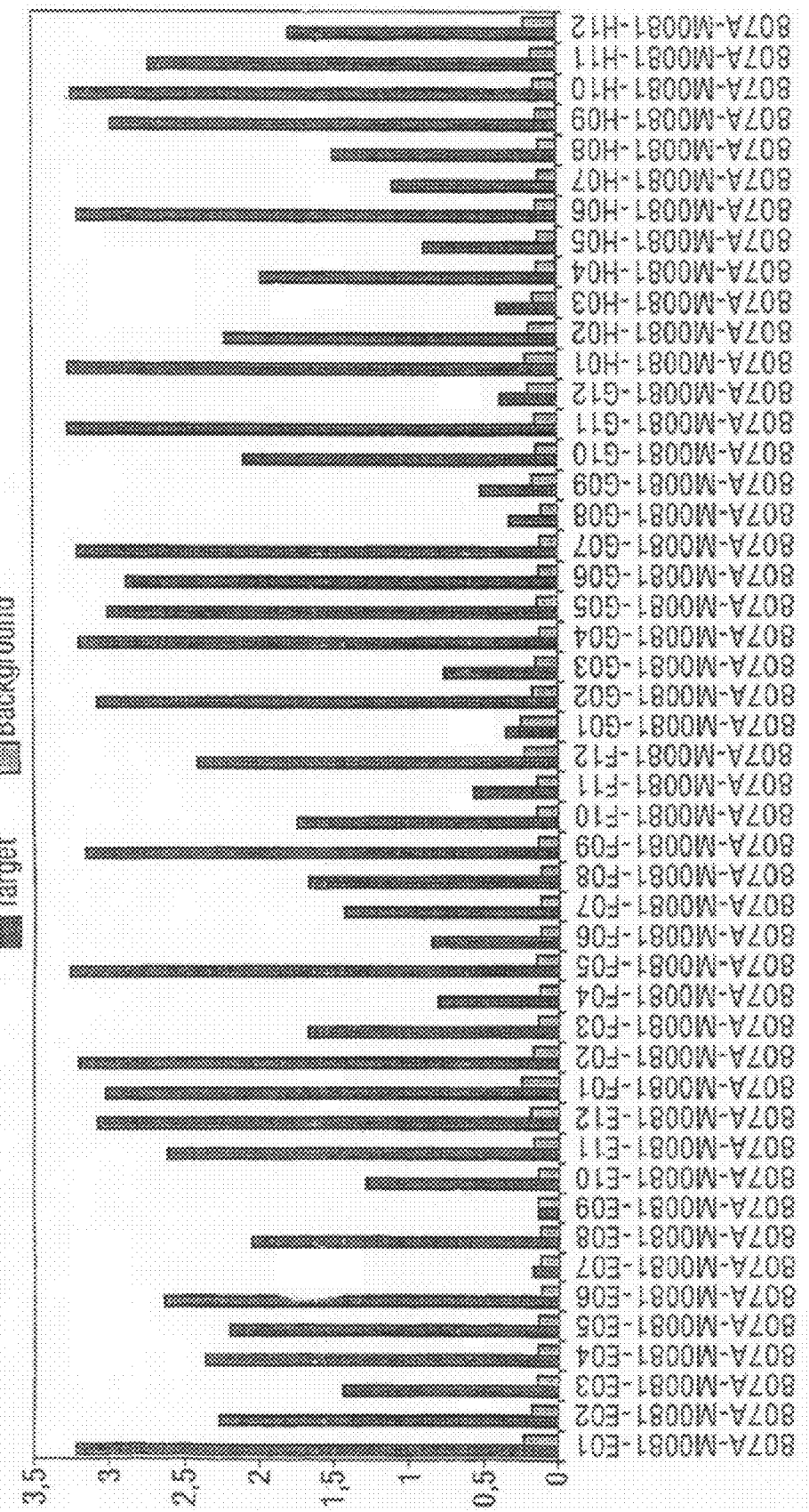

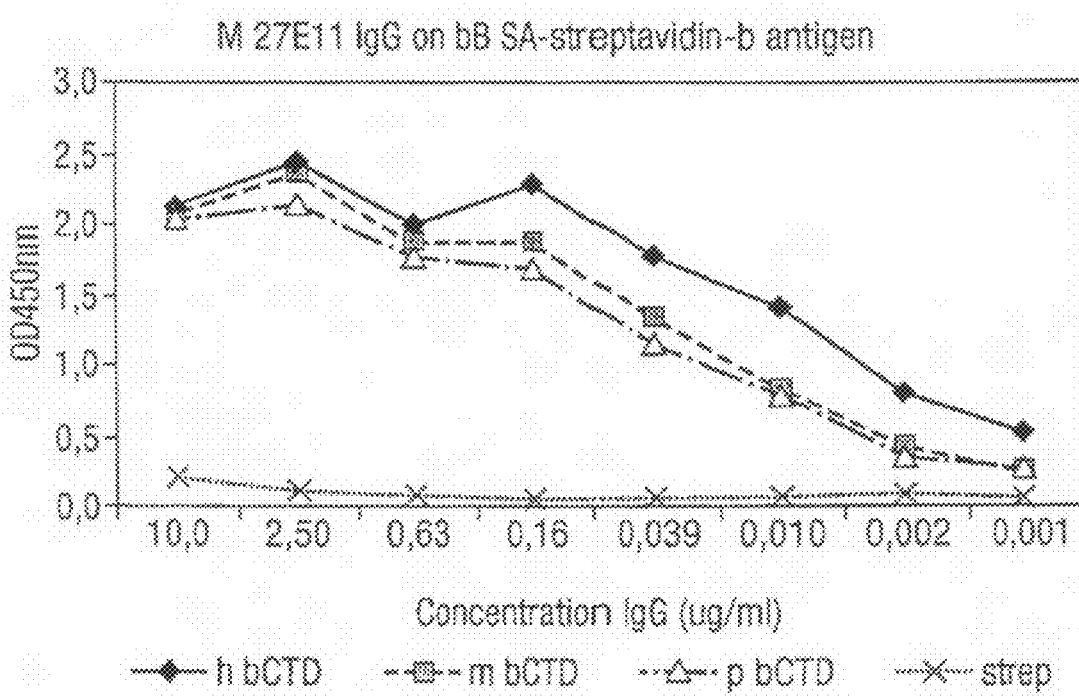

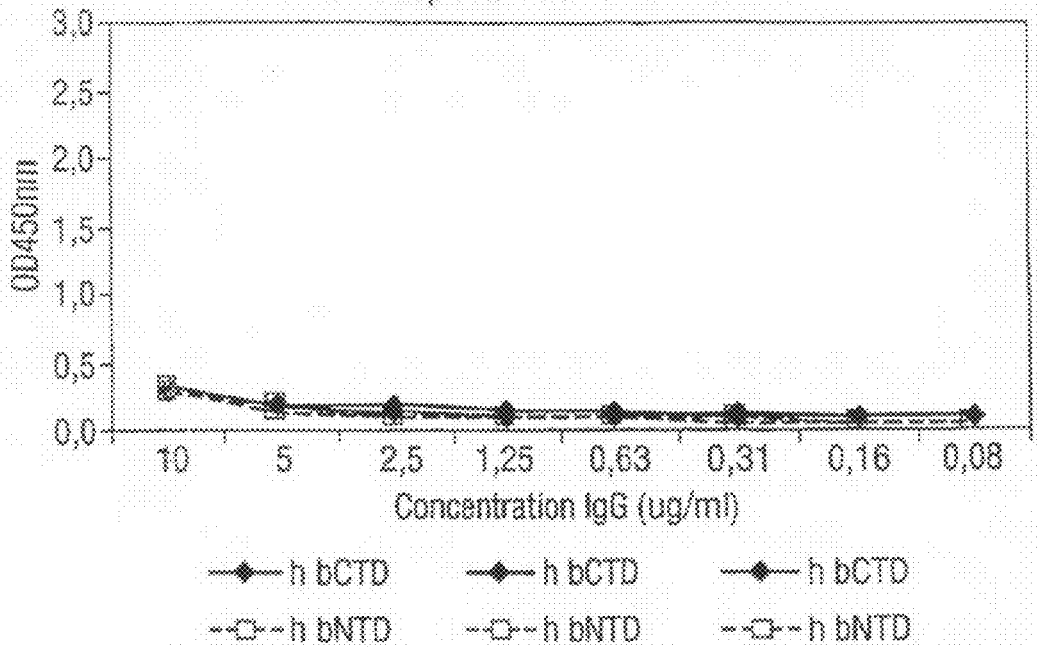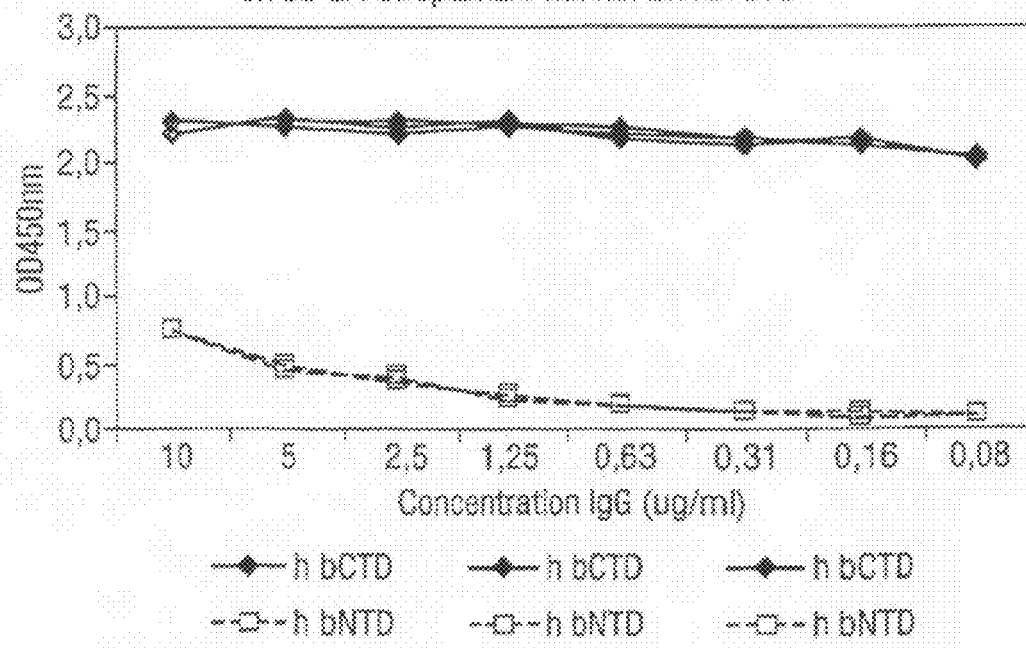

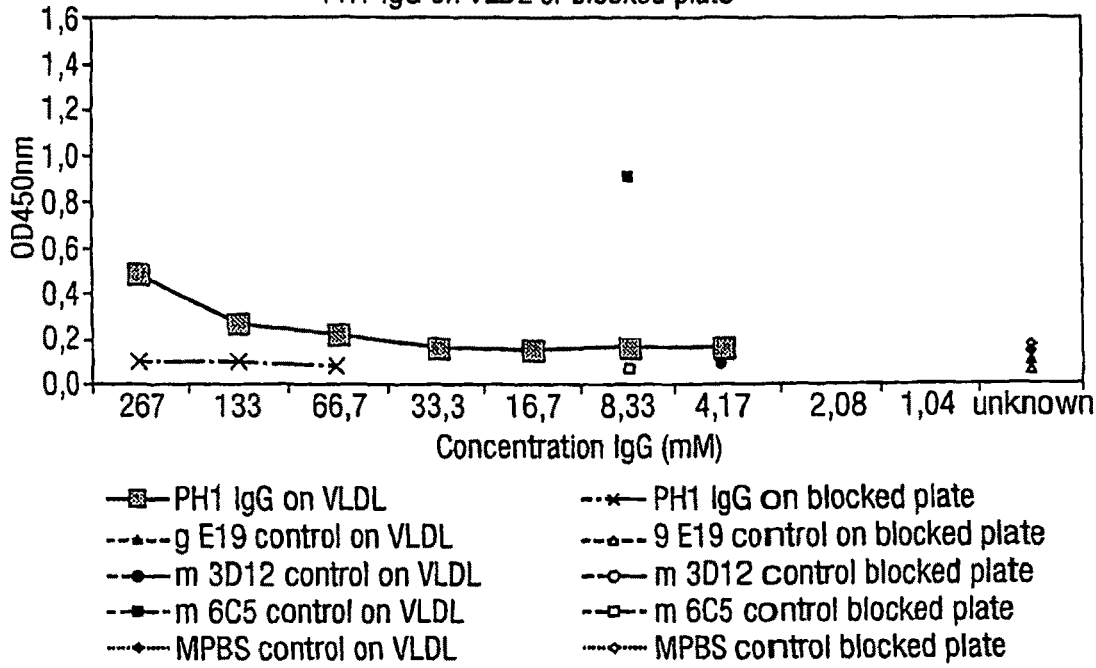
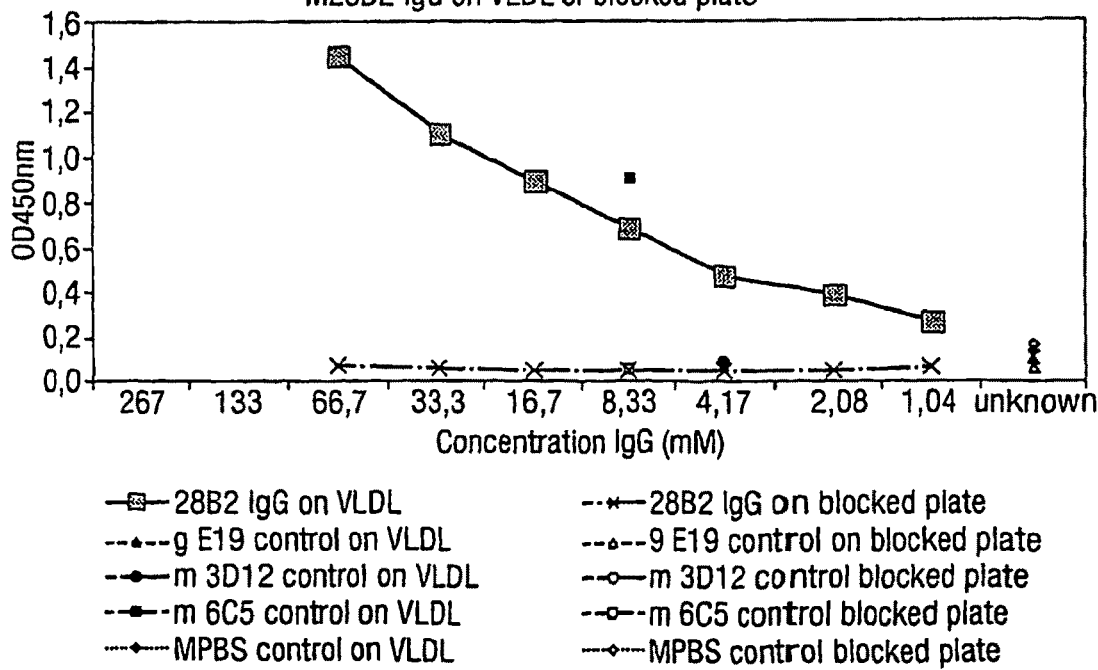

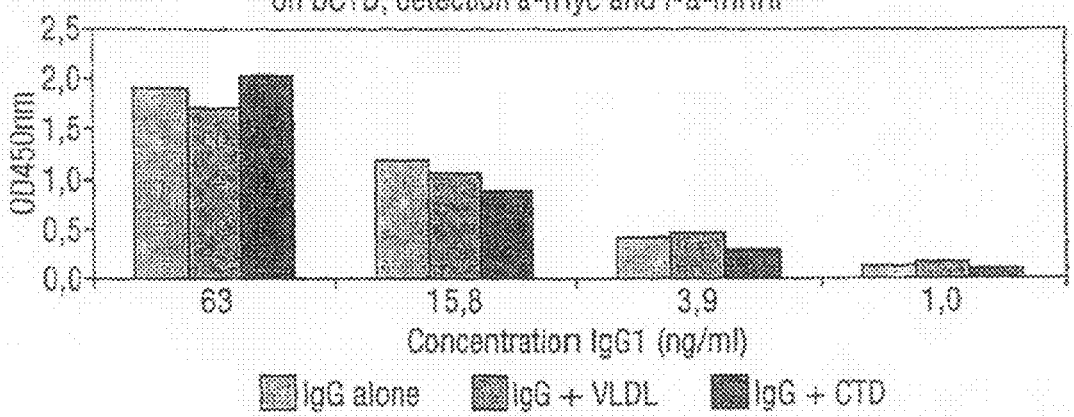
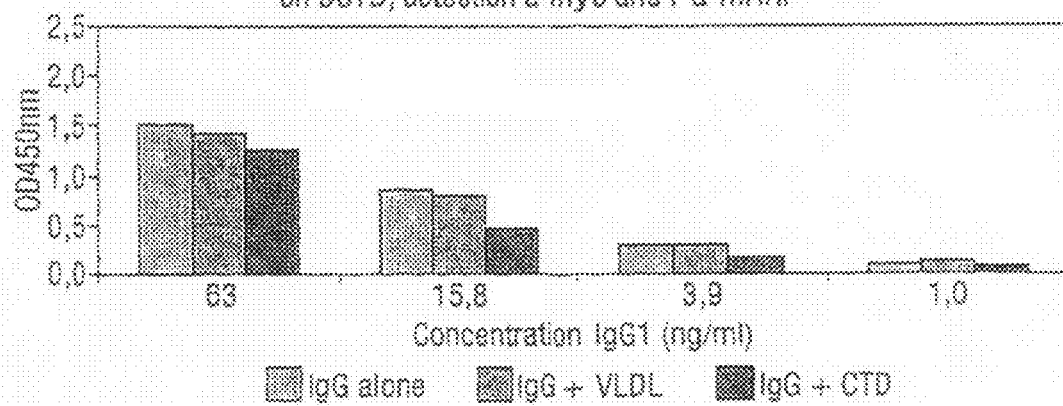

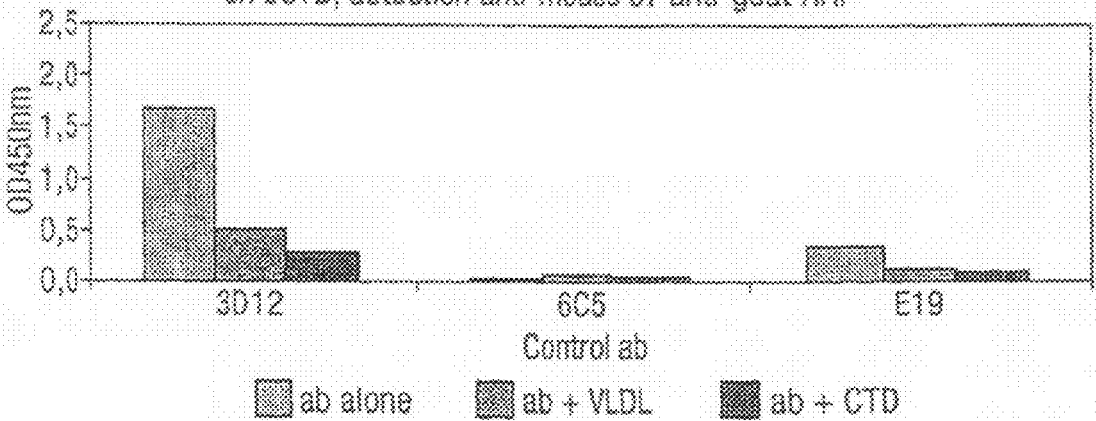
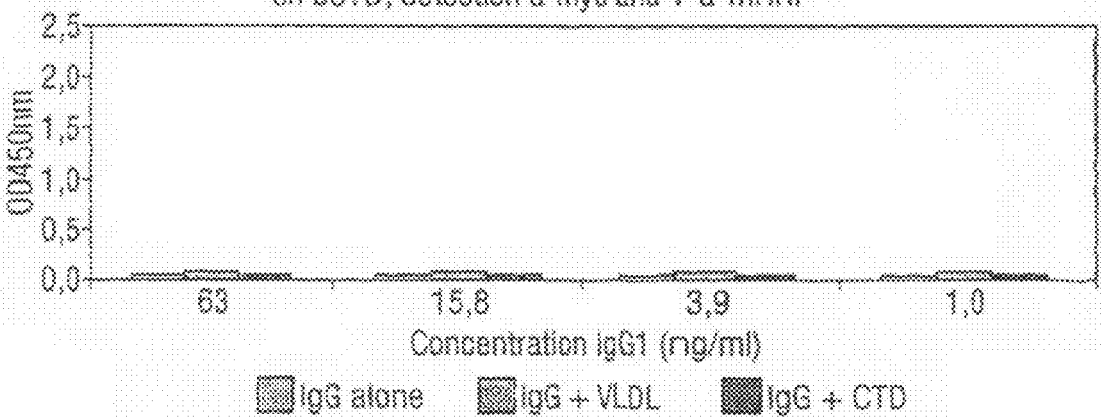

Fig.11A.
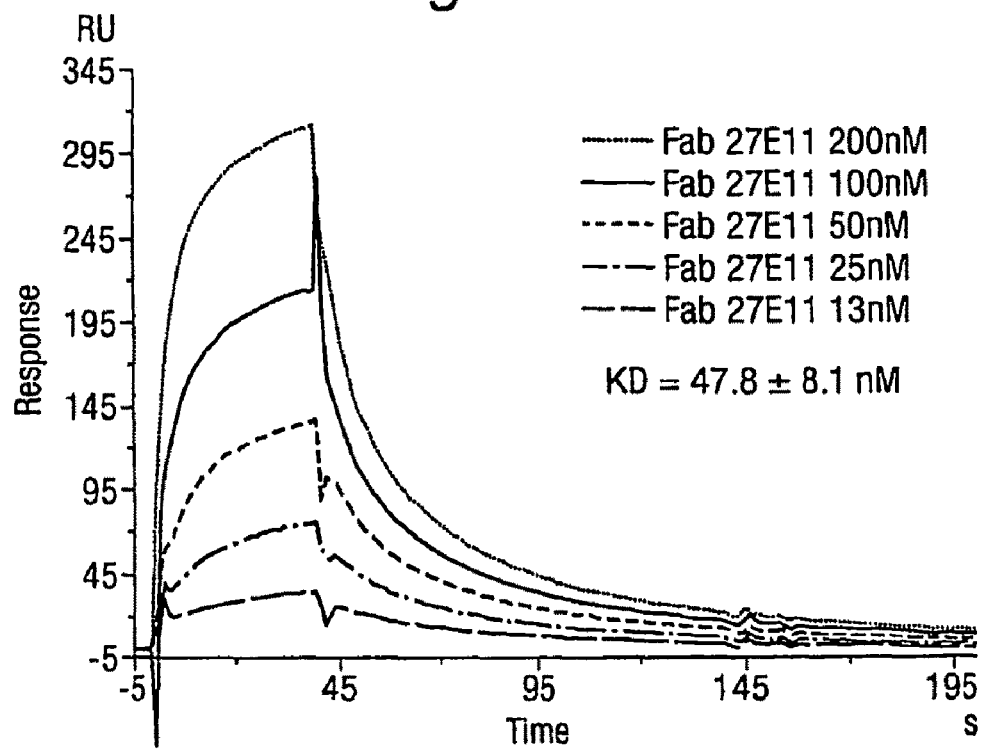
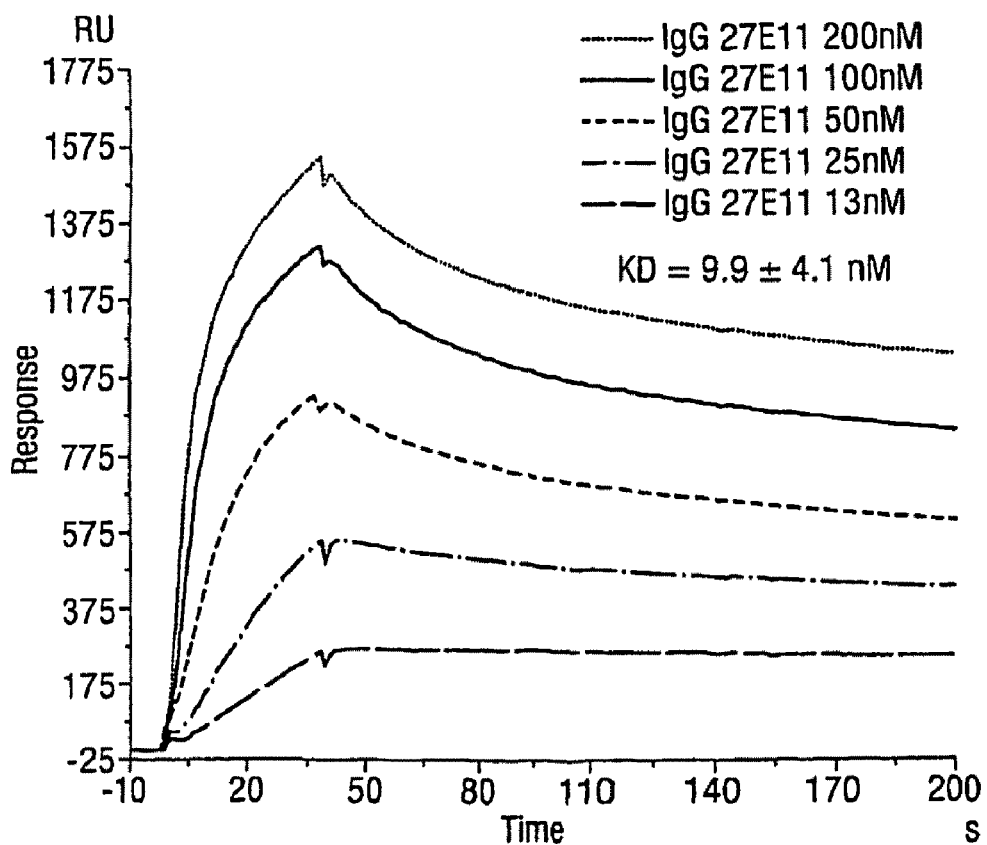

Fig.11B.
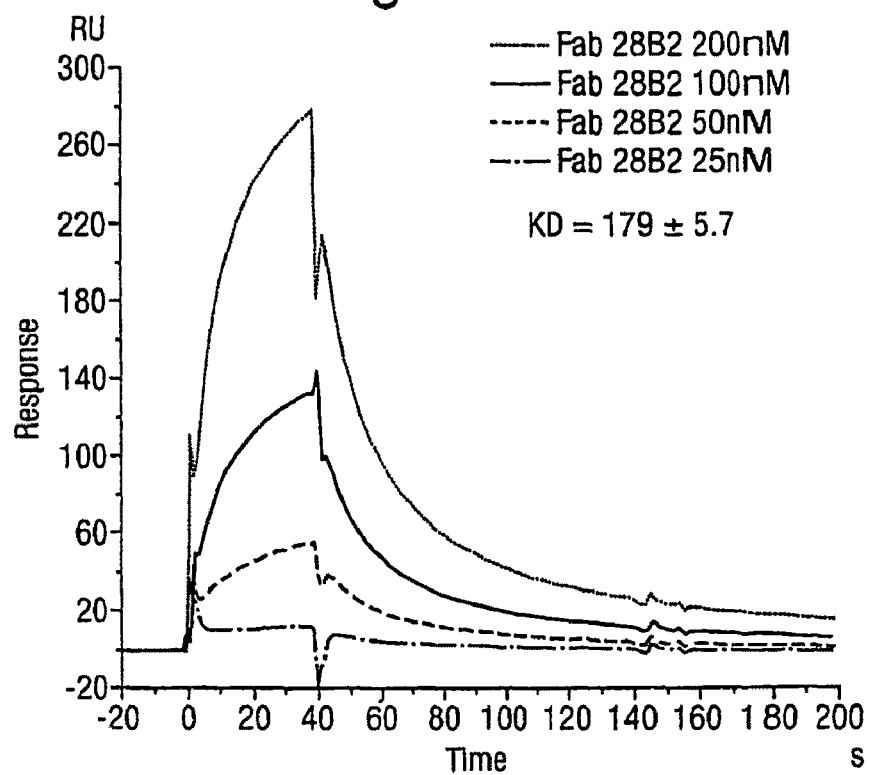
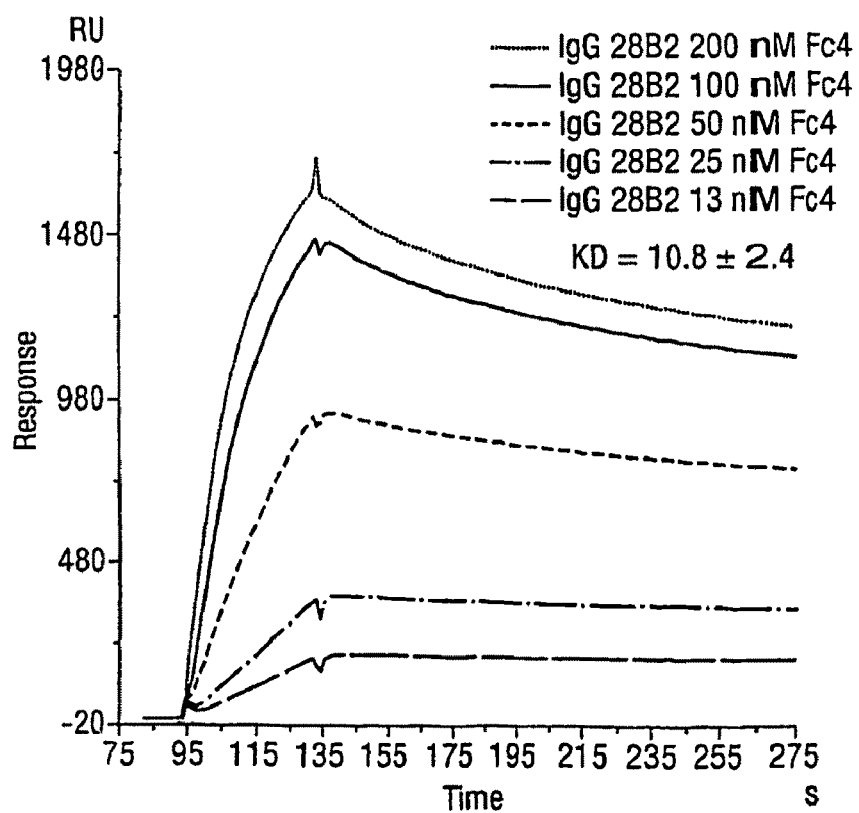

ApoE 10

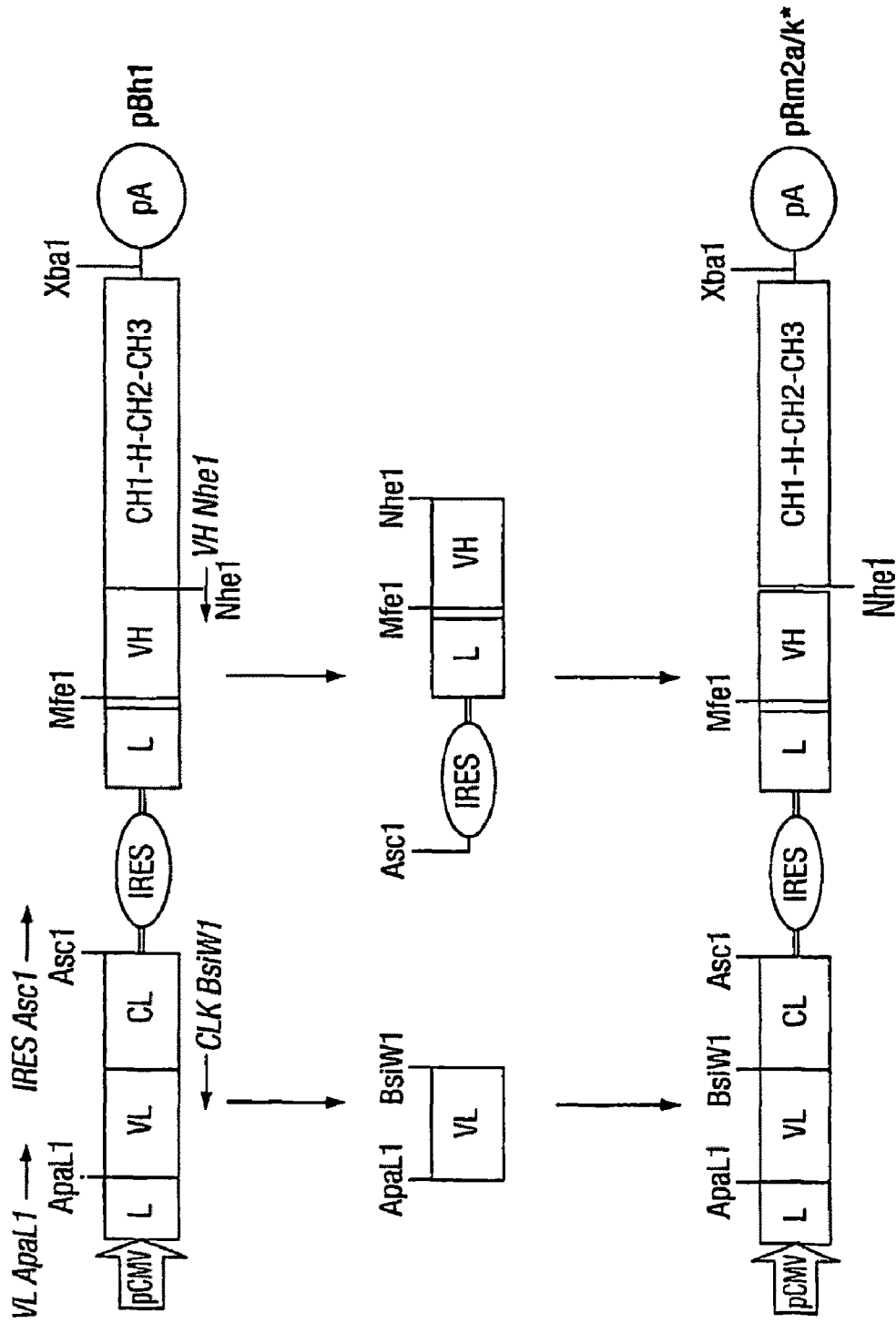

Fig. 15.

```
peptide 1:  biotin-GC-ARMEEMGSRTRDRLDE      aa  1-16  (16+2 aa)
peptide 2:  biotin-GC-VKEQVAEVRAKLEEQA      aa  17-32 (16+2 aa)
peptide 3:  biotin-GC-QQIRLQAEAFQARLKS      aa  33-48 (16+2 aa)
peptide 4:  biotin-GC-WFEPLVEDMQRQWAGL      aa  49-64 (16+2 aa)
peptide 5:  biotin-GC-VEKVQAAVGTSAAPVP      aa  65-80 (16+2 aa)

peptide 6:  biotin-GC-RTRDRLDEVKEQVAEV      aa  9-24  (16+2 aa)
peptide 7:  biotin-GC-RAKLEEQAQQIRLQAE      aa  25-40 (16+2 aa)
peptide 8:  biotin-GC-AFQARLKSWFEPLVED      aa  41-56 (16+2 aa)
peptide 9:  biotin-GC-MQRQWAGLVEKVQAAV      aa  57-72 (16+2 aa)
peptide 10: biotin-GC-GTSAAPVPSDNH          aa  73-84 (12+2 aa)
```

US 8,058,016 B2

METHODS OF USING AN ANTIBODY THAT BINDS TO APOLIPOPROTEIN E

This application is a continuation of application. Ser. No. 10/579,445, filed Oct. 6, 2006, now allowed; which is a U.S. national stage under 35 U.S.C. 371 of Int'l Appln. No. PCT/EP2004/013426; which claims priority benefit of provisional Appln. No. 60/525,174, filed Nov. 28, 2003. The entire contents of each of which are hereby incorporated by reference in this application.

FIELD OF THE INVENTION

The present invention relates to antibodies that specifically bind to a C-terminal fragment of Apolipoprotein E (ApoE). The present invention also provides methods for obtaining such polypeptides and the use of such polypeptides in the diagnosis and treatment of Alzheimer's disease, systemic amyloidosis and other amyloid disorders.

BACKGROUND TO THE INVENTION

Amyloidosis is a progressive, incurable metabolic disease of unknown cause characterized by abnormal deposits of protein in one or more organs or body systems. Amyloid proteins are manufactured, for example, by malfunctioning bone marrow. Amyloidosis, which occurs when accumulated amyloid deposits impair normal body function, can cause organ failure or death. It is a rare disease, occurring in about eight of every 1,000,000 people. It affects males and females equally and usually develops after the age of 40. At least 15 types of amyloidosis have been identified. Each one is associated with deposits of a different kind of protein.

The major forms of amyloidosis are primary systemic, secondary, and familial, or hereditary amyloidosis. There is also another form of amyloidosis associated with Alzheimer's disease. Primary systemic amyloidosis usually develops between the ages of 50 and 60. With about 2,000 new cases diagnosed annually, primary systemic amyloidosis is the most common form of this disease in the United States. Also known as light-chain-related amyloidosis, it may also occur in association with multiple myeloma (bone marrow cancer). Secondary amyloidosis is a result of chronic infection or inflammatory disease. It is often associated with Familial Mediterranean fever (a bacterial infection characterized by chills, weakness, headache, and recurring fever), Granulomatous ileitis (inflammation of the small intestine), Hodgkin's disease, Leprosy, Osteomyelitis and Rheumatoid arthritis.

Familial or hereditary amyloidosis is the only inherited form of the disease. It occurs in members of most ethnic groups, and each family has a distinctive pattern of symptoms and organ involvement. Hereditary amyloidosis is though to be autosomal dominant, which means that only one copy of the defective gene is necessary to cause the disease. A child of a parent with familial amyloidosis has a 50-50 chance of developing the disease.

Amyloidosis can involve any organ or system in the body. The heart, kidneys, gastrointestinal system, and nervous system are affected most often. Other common sites of amyloid accumulation include the brain, joints, liver, spleen, pancreas, respiratory system, and skin.

Alzheimer's disease (AD) is the most common form of dementia, a neurologic disease characterized by loss of mental ability severe enough to interfere with normal activities of daily living, lasting at least six months, and not present from birth. AD usually occurs in old age, and is marked by a decline in cognitive functions such as remembering, reasoning, and planning.

Between two and four million Americans have AD; that number is expected to grow to as many as 14 million by the middle of the 21st century as the population as a whole ages. While a small number of people in their 40s and 50s develop the disease, AD predominantly affects the elderly. AD affects about 3% of all people between ages 65 and 74, about 20% of those between 75 and 84, and about 50% of those over 85. Slightly more women than men are affected with AD, even when considering women tend to live longer, and so there is a higher proportion of women in the most affected age groups.

Several genes have been implicated in AD, including the gene for amyloid precursor protein, or APP, responsible for producing amyloid. Mutations in this gene are linked to some cases of the relatively uncommon early-onset forms of AD. Other cases of early-onset AD are caused by mutations in the presenilin genes, PS-1 and PS-2. A dementia similar to AD eventually affects nearly everyone with Downs syndrome, caused by an extra copy of chromosome 21. Other mutations on other chromosomes have been linked to other early-onset cases.

Potentially the most important genetic link was discovered in the early 1990s on chromosome 19. A gene on this chromosome, apoE, codes for a protein involved in transporting lipids into neurons.

Apolipoprotein E (ApoE) is a 34 kDa glycosylated protein. The main sites of ApoE production are the liver and brain. ApoE is a constituent of very low density lipoprotein (VLDL), a subclass of high density lipoproteins and chylomicrons. Cellular uptake of lipid complexes is mediated by binding of ApoE to the low density lipoprotein (LDL) receptor and other related receptors.

There are three major ApoE isoforms in humans, apoE2, apoE3 and apoE4 which are products of three alleles, $\epsilon2$, $\epsilon3$ and $\epsilon4$. In the general population, the $\epsilon3$ allele is the most common, accounting for 78% of all apoE alleles. The frequency of the $\epsilon4$ allele is increased significantly in the population of late-onset sporadic and familial Alzheimer's disease (AD) patients.

ApoE contains a C-terminal domain (ApoE-CTD) and an N-terminal domain (ApoE-NTD) joined by a random-coil region. The C-terminal domain comprises a lipid binding site and the N-terminal domain binds to lipoprotein receptors. The CTD amino acid sequence is identical in all three isoforms of ApoE. The CTD and NTD may be separated by cleavage with thrombin.

Direct interactions between ApoE and Amyloid $\beta$ (A$\beta$) have been demonstrated in vitro. ApoE is also present in AD plaques. It has been reported that the N-terminal domain of ApoE (ApoE-NTD) mediates binding of apoE to A$\beta$ (Golabek et al., (2000) Biophysical Journal 79: 1008-1015). However, AD plaques containing ApoE have been shown to comprise full-length ApoE at the centre of the plaques and a C-terminal domain fragment of ApoE (ApoE-CTD) at the periphery of the plaques (Cho et al., (2001) J. Neuropathology and Expt. Neurology 60: 342-349). A$\beta_{1-42}$ deposition in plaques has been shown to precede ApoE deposition whilst A$\beta_{1-40}$ deposition follows ApoE depositor, in plaque maturation (Terai et al., (2001), Brain Research 900: 48-56).

The function of ApoE in the brain is not thought to be specific for AD. ApoE appears to play an important role in modifying recovery from acute brain injury. In particular, there is evidence from both clinical and animal studies to suggest that the presence of the ApoE4 isoform is associated with poor neurological recovery from a variety of acute brain injuries.

SUMMARY OF THE INVENTION

The present inventors developed therapeutic antibodies directed to a region of Apolipoprotein E (ApoE) which is exposed in protein aggregates found in amyloid deposits including Alzheimer plaques but which is not accessible, or has only restricted accessibility, in other forms of ApoE such as ApoE in lipoprotein particles in the blood.

Accordingly, the present invention provides:

a human antibody or antibody fragment, which antibody or fragment:
(i) binds to a polypeptide having the amino acid sequence shown in SEQ ID NO: 1 of the C-terminal domain of Apolipoprotein E (ApoE-CTD) or the amino acid sequence of a part thereof; and
(ii) binds to human plaques;

a human antibody or antibody fragment, which antibody or fragment:
(i) binds to a polypeptide having the amino acid sequence shown in SEQ ID NO: 1 of ApoE-CTD or the amino acid sequence of a part thereof; and
(ii) comprises a heavy chain CDR3 region comprising the sequence shown in SEQ ID NO: 20, SEQ ID NO: 512, SEQ ID NO: 513, SEQ ID NO: 514, SEQ ID NO: 515, SEQ ID NO: 516 or SEQ ID NO: 517;

a human antibody or antibody fragment, which antibody or fragment:
(i) binds to a polypeptide having the amino acid sequence shown in SEQ ID NO: 1 of ApoE-CTD or the amino acid sequence of a part thereof; and
(ii) comprises a heavy chain CDR3 region comprising an amino acid sequence selected from the sequences shown in SEQ ID NO: 29, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86 and SEQ ID NO: 89;

a human antibody or antibody fragment, which antibody or fragment binds, in the presence of VLDL, to a polypeptide having the ApoE-CTD amino acid sequence shown in SEQ ID NO: 1 or the amino sequence of a part thereof;

a human antibody or antibody fragment, which antibody or fragment:
(i) binds to human plaques; and
(ii) comprises a heavy chain CDR3 region comprising the sequence shown in SEQ ID NO: 20, SEQ ID NO: 512, SEQ ID NO: 513, SEQ ID NO: 514, SEQ ID NO: 515, SEQ ID NO: 516 or SEQ ID NO: 517;

a human antibody or antibody fragment, which antibody or fragment:
(i) binds to human plaques; and
(ii) comprises a heavy chain CDR3 region comprising an amino acid sequence selected from the sequences shown in SEQ ID NO: 29, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86 and SEQ ID NO: 89;

an antibody or antibody fragment which comprises the heavy chain sequence shown in SEQ ID NO: 136 and the light chain sequence shown in SEQ ID NOS: 521 and 522;

an antibody or antibody fragment which comprises the heavy chain sequence shown in SEQ ID NO: 142 and the light chain sequence shown in SEQ ID NO: 523;

an antibody or antibody fragment which comprises the heavy chain sequence shown in SEQ ID NO: 40 and the light chain sequence shown in SEQ ID NO: 517 and/or 518;

an antibody or antibody fragment which comprises the heavy chain sequence shown in SEQ ID NO: 40 and the light chain sequence shown in SEQ ID NO: 519 and/or 520;

an antibody or antibody fragment which comprises the heavy chain CDR1 sequence shown in SEQ ID NO: 24, the heavy chain CDR2 sequence shown in SEQ ID NO: 25 and the heavy chain CDR3 sequence shown in any one of SEQ ID NOS: 207, 209 and 210;

an antibody or antibody fragment which comprises the heavy chain CDR1 sequence shown in SEQ ID NO: 48, the heavy chain CDR2 sequence shown in SEQ ID NO: 49 and the heavy chain CDR3 sequence shown in any one of SEQ ID NOS: 320, 322 and 323;

an antibody or antibody fragment which comprises the heavy chain CDR1 sequence shown in SEQ ID NO: 66, the heavy chain CDR2 sequence shown in SEQ ID NO: 67 and the heavy chain CDR3 sequence shown in SEQ ID NO: 373;

an antibody or antibody fragment according to any one of the preceding claims which is a monoclonal antibody;

an antibody or antibody fragment according to the invention, for use in a method of treatment of the human or animal body by therapy or in a diagnostic method practised on the human or animal body;

use of an antibody or antibody fragment according to the invention, in the manufacture of a medicament for the treatment or prevention of an amyloid disorder;

a pharmaceutical composition comprising an antibody or antibody fragment according to the invention and a pharmaceutically acceptable carrier or diluent;

a method of treating a subject suffering from an amyloid disorder comprising administering, to said subject a therapeutically effective amount of an antibody or antibody fragment according to the invention;

a method of diagnosing an amyloid disorder in a subject comprising:
(i) administering to said subject an antibody or antibody fragment according to the invention; and
(ii) determining whether or not said antibody or antibody fragment binds to plaques in said subject, wherein binding of said antibody or antibody fragment to plaques is indicative of an amyloid disorder,
thereby determining whether the subject has an amyloid disorder;

a polynucleotide encoding an antibody or antibody fragment according to the invention;

a vector comprising a polynucleotide according to the invention;

a host cell expressing a polypeptide according the invention;

a virus encoding a polynucleotide according to the invention;

a kit for detecting ApoE-CTD, which kit comprises an antibody or antibody fragment according to the invention and means for detecting said an antibody or antibody fragment; and a method for detecting the presence of ApoE-CTD in a sample from a subject, which method comprises:

(i) contacting a sample taken from a subject with an antibody or antibody fragment according to the invention under conditions that permit binding of the an antibody or antibody fragment to ApoE-CTD; and (ii) determining whether or not the an antibody or antibody fragment binds to the sample thereby detecting any ApoE-CTD present in the sample.

BRIEF DESCRIPTION OF THE FIGURES

FIG. 1 shows the binding of known monoclonal antibodies to biotinylated CTD (bCTD) (A) and VLDL (B) by ELISA.

FIG. 2 shows the binding of phage to bCTD (background=0.05) (A) and VLDL (background=0.1) (B).

FIG. 7 shows the binding of control antibody PH1 (A) and 807A-M0028-B02 (M28B02) (B) to bCTD and bNTD.

FIG. 8 shows the binding of control antibody PH1 (A) and 807A-M0028-B02 (M28B02) (B) to coated VLDL.

FIG. 9 shows the results of antibody binding in competition ELISA between coated bCTD (0.05 µg/ml) and an excess of VLDL or CTD in solution. Binding of M27E11 IgG (A), M28B2 IgG (B), control antibody (C) and PH1 IgG (D) is shown.

FIG. 11 shows the Biacore analysis of 807A-M0027-E11 (A) and 807A-M0028-B02 (B) as soluble Fab (top) and IgG (bottom) on a CTD-coated chip.

FIG. 14 is a schematic diagram showing the strategy used to transfer V-regions from pBh1 to pRmk2a.

FIG. 15 shows the sequences of the CTD peptides (SEQ ID NOS: 2 to 11, respectively).

a) In vivo binding of 807A-M0028-B02 4 days after injection;

b) In vivo binding of 807A-M0028-B02 7 days after injection.

Figure 25:
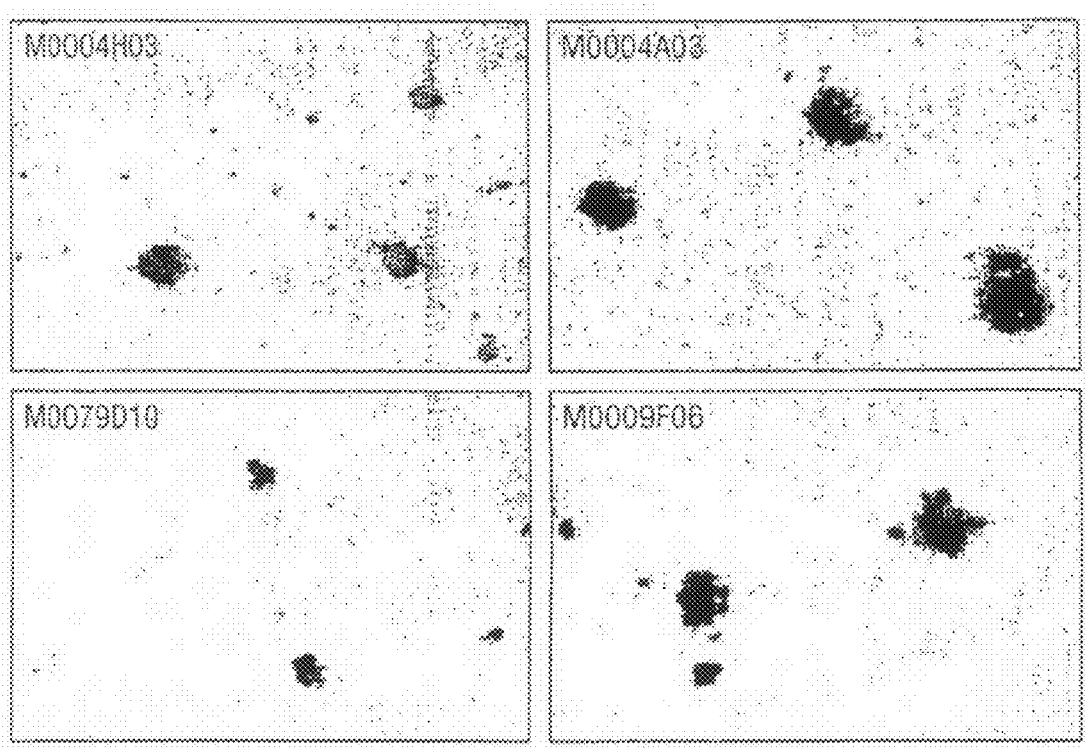

FIG. 25 shows results of a screen of in vivo plaque binding capacity of 807B M0004H03, 807B-M0004-A03, 807B-M0079-D10 and 807B-M0009-F06. Immunohistochemistry expression patterns of anti-CTD hIgG clones B807B-M0004H03, 807B-M0004-A03, 807B-M0079-D10 and 807B-M0009-F06 in APP/PS1 mouse brain sections after in vivo administration is shown.

Figure 26:
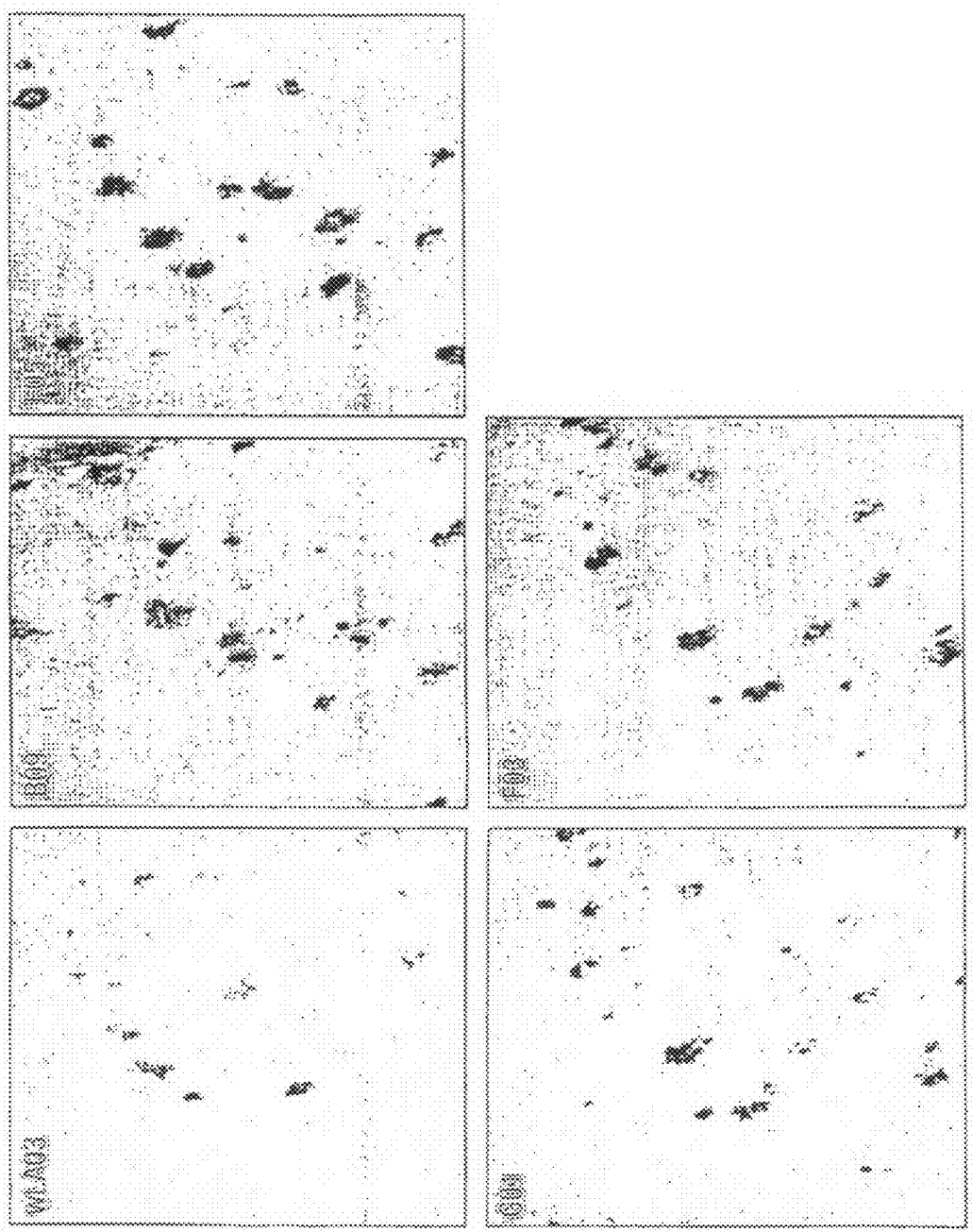

FIG. 26 shows results of an in vitro screen for plaque binding capacity of affinity maturated Fab-clones in human AD brain sections. Wild-type clone 807B-M0004-A03 (wt A03) was compared to affinity maturated clones 807B-M0118-B09 (B09), 807B-M0117-F05 (F05), 807B-M0117-G01 (G01) and 807B-M0118-F03 (F03). Amyloid plaques visualised by anti-CTD binding antibodies (Fab clones) on human AD brain sections.

Figure 27:
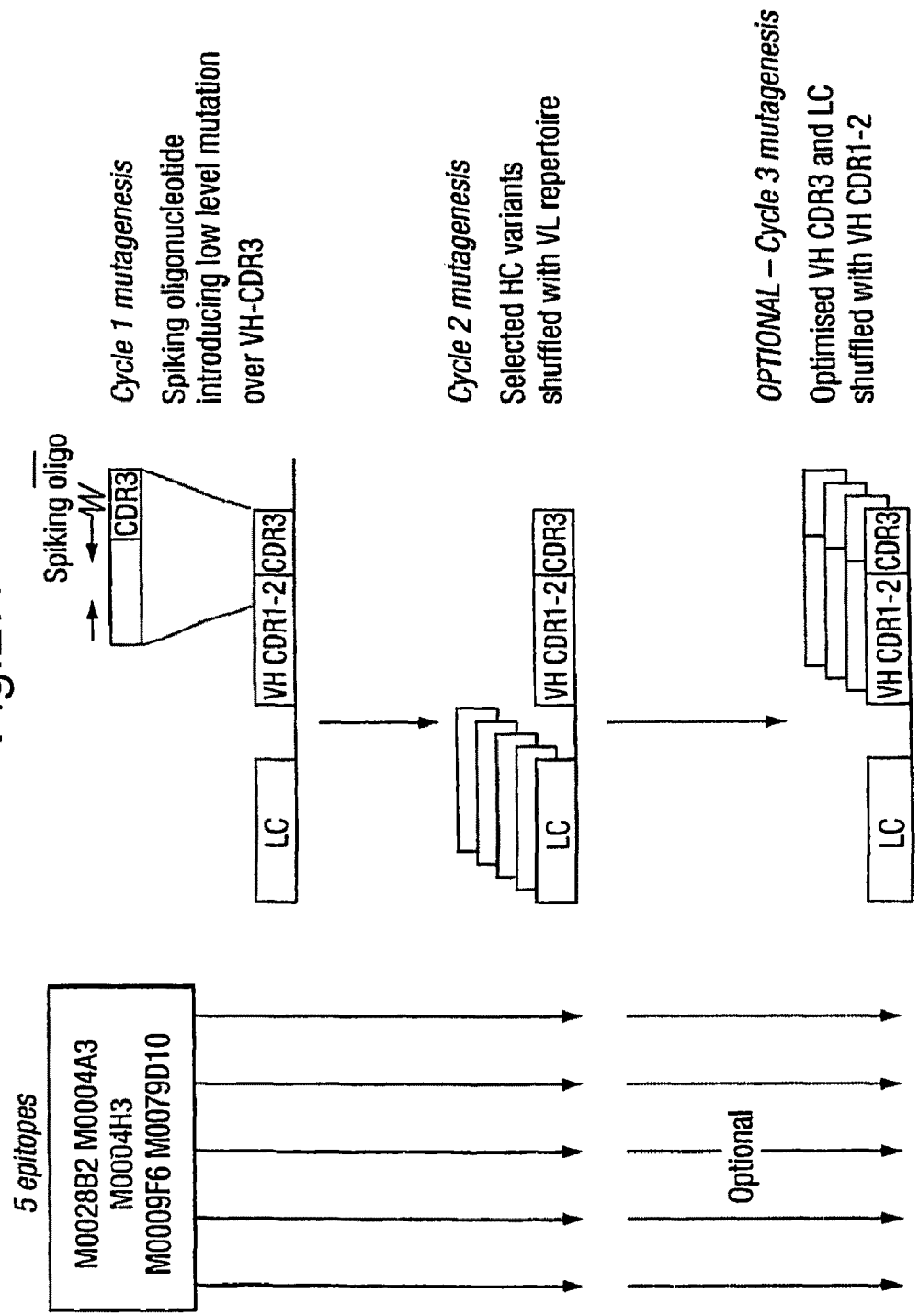

FIG. 27 shows the strategy used for affinity maturation of 807A-M0028-B02, 807B-M0004-H03, 807B-M004-A03, 807B-M0079-D10 and 807B-M0009-F06.

BRIEF DESCRIPTION OF THE SEQUENCES

SEQ ID NO: 1 is the amino acid sequence of the ApoE-CTD.

SEQ ID NO: 2 is the amino acid sequence of peptide 1 (amino acids 1 to 16 of the ApoE-CTD).

SEQ ID NO: 3 is the amino acid sequence of peptide 2 (amino acids 17 to 32 of the ApoE-CTD).

SEQ ID NO: 4 is the amino acid sequence of peptide 3 (amino acids 33 to 48 of the ApoE-CTD).

SEQ ID NO: 5 is the amino acid sequence of peptide 4 (amino acids 49 to 64 of the ApoE-CTD).

SEQ ID NO: 6 is the amino acid sequence of peptide 5 (amino acids 65 to 80 of the ApoE-CTD).

SEQ ID NO: 7 is the amino acid sequence of peptide 6 (amino acids 9 to 24 of the ApoE-CTD).

SEQ ID NO: 8 is the amino acid sequence of peptide 7 (amino acids 25 to 40 of the ApoE-CTD).

SEQ ID NO: 9 is the amino acid sequence of peptide 8 (amino acids 41 to 56 of the ApoE-CTD).

SEQ ID NO: 10 is the amino acid sequence of peptide 9 (amino acids 57 to 72 of the ApoE-CTD).

SEQ ID NO: 11 is the amino acid sequence, of peptide 10 (amino acids 73 to 84 of the ApoE-CTD).

SEQ ID NO: 12 is the amino acid sequence of an epitope in peptide 4 (amino acids 53 to 60 of ApoE-CTD).

SEQ ID NO: 13 is the amino acid sequence of an epitope in peptides 4 and 9 (amino acids 57 to 64 of ApoE-CTD).

SEQ ID NO: 14 is the amino acid sequence of an epitope in peptide 9 (amino acids 61 to 68 of ApoE-CTD).

SEQ ID NO: 15 is the amino acid sequence of an epitope in peptides 1 and 6 (amino acids 9 to 16 of ApoE-CTD).

SEQ ID NO: 16 is the amino acid sequence of an epitope in peptides 4 and 8 (amino acids 49 to 56 of ApoE-CTD).

SEQ ID NO: 17 is the amino acid sequence of an epitope in peptides 3 and 8 (amino acids 41 to 48 of ApoE-CTD).

SEQ ID NO: 18 is the amino acid sequence of peptides 1 and 6 (amino acids 1 to 24 of ApoE-CTD).

SEQ ID NO: 19 is the amino acid sequence of peptides 8 and 9 (amino acids 41 to 72 of ApoE-CTD).

SEQ ID NO: 20 is the amino acid sequence of the consensus CDR3 sequence from antibodies 807A-M0027-E11 and 807A-M0028-B02.

SEQ ID NOS: 21 to 164 are described in Table 8.

SEQ ID NO: 165 is the amino acid sequence of human ApoE4.

SEQ ID NO: 166 is the amino acid sequence of human ApoE3.

SEQ ID NO: 167 is the amino acid sequence of human ApoE2.

SEQ ID NO: 168 is the amino acid sequence of the mature form of human ApoE4.

SEQ ID NO: 169 is the amino acid sequence of the mature form of human ApoE3.

SEQ ID NO: 170 is the amino acid sequence of the mature form of human ApoE2.

SEQ ID NOS: 171 to 206 are described in Table 8.

SEQ ID NOS: 207 to 511 are described in Tables 38 to 42.

SEQ ID NO: 512 is the consensus amino acid sequence of the CDR3 regions of affinity matured clones of 807A-M0028-B02.

SEQ ID NO: 513 is the consensus amino acid sequence of the CDR3 regions of affinity matured clones of 807B-M0004-A03.

SEQ ID NO: 514 is the consensus amino acid sequence of the CDR3 regions of affinity matured clones of 807B-M0004-H03.

SEQ ID NO: 515 is the consensus amino acid sequence of the CDR3 regions of affinity matured clones of 807B-M0009-F06.

SEQ ID NO: 516 is the consensus amino acid sequence of the CDR3 regions of selected affinity matured clones of 807A-M0028-B02.

SEQ ID NO: 517 is the consensus amino acid sequence of the CDR3 regions of selected affinity matured clones of 807B-M0004-A03.

SEQ ID NO: 518 to 527 are defined in Table 21.

DETAILED DESCRIPTION OF THE INVENTION

A. Polypeptides

The present invention provides antibodies that bind to a region on Apolipoprotein E (ApoE) which is exposed in the protein aggregates found in amyloid deposits such as Alzheimer plaques, but which is not present or accessible in other forms of ApoE, such as in lipoprotein particles in the blood.

For the purposes of this invention, the term "antibody", unless specified to the contrary, includes antibody fragments.

Typically, an antibody of the invention binds the C-terminal domain of Apolipoprotein E (ApoE-CTD), i.e. is reactive with ApoE-CTD. An antibody of the invention does not bind to the N-terminal domain of Apolipoprotein E (ApoE-NTD). The antibody typically binds to the form of ApoE present in human plaques in preference to the form of ApoE present in VLDL. Generally, the form of ApoE present in human plaques is ApoE-CTD. An antibody of the invention preferably binds ApoE-CTD in the presence of very low density lipoprotein (VLDL). An antibody of the invention may be one that binds to an epitope in ApoE-CTD, which epitope is not present in ApoE associated with VLDL. For example, the epitope may be one which is one not accessible or exposed to the antibody when ApoE is associated with VLDL. The epitope to which the antibody binds may typically be hidden in full-length ApoE present in VLDL and so the affinity of the antibody for ApoE is substantially less than its affinity for ApoE-CTD. The epitope to which the antibody binds is present only in ApoE-CTD and not in ApoE-NTD and so the antibody is typically devoid of binding to ApoE-NTD. Any binding of the antibody to ApoE-NTD is generally non-specific binding of a substantially lower affinity than the specific binding of the antibody to ApoE-CTD. A substantially lower affinity is generally at least a two fold, three fold, five fold, 10 fold, 50 fold or 100 fold lower affinity.

An antibody of the invention thus preferentially binds or specifically binds to ApoE-CTD. An antibody "preferentially binds" or "specifically binds" to ApoE-CTD when it binds with preferential or high affinity to ApoE-CTD but does not substantially bind, does not bind or binds with only low affinity to other polypeptides. A variety of protocols for binding, competitive binding or immuno-radiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation. Typically an antibody of the invention, is capable of binding to ApoE-CTD having the sequence shown in SEQ ID NO: 1 with an affinity constant of at least $10^7 M^{-1}$, preferably at least $10^8 M^{-1}$, $10^9 M^{-1}$ or $10^{10} M^{-1}$. An antibody of the invention, is preferably capable of preferentially binding to ApoE-CTD with an affinity that is at least two-fold, 10-fold, 50-fold, 100-fold or greater than its affinity for binding to a non-specific polypeptide such as BSA, casein, VLDL, ApoE-NTD or ApoE present in VLDL.

An antibody which specifically binds to ApoE-CTD typically displays at least 2× background binding in an ELISA on immobilised ApoE-CTD but less than 2× background, typically 1× background, to control proteins such as ApoE-NTD or streptavidin.

An antibody of the invention generally binds to human plaques. The term "human plaques" is intended to cover any amyloid deposits comprising at least one protein having an amino acid sequence encoded by a human gene. Preferably the human plaque is present in or derived from human tissue. More preferably the human plaque is present in a sample that has been obtained from a human subject. The human subject may have an amyloid disorder, such as systemic amyloidosis or Alzheimer's disease. The sample may be taken from any tissue or organ containing amyloid plaques. Suitable tissues and organs include brain, tongue, intestines, skeletal muscle, smooth muscle, nerves, skin, ligaments, heart, liver, spleen and kidneys. Where the subject has Alzheimer's disease, the sample is generally a brain section. The brain section is typically obtained post-mortem. Fibrils prepared from any such sample are also included within the term "human plaques".

The human plaque may be present in or derived form a non-human animal which is transgenic for one or more, for example two or three, human proteins, which human protein(s) is/are found in amyloid deposits. The human protein is preferably ApoE but may be amyloid precursor protein (APP) (typically comprising the Swedish mutation) or presenilin.

Binding to human plaques may be determined by any suitable method. For example in an IHC assay, binding of an antibody to human plaques can be said to occur when a positive blind scored IHC signal is obtained after staining with <20 µg/ml antibody in two amyloid deposit samples primarily tested or if one sample is negative in the primary test, at least two out of three samples subsequently tested indicates that an antibody binds to human plaques. The samples are preferably derived from different individuals and sectioned from tissue samples with histologically verified amyloid deposits which are IHC positive for an amyloid marker such as Aβ.

The ability of an antibody to bind to human plaques may be determined in vivo using a mouse or other non-human animal model, such as a rodent or primate, of Alzheimer's disease or systemic amyloidosis.

In such an assay, binding of an antibody to plaques may be determined using IHC. The antibody may be labelled prior to being tested. Binding to the plaque may be defined as positive blind scored IHC staining of amyloid after injection of ≦1 mg antibody, in single or multiple doses, in at least two out of three mice tested. The signal is generally compared to the signal from stained anatomically, sex and age matched tissue from negative isotype matched control antibody injected mice.

The term "epitope" as used herein refers to that portion of a molecule that makes contact with a particular binding polypeptide. An epitope may be linear, comprising an essentially linear amino acid sequence from the antigen or conformational, comprising sequences that are separated by other sequences but come together structurally to form a binding site for the polypeptide.

The epitope in ApoE-CTD to which the antibody binds may appear on ApoE-CTD after cleavage from full-length ApoE. Alternatively the epitope may appear following the interaction of ApoE-CTD with amyloid plaques, for example as a result of binding of ApoE-CTD to Aβ. Cleavage of ApoE and/or binding of ApoE-CTD to amyloid plaques may result in the exposure of new linear (peptide) epitopes and/or to the exposure or formation of new conformational epitopes. The epitope to which a polypeptide of the invention binds may be hidden in VLDL-associated ApoE due to the interaction of ApoE with other components of VLDL. The polypeptide may bind specifically to a complex formed between ApoE-CTD and Aβ.

The amino acid sequence of ApoE-CTD is shown in SEQ ID NO: 1. ApoE-CTD epitopes may thus be formed by a linear or conformational sequence within the sequence of ApoE-CTD as shown in SEQ ID NO: 1. An antibody that binds to ApoE-CTD typically bind to an ApoE-CTD polypeptide having the whole sequence shown in SEQ ID NO: 1 but may also bind to a part of the amino acid sequence of SEQ ID NO: 1 such as to a peptide having an amino acid sequence as shown in any one of SEQ ID NOS: 2 to 19. Preferably, the antibody binds to one or more of the peptides shown in SEQ ID NO: 2, SEQ ID NO: 5, SEQ ID NO: 7, SEQ ID NO: 9, SEQ ID NO: 10, SEQ ID NO: 12, SEQ ID NO: 13, SEQ ID NO: 14, SEQ ID NO: 15, SEQ ID NO: 16, or SEQ ID NO: 17. The part of ApoE-CTD to which the antibody binds is at least a three amino acid fragment of SEQ ID NO: 1, preferably at least a five, six, seven or eight amino acid fragment, more preferably a 10, 12 or 16 amino acid fragment.

The polypeptide (or peptide) to which the antibody binds may be a recombinant polypeptide. The polypeptide may be in solution or, more preferably, may be attached to a solid surface. For example, the polypeptide may be attached to beads, such as magnetic beads.

The polypeptide may be biotinylated. The biotin molecule conjugated to the peptide may be used to immobilize the polypeptide on a solid surface by coupling biotin to streptavidin on the solid surface.

An antibody of the present invention suitable for use in treating or preventing Alzheimer's disease and/or systemic amyloidosis typically tests positive in an ex vivo phagocyte assay. A positive phagocyte assay is defined as positive blind scored confocal microscopy detection of phagocytes that contain amyloid after co-culture on amyloid tissue after applying ≦20 µg/ml of the antibody in at least two out of three cultures tested. The signal is generally compared to the signal from identical co-cultures containing the same concentration of a negative control antibody. A positive phagocyte assay generally also results in the degradation of amyloid, for example as shown by Western blot to be less than one third the density of the Aβ-based remaining after up to three days of co-culture, as compared to blots from identical co-cultures containing the same concentration of a negative-control antibody.

Antibodies and other peptides for therapeutic use are typically of high affinity, preferably having an affinity of <1 nM, for ApoE-CTD, to enable them to function optimally even at the low concentrations in the brain that will build up after systemic injection.

The term "antibody" refers to a protein comprising at least one, and preferably two, heavy chain variable regions (VH) and/or at least one, preferably two, light chain variable regions (VL). The VH and VL regions can be further subdivided into regions of hypervariability, termed "complementarity determining regions (CDR)", interspersed with regions that are more conserved, termed "framework regions (FR)". The extent of the FR and CDRs has been precisely defined (see, Kabat, et al. (1991) *Sequences of Proteins of Immunological Interest, Fifth Edition*, U.S. Department of Health and Human Services, NIH Publication No. 91-3242; Chothia et al. (1987) *J. Mol. Biol.* 196: 901-917, which are incorporated herein by reference in their entirety). Each VH and VL is composed of three CDRs and four FRs arranged from N-terminus to C-terminus in the following order: FR1, CDR1, FR2, CDR2, FR3, CDR3, FR4.

The VH or VL chain of the antibody can further include all or part of a heavy or light chain constant region, to thereby form a heavy or light immunoglobulin chain respectively. In one embodiment, the antibody is a tetramer of two heavy and two light chains, wherein the heavy and light chains are interconnected by, for example, disulphide bonds. The heavy chain constant region is comprised of three domains, CH1, CH2 and CH3. The light chain constant region is comprised of one domain, CL. The variable region of the heavy and light chains contains a binding domain that interacts with antigen. The constant regions of the antibodies typically mediate the binding of the antibody to host tissues and factors, including various cells of the immune system and the first component of the complement system. The term "antibody" includes intact immunoglobulins of types IgA, IgG, IgE, IgD, IgM and subtypes thereof. A preferred immunoglobulin is IgG.

As used herein the term "immunoglobulin" refers to a protein consisting of one or more polypeptides substantially encoded by immunoglobulin genes. The recognised human immunoglobulin genes include the kappa, lambda, alpha (IgA1 and IgA2), gamma (IgG1, IgG2, IgG3, IgG4), delta, epsilon and mu conatant region genes as well as a myriad of immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g. gamma (encoding about 330 amino acids).

An antibody fragment of the invention is typically an antigen-binding fragment. The term "antigen-binding fragment" refers to one or more fragments of a full-length antibody that are capable of specifically binding to ApoE-CTD. Examples of binding fragments include (i) a Fab fragment (a monovalent fragment consisting of the VL, VH, CL and CH1 domains; (ii) a F(ab')$_2$ fragment (a bivalent fragment comprising two Fab fragments linked by a disulphide bridge at the hinge region; (iii) a Fd fragment (consisting of the VH and CH1 domains); (iv) a Fv fragment (consisting of the VH and VL domains of a single arm of an antibody); (v) a dAb fragment (consisting of the VH domain); (vi) an isolated CDR; (vii) a single chain Fv (scFv) (consisting of the VH and VL domains of a single arm of an antibody joined by a synthetic linker using recombinant means such that the VH and VL domains pair to form a monovalent molecule); (viii) diabodies (consisting of two scFvs in which the VH and VL domains are joined such that they do not pair to form a monovalent molecule; the VH of each one of the scFv pairs with the VL domain of the other scFv to form a bivalent molecule); (ix) bi-specific antibodies (consisting of at least two antigen binding regions, each region binding a different epitope). Preferably, the antibody fragment is a Fab fragment or single-chain antibody (scFv).

The sequences of preferred CDR1 domains are shown in SEQ ID NOS: 21, 24, 27, 30, 33, 36, 45, 48, 51, 54, 57, 60, 63, 66, 69, 72, 75, 78, 81, 84, 87, 93, 111, 117 and 123. Other preferred CDR1 domains are variants of these sequences in which one or more amino acids within the sequence have been deleted or, more preferably, substituted. Other preferred CDR1 domains are variants of the sequences shown in any one of SEQ ID NOS: 21, 24, 27, 30, 33, 36, 45, 48, 51, 54, 57, 60, 63, 66, 69, 72, 75, 78, 81, 84, 87, 93, 111, 117 and 123 in which one or more amino acid has been inserted. Preferably, a variant CDR1 domain comprises one or more, for example two, three, four or five substitutions, preferably conservative substitutions. Examples of such CDR1 variant sequences are the LV-CDR1 sequences identified in Tables 38, 39, 40, 41 and 42. Preferred CDR1 sequences include SEQ ID NOS: 33, 219, 226, 218, 326, 93, 325, 391 and 394.

The sequences of preferred CDR2 domains are shown in SEQ ID NOS: 22, 25, 28, 31, 34, 37, 46, 49, 52, 55, 58, 61, 64, 67, 70, 73, 76, 79, 82, 85, 88, 94, 112, 118 and 124. Other preferred CDR2 domains are variants of these sequences in which one or more amino acids within the sequence have been deleted or, more preferably, substituted. Other preferred CDR2 domains are variants of the sequences shown in one of SEQ ID NOS: 22, 25, 28, 31, 34, 37, 46, 49, 52, 55, 58, 61, 64, 67, 70, 73, 76, 79, 82, 85, 88, 94, 112, 118 and 124 in which one or more amino acid has been inserted. Preferably, a variant CDR2 domain comprises one or more, for example two, three, four or five substitutions, preferably conservative substitutions. Examples of such CDR2 variant sequences are the LV-CDR2 sequences identified in Tables 38, 39, 40, 41 and 42. Preferred CDR2 sequences include SEQ ID NOS: 382, 386, 333, 334, 34, 247 and 252.

The sequences of preferred CDR3 domains are shown in SEQ ID NOS: 23, 26, 29, 32, 35, 38, 47, 50, 53, 56, 59, 62, 65, 65, 68, 71, 74, 77, 80, 83, 86, 89, 95, 113, 119 and 125. Other preferred CDR3 domains are variants of these sequences in which one or more amino acids within the sequence have been deleted or, more preferably substituted. Other preferred CDR3 domains are variants of the sequences shown in one of SEQ ID NOS: 23, 26, 29, 32, 35, 38, 47, 50, 53, 56, 59, 62, 65, 65, 68, 71, 74, 77, 80, 83, 86, 89, 95, 113, 119 and 125 in which one or more amino acid has been inserted. Preferably, a variant CDR3 domain comprises one or more, for example two or three, conservative substitutions.

Conservative substitutions are shown in the following Table. Amino acids in the same block in the second column and preferably in the same line in the third column may be substituted for each other.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Examples of variant CDR3 sequences are the HV-CDR3 and LV-CDR3 sequences identified in Tables 38, 39, 40, 41 and 42. Preferred variant CDR3 sequences are shown in SEQ ID NOS: 207, 209, 210, 35, 269, 252, 34, 322, 323, 320, 341, 373 and 378.

Preferred antibodies comprise (i) the VH sequence shown in SEQ ID NO: 39, or a variant thereof, and the VL sequence shown in SEQ ID NO: 42, or a variant thereof; (ii) the VH sequence shown in SEQ ID NO: 40, or a variant thereof, and the VL sequence shown in SEQ ID NO: 43, or a variant thereof; (iii) the VH sequence shown in SEQ ID NO: 41, or a variant thereof, and the VL sequence shown in SEQ ID NO: 44, or a variant thereof.

Other preferred antibodies comprise a heavy chain sequence selected from the sequences shown in SEQ ID NOS: 317, 318, 319, 369, 370, 371, 372 and 397 and optionally a light chain sequence selected from SEQ ID NOS: 43, 295, 294, 304, 347, 348, 357, 362, 406 and 418. More preferred antibodies include antibodies having the following combinations of heavy and light chain sequences: SEQ ID NOS: 319 and 43, SEQ ID NOS: 318 and 295, SEQ ID NOS: 318 and 294, SEQ ID NOS: 317 and 304, SEQ ID NOS: 370 and 347, SEQ ID NOS: 370 and 348, SEQ ID NOS: 371 and 348, SEQ ID NOS: 372 and 348, SEQ ID NOS: 369 and 357, SEQ ID NOS: 370 and 362, SEQ ID NOS: 397 and 406. SEQ ID NOS: 397 and 418.

Variant antibodies may be obtained by any suitable method. Typically variants with improved binding characteristics are selected by affinity maturation.

In a preferred embodiment, the antibody is a recombinant or modified anti-ApoE-CTD antibody, e.g. a chimeric, humanised, deimmunised or an in vitro generated antibody. The term "recombinant" or "modified" antibody as used herein is intended to include all antibodies that are prepared, expressed, created or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) antibodies prepared, expressed, created or isolated by any other means that involves splicing of human immunoglobulin gene sequences to other DNA sequences. Such recombinant antibodies include humanised, CDR grafted, chimeric, deimmunised, in vitro generated antibodies and may optionally include constant regions derived from human germline immunoglobulin sequences.

An antibody according to the invention is a human antibody. The antibody may be a chimeric antibody, a recombinant antibody, a humanised antibody, a monoclonal antibody or a polyclonal antibody. Preferably the antibody is monoclonal.

The antibody may be conjugated to a functional moiety such as a drug, detectable moiety or a solid support.

Also within the scope of the invention are compositions comprising two or more antibodies which bind different epitopes of ApoE-CTD. The antibodies in the composition may bind overlapping epitopes. Antibodies that bind overlapping epitopes competitively inhibit the binding of each other to ApoE-CTD.

The antibody is preferably monospecific, e.g. a monoclonal antibody, or antigen-binding fragment thereof. Bispecific and multivalent antibodies are also provided, which bispecific or multivalent antibodies bind to two or more different epitopes of ApoE-CTD.

An antibody of the invention may be joined to a binding moiety such as biotin. For example, an antibody, preferably an IgG, may be biotinylated by incubation with sulfosuccinimidyl-2-(biotinamido) ethyl-1,3-dithiopropionate. A biotinylated IgG preferably comprises from 1 to 5 such as 2, 3 or 4 biotin groups.

An antibody of the invention may be in substantially isolated form. They may be mixed with carriers or diluents which will not interfere with their intended use and still be regarded as substantially isolated. They may also be in a substantially purified form, in which case they will generally comprise at least 90%, e.g. at least 95%, 98% or 99%, of the polypeptides or dry mass of the preparation.

B. Methods For Identifying Antibodies

The invention also provides a method for identifying an antibody according to the invention. The method typically comprises identifying an antibody that binds to a polypeptide having the amino acid sequence as shown in SEQ ID NO: 1 or the amino acid sequence of a part thereof and that binds to human plaques. Either or both binding assays may be carried out in the presence of VLDL. The methods generally comprise providing a display library and screening the library to identify a member that encodes an antibody that binds to ApoE-CTD or a fragment thereof and/or to human plaques, preferably in the presence of VLDL. A display library is a collection of entities; each entity includes an accessible antibody component and a recoverable component that encodes or identifies the antibody component. The antibody component can be of any length, e.g., from three amino acids to over 300 amino acids for example 30, 100 or 200 amino acids and is typically an antibody fragment, preferably a Fab fragment. In a selection, the antibody component of each member of the library is probed with ApoE-CTD and if the antibody component binds to ApoE-CTD or fragment thereof, the display library member is identified, typically by retention on a support. Display library members that bind ApoE-CTD may also typically tested for binding to ApoE-NTD (negative selection).

Retained display library members are recovered from the support and analysed. The analysis can include amplification and a subsequent selection under similar or dissimilar conditions. For example, positive and negative selections can be alternated. The analysis can also include determining the amino acid sequence of the antibody component and purification of the antibody component for detailed characterisation.

A variety of formats can be used for display libraries and any suitable format may be used in a method of the invention. Preferred formats are phage display and cell-based display such as yeast display.

In phage display, the candidate antibodies are typically covalently linked to bacteriophage coat protein. The linkage results from translation of a nucleic acid encoding the candidate antibodies fused to the coat protein. The linkage can include a flexible peptide linker, a protease site, or an amino acid incorporated as a result of suppression of a stop codon. Phage display is described, for example, in Ladner et al., U.S. Pat. No. 5,223,409; Smith (1985) Science 228:1315-1317; WO 92/18619; WO 91/17271; WO 92/20791; WO 92/15679; WO 93/01288; WO 92/01047; WO 92/02809; WO 90/09690; de Haard et al. (1999) J. Biol. Chem. 274:18218-30; Hoogenboom et al. (1998) Immunotechnology 4: 1-20; Hoogenboom et al. (2000) Immunol. Today 2:371-8; Fuchs et al. (1991) Bio/Technology 9:1370-1372; Hay et al. (1992) Hum. Antibod. Hybridomas 3:81-85; Huse et al. (1989) Science 246: 1275-1281; Griffiths et al. (1993) EMBO J. 12:725-734; Hawkins et al. (1992) J. Mol. Biol. 226:889-896; Clackson et al. (1991) Nature 352:624-628; Gram et al. (1992) Proc. Natl. Acad. Sci. USA 89:3576-3580; Garrard et al. (1991) Bio/Technology 9:1373-1377; Rebar et al. (1996) Methods Enzymol. 267:129-49; Hoogenboom et al. (1991) Nuc. Acids Res. 19:4133-4137; Barbas et al. (1991) Proc. Natl. Acad. Sci. USA 88:7978-7982; and Lee et al. (2003) Trends In Biotechnology 21: 45-52.

Phage display systems have been developed for filamentous phage (phage fl, fd and M13) as well as other bacteriophage (e.g., T7 Bacteriophage and lambdoid phages; see, e.g., Santini (1998) J. Mol. Biol. 282:125-135; Rosenberg et al. (1996) Innovations 6:1-6; Houshmet et al. (1999) Anal. Biochem. 268:363-370). The filamentous phage display systems typically use fusions to a minor coat protein, such as gene III protein, and gene VIII protein, a major coat protein, but fusions to other coat proteins such as gene VI protein, gene VII protein, gene IX protein, or domains thereof can also been used (see, e.g., WO 00/71694). In a preferred embodiment, the fusion is to a domain of the gene III protein, e.g., the anchor domain or "stump," (see, e.g., U.S. Pat. No. 5,658,727 for a description of the gene III protein anchor domain).

The valency of the candidate polypeptides can also be controlled. Cloning of the sequence encoding the polypeptide component into the complete phage genome results in multi-variant display since all replicates of the gene III protein are fused to the polypeptide component. For reduced valency, a phagemid system can be utilised. In this system, the nucleic acid encoding the polypeptide component fused to gene III is provided on a plasmid, typically of length less than 700 nucleotides. The plasmid includes a phage origin of replication so that the plasmid is incorporated into bacteriophage particles when bacterial cells bearing the plasmid are infected with helper phage, e.g., M13K07. The helper phage provides an intact copy of gene III and other phage genes required for phage replication and assembly. The helper phage has a defective origin such that the helper phage genome is not efficiently incorporated into phage particles relative to the plasmid that has a wild type origin.

Bacteriophage displaying the candidate antibodies can be grown and harvested using standard phage preparatory methods, e.g., PEG precipitation from growth media.

After selection of individual display phages, the nucleic acid encoding the selected candidate antibodies can be obtained by infecting cells using the selected phages. Individual colonies or plaques can be picked, the nucleic acid isolated and sequenced.

In a screening procedure to obtain ApoE-CTD binders according to this invention, a display library is contacted with and allowed to bind a target ApoE-CTD molecule, usually immobilised on a solid support. Non-binders are separated from binders. In various ways, the bound phage are liberated from the ApoE-CTD, collected and amplified. Since the phage can be amplified through infection of bacterial cells, even a few binding phage are sufficient to reveal the gene sequence that encodes a binding entity. Using these techniques it is possible to recover a binding phage that is about 1 in 20 million in the population. One or more libraries, displaying 10-20 million or more potential binding polypeptides each, can be rapidly screened to find high-affinity ApoE-CTD binders. When the selection process works, the diversity of the population falls with each round until only good binders remain, i.e., the process converges. Typically, a phage display library will contain several closely related binders (10 to 50 binders out of 10 million). Indications of convergence include increased binding (measured by phage titers) and recovery of closely related sequences.

In a cell-display library the candidate antibodies are displayed on the surface of a cell, e.g., a eukaryotic or prokaryotic cell. Exemplary prokaryotic cells include *E. coli* cells, *B. subtilis* cells and spores (see, e.g., Lu et al. (1995) *Biotechnology* 13:366). Exemplary eukaryotic cells include yeast (e.g., *Saccharomyces cerevisiae, Schizosaccharmyces pombe, Hanseulla,* or *Pichia pastoris*). Yeast surface display is described in, for example, Boder and Wittrup (1997) *Nature Biotech.* 15:553-557. A yeast display system that may be used to display immunoglobulin proteins such as Fab fragments, and yeast mating may be used to generate combinations of heavy and light chains.

Yeast display has clear advantages over phage display in the application of affinity maturation of anti-ApoE-CTD antibodies. The most important advantage is that FACS selection may be used to quantitatively sort each yeast cell for its antigen binding. It is also possible to perform normalised selection so that variations in display level can be corrected, thus avoiding selection on the basis of avidity. This is particularly important when using a multivalent target antigen.

The display library may be a ribosome display library. In a ribosome display to library mRNA and the candidate antibody encoded by the RNA can be physically associated by stabilising ribosomes that are translating the mRNA and have the nascent polypeptide still attached. Typically, high divalent $Mg^{2+}$ concentrations and low temperature are used. See, e.g., Mattheakis at al. (1994) *Proc. Natl. Acad. Sci. USA* 91:9022 and Hanes at al. (2000) *Nature Biotech.* 18:1287-92; Hans at al. (2000) *Methods Enzymol.* 328-404-30 and Schaffitzel et al. (1999) *J. Immunol. Methods* 231:119-35.

Another display library format utilises peptide-nucleic acid fusions. Polypeptide-nucleic acid fusions can be generated by the in vitro translation of mRNA that include a covalently attached puromycin group, e.g., as described in Roberts and Szostak (1997) *Proc. Acad. Sci. USA* 94:12297-12302, and U.S. Pat. No. 6,207,446. The mRNA can then be reverse transcribed into DNA and crosslinked to the polypeptide.

Another display format that may be used is a non-biological display in which the antibody component is attached to a non-nucleic acid tag that identifies the antibody. For example, the tag can be a chemical tag attached to a bead that displays the antibody or a radiofrequency tag (See, e.g., U.S. Pat. No. 5,874,214).

A parental binding domain is selected to serve as a structural template for the candidate antibodies. The binding domain may be a naturally occurring or synthetic protein, or a region or domain of a protein such as an immunoglobulin. The parental binding domain may be selected based on knowledge of a known interaction between the parental binding domain and ApoE-CTD but, but this is not critical. In fact, it is not essential that the parental binding domain have any affinity for ApoE-CTD at all: its purpose is to provide a structure from which a library can be generated, which library will include one or more candidate antibodies that bind specifically to ApoE-CTD.

The candidate antibodies may be Fab fragments, single chain Fv molecules (scFV), single domain antibodies, camelid antibodies and camelized antibodies.

In a preferred embodiment, the parental binding domain comprises an immunoglobulin domain with antigen-binding activity, such as scFv, Fab or IgG. A typical display library displays candidate polypeptides that include a VH domain and a VL domain. As in the case of the Fab and other formats, the displayed antibody can include a constant region as part of a light or heavy chain. In one embodiment, each chain includes one constant region, e.g. as in the case of a Fab. In other embodiments, additional constant regions are displayed.

Display libraries are particularly useful, for example for identifying human or "humanised" antibodies that recognise human antigens. The in vitro display selection process surmounts the inability of a normal human immune system to generate antibodies against self-antigens.

Antibody libraries can be constructed by a number of processes (see, e.g. de Haard et al (1999) *J. Biol. Chem.* 274: 18218-30; Hoogenboom et al (1998) *Immunotechnology* 4:1-20, and Hoogenboom et al (2000) *Immunol. Today* 21:371-8). Further, elements of each process can be combined with those of other processes. The processes can be used such that variation is introduced into a single immunoglobulin domain (e.g. VH or VL) or into multiple immunoglobulin domains (e.g. VH and VL). The variation can be introduced into an immunoglobulin variable domain, e.g. in the region of one or more of CDR1, CDR2, CDR3, FR1, FR2, FR3 and FR4, referring to such regions of either and/or both of heavy and light chain variable domains. In one embodiment, variation is introduced into all three CDRs of a given variable domain. In another preferred embodiment, the variation is introduced into CDR1 and CDR2, e.g. of a heavy chain variable domain. Any combination is feasible.

In a preferred embodiment the parental domain comprises the CDR3 sequence shown in any one of SEQ ID NOS: 23, 26, 29, 32, 35, 38, 47, 50, 53, 56, 59, 62, 65, 68, 71, 74, 77, 80, 83, 86, 89, 95, 113, 119 and 125. Amino acid substitutions at one or both of positions 2 and 3 of SEQ ID NO: 23 or 26 are preferred variations in candidate antibodies. Examples of variant VH-CDR3 sequences generated by antibody spiking are identified in Tables 38, 39, 40, 41 and 42. Preferred CDR3 sequences are shown in SEQ ID NOS: 207, 209, 210, 320, 322, 323 and 373. Consensus sequences for preferred CDR3 sequences are shown in SEQ ID NOS: 512, 513, 514, 515, 516, 517 and 20.

Examples of variant VL-CDR3 sequences generated by light chain shuffling are also shown in Tables 38, 39, 40, 41 and 42. Preferred VL-CDR3 sequences are shown in SEQ ID NOS: 35, 269, 275, 268, 341 and 378.

The parental domain preferably also comprises the other components of the VH chain, and optionally a VL chain, or the other components of the VL chain, and optionally a VH chain.

A second preferred parental domain comprises a CDR1 and/or CDR2 domain with the sequence shown in any one of SEQ ID NOS: 21, 24, 27, 30, 33, 36, 45, 48, 51, 54, 57, 60, 63, 66, 69, 72, 75, 78, 81, 84, 87, 93, 111, 117 and 123 or in SEQ ID NOS: 22, 25, 28, 31, 34, 37, 46, 49, 52, 55, 58, 61, 64, 67, 70, 73, 76, 79, 82, 85, 88, 94, 112, 118 and 124. The candidate polypeptides may be generated by DNA shuffling the CDR1 and/or CDR2 domains. Examples of variant VL-CDR1 and VL-CDR2 sequences are identified in Tables 38, 39, 40, 41 and 42. Preferred CDR1 sequences are shown in SEQ ID NOS: 33, 219, 226, 218, 93, 325, 326, 391 and 394. Preferred CDR2 sequences are shown in SEQ ID NOS: 34, 247, 252, 333, 334, 382 and 386.

A third preferred parental domain comprises the VL sequence shown in any one of SEQ ID NOS: 42, 43, 44, 151, 157, 159 and 161. Candidate polypeptides are typically generated by DNA shuffling of the entire VL sequence. Examples of shuffled light chain sequences are identified in Tables 38, 39, 40, 41 and 42. Preferred shuffled light chain sequences are shown in SEQ ID NOS: 43, 295, 294, 304, 347, 348, 357, 362, 406 and 418.

In one process, antibody libraries are constructed by inserting diverse oligonucleotides that encode CDRs into the corresponding regions of the nucleic acid. The oligonucleotides can be synthesized using monomeric nucleotides or trinucleotides. For example, Knappik et al ((2000) *J. Mol. Biol.* 296:57-86) describes a method for constructing CDR encoding oligonucleotides using trinucleotide synthesis and a template with engineered restriction sites for accepting the oligonucleotides.

In another process, an animal, e.g. a rodent, is immunised with the ApoE-CTD. The animal is optionally boosted with the antigen to further stimulate the response. Then spleen cells are isolated from the animal, and nucleic acid encoding VH and/or VL domains is amplified and cloned for expression in the display library.

In yet another process, antibody libraries are constructed from nucleic acid amplified from naïve germline immunoglobulin genes. The amplified nucleic acid includes nucleic acid encoding the VH and/or VL domain. Sources of immunoglobulin-encoding nucleic acids are described below. Amplification can include PCR, e.g. with primers that anneal to the conserved constant region, or another amplification method.

Nucleic acid encoding immunoglobulin domains can be obtained from the immune cells of, e.g. a human, a primate, mouse, rabbit, camel or rodent. In one example, the cells are selected for a particular property. B cells at various stages of maturity can be selected. In another example, the B cells are naïve.

In one embodiment, fluorescent-activated cell sorting (FACS) is used to sort

B cells that express surface-bound IgM, IgD or IgG molecules. Further, B cells expressing different isotypes of IgG can be isolated. In another preferred embodiment, the B or T cell is cultured in vitro. The cells can be stimulated in vitro, e.g. by culturing with feeder cells or by adding mitogens or other modulatory reagents, such as antibodies to CD40, CD40 ligand or CD20, phorbol myristate acetate, bacterial lipopolysaccharide, concanavalin A, phytohemagglutinin or pokeweed mitogen.

In still another embodiment, the cells are isolated from a subject that has an immunological disorder, e.g. systemic lupus erythematosus (SLE), rheumatoid arthritis, vasculitis, Sjogren syndrome, systemic sclerosis or anti-phospholipid syndrome. The subject can be a human or an animal, e.g. an animal model for the human disease, or an animal having an analogous disorder. In yet another embodiment, the cells are isolated from a transgenic non-human animal that includes a human immunoglobulin locus.

In one preferred embodiment, the cells have activated a program of somatic hypermutation. Cells can be stimulated to undergo somatic mutagenesis of immunoglobulin genes, for example, by treatment with anti-immunoglobulin, anti-CD40 and anti-CD38 antibodies (see, e.g. Bergthorsdottir et al (2001) *J. Immunol.* 166:2228). In another embodiment, the cells are naïve.

The nucleic acid encoding an immunoglobulin variable domain can be isolated from a natural repertoire by the following exemplary method. First, RNA is isolated from the immune cell. Full length (i.e. capped) mRNAs are separated (e.g. by degrading uncapped RNAs with calf intestinal phosphatase). The cap is then removed with tobacco acid pyrophosphatase and reverse transcription is used to produce the cDNAs.

The reverse transcription of the first (antisense) strand can be done in any manner with any suitable primer. See, e.g. de Haard et al (1999) *J. Biol. Chem.* 274:18218-30. The primer binding region can be constant among different immunoglobulins, e.g. in order to reverse transcribe different isotypes of immunoglobulin. The primer binding region can also be specific to a particular isotype of immunoglobulin. Typically, the primer is specific for a region that is 3' to a sequence encoding at least one CDR. In another embodiment, poly-dT primers may be used (and may be preferred for the heavy-chain genes).

A synthetic sequence can be ligated to the 3' end of the reverse transcribed strand. The synthetic sequence can be used as a primer binding site for binding of the forward primer during PCR amplification after reverse transcription. The use of the synthetic sequence can obviate the need to use a pool of different forward primers to fully capture the available diversity.

The variable domain-encoding gene is then amplified, e.g. using one or more rounds. If multiple rounds are used, nested primers can be used for increased fidelity. The amplified nucleic acid is then cloned into a display library vector.

Any method for amplifying nucleic acid sequences may be used for amplification. Methods that maximise, and do not bias, diversity are preferred. Suitable techniques for nucleic acid amplification include the polymerase chain reaction (PCR), transcription-based methods that utilise RNA synthesis by RNA polymerases to amplify nucleic acid (Sarker et al (1989) *Science* 244:331-34), NASBA (U.S. Pat. Nos. 5,130, 238; 5,409,818; and 5,554,517) which utilises cycles of transcription, reverse-transcription and RnaseH-based degradation to amplify a DNA sample, rolling circle amplification (RCA; U.S. Pat. No. 6,143,495) and strand displacement amplification (SDA; U.S. Pat. No. 5,624,825).

After a first set of binding antibodies is identified, the sequence information can be used to design other libraries biased for members having additional desired properties, e.g., discrimination between ApoE-CTD and full-length ApoE, preferably VLDL-associated ApoE. Such techniques make it possible not only to screen a large number of potential binding antibodies but also make it practical to repeat the binding/elution cycles and to build secondary, biased libraries for screening analog-displaying packages that meet initial criteria. Using these techniques, a biased library may be screened to reveal members that bind tightly (i.e., with high affinity) under the screening conditions.

Thus, in one preferred embodiment, display library technology may be used in an iterative mode. A first display library is used to identify one or more antibodies that bind ApoE-CTD and/or human plaques. These identified antibodies are then varied using a mutagenesis method to form a second display library. Higher affinity polypeptides are then selected from the second library, e.g., by using higher stringency or more competitive binding and washing conditions.

In affinity maturation protocols, the variation is preferably generated by amino acid substitutions but may also result from deletion or addition of amino acids.

The amino acid substitutions may be those which are expected to alter the binding properties of the domain without significantly altering its structure, at least for most substitutions. It is preferred that the amino acid positions that are selected for variation (variable amino acid positions) will be surface amino acid positions, that is, positions in the amino acid sequence of the domains which, when the domain is in its most stable conformation, appear on the outer surface of the domain (i.e., the surface exposed to solution). Most preferably the amino acid positions to be varied will be adjacent or close together, so as to maximise the effect of substitutions. In addition, extra amino acids can be added into the structure of the parental binding domain.

In some implementations, the mutagenesis is targeted to regions known or likely to be at the binding interface. Mutagenesis can be directed to the CDR regions of the heavy or light chains as described herein. Further, mutagenesis can be directed to framework regions near or adjacent to the CDRs. Mutagenesis can also be limited to one or a few of the CDRs, e.g., to make precise step-wise improvements.

Effective affinity maturation requires 4 components (i) the rediversification of lead antibody genes (ii) display on either phage or yeast (iii) affinity selection (iv) screening of clones for improved affinity.

Alignment of Fabs showing the required binding properties, for example using a BLAST algorithm (e.g. Karlin and Altschul (1993) PNAS USA 90: 5873-5787) may be used to identify conserved residues in the CDR domains. Sequence similarity amongst the CDR loops may allow a prediction of the direct involvement of any amino acid in antibody affinity or specificity.

For example, the VH-CDR3 loops of antibodies 807A-M0028-B02 and 807A-M0027-E11 (SEQ ID NOS: 23 and 26) show striking similarity and show consensus over 4/6 amino acids (SEQ ID NO: 20). This suggests that the VH-CDR3 plays a role in antibody affinity and specificity.

An optimal antibody mutagenesis strategy introduces a minimal number of mutations at functionally relevant positions. This is achieved by both targeted and non-targeted mutagenesis procedures. Non-targeted mutagenesis procedures include chain shuffling which introduces large block changes in antibodies by rediversifying the whole VL gene or the VH CDR1-2 fragment. Typically, the VH-CDR3 loop is left untouched, as it may make significant contributions to binding affinity and specificity. Examples of chain shuffling are described in the following documents: Marks et al., (1992) Nature Biotech 10: 779-783, Schier et al., (1996) J. Mol. Biol. 255, 28-43, Park et al., (2000) BBRC. 275. 553-557 and Chames et al., (2002) J. Immunol. 1110-1118. Although chain shuffling is a well-validated technique (particularly for antibodies with a low starting affinity) a possible disadvantage is that by making such large block changes in the antibody molecule that there may be an increased chance of disrupting multiple favourable contacts. However this could be compensated by the loss of unfavourable contacts or the generation of new contacts.

Other exemplary non-targeted mutagenesis techniques include: error-prone PCR (Leung et al. (1989) *Technique* 1:11-15), recombination, DNA shuffling using random cleavage (Stemmer (1994) *Nature* 389-391; termed "nucleic acid shuffling"), RACHITT™ (Coco at al. (2001) *Nature Biotech.* 19:354), site-directed mutagenesis (Zooler et al. (1987) *Nucl. Acids Res.* 10:6487-6504), cassette mutagenesis (Reidhaar-Olson (1991) *Methods Enzymol.* 208:564-586) and incorporation of degenerate oligonucleotides (Griffiths at al. (1994) EMBO J. 13:3245).

Targeted mutagenesis procedures include hot spot mutagenesis, parsimonious mutagenesis, saturation mutagenesis, domain randomisation and domain walking. CDR mutagenesis can be done in a stepwise manner that is target CDR1, select an optimised loop and subsequently target CDR2 etc. The single most naturally diverse loop is the VH-CDR3 and it is generally accepted that as this loop is situated centrally in the antibody combining site that this is a critical determinant of antibody specificity and affinity. This means that there is a strong case for specifically targeting this loop.

In one example of iterative selection, the methods described herein are used to first identify an antibody from a display library that binds ApoE-CTD with at least a minimal binding specificity for a target or a minimal activity, e.g., an equilibrium dissociation constant for binding of greater than 1 nM, 10 nM, or 100 nM, and which binds human plaques and or/which retains binding activity in the presence of VLDL-associated ApoE. The nucleic acid sequence encoding the initial identified antibody is used as a template nucleic acid for the introduction of variations, e.g., to identify a second polypeptide that has enhanced properties (e.g., binding affinity, kinetics, or stability) relative to the initial antibody.

Antibodies according to the present invention may be isolated using display technology, in a manner to identify ApoE-CTD binding antibodies exhibiting particular preselected properties of binding and release. According to this methodology, two solution conditions may be preselected, i.e., binding conditions and release conditions. The binding conditions are a set of solution conditions under which is desired that a discovered antibody will bind the target ApoE-CTD; the release conditions are a set of solution conditions under which it is desired that a discovered antibody will not bind the ApoE-CTD (i.e. will dissociate from ApoE-CTD). The two conditions may be selected to satisfy any criterion of the practitioner, such as ease of attaining the conditions, compatibility with other purification steps, lowered cost of switching between conditions compared to other affinity media, etc. Preferably, the two solution conditions are selected so as not to adversely affect the stability or activity of the target protein ApoE-CTD and so as to differ significantly with respect to at least one solution parameter. For example, in conducting the screening for suitable binding peptides described herein, binders are selected that dissociated from the target in the presence of an ethylene glycol-containing buffer, or conditions of lowered pH (i.e. pH 2), or combinations of those conditions, which differ from the conditions employed for binding. Another parameter that can be advantageously varied is the concentration of a salt, for example NaCl, in the binding and elution buffers.

An antibody which binds to ApoE-CTD typically has a minimal binding specificity for ApoE-CTD, for example an equilibrium constant for binding of greater than 1 nM, 10 nM or 100 nM.

Since a slow dissociation rate can be predictive of high affinity, particularly with respect to interactions between antibodies and their targets, methods of off-rate selection can be used to isolate antibodies with a desired kinetic dissociation rate (i.e., reduced) for a binding interaction to an ApoE-CTD.

To select for slow dissociating antibodies from a display library, the library is contacted to an immobilised target, preferably ApoE-CTD. The immobilised target is then washed with a first solution that removes non-specifically or weakly bound antibodies. Then the immobilised target is eluted with a second solution that includes a saturation amount of free target, i.e., replicates of the target that are not attached to the particle. The free target binds to antibodies that dissociate from the target. Rebinding is effectively prevented by the saturating amount of free target relative to the much lower concentration of immobilised target.

The second solution can have solution conditions that are substantially physiological or that are stringent. Typically, the solution conditions of the second solution are identical to the solution conditions of the first solution. Fractions of the second solution are collected in temporal order to distinguish early from late fractions. Later fractions include biomolecules that dissociate at a slower rate from the target than biomolecules in the early fractions.

Further, it is also possible to recover display library members that remain bound to the target even after extended incubation. These can either be dissociated using chaotropic conditions or can be amplified while attached to the target. For example, phage bound to the target can be contacted to bacterial cells.

The ApoE-CTD used in a method of the invention may be in any suitable form. ApoE-CTD typically has the amino acid sequence set out in SEQ ID NO. 1 or the amino acid sequence of a fragment thereof. The fragment of ApoE-CTD is typically at least three amino acids in length, preferably at least five, six, seven or eight amino acids in length and more preferably at least 10, 12 or 16 amino acids in length. Examples of suitable fragments are set out in SEQ ID NOS: 2 to 19. Preferred fragments are those having a sequence shown in any one of SEQ ID NOs: 2, 5, 7, 9, 10, 12, 13, 14, 15, 16 and 17. One or more ApoE-CTD peptide may be used in a screening assay of the invention.

The ApoE-CTD polypeptides are generally produced by recombinant means. Urea-denatured ApoE-CTD which has been recombinantly or naturally produced may be used in a method of the invention. Candidate polypeptides may additionally or alternatively be screened for binding to CTD in a polymeric form (ApoE-CTD binds to fibrils). Binding to a complex of ApoE-CTD and Aβ may also be monitored.

ApoE-CTD may be cleaved from recombinant or naturally occurring ApoE, for example by the action of thrombin.

The ApoE-CTD polypeptide or peptide may be immobilised on a support. Typically immobilisation is achieved by tagging or biotinylating the polypeptide for capture onto a surface. For example, the ApoE-CTD may comprise an S-S biotin group for attachment to streptavadin (for example on streptavadin-coated magnetic beads). Alternatively the ApoE-CTD may comprise a cysteine residue for coupling to a BSA carrier for immobilisation (for example on plastic). In this way a "CTD-coated chip" may be produced. Binding of candidate polypeptide to a CTD-coated chip may be analysed by BIACORE analysis.

Display library members may also be screened for binding to human plaques.

The display library screening methods described herein preferably include a selection or screening process that discards display library members that bind to a non-target molecule. Examples of non-target molecules include: streptavidin and (ii) ApoE-NTD.

In one implementation, a so-called "negative selection" step is used to discriminate between the target and related non-target molecule and a related, but distinct non-target molecule. The display library or a pool thereof is contacted to the non-target molecule. Members of the sample that do not bind the non-target are collected and used in subsequent selections for binding to the target molecule or even for subsequent negative selections. The negative selection step can be prior to or after selecting library members that bind to the target molecule.

In another implementation, a screening step is used. After display library members are isolated for binding to the target molecule, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target. The non-target and target binding data are compared (e.g. using a computer and software) to identify library members that specifically bind to the target MHC-peptide complex.

An antibody or antibody fragment of the invention may bind to ApoE in the presence of VLDL or other lipoprotein particles. An antibody of the invention typically binds to ApoE with a minimal binding specificity for ApoE-CTD, e.g. an equilibrium constant for binding of greater than 1 nM or 100 nM in the presence of VLDL. The VLDL may be present in any suitable form. For example human plasma may be added to the binding assay. Up to 50% human plasma may be added to the assay, for example up to 10%, up to 20%, up to 30% or up to 40% human plasma may be included.

The candidate polypeptides may also be screened for binding to ApoE-NTD. ApoE-NTD may be produced recombinantly or may be cleaved from recombinant or naturally occurring ApoE, for example by the action of thrombin.

In one embodiment, the candidate polypeptides may be screened for binding to astrocytes. It is preferred but not essential, that the selected polypeptides do not bind to astrocytes or bind with a much lower affinity to astrocytes than to ApoE-CTD, for example a two-fold, five-fold, 10-fold, 20-fold or 50-fold lower affinity.

After selecting candidate display library members that bind to ApoE-CTD, each candidate display library member may be further analysed, e.g. to further characterise its binding properties for the target. Each candidate display library member can be subjected to one or more secondary screening assays. The assay can be for a binding property, a catalytic property, a physiological property (e.g. cytotoxicity, renal clearance, immunogenicity), a structural property (e.g. stability, conformation, oligomerisation state) or another functional property. The same assay can be used repeatedly, but with varying conditions, e.g. to determine pH, ionic or thermal sensitivities.

As appropriate, the assays can use the display library member directly, a recombinant antibody produced from the nucleic acid encoding a displayed antibody, or a synthetic antibody synthesised based on the sequence of a displayed antibody. The assays preferably comprise determining whether or not an antibody that binds ApoE-CTD also binds to human plaques, or whether it binds to ApoE-CTD in the presence of VLDL. Exemplary assays for binding properties include ELISA, homogeneous binding assays such as fluorescence resonance energy transfer (FRET) and alpha-screen, surface plasmon resonance (SPR), protein assays and cellular assays.

Antibodies encoded by a display library can also be screened for a binding property using an ELISA. For example, each candidate antibody that binds ApoE-CTD is brought into contact with a microtitre plate whose bottom surface has been coated with ApoE-CTD, VLDL or ApoE-NTD. The plate is washed with buffer to remove non-specifically bound polypeptides. Then the amount of the polypeptide bound to the plate is determined by probing the plate with an antibody that can recognise the polypeptide, e.g. a tag or constant portion of the polypeptide. The antibody is linked to an enzyme such as alkaline phosphatase, which produces a colorimetric product when appropriate substrates are provided. The polypeptide can be purified from cells or assayed in a display library format, e.g. as a fusion to a filamentous bacteriophage coat. In another version of the ELISA, each polypeptide of a diversity strand library is used to coat a different well of a microtitre plate. The ELISA then proceeds using a constant target molecule to query each well. A polypeptide specifically binds ApoE-CTD in an ELISA if it displays at least 2× background on ApoE-CTD but less than 1× background on negative control proteins such as ApoE-NTD or streptavidin.

A homogeneous binding assay is an assay in which the binding interaction of candidate antibody with a target can be analysed after all components of the assay are added without additional fluid manipulations being required. For example, fluorescence resonance energy transfer (FRET) can be used as a homogenous assay (see, for example, Lakowicz et al, U.S. Pat. No. 5,631,169). Another example of a homogenous assay is Alpha Screen (Packard Bioscience, Meriden, Conn., USA).

The homogenous assays can be performed while the candidate polypeptide is attached to the display library vehicle, e.g. a bacteriophage.

The binding interaction of a molecule isolated from a display library and a target can be analysed using Surface Plasmon Resonance (SPR). SPR or Biomolecular Interaction Analysis (BIA) detects biospecific interactions in real time, without labelling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in Szabo et al (1995) *Curr. Opin. Struct. Biol.* 5:699-705 and on-line resources provided by BIAcore International AB (Uppsala, Sweden).

Information from SPR can be used to provide an accurate and quantitative measure of the equilibrium dissociation constant ($K_D$), and kinetic parameters, including $K_{on}$ and $K_{off}$, for the binding of a biomolecule to a target. Such data can be used to compare different biomolecules. For example, proteins encoded by nucleic acid selected from a library of diversity strands can be compared to identify individuals that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g. high affinity and slow $K_{off}$. This information can be combined with structural modelling (e.g. using homology modelling, energy minimisation or structure determination by crystallography or NMR). As a result, an understanding of the physical interaction between the protein and its target can be formulated and used to guide other design processes.

Antibodies identified from the display library can be immobilised on a solid support, for example, on a bead or an array. For a protein array, each of the polypeptides is immobilised at a unique address on a support. Typically, the address is a two-dimensional address. Protein arrays are described below (see, e.g. "Diagnostics").

A candidate antibody identified as binding to ApoE-CTD can be screened by transforming vector nucleic acid sequences that encode the antibody into a host cell such that antibodies are produced within the cell, secreted from the cell, or attached to the cell surface. The cells can be screened for antibodies that bind to ApoE-CTD, for example by detecting a change in a cellular phenotype or a cell-mediated activity. For example, the activity may be cell or complement-mediated cytotoxicity.

In another embodiment, the library of cells is in the form of a cellular array. The cellular array can likewise be screened for any appropriate detectable activity.

C. Producing an Antibody

Standard recombinant nucleic acid methods can be used to express an antibody of the invention. Generally, a nucleic acid sequence encoding the antibody is cloned into, a nucleic acid expression vector. Of course, if the antibody includes multiple polypeptide chains, each chain must be cloned into an expression vector, e.g. the same or different vectors, that are expressed in the same or different cells. If the antibody fragment is sufficiently small, i.e. has less than 50 amino acids, it can be synthesised using automated organic synthetic methods. Methods for producing antibodies are also provided below.

The expression vector for expressing the antibody ligand can include, in addition to the segment encoding the polypeptide ligand or fragment thereof, regulatory sequences, including for example, a promoter, operably linked to the nucleic acid(s) of interest. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXTI, pSG (Stratagene) pSVK3, pBPV, pMSG and pSVL (Pharmacia). One preferred class of preferred libraries is the display library, which is described below.

Methods well known to those skilled in the art can be used to construct vectors containing an antibody of the invention and appropriate transcriptional/translational control signals. These methods include in vitro recombinant DNA techniques, synthetic techniques and in vivo recombination/genetic recombination. See, for example, the techniques described in Sambrook & Russell, *Molecular Cloning: A Laboratory Manual*, 3$^{rd}$ Edition, Cold Spring Harbor Laboratory, NY (2001) and Ausubel et al, *Current Protocols in Molecular Biology* (Greene Publishing Associates and Wiley Interscience, NY (1989)). Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda P and trc. Eukaryotic promoters include CMV immediate early, HSV thymidine kinase, early and late SV40, LTRs from retrovirus, mouse metallothionein-I and various art-known tissue specific promoters.

Generally, recombinant expression vectors will include origins of replication and selectable markers permitting transformation of the host cell, e.g. the ampicillin resistance gene of *E. coli* and *S. cerevisiae* auxotrophic markers (such as URA3, LEI2, HIS3 and TRPl genes), and a promoter derived from a highly expressed gene to direct transcription of a downstream structural sequence. Such promoters can be derived from operons encoding glycolytic enzymes such as 3-phosphoglycerate. kinase (PGK), a-factor, acid phosphatase or heat shock proteins, among others. The polynucleotide of the invention is assembled in appropriate phase with translation initiation and termination sequences, and preferably, a leader sequence capable of directing secretion of translated protein into the periplasmic space or extracellular medium. Optionally, a nucleic acid of the invention can encode a fusion protein including an N-terminal identification peptide imparting desired characteristics, e.g. stabilisation or simplified purification of expressed recombinant product. Useful expression-vectors for bacteria are constructed by inserting a polynucleotide of the invention together with suitable translation initiation and termination signals, optionally in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces* and *Staphylococcus*, although others may also be employed as a matter of choice.

As a representative but non-limiting example, useful expression vectors for bacteria can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega, Madison, Wis., USA).

The present invention further provides host cells containing the vectors of the present invention, wherein the nucleic acid has been introduced into the host cell using known transformation, transfection or infection methods. For example, the host cells can include members of a library constructed from the diversity strand. The host cell can be a eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected, for example by calcium phosphate transfection, DEAE, dextran mediated transfection or electroporation (Davis, L. et al, *Basic Methods in Molecular Biology* (1986)).

Any host/vector system can be used to identify one or more of the target elements of the present invention. These include, but are not limited to, eukaryotic hosts such as HeLa cells, CV-1 cells, COS cells, Sf9 cells and HEK293T cells as well as prokaryotic hosts such as *E. coli* and *B. subtilis*. The most preferred cells are those which do not normally express the particular reporter polypeptide or protein or which expresses the reporter polypeptide or protein at low natural level.

The host of the present invention may also be a yeast or other fungi. In yeast, a number of vectors containing constitutive or inducible promoters may be used. For a review see, *Current Protocols in Molecular Biology*, Vol, 2, Ed. Ausubel et al, Greene Publish. Assoc. & Wiley Interscience, Ch. 13 (1988); Grant et al (1987) "Expression and Secretion Vectors for Yeast", *Methods Enzymol.* 153:516-544 (1987); and *The Molecular Biology of the Yeast Saccharomyces*, Eds. Strathern et al, Cold Spring Harbor Press, Vols. I and II (1982).

The host of the invention may also be a prokaryotic cell such as *E. coli*, other enterobacteriaceae such as *Serratia marescans*, bacilli, various pseudomonads or other prokaryotes which can be transformed, transfected and/or infected.

The present invention further provides host cells genetically engineered to contain the antibodies of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the antibodies in the cell.

The host cell can be a higher eukaryotic host cell, such as a mammalian cell, a lower eukaryotic host cell, such as a yeast cell, or the host cell can be a prokaryotic cell, such as a bacterial cell.

Introduction of the recombinant construct into the host cell can be effected by calcium phosphate transfection, DEAE, dextran mediated transfection or electroporation (David, L. et al, (1986) *Basic Methods in Molecular Biology*). The host cells containing one of the polynucleotides of the invention can be used in a conventional manner to produce the gene product encoded by the isolated fragment (in the case of an ORF).

Any on suitable host/vector system can be used to express one or more of the diversity antibodies of the present invention. Various mammalian cell culture systems can also be employed to express recombinant antibodies.

Antibodies, e.g. Fabs, can be produced in bacterial cells, e.g. *E. coli* cells. For example, if the Fab is encoded by sequences in a phage display vector that includes a suppressible stop codon between the display entity and a bacteriophage protein (or fragment thereof), the vector nucleic acid can be shuffled into a bacterial cell that cannot suppress a stop codon. In this case, the Fab is not fused to the gene III protein and is secreted into the media.

Antibodies can also be produced in eukaryotic cells. In one embodiment, the antibodies (e.g. scFvs) are expressed in a yeast cell such as *Pichia* (see, e.g. Powers et al (2001) *J. Immunol. Methods.* 251:123-35), *Hanseula* or *Saccharomyces*.

In one preferred embodiment, antibodies are produced in mammalian cells. Preferred mammalian host cells for expressing the clone antibodies or antigen-binding fragments thereof include Chinese Hamster Ovary (CHO cells) (including dhfr-CHO cells, described in Urlaub and Chasin ((1980) *Proc. Natl. Acad. Sci. USA* 77:4216-4220), used with a DHFR selectable marker, e.g. as described in Kaufman and Sharp ((1982) *Mol. Biol.* 159:601-621), lymphocytic cell lines, e.g. NS0 myeloma cells and SP2 cells, COS cells and a cell from a transgenic animal, e.g. a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g. origins of replication) and selectable marker genes. The selectable marker gene facilitates selection of host cells into which the vector has been introduced (see, e.g. U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

In an exemplary system for recombinant expression of an antibody, or antigen-binding portion thereof, of the invention, a recombinant expression vector encoding both the antibody heavy and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g. derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carried a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G.

For antibodies that include an Fc domain, the antibody production system preferably synthesises antibodies in which the Fc region is glycosylated. For example, the Fc domain of IgG molecule is glycosylated at asparagine 297 in the CH2 domain. This asparagine is the site for modification with biantennary-type oligosaccharides. It has been demonstrated that this glycosylation is required for effector functions mediated by Fc receptors and complement Clq (Burton and Woof (1992) Adv. Immunol. 51:1-84; Jefferis et al (1998) *Immunol. Rev.* 163:59-76). In one preferred embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

An ApoE-CTD antibody of the invention may be isolated from the display library and its sequence and/or structure may be analysed. The antibody may be produced in any desired quantity using known methods. For example, the antibody may advantageously be produced by a chemical synthesis followed by treatment under oxidising conditions appropriate to obtain the native conformation, i.e., the correct disulfide bond linkages. Synthesis may be carried out by methodologies well known to those skilled in the art (see, Kelley et al., in *Genetic Engineering Principles and Methods*, (Setlow, J. K., ed.), Plenum Press, NY., (1990) vol. 12, pp. 1-19; Stewart et al., *Solid-Phase Peptide Synthesis* (1989), W.H. Freeman Co., San Francisco). Polypeptides according to the invention may also be prepared commercially by companies providing polypeptide synthesis as a service (e.g., BACHEM Bioscience, Inc., King of Prussia, Pa.; Quality Controlled Biochemicals, Inc., Hopkinton, Mass.).

D. Diagnostic Methods

Antibodies that bind to ApoE-CTD and identified by the methods described herein and/or detailed herein have in vitro and in vivo diagnostic, therapeutic and prophylactic utilities.

In one aspect, the present invention provides a diagnostic method for detecting the presence ApoE-CTD in vitro (e.g., a biological sample, such as a biopsy or in vivo (e.g., in vivo imaging in a subject).

The method includes: (i) contacting a sample with an antibody of the invention; and (ii) detecting formation of a complex between the antibody and the sample. The method can also include contacting a reference sample (e.g., a control sample) with the antibody, and determining the extent of formation of the complex between the antibody and the sample relative to the same for the reference sample. A change, e.g., a statistically significant change, in the formation of the complex in the sample or subject relative to the control sample or subject can be indicative of the presence of ApoE-CTD in the sample.

Another method includes: (i) administering an antibody of the invention to a subject; and (ii) detecting formation of a complex between the antibody and the subject. The detection step can include determining location or time of formation of the complex.

The antibody ligand can be directly or indirectly labelled with a detectable substance to facilitate detection of the bound or unbound antibody. Suitable detectable substances include various enzymes, prosthetic groups, fluorescent materials, luminescent materials and radioactive materials.

Complex formation between an antibody of the invention and ApoE-CTD can be detected by measuring or visualising either the antibody bound to the ApoE-CTD or unbound antibody. Conventional detection assays can be used, e.g., an enzyme-linked immunosorbent assay (ELISA), a radioimmunoassay (RIA) or tissue immunohistochemistry. Further to labelling the antibody, the presence of ApoE-CTD can be assayed in a sample by a competition immunoassay utilising standards labelled with a detectable substance and an unlabelled antibody. In one example of this assay, the biological sample, the labelled standards and the antibody are combined and the amount of labelled standard bound to the unlabeled ligand is determined. The amount of ApoE-CTD in the sample is inversely proportional to the amount of labelled standard bound to antibody.

Fluorophore and chromophore labelled antibodies can be prepared. Since antibodies absorb light having wavelengths up to about 310 nm, the fluorescent moieties should be selected to have substantial absorption at wavelengths above 310 nm and preferably above 400 nm. A variety of suitable fluoresces and chromophores are described by Stryer (1968) *Science* 162:526 and Brand, L. at al. (1972) *Annual Review of Biochemistry* 41:843-868. The antibodies can be labelled with fluorescent chromophore groups by conventional procedures such as those disclosed in U.S. Pat. Nos. 3,940,475, 4,289,747 and 4,376,110. One group of fluorescers having a number of the desirable properties described above is the xanthene dyes, which include the fluoresceins and rhodamines. Another group of fluorescent compounds are the naphylamines. Once labelled with a fluorophore or chromophore, the antibody can be used to detect the presence or localisation of the ApoE-CTD in a sample, e.g., using fluorescent microscopy (such as confocal or deconvolution microscopy).

Immunohistochemistry can be performed using the antibodies described herein. For example, the antibody can be synthesised with a label (such as a purification or epitope tag), or can be detectably labelled, e.g., by conjugating a label or label-binding group. For example, a chelator can be attached to the antibody. The antibody is then contacted to a histological preparation, e.g., a fixed section of tissue that is on a microscope slide. After an incubation for binding, the preparation is washed to remove unbound antibody. The preparation is then analysed, e.g., using microscopy, to identify if the antibody bound to the preparation.

Of course, the antibody can be unlabelled at the time of binding. After binding and washing, the antibody is labelled in order to render it detectable.

The antibody can also be immobilised on a protein array. The protein array can be used as a diagnostic tool, e.g., to screen medical samples (such as isolated cells, blood, sera, biopsies, and the like). Of course, the protein array can also include other ligands, e.g., that bind to the ApoE-CTD.

Methods of producing polypeptide arrays are described, e.g., in De Wildt et al. (2000) *Nature Biotech.* 18:989-994; Lueking et al. (1999) *Anal. Biochem.* 270:103-111; Ge (2000) *Nuc. Acids Res.* 28:e3; MacBeath and Schreiber (2000) *Science* 289:1760-1763; WO 01/40803 and WO 99/51773A1. Polypeptides for the array can be spotted at high speed, e.g., using commercially available robotic apparati, e.g., from Genetic MicroSystems and Affymetrix (Santa Clara, Calif., USA) or BioRobotics (Cambridge, UK). The array substrate can be, for example, nitrocellulose, plastic, glass, e.g., surface-modified glass. The array can also include a porous matrix, e.g., acrylamide, agarose or another polymer.

For example, the array can be an array of antibodies, e.g., as described in De Wildt, supra. Cells that produce the polypeptide ligands can be grown on a filter in an arrayed format. Polypeptide production is induced, and the expressed polypeptides are immobilised to the filter at the location of the cell.

An antibody array can be contacted with a labelled target to determine the extent of binding of the target to each immobilised antibody from the diversity strand library. If the target is unlabeled, a sandwich method can be used, e.g., using a labelled probed, to detect binding of the unlabeled target.

Information about the extent of binding at each address of the array can be stored as a profile, e.g., in a computer database. The antibody array can be produced in replicates and used to compare binding profiles, e.g., of a target and a non-target. Thus, antibody arrays can be used to identify individual members of the diversity strand library that have desired binding properties with respect to one or more molecules.

In still another embodiment, the invention provides a method for detecting the presence of a ApoE-CTD containing plaque in vivo. The method includes (i) administering to a subject (e.g., a patient having Alzheimer's disease or systemic amyloidosis) an antibody of the invention, conjugated to a detectable marker; (ii) exposing the subject to a means for detecting said detectable marker bound to the ApoE-CTD containing plaque. For example, the subject is imaged, e.g., by NMR or other tomographic means.

Examples of labels useful for diagnostic imaging in accordance with the present invention include radiolabels such as $^{131}I$, $^{111}In$, $^{123}I$, $^{99m}Tc$, $^{32}P$, $^{125}I$, $^{3}H$, $^{14}C$, and $^{188}Rh$, fluorescent labels such as fluorescein and rhodamine, nuclear magnetic resonance active labels, positron emitting isotopes detectable by a positron emission tomography ("PET") scanner, chemiluminescers such as luciferin and enzymatic markers such as peroxidase or phosphatase. Short-range radiation emitters, such as isotopes detectable by short-range detector probes can also be employed. The polypeptide ligand can be labelled with such reagents using known techniques. Foe example, see Wensel and Meares (1983) *Radioimmunoimaging and Radioimmunotherapy*, Elsevier, N.Y. for techniques relating to the radiolabel of antibodies and D. Colcher et al. (1986) *Methods Enzymol.* 121:802-816.

A radiolabel ligand of this invention can also be used for in vitro diagnostic tests. The specific activity of a isotopically-labelled ligand depends upon the half-life, the isotopic purity of the radioactive label, and how the label is incorporated into antibody.

Procedures for labelling polypeptides with the radioactive isotopes (such as $^{14}C$, $^{3}H$, $^{35}S$, $^{125}I$, $^{32}P$, $^{131}I$) are generally known. For example, tritium labelling procedures are described in U.S. Pat. No. 4,302,438. Iodinating, tritium labelling, and $^{35}S$ labelling procedures, e.g., as adapted for murine monoclonal antibodies, are described, e.g., by Goding, J. W. (*Monoclonal Antibodies: Principles And Practice: Production And Application Of Monoclonal Antibodies In Cell Biology, Biochemistry, And Immunology* 2nd ed., London, Orlando, Academic Press (1986) polypeptide. 124-126) and the references cited therein. Other procedures for iodinating polypeptides, such as antibodies, are described by Hunter and Greenwood (1962) *Nature* 144:945, David et al. (1974) *Biochemistry* 13:1014-1021, and U.S. Pat. Nos. 3,867, 517 and 4,376,110. Radiolabelling elements which are useful in imaging include $^{123}I$, $^{131}I$, $^{111}In$, and $^{99m}Tc$, for example. Procedures for iodinating antibodies are described by Greenwood, F. et al. (1963) *Biochem. J.* 89:114-123; Marchalonis, J. (1969) *Biochem. J.* 113:299-305; and Morrison, M. et al. (1971) *Immunochemistry* 8:289-297. Procedures for $^{99m}Tc$-labeling are described by Rhodes, B. et al. in Burchiel, S. et al. (eds.), *Tumor Imaging: The Radioimmunichemical Detection of Cancer*, New York: Masson 111-123 (1982) and the references, cited therein. Procedures suitable for $^{111}In$-labeling antibodies are described by Hnatowich, D. J. et al. (1983) *J. Immun. Methods* 65:147-157, Hnatowich, D. et al. (1984) *J. Applied Radiation* 35:554-557 and Buckley, R. G. et al. (1984) *F.E.B.S. Lett.* 66:202-204.

In the case of a radiolabelled antibody, the antibody is administered to the patient, is localised to the plaque with which the antibody reacts, and is detected or "imaged" in vivo using known techniques such as radionuclear scanning using e.g., a gamma camera or emission tomography. Alternatively, a position emission transaxial tomography scanner, such as designated Pet VI located at Brookhaven National Laboratory, can be used where the radiolabel emits positrons (e.g., $^{11}C$, $^{18}F$, $^{15}O$, and $^{13}N$).

Magnetic Resonance Imaging (MRI) uses NMR to visualise internal features of a living subject, and is useful for prognosis, diagnosis, treatment, and surgery. MRI can be used without radioactive tracer compounds for obvious benefit. Some MRI techniques are summarised in published European patent application EP-A-0 502 814. Generally, the differences related to relaxation time constants T1 and T2 of water protons in different environments is used to generate an image. However, these differences can be insufficient to provide sharp high resolution images.

The differences in these relation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTS chelates) can be used to attach (and reduce toxicity) of some paramagnetic substances (e.g., $Fe^{+3}$, $Mn^{+2}$, $Gd^{+3}$). Other agents can be in the form of particles, e.g., less than 10 µm to about 10 nM in diameter). Particles can have ferromagnetic, antiferromagnetic or superparamagnetic properties. Particles can include, e.g., magnetic ($Fe_3O_4$), —$Fe_2O_3$, ferrites and other magnetic mineral compounds of transition elements. Magnetic particles may include one or more magnetic crystals with and without nonmagnetic material. The nonmagnetic material can include synthetic or natural polymers such as sepharose, dextran, dextrin, starch and the like.

Antibodies of the invention can also be labelled with an indicating group containing of the NMR-active $^{19}$F atom, or a plurality of such atoms inasmuch as (i) substantially all of naturally abundant fluorine atoms are the $^{19}$F isotope and, thus, substantially all fluorine-containing compounds are NMR-active; (ii) any chemically active polyfluorinated compounds such as trifluoracetic anhydride are commercially available at relatively low cost, and (iii) many fluorinated compounds have been found medically acceptable for use in humans such as the perfluorinated polyethers utilised to carry oxygen as hemoglobin replacements. After permitting such time for incubation, a MRI scan is carried out using an apparatus such as one of those described by Pykett (1982) *Scientific American* 246:78-88.

Also within the scope of the invention are kits comprising an antibody of the invention and instructions for diagnostic use, e.g., the use of the antibody to detect ApoE-CTD, in vitro, e.g., in a sample, e.g., a biopsy from a patient having systemic amyloidosis, or in vivo, e.g., by imaging a subject. The kit can further contain a least one additional reagent, such as a label or additional diagnostic agent. For in vivo use the antibody can be formulated as a pharmaceutical composition.

E. Therapeutic Methods

Polypeptides that bind to ApoE-CTD and identified by the methods described herein and/or detailed herein have therapeutic and prophylactic utilities. For example, these ligands can be administered to cells in culture, e.g. in vitro or ex vivo, or in a subject, e.g. in vivo, to treat, prevent and/or diagnose a variety of disorders such as Alzheimer's disease or systemic amyloidosis.

As used herein, the term "treat" or "treatment" is defined as the application or administration of an anti-ApoE-CTD antibody, alone or in combination with, a second agent to a subject, e.g. a patient, who has a disorder (e.g. a disorder as described herein), a symptom of a disorder or a predisposition toward a disorder, with the purpose to cure, heal, alleviate, relieve, alter, remedy, ameliorate, improve or affect the disorder, the symptoms of the disorder or the predisposition toward the disorder.

As used herein, an amount of an anti-ApoE-CTD polypeptide effective to treat a disorder, or a "therapeutically effective amount" refers to an amount of the ligand which is effective, upon single; or multiple dose administration to a subject, or in prolonging curing, alleviating, relieving or improving a subject with a disorder as described herein beyond that expected in the absence of such treatment.

As used herein, an amount of an anti-ApoE-CTD polypeptide effective to prevent a disorder, or a "prophylactically effective amount" of the polypeptide refers to an amount of an anti-ApoE-CTD polypeptide, e.g. an anti-ApoE-CTD antibody described herein, which is effective, upon single- or multiple-dose administration to the subject, in preventing or delaying the occurrence of the onset or recurrence of a disorder, e.g. Alzheimer's disease.

The terms "induce", "inhibit", "potentiate", "elevate", "increase", "decrease" or the like, e.g. which denote quantitative differences between two states, refer to a difference, e.g. a statistically significant difference, between the two states.

As used herein, the term "subject" is intended to include human and non-human animals. Preferred human animals include a human patient having a disorder characterised by abnormal cell proliferation or cell differentiation. The term "non-human animals" of the invention includes all vertebrates, e.g. non-mammals (such as chickens, amphibians, reptiles) and mammals, such as non-human primates, sheep, dog, cow, pig, etc.

The term "amyloid disorders" is intended to include, but not limited to, Alzheimer's disease, primary systemic amyloidosis, secondary systemic amyloidosis, senile systemic amyloidosis, familial amyloid polyneuropathy I, familial amyloid polyneuropathy III, familial non-neuropathic amyloidosis, hereditary cerebral amyloid angiopathy, Familial British Dementia (FBD), Haemodialysis-related amyloidosis, Familial amyloidosis (Finnish type), Familial subepithelial corneal amyloid, Type II diabetes, Hereditary renal amyloidosis, Pituitary-gland amyloidosis, Injection localized amyloidosis, Medullary carcinoma of the thyroid, Atrial amyloidosis, Familial Danish Dementia (FDD), and Downs syndrome. Related to amyloid diseases wherein amyloid fibrils are detected, comprise, but is not limited to, Spongiform encephalopathies, Sporadic Creutzfeldt-Jakob disease, Familial Creutzfeldt-Jakob disease, Iatropic prion disorders, Variant Creutzfeldt-Jakob disease, Gerstmann-Sträussler-Scheinker Disease (GSS), Kuru, Parkinson's disease, Huntington's disease, Familial amyotrophic lateral sclerosis (ALS), and Chronic obstructive pulmonary disease.

Furthermore, amyloid conditions can be defined as disorders with amyloid deposits in brain, medulla or other organs. An example of such disorders is Alzheimer's disease. Other dementia disorders characterized by amyloid deposits are Spongiform encephalopathies, Sporadic Creutzfeldt-Jakob disease, Familial Creutzfeldt-Jakob disease, Iatropic prion disorders, Variant Creutzfeldt-Jakob disease, Gerstmann-Sträussler-Scheinker Disease (GSS), Kuru, Parkinson's disease, Huntington's disease, Familial British Dementia, Familial Danish Dementia, Down syndrome, Primary Systemic amyloidosis, such as Immunoglobulin-light-chain-related amyloidosis, Secondary Systemic amyloidosis, such as Amyloidosis related to amyloid A protein, Familial systemic amyloidosis, such as Familial transthyretin-associated amyloidosis, Familial apolipoprotein A-I associated amyloidosis, Familial gelsolin associated amyloidosis, Familial fibrinogen A α associated amyloidosis, Familial lyzosome amyloidosis, Senile Systemic amyloidosis, Familial amyloid polyneuropathy I, Familial amyloid polyneuropathy III, Familial non-neuropathic amyloidosis, Hereditary cerebral amyloid angiopathy, Haemodialysis-related amyloidosis, Familial amyloidosis, Finnish type, Familial subepithelial corneal amyloid, Type II diabetes, Hereditary renal amyloidosis, Pituitary-gland amyloidosis, Injection localized amyloidosis, Medullary carcinoma of the thyroid, Atrial amyloidosis, Chronic obstructive pulmonary disease, and Familial amyotrophic lateral sclerosis-ALS. Detailed references can be found in James C. Sacchettini and Jeffery W. Kelly: Nature Reviews, Drug Discovery, Vol. 1 April 2002, 267-275.

In one embodiment, the subject is a human subject. Alternatively, the subject can be a mammal expressing an ApoE-CTD-like antigen with which a polypeptide of the invention cross-reacts. A polypeptide of the invention can be administered to a human subject for therapeutic purposes (discussed further below). Moreover, an anti-ApoE-CTD polypeptide can be administered to a non-human mammal expressing the ApoE-CTD-like antigen to which the polypeptide binds (e.g. a primate, pig or mouse) for veterinary purposes or as an animal model of human disease. Regarding the latter, such animal models may be useful for evaluating the therapeutic efficacy of the polypeptide (e.g. testing of dosages and time courses of administration).

For in vivo embodiments, the contacting step is effected in a subject and includes administering the anti-ApoE-CTD polypeptide to the subject under conditions effective to permit both binding of the ligand to the plaque and the treating, e.g. the destruction of the plaque.

Methods of administering anti-ApoE-CTD polypeptides are described in "Pharmaceutical Compositions". Suitable dosages of the molecules used will depend on the age and weight of the subject and the particular drug used.

The anti-ApoE-CTD ligands can be used directly in vivo to eliminate ApoE-CTD-containing plaques via natural complement-dependent cytoxicity (CDC) or antibody-dependent cellular cytotoxicity (ADCC). The polypeptides of the invention can include complement binding effector domain, such as the Fc portions from IgG1, -2, or -3 or corresponding portions of IgM which bind complement. The treatment can be supplemented by the addition of complement or serum containing complement. Further, phagocytosis of plaques coated with a polypeptide of the invention can be improved by binding of complement proteins.

Antibody-targeted amyloid plaques can be internalised by microglia through type A scavenger receptors (Melanie I. Brazil, Haeyong Chung, and Frederick R. Maxfield. *Effects of Incorporation of Immunoglobulin G and Complement Component C1q on Uptake and Degradation of Alzheimer's Disease Amyloid Fibrils by Microglia* J. Biol. Chem., May 2000; 275: 16941-16947). Alternatively, other mechanisms independent of the microglial Fc receptor might play a role in clearing diffuse, 3D6-immunoreactive, Thio-5-negative plaques and soluble Aβ moieties (Wilcock D M, DiCarlo G, Henderson D, Jackson J, Clarke K, Ugen K E, Gordon M N, Morgan D: *Intracranially administered anti-Abeta antibodies reduce beta-amyloid deposition by mechanisms both independent of and associated with microglial activation*. J Neurosci 2003, 23:3745-3751). Consistent with this hypothesis, Fc-knockout mice also showed reduction of plaque burden after Aβ immunotherapy (Das P, Howard V, Loosbrock N, Dickson D, Murphy M P, Golde T E: *Amyloid-beta immunization effectively reduces amyloid deposition in FcR-gamma-/- knock-out mice*. J Neurosci 2003, 23:8532-8).

Also encompassed by the present invention is a method of killing or ablating which involves using the anti-ApoE-CTD ligand for prophylaxis. For example, these materials can be used to prevent or delay development or progression Alzheimer's disease, systemic amyloidosis or other amyloid disorders.

Use of the therapeutic methods of the present invention to treat Alzheimer's disease or systemic amyloidosis has a number of benefits. Since the polypeptides specifically recognise ApoE-CTD, other tissue is spared and high levels of the agent are delivered directly to the site where therapy is required. Treatment in accordance with the present invention can be effectively monitored with clinical parameters. Alternatively, these parameters can be used to indicate when such treatment should be employed.

F. Pharmaceutical Compositions

In another aspect, the present invention provides compositions, e.g. pharmaceutically acceptable compositions, which include an antibody of the invention formulated together with a pharmaceutically acceptable carrier. As used herein, the term "pharmaceutical compositions" encompasses labelled ligands for in vivo imaging as well as therapeutic compositions.

As used herein, "pharmaceutically acceptable carrier" includes any physiologically compatible solvents, dispersion media, coatings, and the like. Preferably, the carrier is suitable for intravenous, intramuscular, subcutaneous, parenteral, spinal or epidermal administration (e.g. by injection or infusion). Depending on the route of administration, the active compound, i.e. polypeptide may be coated in a material to protect the compound from the action of acids and other natural conditions that may inactivate the compound.

The compositions of this invention may be in a variety of forms. These include, for example, liquid, semi-sold and solid dosage forms, such as liquid solutions (e.g. injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for administration of humans with antibodies. The preferred mode of administration is parental (e.g. intravenous, subcutaneous, intraperitoneal, intramuscular). In a preferred embodiment, the anti-ApoE-CTD polypeptide is administered by intravenous infusion or injection. In another preferred embodiment, the anti-ApoE-CTD ligand is administered by intramuscular or subcutaneous injection.

The phrases "parenteral administration" and administered parentally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnod, intraspinal, epidural and intrasternal injection and infusion.

Pharmaceutical compositions typically must be sterile and stable under the conditions of manufacture and storage.

The composition can be formulated as a solution, microemulsion, dispersion, liposome, or other ordered structure suitable to high drug concentration. Sterile injectable solutions can be prepared by incorporating the active compound (i.e. the polypeptide) in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the present invention can be administered by a variety of methods known in the art, although for many applications, the preferred route/mode of administration is intravenous injection or infusion. For example, for therapeutic applications, the antibody can be administered by intravenous infusion at a rate of less than 30, 20, 10, 5 or 1 mg/min to reach a dose of about 1 to 100 mg/m$^2$ such as 7 to 25 mg/m$^2$. The route and/or mode of administration will vary depending upon the desired results.

Pharmaceutical compositions can be administered with medical devices known in the art. For example, in a preferred embodiment, a pharmaceutical composition of the invention can be administered with a needleless hypodermic injection device, such as the devices disclosed in U.S. Pat. Nos. 5,399,163, 5,383,851, 5,312,335, 5,064,413, 4,941,880, 4,790,824 or 4,596,556. Examples of well-known implants and modules useful in the present invention include: U.S. Pat. No. 4,487,603, which discloses an implantable micro-infusion pump for dispensing medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Of course, many other such implants, delivery systems and modules are also known.

In certain embodiments, the compounds of the invention can be formulated to ensure proper distribution in vivo. For example, the blood-brain barrier (BBB) excludes many highly hydrophilic compounds. To ensure that the therapeutic compounds of the invention cross the BBB, they can be formulated, for example, in liposomes. For methods of manufacturing liposomes, see, e.g. U.S. Pat. Nos. 4,522,811, 5,374, 548 and 5,399,331. The liposomes may comprise one or more moieties which are selectively transported into specific cells or organs, thus enhancing targeted drug delivery (see, e.g. V. V. Ranade (1989) *J. Clin. Pharmacol.* 29:685).

Dosage regimens are adjusted to provide the optimum desired response (e.g. a therapeutic response). For example, a single bolus may be administered, several divided doses may be administered over time or the dose may be proportionally reduced or increased as indicated by the exigencies of the therapeutic situation. It is especially advantageous to formulate parental compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody of the invention is 0.1-20 mg/kg, more preferably 1-10 mg/kg. The antibody can be administered by intravenous infusion at a rate of less than 30, 20, 10, 5 or 1 mg/min to reach a dose of about 1 to 100 mg/m$^2$ or about 5 to 30 mg/m$^2$. For antibody fragments which have lower molecular weights than an IgG, appropriate amounts can be proportionally less. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of an antibody of the invention. The desired therapeutic result is typically a lessening or amelioration of one or more symptom of the disease or disorder from which the individual being treated is suffering. A therapeutic amount of an antibody of the invention may be an amount which serves to slow down or stop production of amyloid deposits, eliminate existing amyloid deposits, alleviate underlying disorders (that give rise to secondary amyloidosis), and relieve symptoms caused by heart or kidney damage. A "therapeutically effective amount" refers to an amount effective, at dosages and for periods of time necessary, to achieve the desired therapeutic result. A therapeutically effective amount of the composition may vary according to factors such as the disease state, age, sex and weight of the individual, and the ability of the polypeptide ligand to elicit a desired response in the individual. A therapeutically effective amount is also one is which any toxic or detrimental effects of the composition is outweighed by the therapeutically beneficial effects. A "therapeutically effective dosage" preferably inhibits a measurable parameter, e.g. plaque formation or growth rate by at least about 20%, more preferably by at least about 40%, even more preferably by at least about 60%, and still more preferably by at least about 80% relative to untreated subjects. The ability of a compound to inhibit a measurable parameter can be evaluated in an animal model system predictive of efficacy in humans. Alternatively, this property of a composition can be evaluated by examining the ability of the compound to inhibit such inhibition in vitro by assays known to the skilled practitioner.

A "prophylactically effective amount" refers to an amount effective, at dosages and for periods of time necessary, to achieve the desired prophylactic result. The desired prophylatic result is the inhibition or delay in the outset or progression of symptoms associated with the disease it is intended to prevent in the individual being treated. Typically, since a prophylactic dose is used in subject prior to or at an earlier stage of disease, the prophylactically effective amount will be less than the therapeutically effective amount.

Also within the scope of the invention are kits comprising an antibody of the invention and instructions for use, e.g. treatment, prophylactic or diagnostic use. In one embodiment, the instructions for diagnostic applications include the use of the antibody to detect the form ApoE-CTD associated with plaques, in vitro, e.g. in a sample, e.g. a biopsy or cells from a patient having Alzheimer's disease or systemic amyloidosis, or in vivo. In another embodiment, the instructions for therapeutic applications include suggested dosages and/or modes of administration in a patient with Alzheimer's disease or systemic amyloidosis. The kit can further contain at least one additional reagent, such as diagnostic or therapeutic agent.

The following invention is further illustrated by the following Examples, which should not be construed as further limiting. The contents of all references, pending patent applications and published patents, cited throughout this application are hereby expressly incorporated by reference in their entirety.

While this invention has been particularly shown and described with references to preferred embodiments thereof, it will be understood by those skilled in the art that various changes in form and details may be made therein without departing from the scope of the invention encompassed by the appended claims.

EXAMPLES

Example 1

Antibody Library Composition

Antibodies that bind to ApoE found in plaques of amyloid disorders that do not bind to VLDL were selected from human phage antibodies in the Dyax phagemid library Fab300. Antibody diversity is present in the library used for the selections on CTD, the diversity in the light and heavy chains are composed as follows:

Heavy Chains

The heavy chain consists of one heavy chain gene segment (V3-23, or DP-47), in which diversity is created using synthetic oligonucleotides in certain positions in the HCDR1 and HCDR2. The distribution pattern is based on a diversity analysis of natural sequences. The appended HCDR3 diversity is derived from natural occurring sequences of the IgM-pool of B-cells from a series of autoimmune donors.

Light Chains

The light chain repertoire is derived from a pool of naturally rearranged light chains sequences, from the same source as the H-CDR3 diversity. This means that we can expect Vkappa and Vlambda genes, based on a diverse range of germline segments and with somatic mutations in or outside the CDRs.

Control Antibodies

The following anti-ApoE antibodies were used as controls:

3D12, a mouse antibody that binds to CTD, VLDL, LDL, ApoE2, ApoE3 and ApoE4 (Colabek et al. Biophysical J., 79:1008-1015);

E19, a goat antibody directed to CTD (Weisgraber (1986), J. Biol. Chem., 261: 2068-2076); and 6C5, a mouse antibody directed to NTD (Castano 1995) J. Biol. Chem., 270: 17610-17615.

Example 2

Preparation and Pretesting of Fibrils

Fibrils were extracted from spleen and kidney. Insoluble amyloid fibrils were extracted from human tissues by repeated rounds of mechanical homogenisation in cold 0.15M NaCl, 0.1% NaN3, with subsequent centrifugation in order to rescue the amyloid in the pellet. Finally the amyloid was dissolved/suspended in water and stored. Amyloid content was verified by Congo red staining of suspension smears. This method of extracting fibrils is known in the art, see for example Skinner et al. Prep. Biochem. 1982; 12(5): 461-476. It was determined that bound and non-bound phage could be separated by washing with 5 Marvel-PBS-Tween (0.1%) washes, 2 PBS-Tween washes and 1 PBS wash.

Example 3

Preparation and Pretesting of Biotinylated CTD (bCTD)

CTD having the amino acid sequence shown in SEQ ID NO: 1 was used. Biotinylation was performed with sulfo-NHS—SS-biotin according to the method described by Pierce using molar ratios of CTD/biotin of 1/2 and 1/10. SDS PAGE revealed that 100% of the material was labelled. In mass-spectrometry at a ratio of 1/10, three to five of the five possible biotinylation sites were labelled with biotin. At a ratio of 1/2 bCTD showed one or two biotins per molecule which is favourable for keeping the structure of the molecule. All CTD and NTD used were labelled with the same protocol at a ratio 1/2 and tested in SDS-page.

Coated bCTD was prepared by coating BSA with biotin, washing, adding streptavidin and, after washing again, adding b-CTD.

To produce denatured bCTD, bCTD was treated with urea and, after washing, bound to streptavidin on biotinylated BSA. To be sure that the bCTD binds and stays on the beads during urea treatment, we measured the amount of bCTD before and after urea treatment and binding to the beads. No loss of bCTD was seen.

Example 4

Selections on Fibrils and ur-bCTD

In the selection strategy the aim was to select for antibodies binding to the complex form of CTD in amyloid fibrils. A first round of selection was performed on fibrils from kidney, a second round of selection was performed on fibrils from spleen and rounds three and four of selection were performed on ur-bCTD. No enrichment was found in rounds two and three but in round four there was an enrichment of 1379. In a second strategy, three rounds of selections on bCTD were performed.

A pre-screening was then carried out to decide which round of selection to chose for a high throughput screen and which antigen should be used. There was no significant difference seen between screening on bCTD and ur-bCTD. It was, therefore, decided to carry out a high throughput screen on the ur-bCTD selection with streptavidin coated bCTD. As a negative control bBSA, streptavidin coated plates were used.

Example 5

Sequence and Binding Analysis

Screening of more than 2000 clones was performed on coated bCTD. ELISA was performed in an automated system. The same method was used to screen for NTD binders. Clones, binding to bCTD and not binding to bNTD were analysed further.

Sequencing was carried out for heavy and light chains genes for clones positive in the high throughput bCTD phage ELISA. Dyax's proprietary 'Webphage' software was used to analyse the sequences of clones.

752 clones were screened after round 3 (23 positives) and 216 clones after round 4 (216 positives) of the selections on fibrils and ur-bCTD. 940 clones were screened after round 2 of selections on bCTD. The number of positive clones in ELISA using bCTD was 463. The number of correct sequences obtained was 163.

To analyse the sequence data, comparisons of sequences at different levels were carried out, including the following:

(1) overall diversity=number of different sequences, will identify a clone as different if one amino acid difference is found (dubbed VH+VL diversity)=163

(2) heavy chain diversity=number of clones with a different heavy chain, ignoring the light chain sequence=152

(3) HCDR3 diversity=the number of clones with a different heavy chain CDR3=54 (+2 clones with amber HCDR3).

This three-level analysis was carried out for two reasons:

Firstly, it is generally accepted that the heavy chain, and, in that domain, its HCDR3 region, are of major importance for the epitope recognition of the antibody. All antibodies with an identical H-CDR3 sequence were grouped.

Secondly, the design of the diversity of the library is such that antibody variants that have an identical HCDR3 with mutations in the other CDRs of the heavy chain, and sometimes identical, sometimes different light chains are expected.

Example 6

Binding of Antibodies to bCTD and VLDL

To monitor binding to VLDL, VLDL was coated on a microtiter plate, and incubated with the test antibodies. A secondary antibody-HRP detection method is used to detect bound antibodies. Staining is performed with tetramethylbenzidine (TMB) and $H_2O_2$. Only non-bound antibody is washed away. Binding to VLDL will give a high signal in ELISA.

As a positive control we used monoclonal antibodies against ApoE. Two antibodies (3D12, E19), binding to CTD and VLDL, were positive in bCTD ELISA (FIG. 1A) and in VLDL ELISA (FIG. 1B). Another antibody (6C5) that binds to NTD does not bind to bCTD but binds well to VLDL. This NTD site is not covered by VLDL and could give a measure of coating quality of ApoE itself. Since of this antibody signal is high, we can conclude that enough ApoE is coated to perform the VLDL ELISA like it is.

For phage antibodies (FIG. 2), we made a classification in 3 groups: antibodies that are always positive (more than 3 times of negative phage binding), antibodies that are sometimes positive, sometimes negative (sometimes 2 times negative phage binding, sometimes negative) and negative antibodies. For the doubtful antibodies the ELISA is possibly not sensitive enough, or the antibodies are just not binding or probably the affinity is not high enough to see a high signal or there could be a cross-reaction with VLDL (epitope partially on VLDL, partially on covered CTD) etc.

Example 7

VLDL Assay Development and Automation

Figure 3B:
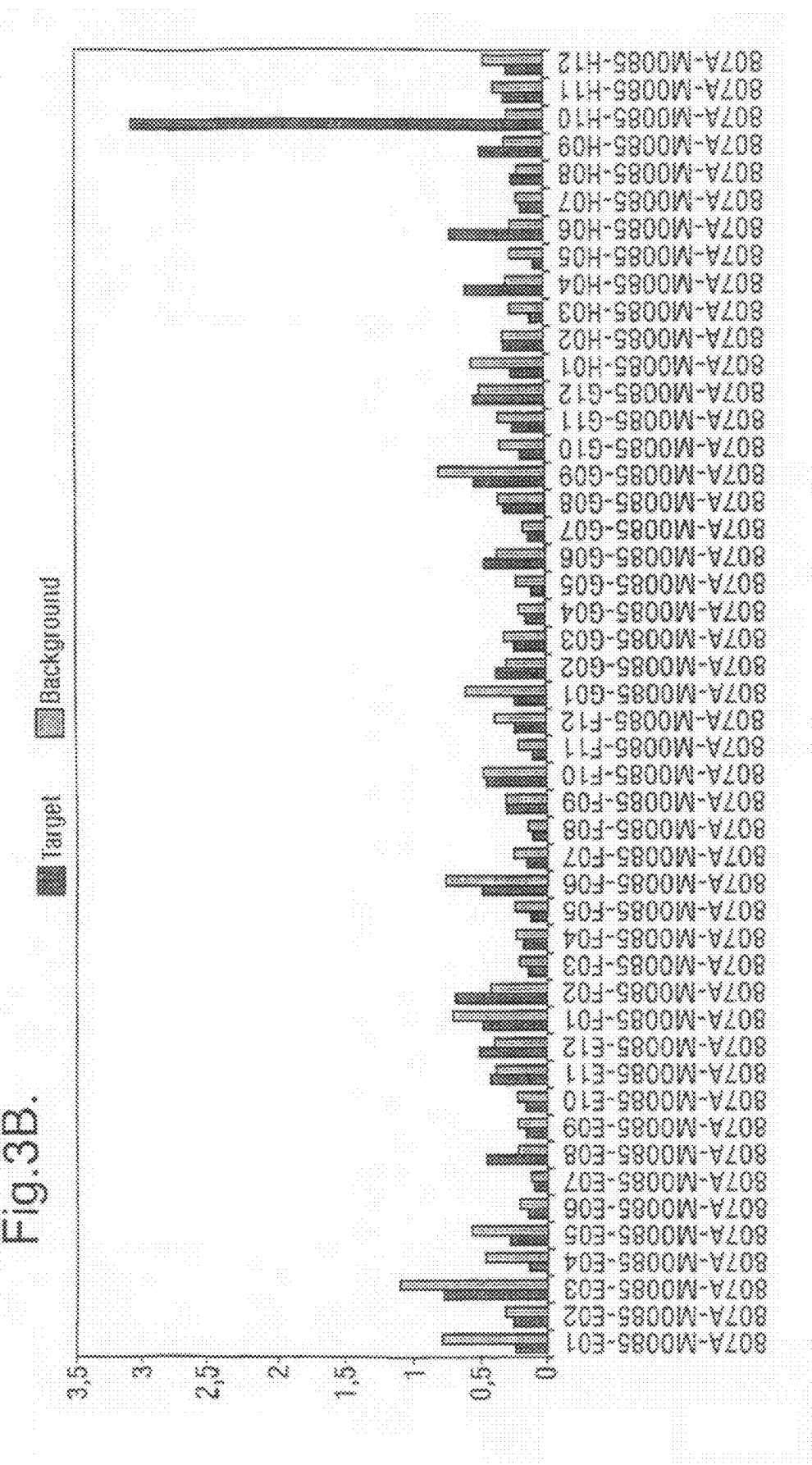
FIG. 3 shows an example of bCTD (A) and VLDL (B) ELISA on 203 phage clones.

The VLDL ELISA was performed for all 203 bCTD positive phage clones. 6 clones were found which were always positive (more than 3 times the background). Other clones produced a signal higher than 2 times the background (FIG. 3). These clones are not excluded from further testing at this stage. Only 6 clones were positive, with a high signal, to VLDL. Tests were carried out 3 times, and the same results were obtained. In parallel binding of antibodies to bNTD was tested. No antibodies bound to bNTD. Clones that bound to VLDL were not tested further.

Example 8

Recloning of Phage to Fab, Specificity Tests

Because of the low amount of VLDL binders in coated VLDL ELISA and because of the variable results of the VLDL competition ELISA, we batch recloned in parallel all different 157 clones from Fab on phage into soluble Fab. It was expected that many Fabs will not bind to bCTD because of their monovalent nature versus the multivalent phage, thus enabling low affinity binders to be excluded by means of Fab ELISA signals on bCTD.

After recloning, 85 antibodies bound specifically to bCTD. No new VLDL or NTD binders were found. The amino acid sequences of CDR regions of the VH and VL chains of these antibodies are shown in Tables 9 and 10.

Example 9

Epitope Mapping

Binding to identical epitopes is tested by monitoring competition between Fab and phage antibodies. A limited amount of phage and a maximal amount of Fab is added to an ELISA well coated with bCTD. After binding steps, phage is detected by a peroxidase reaction after incubating with an anti-M13 HRP antibody. Because of the high concentration of Fab added, phage directed to the same epitope as the Fab will be competed off and the Fab signal will be decreased.

Antibodies from the same VH-CDR3 group recognise overlapping epitopes. This criterion was used to exclude clones for immunohistochemistry (IHC): Only clones with the highest/slowest off-rate were tested. All clones not belonging to a big VH-CDR3 group were tested in IHC.

Antibodies 807A-M0026-F05 and 807A-M0027-E11 did not cross-react with each other. However, both cross-reacted with antibody 807A-M0028-A07, indicating that both antibodies recognise a similar but not the same epitope.

Antibody 807A-M0028-B02 possibly recognises another epitope than antibodies 807A-M0026-F05 and antibody 807A-M0027-E11.

Example 10

Off-rate Measurements

To optimise Biacore measurements, we used a Biacore chip coated with streptavidin to bind bCTD. First we analysed antibodies 3D12 and E19 for binding to the chip. We also recloned a Fab that we recovered from the pre-screening (not binding to VLDL, positive in Fab ELISA). Mab 3D12 did not bind in Biacore, probably due to low affinity. Ab E19 and non-purified Fab 1F7 (dialysed periplasmic fraction) did bind to the bCTD chip. As a control we used a channel coated with bBSA; neither antibody bound to this surface.

Off-rate ranking of selected Fabs was determined with this bCTD chip using periplasmic extracts (important for ranking clones, now and during affinity maturation studies). Table 1 shows a representative list of off-rates.

Affinity determination was determined on a low density of bCTD on the chip using purified Fab fragments.

Example 11

Immunohistochemistry

Immunohistochemistry (IHC) on the antibodies with the slowest off-rate of the identical VH-CDR3 groups and all antibodies having a different VH-CDR3 (single clones) were tested in IHC performed on frozen tissue slides.

For IHC and affinity measurement purified Fabs were used. Antibody fragments (Fabs) were expressed in bacteria (typically in 400-ml cultures, 4 hours IPTG induction) and purified from periplasmic extracts by Immobilized Metal Affinity Chromatography (IMAC). Periplasmic extracts were prepared by “osmotic shock” treatment of the bacteria. The samples were loaded on a 1 ml Co-IDA column and eluted with a 0-150 mM linear gradient of imidazole. Protein preparations were dialyzed against PBS and analyzed by non-reducing SDS-PAGE.

Only 3 antibodies bound as Fab on AD plaques: 807A-M0027-E11, 807A-M0028-B02 and 807A-M0026-F05.

Antibody 807A-M0027-E11 detects Alzheimer’s Disease (AD) plaques in IHC. It is important that antibodies specifically recognise plaques in tissue and not to Apolipoprotein E exposed in serum. Typically, an antibody of the invention binds to plaques of at least two patients having AD and to patients potentially also having systemic amyloidosis. Therefore, IHC was performed in the presence of fresh plasma. In IHC staining with 807A-M0027-E11, as phage and as Fab, in the presence of even 50% plasma, the signal was not quenched. Also the addition of VLDL in solution did not change the staining. This is in contrast with the 6C5 control antibody, directed to NTD, the signal of which was quenched by fresh plasma or VLDL solution. SFab antibody 807A-M0028-B02 stained positive on AD plaques and also astrocytes. SFab antibody 807A-M0026-F05 stained AD plaques weakly. The staining pattern for this antibody is not very strong, caused by low affinity of this antibody. The antibodies were positive in tissues of more than 1 patient.

Other sFab antibodies: 807A-M0039-C10, 807A-M0037-D01, 807A-M0046-A06 and 807A-M0039-C10 only detected astrocytes on AD brain tissue.

Example 12

Affinity Measurement of sFabs Binding to Plaques in IHC

Figure 4A:
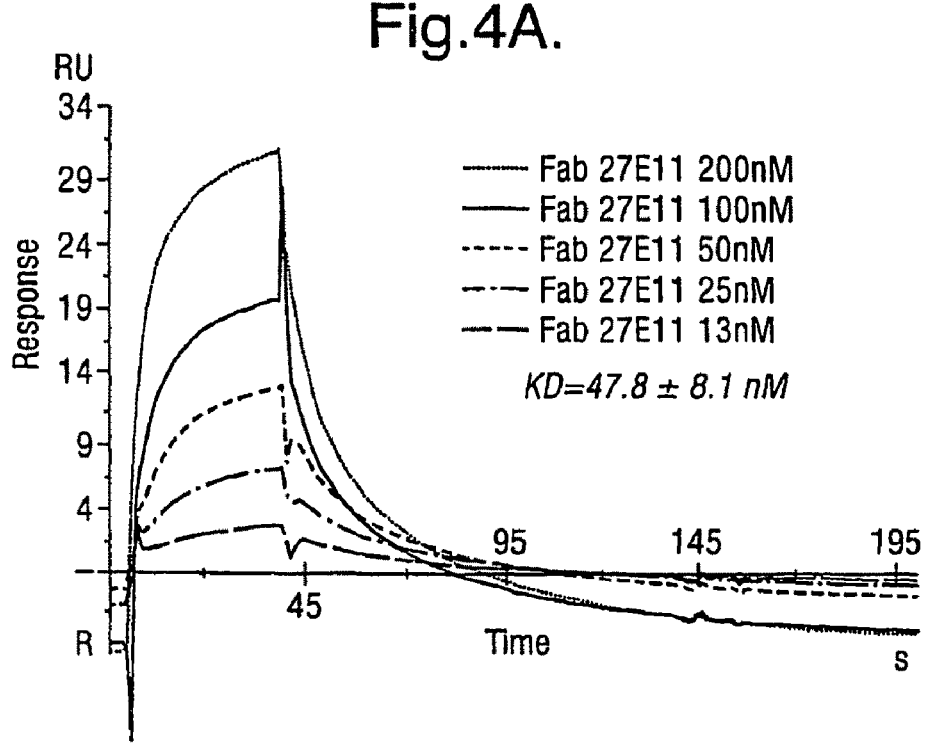
FIG. 4 shows Biacore affinity analysis on bCTD coated of sFab antibodies M27E11 (A), M28B02 (B) and M26F05 (C) and Biacore affinity analysis with Fab M27E11 coated on the chip (D).
Figure 4B:
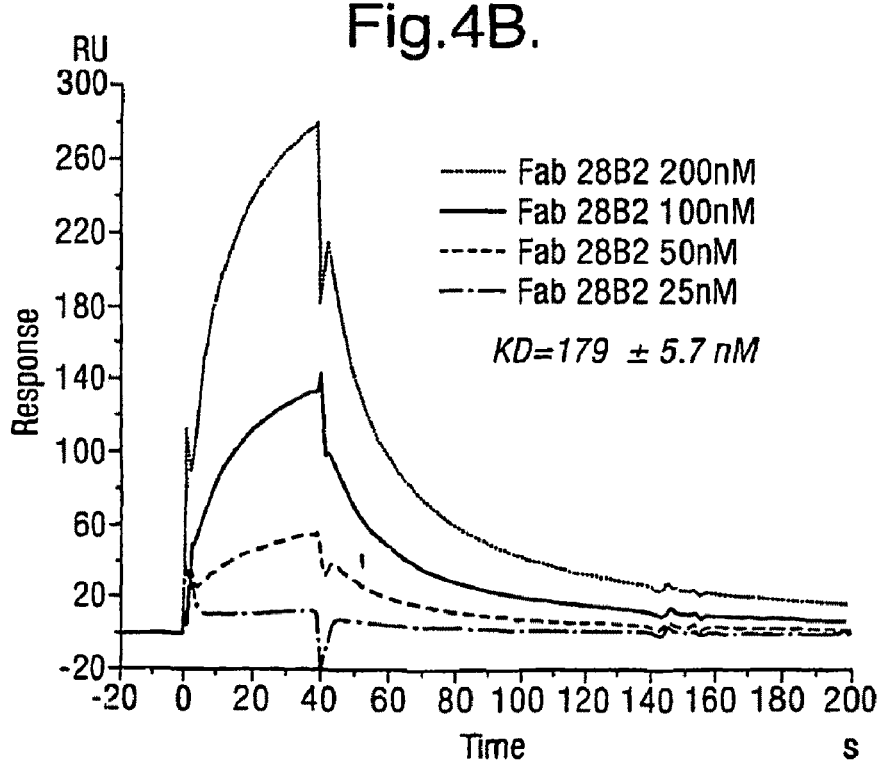
Figure 4C:
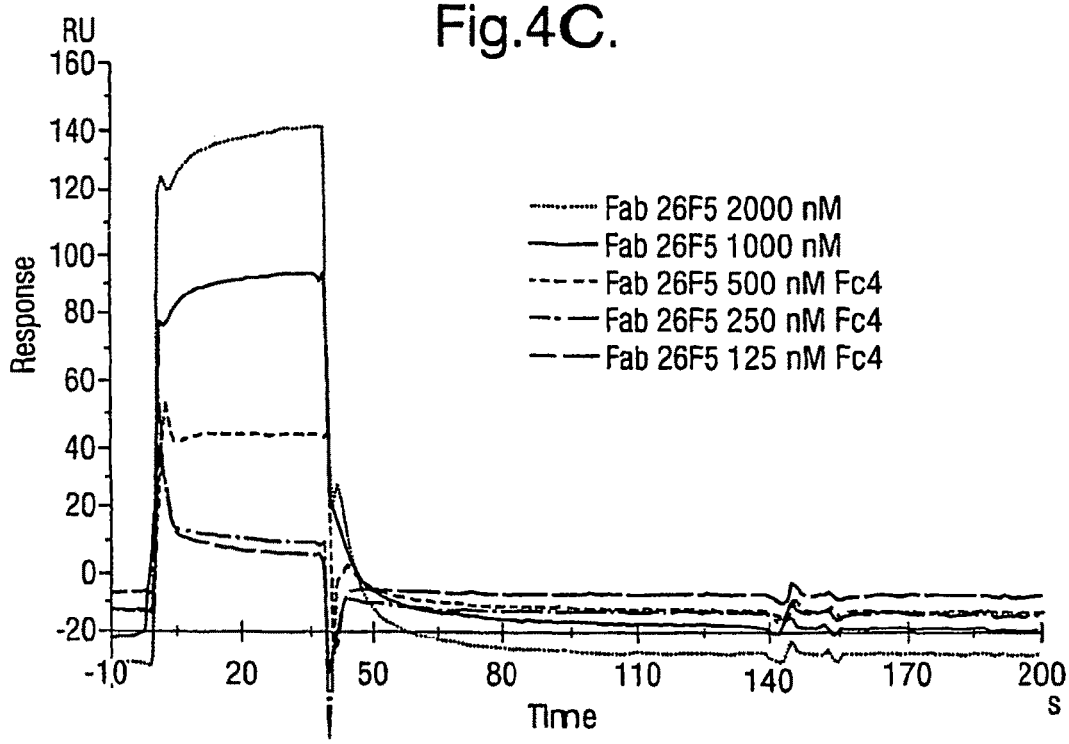

The three Fabs 807A-M0027-E11, 807A-M0028-B02 and 807A-M0026-F05 were extensively studied in Biacore analysis. First bCTD was coated on a streptavidin chip, then sFabs were run over the chip at different concentrations and binding resonance units (RU) were measured. As a negative control, one channel of the chip was saturated with biotin-BSA. FIG. 4A shows the analyses of sFab antibody 807A-M0027-E11 on bCTD resulting in an affinity is 47.8 nM. The affinity of sFab antibody 807A-M0028-B02 showed a similar pattern, with an affinity of 179 nM (FIG. 4B). Antibody 807A-M0026-F05 has such a low affinity (in the µM range) that it is difficult to measure (FIG. 4C).

Figure 4D:
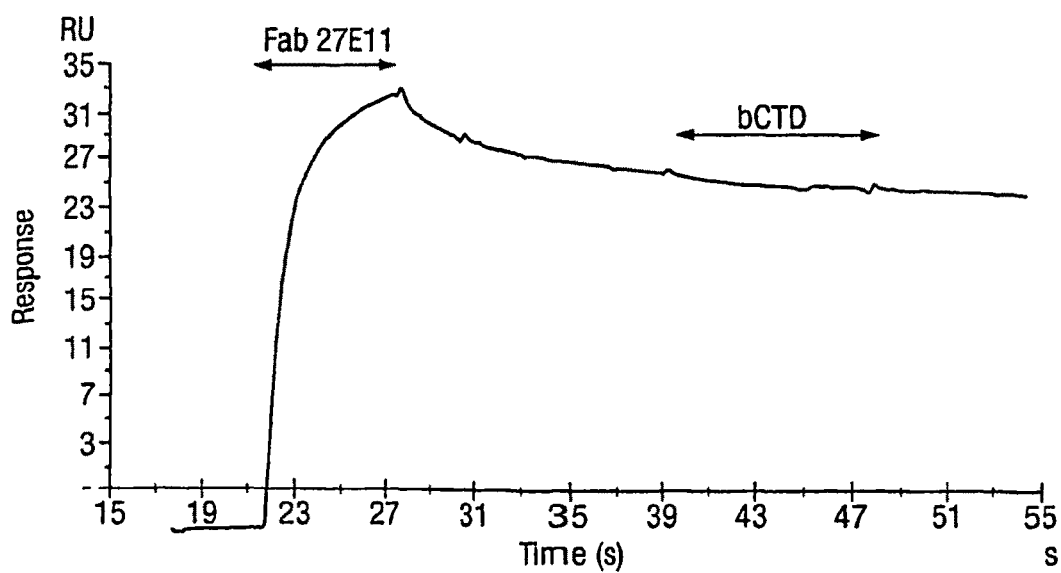

In contrast, when sFabs were coupled to a CM5 chip via an anti-Fc antibody, no binding was observed for antibody 807A-M0027-E11 (see FIG. 4D), nor for antibody 807A-M0028-B02.

The different results reversing the coating and analyte, in the two different Biacore measurements suggest that both, antibody 807A-M0027-E11 and 807A-M0028-B02 only bind to coated bCTD and not to bCTD in solution.

Example 13

Antibody Reformatting, Expression and Purification of IgGs

Antibody (Batch) Reformatting to IgG1
85 clones showed specific binding to CTD as soluble Fab. Of these the 30 candidates that had been chosen for IHC studies were reformatted to complete human IgG1 antibodies.

A pool of 157 CTD-specific Fabs, that contained all 85 "soluble Fab binders", was used for simultaneous, restriction digestion based batch-reformatting into the human IgG1 expression vector pBh1.

Figure 5:
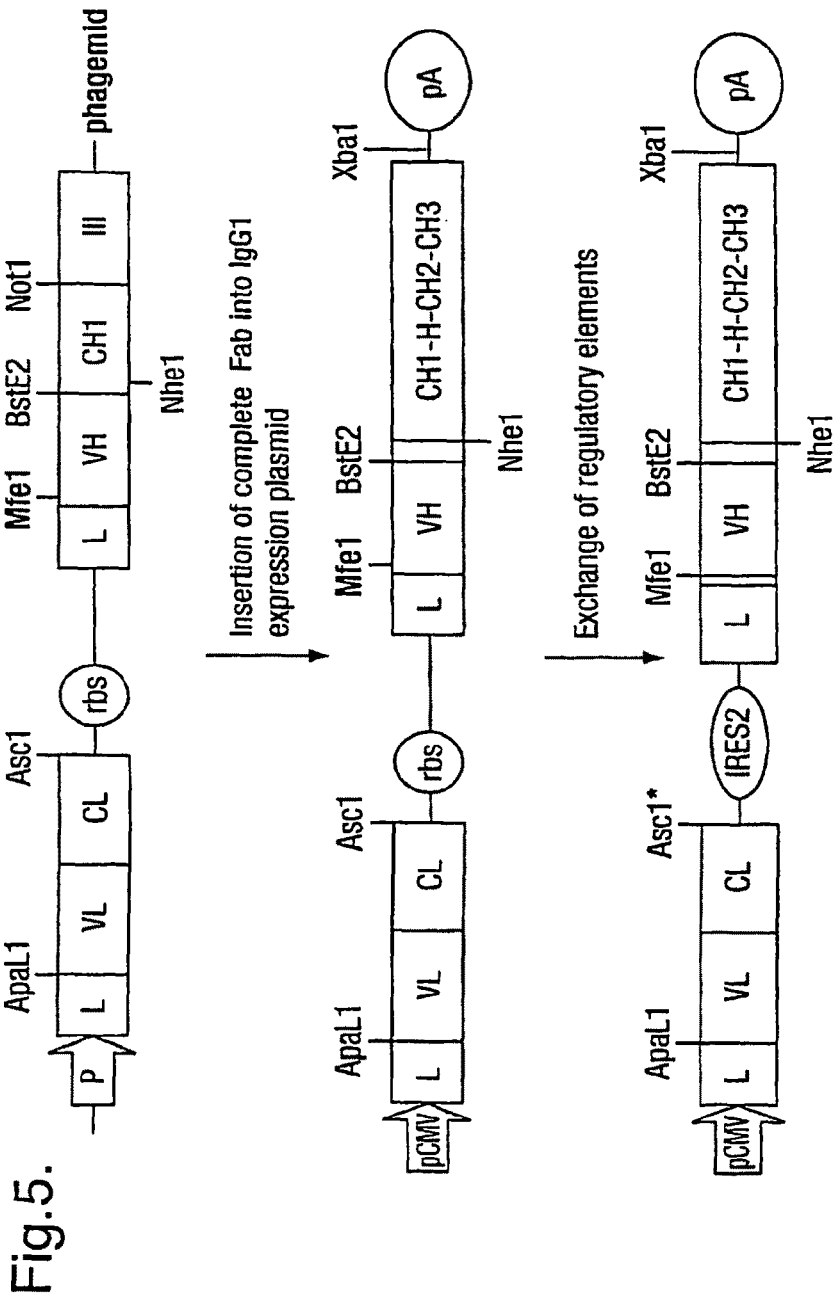
FIG. 5 is a schematic diagram showing the strategy of transfer of Fab to pBh1.

The batch-reformatting strategy involved two cloning steps, and is illustrated in FIG. 5. In the first step, complete Fab fragments are inserted into pBh1. In the second step, internal/regulatory sequences are exchanged.

To "re-identify" the initial Fabs, about 300 individual clones were analysed by DNA-sequencing. 72 of the 85 "soluble Fab binders" were found back. Notably, 29 of 30 of the prioritised candidates chosen for IHC (as phage and soluble Fab) were obtained as IgG1 constructs by batch reformatting.

11 of the 13 remaining "soluble Fab binders" could be reformatted individually into the human IgG1 expression vector pRh1. Identity of the reformatted antibodies to their Fab counterparts was verified by sequencing. Besides initial PCR-amplification of the complete Fab-insert, the cloning approach is identical with the batch-reformatting strategy depicted in FIG. 5.

Expression and Purification of IgG1 Antibodies
Reformatted IgG1-antibodies were expressed in transiently transfected HEK293T cells. Antibodies were purified from culture supernatant of ~5×10$^6$ transfected cells (per flask), kept in culture for about one week. Purification was carried out by Protein-A-based affinity chromatography. Purified antibodies were dialyzed against PBS and analysed on SDS-gel under reducing and non-reducing conditions.
Biotinylation of IgG Antibodies
Biotinylation of antibodies was performed in PBS, incubating the purified antibodies for 2 hours with a 15-fold molar excess of Sulfosuccinimidyl-2-(biotinamido)ethyl-1,3-dithiopropionate. The level of biotin-incorporation (i.e. the average number of biotin groups per antibody molecule) was determined using the HABA [2-(4'-hydroxyazobenzene)benzoic acid] method (Pierce). Using this approach, we found that all biotinylated antibodies contained 3 to 4 biotin groups per molecule.

Example 14

Specificity Tests with IgG1 Antibodies

Binding of IgG1 Antibodies to Other Species
Cross-reactivity of the human antibodies on bCTD of these species was tested to try to identify antibodies that can be studied in mouse and primate models.

The antibodies (807A-M0028-B02, 807A-M0027-E11, 807A-M0026-F05) that bound to plaques in AD tissues as sFab, were reformatted to hIgG1 and tested for their binding capacity on recombinant mouse CTD (mbCTD), recombinant primate CTD (pbCTD) and recombinant human CTD (hbCTD) that was biotinylated.

Figure 6A:
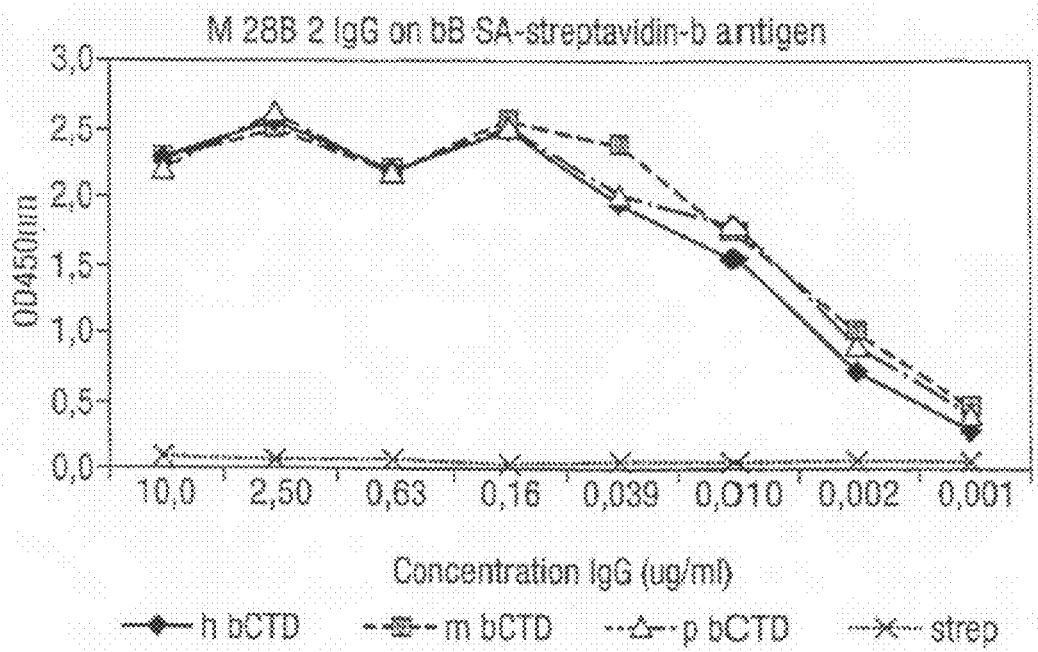
FIG. 6 shows the binding of antibodies 807A-M0028-B02 (M28B02) (A), 807A-M0026-F05 (M26F05) (B) and 807A-M0027-E11 (M27E11) (C) to human CTD, murine CTD and primate CTD.

Antibodies 807A-M0028-B02 and 807A-M0027-E11 (FIGS. 6A and 6C) did bind to CTD of the three different species. Both antibodies bound to the same extent suggesting that the epitopes recognised by the antibodies are the same in these species.

Figure 6B:
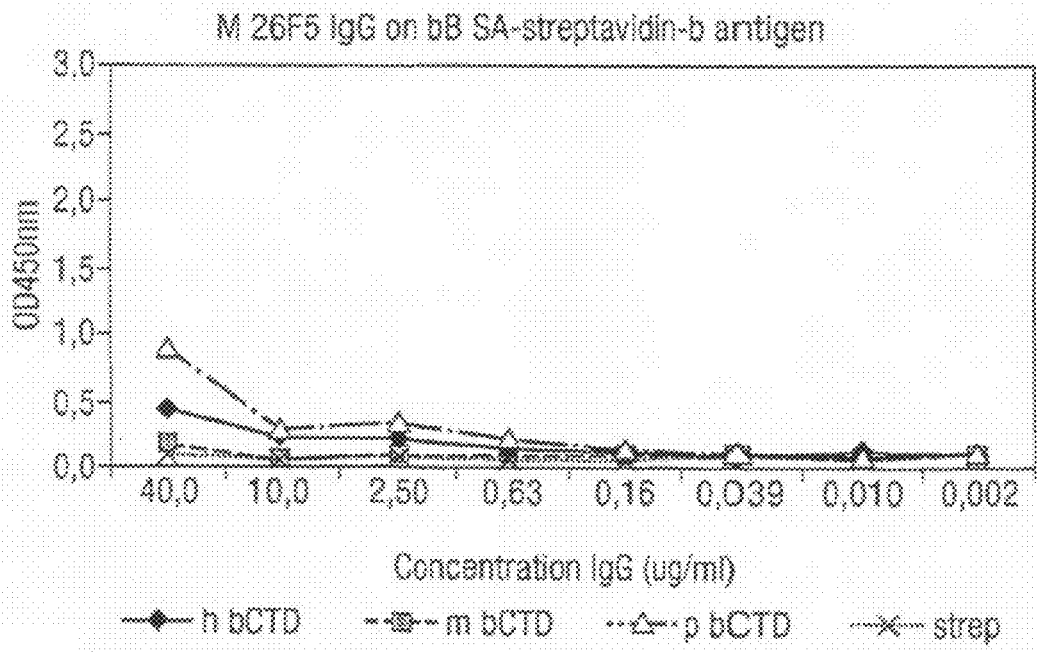
Figure 10:
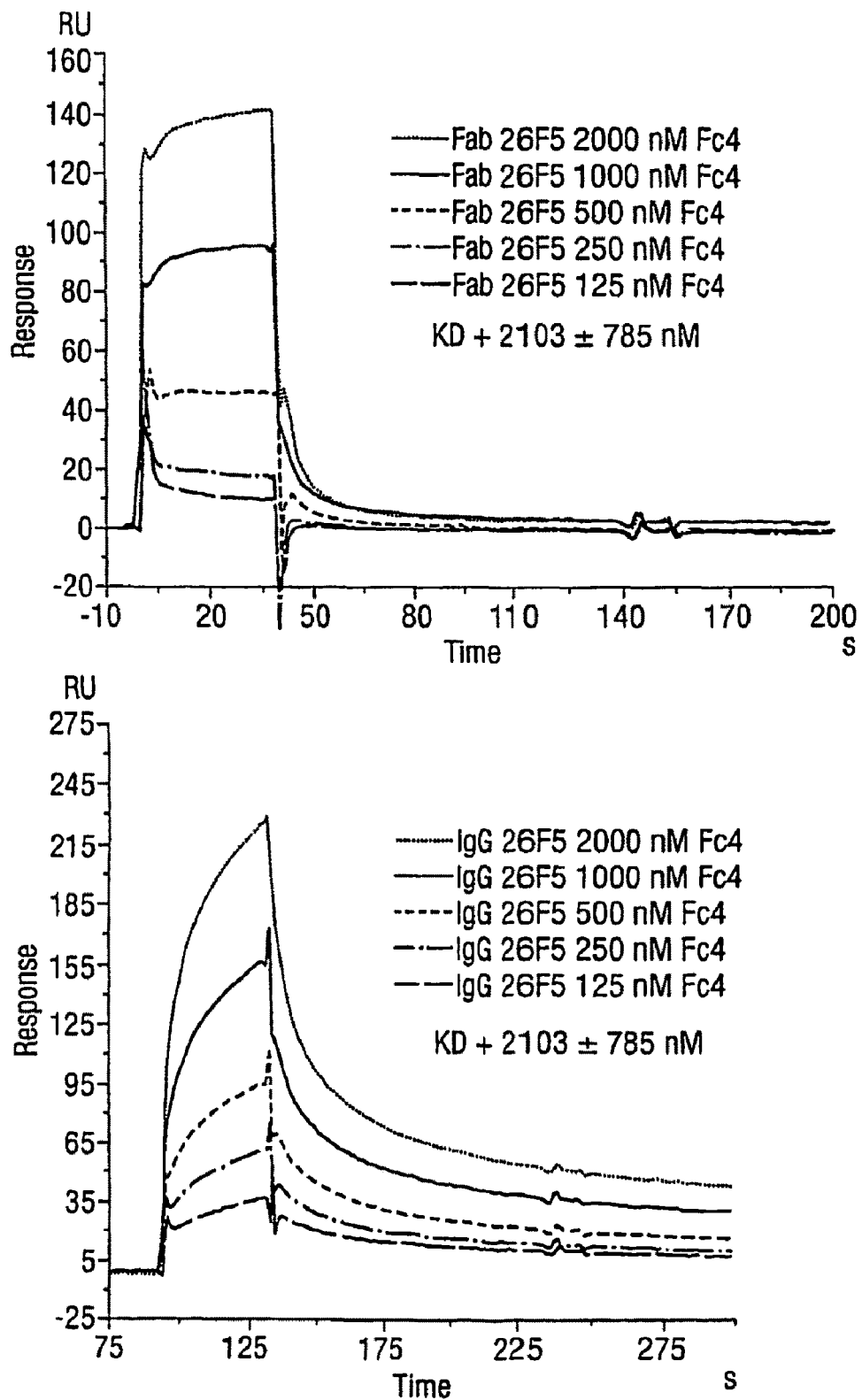
FIG. 10 shows the Biacore analysis of 807A-M0026-F05 (M26F05) as soluble Fab (top) and IgG (bottom) on a CTD-control chip.

Antibody 807A-M0026-F05 (FIG. 6B) binds to pCTD and hCTD but not to mouse CTD, suggesting that the antibody is directed against an epitope that is not present in mice or that concentration used is not high enough. The low O.D. in this ELISA can be explained by the low affinity of this antibody.
Binding of IgG1 Antibodies to bNTD
807A-M0027-E11 and 807A-M0026-F05 did not bind to bNTD. Antibody 807A-M0028-B02 did bind at very high concentrations (10 and 5 µg/ml). To check if this was related to specific binding, we tried to compete with 1000 times more bNTD in solution (540 ug/ml in solution, 0.5 ug/ml coated) (FIG. 7). The non-specific signal did not decrease in competition. The signal is most probably due to the high amounts of antibody added, as also seen for the anti-MUC1 antibody PH1 (FIG. 7).
Binding of IgG1 Antibodies to VLDL
Binding of antibodies to coated VLDL was tested in ELISA. Unlike the phage and the Fabs of the plaque binders, antibodies 807A-M0028-B02 (FIG. 8) and 807A-M0027-E11 are binding to VLDL to the same extent. When compared to the binding of a non-CTD binder (PH1, which is a MUC1 binder) this binding seems to be specific.

Because VLDL is composed of ApoE and a lipid, the coated VLDL could change its conformation during treatment in ELISA and it could be that the CTD is not covered by the lipid anymore. Therefore we did a competition test with the antibodies in solution, bCTD bound to the plate and an excessive amount of CTD or VLDL in solution (FIG. 9). In this assay we could not see inhibition with VLDL for the human antibodies (FIGS. 9A and B) and little inhibition with CTD for antibody 807A-M0028-B02 (FIG. 9B). In contrast, the commercial antibodies 3D12 and E19 directed against CTD were clearly inhibited by VLDL as well as by CTD. The 6C5 monoclonal directed to NTD did not bind in this assay.

These results suggest that the human antibodies (807A-M0028-B02, 807A-M0027-E11) are not binding to VLDL in solution and recognise CTD in solution to a lesser extent than coated bCTD.

Conclusion

Two of the three antibodies binding to plaques in AD (807A-M0028-B02, 807A-M0027-E11) are cross-reactive with pCTD and mCTD. The third antibody (807A-M0026-F05) does not cross-react with mCTD and binds pCTD. The antibodies of interest do not bind to NTD. Two antibodies (807A-M0028-B02, 807A-M0027-E11) bind to coated VLDL, when high antibody concentrations were used. Antibody 807A-M0026-F05 does not show these properties but this could be related to the affinity of the antibody.

Example 15

Biacore Analysis

To compare Fab and IgG1 binding and to study the nature of binding of the human antibodies on CTD in solution, Biacore was extensively used.

Comparison of Fabs and IgGs in Biacore

FIGS. 10, 11, 12 and 13 summarize the results of the Biacore analysis of the CTD-specific clones 807A-M0026-F05, 807A-M0027-E11 and 807A-M0028-B02. As expected all three plaque binders bind better to bCTD on the chip as IgG1 compared with their original Fab format. IgG1 Antibody 807A-M0027-E11 binds 3 times better than antibody 807A-M0028-B02 while antibody 807A-M0026-F05 binds with a very low micro molar avidity to the chip.

The avidity measured (Table 2) is higher when measured 50 seconds after the injection of the antibody is stopped as compared with the avidity measured immediately after injection stop. This difference is probably due to the rebinding of the antibody to the chip when free bCTD is available on the chip.

Binding of Antibodies to Captured CTD

Because of the inconsistency of VLDL ELISA in which the human IgG1 antibodies bind to coated bCTD/VLDL but not CTD/VLDL in solution, additional Biacore experiments were performed (see also Biacore on Fabs). In these experiments bCTD or ApoE was captured. First anti-hFc antibody was coupled to the chip, followed by binding of the specific antibodies, followed by the injection of bCTD or ApoE.

Figure 12:
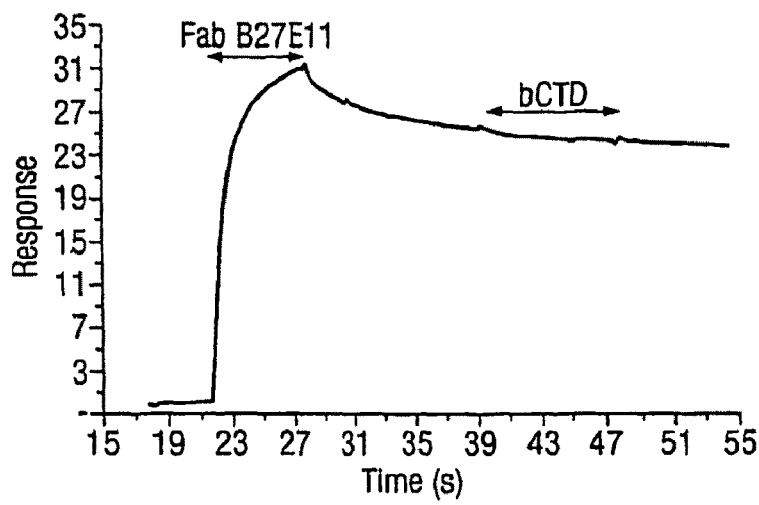
FIGS. 12 and 13 show the binding of bCTD in solution to Fab 807A-M0027-E11 (M27E11) indirectly coupled to a Biacore chip.
Figure 13:
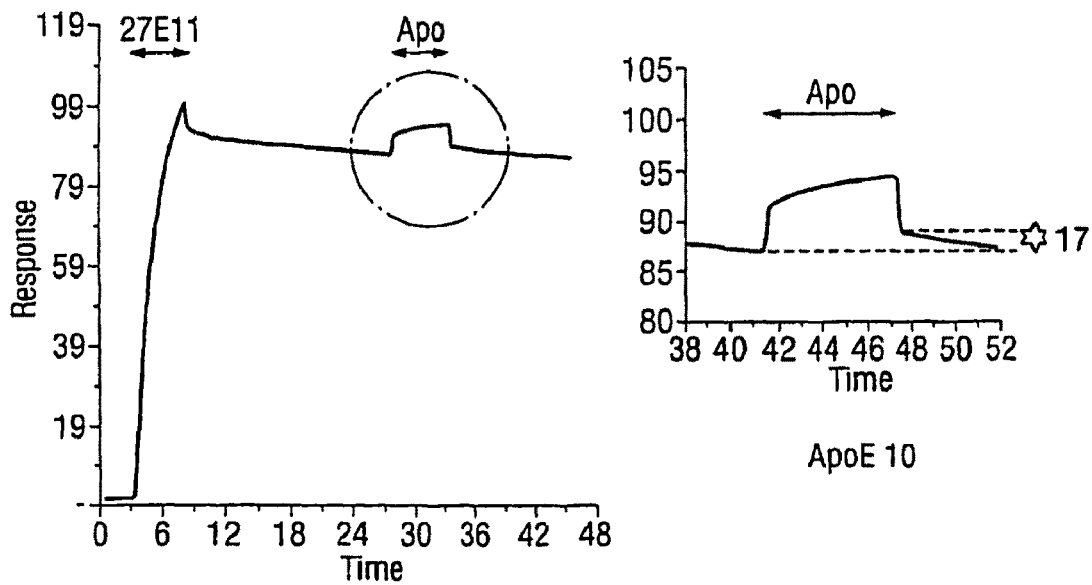

FIG. 12 shows that Fab antibody 807A-M0027-E11, indirectly coupled to the chip, does not bind bCTD (280 nM). The same curves (data not shown) were obtained by using Fab antibody 807A-M0028-B02 and when IgG1 of both antibodies was used. The test was performed with ApoE originating from human serum. Only a very small amount of ApoE (17 RU, <1%) was bound to the antibody (FIG. 13).

Conclusion

In Biacore, IgG1 antibodies 807A-M0027-E11 and 807A-M0028-B02 bind to coated bCTD with nM avidity while IgG1 antibody 807A-M0026-F05 binds with µM avidity. Affinity measurements on antigen in solution do show that both antibodies 807A-M0027-E11 and 807A-M0028-B02 do not capture bCTD nor ApoE efficiently. These results confirm the results seen by VLDL/CTD competition ELISA: antibodies 807A-M0027-E11 and 807A-M0028-B02 bind better to coated bCTD than to CTD in solution.

Example 16

Additional Testing to Study Binding of Antibodies to Natural CTD, to Peptides

SDS-PAGE Analysis of the Purified hApoE

The purified, hApoE was analyzed by reducing SDS-PAGE followed by Coomassie staining. As expected, the protein migrated as one major band of ~35 kDa, but there was also a broad band at ~70 kDa and a faint smear from 70 kDa to ~200 kDa. Both the 35 kDa band and the higher molecular weight species were shown by western-blot to contain hApoE.

Immunoprecipitation of Purified hApoE

Purified hApoE was immunoprecipitated with 807A-M0028-B02, 807A-M0027-E11 and 807A-M0026-F05. As a positive control, we used E19, a goat anti-hApoE antibody. As a negative control, we used the PH1 antibody. Untreated, purified hApoE was also included as a reference. The samples were analyzed by SDS-gel, the proteins were transferred to a nitrocellulose membrane and hApoE was detected by western-blot.

As expected, the E19, the 807A-M0028-B02 and the 807A-M0027-E11 antibodies were able to specifically immunoprecipitate hApoE, although not very efficiently. Interestingly, the E19 antibody seemed to be specific for the 35 kDa band, whereas the 807A-M0028-B02 and 807A-M0027-E11 antibodies were more specific for the high molecular weight species. The 807A-M0026-F05 was by contrast unable to immunoprecipitate hApoE, probably due to the low affinity of the antibody.

Immunoprecipitation of Cell Lysates

Cell lysates of PBMC were immunoprecipitated using 807A-M0028-B02, 807A-M0027-E11 and 807A-M0026-F05, as well as E19 (positive control) and M43G5, M43F8, PH1, A2, herceptin and a human IgG1 Kappa Myeloma antibody (negative controls). Samples were analyzed by SDS-PAGE under reducing conditions followed either by silver staining or Western-blot.

Only E19 immunoprecipitated a band of the expected size (i.e. ~35 kDa).

The material immunoprecipitated with E19 also gave a very faint signal in Western-blot. This suggests that some hApoE is captured by E19 in the cell lysates, although this finding must be regarded with care since (1) 807A-M0028-B02 and 807A-M0027-E11 did not immunoprecipitate any hApoE from the cell lysates, (2) 807A-M0026-F05, which was shown to be unable immunoprecipitate hApoE, also gave a weak signal in Western-blot and (3) A2 and 807A-M0043-F08, two irrelevant antibodies, gave strong signals in Western-blot.

Importantly, the three antibodies investigated here (807A-M0028-B02, 807A-M0027-E11 and 807A-M0026-F05) did not seem to immunoprecipitate any major component of the cell lysates. The background for 807A-M0027-E11 was a little bit higher, but not higher than e.g. PH1. These results indicate that the overall specificity of the antibodies, 807A-M0028-B02, 807A-M0026-F05 and 807A-M0027-E11, is due to the binding to CTD.

Immunoprecipitations of VLDL

Binding of antibodies to VLDL was also tested by immunoprecipitation. 10% VLDL was used in these tests. As detection antibody 6C5 was used. After 5 minutes development of a Western blot with the ECL method, no ApoE was detected for the human antibodies of interest. After overnight development antibody 807A-M0027-E11 and 807A-M0028-B02 were detected as faint bands when compared with the VLDL control (non-immunoprecipitated VLDL, 10% of the amount that was used for immunoprecipitation). Immunoprecipitation with the 6C5 antibody showed a more extensive band than with the human antibodies.

Discussion

807A-M0028-B02 and 807A-M0027-E11, but not 807A-M0026-F05, preferentially immunoprecipitate a high molecular weight from of hApoE purified from plasma. The nature of these species remains unclear, although it is clear that they contain hApoE and must form very stable complexes. These antibodies do not interact significantly with major cellular components. Immunoprecipitation of VLDL with the antibodies is possible, although the amount might be very low.

Example 17

In vivo Studies

Mice were bred to express in the brain the human gene for amyloid precursor protein (APP): Swedish mutation K670N, M671L, APP Line 2576, driven by the hamster prion promoter (Hsia et al Science 1996, 274:99-102), alone or in combination with a mutated human presenilin 1 (PS1): M146L driven by the platelet derived growth factor (Duff et al, Nature 1996, 383 (6602):710-3, Holcomb et al, Nature Med 1998, 4:97-100).

For studies requiring expression of human ApoE mice were bred that either expressed the human ApoE4 driven by the glial fibrillary acidic protein (GFAP) promoter with or without the mouse ApoE gene knocked out (Sun et al, J Neurosci, 1998, 18:3261-3272) in combination with humAPP:Swe and humPS1:M146L or humAPP:Swe only.

Monoclonal antibodies (mAb) of the human immunoglobulin G1 (hIgG1) isotype to C-terminal domain (CTD) of Apolipoprotein E (ApoE) were injected intra-peritoneally at a concentration of e.g. 10 mg/kg in non transgenic or transgenic mice. Some mice were injected once and sacrificed 2 days after injection and some were injected twice, with the repeated dose injected after 2 days, and then sacrificed after an additional 2 days i.e. 4 days after the initial injection. The concentration of injected antibody was monitored by ELISA to CTD binding hIgG. Brains from mice injected with a streptavidin specific monoclonal antibody served as negative controls. The sampled brains were immediately frozen to −70° C. and then subjected to freeze sectioning.

Staining for presence of human IgG in brain sections showed homogeneously stained plaques evenly spread trough cortex and hipocampus. No other brain structures showed staining after in vivo exposure. In contrast, several structures along with the amyloid plaques were stained after ex vivo exposure. 70% of the plaques that were accessible for staining ex vivo by anti-ApoE CTD antibody or with a mAb to Ab were stained after the 2-day (n=3) or 4-day (n=3) in vivo exposure with the anti-ApoE CTD antibody. The in vivo exposure for 2 or 4 days at the given dose did not saturate the available binding sites as indicated by the additional staining intensity obtained after ex vivo addition of more anti-CTD antibody.

Antibodies, as macromolecules in general, do not pass freely over the blood brain barrier (BBB). The passage of IgG is considered to be very limited and concentrations in CSF under 0.5% of the plasma concentration has been reported (Elovaara et al, 1987 Eur Neurol 26:229-34, Ganrot & Laurell 1974, Clinical Chemistry 20:571-3). Staining for presence of the intraperitoneally injected human IgG in brain sections revealed that the ApoE CTD specific antibody reached the cerebral plaques evenly throughout the different brain regions in these transgenic mice indicating sufficient BBB passage for staining by immunohistochemistry (IHC) technique. Alzheimer's disease (AD) plaques are complex structures varying in size and density. The cerebral amyloid plaques found in these transgenic mice are considered to represent the small diffuse and medium size plaques found in AD. The plaques were homogeneously stained indicating that the mAb did not only reach the outer layer of the plaques but penetrated the whole plaque structure. 70% of the plaques accessible for staining ex vivo were stained after the in vivo exposure. Considering that the dose of 10 mg/kg administered interperitoneally did not saturate the available plaque-binding sites, a non-saturated level of antibodies may still result in an antibody mediated plaque breakdown by FcR bearing phagocytic cells.

Example 18

Reformatting of Antibodies to Mouse IgG2a

For in vivo testing the variable regions of antibodies 807A-M0028-B02, 807A-M0027-E11, 807A-M0026-F05 and a control antibody (anti-Streptavidin clone A2) were recloned into vector that contains mouse IgG2a constant regions of the heavy chain and mouse Ckappa and the variable regions of antibodies.

These clones were transferred from a human IgG1 expression vector (pBh1) to a construct for expression of mouse IgG2a antibodies (pRmk2a), that besides the constant heavy chain region, also contains the mouse constant kappa light chain gene. The VL and VH regions were lifted from the human IgG1 expression plasmid via PCR, and cloned sequentially into pRmk2a. VL was inserted as an ApaL1/BsiW1 fragment, 3' of the antibody leader and 5' of the constant kappa gene. In case of the VH region, the 5' adjacent IRES motif was also included in the PCR amplification product; an Asc1/Nhe1 fragment was inserted in pRmk2a. Integrity of the constructs was verified by DNA sequencing. The cloning strategy is depicted in FIG. 14.

Example 19

Preparation of Peptides 10 peptides (length 16 amino acids) covering the full ApoE CTD were synthesized.

The peptides contain an 8 amino acid overlap between each other as shown in FIG. 15. The peptides contain an S-S Biotin group that enables binding to Streptavidin (magnetic beads selections). In addition each peptide contains a Cystein that can be coupled to a carrier protein (BSA).

Peptides were solubilised in dimethylformamide (DMF), and subsequently diluted in water. All peptides, except peptide 4 were soluble in DMF at a concentration of less then 10%. Coupling was performed in 10% DMF for all peptides, except for peptide 4 which was coupled in 30% DMF. An excess of maleimide-activated BSA was used to bind to the peptides. After incubation an excess of Cystein was used to occupy possible free cysteines. The BSA coupled peptides (bpeptide-BSA) were used for selections.

Example 20

Binding of Antibodies to Overlapping Peptides

Antibodies 807A-M0026-F05, 807A-M0028-B02 and 807A-M0027-E11 identified in Example 5 were tested for their binding to overlapping peptides. This was done firstly to test which peptides could be preferentially used in further selections: bpeptide-BSA or bpeptide and secondly to see whether the antibodies selected in Example 5 were binding to the overlapping peptides and if so, whether the epitopes they recognised were different and supported the epitope mapping by competition results as performed in Example 9. Both human antibodies and mouse antibodies were compared in this way.

For the human antibodies, peptide mapping was performed with IgG1 as well as with the phage displayed Fab. For example, clone 807A-M0026-F05 recognised bpeptide-BSA 4 and 8 as phage Fab fragment as well as whole IgG1. The ELISA was not sensitive enough to show binding to bpeptide 4 and 8 for this antibody. Therefore, we decided that it would be best to start the selections on bpeptide-BSA to capture the majority of peptide binders and then, if necessary, use the bpeptide in a later round of selection. Remarkably, antibody 807A-M0026-F05 bound better to CTD than to peptide compared with the murine monoclonal antibodies. Antibody 807A-M0028-B02 bound to peptide 4. Antibody 807A-M0027-E11 did not significantly bind to any of the overlapping peptides.

In Example 9 we found that the epitope recognized by antibody 807A-M0026-F05 and antibody 807A-M0027-E11 was covered by a large group of antibodies. Both antibodies did not compete with each other. Since the affinity for CTD for antibody 807A-M0026-F05 is very low as compared with antibody 807A-M0027-E11, one would expect that, if they recognise the same epitope, antibody 807A-M0027-E11 would have bound more strongly to peptides 4 and 8 than antibody 807A-M0026-F05. Therefore, one could conclude that both antibodies recognise related but not identical epitopes. Antibody 807A-M0028-B02 bound to peptide 4 and was different from the antibody group of the two other antibodies in competition epitope mapping and could recognise a different epitope.

We also tested control mouse antibodies on overlapping peptides. Antibodies 3H1, 12D10 and E19 bind to peptides 3, 10 and 5+10 respectively. In contrast with the human antibodies, all control antibodies bind to about the same extent to peptide and bCTD.

Example 21

Selections and Screening on Peptides

Three rounds of selection were carried out on 10 overlapping biotinylated peptides conjugated to BSA (b-peptide-BSA) and one round of selection on the corresponding biotinylated peptides (b-peptide). Selection was performed on 10 individual peptides using Streptavidin-magnetic beads. To handle this high number of selections in between selection rounds no titration of input/output was performed (liquid amplification).

Figure 16:
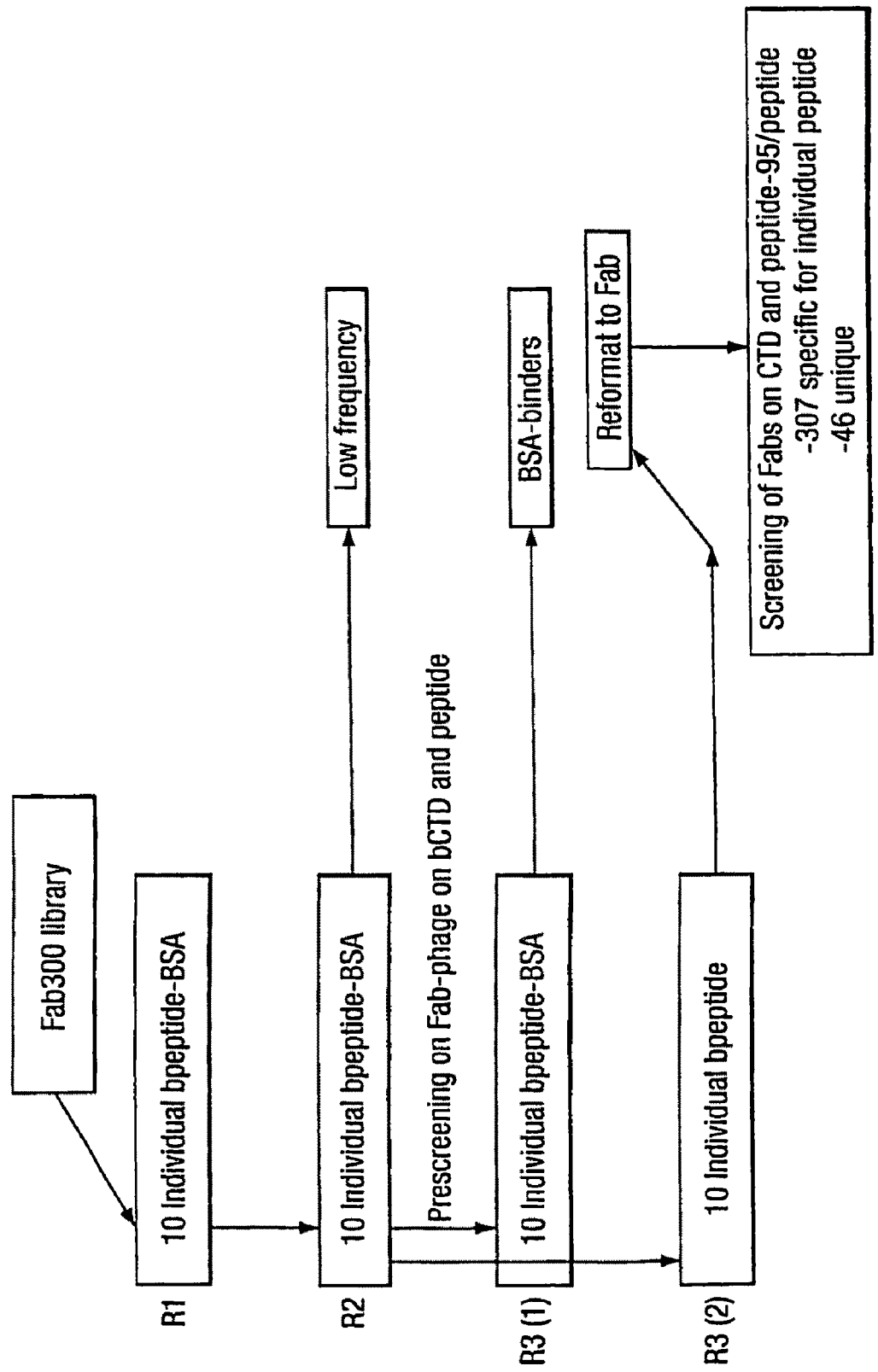
FIG. 16 shows the selection campaign of Example 21.

The procedure used is set out in FIG. 16. First, three rounds of selection for binding to bpeptide-BSA was carried out using the automated Kingfisher system. Pre-screening of round 2 and 3 with Fab-displayed on phage showed that the frequency of positive clones was low in round 2 and that many clones were binding to BSA in round 3, despite extensive depletion and subtraction on BSA. Most likely the binders were directed to the linker molecules on the BSA that we used for coupling the peptides. Therefore another round 3 selection on bpeptides was performed. For this selection background binding was negligible.

To reduce sequencing efforts, phage-Fab clones were batch reformatted to produce sFabs and the large screening of the clones (ELISA and sequencing) was performed at sFab level. 307 antibodies were found positive in ELISA of which 46 were unique as was determined by sequencing as shown in Tables 11 and 12.

Example 22

Selections and Screening on Fibrils and Peptides

Two rounds of selection were carried out on fibrils originating from an organ with amyloid plaques, 2 rounds on 10 corresponding b-BSA-peptides and 1 round on 10 corresponding b-peptides.

Figure 17:
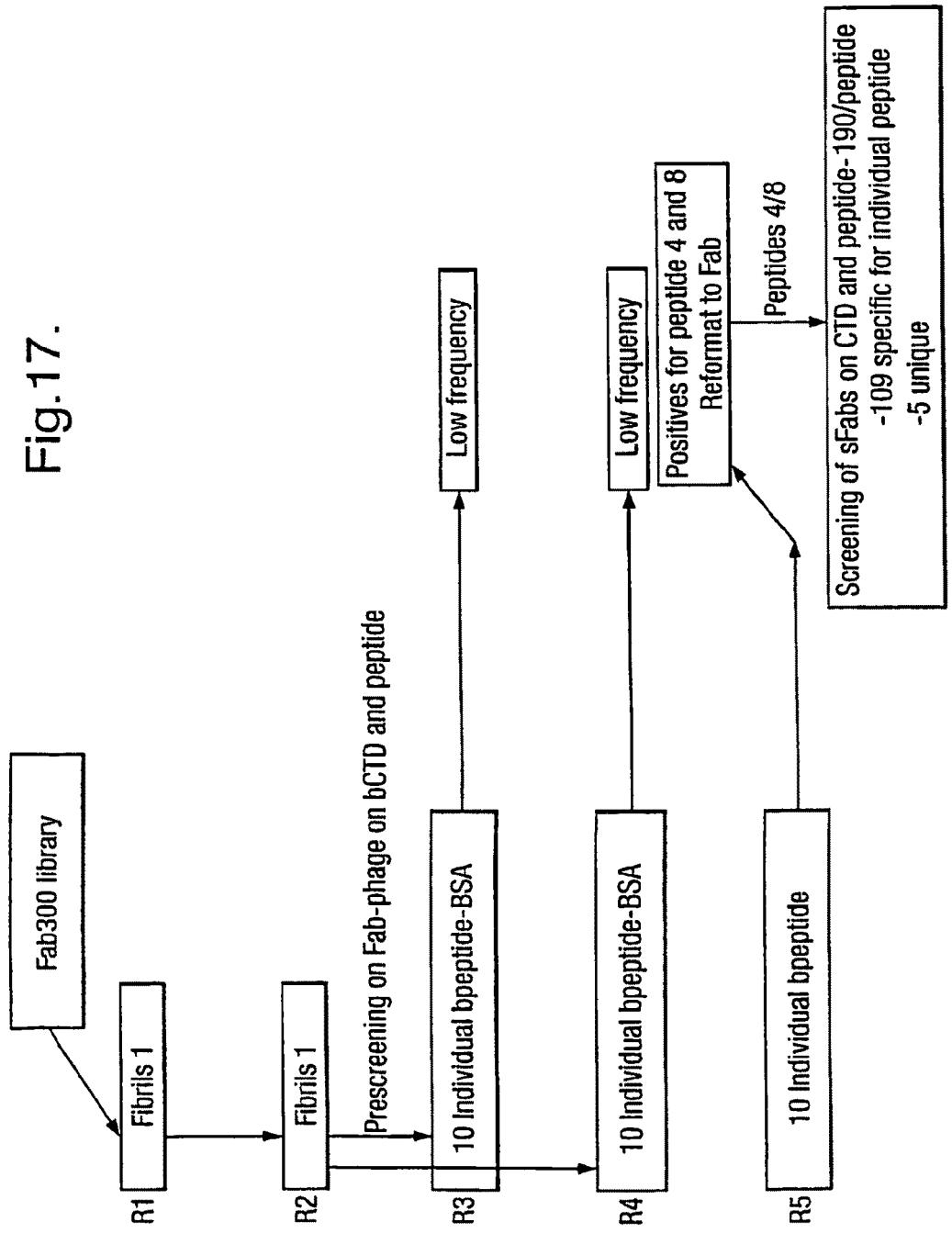
FIG. 17 shows the selection campaign of Example 22.

The procedure used is summarised in FIG. 17. Round 3 and round 4 were performed on individual bpeptides-BSA. After pre-screening few positive clones were found. Therefore a fifth round of selection was carried out using bpeptides. In a pre-screen, positive clones for peptide 4 and 8 were found. For these two selections we screened sFab after batch reformatting. In total 390 sFabs were screened, 109 were positive in ELISA and 4 clones were unique. The amino acid sequences of the VH and VL chains of these unique clones are shown in Tables 11 and 12. In these strategies most clones did show unique VH-CDR3s (Table 12), and high enrichment was found: one clone was enriched 148 times and was found in strategy B1 as well as in strategy B2. This is in contrast with selections of Example 5.

Few clones (Table 13) bound to bCTD, which makes them unique as compared to results in Example 20 where bCTD binders bound weakly or not at all to peptides. In the selection campaigns of Examples 21 and 22 no Fabs were binding to VLDL nor to NTD.

11 Fabs were found positive in IHC, 10 of these Fabs originate from the selection campaign of Example 11 and one originates from the selection campaigns of both Examples 21 and 22.

Example 23

Selections and Screening on ur-bCTD and Peptides

Figure 18:
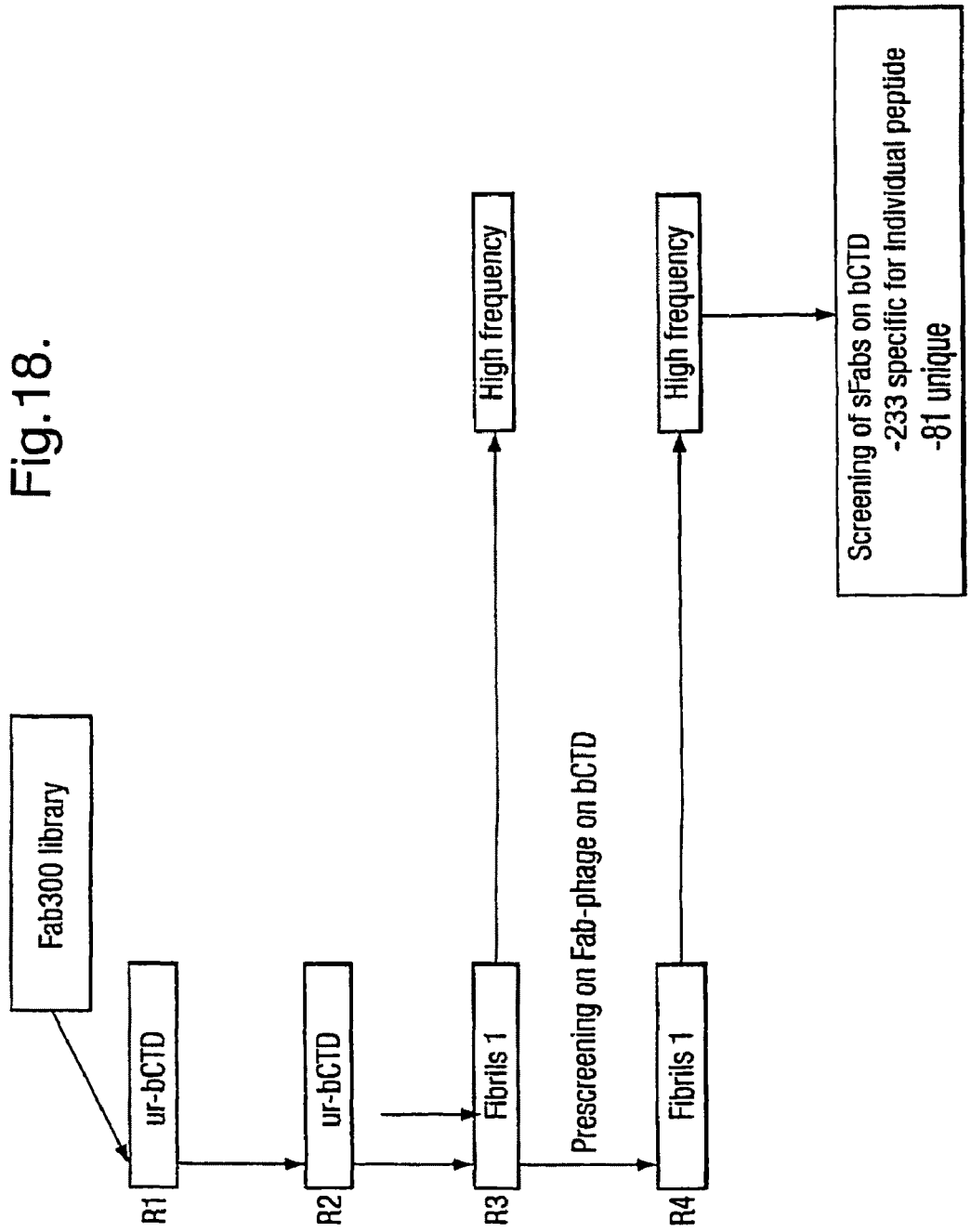
FIG. 18 shows the selection campaign of Example 23.
Figure 19:
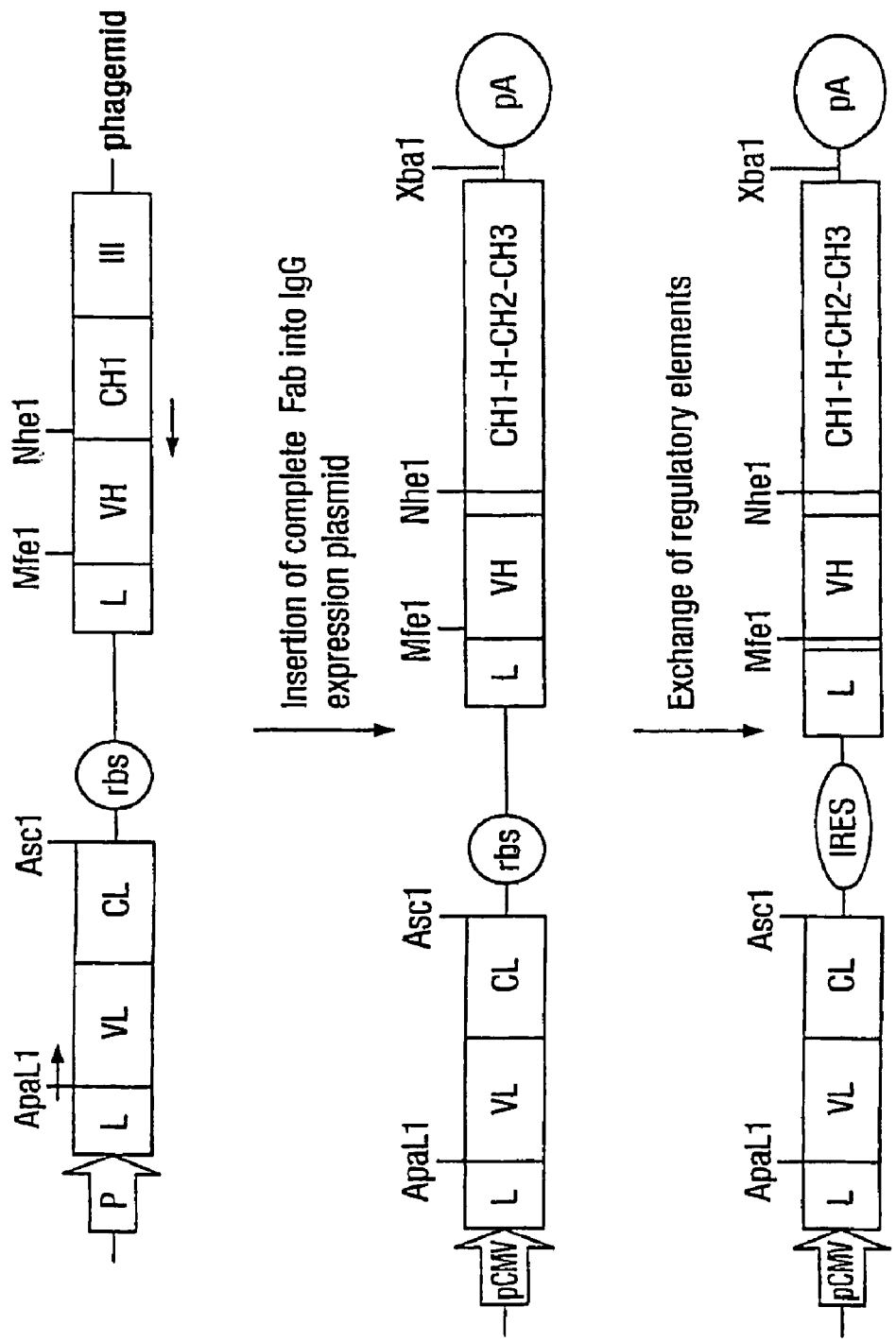
FIG. 19 shows a 'cut and paste' antibody reformatting strategy.

Two rounds of selection were carried out on urea treated biotinylated CTD (ur-bTD) followed by two rounds on fibrils originating from an organ with amyloid plaques. The procedure used is summarised in FIG. 18.

Two rounds of selection on urea-CTD antigen were performed followed by 2 selection rounds on fibrils 1 from an AD patient. In this strategy pre-screening was done after the $3^{rd}$ and $4^{th}$ round of selection. Frequencies were 82/95 and 83/95 respectively. During pre-screening we used ur-bCTD and bCTD and no difference was found between both types of antigen. After the third selection round, many clones were retained that bound to bCTD but not to fibrils while after 2 rounds of selection on the fibrils ($4^{th}$ round of selection) the chance that these binders are retained was less. Therefore, large scale screening was performed on the $4^{th}$ round of selection. 950 sFabs were screened on ur-bCTD. 233 clones were positive in ELISA as soluble Fab, 83 were unique. The amino acid sequences of the VH and VL chains of these uniques Fabs are shown in Tables 14 and 15. In VLDL ELISA, 5 Fabs bound were positive or had questionable binding.

No Fabs Bound to bNTD.

Many Fabs belonged to large families of identical VH-CDR3 groups; one individual antibody was enriched 247 times. Testing in IHC was performed on individual clones (not belonging to a large VH-CDR3 group) and clones belonging to a large VH-CDR3 group that were selected for a slow off-rate.

In a first IHC screen, 6 Fabs bound to plaques of AD patients. The properties of the bCTD binders are summarised in Table 17.

Example 24

Production of Candidate Clones as Soluble Fabs for IHC

Fabs were produced for further analysis. ELISAs were performed on periplasmic fractions of 100 µl cultures. Biacore off-rate measurement on periplasmic fractions of 50 ml cultures of all clones found in tables with Biacore results.

About 90 soluble Fab proteins were produced for testing in IHC. At least 10 µg was required for initial analysis. Because of wide variation in soluble Fab expression levels, the protein had to be purified either from the peripheral extract of 50 ml bacterial cultures, or from peripheral extracts of 400 ml cultures, by IMAC chromatography, using 96-well filter plates and a vacuum manifold. The yields mainly ranged between 10-100 µg.

Large Scale Production of IHC Positive Soluble Fabs 15 of the candidate Fabs turned out to be positive/potentially positive in IHC on plaque tissue. Of these clones more soluble Fab protein were prepared for additional testing.

Soluble Fab proteins were prepared from the periplasmic extracts of 400 ml bacterial cultures.

Example 25

Epitope Mapping, Comparison with Preliminary IHC Results

High throughput Fab screening was performed on the peptides they were selected on and also on a non-overlapping peptide as a control. In epitope mapping all peptide positive antibodies were screened for their binding reactivity to all other peptides. Table 13 contains detailed results.

Two Fabs bound to all peptides (most likely to the BSA-linker) and were considered as non-specific.

No Fabs were identified that were specific for peptide 5 and 10 (although the pre-screening Fab on phage showed some positive binders).

49 different Fabs bound specifically to peptides. 39 of the specific Fabs only bound to the peptide they were selected on. One Fab selected on peptide 1 also recognised peptide 6. 3 Fabs originating from the peptide 4 selection also bound to peptide 9 and 3 Fabs originating from the peptide 9 selections recognised peptide 4. Further, 3 peptides selected on peptide 8 also bound to peptide 4. Only 9 Fabs bound also to bCTD. This suggests that most of these Fabs bind to an epitope that is not present in the recombinant bCTD and recognise another (possibly stretched) structure that could potentially also be found in plaques. The region that covers peptide 3 and peptide 4 is recognised as a 'selection dominant epitope', containing 39 of all 49 specific Fabs and 8 of 9 bCTD binders. Interestingly, this area of ApoE is thought to be involved in the binding to VLDL particles.

Hypothesis Taking into Account for the IHC Screen 39 of the 49 specific Fabs bound to peptide but not to bCTD. This suggests that these Fabs are not likely to recognize natural Apo-E contained in for example VLDL particles. If such a Fab would bind in IHC it could indicate that such an epitope is unique and only found on plaques and that these Fabs would be important leads for further investigation.

Indeed, preliminary IHC data shows that four of these Fabs possibly bind to tissue in AD patients. These four Fabs all bind to peptide 4 and not to the overlapping peptides, suggesting that they recognise similar (overlapping) epitopes (group 1), probably epitope containing amino acids of LVED-MQRQ (SEQ ID NO: 12) or a secondary structure only present in peptide 4 and plaques.

Two other Fabs, positive in IHC and selected on peptide 4, bind to peptides 4 and 9 and to a conformation that is not present or not as prevalent in bCTD. Possibly the epitope for these two antibodies include sequence MQRQWAGL (SEQ ID NO: 13) (group 2).

Another Fab possibly positive in IHC, selected on peptide 9, only recognises peptide 9 and not overlapping peptide nor bCTD and could recognise either the epitope WAGLVEKV (SEQ ID NO: 14) or a conformation only present in peptide 9 (group 3) and plaques.

10 of 49 specific Fabs bind to peptide and bCTD, suggesting that these antibodies recognize a more conformational epitope.

One Fab binds to peptide 1, 6 and bCTD. This epitope (RTRDRLDE, SEQ ID NO: 15) is not predicted to be inside of the binding site of VLDL (group 4).

Two antibodies, obtained from selections on peptides 4 and 9, recognise both peptides (epitope MQRQWAGL, SEQ ID NO: 13) and CTD and therefore are different from Fabs of group 2 (group 5).

One antibody, selected to peptide 8, binds to peptide 4, 8 (epitope WFEPLVED, SEQ ID NO: 16) and bCTD (group 6).

Thus, according to this hypothesis the Fabs identified in Examples 21 and 22, can be divided into six different groups of Fabs that each recognize distinct epitopes.

Example 26

Biacore Off-rate Analysis of the Fabs Identified in the Strategies of Examples 21 and 22

Off-rate analysis of soluble Fabs was performed on all 10 peptides. Periplasmic fractions from all unique Fab of Examples 21 and 22 were made and tested. The results confirm the epitope mapping by ELISA.

Fabs that bind to more peptides and/or to bCTD most often show the about the same off-rate for those molecules. In contrast, RU's (measure for the amount of antibody bound) are often highest for the peptide to which the Fabs were selected on.

The strategies of Examples 21 and 22 did not result in the identification of antibodies belonging to large families of identical VH-CDR3s. Therefore, off-rate measurements were not used as a criterion for IHC.

Example 27

Epitope Mapping of the Antibodies of Example 23 and Comparison with Preliminary IHC Results In the automated screening, Fabs were screened for their binding reaction towards ur-bCTD and streptavidin BSA as negative control. No antibodies bound to NTD. Table 16 contains detailed results.

In total 81 different antibodies, binding to ur-bCTD and CTD were found. 5 of those antibodies bound to coated VLDL. None bound to bNTD. 20 antibodies, also bound to peptide. As in the strategies of Examples 21 and 22 we found a selection dominant epitope around peptides 3 and 4.

Five antibodies of the 81 bound in IHC. Only one of these antibodies bound to peptide. This antibody binds with low RU (Biacore) to peptide 4 and high RU. Interestingly, this antibody was also found using the strategies of Examples 21 and 22. The other four antibodies could be compared with antibodies 807A-M0028-B02 and 807A-M0027-E11 of Example 5.

Example 28

Reformatting of Candidate Fabs to Human IgG1

Most of the IHC positive clones described above can be individually reformatted to the Dyax hIgG1 expression construct pBh1 in two restriction endonuclease based ("cut and paste") cloning steps (see FIG. 5).

With the exception of the amber-stop containing clones, 807B-M0079-D10 (807B-M0027-D08) and 807B-M0081-A11 (807B-M0081-F12), and the clone 807B-M0009-C03, reformatting of Fab to IgG was carried out and the IgGs transiently expressed in Hek293T cells.

The amber-stop mutation in the CDR2 of 807B-M0079-D10 is corrected on the "phagemid level", before the clone is reformatted using the procedure outlined above.

The amber-mutation at the 5'-end of VL of 807B-M0081-A11 is repaired using a different reformatting strategy/"PCR-based reformatting to the hIgG1 expression construct pRh1". Due to the fact that the amber-stop mutation lies within the sequence of our "CJ-kappa-lifting primer", the stop mutation is corrected during PCR amplification of the Fab fragment. The cloning strategy of PCR/Fab fragments to pRh1 is the same as the "cut and paste" approach to pBh1.

Example 29

Conclusions 229 candidate Fabs binding to CTD were isolated from a variety of selection procedures with Dyax' human Fab300 library. Two of the procedures included selections on peptide (Examples 21 and 22). In the selection procedure of Example 23 the successful selection of Example 5 was reversed by first selecting on ur-bCTD and then on fibrils. Also in contrast with Example 5, we did not screen phage but first performed a batch recloning from phage Fab to Fab.

Very few (five) were reactive, as Fab antibody, with coated VLDL. No Fab was positive for bNTD.

In the strategies of Example 21 and 22, some clones were enriched and we observed VH-CDR3 groups with few individual clones.

Fab antibodies from the strategies of Example 21 and 22 recognise a selection dominant epitope around peptides 3 and 4. In the strategy of Example 23, the same dominant epitope is found.

In IHC screening, 15 antibodies were found positive for binding to plaques in IHC in a first screen. An overview of the characteristics of the Fab clones positive in the first IHC screen is shown in Table 17.

Example 30

Properties of IgG1 of the 15 Fabs Positive in IHC

The 15 Fabs which were positive in Fab-IHC were reformatted to IgG1. Of these antibodies, nine were found positive in IgG1-IHC.

Almost all IgG antibodies bound to peptide in peptide epitope mapping. This is probably due to the higher avidity of the IgG1 as compared to the Fab. For the antibodies selected on peptide 4 which only bound to peptide 4 as Fab, some also bound to peptide 9 as IgG. For the antibodies originally from the screen described in Example 23, the IgG antibodies bound to peptides 4 and 8, peptide 9 or peptide 7 only one antibody, 807B-M0083E11, did not bind to any peptide.

Human CTD, mouse CTD and primate CTD were compared to each other. Several IgG antibodies bound to bCTD of each of the three species.

Although there was no binding to coated VLDL in Fab ELISA, in IgG1 ELISA several but not all antibodies bound to VLDL.

All IgG antibodies showed an improved binding compared to Fabs in Biacore analysis when bCTD was coated on the chip.

The IgG1 results are summarised in Table 18.

Example 31

Effect of VLDL on Binding of 807A-M0028-B02 to CTD in Amyloid Deposits

To analyse binding of 807A-M0028-B02 to CTD in amyloid deposits in presence of lipoprotein particles, immunohistochemistry was performed in presence or absence of VLDL to see whether the presence of VLDL would lead to a decreased staining intensity of plaques.

Figure 20:
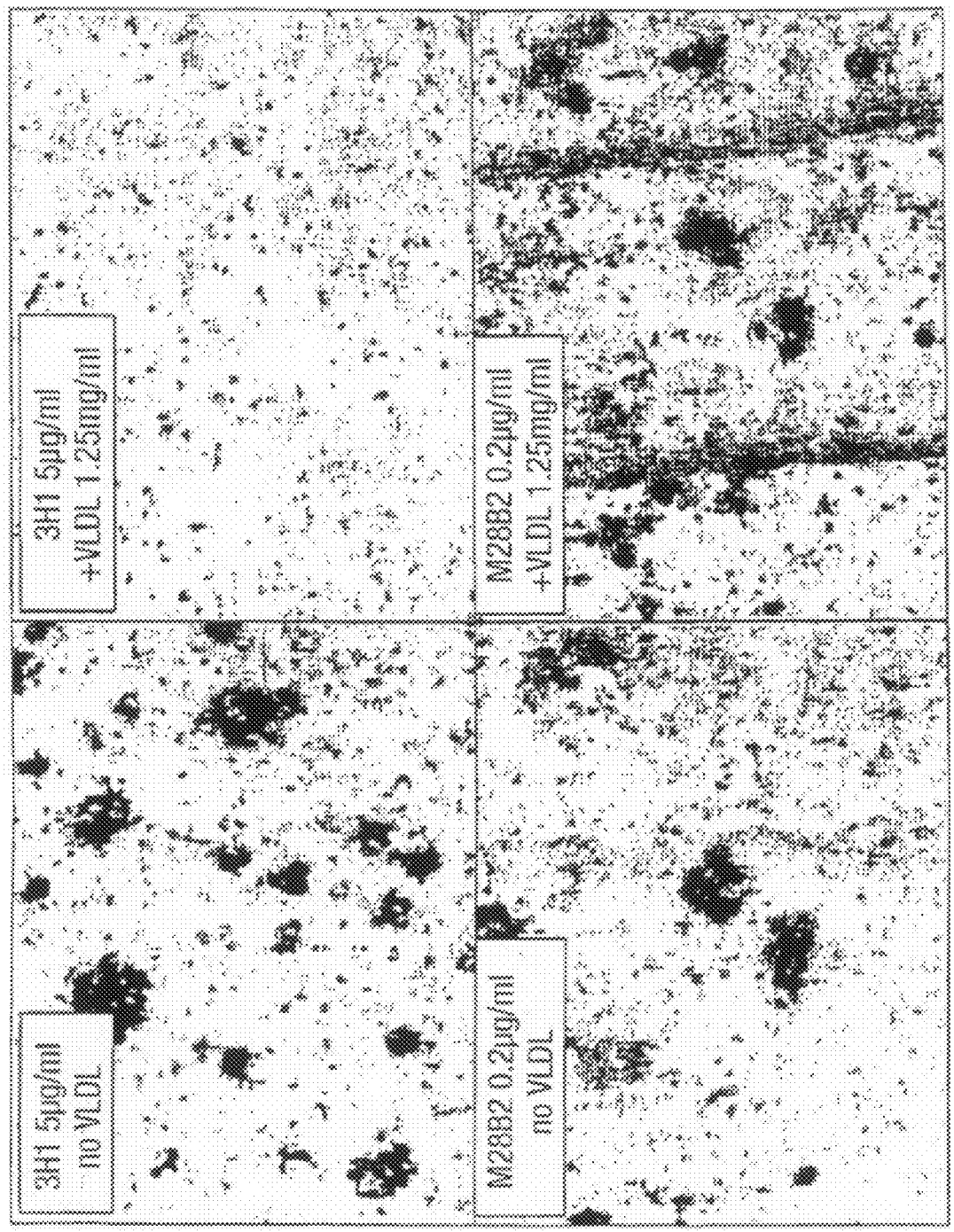
FIG. 20 shows that 807A-M0028-B02 plaque binding in human AD brain sections is not blocked in presence of VLDL. Binding of 807A-M0028-B02 to human amyloid plaques in vitro was not affected by the presence of VLDL indicating that the antibody has very low affinity for CTD in VLDL relative to CTD in plaques.
Figure 21:
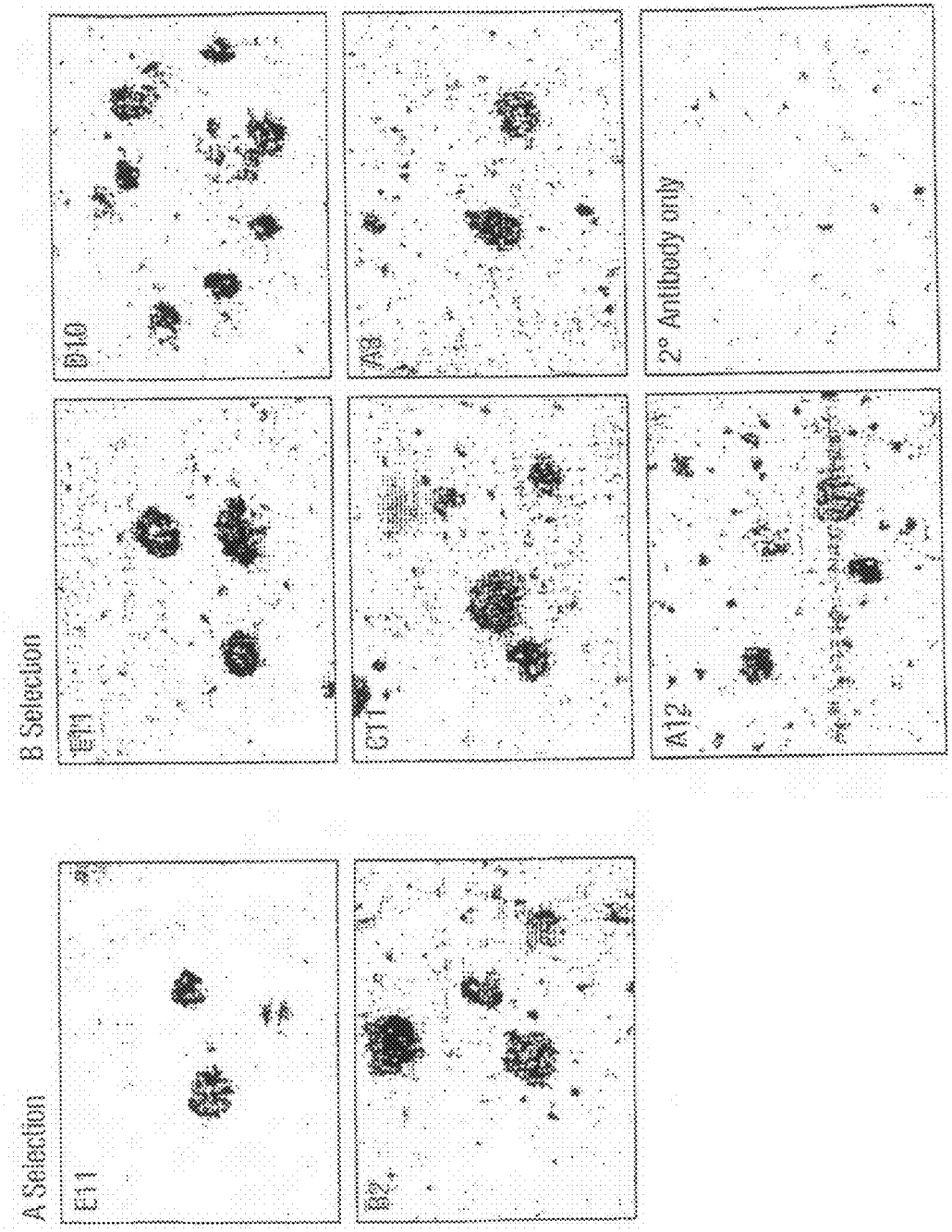
FIG. 21 shows the results of an in vitro immunohistochemistry (IHC) screen of sFab antibody clones on human AD brain sections. Several antibodies (Fab clones) from different selections were identified that bind to AD plaques by immunohistochemistry. Note that individual clones may have the same short name i.e. E11 but are from different selections and not identical. (C11=807B-M0004-H03; (selection A) E11=807A-M0027-E11; B2=807A-M0028-B02; (selection B) E11=807B-M0083-E11; D10=807B-M0079D10; A3=807B-M0004-A03; A12=807B-M0013-A12)

The 807A-M0028-B02 antibody was serially diluted and mixed with VLDL prior incubation of both APP/PS1 and human AD brain sections. No quenching of signal was observed even at the lowest antibody concentration (0.04 µg/ml). In contrast, a commercial antibody to CTD (3H1) was completely quenched already at a high concentration of antibody (5 µg/ml) (FIG. 20).

Example 32

Effect of 807A-M0028-B02 Antibodies on Phagocytic Activity of Microglial/Macrophage Cells To evaluate the effects of 807A-M0028-B02 on phagocytosis activity, a phagocytosis assay of CTD immobilized on Avidin-coated FluoSphere fluorescent microspheres (Molecular Probes) was developed.

The biotinylated CTD immobilized on 1.2 µm yellow-green latex FluoSpheres®NeutrAvidin™ labeled microspheres (Molecular Probes Europe BV, Leiden, The Netherlands) were resuspended with different concentrations of IgG converted clone 807A-M0028-B02 diluted in OPTI-MEM medium supplemented with 1% BSA (Tissue culture tested, Invitrogen AB, Sweden) and 2% ITS-X (Gibco, Invitrogen AB, Sweden) serum supplement (CM) and incubated for 30 min at +4° C.THP-1 cells ($10^6$ cells $ml^{-1}$) in CM with or without 2.0% $NaN_3$, the inhibitor of phagocytosis, were added at a ratio of 1:100 (cells:beads). To allow binding to $F_c$-receptors, cells were synchronised at +4° C. for 20 min and the cell-free beads were removed by low-speed centrifugation (200 g, 10 min, +4° C.). The cell pellets were resuspended in CM and incubated at 37° C. for 40 min in a $CO_2$-incubator. After trypsinisation, the cell suspension was taken in sterile conditions, layered over a 7.5% bovine serum albumin (BSA) cushion and centrifuged at 150×g for 10 min at +4° C., to remove non-internalised beads. The cell pellets were resuspended in 0.3 ml of 2% PFA in PBS. The results were expressed as the percent of the control, i.e. amount of phagocytic cells containing two or more beads in presence vs. in absence of antibodies, as determined by flow cytometry. A FACScan™ (Becton Dickinson, San Jose, Calif.) with an air-cooled argon laser providing an excitation at 488 nm was used. A total of 10000 events were acquired for each sample and stored in the list mode data format. The fluorescence emission was collected at 520 nm (FL1) for the phagocytosis. Data collection and analysis were performed with a Consort 30 system and LYSIS-II program. The data were analyzed, once displayed as two-parameter complexity and cell size, in the process of gating and as fluorescence (FL1) frequency distribution histogram to analyze the phagocytosis. EC50, the concentration that induced 50% increase of phagocytic activity was determined for each antibody tested using dose-responsive curves built with the percentages of phagocytic activity, versus the range of concentrations (0.01-5 µg/ml). Then, the EC50 were extrapolated from these curves and used to compare the relative efficiency of phagocytic stimulation of the antibodies. The IgG converted clone 807A-M0028-B02 demonstrated high efficiency (EC50=34±15 ng/ml) to stimulate THP-1 cells. The results thus indicate that 807A-M0028-B02 specifically directed the in vitro phagocytic uptake of CTD-bearing beads by human macrophage/microglia-like cells in a concentration-dependent fashion.

Example 33

Germ Line Correction of Clones Found in Selections Described in Example 4, Example 21 and Example 22

Of the antibodies described in Table 18, five of them (807A-M0028-B02, 807B-M0004-H03, 807B-M0009-F06, 807B-M0004-A03 and 807B-M0079-D10) have been investigated further. Somatic mutations in the variable part of the light chains of these antibodies have been found in all clones. Some of the clones also contained mutations in the constant part of the light chain (Table 21). Sequence alignments with genomic and known germline sequences have been performed, and the correct amino acids have been identified (indicated in bold in Table 19 and Table 20). The VL chains of the corrected clones are described in Table 19, and the constant parts of the IgG are described in Table 20.

To ensure that the IgG molecules are germline, the somatic mutations are corrected at the DNA level in the five antibodies, and all five germline-corrected IgG1 s were expressed (transiently in HEK 293T cells). Comparative binding analysis was performed in Biacore (Example 34), CTD-ELISA and IHC to ensure that the germline-corrected antibodies are still functional. The results are summarised in Table 23.

Example 34

Biacore Analysis of Germ Line Corrected IgGs

The germline-corrected clones described in Tables 19 and 20 were analysed in Biacore. The analysis was performed by running the IgGs at different concentrations over a surface with coated bCTD. A surface with a biotinylated control IgG was used as a negative surface.

Biacore analysis of clones 807A-M0028-B02, 807A-M0028-B02.1 and 807A-M0028-B02.2 showed that the three IgG molecules bind to bCTD with similar kinetics (similar on-rate and off-rate). The affinity of the IgG is not significantly altered. The same results were obtained when comparing 807B-M0004-A03 with 807B-M0004-A03.1.

Biacore analysis of 807B-M0004-H03 and 807B-M0004-H03.1 indicated that 807B-M0004-H03.1 binds with a different kinetic to the parental clone. However, this did not influence the affinity value significantly. The clone 807B-M0009-F06.1 had lost its binding capacity to bCTD as shown in CTD-ELISA and Biacore analysis and CTD-ELISA.

Example 35

Binding of Antibodies to ApoE-CTD by ELISA

Figure 22:
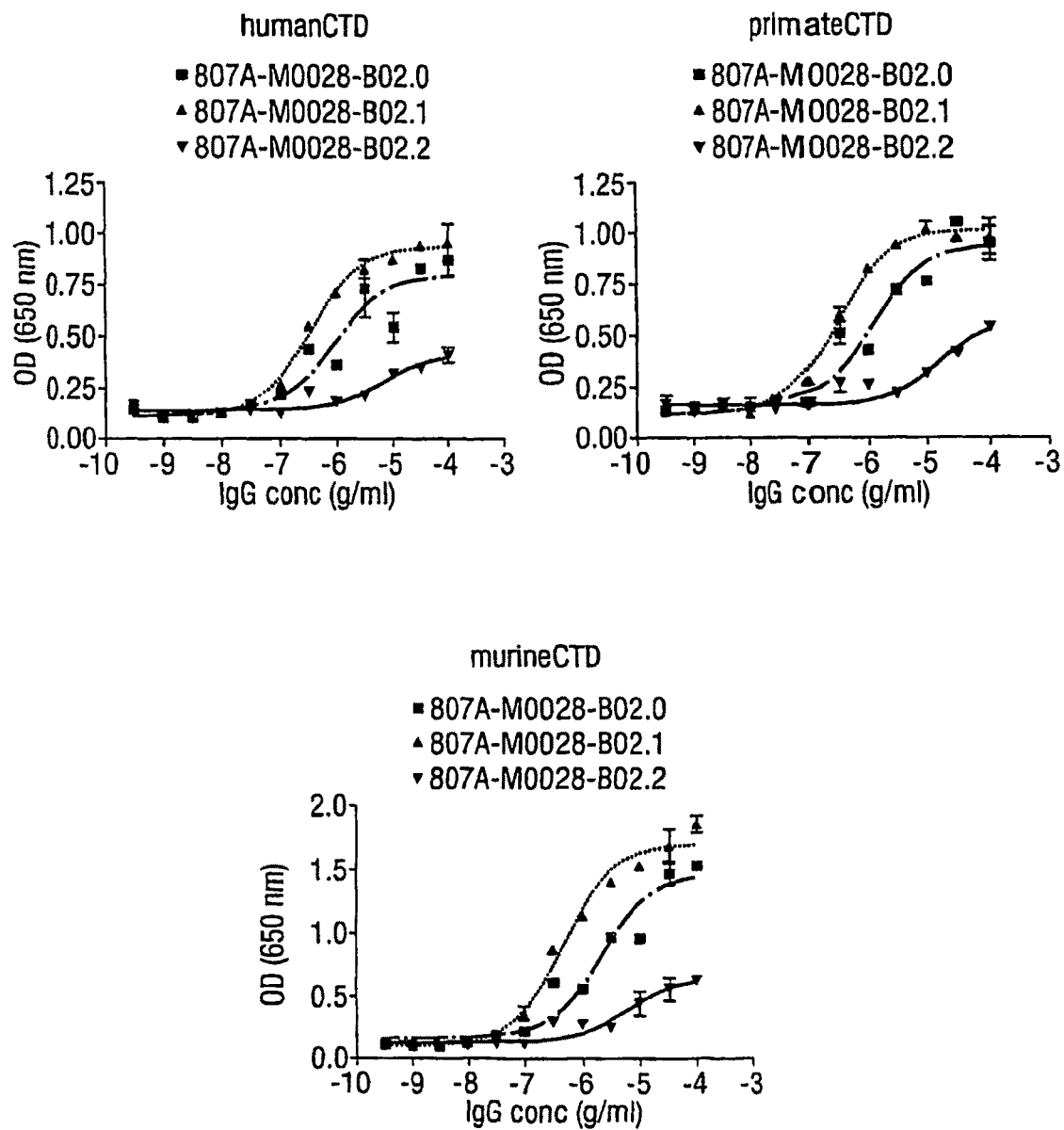
FIG. 22 shows representative results (duplicate samples) of the concentration dependent binding of 807A-M0028-B02, 807A-M0028-B02.1 and 807A-M0028-B02.2 to human, primate and murine ApoE-CTD.

Antibodies were screened for ApoE-CTD binding capacity using a coated ApoE-CTD ELISA. Human, marmoset or murine ApoE-CTD was coated on a microtiter plate followed by incubation with test antibodies. After this, the amount of antibody bound was determined by detection with secondary HRP-antibody and tetramethylbenzidine (TMB) substrate. ApoE-CTD binding gives a high signal measured as optical density (OD) in the ELISA. Binding of 807A-M0028-B02, 807A-M0028-B02.1 and 807A-M0028-B02.2 are exemplified in FIG. 22. Results are disclosed in Table 22.

Example 36

Binding of Antibodies to Human Lipoproteins

Figure 23:
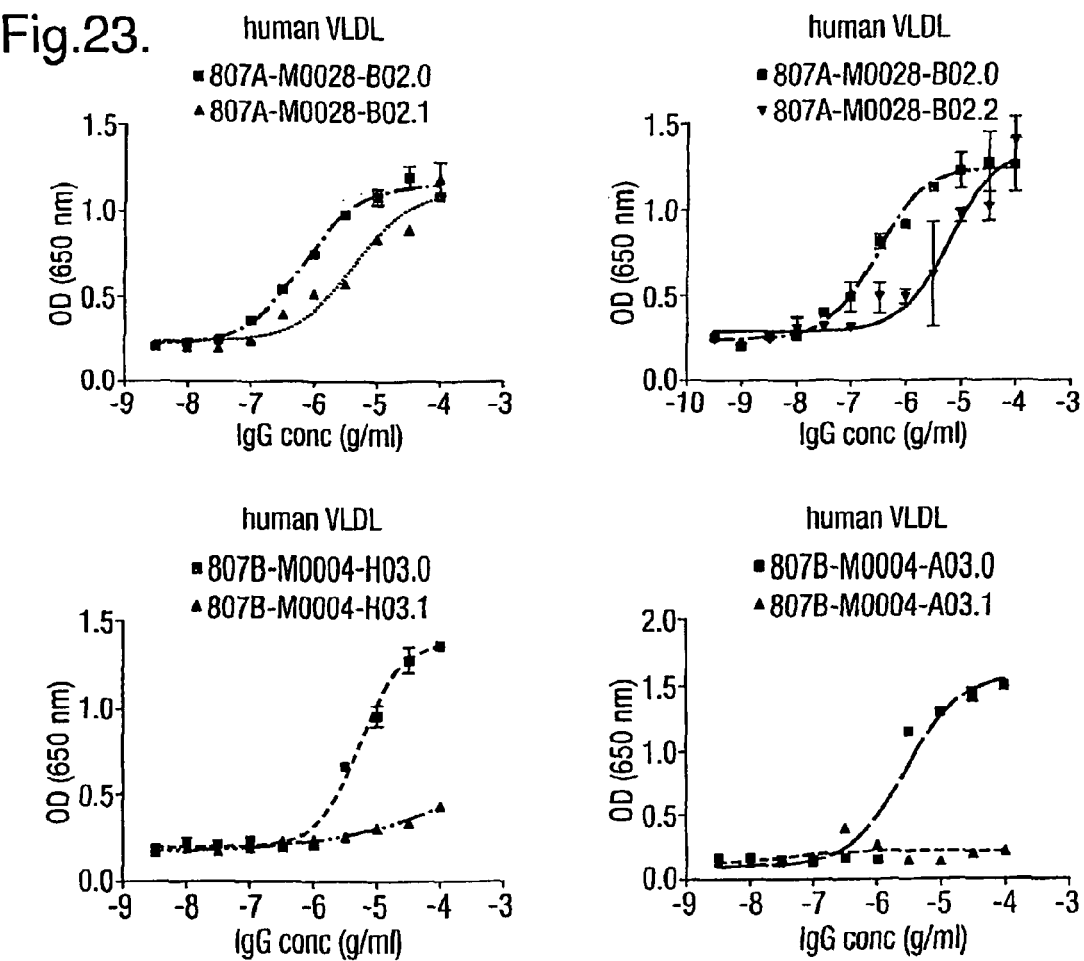
FIG. 23 shows representative results (duplicate samples) of the concentration dependent binding of 807A-M0028-B02, 807A-M0028-B02.1, 807A-M0028-B02.2, 807B-M0004-H03, 807B-M0004-H03.1, 807B-M0004-A03 and 807B-M0004-A03.1 to human VLDL.

Antibodies were screened for lipoprotein binding capacity using a coated VLDL ELISA. Human VLDL was coated on a microtiter plate followed by incubation with test antibodies. After this, the amount of antibody bound was determined by detection with secondary IMP-antibody and tetramethylbenzidine (TMB) substrate. VLDL binding gives a high signal measured as optical density (OD) in the ELISA. Binding of 807A-M0028-B02, 807A-M0028-B02.1, 807A-M0028-B02.2, 807B-M0004-H03.0, 807B-M0004-H03.1, 807B-M0004-A03 and 807B-M0004-A03.1 are exemplified in FIG. 23. Results are disclosed in Table 22.

Example 37

Figure 24A:
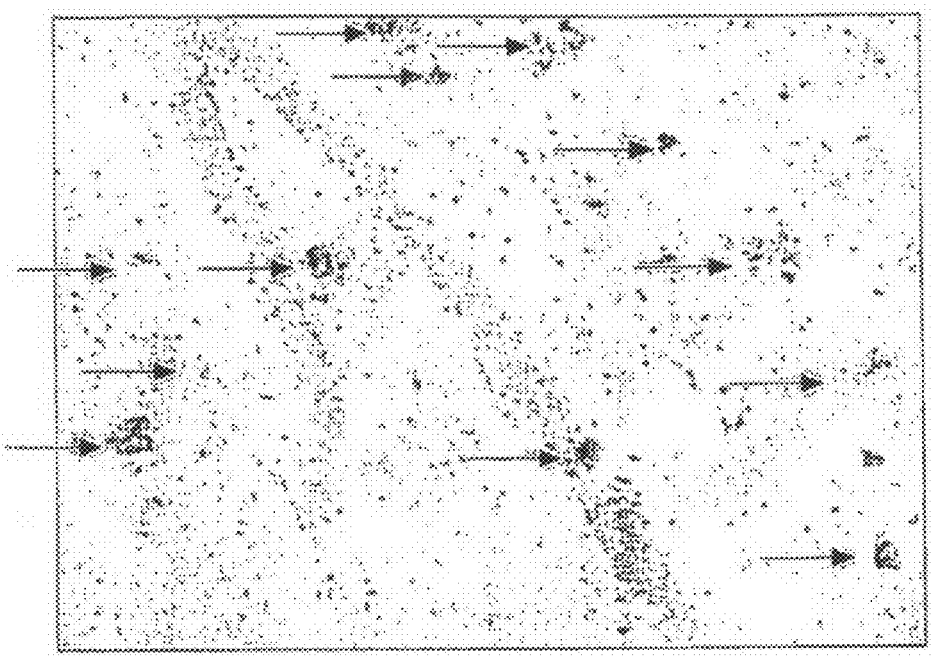
FIG. 24 shows the detection of 807A-M0028-B02 plaque binding in brain tissue sections from APP/PS1 mouse.
Figure 24B:
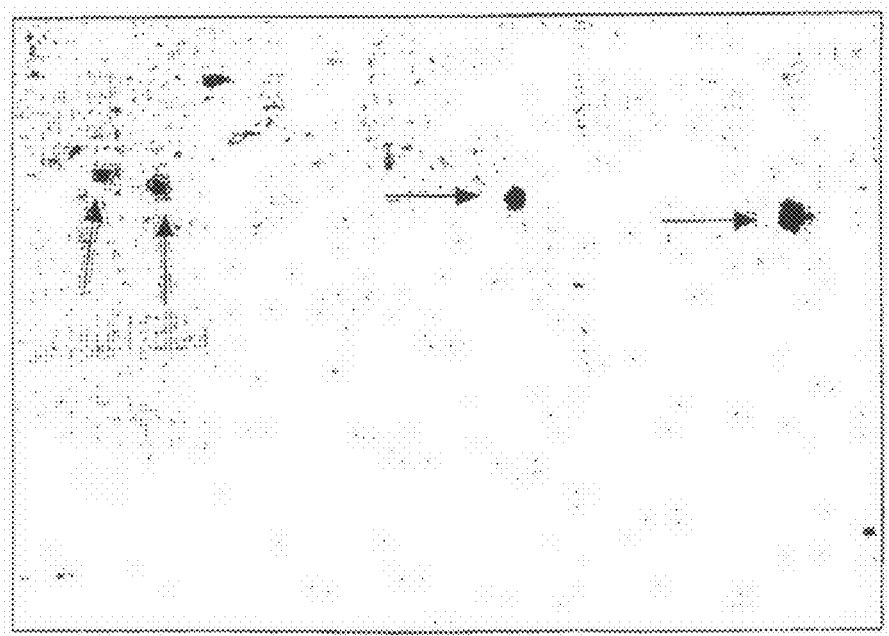

In vivo Binding of 807A-M0028-B02, 807B-M0004H03, 807B-M0004-A03, 807B-M0079-D10, 807B-M0009-F06 to Mouse Cerebral Plaques and in vitro Binding of Fab Clones to Human AD Cerebral Plaques In vivo binding of 807A-M0028-B02, B807B-M0004H03, 807B-M0004-A03, 807B-M0079-D10 and 807B-M0009-F06 to cerebral plaques (immunodecoration) was demonstrated by i.p. or i.v. injections into APP/PS1 transgenic mice (FIGS. 24 and 25). Immunodecoration was observed already two days after a single dose administration of 10 mg/kg of 807A-M0028-B02. Binding of 807A-M0028-B02, B807B-M0004H03, 807B-M0004-A03, 807B-M0079-D10 and 807B-M0009-F06 was only observed on plaques while no staining of astrocytes or any other brain structure was detected (FIGS. 24 and 25). It was demonstrated that a substantial number of plaques were immunodecorated with respective clones by comparing the total plaque burden in each mouse that was determined by staining with a monoclonal antibody to Aβ (6E10) on adjacent sections.

In vitro binding of affinity maturated clones to amyloid plaques in human AD brain sections was also demonstrated by Immunohistochemistry (FIG. 25)

In vitro binding of different wild type clones in human AD plaques is visualised in FIG. 26.

Example 38

Affinity Maturation of 807A-M0028-B02, 807B-M0004H03, 807B-M0004-A03, 807B-M0079-D10, 807B-M0009-F06 by VH-CDR3 Spiking Spiking mutagenesis was used to introduce low level mutations over the full length of the VH-CDR3 of each of 807A-M0028-B02, 807B-M0004H03, 807B-M0004-A03, 807B-M0079-D10 and 807B-M0009-F06 in the context of the original wild-type residues (see FIG. 29). PCR was carried out using an oligonucleotide carrying a region of spiked diversity over the length of the VH-CDR3 sequence of each antibody bracketed by regions of homology with the target V gene in the FR3 and FR4 regions together with a specific primer homologous to the FR1 region capable of annealing to the 5' end of the target V gene.

For antibodies 807A-M0028-B02, 807B-M0009-F06 and 807B-M0004-H03, diversification of the VH-CDR3 was realized through a one step PCR amplification. This PCR was performed using a 5' primer complementary to the light chain constant region and the 3' specific spiked oligonucleotides. The PCRs were then performed in a volume of 50 µl using the advantage 2 PCR enzyme system (Clontech) and 10 pmoles of each primer for 25 cycles (1 min at 95° C., 1 min at 60° C., and 2 min at 68° C.). A primer concentration of 100nM was chosen in order to cover the entire diversity carried by the spiked oligonucleotides. 100 to 200 reactions were needed to obtain ~6 µg of PCR products. All products were purified using the GFX purification it (Amersham).

The resulting PCR products of 730 bp contain an internal XbaI site and an BstEII site, incorporated in the oligonucleotides. These sites were used to clone the products into a display vector.

Diversification of the VH CDR3 of 807B-M0004-A03 and 807B-M0079-D10 was realized in two steps: after primary amplification as described above, the resulting PCR products of 730 bp were re-amplified with a combination of a 5' end nested forward primer, appended with a SfiI site, and a 3' end Nhe1-tagged CH1 reverse primer. The PCRs were then performed in a volume of 50 µl using the advantage 2 PCR enzyme system (Clontech) and 10 pmoles of each primer for 20 cycles (1 min at 95° C., 3 min at 68° C.); 100 to 200 reactions were needed to obtain ~6 µg of PCR products. The number of cycles was kept quite low (20 cycles) in order to maintain maximal diversity, introduced in the first PCR step. To ensure again maximal diversity, for each reaction, 50 ng of the first PCR product was used as template to initiate the second PCR reaction. All products were purified using the GFX purification kit (Amersham).

The PCR products and vector backbones were digested using 50 U/µg DNA of either XbaI and BstEII (for 807A-M0028-B02, 807B-M0009-F06 and 807B-M0004-H03) or SfiI and NheI (for 807B-M0004-A03 and 807B-M0079-D10).

The resulting cleaved products (both vectors and PCR fragments) were gel purified, 1.6 µg of each DNA fragment was ligated into 10 µg of similarly cut phagemid vector backbone using $T_4$ DNA ligase (NEB) and the ligation mixture for each spiked library was introduced into *E. coli* TG1 cells by electroporation.

Phagemid particles were rescued from the libraries using helper phage M13-KO7 (Marks et al., (J. Mol. Biol. 222, 581 (1991)) using enough bacteria from each library for inoculation in order to represent each clone at least once.

The diversity in the VH-CDR3 of each library was evaluated by sequencing. 96 isolates were randomly picked for each library and the VH-CDR3 regions were sequenced and compared to the reference wild type VH-CDR3 sequences.

For clones of 807B-M0079-D10 and 807B-M0004-A03 the full VH sequence was determined and compared to the VH reference regions outside VH-CDR3.

A selection procedure consisting of two rounds of selection was used to preferentially enrich the higher affinity clones in the library over the lower affinity clones. The first round of affinity selection was carried out using a reduced antigen concentration relative to the concentration used to select the wild-type antibody. The optimum reduced antibody concentration was determined empirically using the wild-type antibody and a control antibody. The second round was performed at a further reduced antigen concentration in the presence of competing soluble Fab or IgG. The selection conditions used are detailed in Table 3.

To determine if enrichment of antigen positive clones had occurred, 46 randomly picked clones from before and after the first round of selection for each antibody to be matured were tested in an antigen ELISA. In all cases, enrichment of antigen positive clones after just one round of selection was observed.

After selection, the geneIII stump was removed from the vector to allow soluble Fab expression. 200 clones were randomly picked, screened by ELISA and their heavy chains sequenced. The Dyax WEBPHAGE database was used to link ELISA data to the respective sequences. The VH-CDR3 sequences of the clones found to be positive in the screening assay (OD signal=3× background) were analysed further.

For the clones 807B-M0079-D10 and 807B-M0004-AO3 the full VH region was amplified and cloned and so the full VH sequence was obtained and compared to the VH reference sequence in order to check for any mutations outside VH CDR3. Clones containing mutations in framework regions were discarded but clones with mutations in the VH-CDR1-CDR2 were kept.

The results of amino acid frequency analysis of selected clones are presented in Tables 24 to 30. In the VH-CDR3, some amino acid positions are very conserved whilst others are frequently mutated.

Biacore screening was used to select five CDR3-mutated Fabs based on off rate or $K_D$. CDR3-mutated Fabs were expressed in bacteria. Periplasmic extracts were prepared, and screened in Biacore. The best clones were selected based on either off-rates or $K_D$ for binding to hCTD or a peptide as shown in Table 4.

The biotinylated peptides or human CTD were coated on streptavidin chips. Periplasmic extracts from 10 ml cultures were diluted ½ in HBS+0.1% BSA. Samples were injected at 30 µl/min for 3 minutes using the kinject program. Following a 3 minute dissociation, any remaining sample was stripped from chip surface. Off rates were measured on a time window of 1 min (between 10-70s). These data are presented in Tables 31 to 35.

On rates can be calculated from Biacore curves if both $k_{off}$ and the Fab concentration are known. Under conditions of full Mass Transfer Limitation (MLT) like those encountered when working with very high density chips and low flow rates, the Biacore signal depends only on the concentration of the analyte run over the chip surface. Fab concentrations in crude samples can be determined from a standard curve obtained by running different concentrations of a purified Fab on a high density Protein A chip. Using the Fab concentrations obtained that way and the $k_{off}$ values, we calculated $k_{on}$ data from the Biacore curves. The equilibrium dissociation constant $K_D$ was obtained from $k_{off}/k_{on}$. These data are presented in Tables 31 to 35. Note that the 807B-M0079-D10 does not bind to Protein A. Therefore, only $k_{off}$ values are presented for this clone.

Five variants were successfully selected for 807B-M0004-A03, 807B-M0004-H03, 807B-M0009-F06 and 807A-M0028-B02. The selected variants are identified in Table 36. No clones with significantly improved $K_{off}$ were found for 807B-M0079-D10 (no $K_D$ data available for this clone).

The selected Fabs were produced in *E. coli* and purified from periplasmic extracts by Immobilized Metal Affinity Chromatography. The quality of the preparations was checked on reducing and non reducing SDS-PAGE.

The purified Fabs were used to accurately determine the equilibrium dissociation constant $K_D$.

Biotinylated peptides or human CTD were coated on streptavidin chips. Experiments were performed in HBS running buffer. Purified Fabs were diluted to 200 nM and serial ½ dilutions to 12.5 nM were made and run in duplicates. For association, samples were injected at 30-40 μl/min using the kinject program. Following a 3 minute dissociation, any remaining sample was stripped from the chip surface. Sensorgrams were analyzed using the simultaneous ka/kd fitting program in the BIAevaluation software 3.1. The data are summarized in Table 36. The best clones selected from Biacore screening exhibit an affinity 2 to 3-fold higher than the original clone for 807B-M0004-A03, 807B-M0009-F06 and 807A-M0028-B02. In the case of 807B-M0004-H03, the Biacore signals did not allow an accurate comparison of the different clones.

Purified Fabs were also tested by immunohistochemistry. Table 37 shows the names of the chosen clones together with the wild type clones and indicates whether they stain plaques in immunohistochemistry.

Example 39

Light Chain Shuffling of the Antibody Variants Selected from Example 38

As a starting point for light chain shuffling (cycle 2 in FIG. 29), the heavy chains corresponding to the VH-CDR3 improved variants from Example 38 (cycle 1 in FIG. 29) were used together with wild-type (WT) clones.

The WT clone 807B-M0009-F06 was not included because the affinity of this clone was significantly lower compared to the selected variants from cycle 1. For antibody 807B-M0079-D10, as no improved affinity variant was found in cycle 1, the LC shuffling was performed on the WT clone alone.

In this Example, the non-affinity matured antibodies have been designated as the wild type (WT) clone and the selected variants from cycle 1 as parental clones.

The selected heavy chain variants from cycle 1 were cloned into the FAB310 vector backbone containing a repertoire of 5 to 6 heaving chains (HC) shuffled with approximately $10^8$ light chains (LC) to create combinatorial diversity.

For every clone, a Qiagen DNA preparation was performed on a TG1 culture. 10 μg of DNA was then cleaved using SfiI and NotI restriction enzymes, generating a heavy chain fragment size of 650 bp. The FAB310 vector backbone was similarly cut.

The resulting cleaved products (both vector and fragments) were gel purified and, for each library, the different heavy chain variant fragments were pooled in equal amounts and 3 μg of the pooled fragments were ligated with 6 μg of cleaved phagemid vector backbone using $T_4$ DNA ligase (NEB). Desalted ligation mixtures for each library were introduced into *E. coli* TG1 cells by electroporation.

The library sizes achieved were such that each heavy chain variant was combined with at least one copy of each member of the light chain repertoire.

Heavy chain sequences were determined for 50 isolates, randomly picked from each library.

The light chain sequences of 48 isolates randomly picked from the 807A-M0028-B02-derived unselected library and 48 from the 807B-M0009-F06-derived unselected library. 63 unique functional light chains were obtained.

Phagemid particles were rescued with helper phage M13-KO7 (Marks et al. J. Mol. Biol. 222, 581 (1991)) using enough bacteria from each library for inoculation in order to represent each clone at least once.

The 5 light chained shuffled libraries were selected for improved affinity variants. Prior to selections the libraries were depleted for streptavidin binding antibodies by pre-incubating the libraries with 100 μl streptavidin paramagnetic beads in 1 ml % MPBS. For each library three concentrations of antigen were used to determine the optimal concentration for the second round of selection (Table 5). The incubation time of the phage with bead-target complex was reduced to 0.5 hour and 11 cycles of programmed washing was used in the Kingfisher device. After selection the bound phage were eluted and infected with *E. coli* (TG1 OD of 0.5) and the liquid amplified overnight at 30° C. with shaking at 250 rpm in 25 ml 2×TY/Ampicillin (100 ug/ml) Glucose (2% w/v). Cells were concentrated and glycerol stocks were made in order to perform the round 2 selection.

Unselected library and output was titrated to get single colonies for picking and screening. From the unselected library and output library 47 colonies were picked and screened in a phage ELISA (Coated antigen 0.5 μg/ml for all antigens via b-BSA plus streptavidin).

All selection arms resulted in the enrichment of antigen binding clones. Based on these results an antigen concentration was chosen for the second round of selection.

The conditions for the round 2 selection were chosen to be more stringent and were designed to select for improved (faster) $k_{on}$ and improved (slower) $k_{off}$. Three strategies were used as outlined in Table 6: Strategy I—further lowering of antigen concentrations; strategy II—further lowering of antigen concentration and reduced incubation time with antigen ($k_{on}$ selection); strategy III—further lowering of antigen concentration and increased stringency washing ($k_{off}$ selection). Selection was performed in a KingFisher automated device and an input of approximately $10^{12}$ phages were used. Prior to selections the libraries were depleted for streptavidin binding antibodies as described above. After selection the bound phage were eluted and used to infect *E. coli* as described previously. Cells were concentrated and glycerol stocks were made.

The output of round 2 was pre-screened in ELISA to determine the percentage of antigen binding clones. Sequence analysis of a limited number of clones was performed to determine if any particular clone was dominating selection and if there are any dominant light chain families in the selected clones.

Each of the round 2 phage outputs (15 in total) were re-cloned in batch in order to produce soluble Fabs. This was achieved through the removal of the geneIII stump from the vector.

200 clones were randomly picked and screened by ELISA for their binding to their respective antigen. Antibody sequences were determined for the positive hits only. The storage and initial sequence analysis was conducted via Dyax WEBPHAGE database.

For libraries 807B-M0004-A03, 807B-M079-D10 and 807A-M0004-H03, antibodies enriched between 2 to 8 times were selected. For libraries 807A-M0028-B02 and 807B-M009-F06, all clones were taken since number of unique clones was low. The light and heavy chain sequences from all ELISA positive and unique hits are shown in Tables 38 to 42.

After Biacore analysis of the potential affinity matured binders, a few were found to have a higher affinity. Only libraries 807B-M0004-A03, 807A-M0028-B02 and 807B-M004-H03 gave affinity matured antibodies with a higher affinity than the WT and parental clones. The light chain sequence of those selected clones was aligned to the germline. Interestingly, the same amino acid positions seem to be diversified among all the selected clones belonging to the same germline. The same amino acid positions seem to be diversified among all the selected clones belonging to the same germline.

For library 807B-M0004-A03, although clones M148E08 and M150E03 have exactly the same heavy chain sequence and light chains which differ by two amino acids, clone M150E03 has a 3.2× improved affinity compared to M148E08, suggesting that only two amino acids located in FR1 are responsible for this improvement.

For libraries 807B-M0028-B02 and 807B-M0004-A03, most of the diversification observed in the CDR and FR was reversion to the germline sequence compared to wild-type.

Only a few conservative variations were observed in FR3 of 807A-M0028 B02 library-derived clones.

For Biacore analysis, all clone variants were grown in small cultures (typically 10 ml), periplasmic extracts (PE) were prepared and the Fab concentration in the PEs was measured by running the samples on a Protein A/G chip. The PEs were then diluted to the same Fab concentration (25-50 nM) and run over a target-coated chip (peptide 4, 8, 9 or CTD). The best clones were identified based either on the amplitude of the association and dissociation phases (807A-M0028-B02, 807B-M0004-A03, 807B-M0009-F06) or on the value of the Biacore signal at equilibrium (807B-M0004-H03). Clones derived from 807B-M0079-D10 do not bind to Protein A/G chips and were thus ranked only based on their off-rates Clones derived from 807B-M0004-H03 were ranked based on the value of the Biacore signal at equilibrium which reflects the equilibrium dissociation constant $K_D$: the higher the Biacore signal at equilibrium, the better the affinity.

Clones derived from 807B-M0079-D10 were ranked based only on $k_{off}$.

Four and five variants were selected for 807A-M0028-B02 and 807B-M0004-A03, respectively. None of the isolated 807B-M0009-F06 variants seemed to exhibit an affinity higher than the best variants obtained from CDR3 spiking. For 807B-M0004-H03, two variants were selected based on the value of the Biacore signal at equilibrium. None of the 807B-M0079-D10 variants could be selected based on off-rate analysis.

The selected clones selected were produced in *E. coli* and purified from periplasmic extracts. This material was used to measure accurately the equilibrium dissociation constant $K_D$ in Biacore. The data are summarized in Table 7. The best clones isolated from light chain shuffling exhibit an affinity ~5-times better than the corresponding original wild type clones or the best clones isolated from CDR3 spiking.

The clones selected following light chain shuffling are shown in Tables 43 and 44.

TABLE 1

Off-rate measurement of sFabs originating from selections on fibrils and ur-bCTD

| Initial name | HCDR3 | koff ($e^{-3}s^{-1}$) | RU |
|---|---|---|---|
| 807A-M0027-C11 | AVGYGDYGDY | 13, 30 | 79, 2 |
| 807A-M0027-H05 | DFFTSYFDH | 16, 90 | 182, 0 |
| 807A-M0026-F11 | DLWFGEWDY | 28, 10 | 165, 8 |
| 807A-M0026-H09 | DLWFGEWDY | 25, 10 | 138, 0 |
| 807A-M0027-E12 | DLWFGEWDY | 8, 95 | 419, 9 |
| 807A-M0028-B12 | DLWFGEWDY | 18, 80 | 335, 5 |
| 807A-M0029-G10 | DLWFGEWDY | 23, 80 | 212, 0 |
| 807A-M0027-G01 | DRGVSLLGAFDI | 30, 00 | 231, 3 |
| 807A-M0028-A07 | ESIAVAGVDY | 53, 60 | 367, 0 |
| 807A-M0026-F05 | GRGNYDFWSAGYYYYYMDV | > | 158, 0 |
| 807A-M0028-G07 | QEVWQWPAQFDS | 35, 30 | 131, 7 |
| 807A-M0027-E11 | SLDLDY | 40, 50 | 412, 3 |
| 807A-M0026-G08 | SSGIYYGYYMDV | 38, 80 | 594, 1 |
| 807A-M0028-B02 | SVLLDY | 28, 00 | 454, 6 |
| 807A-M0028-B06 | DRGVSLLGAFDI | 13, 50 | 100, 3 |
| 807A-M0027-D05 | EPIWGYYYYGMDV | 9, 16 | 377, 8 |

TABLE 2

Comparison of Fab and IgG binding on CTD-coated chip for the candidate clones 807A-M0026-F05 (26F5), 807A-M0027-E11 (27E11) and 807A-M0028-B02 (28B2)

| Clone | Format | Surface | ka (1/Ms) e5 | kd (1/s) e−3 | KD (nM) |
|---|---|---|---|---|---|
| 27E11 | Fab | HD | 9.5 | 45.5 | 47.8 ± 8.1 |
|  | IgG | HD | 7.5 | 7.4* | 9.9 ± 4.1 |
|  |  |  | 8.1 | 2.1# | 2.6 ± 1.1 |
|  |  | LD | 10.1 | 7.7* | 7.6 ± 3.2 |
|  |  |  | 11.1 | 2.1# | 1.9 ± 0.8 |
| 28B2 | Fab | HD | 2.5 | 44.2 | 179 ± 5.7 |
|  | IgG | HD | 3.7 | 4.0 | 10.8 ± 2.4 |
|  |  | LD | 5.2 | 6.4 | 12.3 ± 3.7 |
| 26F5 | Fab | HD | n.f. | n.f. | n.d. |
|  | IgG | HD | 0.2 | 42 | 2103 ± 785 |
|  |  | LD | n.f. | n.f. | n.d. |

*kd measured directly after injection stop.
kd measured ~50 sec after injection stop.
n.f. no fit
n.d. not determined

TABLE 3

| Antibody | Round 1 selection | Round 2 selection |
|---|---|---|
| 807A-M0028-B02 | 3 nM bCTD or 1 tube of fibrils | 0.3 nM bCTD + 5 µM wt Fab or 0.3 nM IgG1 |
| 807B-M0004-A03 | 5.7 nM p4 | 0.057 nM p4 + 5 µM wt Fab or 0.01 nM IgG1 |
| 807B-M0004-H03 | 5.7 nM p4 | 0.57 nM p4 + 5 µM wt Fab or 0.3 nM IgG1 |
| 807B-M0009-F06 | 5.7 nM p9 | 0.057 nM p9 + 5 µM wt Fab or 0.3 nM IgG1 |
| 807B-M0079-D10 | 5.7 nM p8 | 0.057 nM p8 + 5 µM wt Fab or 0.3 nM IgG1 |

TABLE 4

| Original clone | $K_D$ (nM) | Number of clones screened |
|---|---|---|
| 807A-M0028-B02 | 150 (on hCDT) | 72 |
| 807B-M0004-A03 | 98 (on p4) | 39 |
| 807B-M0004-H03 | 200 (on p4) | 54 |
| 807B-M0009-F06 | 172 (on p9) | 24 |
| 807B-M0079-D10 | 26 (on p8) | 33 |

TABLE 5

Percentage of antigen binding clones retrieved from the round 1 selections at decreasing antigen concentrations

| Library | Round | Antigen | Ag concentrations | | |
|---|---|---|---|---|---|
| A03 Hit rate % | 1 | P4 | 57 nM, | 5.7 nM, | 0.57 nM |
| Input | | | 2% | 2% | 2% |
| Output | | | 62% | 51% | 83% |
| H03 Hit rate % | 1 | P4 | 570 nM, | 57 nM, | 5.7 nM |
| Input | | | 2% | 0% | 0% |
| Output | | | 72% | 72% | 81% |
| F06 Hit rate % | 1 | P9 | 57 nM, | 5.7 nM, | 0.57 nM |
| Input | | | 0% | 0% | 0% |
| Output | | | 6% | 4% | 2% |
| D10 Hit rate % | 1 | P8 | 57 nM, | 5.7 nM, | 0.57 nM |
| Input | | | 0% | 0% | 0% |
| Output | | | 34% | 45% | 38% |
| B2 Hit rate % | 1 | CTD | 300 nM, | 30 nM, | 3 nM |
| Input | | | 2% | 2% | 2% |
| Output | | | 28% | 21% | 17% |

TABLE 6

Conditions used for the second round selection strategies

| Strategy | Library | Round | Antigen | Ag conc (nM) | Incubation time (mins) | Washing |
|---|---|---|---|---|---|---|
| I | A3 | 2 | Pep-4 | 0.057 | 30 | 11 × 5 mins |
| I | H3 | 2 | Pep-4 | 5.7 | 30 | 11 × 5 mins |
| I | D10 | 2 | Pep-8 | 0.057 | 30 | 11 × 5 mins |
| I | B2 | 2 | b-CTD | 10 | 30 | 11 × 5 mins |
| I | F6 | 2 | Pep-9 | 5.7 | 30 | 11 × 5 mins |
| II | A3 | 2 | Pep-4 | 0.57 | 3 | 11 × 5 mins |
| II | H3 | 2 | Pep-4 | 5.7 | 3 | 11 × 5 mins |
| II | D10 | 2 | Pep-8 | 0.57 | 3 | 11 × 5 mins |
| II | B2 | 2 | b-CTD | 30 | 3 | 11 × 5 mins |
| II | F6 | 2 | Pep-9 | 5.7 | 3 | 11 × 5 mins |
| III | A3 | 2 | Pep-4 | 0.57 | 30 | 3 × 5 mins + 3 × 45 mins + 3 × 5 mins |
| III | H3 | 2 | Pep-4 | 5.7 | 30 | 3 × 5 mins + 3 × 45 mins + 3 × 5 mins |
| III | D10 | 2 | Pep-8 | 0.57 | 30 | 3 × 5 mins + 3 × 45 mins + 3 × 5 mins |
| III | B2 | 2 | b-CTD | 30 | 30 | 3 × 5 mins + 3 × 45 mins + 3 × 5 mins |
| III | F6 | 2 | Pep-9 | 5.7 | 30 | 3 × 5 mins + 3 × 45 mins + 3 × 5 mins |

TABLE 7

| Clone name | $k_{on}$ (1/Ms) | $k_{off}$ (1/s) | $K_D$ (nM) | |
|---|---|---|---|---|
| M0004A03 WT | 4.19E+05 | 3.31E−02 | 79 | * |
| M0004A03-M0148-E08 | 9.51E+05 | 4.85E−02 | 51 | * |
| M0004A03-M0149-F02 | 6.51E+05 | 2.41E−02 | 37 | * |
| M0004A03-M0149-G11 | 4.12E+05 | 1.73E−02 | 42 | * |
| M0004A03-M0150-E03 | 6.08E+05 | 9.89E−03 | 16 | * |
| M0004A03-M0151-D09 | 5.35E+05 | 1.61E−02 | 30 | * |

TABLE 7-continued

| Clone name | $k_{on}$ (1/Ms) | $k_{off}$ (1/s) | $K_D$ (nM) | |
|---|---|---|---|---|
| M0028B02-M0168-D10 | 6.97E+04 | 2.97E−03 | 43 | * |
| M0028B02-M0169-F03 | 1.73E+05 | 1.78E−03 | 10 | * |
| M0028B02-M0171-E03 | 1.02E+05 | 2.61E−03 | 26 | * |
| M0028B02-M0171-G02 | 8.99E+04 | 4.55E−03 | 51 | * |

* Kinetic analysis, 1:1 model

TABLE 8

Description of SEQ ID NOS: 21-164 and 171-206

| Antibody Name | VH-CDR1 | VH-CDR2 | VH-CDR3 | VH | VL-CDR1 | VL-CDR2 |
|---|---|---|---|---|---|---|
| 807A-M0027-E11 | SEQ ID NO: 21 | SEQ ID NO: 22 | SEQ ID NO: 23 | SEQ ID NO: 39 | SEQ ID NO: 30 | SEQ ID NO: 31 |
| 807A-M0028-B02 | SEQ ID NO: 24 | SEQ ID NO: 25 | SEQ ID NO: 26 | SEQ ID NO: 40 | SEQ ID NO: 33 | SEQ ID NO: 34 |
| 807A-M0026-F05 | SEQ ID NO: 27 | SEQ ID NO: 28 | SEQ ID NO: 29 | SEQ ID NO: 41 | SEQ ID NO: 36 | SEQ ID NO: 37 |
| 807B-M0001-B07 | SEQ ID NO: 45 | SEQ ID NO: 46 | SEQ ID NO: 47 | SEQ ID NO: 135 | SEQ ID NO: 90 | SEQ ID NO: 91 |
| 807B-M0004-A03 | SEQ ID NO: 48 | SEQ ID NO: 49 | SEQ ID NO: 50 | SEQ ID NO: 136 | SEQ ID NO: 93 | SEQ ID NO: 94 |
| 807B-M0004-A05 | SEQ ID NO: 51 | SEQ ID NO: 52 | SEQ ID NO: 53 | SEQ ID NO: 137 | SEQ ID NO: 96 | SEQ ID NO: 97 |
| 807B-M0004-C04 | SEQ ID NO: 54 | SEQ ID NO: 55 | SEQ ID NO: 56 | SEQ ID NO: 138 | SEQ ID NO: 99 | SEQ ID NO: 100 |
| 807B-M0004-C05 | SEQ ID NO: 57 | SEQ ID NO: 58 | SEQ ID NO: 59 | SEQ ID NO: 139 | SEQ ID NO: 102 | SEQ ID NO: 103 |
| 807B-M0004-F06 | SEQ ID NO: 60 | SEQ ID NO: 61 | SEQ ID NO: 62 | SEQ ID NO: 140 | SEQ ID NO: 105 | SEQ ID NO: 106 |
| 807B-M0004-F10 | SEQ ID NO: 63 | SEQ ID NO: 64 | SEQ ID NO: 65 | SEQ ID NO: 141 | SEQ ID NO: 108 | SEQ ID NO: 109 |
| 807B-M0004-H03 | SEQ ID NO: 66 | SEQ ID NO: 67 | SEQ ID NO: 68 | SEQ ID NO: 142 | SEQ ID NO: 111 | SEQ ID NO: 112 |
| 807B-M0009-C03 | SEQ ID NO: 69 | SEQ ID NO: 70 | SEQ ID NO: 71 | SEQ ID NO: 143 | SEQ ID NO: 114 | SEQ ID NO: 115 |
| 807B-M0009-F06 | SEQ ID NO: 72 | SEQ ID NO: 73 | SEQ ID NO: 74 | SEQ ID NO: 144 | SEQ ID NO: 117 | SEQ ID NO: 118 |
| 807B-M0013-A12 | SEQ ID NO: 75 | SEQ ID NO: 76 | SEQ ID NO: 77 | SEQ ID NO: 145 | SEQ ID NO: 120 | SEQ ID NO: 121 |
| 807B-M0079-D10 | SEQ ID NO: 78 | SEQ ID NO: 79 | SEQ ID NO: 80 | SEQ ID NO: 146 | SEQ ID NO: 123 | SEQ ID NO: 124 |
| 807B-M0081-F12 | SEQ ID NO: 81 | SEQ ID NO: 82 | SEQ ID NO: 83 | SEQ ID NO: 147 | SEQ ID NO: 126 | SEQ ID NO: 127 |
| 807B-M0081-H03 | SEQ ID NO: 84 | SEQ ID NO: 85 | SEQ ID NO: 86 | SEQ ID NO: 148 | SEQ ID NO: 129 | SEQ ID NO: 130 |
| 807B-M0083-E11 | SEQ ID NO: 87 | SEQ ID NO: 88 | SEQ ID NO: 89 | SEQ ID NO: 149 | SEQ ID NO: 132 | SEQ ID NO: 133 |

| Antibody Name | VL-CDR3 | VL | Polynucleotide encoding VH | Polynucleotide encoding VL |
|---|---|---|---|---|
| 807A-M0027-E11 | SEQ ID NO: 32 | SEQ ID NO: 42 | SEQ ID NO: 174 | SEQ ID NO: 173 |
| 807A-M0028-B02 | SEQ ID NO: 35 | SEQ ID NO: 43 | SEQ ID NO: 176 | SEQ ID NO: 175 |
| 807A-M0026-F05 | SEQ ID NO: 38 | SEQ ID NO: 44 | SEQ ID NO: 172 | SEQ ID NO: 171 |
| 807B-M0001-B07 | SEQ ID NO: 92 | SEQ ID NO: 150 | SEQ ID NO: 178 | SEQ ID NO: 177 |
| 807B-M0004-A03 | SEQ ID NO: 95 | SEQ ID NO: 151 | SEQ ID NO: 180 | SEQ ID NO: 179 |
| 807B-M0004-A05 | SEQ ID NO: 98 | SEQ ID NO: 152 | SEQ ID NO: 182 | SEQ ID NO: 181 |
| 807B-M0004-C04 | SEQ ID NO: 101 | SEQ ID NO: 153 | SEQ ID NO: 184 | SEQ ID NO: 183 |
| 807B-M0004-C05 | SEQ ID NO: 104 | SEQ ID NO: 154 | SEQ ID NO: 186 | SEQ ID NO: 185 |
| 807B-M0004-F06 | SEQ ID NO: 107 | SEQ ID NO: 155 | SEQ ID NO: 188 | SEQ ID NO: 187 |
| 807B-M0004-F10 | SEQ ID NO: 110 | SEQ ID NO: 156 | SEQ ID NO: 190 | SEQ ID NO: 189 |
| 807B-M0004-H03 | SEQ ID NO: 113 | SEQ ID NO: 157 | SEQ ID NO: 192 | SEQ ID NO: 191 |
| 807B-M0009-C03 | SEQ ID NO: 116 | SEQ ID NO: 158 | SEQ ID NO: 194 | SEQ ID NO: 193 |
| 807B-M0009-F06 | SEQ ID NO: 119 | SEQ ID NO: 159 | SEQ ID NO: 196 | SEQ ID NO: 195 |
| 807B-M0013-A12 | SEQ ID NO: 122 | SEQ ID NO: 160 | SEQ ID NO: 198 | SEQ ID NO: 197 |
| 807B-M0079-D10 | SEQ ID NO: 125 | SEQ ID NO: 161 | SEQ ID NO: 200 | SEQ ID NO: 199 |
| 807B-M0081-F12 | SEQ ID NO: 128 | SEQ ID NO: 162 | SEQ ID NO: 206 | SEQ ID NO: 205 |
| 807B-M0081-H03 | SEQ ID NO: 131 | SEQ ID NO: 163 | SEQ ID NO: 202 | SEQ ID NO: 201 |
| 807B-M0083-E11 | SEQ ID NO: 134 | SEQ ID NO: 164 | SEQ ID NO: 204 | SEQ ID NO: 203 |

TABLE 9

Amino acid sequences of the VL chains of the antibodies identified using the screening strategy of Example 5

| Initial Name | LV-FR1 | LV-CDR1 | LV-FR2 | LV-CDR2 | LV-FR3 | LV-CDR3 | LV-FR4 |
|---|---|---|---|---|---|---|---|
| 807A-M0027-C11 | QDIQMTQSPSTLSASVGD RVTITC | RASQSVSSWLA | WYQQKPGAAPRLLIY | KASSLQT | GVPSRFSGGGSGTEFTLT ISSLQPDDFATYYC | QQSYSTPT | FGGGTK VEIK |
| 807A-M0043-F08 | QDIQMTQSPSSVSASVGD RVTITC | RASQGISSWLA | WYQQKPGKAPKLLIY | AASSLQS | GVPSRFSGSGSGTDFTLT ISSLQPEDFATYYC | QQANSFPPT | FGQGTK VEIQ |
| 807A-M0039-E07 | QSELTQPPSASGSPGQSV TISC | TGTSSDVGGYNYVS | WYQQHPGKAPKLMIY | EVSKRPS | GVPDRFSGSKSVTSASLA ITGLQAEDEADYYC | QSYDSSLSGYV | FGSGTK VTVL |

TABLE 9-continued

Amino acid sequences of the VL chains of the antibodies identified using the screening strategy of Example 5

| Initial Name | LV-FR1 | LV-CDR1 | LV-FR2 | LV-CDR2 | LV-FR3 | LV-CDR3 | LV-FR4 |
|---|---|---|---|---|---|---|---|
| 807A-M0039-D11 | QDIQMTQSPSSLSASVGD RVTMTC | QASQDIRNYIN | WYQQKPGKAPKLLIN | DASNLEP | GVPSRFRGSGYGTDFSFS ISSLQSEDIATYYC | QQYDSVPIT | FGQGTR VEIK |
| 807A-M0037-F10 | QSALTQPPSASGTPGQRV TISC | SGRSSNIGSNSVN | WYQQLPGTAPKLLIY | SNNQRPS | GVPDRFSGSKSGTSASLA ISGLRSEDEADYYC | AAWDDSLSGVV | FGGGTK LTVL |
| 807A-M0028-B06 | QDIQMTQSPDTLSLSPGDR ATLSC | RASQSVSSNYLA | WYHQKPGQAPRLVIY | NTSRRAT | GIPDRFSGSGSGTDFTLT ISRLDPEDFGVYYC | QQYAYGRSPGYP | FGQGTR LEIK |
| 807A-M0046-F05 | QDIQMTQSPGTLSLSPGER ATLSC | RASQSVSSSYLA | WYQQKPGQTPRLLIY | GASSRAT | GIPDRFSGSGSGTDFTLT ISRLEPEDFAVYYC | QQYGSSPYT | FGQGTK LEIR |
| 807A-M0041-F03 | QDIQMTQSPSTLSASVGD RVAITC | RASQGINRWLA | WYQQKPGKAPKLLIY | KASALES | GVPSRFSGSVSGTQFTLT ISSLQPDDFATYYC | QHYYTYPYA | FGQGTK LEIK |
| 807A-M0043-E08 | QYELTQPPSASGSPGQSV TISC | TGTSSDVGAYNYVS | WYQQHPGKAPKLIIY | EVNKRPS | GVPDRFSASKSGNTASLT VSGLQAEDEADYYC | NSYAGSNSLI | FGGGTK LTVL |
| 807A-M0042-D05 | QDIQMTQSPATLSVSPGD RVTLSC | RASQSVGSTLA | WYQQKPGQAPRLLIY | GAVTRAT | GVPARFSASASGPDFTLT ISSLQSEDFAVYYC | QQYGGSPWYT | FGQGTK LEIK |
| 807A-M0029-G10 | QDIQMTQSPSSLSASVGD RVTITC | RASQSISSYLN | WYQQKPGKAPKLLIY | AASSLQS | GVPSRFSGSGSGTDFTLI ISDLQPEDFATYYC | QQSYTTPFT | FGPGTT VDIK |
| 807A-M0046-G03 | QDIQMTQSPSSLSASVGD RVTITC | RASQGITNWVA | WYQQKPGKAPKLLIY | GASRLQS | GVPSRFSGSGSGTDFSLT ISSLQPEDFATYYC | QQSYSSLFT | FGPGTK VDIK |
| 807A-M0037-D06 | QDIQMTQSPSSLSASVGD RVTITC | RTSQDVRNWVA | WYQQKPGKAPNLLIY | MASTLQS | GVPSRFSGSGSGTDFTLT ISSLQPEDFATYFC | QQADTFPWT | FGPGTK VDIK |
| 807A-M0043-E07 | QDIQMTQSPSSLSASVGD RVTITC | RASQNVNTFLN | WYQHKAGKAPKLLIY | AASSLQS | GVPSRFSGTGSGTDFTLT ISSLQPEDFATYYC | QQSYSDPLT | FGGGTK VEIK |
| 807A-M0027-E11 | QDIQMTQSPSSLSASVGD RVTITC | RASQRIRKNLH | WYQQKPGKAPNLLIY | DASSNER | GVPSRFSGRGSGTEFTLT ISSLQPEDLATYYC | QQSFSSPWT | FGQGTK VEIK |
| 807A-M0046-A11 | QDIQMTQSPSSLSASVGD RVTITC | RASQSISSYLN | WYQQKPGKAPKLLIY | AASSLQS | GVPSRFSGSGSGTDFTLT ISSLQPEDFATYYC | QQSYSTPLT | FGGGTK VEIK |
| 807A-M0041-E01 | QDIQMTQSPSSLSASVGD RVTITC | HASQDIANYLS | WYQQKPGKAPKLLIY | DAFNLET | GVPSRFSGSGSGTDFTLT ISSLQPEDIATYYC | QQFEDLFSLT | FGPGTR VDLK |
| 807A-M0044-B07 | QDIQMTQSPGILSLSPGER ATLSC | RASQNLIFNFLA | WYQHKPGQAPRLLIY | GSSTRAT | GIPDRFSGSGSGTDFTLT INRLEPEDFAVYYC | QQYHTSSFT | FGPGTK VDIK |
| 807A-M0028-B02 | QDIQMTQSPSSLSASVGD RVTITC | RTSQDIRNHLG | WFQQKPGKAPQRLIR | EASILQS | GVPSTFYGSGYGREFTLT ISSLQPEDFATYYC | LQYDSFPYT | FGQGTK LEIK |
| 807A-M0039-E06 | QDIQMTQSPSSVSASVGD RVTITC | RASQGISSWLA | WYQQKPGKAPKLLIY | AASSLQS | GVPSRFSGSGSGTDFTLT ISSLQPEDFASYFC | QQSYSSPGIT | FGPGTK VEIK |
| 807A-M0040-A03 | QSELTQPPSVSVSPGQTA TITC | SGDKLGDKYAS | WYQQRPGQSPVLVIY | QDTKRPS | GIPERFSGSNSGNTATLT ISGTQTMDEADYYC | QAWGSSPVV | FGGGTR LTVL |

TABLE 9-continued

Amino acid sequences of the VL chains of the antibodies identified using the screening strategy of Example 5

| Initial Name | LV-FR1 | LV-CDR1 | LV-FR2 | LV-CDR2 | LV-FR3 | LV-CDR3 | LV-FR4 |
|---|---|---|---|---|---|---|---|
| 807A-M0044-G07 | QDIQMTQSPSSVSASVGD RVTITC | RASQVISTWLS | WYQQKPGKAPKLLIY | TASTLQS | GVPARFSGSGSGTDFTLT INNLQPEDFATYYC | QQANSFPIT | FGGGTK VEIN |
| 807A-M0044-E08 | QSPSSVSTSVGDRVTITCR ASQ | LDIQMTDISTWLA | WYQQKPGKAPKLLIY | AASTLES | GVPSRFSGSGSGTDFTLT ISSLQPEDFATYYC | QQAYSFPIT | FGQGTR LEIK |
| 807A-M0038-A09 | QSALTQPPSVSVAPGQTA RITC | GGNNIGTKIVN | WYQQRPGQAPVVVVY | DNSDRPS | GIPERFSGSNSGNTATLT ISRVEAGDEADYYC | QLWDSSSDHPI | FGTGTK VTVL |
| 807A-M0037-C08 | QDIQMTQSPSSVSASVGD RVTITC | RASQGISSWLA | WYQQKPGKAPKLLIY | AASSLQS | GVPSRFSGSASGADFTLT ISSLQPEDFATYYC | QQTYDTPFT | FGPGTT VDLK |
| 807A-M0039-H09 | QDIQMTQSPSSLPASVGD SVTVTC | RTSQSISDYVN | WYQQKPGKAPNLLIY | AASTLQG | GVPSRFSGSASGTNFSLT IDDLQPEDFATYYC | QQTFFSPPT | FGQGTR VEIK |
| 807A-M0039-D05 | QDIQMTQSPSSLSASVGD RVTITC | RASQDIRDDLG | WYQQKPGKAPKRLIY | AASSLQS | GVPSRFSGSGSGTEFTLT ISSLQPEDFATYYC | QQHNNYPSFT | FGPGTR LDIK |
| 807A-M0042-F12 | QSELTQPPSASGTPGQRV TISC | SGGYSNMGSNYAH | WYQQLPGTAPKLLIY | NNNQRPS | GVPDRFSGSKSGTSASLA ISGLQSEDEADYYC | AAWDDSLNGWV | FGGGTK LTVL |
| 807A-M0043-H05 | QSELTQPASVSGSPGQSIT ISC | TGTNTDVGGYNYVA | WYQQHPGKAPKLMIY | DVSNRPS | GVSTRFSGSKSGDTASLT ISGLQTEDEADYYC | SSSFTSRSTHV | FGTGTK VTVL |
| 807A-M0042-C03 | QDIQMTQSPATLSLSPGER ATLSC | RASQSVSSSYLA | WYQQKPGQAPRLLIY | GASSRAT | GIPDRFSGSGSGTDFTLT ISRLEPEDFASYFC | QQSYSSPGIT | FGPGTK VEIK |
| 807A-M0040-C03 | QDIQMTQSPGTLSLSPGER ATLSC | RASQIFSSSYVA | WYQQKPGQAPRLLIY | GASSRAS | GIPDRFSGSGSGTDFTLT ISRLEPEDFAVYWC | QQSSSSPPT | FGQGTR VEVR |
| 807A-M0046-C05 | QDIQMTQSPSSLSASVGD RVTITC | RASQSISSYLN | WYQQKPGKAPKVLIY | GTSSLQS | GVPSRFSGSGSRTDFTLT ISSLQPEDFGIYYC | QQSYNTPPT | FGQGTK LEIK |
| 807A-M0027-D05 | QDIQMTQSPSSLSASVGD RVTITC | RASQSISSYLN | WYQQKPGKAPKLLIY | AASSLQS | GVPSRFSGSGSGTDFTLT ISSLQPEDFATYYC | QQTYTTPAWT | FGQGTK VEIR |
| 807A-M0040-B11 | QSVLTQPPSASGTPGQRV TISC | SGSSSNIGSNNVN | WYQQLPGTAPKLLIY | SNDQRPS | GVPDRFSGSKSATSASLA ISGLQSEDEADYHC | AAWDDSLNGPV | FGGGTK LTVL |
| 807A-M0039-B02 | QDIQMTQSPSTLSASVGD RVTITC | RASQISSWLA | WYQQKPGKAPKLLIY | TASSLES | GVPSRFSAGGSGTEFTLT ISSLQPDDFGTYYC | QQYNSYSLT | FGGGTK VEIK |
| 807A-M0041-C07 | QDIQMTQSPSSLSASLGDR VTITC | RASQGISNSLA | WYQQKPGKAPKLLIS | AASTLQT | GVPSRFSGSGSGTDFTLI TNLQPDDFATYYC | QQINGYPVT | FGAGTK VEIK |
| 807A-M0041-H04 | QSELTQPPSASGTPGQRVI ISC | SGSGSNIGSNIVS | WFQQLPGAAPRLLIY | NDHRRPS | GVPDRFSGSKSGTSASLA ITGLRSEDETDYYC | AAWDDSLSAVV | FGGGTK LTVL |
| 807A-M0028-G07 | QYELTQPPSVSVAPGQTA RITC | GGNNIGSKNVH | WYQQKPGQAPVLVVY | DDTDRPS | GIPERFSGSNSGDTATLT ISWVEAGDEAKYHC | HVWDSSSDHYV | FGTGTA VTVL |
| 807A-M0041-A09 | QDIQMTQSPATLSLSPGER ATLSC | RASQSVSNNLA | WYQQKPGQAPRLLIS | GASTRAT | GIPARFSGSGSGTEFTLT INSLQSEDSAVYYC | QQYDNWPPFT | FGPGTK VDIK |

TABLE 9-continued

Amino acid sequences of the VL chains of the antibodies identified using the screening strategy of Example 5

| Initial Name | LV-FR1 | LV-CDR1 | LV-FR2 | LV-CDR2 | LV-FR3 | LV-CDR3 | LV-FR4 |
|---|---|---|---|---|---|---|---|
| 807A-M0042-B10 | QSALTQPASVSGSPGQSITISC | SGTDSDVGGYNHVS | WYQQHPGKAPKLIIY | DVDHRPS | GISNRFSGSKSGNTASLTISGLQAEDEADYYC | SSYRSGSTYV | FGTATKVTVL |
| 807A-M0041-E06 | QSVLTQPPSTSGTPGQRVTISC | SGSNSNIGSKTVN | WYQQLPGTAPKLLIY | MNYERPS | GVPDRFSGSKSGTSASLAISGLQSEDEADYYC | AAWDDSLSGPV | FGGGTKLTVL |
| 807A-M0037-D10 | QDIQMTQSPSSLSASVGDRVTITC | RASQSIYTSLN | WYQQKPGKAPRLLIS | DASNLQS | GVPSRFSGSGSGTDFTLTIASLQPDDFATYHC | QQSYRLFPT | FGQGTRLEIK |
| 807A-M0044-F04 | QDIQMTQSPATLSVSPGGRATLSC | RASQSVRKNVA | WYQQKPGQPPRLLIY | GASTRAT | GVPARFSGSGSGTEFTLTISRMQPEDFVVYHC | QQYSSWPA | FGQGTMVEIN |
| 807A-M0043-D10 | QDIQMTQSPATLSVSPGEGATLSC | RASQSVSSGLA | WYQQKPGQSPRLLIY | DISTRAT | GIPARFSGSGSGTEFTLTISSLQSEDFAVYYC | QQYKDWPLT | FGGGTQVEIK |
| 807A-M0043-G06 | QDIQMTQSPSYLSASVGDRVTITC | RASQTISRYLN | WYQQKPGNAPKLLIY | AASTLQS | GVPSRFSGSGSGTDFTLAISSLQPEDFATYYC | QNSYSSPYT | FGQGTNVELK |
| 807A-M0037-G01 | QDIQMTQSPATLSVSPGERATLSC | RASQSVSSNLA | WYQQKPGQAPRLLIY | GASTRAT | GIPARFSGSGSGTEFTLTISSLQSEDFAVYYC | QQYGSSPPIT | FGQGTRLEIK |
| 807A-M0044-E11 | QSALTQPASVSGSPGQSITISC | TGTSTDVGGYNYVS | WYQKHPGKAPKLMIY | DVSNRPS | GVSNRFSGSKSGNTASLTISGLQAEDEADYYC | SSYTNTITVV | FGGGTKLTVL |
| 807A-M0043-A10 | QDIQMTQSPSSLSASVGDRVTITC | RASQSISSYLN | WYQQKPGKAPKLLIY | TTSFVQS | GVPSRFSGSGSGTDFTLTISSLQPEDFATYYC | QQSYTIPTT | FGGGTKVDVK |
| 807A-M0045-B03 | QYELTQPASVSGSPGQSITISC | TGTSSDVGAFNYVS | WYQHHPGKAPKLLLY | EVTNRPS | GVSDRFSGSKSGNTASLTASYTRTRSLAISGLQAEDEADYHC | ASYTRTRSLA | FGGGTRLTVL |
| 807A-M0038-A08 | QDIQMTQSPSSLSASVGDRVTITC | RASQSIRIYLN | WYQQKPGKAPKLLIY | AASKLED | GVPSRFSGSGTGTDFTLTIRSLQPEDFASYFC | QQSYSSPGIT | FGPGTKVEIK |
| 807A-M0039-C02 | QDIQMTQSPGTLSLSPGDRATLSC | RASQSVGSDYLA | WYQQKPGQAPRLLIF | AASTRAT | GIPDRFSGSGSATDFTLTISSLEPEDFAVYFC | QQYASPPRT | FGQGTKVEIK |
| 807A-M0027-G01 | QSELTQPPSASGTPGQRVTISC | SGGYSNMGSNYAH | WYQQLPGTAPKLLIY | NNNQRPS | GVPDRFSGSKSGTSASLAISGLRSEDEADYYC | AAWDDSLSGPV | FGGGTKLTVL |
| 807A-M0039-B08 | QDIQMTQSPSSLSASVGDRVTITC | RASQGISNFLA | WYQQKPGKAPKVLIY | DASTLRS | GVPSRFSGSGSGTDFTLTIDSLQPEDFATYYC | QQYYRYPLT | FGGGTKVEIK |
| 807A-M0046-E12 | QDIQMTQSPSSLSASVGDRVTITC | RASQGIRNDLG | WYQQKPGKAPKRLIY | GASSLQS | GVPSRFSGSGSGTEFTLTISSLQPEDFATYYC | LQHNSYPLT | FGGGTKVEIK |
| 807A-M0041-A08 | QSELTQPASVSGSPGQSITISC | GTSSDVGGYNYVS | WYQQHPGKAPKLMIY | DVSNRPS | GVSNRFSGSKSGNTASLTISGLQAEDEADYYC | SSYTSSSTLDPYA | FGTGTKVTVL |
| 807A-M0037-C09 | QDIQMTQSPSSLSASVGDRVTVTC | RASQGIRNNLA | WYQQRPGKAPKRLIY | GASNLHS | GVPSRFSGSGSGTEFTLTISSLQPEDFATYYC | LQHNNYPYS | FGQGTKLEIK |
| 807A-M0040-G01 | QDIQMTQSPSSLSASVGDRVTITC | RASQGIHNYVN | WYQQKPGKAPKLLIY | AASSLQS | GVPSRFSGSGSATDFTLTISSLQPEDFATYYC | QQSFNTPFT | FGPGTRVDIK |

TABLE 9-continued

Amino acid sequences of the VL chains of the antibodies identified using the screening strategy of Example 5

| Initial Name | LV-FR1 | LV-CDR1 | LV-FR2 | LV-CDR2 | LV-FR3 | LV-CDR3 | LV-FR4 |
|---|---|---|---|---|---|---|---|
| 807A-M0045-E04 | QDIQMTQSPSSLSASVGD RVTITC | RASQGIRKDLG | WYQQRPGKAPKLLIY | GASSLLN | GVPSRFSGSGSGTDFTLT ISSLQPEDFATYYC | LQDNDYPFT | FGPGTK VEIR |
| 807A-M0041-H05 | QSALTQPPSVSGAPGQRV TISC | TGSSSNIGAPYDVH | WYQQVPGTAPKVLIY | GNNHRPS | GVPDRFSGSKSGTSASLA ISGLQAEDEAHYYC | QSYDSSLSGPI | FGGGTT LTVL |
| 807A-M0043-A08 | QSALTQPASVSGSPGQSIT ISC | TGTSNDVGGYNSVS | WYQQHPGKAPKLLIY | DVTNRPS | GVSNRFSTSQSANTASLT ISGLQPEDEAEYFC | SSYTTRSTWV | FGGGTK LTVL |
| 807A-M0038-C09 | QDIQMTQSPDSLAVSLGER ATINC | KSSQSVLYSSNNKN YLA | WYQQKPGQPPKLLIY | WASIRES | GVPDRFSGSGSGTDFTLT ISSLQAEDVAVYYC | QQYYSTPTWT | FGQGTK VEIK |
| 807A-M0042-F09 | QDIQMTQSPSSLSASVGD RVTITC | RASQGIRHDLG | WYQQKPGKAPKRLIY | AASSLQN | GVPSRFSGSGSGTEFTLT ISSLQPEDFATYYC | LQHNSYPWT | FGQGTK VEIK |
| 807A-M0045-B12 | QDIQMTQSPSSLSASVGD RVTITC | RTSQNINTYLN | WYQQKPGKAPRLLIY | AASSLQS | GVPSRFSGSGFGTDFTLT ISSLQPEDFGIYYC | EQSYNVPRT | FGQGTR LDIK |
| 807A-M0044-C04 | QDIQMTQSPSSLSASVGD RVTITC | RASQTISNYLN | WYQQKPGKAPKLLIY | ATSTLQS | GVPSRFSGSGSGTDFTLT ITSLQPEDFATYYC | QQTYNTPGT | FGQGTK LEIK |
| 807A-M0026-F11 | QSVLTQPASVSGSPGQSIT ISC | TGTSSDVGIYNYVS | WYQQHPGKAPKLMIY | DVSNRPS | GVSNRFSGSKSGNTASLT ISGLQAEDEADYYC | SSYTSSSTPYV | FGRGRK VTVL |
| 807A-M0027-E12 | QDIQMTQSPGTLSLSPGER ATLSC | RASRSLFSTYLA | WYQQKPGQPPRLLIY | GASTRAT | GIPDRFSGSGSGTDFTLT ISRLEPEDSALYYC | QQYVSSQLT | FGGGTK VEIK |
| 807A-M0028-B12 | QDIQMTQSPLSLSASAGDR VTITC | RASQNINRYLN | WYQQKPGKAPRLLIY | AASNLQS | GVPSRFSGSQSGTDFTLT ISSLQPEDFATYYC | QQSFSPPIT | FGQGTR LDIK |
| 807A-M0026-G08 | QDIQMTQSPSSLSASAGD RVTITC | RANQGIRNNLA | WFQQKPGKAPKSLIY | DASSLQS | GVPSKFSGTGSGTEFTLT IGSLQPEDSATYYC | QQYFTFPLT | FGGGTK VEIK |
| 807A-M0043-A07 | QDIQMTQSPSSVSASVGD RVTITC | RASQGISSWLA | WYQQKPGKAPKLLIY | AASSLQS | GVPSRFSGSGSGTDFTLT ISSLQPEDFATYYC | QQANSFPLT | FGGGTK VEIK |
| 807A-M0042-F04 | QDIQMTQSPATLSLSPGES ATLSC | RASQSVNDYLA | WYQQKPGQAPRLLIY | DSSNRAT | GIPARFSGSGSGTDFTLT ISSLEPEDFATYYC | QQANSFPPT | FGQGTK VEIK |
| 807A-M0045-H09 | QDIQMTQSPSSLSASVGD RVTITC | RASQSISSYLN | WYQQKPGKAPKLLIY | VASSLQS | GVPSRFSGSGSGTDFTLT ISSLQPEDFATYYC | QQSYSIPPT | FGQGTR VEIK |
| 807A-M0046-D04 | QDIQMTQSPGTLSLSPGES ATLSC | RASQSISSYLN | WYQQKQGKAPKLLMF | AASSLKS | GIPDRFSGRGSGTDFSLT ISRLEPEDFAVYYC | QQYEFSPEN | FGQGTK LQIK |
| 807A-M0040-G04 | QDIQMTQSPATLSASVGD RVTITC | RASQSISSYLN | WYQQKPGKAPKLLIY | AASSLQS | GVPSRFSGSGSGTDFTLT ISSLQPEDFATYYC | QQSYSTPHT | FGQGTK LEIK |
| 807A-M0045-B01 | QSVLTQPASVSGSPGQSIT ISC | TGTNTDVGGYNYVS | WYQQNPGEAPKLIIY | EVNHRPS | GVSDRFSGSKSGNTASLT ISGLQADDETDYYC | SSYTNRNGYV | FGRGRK VTVL |
| 807A-M0040-A08 | QSVLTQPPSASGTPGQRVI ISC | SGSSSNIGSNIVS | WFQQVPGAAPRLLIY | NDHRRPS | GVPDRFSGSKSGTSASLA ISGLQSEDDADYYC | ASWDDSLNGVL | FGGGTK LTVL |

TABLE 9-continued

Amino acid sequences of the VL chains of the antibodies identified using the screening strategy of Example 5

| Initial Name | LV-FR1 | LV-CDR1 | LV-FR2 | LV-CDR2 | LV-FR3 | LV-CDR3 | LV-FR4 |
|---|---|---|---|---|---|---|---|
| 807A-M0026-F05 | QDIQMTQSPGTLSLSPGERATLSC | RASQSIGSRYLA | WYQQKPGQAPRLLIY | DASKRAT | GVPVRFSGSGSGTDFTLTISSLGPEDFAVYYC | QQGYNWPPWT | FGQGTKVEIK |
| 807A-M0037-H02 | QDIQMTQSPGTLSLSPGERATLSC | RASQSVSSSYLA | WYQQKPGQAPSLLIY | DMSTRAP | GIPERFSGSGSGTDFTLTISRLEPEDFAVYYC | QQYGSSVA | FGGGTKVEMK |
| 807A-M0042-A06 | QSALTQPPSASGTPGQRVTISC | SGGYSNMGSNYAH | WYQQLPGTAPKLLIY | NNNQRPS | GVPDRFSGSKSGTSASLAISGLRSEDEADYYC | AAWDDSLSGPV | FGGGTKLTVL |
| 807A-M0028-A07 | QDIQMTQSPSSLSASIGDRVTITC | RASQGISNYLA | WYQQKPGKVPNLLIY | AASTLQS | GVPSRFSGSGSGTDFTLTISSLQPEDVATYYC | QKYNSAPRT | FGQGTKVEIK |
| 807A-M0043-G01 | QDIQMTQSPSSLSASVGDRVTITC | RPSQSTSNWLA | WYQQKPGKAPKLLIY | KASILES | GVPSRFSGSGSGTEFTLTISSLQPDDFATYYC | QQYDSYWT | FGQGTKIEIK |
| 807A-M0046-F04 | QDIQMTQSPSSLSASVGDRVTITC | RASQSISTYLN | WYQHKPGNAPNLLIY | GASSLKR | GVPSRFSGSGSETEFTLTISSLQPEDFATYYC | QQSYSAPLI | FGGGTKVEIR |
| 807A-M0037-F03 | QDIQMTQSPGTLSLSPGERATLSC | RASQSISSRYLA | WYQQKAGQAPRLLMY | GASRAT | GIPARFSGSGSGTDFTLTISSLQPEDFATYYC | QSYEYPLT | FGQGTKLEIK |
| 807A-M0039-C10 | QSALTQPRSVSGSPGQSVTISC | TGTYSDVGNYYSVS | WYQQHPGKAPKFIIY | DVTKRPS | GVPDRFSGSKSGNTASLTISGLQAEDEADYYC | CSYAGSYTLL | FGGGTKLTVL |

TABLE 10

Amino acid sequences of the VH chains of the antibodies identified using the screening strategy of Example 5

| Initial Name | FR1 | CDR1 | FR2 | CDR2 | FR3 | CDR3 | FR4 |
|---|---|---|---|---|---|---|---|
| 807A-M0027-C11 | EVQLLESGGGLVQPGGSLRLSCAASGFTFS | EYGMS | WVRQAPGKGLEWVS | VISPSGGGTEYADSVKG | RFTISRDNSKNTLYLQMNSLRAEDTAVYYCAR | AVGYGDYGDY | WGQGTLVTVSS |
| 807A-M0043-F08 | EVQLLESGGGLVQPGGSLRLSCAASGFTFS | EYTML | WVRQAPGKGLEWVS | GIWPSGGPTFYADSVKG | RFTISRDNSKNTLYLQMNSLRAEDTAVYYCAR | ELDTAMAPPSDAFDI | WGQGTMVTVSS |
| 807A-M0039-E07 | EVQLLESGGGLVQPGGSLRLSCAASGFTFS | FYFMG | WVRQAPGKGLEWVS | SISSSGGMTTYADSVKG | RFTISRDNSKNTLYLQMNSLRAEDTAVYYCAR | DLWFGEWDY | WGQGTLVTVSS |
| 807A-M0039-D11 | EVQLLESGGGLVQPGGSLRLSCAASGFTFS | FYGMG | WVRQAPGKGLEWVS | YISPSGGSTTYADSVKG | RFTISRDNSKNTLYLQMNSLRAEDTAVYYCAR | DLWFGEWDY | WGQGTLVTVSS |
| 807A-M0037-F10 | EVQLLESGGGLVQPGGSLRLSCAASGFTFS | FYGMG | WVRQAPGKGLEWVS | YISSSGGLTFYADSVKG | RFTISRDNSKNTLYLQMNSLRAEDTAVYYCAR | DLWFGEWDY | WGQGTLVTVSS |
| 807A-M0028-B06 | EVQLLESGGGLVQPGGSLRLSCAASGFTFS | FYQMN | WVRQAPGKGLEWVS | SIYPSGGLTYYADSVKG | RFTISRDNSKNTLYLQMNSLRAEDTAVYYCAR | DRGVSLLGAFDI | WGQGTMVTVSS |
| 807A-M0046-F05 | EVQLLESGGGLVQPGGSLRLSCAASGFTFS | FYRMT | WVRQAPGKGLEWVS | SISSSGGGTPYADSVKG | RFTISRDNSKNTLYLQMNSLRAEDTAVYYCAR | DLWFGEWDY | WGQGTLVTVSS |

TABLE 10-continued

Amino acid sequences of the VH chains of the antibodies identified using the screening strategy of Example 5

| Initial Name | FR1 | CDR1 | FR2 | CDR2 | FR3 | CDR3 | FR4 |
|---|---|---|---|---|---|---|---|
| 807A-M0041-F03 | EVQLLESGGGLVQPGGSLRLSCAASGFTFS | FYSMF | WVRQAPGKGLEWVS | YIYPSGGWTNYADSVKG | RFTISRDNSKNTLYLQMNSLRAEDTAVYYCAR | SVVGWGLDY | WGQGTLVTVSS |
| 807A-M0043-E08 | EVQLLESGGGLVQPGGSLRLSCAASGFTFS | FYSMG | WVRQAPGKGLEWVS | YIYPSGGTTYADSVKG | RFTISRDNSKNTLYLQMNSLRAEDTAVYYCAR | DLWFGEWDY | WGQGTLVTVSS |
| 807A-M0042-D05 | EVQLLESGGGLVQPGGSLRLSCAASGFTFS | FYSMV | WVRQAPGKGLEWVS | SISPSGGQTDYADSVKG | RFTISRDNSKNTLYLQMNSLRAEDTAVYYCAR | DLWFGEWDY | WGQGTLVTVSS |
| 807A-M0029-G10 | EVQLLESGGGLVQPGGSLRLSCAASGFTFS | FYTMV | WVRQAPGKGLEWVS | VISPSGGLTHYADSVKG | RFTISRDNSKNTLYLQMNSLRAEDTAVYYCAR | DLWFGEWDY | WGQGTLVTVSS |
| 807A-M0046-G03 | EVQLLESGGGLVQPGGSLRLSCAASGFTFS | FYYMS | WVRQAPGKGLEWVS | RISPSGGLTHYADSVKG | RFTISRDNSKNTLYLQMNSLRAEDTAVYYCAR | DFFTSYFDY | WGQGTLVTVSS |
| 807A-M0037-D06 | EVQLLESGGGLVQPGGSLRLSCAASGFTFS | HYLMV | WVRQAPGKGLEWVS | GISPSGGGTNYADSVKG | RFTISRDNSKNTLYLQMNSLRAEDTAVYYCAK | GPGYSYGYYYYGMDV | WGQGTTVTVSS |
| 807A-M0043-E07 | EVQLLESGGGLVQPGGSLRLSCAASGFTFS | KYPMQ | WVRQAPGKGLEWVS | SISPSGGSTVYADSVKG | RFTISRDNSKNTLYLQMNSLRAEDTAVYYCAR | GVTTVPRYYYYYYVMDV | WGKGTTVTVSS |
| 807A-M0027-E11 | EVQLLESGGGLVQPGGSLRLSCAASGFTFS | KYSMH | WVRQAPGKGLEWVS | GIYSSGGKTIYADSVKG | RFTISRDNPKNTLYLQMNSLRAEDTAVYYCAR | SLDLDY | WGQGTLVTVSS |
| 807A-M0046-A11 | EVQLLESGGGLVQPGGSLRLSCAASGFTFS | LYGMV | WVRQAPGKGLEWVS | RISPSGGYTGYADSVKG | RFTISRDNSKNTLYLQMNSLRAEDTAVYYCAR | DLWFGEWDY | WGQGTLVTVSS |
| 807A-M0041-E01 | EVQLLESGGGLVQPGGSLRLSCAASGFTFS | LYRMG | WVRQAPGKGLEWVS | SISPSGGWTRYADSVKG | RFTISRDNSKNTLYLQMNSLRAEDAVYYCAR | DLWFGEWDY | WGQGTLVTVSS |
| 807A-M0044-B07 | EVQLLESGGGLVQPGGSLRLSCAASGFTFS | MYGML | WVRQAPGKGLEWVS | RISPSGGFTNYADSVKG | RFTISRDNSKNTLYLQMNSLRAEDTAVYYCAR | DLWFGEWDY | WGQGTLVTVSS |
| 807A-M0028-B02 | EVQLLESGGGLVQPGGSLRLSCAASGFTFS | MYMMD | WVRQAPGKGLEWVS | SIWPSGGQTWYADSVKG | RFTISRDNSKNTLYLQMNSLRAEDTAVYYCAR | SVLLDY | WGQGTLVTVSS |
| 807A-M0039-E06 | EVQLLESGGGLVQPGGSLRLSCAASGFTFS | NYVMH | WVRQAPGKGLEWVS | VISPSGGATIYADSVKG | RFTISRDNSKNTLYLQMNSLRAEDTAVYYCAR | DWGPFEAFDI | WGQGTMVTVSS |
| 807A-M0040-A03 | EVQLLESGGGLVQPGGSLRLSCAASGFTFS | QYNMG | WVRQAPGKGLEWVS | YISSSGGITWYADSVKG | RFTISRDNSKNTLYLQMNSLRAEDTAVYYCAR | DFFTSYFDY | WGQGTLVTVSS |
| 807A-M0044-G07 | EVQLLESGGGLVQPGGSLRLSCAASGFTFS | TYSMH | WVRQAPGKGLEWVS | YIGSSGGFTMYADSVKG | RFTISRDNSKNTLYLQMNSLRAEDTAVYYCAR | GLYR | WGQGTLVTVSS |
| 807A-M0044-E08 | EVQLLESGGGLVQPGGSLRLSCAASGFTFS | TYWMI | WVRQAPGKGLEWVS | SISSSGGWTMYADSVKG | RFTISRDNSKNTLYLQMNSLRAEDTAVYYCAR | EDNYYGMDV | WGQGTTVTVSS |
| 807A-M0038-A09 | EVQLLESGGGLVQPGGSLRLSCAASGFTFS | VYSMA | WVRQAPGKGLEWVS | GIWPSGGPTAYADSVKG | RFTISRDNSKNTLYLQMNSLRAEDTAVYYCAR | EDFWSGLEDV | WGKGTTVTVSS |
| 807A-M0037-C08 | EVQLLESGGGLVQPGGSLRLSCAASGFTFS | WYAMD | WVRQAPGKGLEWVS | RIRPSGGNTDYADSVKG | RFTISRDNSKNTLYLQMNSLRAEDTAVYYCAR | EPIWGYYYYMDV | WGQGTTVTVSS |

TABLE 10-continued

Amino acid sequences of the VH chains of the antibodies identified using the screening strategy of Example 5

| Initial Name | FR1 | CDR1 | FR2 | CDR2 | FR3 | CDR3 | FR4 |
|---|---|---|---|---|---|---|---|
| 807A-M0039-H09 | EVQLLESGGGLVQPGG SLRLSCAASGFTFS | WYAMD | WVRQAPGKGLEWVS | RIRSSGGLTHYADSVKG | RFTISRDNSKNTLYLQMNS LRAEDTAVYYCAR | EPIWGYYYYG MDV | WGQGTT VTVSS |
| 807A-M0039-D05 | EVQLLESGGGLVQPGG SLRLSCAASGFTFS | WYAMD | WVRQAPGKGLEWVS | SIYPSGGWTEYADSVKG | RFTISRDNSKNTLYLQMNS LRAEDTAVYYCAR | GLGMDV | WGQGTT VTVSS |
| 807A-M0042-F12 | EVQLLESGGGLVQPGG SLRLSCAASGFTFS | WYAMS | WVRQAPGKGLEWVS | SIYSSGGKTGYADSVKG | RFTISRDNSKNTLYLQMNS LRAEDTAVYYCAR | EPIWGYYYYG MDV | WGQGTT VTVSS |
| 807A-M0043-H05 | EVQLLESGGGLVQPGG SLRLSCAASGFTFS | WYAMV | WVRQAPGKGLEWVS | YIRSSGGHTVYADSVKG | RFTISRDNSKNTLYLQMNS LRAEDTAVYYCAR | EPIWGYYYYG MDV | WGQGTT VTVSS |
| 807A-M0046-H06 | EVQLLESGGGLVQPGG SLRLSCAASGFTFS | WYDMD | WVRQAPGKGLEWVS | SISSSGGFTTYADSVKG | RFTISRDNSKNTLYLQMNS LRAEDTAVYYCAR | EPIWGYYYYG MDV | WGQGTT VTVSS |
| 807A-M0042-C03 | EVQLLESGGGLVQPGG SLRLSCAASGFTFS | WYDMD | WVRQAPGKGLEWVS | SIVSSGGLTDYADSVKG | RFTISRDNSKNTLYLQMNS LRAEDTAVYYCAR | QEVWQWPAQF DS | WGQGTL VTVSS |
| 807A-M0040-C03 | EVQLLESGGGLVQPGG SLRLSCAASGFTFS | WYDME | WVRQAPGKGLEWVS | VIGPSGGPTHYADSVKG | RFTISRDNSKNTLYLQMNS LRAEDTAVYYCAR | EPIWGYYYYG MDV | WGQGTT VTVSS |
| 807A-M0046-C05 | EVQLLESGGGLVQPGG SLRLSCAASGFTFS | WYDME | WVRQAPGKGLEWVS | WISSSGGTTWYADSVKG | RFTISRDNSKNTLYLQMNS LRAEDTAVYYCAR | EPIWGYYYYG MDV | WGQGTT VTVSS |
| 807A-M0027-D05 | EVQLLESGGGLVQPGG SLRLSCAASGFTFS | WYDMF | WVRQAPGKGLEWVS | SIYSSGGITYYADSVKG | RFTISRDNSKNTLYLQMNS LRAEDTAVYYCAR | EPIWGYYYYG MDV | WGQGTT VTVSS |
| 807A-M0040-B11 | EVQLLESGGGLVQPGG SLRLSCAASGFTFS | WYDMG | WVRQAPGKGLEWVS | SISPSGGSTTYADSVKG | RFTISRDNSKNTLYLQMNS LRAEDTAVYYCAR | EPIWGYYYYG MDV | WGQGTT VTVSS |
| 807A-M0039-B02 | EVQLLESGGGLVQPGG SLRLSCAASGFTFS | WYDMH | WVRQAPGKGLEWVS | SISPSGGLTYYADSVKG | RFTISRDNSKNTLYLQMNS LRAEDTAVYYCAR | QEVWQWPAQF DS | WGQGTL VTVSS |
| 807A-M0041-C07 | EVQLLESGGGLVQPGG SLRLSCAASGFTFS | WYDMH | WVRQAPGKGLEWVS | SISPSGGLTYYADSVKG | RFTISRDNSKNTLYLQMNS LRAEDTAVYYCAR | QEVWQWPAQF DS | WGQGTL VTVSS |
| 807A-M0041-H04 | EVQLLESGGGLVQPGG SLRLSCAASGFTFS | WYDMH | WVRQAPGKGLEWVS | SISSSGGDTTYADSVKG | RFTISRDNSKNTLYLQMNS LRAEDTAVYYCAR | EPIWGYYYYG MDV | WGQGTT VTVSS |
| 807A-M0028-G07 | EVQLLESGGGLVQPGG SLRLSCAASGFTFS | WYDMH | WVRQAPGKGLEWVS | YISPSGGWTGYADSVKG | RFTISRDNSKNTLYLQMNS LRAEDTAVYYCAR | QEVWQWPAQF DS | WGQGTL VTVSS |
| 807A-M0041-A09 | EVQLLESGGGLVQPGG SLRLSCAASGFTFS | WYDMN | WVRQAPGKGLEWVS | RISPSGGSTRYADSVKG | RFTISRDNSKNTLYLQMNS LRAEDTAVYYCAR | EPIWGYYYYG MDV | WGQGTT VTVSS |
| 807A-M0042-B10 | EVQLLESGGGLVQPGG SLRLSCAASGFTFS | WYDMN | WVRQAPGKGLEWVS | SIGSSGGETRYADSVKG | RFTISRDNSKNTLYLQMNS LKAEDTAVYYCAR | EPIWGYYYYG MDV | WGQGTT VTVSS |
| 807A-M0041-E06 | EVQLLESGGGLVQPGG SLRLSCAASGFTFS | WYDMQ | WVRQAPGKGLEWVS | SISSSGGLTTYADSVKG | RFTISRDNSKNTLYLQMNS LRAEDTAVYYCAR | EPIWGYYYYG MDV | WGQGTT VTVSS |
| 807A-M0037-D10 | EVQLLESGGGLVQPGG SLRLSCAASGFTFS | WYDMR | WVRQAPGKGLEWVS | SISSSGGRTVYADSVKG | RFTISRDNSKNTLYLQMNS LRAEDTAVYYCAR | EPIWGYYYYG MDV | WGQGTT VTVSS |

TABLE 10-continued

Amino acid sequences of the VH chains of the antibodies identified using the screening strategy of Example 5

| Initial Name | FR1 | CDR1 | FR2 | CDR2 | FR3 | CDR3 | FR4 |
|---|---|---|---|---|---|---|---|
| 807A-M0044-F04 | EVQLLESGGGLVQPGGSLRLSGAASGFTFS | WYDMS | WVRQAPGKGLEWVS | RIGSSGGATQYADSVKG | RFTISRDNSKNTLYLQMNSLRAEDTAVYYCAR | EPIWGYYYYGMDV | WGQGTTVTVSS |
| 807A-M0043-D10 | EVQLLESGGGLVQPGGSLRLSCAASGFTFS | WYDMS | WVRQAPGKGLEWVS | YIVPSGGVTLYADSVKG | RFTISRDNSKNTLYLQMNSLRAEDTAVYYCAR | EPIWGYYYYGMDV | WGQGTTVTVSS |
| 807A-M0043-G06 | EVQLLESGGGLVQPGGSLRLSCAASGFTFS | WYDMV | WVRQAPGKGLEWVS | SIVSSGGETRYADSVKG | RFTISRDNSKNTLYLQMNSLRAEDTAVYYCAR | EPIWGYYYYGMDV | WGQGTTVTVSS |
| 807A-M0037-G01 | EVQLLESGGGLVQPGGSLRLSCAASGFTFS | WYDMV | WVRQAPGKGLEWVS | YIRPSGGITFYADSVKG | RFTISRDNSKNTLYLQMNSLRAEDTAVYYCAR | QEVWQWPAQFDS | WGQGTLVTVSS |
| 807A-M0044-E11 | EVQLLESGGGLVQPGGSLRLSCAASGFTFS | WYDMV | WVRQAPGKGLEWVS | YIVPSGGETSYADSVKG | RFTISRDNSKNTLYLQMNSLRAEDTAVYYCAR | EPIWGYYYYGMDV | WGQGTTVTVSS |
| 807A-M0043-A10 | EVQLLESGGGLVQPGGSLRLSCAASGFTFS | WYDMY | WVRQAPGKGLEWVS | GIGPSGGSTYYADSVKG | RFTISRDNSKNTLYLQMNSLRAEDTAVYYCAR | EPIWGYYYYGMDV | WGQGTTVTVSS |
| 807A-M0045-B03 | EVQLLESGGGLVQPGGSLRLSCAASGFTFS | WYDMY | WVRQAPGKGLEWVS | SIRSSGGLTNYADSVKG | RFTISRDNSKNTLYLQMNSLRAEDTAVYYCAR | EPIWGYYYYGMDV | WGQGTTVTVSS |
| 807A-M0038-A08 | EVQLLESGGGLVQPGGSLRLSCAASGFTFS | WYDMY | WVRQAPGKGLEWVS | SISPSGGITAYADSVKG | RFTISRDNSKNTLYLQMNSLRAEDTAVYYCAR | QEVWQWPAQFDS | WGQGTLVTVSS |
| 807A-M0039-C02 | EVQLLESGGGLVQPGGSLRLSCAASGFTFS | WYDMY | WVRQAPGKGLEWVS | SISPSGGITAYADSVKG | RFTISRDNSKNTLYLQMNSLRAEDTAVYYCAR | QEVWQWPAQFDS | WGQGTLVTVSS |
| 807A-M0027-G01 | EVQLLESGGGLVQPGGSLRLSCAASGFTFS | WYEMG | WVRQAPGKGLEWVS | SIGPSGGETIYADSVKG | RFTISRDNSKNTLYLQMNSLRAEDTAVYYCAR | DRGVSLLGAFDI | WGQGTMVTVSS |
| 807A-M0039-B08 | EVQLLESGGGLVQPGGSLRLSCAASGFTFS | WYEMG | WVRQAPGKGLEWVS | SIYSSGGQTVYADSVKG | RFTISRDNSKNTLYLQMNSLRAEDTAVYYCAR | QEVWQWPAQFDS | WGQGTLVTVSS |
| 807A-M0046-E12 | EVQLLESGGGLVQPGGSLRLSCAASGFTFS | WYEMN | WVRQAPGKGLEWVS | RIYPSGGPTWYADSVKG | RFTISRDNSKNTLYLQMNSLRAEDTAVYYCAR | EPIWGYYYYGMDV | WGQGTTVTVSS |
| 807A-M0041-A08 | EVQLLESGGGLVQPGGSLRLSCAASGFTFS | WYFMH | WVRQAPGKGLEWVS | SIYPSGGTTEYADSVKG | RFTISRDNSKNTLYLQMNSLRAEDTAVYYCAR | EPIWGYYYYGMDV | WGQGTTVTVSS |
| 807A-M0037-C09 | EVQLLESGGGLVQPGGSLRLSCAASGFTFS | WYGMG | WVRQAPGKGLEWVS | YISSSGGLTIYADSVKG | RFTISRDNSKNTLYLQMNSLRAEDTAVYYCAR | DLWFGEWDY | WGQGTLVTVSS |
| 807A-M0040-G01 | EVQLLESGGGLVQPGGSLRLSCAASGFTFS | WYGMS | WVRQAPGKGLEWVS | RIVSSGGPTGYADSVKG | RFTISRDNSKNTLYLQMNSLRAEDTAVYYCAR | EPIWGYYYYGMDV | WGQGTTVTVSS |
| 807A-M0045-E04 | EVQLLESGGGLVQPGGSLRLSCAASGFTFS | WYGMV | WVRQAPGKGLEWVS | SIYPSGGTTQYADSVKG | RFTISRDNSKNTLYLQMNSLRAEDTAVYYCAR | DLWFGEWDY | WGQGTLVTVSS |
| 807A-M0041-H05 | EVQLLESGGGLVQPGGSLRLSCAASGFTFS | WYNMD | WVRQAPGKGLEWVS | SIGSGGPTKYADSVKG | RFTISRDNSKNTLYLQMNSLRAEDTAVYYCAR | EPIWGYYYYGMDV | WGQGTTVTVSS |
| 807A-M0043-A08 | EVQLLESGGGLVQPGGSLRLSCAASGFTFS | WYNMG | WVRQAPGKGLEWVS | YIGPSGGETYYADSVKG | RFTISRDNSKNTLYLQMNSLRAEDTAVYYCAR | EPIWGYYYVGMDV | WGQGTTVTVSS |

TABLE 10-continued

Amino acid sequences of the VH chains of the antibodies identified using the screening strategy of Example 5

| Initial Name | FR1 | CDR1 | FR2 | CDR2 | FR3 | CDR3 | FR4 |
|---|---|---|---|---|---|---|---|
| 807A-M0038-C09 | EVQLLESGGGLVQPGGSLRLSCAASGFTFS | WYNMQ | WVRQAPGKGLEWVS | VISPSGGGTYYADSVKG | RFTISRDNSKNTLYLQMNSLRAEDTAVYYCAR | VKWDHSPLFDP | WGQGTLVTVSS |
| 807A-M0042-F09 | EVQLLESGGGLVQPGGSLRLSCAASGFTFS | WYNMV | WVRQAPGKGLEWVS | WISSSGGMTRYADSVKG | RFTISRDNSKNTLYLQMNSLRAEDTAVYYCAR | DLWFGEWDY | WGQGTLVTVSS |
| 807A-M0045-B12 | EVQLLESGGGLVQPGGSLRLSCAASGFTFS | WYPMY | WVRQAPGKGLEWVS | VIYPSGGHTKYADSVKG | RFTISRDNSKNTLYLQMNSLRAEDTAVYYCAR | EPIWGYYYYGMDV | WGQGTTVTVSS |
| 807A-M0044-C04 | EVQLLESGGGLVQPGGSLRLSCAASGFTFS | WYQME | WVRQAPGKGLEWVS | SISSSGGTTDYADSVKG | RFTISRDNSKNTLYLQMNSLRAEDTAVYYCAR | EPIWGYYYYGMDV | WGQGTTVTVSS |
| 807A-M0026-F11 | EVQLLESGGGLVQPGGSLRLSCAASGFTFS | WYQMS | WVRQAPGKGLEWVS | SISSSGGHTFYADSVKG | RFTISRDNSKNTLYLQMNSLRAEDTAVYYCAR | DLWFGEWDY | WGQGTLVTVSS |
| 807A-M0027-E12 | EVQLLESGGGLVQPGGSLRLSCAASGFTFS | WYRMT | WVRQAPGKGLEWVS | SISPSGGVTLYADSVKG | RFTISRDNSKNTLYLQMNSLRAEDTAVYYCAR | DLWFGEWDY | WGQGTLVTVSS |
| 807A-M0028-B12 | EVQLLESGGGLVQPGGSLRLSCAASGFTFS | WYSMG | WVRQAPGKGLEWVS | WISSSGGGTPYADSVKG | RFTISRDNSKNTLYLQMNSLRAEDTAVYYCAR | DLWFGEWDY | WGQGTLVTVSS |
| 807A-M0026-G08 | EVQLLESGGGLVQPGGSLRLSCAASGFTFS | WYSMH | WVRQAPGKGLEWVS | SIRSSGGWTKYADSVKG | RFTISRDNSKNTLYLQMNSLRAEDTAVYYCAR | SSGIYYGYYMDV | WGKGATVTVSS |
| 807A-M0043-A07 | EVQLLESGGGLVQPGGSLRLSCAASGFTFS | WYSML | WVRQAPGKGLEWVS | YIYPSGGATFYADSVKG | RFTISRDNSKNTLYLQMNSLRAEDTAVYYCAR | GRSTFDI | WGQGTMVTVSS |
| 807A-M0042-F04 | EVQLLESGGGLVQPGGSLRLSCAASGFTFS | WYSMN | WVRQAPGKGLEWVS | GISSSGGMTHYADSVKG | RFTISRDNSKNTLYLQMNSLRAEDTAVYYCAR | EPIWGYYYYGMDV | WGQGTTVTVSS |
| 807A-M0045-H09 | EVQLLESGGGLVQPGGSLRLSCAASGFTFS | WYTMG | WVRQAPGKGLEWVS | SIVSSGGYTPYADSVKG | RFTISRDNSKNTLYLQMNSLRAEDTAVYYCAR | EPIWGYYYYGMDV | WGQGTTVTVSS |
| 807A-M0046-D04 | EVQLLESGGGLVQPGGSLRLSCAASGFTFS | WYTMH | WVRQAPGKGLEWVS | SIRSSGGMTDYADSVKG | RFTISRDNSKNTLYLQMNSLRAEDTAVYYCAR | SSGIVYGYYMDV | WGKGATVTVSS |
| 807A-M0040-G04 | EVQLLESGGGLVQPGGSLRLSCAASGFTFS | WYTMQ | WVRQAPGKGLEWVS | SIYPSGGDTKYADSVKG | RFTISRDNSKNTLYLQMNSLRAEDTAVYYCAR | EPIWGYYYYGMDV | WGQGTTVTVSS |
| 807A-M0045-B01 | EVQLLESGGGLVQPGGSLRLSCAASGFTFS | WYTMV | WVRQAPGKGLEWVS | SIRSSGGQTKYADSVKG | RFTISRDNSKNTLYLQMNSLRAEDTAVYYCAR | EPIWGYYYVGMDV | WGQGTTVTVSS |
| 807A-M0040-A08 | EVQLLESGGGLVQPGGSLRLSCAASGFTFS | WYTMV | WVRQAPGKGLEWVS | SIVPSGGDTHYADSVKG | RFTISRDNSKNTLYLQMNSLRAEDTAVYYCAR | EPIWGYYYYGMDV | WGQGTTVTVSS |
| 807A-M0026-F05 | EVQLLESGGGLVQPGGSLRLSCAASGFTFS | YYAMQ | WVRQAPGKGLEWVS | SLYPSGGNTSYADSVKG | RFTISRDNSKNTLYLQMNSLRAEDTAVYYCAR | GRGNYDFWSAGYYYYMDV | WGKGTTVTVSS |
| 807A-M0037-H02 | EVQLLESGGGLVQPGGSLRLSCAASGFTFS | YYGMV | WVRQAPGKGLEWVS | RISPSGGMTDYADSVKG | RFTISRDNSKNTLYLQMNSLRAEDTAVYYCAR | DLWFGEWDY | WGQGTPVTVSS |
| 807A-M0042-A06 | EVQLLESGGGLVQPGGSLRLSCAASGFTFS | YYHMD | WVRQAPGKGLEWVS | SIVSSGGFTAYADSVKG | RFTISRDNSKNTLYLQMNSLRAEDTAVYYCAR | DRGVSLLGAFDI | WGQGTMVTVSS |

TABLE 10-continued

Amino acid sequences of the VH chains of the antibodies identified using the screening strategy of Example 5

| Initial Name | FR1 | CDR1 | FR2 | CDR2 | FR3 | CDR3 | FR4 |
|---|---|---|---|---|---|---|---|
| 807A-M0028-A07 | EVQLLESGGGLVQPGGSLRLSCAASGFTFS | YRRMA | WVRQAPGKGLEWVS | SIYSSGGMTLYADSVKG | RFTISRDNSKNTLYLQMNSLRAEDTAVYYCAK | ESIAVAGVDY | WGQGTLVTVSS |
| 807A-M0043-G01 | EVQLLESGGGLVQPGGSLRLSCAASGFTFS | YYSMI | WVRQAPGKGLEWVS | RISPSGGQTNYADSVKG | RFTISRDNSKNTLYLQMNSLRAEDTAVYYCAR | DLWFGEWDY | WGQGTLVTVSS |
| 807A-M0046-F04 | EVQLLESGGGLVQPGGSLRLSCAASGFTFS | YYSMT | WVRQAPGKGLEWVS | SISPSGGGTGYADSVKG | RFTISRDNSKNTLYLQMNSLRAEDTAVYYCAR | DLWFGEWDY | WGQGTLVTVSS |
| 807A-M0037-F03 | EVQLLESGGGLVQPGGSLRLSCAASGFTFS | YYSMV | WVRQAPGKGLEWVS | WISSSGGSTNYADSVKG | RFTISRDNSKNTLYLQMNSLRAEDTAVYYCAR | DLWFGEWDY | WGQGTLVTVSS |
| 807A-M0039-C10 | EVQLLESGGGLVQPGGSLRLSCAASGFTFS | YYSMV | WVRQAPGKGLEWVS | WISSSGGSTNYADSVKG | RFTISRDNSKNTLYLQMNSLRAEDTAVYYCAR | DLWFREWDY | WGQGTLVTVSS |

TABLE 11

Amino acid sequences of the VL chains of the antibodies identified using the screening strategies of Examples 21 and 22

| Antibody Name | VL-FR 1 | VL-CDR 1 | VL-FR 2 | VL-CDR 2 | VL-FR 3 | VL-CDR 3 | VL-FR 4 |
|---|---|---|---|---|---|---|---|
| 807B-M0001-A09 | QSVLTQPPSASGTPGQRVTISC | SGSSSNIGTYPVN | WYQQLPGAAPKLLIY | STDQRPS | GVPDRFSGSKSGTSASLAISGLQSEDESDYYC | AAWDDSLNGLWV | FGGGTKVTVL |
| 807B-M0001-B07 | QYELTQPPSVSGTPGQRVTISC | SGSSSNIGSEYVY | WFQQLPGTAPRLLIY | RNDQRPS | GVPDRFSGSKSGTSASLAISGLQSEDEADYYC | AAWDDSLPGWC | SGGGTKLTVL |
| 807B-M0001-C10 | QYELTQPPSASGTPGQTVTISC | SGSSSNIGTNFVY | WYQQLPGTAPKLLIY | RSIKRPS | GVPDRFSGSKSGTSASLAISGLRSEDEADYYC | AAWDDSLSGVV | FGGGTKLTVL |
| 807B-M0001-G03 | QSALTQPPSASGTPGQRVTFSC | SGSSSNIGINSVN | WYQQLPGTAPKLLIY | SNNQRPS | GVPDRFSGSKSGTSASLAISGLRSEDEADYYC | AAWDDSLAGWV | FGGGTKVTVL |
| 807B-M0004-A03 | QSELTQPPSASGTPGQRVTISC | SGSSSNIGSNTVN | WYQQLPGTAPKLLIY | NNNQRPS | GVPDRFSGSKSGTSASLAISGLQSEDEADYYC | AAWHDGLNGPV | FGGGTKLTVL |
| 807B-M0004-A05 | QDIQMTQSPATLSLSPGERATLSC | KASQSVRAFIA | WYQQKPGQAPRLLIS | GASNRAT | GIPDRFSGGGSGTDFTLTISRLEPEDFAVYYC | QQYGSSRYT | FGQGTKLEIK |
| 807B-M0004-B10 | QDIQMTQSPSSLSASVGDRVTITC | RASQSISTYLN | WYQQKPGKAPKLLIF | ATSRLQS | EVPSRFSGSGSGTDFTLTISSLQPEDFATYYC | QQSYSPPRT | FGQGTKLDIN |
| 807B-M0004-C01 | QDIQMTQSPLSLPVSLGQKASISC | RSSQSLVHTDGTTYLS | WFQQRPGQSPRRLVY | KVSDRGS | GVPDRFSGSGSGIDFTLKISRVEAEDVGLYYC | MQGTHWPPT | FGQGTKLEIK |
| 807B-M0004-C04 | QDIQMTQSPSSLPVTPGEPASISC | RSSQSLLHSSGYNYLD | WYLQKPGQSPQLLIY | LGSNRAS | GVPDRFTGSGSGTDFTLKISRVEAEDVGVYYC | MQALQTPT | FGGGTKVDIK |
| 807B-M0004-C05 | QDIQMTQSPATLSVSPGERATLSC | RASQSVSSNLA | WYQQKPGQAPRLLIY | GASTRAT | GVPARFSGSGSGTDFTLSISSLQPEDFATYYC | QQYAGHPIT | FGQGTRLEIK |

TABLE 11-continued

Amino acid sequences of the VL chains of the antibodies identified using the screening strategies of Examples 21 and 22

| Antibody Name | VL-FR 1 | VL-CDR 1 | VL-FR 2 | VL-CDR 2 | VL-FR 3 | VL-CDR 3 | VL-FR 4 |
|---|---|---|---|---|---|---|---|
| 807B-M0004-D10 | QSELTQPSSASETPGQRVTISC | SGSSSNIGSNLVY | WYQQVPGTALKLLIY | RNDQRPS | GVPDRFSGSKSGTSASLAISGLRSEDEADYFC | VSWDGSLSGWV | FGGGTRLTVL |
| 807B-M0004-F06 | QSELTQAASVSGSPGQSITLSC | TGATRDVS | WYQQHPGKAPKLVL | YEVSSRPS | GVSDRFSGSMSGNTASLTISGLQAEDEADYYC | SSTTSRAPRVV | FGGGTKLTVL |
| 807B-M0004-F07 | QDIQMTQSPATLSLSPGERATLSC | RASQSVSSYLA | WYQQKPGQAPRLLIY | DAFNRAT | GIPARFSGSGSGTDFTLTISSLEPEDFAVYYC | QQRSNWPLT | FGGGTKVEIK |
| 807B-M0004-F10 | QDIQMTQSPLSLPVTPGEPASISC | RSSQSLMHRNGHHFFD | WYLQKPGQSPQLLIY | WASNRAP | GVPDRFSGSGSGTDFTLKISRVEAEDVGIYYC | MQALQTPYT | FGQGTKLEIK |
| 807B-M0004-G08 | QDIVMTQTPPSLPVNPGEPASISC | RSSQSLVHSDGNTYLN | WFQQRPGQSPRRLIS | KVSNRDS | GVPDRFSGSGAGTDFTLNISRVEAEDVGDYYC | MQVTEFPLT | FGGGTKVEIK |
| 807B-M0004-H03 | QDIQMTQSPSSLSASIGDRVTISC | QASQNIDNYLN | WYQQKPGKAPKLLIY | AASSLQS | GVPSRFSGSGSGTDFTLTISSLQPEDFATYYC | QQSYSTPRT | FGGGTKVEIK |
| 807B-M0008-A03 | QSALTQPASVSGSPGQSITISC | TGTSNDVGGYNYVS | WYQQHPGIAPKVVIY | EVSNRPS | GVSDRFSGSKAGNTASLTISGLQAEDEADYYC | NSYTSSRTWV | FGGGTKVTVL |
| 807B-M0008-A08 | QDIQMTQSPSSLSASVGDRVTITC | RASQSISSYLN | WYQQKPGKAPKLLIY | AASSLQS | GVPSRFSGSGSGTDFTLTISSLQPEDFATYYC | QQSYSTPLT | FGGGTKVEIK |
| 807B-M0008-B04 | QYELTQPPSASGTPGQRVTISC | SGTLSNIGTNIVS | WFQQLPGTAPKLLIY | NDHRRPS | GVPDRFSGSKSATSASLAISGLQSEDEADYYC | AAWDDSLNGW | FGGGTKLTVL |
| 807B-M0008-B08 | QDIQMTQSPSSLSASVGDRVTITC | RASQSISTYLN | WYQEKPGKAPELLIF | AASSLQG | GVPSRFSGSGSGTDFTLTISSLQPEDLATYYC | QQSYDIPLS | FGGGTKVEIK |
| 807B-M0008-D02 | QDIQMTQSPATLSLSLGERANFSC | RASEYISTYLA | WYQQKPGQAPRLLIY | DASVRAP | GTPARFSGTGSGTDFTLTISSLQPDDFAVYFC | QERYDWPLT | FGPGTRLDVK |
| 807B-M0008-D05 | QSALTQPPSASGTPGQRVTISC | SGSSSNIGRNFVY | WYRQLPGTAPKLLIY | ENNQRPS | GVPDRFSGSKSGTSASLAISGLRSEDEADYHC | AAWDDSLSGLV | FGGGTKLTVL |
| 807B-M0008-E01 | QDIQMTQSPGTLSLSPGERGTLSC | RASQSVSSRYLA | WYQQKPGQAPRLLIY | GASSRAP | GIPDRFSGSGSGTDFTLTISSLEPEESAVYYC | QQYGSSPVT | FGGGTKVEIK |
| 807B-M0008-E06 | QYELTQPPSASGTPGQRVTISC | SGSSSNIGSNYVY | WHQQLPGTAPKLLIS | RNNQRPS | GVPDRFSGSKSGTSASLAISGLRSEDEADYYC | AAWDDSLSGYV | FGAGTKVTVL |
| 807B-M0008-G11 | QSVLTQPASVSGSPGQSITISC | TGASSDVGGSNFVS | WYQQHPGKAPKLIIY | DVSNRPS | GVSNRFSGSKSGNTASLTISGLQAEDDDDTDYYC | SSYTSSSLVV | FGGGTKLTVL |
| 807B-M0009-A06 | QSVLTQPPSASGTPGQRVSISC | SGSSSNIGSYYVY | WYQHLPGTAPKLLIY | RNNQRPS | GVPDRFSGSKSGTSASLAISGLRSEDESDYYC | AAWDDRLSTWV | FGGGTKLTVL |
| 807B-M0009-A09 | QYELTQPPSVSVSPGQTASITC | SGDKLGDKYAS | WYQQKPDQSPVLVIY | QDRKRPS | GIPERFSGSNSGNTATLTISGTQAMDEADYYC | QAWDSNTVV | FGGGTKLTVL |
| 807B-M0009-B07 | QDIQMTQSPGTLSLSPGERATLSC | RASQSVSSSYLA | WYQQKPGQAPRLLIY | GASSRAT | GIPDRFSGSGSGTDFTLTISRLEPEDFAVYYC | QQYGSSGWT | FGQGTKVEIK |

TABLE 11-continued

Amino acid sequences of the VL chains of the antibodies identified using the screening strategies of Examples 21 and 22

| Antibody Name | VL-FR 1 | VL-CDR 1 | VL-FR 2 | VL-CDR 2 | VL-FR 3 | VL-CDR 3 | VL-FR 4 |
|---|---|---|---|---|---|---|---|
| 807B-M0009-C02 | QYELTQPPSVSVSPGQTASITC | SGDKLGDKYTS | WHQQKPGQSPVLVIY | QDRKRPS | GIPERFSGSNSGNTATLTISGTQAMDEADYYC | QAWDSNTVV | FGGGTKLTVL |
| 807B-M0009-C03 | QSELTQPPSASGTPGQRVTISC | SGSSSNIGSNYVY | WYQQLPGTAPKLLIY | RNNQRPS | GVPDRFSGSKSGTSASLAISGLQSEDEADYYC | AAWDDSLNAWV | FGGGTKLTVL |
| 807B-M0009-F06 | QDIQMTQSPLSLPVTPGEPASISC | KSSQSLLHSNGYNYLD | WYLQKPGQSPQLLIS | LGSNRAS | GVPARFSGSGSGTDFTLKISRVEAEDVGYYC | MQALQTIT | FGQGTRLEIK |
| 807B-M0009-G03 | QSVLTQSPSASASLGASVRVTC | TLSSGHSNYDIA | WHQQQPEKGPRY | LMKLNSD | GIPDRFSGSSSGTERYLTISSLQSEDEADYYC | QTWGTGLRV | FGGGTKLTVL |
| 807B-M0023-C03 | QSELTQPPSVSVSPGQTATITC | SGYDLGAKFVS | WYQQKSGQSPVLVM | YQDNKRPS | GIPERFSGSNSGNTATLTISGTQAMDEADYYC | QVWDSPSYI | FGTGTTVTVL |
| 807B-M0023-G05 | QDIQMTQSPGTLSLSPGERATLSC | RASQSVSSSYLA | WYQQKPGQAPRLLIY | GASSRAT | GIPDRFSGSGSGTDFTLTISSLHPEDFATYFC | QQGNSFPIT | FGQGTRLEIK |
| 807B-M0024-H08 | QDIQMTQSPSSLSASVGDRVSITC | RASQSISSHLN | WYQQKPGKVPKVLIY | GASRLQS | GVPSRFSGSGSGTDFTLTINSLQPEDFATYYC | QQSYRAPVFT | FGPGTKVDV |
| 807B-M0025-B05 | QSVLTQPPSASGTPGQRVTISC | SGSSSNIGRNPVN | WYQHLPGTAPKLLIY | GDNQRPS | GVPDRFSGSRSGTSASLAISGLQSEDEADYYC | AAWDDSLYGPV | FGGGTKLTVL |
| 807B-M0027-E08 | QSALTQPPSVSVSPGQTASITC | AGDELGNKYAS | WYQQKPGQSPVLVIY | QDRKRPS | GIPERFSGSHSGNTATLTISGTQALDEADYYC | QSWDSSSVI | FGGGTKVTVL |
| 807B-M0042-A05 | QDIQMTQSPSAMSASVGDRVTITC | RASQGISNYLA | WFQQKPGKVPKRLIY | AASSLQS | GVPSRFSGSGSGTEFTLTISSLQPEDFATYYC | LQHNSYPLT | FGGGTKVEIK |
| 807B-M0042-B05 | QSALTQPPSASGTPGQRVTISC | SGSSSNIGSHYVY | WYQQLPGTDPKLLIY | KSIQRPS | GVPDRFSGSKSGTSASLAISGLRSDDEGDYYC | AAWDDSLSGSYV | FGTGTKVTVL |
| 807B-M0046-E03 | QDIQMTQSPSSVSASVGDRVTLTC | RASQDISSWLA | WYQQKPGKAPKLLIY | AASRLQS | GVPSRFSGSGSGTDFSLTISSLQPDDFATYYC | QQSHSFPLS | FGGGTKVEIK |
| 807B-M0050-A04 | QDIQMTQSPSSLSVSPGERATLSC | RASQTISNDLA | WYQQTPGQAPRLLIY | GASSRAT | GIPDRFSGSGSGTDFTLTISNLQPEDFATYFC | QQADSPPLT | FGGGTKVEIK |
| 807B-M0050-B09 | QDIQMTQSPDSLAVSLGERATINC | QSSQSVLYSSNNKNYLA | WYQQKPGQPPKLLIY | GASTRES | GVPDRFSGSGSGTDFTLTISSLQAEDVAVYYC | QQYYTTPLT | FGGGTKVEIK |
| 807B-M0050-E04 | QDIQMTQSPSSVSASVGDRVTITC | RASQGISSWLA | WYQQKPGKAPKLLIY | PASSLQS | GVPSRFSGSGSGTDFTLTISSLQPEDFATYYC | QQGTSFPLT | FGGGTKVEIK |
| 807B-M0050-G01 | QDIQMTQSPSTLSASVGDRVTITC | RASQSISTWLA | WYQQKPGKAPKLLIY | KAFSLEG | GVPSRFSGSGSGTEFTLTISSLQPEDFATYYC | QQSYSPPLT | FGGGTKVDIR |
| 807B-M0050-G05 | QDIQMTQSPSSLSASVGDRVTITC | RASQGISNYLA | WYQQKPGKVPKLLIY | AASTLQS | GVPSRFSGSGSGTDFTLTISSLQPEDVATYYC | QNYNRAPRT | FGQGTKVEIK |
| 807B-M0050-H05 | QDIQMTQSPPSVSASVGDRVTITC | RASQVITRWLA | WYQQKPGQAPKLLIY | SASSLQS | GVPSRFSGSGSGTDFTLTISSLQPEDFATYYC | QQATSFPLT | FGGGTKVEIK |

TABLE 11-continued

Amino acid sequences of the VL chains of the antibodies identified using the screening strategies of Examples 21 and 22

| Antibody Name | VL-FR 1 | VL-CDR 1 | VL-FR 2 | VL-CDR 2 | VL-FR 3 | VL-CDR 3 | VL-FR 4 |
|---|---|---|---|---|---|---|---|
| 807B-M0050-H10 | QDIQMTQSPLSLSASV GDRVTITC | RASQSISS YLN | WYQHKPGKAPRLLIY | GASSLQN | GVPSRFTGSGTGTDFTLTISSLQPE DFATYYC | QQSFTTPLT | FGGGTKVE IK |

TABLE 12

Amino acid sequences of the VH chains of the antibodies identified using the screening strategies of Examples 21 and 22

| Isolate Name | VH-FR 1 | VH-CDR 1 | VH-FR 2 | VH-CDR 2 | VH-FR 3 | VH-CDR 3 | VH-FR 4 |
|---|---|---|---|---|---|---|---|
| 807B-M0001-A09 | EVQLLESGGGLVQPGGSLR LSCAASGFTFS | RYPMF | WVRQAPGK GLEWVS | SISSSGGYT VYADSVKG | RFTISRDNSKNTLYLQM NSLRAEDTAVYYCAR | VGKGAYYYAMDV | WGQGTTVTVSS |
| 807B-M0001-B07 | EVQLLESGGGLVQPGGSLR LSCAASGFTFS | FYGMV | WVRQAPGK GLEWVS | SISPSGGYT LYADSVKG | RFTISRDNSKNTLYLQM NSLRAEDTAVYYCAK | DGRRPHYGSGRW AY | WGQGTLVTVSS |
| 807B-M0001-C10 | EVQLLESGGGLVQPGGSLR LSCAASGFTFS | QYVMF | WVRQAPGK GLEWVS | SISSSGGKT SYADSVKG | RFTISRDNSKNTLYLQM NSLRAEDTAVYYCAR | RLKIYDSSGYYY YVGMDV | WGQGTTVTVSS |
| 807B-M0001-G03 | EVQLLESGGGLVQPGGSLR LSCAASGFTFS | SYAMS | WVRQAPGK GLEWVS | SISPSGGFT PYADSVKG | RFTISRDNSKNTLYLQM NSLRAEDTAVYYCAR | VGKGAYYYAWDV | WGQGTTVTVSS |
| 807B-M0004-A03 | EVQLLESGGGLVQPGGSLR LSCAASGFTFS | RYLMM | WVRQAPGK GLEWVS | VISPSGGRT WYADSVKG | RFTISRDNSKNTLYLQM NSLRAEDTAVYYCVR | SIAAAGTDY | WGQGTLVTVSS |
| 807B-M0004-A05 | EVQLLESGGGLVQPGGSLR LSCAASGFTFS | NYFMI | WVRQAPGK GLEWVS | WISPSGGTT QYADSVKG | RFTISRDNSKNTLYLQM NSLRAEDTAVYYCAR | EAGY | WGQGTLVTVSS |
| 807B-M0004-B10 | EVQLLESGGGLVQPGGSLR LSCAASGFTFS | KYVMI | WVRQAPGK GLEWVS | SISPSGGDT TYADSVKG | RFTISRDNSKNTLYLQM NSLRAEDTAVYYCAR | DLGSNWGTGVVW N | WGQGTLVTVSS |
| 807B-M0004-C01 | EVQLLESGGGLVQPGGSLR LSCAASGFTFS | NYNMH | WVRQAPGK GLEWVS | SIYSSGGTT LYADSVKG | RFTISRDNSKNTLYLQM NSLRAEDTAVYYCAR | LVADEWIDAFDI | WGQGTMVTVSS |
| 807B-M0004-C04 | EVQLLESGGGLVQPGGSLR LSCAASGFTFS | AYYMG | WVRQAPGK GLEWVS | VIRPSGGKT KYADSVKG | RFTISRDNSKNTLYLQM NSLRAEDTAVYYCAR | GPHGQGGVDS | WGQGTLVTVSS |
| 807B-M0004-C05 | EVQLLESGGGLVQPGGSLR LSCAASGFTFS | EYFMT | WVRQAPGK GLEWVS | SIRPSGGKT RYADSVKG | RFTISRDNSKNTLYLQM NSLRAEDTAVYYCAR | VSRYYNNGAYRL DAFDI | WGPGTVVTVSS |
| 807B-M0004-D10 | EVQLLESGGGLVQPGGSLR LSCAASGFTFS | WYQMS | WVRQAPGK GLEWVS | VISPSGGRT IYADSVKG | RFTISRDNSKNTLYLQM NSLRAEDTAVYYCAR | QGLLTAFDI | WGQGTMVTVSS |
| 807B-M0004-F06 | EVQLLESGGGLVQPGGSLR LSCAASGFTFS | AYRMA | WVRQAPGK GLEWVS | YISSSGGVT SYADSVKG | RFTISRDNSKNTLYLQM KSLRAEDTAVYYCAR | GTHLPGVDY | WGQGTLVTVSS |
| 807B-M0004-F07 | EVQLLESGGGLVQPGGSLR LSCAASGFTFS | EYYMT | WVRQAPGK GLEWVS | SIRPSGGAT RYADSVKG | RFTISRDNSKNTLYLQM NSLRAEDTAVYYCAR | EPIWGYYYGMD V | WGQGTTVTVSS |
| 807B-M0004-F10 | EVQLLESGGGLVQPGGSLR LSCAASGFTFS | GYIMA | WVRQAPGK GLEWVS | GIGSSGGLT AYADSVKG | RFTISRDNSKNTLYLQM NSLRAEDTAVYYCAR | EAGY | WGQGTLVTVSS |
| 807B-M0004-G08 | EVQLLESGGGLVQPGGSLR LSCAASGFTFS | TYAMA | WVRQAPGK GLEWVS | SIRSSGGVT KYADSVKG | RFTISRDNSKNTLYLQM NSLRAEDTAVYYCAR | GGAVAGY | WGQGTLVTVSS |
| 807B-M0004-H03 | EVQLLESGGGLVQPGGSLR LSCAASGFTFS | SYPMV | WVRQAPGK GLEWVS | GIWSSGGLT YYADSVKG | RFTISRDNSKNTLYLQM NSLRAEDTAVYYCAR | EGSAGVVKGPAR YYYYYMDV | WGKGTTVTVSS |
| 807B-M0008-A03 | EVQLLESGGGLVQPGGSLR LSCAASGFTFS | HYTMY | WVRQAPGK GLEWVS | GISPSGGVT PYADSVKG | RFTISRDNSKNTLYLQM NSLRAEDTAVYYCAR | AGSGGSFDY | WGQGTLVTVSS |
| 807B-M0008-A08 | EVQLLESGGGLVQPGGSLR LSCAASGFTFS | KYLMM | WVRQAPGK GLEWVS | YIWPSGGTD YADSVKG | RFTISRDNSKNTLYLQM NSLRAEDTAVYYCAK | VRTSRINGSFD Y | WGQGTLVTVSS |
| 807B-M0008-B04 | EVQLLESGGGLVQPGGSLR LSCAASGFTFS | RYPMS | WVRQAPGK GLEWVS | SISPSGGPT SYADSVKG | RFTISRDNSKNTLYLQM NSLRAEDTAVYYCAR | SGPYYFDY | WGQGTLVTVSS |
| 807B-M0008-B08 | EVQLLESGGGLVQPGGSLR LSCAASGFTFS | HYPMS | WVRQAPGK GLEWVS | SISPSGGFT MYADSVKG | RFTISRDNSKNTLYLQM NSLRAEDTAVYYCAR | FEYSSSSGISWF DP | WGQGTLVTVSS |

TABLE 12-continued

Amino acid sequences of the VH chains of the antibodies identified using the screening strategies of Examples 21 and 22

| Isolate Name | VH-FR 1 | VH-CDR 1 | VH-FR 2 | VH-CDR 2 | VH-FR 3 | VH-CDR 3 | VH-FR 4 |
|---|---|---|---|---|---|---|---|
| 807B-M0008-D02 | EVQLLESGGGLVQPGGSLR LSCAASGFTFS | KYGMT | WVRQAPGK GLEWVS | SIRPSGGIT KYADSVKG | RFTISRDNSKNTLYLQM NSLRAEDTAVYYCAR | ENYGPDY | WGQGTLVTVSS |
| 807B-M0008-D05 | EVQLLESGGGLVQPGGSLR LSCAASGFTFS | TYHMF | WVRQAPGK GLEWVS | GISSSGGST RYADSVKG | RFTISRDNSKNTLYLQM NSLRAEDTAVYYCAR | VSVTTNAFDI | WGQGTMVTVSS |
| 807B-M0008-E01 | EVQLLESGGGLVQPGGSLR LSCAASGFTFS | TYAMT | WVRQAPGK GLEWVS | SISSSGGT KYADSVKG | RFTISRDNSKNTLYLQM NSLRAEDTAVYYCAR | HGYSSGWPPFDY | WGQGTLVTVSS |
| 807B-M0008-E06 | EVQLLESGGGLVQPGGSLR LSCAASGFTFS | HYPMS | WVRQAPGK GLEWVS | SIVPSGGYT LYADSVKG | RFTISRDNSKNTLYLQM NSLRAEDTAVYYCAR | HNRAIGTFDY | WGQGTLVTVSS |
| 807B-M0008-G11 | EVQLLESGGGLVQPGGSLR LSCAASGFTFS | SYAMI | WVRQAPGK GLEWVS | GISPSGGQT VYADSVKG | RFTISRDNSKNTLYLQM NSLRAEDTAVYYCAR | AGSGGSFDY | WGQGTLVTVSS |
| 807B-M0009-A06 | EVQLLESGGGLVQPGGSLR LSCAASGFTFS | VYNMV | WVRQAPGK GLEWVS | VISPSGGST YYADSVKG | RFTISRDNSKNTLYLQM NSLRAEDTAVYYCAR | DRGYCSGNTCYI DAFDI | WGQGTMVTVSS |
| 807B-M0009-A09 | EVQLLESGGGLVQPGGSLR LSCAASGFTFS | RYPMA | WVRQAPGK GLEWVS | GISSSGGLT SYADSVKG | RFTISRDNSKNTLYLQM NSLRAEDTAVYYCAR | FVGAKPADY | WGQGTLVTVSS |
| 807B-M0009-B07 | EVQLLESGGGLVQPGGSLR LSCAASGFTFS | FYWMV | WVRQAPGK GLEWVS | GISPSGGPT KYADSVKG | RFTISRDNSKNTLYLQM NSLRAEDTAVYYCAR | EPIWGYYYYGMD V | WGQGTTVTVSS |
| 807B-M0009-C02 | EVQLLESGGGLVQPGGSLR LSCAASGFTFS | SYPMT | WVRQAPGK GLEWVS | GISSSGGST AYADSVKG | RFTISRDNSKNTLYLQM NSLRAEDTAVYYCAK | VTGGDFDY | WGQGTLVTVSS |
| 807B-M0009-C03 | EVQLLESGGGLVQPGGSLR LSCAASGFTFS | KYQMT | WVRQAPGK GLEWVS | VISSSGGDT AYADSVKG | RFTISRDNSKNTLYLQM NSLRAEDTAVYYCAR | DRGYCSGNTCYI DAFDI | WGQGTMVTVSS |
| 807B-M0009-F06 | EVQLLESGGGLVQPGGSLR LSCAASGFTFS | PYWMF | WVRQAPGK GLEWVS | GIVSSGGMT GYADSVKG | RFTISRDNSKNTLYLQM NSLRAEDTAVYYCAR | VGMSTYAFDI | WGQGTMVTVSS |
| 807B-M0009-G03 | EVGLLESGGGLVQPGGSLR LSCAASGFTFS | PYRMA | WVRQAPGK GLEWVS | SISPSGGHT GYADSVKG | RFTISRDNSKNTLYLQM NSLRAEDTAVYYCAR | ESDGTTSAYFDY | WGQGTLVTVSS |
| 807B-M0023-C03 | EVQLLESGGGLVQPGGSLR LSCAASGFTFS | SYMMG | WVRQAPGK GLEWVS | YIYPSGGWT YYADSVKG | RFTISRDNSKNTLYLQM NSLRAEDTAVYYCAR | GRSWGRYFQH | WGQGTLVTVSS |
| 807B-M0023-G05 | EVQLLESGGGLVQPGGSLR LSCAASGFTFS | MYWMG | WVRQAPGK GLEWVS | SISPSGGFT MYADSVKG | RFTISRDNSKNTLYLQM NSLRAEDTAVYYCAR | GLYR | WGQGTLVTVSS |
| 807B-M0024-H08 | EVQLLESGGGLVQPGGSLR LSCAASGFTFS | AYNMD | WVRQAPGK GLEWVS | SIYPSGGHT NYADSVKG | RFTISRDNSKNTLYLQM NSLRAEDTAVYYCAR | GKRIAARGGYYF DY | WGQGTLVTVSS |
| 807B-M0025-B05 | EVQLLESGGGLVQPGGSLR LSCAASGFTFS | NYSMV | WVRQAPGK GLEWVS | SIVPSGGFT LYADSVKG | RFTISRDNSKNTLYLQM NSLRAEDTAVYYCAR | HGSSWTFDY | WGQGTLVTVSS |
| 807B-M0027-E08 | EVQLLESGGGLVQPGGSLR LSCAASGFTFS | NYRME | WVRQAPGK GLEWVS | SIWSSGGLT KqADSVKG | RFTISRDNSKNTLYLQM NSLRAEDTAVYYCAR | GLYR | WGQGTLVTVSS |
| 807B-M0042-A05 | EVQLLESGGGLVQPGGSLR LSCAASGFTFS | HYQMK | WVRQAPGK GLEWVS | SIGSSGGST SYADSVKG | RFTISRDNSKNTLYLQM NSLRAEDTAVYYCAR | GPL | WGQGTLVTVSS |
| 807B-M0042-B05 | EVQLLESGGGLVQPGGSLR LSCAASGFTFS | NYHMD | WVRQAPGK GLEWVS | SISPSGGIT KYADSVKG | RFTISRDNSKNTLYLQM NSLRAEDTSVYYCAG | GVGATAGI | WGQGTMVTVSS |
| 807B-M0046-E03 | EVQLLESGGGLVQPGGSLR LSCAASGFTFS | PYAMI | WVRQAPGK GLEWVS | YISPSGGKT QYADSVKG | RFTISRDNSKNTLYLQM NSLRAEDTAVYYCAK | DQQTDYFDY | WGQGTLVTVSS |
| 807B-M0050-A04 | EVQLLESGGGLVQPGGSLR LSCAASGFTFS | QYNMN | WVRQAPGK GLEWVS | GISSSGGPT VYADSVKG | RFTISRDNSKNTLYLQM NSLRAEDTAVYYCAR | FRCTSTSCFSDY | WGQGTLVTVSS |
| 807B-M0050-B09 | EVQLLESGGGLVQPGGSLR LSCAASGFTFS | NYGML | WVRQAPGK GLEWVS | VISSSGGYT FYADSVKG | RFTISRDNSKNSLYLQM NSLRAEDTAVYYCAR | VGATGPFDI | WGQGTMVTVSS |
| 807B-M0050-E04 | EVQLLESGGGLVQPGGSLR LSCAASGFTFS | RYSMM | WVRQAPGK GLEWVS | GISPSGGPT SYADSVKG | RFTISRDNSKNTLYLQM NSLRAEDTAVYYCAR | ENIEYSSSFPNM GRPHYYYYGMD V | WGQGTTVTVSS |
| 807B-M0050-G01 | EVQLLESGGGLVQPGGSLR LSCAASGFTFS | RYEMY | WVRQAPGK GLEWVS | VISSSGGTT FYADSVKG | RFTISRDNSKNTLYLQM NSLRAEDTAVYYCAR | GGDNWNYLSV | WGQGTTVTVSS |

TABLE 12-continued

Amino acid sequences of the VH chains of the antibodies identified using the screening strategies of Examples 21 and 22

| Isolate Name | VH-FR 1 | VH-CDR 1 | VH-FR 2 | VH-CDR 2 | VH-FR 3 | VH-CDR 3 | VH-FR 4 |
|---|---|---|---|---|---|---|---|
| 807B-M0050-G05 | EVQLLESGGGLVQPGGSLR LSCAASGFTFS | PYPMD | WVRQAPGK GLEWVS | VISSSGGTT YYADSVKG | RFTISRDNSKNTLYLQM NSLRAEDTAVYYCAR | VGMSTYAFDI | WGQGTMVTVSS |
| 807B-M0050-H05 | EVQLLESGGGLVQPGGSLR LSCAASGFTFS | NYVMH | WVRQAPGK GLEWVS | SIGPSGGGT EYADSVKG | RFTISRDNTKNTLYLQM NSLRAEDTAVYYCAR | DRGYCSGNTCYI DAFDI | WGQGTMVTVSS |
| 807B-M0050-H10 | EVQLLESGGGLVQPGGSLR LSCAASGFTFS | TYPMQ | WVRQAPGK GLEWVS | VISSSGGYT QYADSVKG | RFTISRDNSKNTLYLQM NSLRAEDTAVYYCAS | MRVDYGDNYGMD V | WGQGTTVTVSS |

TABLE 13

| Isolate Name | Peptide | Enrichment VH | CDR3 | Peptide Mapping 1 | 2 | 3 | 4 | 5 | 6 | 7 | 8 | 9 | 10 | bCTD | Fab IHC | Group |
|---|---|---|---|---|---|---|---|---|---|---|---|---|---|---|---|---|
| 807B-MO001-A09 | E22-P1 | 6 | 8 | + | | | | | | | | | | | +/− | 4 |
| 807B-MO001-B07 | E22-P1 | 2 | 2 | + | | | | | + | | | | | + | | |
| 807B-MO001-C10 | E22-P1 | 1 | 1 | + | | | | | | | | | | | | |
| 807B-MO001-G03 | E22-P1 | 2 | 8 | + | | | | | | | | | | | | |
| 807B-MO042-A05 | E22-P2 | 1 | 1 | | + | | | | | | | | | | | |
| 807B-MO042-B05 | E22-P2 | 7 | 7 | | + | | | | | | | | | | | |
| 807B-MO050-A04 | E22-P3 | 19 | 19 | | | + | | | | | | | | | | |
| 807B-MO050-B07 | E22-P3 | 20 | 20 | | | + | | | | | | | + | | | |
| 807B-MO050-B09 | E22-P3 | 4 | 4 | | | + | | | | | | | | | | |
| 807B-MO050-E04 | E22-P3 | 1 | 1 | | | + | | | | | | | | | | |
| 807B-MO050-G01 | E22-P3 | 2 | 2 | | | + | | | | | | | | | | |
| 807B-MO050-G05 | E22-P3 | 2 | 3 | | | + | | | | | | | | | | |
| 807B-MO050-H05 | E22-P3 | 1 | 8 | | | + | | | | | | | | | | |
| 807B-MO050-H10 | E22-P3 | 1 | 1 | | | + | | | | | | | | | | |
| 807B-MO004-A03 | E22-P4 | 5 | 5 | | | | + | | | | | + | + | | + | 5 |
| 807B-MO004-A05 | E22-P4 | 2 | 3 | | | | + | | | | | | | | +/− | 1 |
| 807B-MO004-B10 | E22-P4 | 3 | 3 | | | | + | | | | | | | | | |
| 807B-MO004-C01 | E22-P4 | 2 | 2 | | | | + | | | | | | | | | |
| 807B-MO004-C04 | E22-P4 | 1 | 1 | | | | + | | | | | | | | +/− | 1 |
| 807B-MO004-C05 | E22-P4 | 1 | 1 | | | | + | | | | | | | | +/− | 1 |
| 807B-MO004-D10 | E22-P4 | 1 | 1 | | | | + | | | | | | | | | |
| 807B-MO004-F06 | E22-P4 | 2 | 2 | | | | + | | | | | | | | +/− | 1 |
| 807B-MO004-F07 | E22-P4 | 1 | 4 | | | | + | | | | | | | | | |
| 807B-MO004-F10 | E22-P4 | 1 | 3 | | | | + | | | | | + | | | +/− | 2 |
| 807B-MO004-G08 | E22-P4 | 1 | 1 | | | | + | | | | | | | | | |
| 807B-MO004-H03 | E22-P4 | 1 | 1 | | | | + | | | | | + | | | + | 2 |
| 807B-MO023-C03 | E23-P4 | 1 | 1 | | | | + | | | | | | | | | |
| 807B-MO023-G05 | E23-P4 | 1 | 149 | | | | + | | | | | | | | | |
| 807B-MO024-H08 | E23-P4 | 4 | 4 | | | | + | | | | | | | | | |
| 807B-MO046-E03 | E22-P7 | 3 | 3 | | | | | | | + | | | | | | |
| 807B-MO008-A03 | E22-P8 | 2 | 3 | | | | | | | | + | | | | | |
| 807B-MO008-A08 | E22-P8 | 1 | 1 | | | | | | | | + | | | | | |
| 807B-MO008-B04 | E22-P8 | 2 | 2 | | | | | | | | + | | | | | |
| 807B-MO008-B08 | E22-P8 | 1 | 1 | | | | | | | | + | | | + | | |
| 807B-MO008-D02 | E22-P8 | 5 | 5 | | | | | | | | + | | | | | |
| 807B-MO008-D05 | E22-P8 | 2 | 2 | | | | | | | | + | | | | | |
| 807B-MO008-E01 | E22-P8 | 2 | 2 | | | | | | | | + | | | | | |
| 807B-MO008-E06 | E22-P8 | 1 | 1 | | | | | | | | + | | | | | |
| 807B-MO008-G11 | E22-P8 | 1 | 3 | | | | | | | | + | | | | | |
| 807B-MO008-G12 | E22-P8 | 1 | 1 | | | | | | | | + | | | | | |
| 807B-MO025-B05 | E23-P8 | 1 | 1 | | | | | | | | + | | | + | | |
| 807B-MO027-E08 | E23-P8 | 148 | 149 | | | | + | | | | + | | | + | + | 6 |
| 807B-MO009-A06 | E22-P9 | 5 | 8 | | | | + | | | | | + | | | | |
| 807B-MO009-A09 | E22-P9 | 15 | 15 | | | | | | | | | + | | | | |
| 807B-MO009-B07 | E22-P9 | 4 | 5 | + | + | +/− | + | + | + | + | + | + | | | | |
| 807B-MO009-C02 | E22-P9 | 13 | 13 | | | | | | | | | + | | | | |
| 807B-MO009-C03 | E22-P9 | 2 | 8 | | | | + | | | | | + | | | +/− | 5 |
| 807B-MO009-F06 | E22-P9 | 1 | 3 | | | | | | | | | + | | | | 3 |
| 807B-MO009-G03 | E22-P9 | 1 | 1 | | | | + | | | | | + | | | | |

TABLE 14

Amino acid sequences of the VL chains of the antibodies identified using the screening strategy of Example 23

| Isolate Name | FR 1 | CDR 1 | FR 2 | CDR 2 | FR 3 | CDR 3 | FR 4 |
|---|---|---|---|---|---|---|---|
| 807B-M0011-C07 | QYELTQPPSASGS PGQSVTISC | TGTSSDVGTYKYVS | WYQQHPDKAPR LIIY | EVNRRPS | GVPDRFSGSKSGNTAS LTISGLQAEDEADYYC | YSHATGNNYV | FGTGTKVTVL |
| 807B-M0012-C09 | QSELTQPPSASGT PGRVTISC | SGTLSNIGTNIVS | WFQQLPGTAPK LLIY | NDHRRPS | GVPDRFSGSKSATSAS LAISGLQSEDEADYYC | AAWDDSLNGVV | FGGGTKLTVL |
| 807B-M0012-D09 | QDIQMTQSPATLS LSPGERATLSC | RASQSVSSYLA | WYQQKPGQAPR LLIY | DASNRAT | GIPARFSGSGSGTDFT LTISSLEPEDFAVYYC | QQRSNWPRYT | FGQGTKLEIK |
| 807B-M0012-F10 | QDIQMTQSPSFLS ASVGDRVTITC | RASQGISNYLA | WYQQKPGKAPK LLIY | VASALQS | GVPSRFSGSGSGTEFT LTISSLQPEDFATYYC | QQYYSYSA | FGQGTRVEIK |
| 807B-M0012-F12 | QDIQMTQSPATLS VSPGERATLSC | RASQSVSSNLA | WYQQKPGQAPR LLIY | AASSLQS | GVPSRFSGSGSGTDFT LTVSSLQPEDFATYYC | QQTYSTPWT | FGQGTKLEIK |
| 807B-M0012-G05 | QDIQMTQSPGTLS LSPGERATLSC | RASRSLFSTYLA | WYQQKPGQPPR LLIY | GASTRAT | GIPDRFSGSGSGTDFT LTISRLEPEDSALYYC | QQYVSSQLT | FGGGTKVEIK |
| 807B-M0013-A12 | QDIQMTQSPSTLS ASVGDRVTITC | RASQSISRWLA | WYQQKPGKAPK LLIY | AASSLQS | GVPSRFSGSGSGTDFT LTISSLQPEDFATYYC | QQSYSTPLT | FGGGTKVEIK |
| 807B-M0013-B04 | QDIQMTQSPSSLP ASVGDRVTITC | RASQNIVTYLN | WYQQKPGKAPK LLIY | AASSLQS | GVPSRFSGSGSGTDFT LTISSLQPEDFATYYC | QQSYSMSSWT | FGQGTNLEIK |
| 807B-M0013-C03 | QDIQMTQSPDSLS ASVGDRVTITC | RASQSISSYLN | WYQQKPGKAPK LLIY | AASSLQS | GVPSRFSGSGSGTDFT LTISSLQPEDFATYYC | QQSYSTPPYT | FGQGTKLEIK |
| 807B-M0013-F06 | QYELTQPPSASGT PGRVTISC | SGSGSNIGSNLVY | WYQQLPGTAPK LLIY | RNTQRPS | GVPDRFSASKSGTSAS LAISGLRSEDEADYHC | ATWDDSLGGVV | FGGGTKLTVL |
| 807B-M0013-G05 | QDIQMTQSPGTLS LSPGERATLSC | RASQSLSSSYLA | WYQQKPGQPPR LLIY | GASRRAT | GIPDRFSGSGSGTDFT LTISRLEPEDFAVYYC | QHYGRSPLFT | FGPGTTVDIK |
| 807B-M0014-D07 | QDIQMTQSPATLS LSPGESTTLSC | RASQSVSRYVA | WYQQKPGQSPR LVIY | DASNRAT | GIPARFSGSGSGTDFT LTITSLEPEDFGIYYC | LQRSNWPFT | FGPGTKVEIK |
| 807B-M0014-D09 | QDIQMTQSPSSFS ASTGDRVTITC | RASQGVGSYLA | WYQQKPGKAPK LLIY | GAYTLQS | GVPSRFSGSGSGTDFT LIISGLQSEDFATYYC | QQYYSYPFT | FGPGTKVDIK |
| 807B-M0014-E08 | QDIQMTQSPSSLS ASVGDRVTITC | RASQDIRDDLG | WYQQKPGKAPK RLIY | AASSLQS | GVPSRFSGSGSGTEFT LTISSLQPEDFATYYC | QQHNNYPSFT | FGPGTRLDIK |
| 807B-M0014-F07 | QDIQMTQSPSSLS ASVGDRVAITC | RASQSIDTYLN | WYQQKPGKAPK LLIY | AASKLED | GVPSRFSGSGTGTDFT LTIRSLQPEDFASYFC | QQSYSSPGIT | FGPGTKVEIK |
| 807B-M0016-C06 | QDIQMTQSPSSLS ASVGDRVTITC | RASQSINTYLN | WYQQKPGQAPK LLIY | ASSTLQR | GVPSRFSGSGSGTDFT LTISSLQLEDFATYFC | QQSYSPPLYT | FGQGTKLDLK |
| 807B-M0016-D01 | QDIQMTQSPSSLS ASVGDRVTITC | RASQSIDNYLN | WYQQKPGIAPK LLIY | TASSLQS | GVPSRFSGSGSGTDFT LTISSLQPEDFATYYC | QQSYTTPHT | FGQGTKLEIR |
| 807B-M0016-D08 | QDIQMTQSPSSLS ASVGDRVAITC | RASQSISSFLN | WYQQKPGKAPN LLIY | GASSLQS | GVPSRFSGSGSGTDFT LTISSLQPEDFATYYC | QQSYSTPYT | FGQGTKLEIK |
| 807B-M0016-E01 | QDIQMTQSPSSLS ASVGDRITITC | RASQSIGRYLN | WYQQKPGKAPK LLIY | TASSLQS | GVPSRFSGSGSGTDFT LTISSLQPEDFATYYC | QQSFTTPHT | FGLGTKLEIE |
| 807B-M0016-F04 | QDIQMTQSPATLS ASVGDRVTFTC | RASQSVNNWVA | WYQQKPGGAPE GLIY | KASHLQS | GVPSRFSGGGSGTVFT LTITSLQPDDFATYYC | QQYQTYPYT | FGQGTRLDMK |
| 807B-M0016-F05 | QDIQMTQSPSSLS ASVGDSVTITC | RASQSISTYLN | WYQQKPGKAPK LLIS | APSRLQS | GVPSRFSDSGSGTDFT LAISSLQPEDFATYYC | QQSYSTPVT | FGQGTKLEIK |
| 807B-M0016-F08 | QSALTQPRSVSGS PGQSVTISC | TGTSSDVGGYNYVS | WYQQHPGKAPK LMIY | DVSKRPS | GVPDRFSGSKSGNTAS LTISGLQAEDEADYYC | CSYAGNYSVV | FGGGAKLSVL |
| 807B-M0017-B05 | QDIQMTQSPGTLS LSPGERATLSC | RASQSVHSSYLA | WYQQKPGQAPR LLIY | GTSSRAT | GIPDRFSGNGFGTDFT LTISRLEPEDFAVYYC | QQYGSSPIT | FGQGTRLEIK |
| 807B-M0017-B06 | QYELTQPPSASGS PGQSVTISC | TGTSSDVGAYNYVS | WYKIHPGKAPK LMIY | DVNNRPS | GVSNRFSGSKSGNTAS LTISGLQAEDEADYYC | CSYAGSSTQV | FGTGTKVTVL |
| 807B-M0017-E05 | QDIQMTQSPGTLS LSPGERATLSC | RASQSVTSSYLA | WYQQKPGQAPR LLIY | GASSRAT | GIPDRFSGSGSGADFT LTISRLEPEDFAVYYC | QQYGTSPYT | FGQGTKLEIK |

TABLE 14-continued

Amino acid sequences of the VL chains of the antibodies identified using the screening strategy of Example 23

| Isolate Name | FR 1 | CDR 1 | FR 2 | CDR 2 | FR 3 | CDR 3 | FR 4 |
|---|---|---|---|---|---|---|---|
| 807B-M0018-C12 | QSELTQPPSASGS PGQTVTISC | TGSSRDIGNYNYVS | WYQQFPGKAPK LIIY | DVRKRPS | GVSDRFSGSKSGNTAF LTVSGLQTEDEADYFC | GSYTGTNNV | FGPGTSVTVL |
| 807B-M0018-E09 | QDIQMTQSPGTLS LSPGERATLSC | RASQSVSSSYLA | WYQQKPGQAPR LLIY | GASSRAT | GIPDRFSGSGSGTDFT LTISRLEPEDFAVYYC | QQYGSSRVT | FGGGTKVEIK |
| 807B-M0018-G02 | QDIQMTQSPSSLS ASIGDRVTITC | RASQDIRDDLG | WYQQKPGKAPK RLIY | AASSLQS | GVPSRFSGSGSGTEFT LTISSLQPEDFATYYC | LQHNTFPSFT | FGPGTKVDIK |
| 807B-M0019-A04 | QDIQMTQSPGTLS LSPGERATLSC | RASQSVSSSYLA | WYQQKPGQAPR LLIY | GASSRAT | GIPDRFSGSGSGTDFT LTISRLEPEDFAVYYC | QQYGSSSIT | FGQGTRLEIK |
| 807B-M0019-A10 | QDIQMTQSPLSLS ASIGDRVTITC | RASQDIRSDLG | WYQQKPGKAPK LLIY | GASTLQS | GVPSRFSGSGSGADFT LIISNLQPEDFATYYC | LQDYNYPRT | FGQGTKVEIK |
| 807B-M0019-C01 | QSALTQPASVSGS PGQPITISC | SGTSSDVGGYNYVS | WYQQHPGKAPK LVIY | DVSNRPS | GISYRFSGSKSVNTAS LTISGLQAEDEADYFC | SSYTSNSTLV | FGGGTQADRP |
| 807B-M0019-F06 | QSELTQPASVSGS PGQSITISC | TGTSSDVGSYNLVS | WYQQHPGKAPK LMIY | EGSKRPS | GVSNRFSGSKSGNTAS LTISGLQAEDEADYYC | CSYAGSSTLV | FGGGTKLTVL |
| 807B-M0019-G07 | QDIQMTQSPATLS ASVGDRVTITC | RASQGLASWLA | WYQQKPGKAPN LLIY | KASNLKS | GVPSRFSGSESGTEFT LTISSLQPDDFATYFC | HQYYSNSWT | FGQGTKVEIK |
| 807B-M0020-D01 | QDIQMTQSPSSLS ASVGDRVSIT. | RASQTIRDYLH | WYQQKPGKAPK LLIY | AASSLQV | GVPSRFSGSGSGTDFT LTISSLQPEDLATYYC | QQTYSTLIT | FGQGTRLEIK |
| 807B-M0020-F06 | QDIQMTQSPGTLS LSPGERATLSC | RASQSISYNYLA | WYQQKPGQAPR LLIY | DASNRAT | GIPARFSGSGSGTDFT LTISSLEPEDFAVYYC | QQRSNWPPGLT | FGGGTKVEIK |
| 807B-M0020-F12 | QDIQMTQSPSSLS ASVGDRVTITC | RASQDIRNYLA | WFQQKPGKAPK SLIY | GASSLQG | GVPSKFSGSGSGTDFT LTISGLQPEDFATYYC | QQYNSYPLT | FGGGTKVEVK |
| 807B-M0020-G01 | QSELTQPASVSGS PGQSITISC | TGTSSDVGSYNLVS | WYQQHPGKAPK LMIY | EGSKRPS | GVSNRFSGSKSGNTAS LTISGLQAEDEADYYC | CSYAGSSTYV | FGTGTKVTVL |
| 807B-M0079-B09 | QDIQMTQSPSSLS ASVGDRVTITC | RASQSISSYLN | WYQQKPGNAPR LLIY | SASTLNS | GVPSRFSGSGSGTHFT LTISSLQPEDFGIYYC | QQANSLPFT | FGQGTKLEIK |
| 807B-M0079-D10 | QSALTQPPSVSVS PGQTASITC | AGDELGNKYAS | WYQQKPGQSPV LVIY | QDRKRPS | GIPERFSGSHSGNTAT LTISGTQALDEADYYC | QSWDSSSVI | FGGGTKVTVL |
| 807B-M0079-H01 | QDIQMTQSPSSLS ASVGDRVTITC | RASQSISSYLN | WYQQKPGKAPK LLIY | AASSLQS | GVPSRFSGSGSGTDFT LTISSLQPEDFATYYC | QQSYSTPFT | FGPGTKVDIK |
| 807B-M0079-H05 | QDIQMTQSPSSLS ASVGDRVTITC | RASQGINSWLA | WYQQRPGKAPR SLIY | AATNLQN | GVPSRFSGSGSGTLFT LTINNLQPEDFATYYC | QQYQNYPYT | FGQGTKLDIE |
| 807B-M0080-A02 | QDIQMTQSPLSLS ASVGDRVTIPC | RASQSISTYLN | WYQQKPGKAPK ILIY | AASSLQS | GVPSRFSGSGSGTDFT LTISSLQPEDFATYFC | QQSYTTPLT | FGGGTKVEIK |
| 807B-M0080-C04 | QSALTQPPSASGT PGQTVAISC | SGTSNIGSNNVN | WYQQLPGTAPK LLMY | TTNYRPS | GVPARFSGSKSGTSAS LAISGLQSEDEADYYC | AAWDDSLNGPNVV | FGGGTKLTVL |
| 807B-M0080-F10 | QDIQMTqSPSVS ASIGDRVTITC | RASQGISIWLA | WYQQKPGKAPK LLIY | GASSLQS | GAPSRFSGSGSGTDFT LTISSLQPEDFATYYC | QQANSFPLT | FGGGTKVEIK |
| 8075-M0081-C03 | QDIQMTQSPSTLS ASVGDRVTITC | RASQSINRWLA | WYQQKPGKAPK LLIY | KASNLES | GAPSRFSGSGSGTEFT LTISSLQPDDFGTYYC | QQYHSYPWT | FGQGTKVDVK |
| 807B-M0081-C05 | QSALTQPPSVSGA PGQRVTISC | TGSSSNIGAPYDVH | WYQQVPGTAPK VLIY | GNNHRPS | GVPDRFSGSKSGTSAS LAISGLQAEDEAHYYC | QSYDSSLSGPI | FGGGTTLTVL |
| 807B-M0081-D08 | QDIQMTQSPSSVS ASVGDRVTITC | RASQGISSWLA | WYQQKPGKAPK LLIY | AASSLQS | GVPSRFSGSGSGTDFT LTISSLQPEDFATYYC | QQANSFPPT | FGQGTKVEIQ |
| 807B-M0081-E08 | QDIQMTQSPSSLP ASVGDRVTITC | RASRNIGKYLN | WYQQIRGRAPR LLVY | LASSVQT | GVPPRFSGSGSGTDFS LIISSLQPEDFATYYC | QQSYAAPLT | FGGGTKVEIK |
| 807B-M0081-F12 | QDIQMTqSPSSLS ASVGDRVTITC | RASQSISSYLN | WYQQKPGKAPK LLIY | AASSLQS | GVPSRFSGSGSGTEFS LSISSLQPEDFATYYC | QQANSFPLT | FGGGTKVEIK |
| 807B-M0081-G04 | QDIQMTQSPDTLS LSPGERATLSC | RASQSISTSLA | WYHQRPGQAPR LLIY | DASNRAT | GVPARFSGTGSGTDFT LTISSLEPEDFAVYYC | QQRSNWPYT | FGQGTKLEIK |

TABLE 14-continued

Amino acid sequences of the VL chains of the antibodies identified using the screening strategy of Example 23

| Isolate Name | FR 1 | CDR 1 | FR 2 | CDR 2 | FR 3 | CDR 3 | FR 4 |
|---|---|---|---|---|---|---|---|
| 807B-M0081-G11 | QDIQMTQSPSSLS ASVGDRVAITC | RASQSIDTYLN | WYQQKPGKAPK LLIY | AASKLED | GVPSRFSGSGTGTDFT LTIRSLQPEDFASYFC | QQSYSSPGIT | FGPGTKVEIK |
| 807B-M0081-H03 | QYELTQPPSASGS PGQSVTISC | TGTSSDVGGYNYVS | WYQQHPGKAPK FMIY | EVNKRPS | GVPDRFSGSKSGNTAS LTVSGLQAEDEADYYC | SSYAGRNFVV | FGGGTKLTVL |
| 807B-M0081-H07 | QDIQMTQSPSSLS ASVGDRVTITC | RASQSISSYLN | WYQQKPGKAPK LLIY | AASSLQS | GVPSRFSGSGSGTDFT LIISDLQPEDFATYYC | QQSYTTPFT | FGPGTTVDIK |
| 807B-M0082-B07 | QSALTQPASVSGS PGQSITISC | TGTSSDVGGYNYVS | WYQQHPGKAPK LMIY | DVSNRPS | GVSNRFSGSKSGNTAS LTISGLQAEDEADYYC | SSYTSRSTYV | FGTGTKVTVL |
| 8075-M0082-E01 | QDIQMTQSPSSLS ASVGDRVAITC | RASQSIDTYLN | WYQQKPGKAPK LLIY | AASSLQS | GVPSRFSGSGSGTDFT LTVSSLQPEDFATYYC | LQSNTFPFT | FGPGTKVDIT |
| 807B-M0082-E08 | QDIQMTQSPSSLS ASIGDRVTITC | RASQSISSYLN | WYQQKQGKAPK LLMF | AASSLKS | GVPSRFSGSGSGTDFT LTISNLQPEDFATYYC | QQTYSSPWT | FGQGTKVEIR |
| 807B-M0082-H06 | QDIQMTQSPSSLS ASVGDRVTVTC | RASQGIRNNLA | WYQQRPGKAPK RLIY | GASNLHS | GVPSRFSGSGSGTEFT LTISSLQPEDFATYYC | LQHNNYPYS | FGQGTKLEIK |
| 807B-M0083-B10 | QDIQMTQSPSSVS ASVGDRVTIIC | RASQDIHTWLA | WYQQKPGKAPK LLIY | AASSLQS | GVPSRFSGSGSGTDFT LTISSLQPEDFATYYC | QQSYSTPRT | FGQGTKVEIK |
| 807B-M0083-E10 | QDIQMTQSPGTLS LSPGERATLSC | RASQSISSRYLA | WYQQKAGQAPR LLMY | GASRAT | GIPARFSGSGSGTDFT LTISSLQPEDFATYYC | QQSYEYPLT | FGQGTKLEIK |
| 807B-M0083-E11 | QSALTQPPSVSVA PGQTARITC | GGNNIGTKIVN | WYQQRPGQAPV VVVY | DNSDRPS | GIPERFSGSNSGNTAT LTISRVEAGDEADYYC | QLWDSSSDHPI | FGTGTKVTVL |
| 807B-M0084-C03 | QYELTQPPSVSVA PGQTARISC | GGSNIGSKSVH | WYQQKSGQAPV LVVY | DDSDRPS | GIPERFFGSNSGRTAT LTISGVEVGDEADYYC | QVWDSSSDDYV | FAAGTKLSVL |
| 807B-M0084-C11 | QDIQMTQSPSSLS ASVGDRVTITC | RASQSIATFLN | WYQQKPGKAPN LLIS | GAFNLQS | GVPSRFSGSGSGTDFT LTISSLQPEDFATYYC | QHSYGTPT | FGQGTKVEIK |
| 807B-M0084-E07 | QDIQMTQSPSSLP ASVGDRVTITC | RASQSISRYLN | WYQQKPGKAPK VMIY | DASTLQS | GVPSRFSGSGSGTDFT LTISNLQPEDFATYYC | QQSYITPRT | FGQGTKVEIK |
| 807B-M0084-F03 | QDIQMTQSPATLS VSPGERATLSC | RASQSVSNNLA | WYQQKPGQAPR LLIY | AASTRAT | GIPARFSGSGSGTDFT LTISSLEPEDFAVYYC | QQYYYTPPT | FGRGTKVEIN |
| 807B-M0084-F08 | QDIQMTQSPATLS VSPGARATLSC | RASQSVRNNLA | WYQQKPGQAPR LLIY | GASTRAT | DIPARFSGGGSGTEFT LTISSLQPDDFATYYC | QHEET | FGQGTKVEIK |
| 807B-M0084-H05 | QSALTQPPSVSAA PGQRVTISC | SGGTSNIQYNGVN | WYQQLPGKAPK LLIY | FDDLLPS | GVSDRFSGSKSGTSAS LAISGLRSEDEADYYC | AAWDDSLSGVV | FGGGTKLTVL |
| 807B-M0085-B12 | QDIQMTQSPSSVS ASVGDRVTITC | RASQGISSWLA | WYQQKPGKAPK LLIY | AASSLQS | GVPSRFSGSGSGTDFT LTISSLQPEDFATYYC | QQANSFPLT | FGGGTKVEIK |
| 807B-M0085-C01 | QDIQMTQSPATLS VSPGERATLSC | RASQSVSSNLA | WYQQKPGQAPR LLIY | GASTRAT | GIPARFSGSGSGTDFT FTISSLQPEDIATYFC | QQYINLPIT | FGQGTRLEIK |
| 807B-M0085-E10 | QDIQMTQSPSSLS ASVGDRVTITC | QASQDISKYLN | WYQQRPGKAPE LLIY | DASNLEP | GVPSRFSGSGSTHFT FTISSLQPEDFATYYC | QQFDNFPLT | FGPGTRLDIK |
| 807B-M0085-G03 | QDIQMTQSPLSLS ASVGDRVTITC | RASQSISSYLN | WYQQKPGKAPK LLIY | AASSLQS | GVPSRFSGSGSGTDFT LTISSLQPEDFATYYC | QQSYSTPLYT | FGQGTKLEIK |
| 807B-M0085-G07 | QDIQMTQSPGTLS LSPGERATLSC | RASQSVSSSYLA | WYQQKPGQAPR LLIY | GASSRAT | GIPDRFSGSGSGTDFT LTISRLEPEDFAVYYC | QSGVT | FGGGTKVEIK |
| 807B-M0085-G08 | QDIQMTQSPGTLS LSPGERATLSC | RASQSVSRSSLA | WYQQKPGQAPR LLIY | GASSRAT | GIPDRFSGSGSGTDFT LTISRLEPEDFAVYYC | QQYGNSPGGT | FGQGTKVEIK |
| 807B-M0086-C06 | QSALTQPPSASGT PGQKVTISC | SGGSSNIGSNIVN | WYQQVPGMAPK LLYTNNRRPS | TNNRRPS | GVPDRFSGSKSGTSAS LAISGLRSEDEADYYC | AAWDDSLSGGV | FGGGTKLTVI |
| 807B-M0086-D03 | QDIQMTQSPSSLS ASVGDRVTITC | RASQSISSYLN | WYQQKPGKAPK LLIY | VASSLQS | GVPSRFSGSGSGTDFT LTISSLQPEDFATYYC | QQSYSIPPT | FGQGTRVEIK |
| 807B-M0086-E08 | QDIQMTQSPGTLS LSPGERATLSC | SVSQSVSSNYLA | WYQQKPGQSPR LLIY | GASARAT | GIPDRFSGSGSRTDFT LTISRLEPEDFAVYYC | QQYVTTPPT | FGQGTKVEIK |

TABLE 14-continued

Amino acid sequences of the VL chains of the antibodies identified using the screening strategy of Example 23

| Isolate Name | FR 1 | CDR 1 | FR 2 | CDR 2 | FR 3 | CDR 3 | FR 4 |
|---|---|---|---|---|---|---|---|
| 807B-M0086-G03 | QDIQMTqSPSFLS ASVGDRVSVTC | RASQVLRRPLA | WYQQKAGKAPK LLIS | AFSILES | GVPSRFSAGGSGTEFT LTINSLQAEDFATYYC | QQVSSYPLT | FGGGPRVEIK |

TABLE 15

Amino acid sequences of the VH chains of the antibodies identified using the screening strategy of Example 23

| Isolate Name | FR1 | CDR 1 | FR 2 | CDR 2 | FR 3 | CDR 3 | FR 4 |
|---|---|---|---|---|---|---|---|
| 807B-M0011-C07 | EVQLLESGGGLVQPG GSLRLSCAASGFTFS | WYSMD | WVRQAPGKGLEWVS | GIGPSGGRTRY ADSVKG | RFTISRDNSKNTLYLQMNS LRAEDTAVYYCAR | EPIWGYYY YGMDV | WGQGTTVTSS |
| 807B-M0012-C09 | EVQLLESGGGLVQPG GSLRLSCAASGFTFS | WYTMD | WVRQAPGKGLEWVS | GISPSGGATNY ADSVKG | RFTISRDNSKNTLYLQMNS LRAEDTAVYYCAR | GLRYFDFY YYYGMDV | WGQGTTVTSS |
| 807B-M0012-D09 | EVQLLESGGGLVQPG GSLRLSCAASGFTFS | LYQMA | WVRQAPGKGLEWVS | SISSSGGLTDY ADSVKG | RFTISRDNSKNTNTLQMNS LRAEDTAVYYCAR | DLWFGEWD Y | WGQGTLVTSS |
| 807B-M0012-F10 | EVQLLESGGGLVQPG GSLRLSCAASGFTFS | WYNMS | WVRQAPGKGLEWVS | YIYPSGGITIY ADSVKG | RFTISRDNSKNTNTLQMNS LRAEDTAVYYCAR | ERGTIFND AFDI | WGQGTMVTSS |
| 807B-M0012-F12 | EVQLLESGGGLVQPG GSLRLSCAASGFTFS | WYDMD | WVRQAPGKGLEWVS | SIYPSGGLTGY ADSVKG | RFTISRDNSKNTLYLQMNS LRAEDTAVYYCAR | EPIWGYYY YGMDV | WGQGTTVTSS |
| 807B-M0012-G05 | EVQLLESGGGLVQPG GSLRLSCAASGFTFS | WYRMT | WVRQAPGKGLEWVS | SISPSGGVTLY ADSVKG | RFTISRDNSKNTLYLQMNS LRAEDTAVYYCAR | DLWFGEWD Y | WGQGTLVTSS |
| 807B-M0013-A12 | EVQLLESGGGLVQPG GSLRLSCAASGFTFS | HYGMS | WVRQAPGKGLEWVS | SIRSSGGRTWY ADSVKG | RFTISRDNSKNTLYLQMNS LRAEDTAVYYCAK | GSLSSGWD Y | WGQGTLVTSS |
| 807B-M0013-B04 | EVQLLESGGGLVQPG GSLRLSCAASGFTFS | HYDMV | WVRQAPGKGLEWVS | VIVPSGGATAY ADSVKG | RFTISRDNSKNTLYLQMNS LRAEDTAVYYCAR | EDFWSGLE DV | WGKGTTVTSS |
| 807B-M0013-C03 | EVQLLESGGGLVQPG GSLRLSCAASGFTFS | WYNMA | WVRQAPGKGLEWVS | SISPSGGHTKY ADSVKG | RFTISRDNSKNTLYLQMNS LRAEDTAVYYCAR | DLWFGEWD Y | WGQGTLVTSS |
| 807B-M0013-F06 | EVQLLESGGGLVQPG GSLRLSCAASGFTFS | KYVMT | WVRQAPGKGLEWVS | VISSSGGPTDY ADSVKG | RFTISRDNSKNTLYLQMNS LRAEDTAVYYCAR | WGVRGVIP FDY | WGQGTLVTSS |
| 807B-M0013-G05 | EVQLLESGGGLVQPG GSLRLSCAASGFTFS | WYSMI | WVRQAPGKGLEWVS | YIGPSGGPTRY ADSVKG | RFTISRDNSKNTLYLQMNS LRAEDTAVYYCAR | EPIWGYYY YGMDV | WGQGTTVTSS |
| 807B-M0014-D07 | EVQLLESGGGLVQPG GSLRLSCAASGFTFS | WYTMT | WVRQAPGKGLEWVS | SISSSGGVTKY ADSVKG | RFTISRDNSKNTLYLQMNS LRAEDTAVYYCAR | GRWLAPFD Y | WGQGTLVTSS |
| 807B-M0014-D09 | EVQLLESGGGLVQPG GSLRLSCAASGFTFS | YYIMA | WVRQAPGKGLEWVS | SISPSGGGTVY ADSVKG | RFTISRDNSKNTLYLQMNS LRAEDTAVYYCAR | ATCTGGSC YRFDY | WGQGTTVTSS |
| 807B-M0014-E08 | EVQLLESGGGLVQPG GSLRLSCAASGFTFS | WYAMD | WVRQAPGKGLEWVS | SIYPSGGWTEY ADSVKG | RFTISRDNSKNTLYLQMNS LRAEDTAVYYCAR | GLGMDV | WGQGTTVTSS |
| 807B-M0014-F07 | EVQLLESGGGLVQPG GSLRLSCAASGFTFS | WYDMF | WVRQAPGKGLEWVS | SISPSGGFTQY ADSVKG | RFTISRDNSKNTLYLQMNS LRAEDTAVYYCAR | QEVWQWPA QFDS | WGQGTTVTSS |
| 807B-M0016-C06 | EVQLLESGGGLVQPG GSLRLSCAASGFTFS | LYGMS | WVRQAPGKGLEWVS | SIGPSGGHTFY ADSVKG | RFTISRDNSKNTLYLQMNS LRAEDTAVYYCAR | DLWFGEWD Y | WGQGTLVTSS |
| 807B-M0016-D01 | EVQLLESGGGLVQPG GSLRLSCAASGFTFS | WYNMG | WVRQAPGKGLEWVS | GISPSGGTTTY ADSVKG | RFTISRDNSKNTLYLQMNS LRAEDTAVYYCAR | DLWFGEWD Y | WGQGTLVTSS |
| 807B-M0016-D08 | EVQLLESGGGLVQPG GSLRLSCAASGFTFS | WYGMV | WVRQAPGKGLEWVS | SIYPSGGTTQY ADSVKG | RFTISRDNSKNTLYLQMNS LRAEDTAVYYCAR | DLWFGEWD Y | WGQGTLVTSS |
| 807B-M0016-E01 | EVQLLESGGGLVQPG GSLRLSCAASGFTFS | WYDMQ | WVRQAPGKGLEWVS | SISSSGGLTTY ADSVKG | RFTISRDNSKNTLYLQMNS LRAEDTAVYYCAR | EPIWGYYY YGMDV | WGQGTTVTSS |
| 807B-M0016-F04 | EVQLLESGGGLVQPG GSLRLSCAASGFTFS | NYNMH | WVRQAPGKGLEWVS | VISPSGGGTWY ADSVKG | RFTISRDNSKNTLYLQMNS LRAEDTAVYYCAR | DFFTSYFD Y | WGQGTLVTSS |
| 807B-M0016-F05 | EVQLLESGGGLVQPG GSLRLSCAASGFTFS | WYRMT | WVRQAPGKGLEWVS | SISPSGGVTLY ADSVKG | RFTISRDNSKNTLYLQMNS LRAEDTAVYYCAR | DLWFGEWD Y | WGQGTLVTSS |

TABLE 15-continued

Amino acid sequences of the VH chains of the antibodies identified using the screening strategy of Example 23

| Isolate Name | FR1 | CDR 1 | FR 2 | CDR 2 | FR 3 | CDR 3 | FR 4 |
|---|---|---|---|---|---|---|---|
| 807B-M0016-F08 | EVQLLESGGGLVQPGGSLRLSCAASGFTFS | MYHMG | WVRQAPGKGLEWVS | GISPSGGTTTYADSVKG | RFTISRDNSKNTLYLQMNSLRAEDTAVYYCAR | DLWFGEWDY | WGQGTLVTVSS |
| 807B-M0017-B05 | EVQLLESGGGLVQPGGSLRLSCAASGFTFS | WYTMF | WVRQAPGKGLEWVS | GIWPSGGKTDYADSVKG | RFTISRDNSKNTLYLQMNSLRAEDTAVYYCAK | EGVIAVAGPYRD | WGQGTLVTVSS |
| 807B-M0017-B06 | EVQLLESGGGLVQPGGSLRLSCAASGFTFS | WYEMG | WVRQAPGKGLEWVS | SISPSGGYTSYADSVKG | RFTISRDNSKNTLYLQMNSLRAEDTAVYYCAR | DLWFGEWDY | WGQGTLVTVSS |
| 807B-M0017-E05 | EVQLLESGGGLVQPGGSLRLSCAASGFTFS | WYQMA | WVRQAPGKGLEWVS | GISSSGGTTTYADSVKG | RFTISRDNSKNTLYLQMNSLSAEDTAVYYCAR | DLWFGEWDY | WGQGTLVTVSS |
| 807B-M0018-C12 | EVQLLESGGGLVQPGGSLRLSCAASGFTFS | FYRMG | WVRQAPGKGLEWVS | SISSSGGLTDYADSVKG | RFTISRDNSKNTLYLQMNSLRAEDTAVYYCAR | DLWFGEWDY | WGQGTLVTVSS |
| 807B-M0018-E09 | EVQLLESGGGLVQPGGSLRLSCAASGFTFS | WYGMA | WVRQAPGKGLEWVS | YISPSGGGTSYADSVKG | RFTISRDNSKNTLYLQMNSLRAEDTAVYYCAR | DLWFGEWDY | WGQGTLVTVSS |
| 807B-M0018-G02 | EVQLLESGGGLVQPGGSLRLSCAASGFTFS | KYVMN | WVRQAPGKGLEWVS | SISSSGGQTSYADSVKG | RFTISRDNSKNTLYLQMNSLRAEDTAVYYCAR | GERAAAGTQHYYYYGMDV | WGQGTTVTVSS |
| 807B-M0019-A04 | EVQLLESGGGLVQPGGSLRLSCAASGFTFS | YYDMW | WVRQAPGKGLEWVS | RIVSSGGWTMYADSVKG | RFTISRDNSKNTLYLQMNSLRAEDTAVYYCAR | GRSLYYDFWSGYYPNTYYYYMDV | WGKGTTVTVSS |
| 807B-M0019-A10 | EVQLLESGGGLVQPGGSLRLSCAASGFTFS | YYDMS | WVRQAPGKGLEWVS | SIWSSGGNTMYADSVKG | RFTISRDNSKNTLYLQMNSLRAEDTAVYYCAR | GGGFGVYHHYYDMDV | WGQGTTVTVSS |
| 807B-M0019-C01 | EVQLLESGGGLVQPGGSLRLSCAASGFTFS | WYGMG | WVRQAPGKGLEWVS | YISSSGGHTKYADSVKG | RFTISRDNSKNTLYLQMNSLRAEDTAVYYCAR | DLWFGEWDY | WGQGTLVTVSS |
| 807B-M0019-F06 | EVQLLESGGGLVQPGGSLRLSCAASGFTFS | WYPMD | WVRQAPGKGLEWVS | SISPSGGFTQYADSVKG | RFTISRDNSKNTLYLQMNSLRAEDTAVYYCAR | DLWFGEWDY | WGQGTLVTVSS |
| 807B-M0019-G07 | EVQLLESGGGLVQPGGSLRLSCAASGFTFS | FYPMV | WVRQAPGKGLEWVS | WISSSGGTTSYADSVKG | RFTISRDNSKNTLYLQMNSLRAEDTAVYYCAR | DLWFGEWDY | WGQGTLVTVSS |
| 807B-M0020-D01 | EVQLLESGGGLVQPGGSLRLSCAASGFTFS | WYVMT | WVRQAPGKGLEWVS | GISSSGGMTEYADSVKG | RFTISRDNSKNTLYLQMNSLRAEDTAVYYCAR | DLWFGEWDY | WGQGTLVTVSS |
| 807B-M0020-F06 | EVQLLESGGGLVQPGGSLRLSCAASGFTFS | VYNMY | WVRQAPGKGLEWVS | SISPSGGFTTYADSVKG | RFTISRDNSKNTLYLQMNSLRAEDTAVYYCAR | DTSGWYEEEDY | WGQGTLVTVSS |
| 807B-M0020-F12 | EVQLLESGGGLVQPGGSLRLSCAASGFTFS | IYEMA | WVRQAPGKGLEWVS | SISSSGGWTKYADSVKG | RFTISRDNSKNTLYLQMNSLRAEDTAVYYCAR | DLWFGEWDH | WGQGTLVTVSS |
| 807B-M0020-G01 | EVQLLESGGGLVQPGGSLRLSCAASGFTFS | FYYMS | WVRQAPGKGLEWVS | GISPSGGTTQYADSVKG | RFTISRDNSKNTLYLQMNSLRAEDTAVYYCAR | DLWFGEWDY | WGQGTLVTVSS |
| 807B-M0079-B09 | EVQLLESGGGLVQPGGSLRLSCAASGFTFS | FYAMQ | WVRQAPGKGLEWVS | YISSSGGHTHYADSVKG | RFTISRDNSKNTLYLQMNSLRAEDTAVYYCAR | GAGALGY | WGQGTLVTVSS |
| 807B-M0079-D10 | EVQLLESGGGLVQPGGSLRLSCAASGFTFS | NYRME | WVRQAPGKGLEWVS | SIWSSGGLTKQADSVKG | RFTISRDNSKNTLYLQMNSLRAEDTAVYYCAR | GLYR | WGQGTLVTVSS |
| 807B-M0079-H01 | EVQLLESGGGLVQPGGSLRLSCAASGFTFS | WYDMD | WVRQAPGKGLEWVS | RIWPSGGSTHYADSVKG | RFTISRDNSKNTLYLQMNSLRAEDTAVYYCAR | EPIWGYYYYGMDV | WGQGTTVTVSS |
| 807B-M0079-H05 | EVQLLESGGGLVQPGGSLRLSCAASGFTFS | QYMMG | WVRQAPGKGLEWVS | SISSGGWTAYADSVKG | RFTISRDNSKNTLYLQMNSLRAEDTAVYYCAK | DGGTWDFDY | WGQGTLVTVSS |
| 807B-M0080-A02 | EVQLLESGGGLVQPGGSLRLSCAASGFTFS | WYNMG | WVRQAPGKGLEWVS | SIGPSGGHTMYADSVKG | RFTISRDNSKNTLYLQMNSLRAEDTAVYYCAR | DLWFGEWDY | WGQGTLVTVSS |
| 807B-M0080-C04 | EVQLLESGGGLVQPGGSLRLSCAASGFTFS | WYSME | WVRQAPGKGLEWVS | SIVSSGGHTIYADSVKG | RFTISRDNSKNTLYLQMNSLRAEDTAVYYCAR | EPIWGYYYYGMDV | WGQGTTVTVSS |
| 807B-M0080-F10 | EVQLLESGGGLVQPGGSLRLSCAASGFTFS | DYVMN | WVRQAPGKGLEWVS | SIYPSGGLTRYADSVKG | RFTISRDNSKNTLYLQMNSLRAEDTAVYYCAR | GAGALGY | WGQGTLVTVSS |
| 807B-M0081-C03 | EVQLLESGGGLVQPGGSLRLSCAASGFTFS | WYWMG | WVRQAPGKGLEWVS | GISSSGGRTVYADSVKG | RFTISRDNSKNTLYLQMNSLRAEDTAVYYCAR | GHWGWFDP | WGQGTLVTVSS |

TABLE 15-continued

Amino acid sequences of the VH chains of the antibodies identified using the screening strategy of Example 23

| Isolate Name | FR1 | CDR 1 | FR 2 | CDR 2 | FR 3 | CDR 3 | FR 4 |
|---|---|---|---|---|---|---|---|
| 807B-M0081-C05 | EVQLLESGGGLVQPGGSLRLSCAASGFTFS | WYNMD | WVRQAPGKGLEWVS | SIGPSGGPTKYADSVKG | RFTISRDNSKNTLYLQMNSLRAEDTAVYYCAR | EPIWGYYYYGMDV | WGQGTTVTVSS |
| 807B-M0081-D08 | EVQLLESGGGLVQPGGSLRLSCAASGFTFS | EYTML | WVRQAPGKGLEWVS | GIWPSGGPTFYADSVKG | RFTISRDNSKNTLYLQMNSLRAEDTAVYYCAR | ELDTAMAPPSDAFDI | WGQGTMVTVSS |
| 807B-M0081-E08 | EVQLLESGGGLVQPGGSLRLSCAASGFTFS | MYNMY | WVRQAPGKGLEWVS | RIGSSGGMTDYADSVKG | RFTISRDNSKNTLYLQMNSLRAEDTAVYYCAR | EPIWGYYYYGMDV | WGQGTTVTVSS |
| 807B-M0081-F12 | EVQLLESGGGLVQPGGSLRLSCAASGFTFS | WYLMH | WVRQAPGKGLEWVS | SIVPSGGTTVYADSVKG | RFTISRDNSKNTLYLQMNSLRAEDTAVYYCAR | DLWFGEWDY | |
| 807B-M0081-G04 | EVQLLESGGGLVQPGGSLRLSCAASGFTFS | WYSMV | WVRQAPGKGLEWVS | VISSSGGFTGYADSVKG | RFTISRDNSKNTLYLQMNSLRAEDTAVYYCAR | DLWFGEWDY | WGQGTLVTVSS |
| 807B-M0081-G11 | EVQLLESGGGLVQPGGSLRLSCAASGFTFS | WYDMV | WVRQAPGKGLEWVS | GIWPSGGFTNYADSVKG | RFTISRDNSKNTLYLQMNSLRAEDTAVYYCAR | HPVSSGFDY | WGQGTLVTVSS |
| 807B-M0081-H03 | EVQLLESGGGLVQPGGSLRLSCAASGFTFS | WYSMV | WVRQAPGKGLEWVS | SIGPSGGMTRYADSVKG | RFTISRDNSKNTLYLQMNSLRAEDTAVYYCAR | DQGITMVQGAMGY | WGQGTLVTVSS |
| 807B-M0081-H07 | EVQLLESGGGLVQPGGSLRLSCAASGFTFS | FYTMV | WVRQAPGKGLEWVS | VISPSGGLTHYADSVKG | RFTISRDNSKNTLYLQMNSLRAEDTAVYYCAR | DLWFGEWDY | WGQGTLVTVSS |
| 807B-M0082-B07 | EVQLLESGGGLVQPGGSLRLSCAASGFTFS | YYSMT | WVRQAPGKGLEWVS | SISPSGGGTGYADSVKG | RFTISRDNSKNTLYLQMNSLRAEDTAVYYCAR | DLWFGEWDY | WGQGTLVTVSS |
| 807B-M0082-E01 | EVQLLESGGGLVQPGGSLRLSCAASGFTFS | WYGMS | WVRQAPGKGLEWVS | WISPSGGMTKYADSVKG | RFTISRDNSKNTLYLQMNSLRAEDTAVYYCAR | DLWFGEWDY | WGQGTLVTVSS |
| 807B-M0082-E08 | EVQLLESGGGLVQPGGSLRLSCAASGFTFS | WYDMD | WVRQAPGKGLEWVS | SISSSGGFTTYADSVKG | RFTISRDNSKNTLYLQMNSLRAEDTAVYYCAR | EPIWGYYYYGMDV | WGQGTTVTVSS |
| 807B-M0082-H06 | EVQLLESGGGLVQPGGSLRLSCAASGFTFS | WYGMG | WVRQAPGKGLEWVS | YISSSGGLTIYADSVKG | RFTISRDNSKNTLYLQMNSLRAEDTAVYYCAR | DLWFGEWDY | WGQGTLVTVSS |
| 807B-M0083-B10 | EVQLLESGGGLVQPGGSLRLSCAASGFTFS | YYAMG | WVRQAPGKGLEWVS | WISSSGGSTHYADSVKG | RFTISRDNSKNTLYLQMNSLRAEDTAVYYCAR | DLWFGEWDY | WGQGTLVTVSS |
| 807B-M0083-E10 | EVQLLESGGGLVQPGGSLRLSCAASGFTFS | YYSMV | WVRQAPGKGLEWVS | WISSSGGSTNYADSVKG | RFTISRDNSKNTLYLQMNSLRAEDTAVYYCAR | DLWFGEWDY | WGQGTLVTVSS |
| 807B-M0083-E11 | EVQLLESGGGLVQPGGSLRLSCAASGFTFS | VYSMA | WVRQAPGKGLEWVS | GIWPSGGPTAYADSVKG | RFTISRDNSKNTLYLQMNSLRAEDTAVYYCAR | EDFWSGLEDV | WGKGTTVTVSS |
| 807B-M0084-C03 | EVQLLESGGGLVQPGGSLRLSCAASGFTFS | WYDMM | WVRQAPGKGLEWVS | YIYSSGGSTRYADSVKG | RFTISRDNSKKTLYLQMNSLRAEDTAVYYCAR | EPIWGYYYYGMDV | WGQGTTVTVSS |
| 807B-M0084-C11 | EVQLLESGGGLVQPGGSLRLSCAASGFTFS | FYRMA | WVRQAPGKGLEWVS | VISPSGGHTYYADSVKG | RFTISRDNSKNTLYLQMNSLRAEDTAVYYCAR | DFFTSYFDY | WGQGTLVTVSS |
| 807B-M0084-E07 | EVQLLESGGGLVQPGGSLRLSCAASGFTFS | WYRMA | WVRQAPGKGLEWVS | SISSSGGDTQYADSVKG | RFTISRDNSKNTLYLQMNSLRAEDTAVYYCAR | DLWFGEWDY | WGQGTLVTVSS |
| 807B-M0084-F03 | EVQLLESGGGLVQPGGSLRLSCAASGFTFS | WYVMD | WVRQAPGKGLEWVS | SISPSGGGTLYADSVKG | RFTISRDNSKNTLYLQMNSLRAEDTAVYYCAR | DLHYGSVLDF | WGQGTLVTVSS |
| 807B-M0084-F08 | EVQLLESGGGLVQPGGSLRLSCAASGFTFS | WYGMA | WVRQAPGKGLEWVS | YISPSGGGTSYADSVKG | RFTISRDNSKNTLYLQMNSLRAEDTAVYYCAR | DLWFGEWDY | WGQGTLVTVSS |
| 807B-M0084-H05 | EVQLLESGGGLVQPGGSLRLSCAASGFTFS | WYTME | WVRQAPGKGLEWVS | GIYSSGGTTTYADSVKG | RFTISRDNSKNTLYLQMNSLRAEDTAVYYCAR | EPIWGYYYYGMDV | WGQGTTVTVSS |
| 807B-M0085-B12 | EVQLLESGGGLVQPGGSLRLSCAASGFTFS | WYGMV | WVRQAPGKGLEWVS | SISPSGGQTFYADSVKG | RFTISRDNSKNTLYLQMNSLRAEDTAVYYCAR | EPIWGYYYYGMDV | WGQGTTVTVSS |
| 807B-M0085-C01 | EVQLLESGGGLVQPGGSLRLSCAASGFTFS | WYTMD | WVRQAPGKGLEWVS | GISPSGGYTTYADSVKG | RFTISRDNSKNTLYLQMNSLRAEDTAVYYCAR | GTVLLWFQESGGHFDY | WGQGTPVTVSS |
| 807B-M0085-E10 | EVQLLESGGGLVQPGGSLRLSCAASGFTFS | WYQMS | WVRQAPGKGLEWVS | GISSSGGSTQYADSVKG | RFTISRDNSKNTLYLQMNSLRAEDTAVYYCAR | DLWFGEWDY | WGQGTLVTVSS |
| 807B-M0085-G03 | EVQLLESGGGLVQPGGSLRLSCAASGFTFS | WYVMM | WVRQAPGKGLEWVS | SIVPSGGGTGYADSVKG | RFTISRDNSKNTLYLQMNSLRAEDTAVYYCAR | ENYGPDY | WGQGTLVTVSS |

TABLE 15-continued

Amino acid sequences of the VH chains of the antibodies identified using the screening strategy of Example 23

| Isolate Name | FR1 | CDR 1 | FR 2 | CDR 2 | FR 3 | CDR 3 | FR 4 |
|---|---|---|---|---|---|---|---|
| 807B-M0085-G07 | EVQLLESGGGLVQPGGSLRLSCAASGFTFS | WYAMD | WVRQAPGKGLEWVS | SIVPSGGRTLYADSVKG | RFTISRDNSKNTLYLQMNSLRAEDTAVYYCAR | EPIWGYYY YGMDV | WGQGTTVTVSS |
| 807B-M0085-G08 | EVQLLESGGGLVQPGGSLRLSCAASGFTFS | FYGMG | WVRQAPGKGLEWVS | RIRPSGGMTSYADSVKG | RFTISRDNSKNTLYLQMNSLRAEDTAVYYCAR | DLWFGEWDY | WGQGTLVTVSS |
| 807B-M0086-C06 | EVQLLESGGGLVQPGGSLRLSCAASGFTFS | WYSMV | WVRQAPGKGLEWVS | WISSSGGFTKYADSVKG | RFTISRDNSKNTLYLQMNSLRAEDTAVYYCAR | DLWFGEWDY | WGQGTLVTVSS |
| 807B-M0086-D03 | EVQLLESGGGLVQPGGSLRLSCAASGFTFS | WYTMG | WVRQAPGKGLEWVS | SIVSSGGYTPYADSVKG | RFTISRDNSKNTLYLQMNSLRAEDTAVYYCAR | EPIWGYYY YGMDV | WGQGTTVTVSS |
| 807B-M0086-E08 | EVQLLESGGGLVQPGGSLRLSCAASGFTFS | WYDMH | WVRQAPGKGLEWVS | WIVPSGGITEYADSVKG | RFTISRDNSKNTLYLQMNSLRAEDTAVYYCAR | QEVWQWPA QFDS | WGQGTLVTVSS |
| 807B-M0086-G03 | EVQLLESGGGLVQPGGSLRLSCAASGFTFS | EYKMN | WVRQAPGKGLEWVS | YIYPSGGFTHYADSVKG | RFTISRDNSKNTLYLQMNSLRAEDTAVYYCAR | SVVGWGLDY | WGQGTLVTVSS |

TABLE 16

| | Enrichment | | | | Peptide Mapping | | | | | | | | | | koff | | Fab |
|---|---|---|---|---|---|---|---|---|---|---|---|---|---|---|---|---|---|
| Isolate Name | VH | CDR3 | bCTD | VLDL | 1 | 2 | 3 | 4 | 5 | 6 | 7 | 8 | 9 | 10 | (e-3) | RU | IHC |
| 807B-M0011-CO7 | 3 | 20 | + | | | | | | | | | | | | 11.6 | 325 | |
| 807B-M0012-CO9 | 12 | 12 | + | | | | | | | | | | | | 11.7 | 156 | |
| 807B-M0012-DO9 | 1 | 299 | + | | | | | | | | | | | | 14.8 | 159 | |
| 807B-M0012-F10 | 1 | 1 | + | | | | | | | | | | | | 5.5 | 50.5 | |
| 807B-M0012-F12 | 2 | 20 | + | | | | | | | | | | | | 3.0 | 246 | |
| 807B-M0012-GO5 | 15 | 299 | + | | | | | | | | | | | | 7.9 | 157 | |
| 807B-M0013-A12 | 3 | 3 | + | | | | | | | | | | | | 6.8 | 63.9 | + |
| 807B-M0013-BO4 | 1 | 4 | + | | | | | | | | | | | | 12.5 | 101 | |
| 807B-M0013-CO3 | 1 | 299 | + | | | | + | | | | | | | | 38.4 | 177 | |
| 807B-M0013-FO6 | 1 | 1 | + | | | | + | | | | + | | | | 9.3 | 162 | |
| 807B-M0013-GO5 | 1 | 20 | + | +/- | | | + | | | | | | | | 17.5 | 136 | |
| 807B-M0014-DO7 | 10 | 10 | + | | | | | | | | | + | | | 8.1 | 206 | |
| 807B-M0014-DO9 | 13 | 13 | + | | | | | | | | | + | | | 5.2 | 80.4 | |
| 807B-M0014-EO8 | 2 | 2 | + | | | | + | | | | | | | | 18.6 | 151 | |
| 807B-M0014-FO7 | 1 | 2 | + | | | | | | | | | | | | 8.6 | 205 | |
| 807B-M0016-CO6 | 5 | 299 | + | | | | | | | | | | | | 7.2 | 74.2 | |
| 807B-M0016-DO1 | 1 | 299 | + | | | | | | | | | | | | 8.5 | 74 | |
| 807B-M0016-DO8 | 1 | 299 | + | | | | + | | | | | | | | 12.4 | 80.3 | |
| 807B-M0016-EO1 | 1 | 20 | + | | | | | | | | | | | | 8.0 | 465 | |
| 807B-M0016-FO4 | 1 | 2 | + | | | | | | | | | | | | 13.5 | 58.9 | |
| 807B-M0016-FO5 | 15 | 299 | + | | | | | | | | | | | | 9.0 | 69 | |
| 807B-M0016-FO8 | 1 | 299 | + | | | | | | | | | | | | 18.5 | 113 | |
| 807B-M0017-BO5 | 1 | 1 | + | +/- | | | | | | | | | | | 26.1 | 248 | |
| 807B-M0017-BO6 | 1 | 299 | + | | | | | | | | | | | | 8.8 | 120 | |
| 807B-M0017-EO5 | 1 | 299 | + | | | | | | | | | | | | 4.7 | 71.1 | |
| 807B-M0018-C12 | 2 | 299 | + | | | | | | | | | | | | 11.0 | 107 | |
| 807B-M0018-EO9 | 3 | 299 | + | | | | | | | | | | | | 10.5 | 66.8 | |
| 807B-M0018-GO2 | 1 | 1 | + | | | | | | | | | + | | | 21.1 | 98.9 | |
| 807B-M0019-AO4 | 1 | 1 | + | | | | | | | | | | | | 5.4 | 31.1 | |
| 807B-M0019-A10 | 1 | 1 | + | | | | | | | | | | | | 7.1 | 51 | |
| 807B-M0019-CO1 | 1 | 299 | + | | | | | | | | | | | | 10.6 | 80.1 | |
| 807B-M0019-FO6 | 1 | 299 | + | | | | | | | | | | | | 7.7 | 99.4 | |
| 807B-M0019-GO7 | 1 | 299 | + | | | | | | | | | | | | 5.2 | 31.2 | |
| 807B-M0020-DO1 | 1 | 299 | + | | | | | | | | | | | | 3.9 | 51.2 | |
| 807B-M0020-FO6 | 1 | 1 | + | | | | | | | | | | | | 4.9 | 53.2 | |
| 807B-M0020-F12 | 1 | 1 | + | | | | | | | | | | | | 9.9 | 67.4 | |
| 807B-M0020-GO1 | 1 | 299 | + | | | | | | | | | | | | 12.7 | 68 | |
| 807B-M0079-BO9 | 1 | 2 | + | +/+ | | | | | + | | | | | | 8.3 | 438 | |
| 807B-M0079-D10 | | | + | +/- | | | + | | | | + | + | | | 4.3 | 100 | + |
| 807B-M0079-HO1 | 1 | 20 | + | | + | + | + | | | | | | | | 2.5 | 256 | |
| 807B-M0079-HO5 | 1 | 1 | + | | | | | | | | | | | | 2.0 | 99.3 | |
| 807B-M0080-AO2 | 1 | 299 | + | | | | | | | | | | | | 2.5 | 86.8 | |
| 807B-M0080-CO4 | 1 | 20 | + | | | | | | | | | | | | 2.5 | 162 | |
| 807B-M0080-DO6 | 1 | 1 | + | | | | | + | | | | | | | 2.4 | 72.7 | |
| 807B-M0080-F10 | 1 | 2 | + | | | | | | + | | | | | | 2.7 | 49.2 | |
| 807B-M0081-CO3 | 1 | 1 | + | | | | | | | | | + | | | 2.2 | 84.6 | |
| 807B-M0081-CO5 | 1 | 20 | + | | | | | | | | | | | | 2.6 | 158 | |
| 807B-M0081-DO8 | 1 | 1 | + | | | | | | + | | | | | | 4.0 | 55.1 | |

TABLE 16-continued

| Isolate Name | Enrichment VH | CDR3 | bCTD | VLDL | Peptide Mapping 1 | 2 | 3 | 4 | 5 | 6 | 7 | 8 | 9 | 10 | koff (e-3) | RU | Fab IHC |
|---|---|---|---|---|---|---|---|---|---|---|---|---|---|---|---|---|---|
| 807B-M0081-E08 | 1 | 20 | + | | | | | | | | | | | | 5.7 | 65.1 | |
| 807B-M0081-F12 | 249 | 299 | + | | | | | | | | | | | | 6.1 | 128 | + |
| 807B-M0081-G04 | 1 | 299 | + | | | | | | | | | | | | 2.6 | 64.1 | |
| 807B-M0081-G11 | 1 | 1 | + | | | | | | | + | | | | | 3.6 | 83.6 | |
| 807B-M0081-H03 | 1 | 1 | + | | | | | | | | | | | | 9.7 | 346 | +/− |
| 807B-M0081-H07 | 1 | 299 | + | | | | | | | | | | | | 2.3 | 56.4 | |
| 807B-M0082-B07 | 1 | 299 | + | +/− | | | | | | | | | | | 2.8 | 46.4 | |
| 807B-M0082-C11 | 1 | 1 | + | | | | | | | | | | | | 4.0 | 244 | |
| 807B-M0082-E01 | 2 | 299 | + | | | | | | + | + | | | | | 4.7 | 68.8 | |
| 807B-M0082-E08 | 1 | 20 | + | | | | | | | | | | | | 3.0 | 154 | |
| 807B-M0082-F04 | 1 | 20 | + | | | | | | | | | | | | 3.1 | 136 | |
| 807B-M0082-F11 | 1 | 299 | + | | | | | | | | | | | | 6.1 | 32.5 | |
| 807B-M0082-H06 | 2 | 299 | + | | | | | + | | | | | | | 5.1 | 103 | |
| 807B-M0083-B10 | 1 | 299 | + | | | | | | | + | + | | | | 2.9 | 45 | |
| 807B-M0083-E10 | 1 | 299 | + | | | | | | | + | | | | | 3.7 | 47.9 | |
| 807B-M0083-E11 | 3 | 4 | + | | | | | | | | | | | | 5.1 | 34.6 | + |
| 807B-M0084-C03 | 1 | 20 | + | | | | | | | | | | | | 2.0 | 53.9 | |
| 807B-M0084-C11 | 1 | 2 | + | | | | | | | | | | | | 3.7 | 52.5 | |
| 807B-M0084-E07 | 1 | 299 | + | | + | | | | | + | | + | | | 4.4 | 46.7 | |
| 807B-M0084-F03 | 1 | 1 | + | | | | | | | | | | | | 3.6 | 49.6 | |
| 807B-M0084-F08 | 3 | 299 | + | | | | | | | | | | | | 5.8 | 51.5 | |
| 807B-M0084-H05 | 2 | 20 | + | + | | | | | | | | | | | 2.4 | 118 | |
| 807B-M0085-B12 | 1 | 20 | + | | | | | | | + | | | | | 7.9 | 95.3 | |
| 807B-M0085-C01 | 1 | 1 | + | | | | | | | | | | | | 5.5 | 69.7 | |
| 807B-M0085-E01 | 1 | 20 | + | | | | | | | | | | | | 2.8 | 49.5 | |
| 807B-M0085-E10 | 1 | 299 | + | | + | + | | | + | + | | + | + | + | 5.8 | 47.5 | |
| 807B-M0085-G03 | 1 | 1 | + | | | | | | | | | | | | 2.2 | 52.8 | |
| 807B-M0085-G07 | 1 | 20 | + | | | | | | | | | | | | 4.2 | 83.7 | |
| 807B-M0085-G08 | 1 | 299 | + | | | | | | | | | | + | | 3.8 | 42.2 | |
| 807B-M0086-C06 | 1 | 299 | + | | | | | | | | | | | | 4.8 | 59.5 | |
| 807B-M0086-D03 | 1 | 20 | + | | | | | | | | | | | | 3.7 | 159 | |
| 807B-M0086-E08 | 1 | 2 | + | | | | | | | | | | | | 2.6 | 73 | |
| 807B-M0086-G03 | 2 | 2 | + | | | | | | | | | | | | 3.7 | 43.8 | |

TABLE 17

Fab Binding Data to CTD and peptides

| Isolate name | Strategy | CTD IHC | ELISA | peptide | group | Affinity Biacore (nM) CTD | p1 | p4 | p6 | p8 | p9 | VLDL ELISA |
|---|---|---|---|---|---|---|---|---|---|---|---|---|
| 807B-M0001-B07 | E22 P1 | +/− | + | p1, p6 | 4 | 46 | 245 | | 396 | | | − |
| 807B-M0004-A03 | E22 P4 | ++ | + | p4, p9 | 5 | low RU* | | 98 | | | low RU* | − |
| 807B-M0004-A05 | E22 P4 | +/− | − | p4 | 1 | no RU** | | 208 | | | | − |
| 807B-M0004-C04 | E22 P4 | +/− | − | p4 | 1 | no RU** | | 509 | | | | − |
| 807B-M0004-C05 | E22 P4 | +/− | − | p4 | 1 | no RU** | | 225 | | | | − |
| 807B-M0004-F06 | E22 P4 | +/− | − | p4 | 1 | no RU** | | 361 | | | | − |
| 807B-M0004-F10 | E22 P4 | +/− | − | p4, p9 | 2 | no RU** | | 104 | | | low RU* | − |
| 807B-M0004-H03 | E22 P4 | ++ | − | p4, p9 | 2 | no RU** | | 200 | | | low RU* | − |
| 807B-M0009-C03 | E22 P9, E24 P3 | +/− | + | p4, p9 | 5 | no RU** | | 728 | | | 163 | − |
| 807B-M0009-F06 | E22 P9, E24 P3 | +/− | − | p9 | 3 | no RU** | | | | | 172 | − |
| 807B-M0013-A12 | E24 | ++ | + | no | 7 | no RU** | | | | | | − |
| 807B-M0079-D10 | E22&E23 P9, E24 | ++ | + | p4, p8 | 6 | 59.17 | | low RU* | | 25.79 | | − |
| 807B-M0081-F12 | E24 | + | + | no | 8 | low RU* | | | | | | − |
| 807B-M0081-H03 | E24 | +/− | + | no | 9 | 10 | | | | | | − |
| 807B-M0083-E11 | E24 | ++ | + | no | 10 | low RU* | | | | | | − |
| 807A-M0028-B02 | E5 | + | + | no | | | | | | | | − |
| 807A-M0026-F05 | E5 | + | + | p3, p8 | | | | | | | | − |
| 807A-M0027-E11 | E5 | + | + | no | | | | | | | | − |

*low RU: RUs are low, affinity was not measured
**no RU: no binding observed

TABLE 18

IgG Binding Data to CTD and peptides

| Isolate name | Strategy | CTD IHC | CTD ELISA | CTD peptide | Affinity Biacore (nM) hCTD | mCTD | pCTD | p1 | p4 | p8 | p9 | VLDL ELISA (O.D)† | ELISA hCTD | mCTD | pCTD |
|---|---|---|---|---|---|---|---|---|---|---|---|---|---|---|---|
| 807B-M0001-B07 | E22 P1 | + | + | p1, p6 | 5 | <h, pCTD | 6 | 8.04 | | | | 2.14 | +++ | ++ | +++ |
| 807B-M0004-A03 | E22 P4 | +++ | + | (p1, p6) p4, p8, p9 | 3 | | 3 | | 0.17 | | low RU* | 0.273 | + | + | ++ |
| 807B-M0004-A05 | E22 P4 | − | + | p4, p9 | 167 | no RU** | no RU** | | 17.42 | | | 0.214 | +/− | +/− | +/− |
| 807B-M0004-C04 | E22 P4 | − | +/− | p4, p9 | no RU** | no RU** | no RU** | | 8.68 | | | 0.242 | +/− | +/− | +/− |
| 807B-M0004-C05 | E22 P4 | − | − | p4, p9 | no RU** | no RU** | no RU** | | 0.97 | | | 0.233 | +/− | +/− | +/− |
| 807B-M0004-F06 | E22 P4 | − | | | no RU** | no RU** | no RU** | | 6.72 | | | 0.248 | +/− | +/− | +/− |
| 807B-M0004-F10 | E22 P4 | (+) | + | p4, p8, p9 | 25 | no RU** | 23 | | 1.00 | | 13.74 | 1.11 | ++ | +/− | +/− |
| 807B-M0004-H03 | E22 P4 | +(+) | + | p4, p9, (p8) | 45 | no RU** | 43 | | 11.55 | | low RU* | 0.309 | ++ | +(+) | ++ |
| 807B-M0009-C03 | E22 P9, E24 P3 | (+) | + | p4, p9 | 23 | no RU** | 4 | | 1.00 | | 0.27 | 2.528 | +++ | +++ | +++ |
| 807B-M0009-F06 | E22 P9, E24 P3 | ++ | − | p4, p9 | 34 | 234 | 28 | | no RU** | | 10.6 | 1.202 | +/− | +/− | +/− |
| 807B-M0013-A12 | E24 | +++ | + | (p3, p9) p4, p8 | 27 | 23 | 26 | | | | | 0.462 | ++ | +/− | +/− |
| 807B-M0079-D10 | E22&E23 P9, E24 | (+) | + | p4, p8 | 1 | 2 | 1 | | 43.64 | 1.05 | | 0.2 | +++ | +++ | +++ |
| 807B-M0081-F12 | E24 | | + | (p9) | 15 | 16 | 19 | | no RU** | | | 0.285 | ++ | + | + |
| 807B-M0081-H03 | E24 | (+) | + | (p7) | 9 | 18 | 7 | | no RU** | | | 2.88 | +++ | +++ | +++ |
| 807B-M0083-E11 | E24 | − | + | no | 12 | 64 | 25 | | no RU** | | | 0.221 | + | − | − |
| 807A-M0028-B02 | E5 | + | + | P4 | 9 | 7 | 5 | | | | | 2.679 | | | |
| 807A-M0026-F05 | E5 | + | | | | | | | | | | | | | − |
| 807A-M0027-E11 | E5 | + | | | | | | | | | | | | | − |

*low RU: RUs are low, affinity was not measured
**no RU: no binding observed
†VLDL ELISA: VLDL is coated, 5 μg/ml of appropriate hIgG is added O.D. of 2x background is 0.420

TABLE 19

Amino acid sequences of the VL chains of the Germline-corrected antibodies

| Initial Name | LV-FR1 | LV-CDR1 | LV-FR2 | LV-CDR2 | LV-FR3 | LV-CDR3 | LV-FR4 |
|---|---|---|---|---|---|---|---|
| 807A-M0028-B02.1 | DIQMTQSPSSLSA SVGDRVTITC | RTSQDIRNHLG | WFQQKPGKAP QRLIR | EASILQS | GVPSTFYGSGYGRE FTLTISSLQPEDFA TYYC | LQYDSFPYT | FGQGTKLEIK |
| 807A-M0028-B02.2 | DIQMTQSPSSLSA SVGDRVTITC | RTSQDIRNHLG | WYQQKPGKAP KRLIY | EASILQS | GVPSRFSGSGSGTE FTLTISSLQPEDFA TYYC | LQYDSFPYT | FGQGTKLEIK |
| 807B-M0004-H03.1 | DIQMTQSPSSLSA SVGDRVTITC | QASQNIDNYLN | WYQQKPGKAP KLLIY | AASSLQS | GVPSRFSGSGSGTD FTLTISSLQPEDFA TYYC | QQSYSTPRT | FGQGTKVEIK |
| 807B-M0009-F06.1 | DIVMTQSPLSLPV TPGEPASISC | KSSQSLLHSNGYNYLD | WYLQKPGQSP QLLIY | LGSNRAS | GVPDRFSGSGSGTD FTLKISRVEAEDVG VYYC | MQALQTIT | FGQGTRLEIK |
| 807B-M0004-A03.1 | QSVLTQPPSASG TPGQRVTISC | SGSSSNIGSNTVN | WYQQLPGTAP KLLIY | NNNQRPS | GVPDRFSGSKSGTS ASLAISGLQSEDEA DYYC | AAWHDGLNGPV | FGGGTKLTVL |

TABLE 19-continued

Amino acid sequences of the VL chains of the Germline-corrected antibodies

| Initial Name | LV-FR1 | LV-CDR1 | LV-FR2 | LV-CDR2 | LV-FR3 | LV-CDR3 | LV-FR4 |
|---|---|---|---|---|---|---|---|
| 807B-M0079-D10.1 | SYELTQPPSVSVS PGQTASITC | AGDELGNKYAS | WYQQKPGQSP VLVIY | QDRKRPS | GIPERFSGSNSGNT ATLTISGTQAMDEA DYYC | QSWDSSSVI | FGGGTKLTVL |

TABLE 20

Amino acid sequences of the CL chains of the Germline-corrected antibodies

| Name | Germ line | Sequence of constant region of light chain |
|---|---|---|
| 807A-M0028-B02.1 | Kappa | RTVAAPSVFIFPPSDEQLKSGTASVVC LLNNFYPREAKVQWKVDNALQSGNSQE SVTEQDSKDSTYSLSSTLTLSKADYEK HKVYACEVTHQGLSSPVTKSFNRGEC |
| 807A-M0028-B02.2 | Kappa | RTVAAPSVFIFPPSDEQLKSGTASVVC LLNNFYPREAKVQWKVDNALQSGNSQE SVTEQDSKDSTYSLSSTLTLSKADYEK HKVYACEVTHQGLSSPVTKSFNRGEC |
| 807B-M0004-A03.1 | Lambda | GQPKAAPSVTLFPPSSEELQANKATLV CLISDFYPGAVTVAWKADSSPVKAGVE TTTPSKQSNNKYAASSYLSLTPEQWKS HKSYSCQVTHEGSTVEKTVAPTECS |
| 807B-M0079-D10.1 | Lambda | GQPKAAPSVTLFPPSSEELQANKATLV CLISDFYPGAVTVAWKADSSPVKAGVE TTTPSKQSNNKYAASSYLSLTPEQWKS HRSYSCQVTHEGSTVEKTVAPTECS |

TABLE 21

Description of SEQ ID NOS: 539-548

| Antibody | VL chain sequence | CL chain sequence |
|---|---|---|
| 807A-M0028-B02.1 | SEQ ID NO: 518 | SEQ ID NO: 519 |
| 807A-M0028-B02.2 | SEQ ID NO: 520 | SEQ ID NO: 521 |
| 807B-M0004-H03.1 | SEQ ID NO: 524 | — |
| 807B-M0009-F06.1 | SEQ ID NO: 525 | — |
| 807B-M0004-A03.1 | SEQ ID NO: 522 | SEQ ID NO: 523 |
| 807B-M0079-D10.1 | SEQ ID NO: 526 | SEQ ID NO: 527 |

TABLE 22

IgG Binding Data to CTD and peptides

| Isolate name | Strategy | CTD IHC[2] | CTD ELISA | peptide | Affinity Biacore (nM) hCTD | mCTD | pCTD | p1 |
|---|---|---|---|---|---|---|---|---|
| 807B-M0001-B07 | E22 P1 | + | + | p1, p6 | 5 | <h, pCTD | 6 | 8.04 |
| 807B-M0004-A03 | E22 P4 | +++ | + | (p1, p6) p4, p8, p9 | 3 | | 3 | |
| 807B-M0004-A05 | E22 P4 | − | + | p4, p9 | 167 | no RU[3] | no RU[3] | |
| 807B-M0004-C04 | E22 P4 | − | +/− | p4, p9 | no RU[3] | no RU[3] | no RU[3] | |
| 807B-M0004-C05 | E22 P4 | − | − | p4, p9 | no RU[3] | no RU[3] | no RU[3] | |
| 807B-M0004-F06 | E22 P4 | − | | | no RU[3] | no RU[3] | no RU[3] | |
| 807B-M0004-F10 | E22 P4 | (+) | + | p4, p8, p9 | 25 | no RU[3] | 23 | |
| 807B-M0004-H03 | E22 P4 | +(+) | + | p4, p9, (p8) | 45 | no RU[3] | 43 | |
| 807B-M0009-C03 | E22 P9, E24 P3 | (+) | + | p4, p9 | 23 | no RU[3] | 4 | |
| 807B-M0009-F06 | E22 P9, E24 P3 | ++ | − | p4, p9 | 34 | 234 | 28 | |
| 807B-M0013-A12 | E24 | +++ | + | (p3, p9), p4, p8 | 27 | 23 | 26 | |
| 807B-M0079-D10 | E22&E23 P9, E24 | (+) | + | p4, p8 | 1 | 2 | 1 | |
| 807B-M0081-F12 | E24 | [1]n.d. | + | (p9) | 15 | 16 | 19 | |
| 807B-M0081-H03 | E24 | (+) | + | (p7) | 9 | 18 | 7 | |
| 807B-M0083-E11 | E24 | − | + | no | 12 | 64 | 25 | |
| 807A-M0028-B02 | E5 | + | + | P4 | 9 | 7 | 5 | |

TABLE 22-continued

IgG Binding Data to CTD and peptides

| 807A-M0026-F05 | E5 | (+) |
| 807A-M0027-E11 | E5 | + |

| Isolate name | Affinity Biacore (nM) | | | VLDL ELISA[5] | ELISA[6] | | |
|---|---|---|---|---|---|---|---|
| | p4 | p8 | p9 | | hCTD | mCTD | pCTD |
| 807B-M0001-B07 | | | | ++ | +++ | ++ | +++ |
| 807B-M0004-A03 | 0.17 | | low RU[4] | ++ | +++ | ++ | + |
| 807B-M0004-A05 | 17.42 | | | − | +/− | +/− | +/− |
| 807B-M0004-C04 | 8.68 | | | − | +/− | +/− | +/− |
| 807B-M0004-C05 | 0.97 | | | − | +/− | +/− | +/− |
| 807B-M0004-F06 | 6.72 | | | − | +/− | +/− | +/− |
| 807B-M0004-F10 | 1.00 | | 13.74 | + | ++ | +/− | +/− |
| 807B-M0004-H03 | 11.55 | | low RU[4] | ++ | + | − | − |
| 807B-M0009-C03 | 1.00 | | 0.27 | ++ | +++ | +++ | +++ |
| 807B-M0009-F06 | no RU[3] | | 10.6 | +++ | +++ | + | + |
| 807B-M0013-A12 | | | | ++ | ++ | +/− | +/− |
| 807B-M0079-D10 | 43.64 | 1.05 | | +++ | +++ | +++ | +++ |
| 807B-M0081-F12 | no RU[3] | | | + | ++ | + | + |
| 807B-M0081-H03 | no RU[3] | | | +++ | +++ | +++ | +++ |
| 807B-M0083-E11 | no RU[3] | | | − | + | − | − |
| 807A-M0028-B02 | | | | +++ | +++ | +++ | +++ |
| 807A-M0026-F05 | | | | +++ | +++ | [1]n.d | [1]n.d |
| 807A-M0027-E11 | | | | +++ | +++ | [1]n.d | [1]n.d |

[1]n.d.: Not done
[2]IHC: tissue from human AD cortex used. 1 µg/ml of appropriate hIgG added
[3]no RU: no binding observed
[4]low RU: RUs are low, affinity was not measured
[5]VLDL ELISA: human VLDL coated 0.0003-100 µg/ml of appropriate hIgG tested for binding
[6]ELISA: human, mouse or primate CTD coated, 0.0003-100 µg/ml of appropriate hIgG tested for binding

TABLE 23

Binding of germ line corrected IgG to CTD and tissue

| Isolate name | Peptide | Affinity (Biacore (nM)) | VLDL ELISA[2] | IHC[3] (tissue) | ELISA[4] | | | In vitro phagocytosis EC50 ± SEM (ng/ml) |
|---|---|---|---|---|---|---|---|---|
| | | | | | hCTD | mCTD | pCTD | |
| 807A-M0028-B02 | P4 | 10.8 | +++ | ++ | +++ | +++ | +++ | 34 +/− 15 |
| 807A-M0028-B02.1 | n.d.[1] | 13 | ++ | ++ | +++ | +++ | ++ | 67 +/− 38 |
| 807A-M0028-B02.2 | n.d.[1] | | +++ | ++ | + | + | + | 27 +/− 7 |
| 807B-M0004-H03 | p4, p9, (p8) | 12.5 | ++ | ++ | + | − | + | 53 +/− 25 |
| 807B-M0004-H03.1 | n.d.[1] | 17.7 | − | +++ | +++ | − | ++ | 22 +/− 16 |
| 807B-M0009-F06 | p4, p9 | 14.8 | +++ | ++ | +++ | + | ++ | 23 +/− 9 |
| 807B-M0009-F06.1 | n.d.[1] | very low binding | − | + | − | − | − | 42 +/− 17 |
| 807B-M0004-A03 | (p1, p6) p4, p8, p9 | 12.2 | ++ | ++ | +++ | + | ++ | 205 +/− 81 |
| 807B-M0004-A03.1 | n.d.[1] | 24.4 | − | +[3]* | +++ | + | + | 78 +/− 43 |

TABLE 23-continued

Binding of germ line corrected IgG to CTD and tissue

| Isolate name | Peptide | Affinity (Biacore (nM)) | VLDL ELISA[2] | IHC[3] (tissue) | ELISA[4] hCTD | ELISA[4] mCTD | ELISA[4] pCTD | In vitro phagocytosis EC50 ± SEM (ng/ml) |
|---|---|---|---|---|---|---|---|---|
| 807B-M0079-D10 | p4, p8 | n.d.[1] | +++ | ++ | +++ | +++ | +++ | 7 +/− 1.4 |
| 807B-M0079-D10.1 | n.d.[1] | n.d.[1] | ++ | ++ | +++ | +++ | +++ | 19 +/− 15 |

[1]n.d.: Not done.
[2]VLDL ELISA: human VLDL is coated 0.0003-100 μg/ml of appropriate hIgG is tested for binding
[3]IHC: Brain tissue sections from APP/PS1 mouse was used. 1.5-1.8 μg/ml of appropriate hIgG is added,
[3]*reactivity to mCTD lower than to hCTD
[4]CTD ELISA: human, mouse or primate CTD is coated, 0.0003-100 μg/ml of appropriate hIgG is tested for binding

TABLE 24

807B-M0004-A03 = 39 clones selected for Fab production

| AminoAc | 1 (WT = S) | 2 (WT = I) | 3 (WT = A) | 4 (WT = A) | 5 (WT = A) | 6 (WT = G) | 7 (WT = T) | 8 (WT = D) | 9 (WT = Y) |
|---|---|---|---|---|---|---|---|---|---|
| A | | | 88% | 65% | 60% | | | | |
| D | | | | 9% | | | | 98% | 2% |
| E | | | | 7% | | | | 2% | |
| G | 2% | | 5% | 2% | | 84% | | | |
| H | | | | | | | | 2% | 21% |
| I | | 98% | | | | | 2% | | |
| K | | | | | | | | 5% | |
| L | | | | | | | | | 2% |
| M | | 2% | | | | | | | |
| N | | | | 5% | | | 10% | | |
| P | | | | | 5% | | | | |
| Q | | | 2% | | | | | | |
| R | 5% | | | | | 16% | 2% | | 5% |
| S | 91% | | 5% | 14% | 19% | | | | |
| T | 2% | | | 2% | 7% | | 79% | | |
| V | | | | 5% | | | | | |
| Y | | | | | | | | | 70% |

TABLE 25

807B-M0004-H03 = 54 clones selected for Fab production: part 1

| AminoAc | 1 (WT = E) | 2 (WT = G) | 3 (WT = S) | 4 (WT = A) | 5 (WT = G) | 6 (WT = V) | 7 (WT = V) | 8 (WT = K) | 9 (WT = G) | 10 (WT = P) |
|---|---|---|---|---|---|---|---|---|---|---|
| A | 2% | 2% | 5% | 82% | 9% | 5% | | | 4% | 5% |
| D | 4% | | | | | | 2% | | | |
| E | 95% | | | | 2% | 4% | | | | |
| F | | | | | | 4% | 4% | | 2% | |
| G | | 73% | | 2% | 46% | | | | 73% | |
| H | | | | | | | | | | 2% |
| I | | | | | | | 7% | 7% | | |
| K | | | | | | 2% | | 84% | | |
| L | | | 5% | | | 9% | 9% | | | 5% |
| M | | | 2% | | | 4% | 2% | | | |
| N | | | | | | | | 4% | | |
| P | | | 5% | | | | | 2% | | 77% |
| Q | | | | | | | | 2% | | 2% |
| R | | 18% | 2% | 9% | 38% | 4% | | 2% | 11% | 5% |
| S | | 4% | 75% | | | | 2% | | | 4% |
| T | | | | | | 2% | | | | |
| V | | 4% | | 7% | 4% | 66% | 77% | | | |
| W | | | 4% | | | | | | 9% | |
| Y | | | | | | | | | | |
| Stop | | | 2% | | | | | | | |

TABLE 26

807B-M0004-H03 = 54 clones selected for Fab production: part 2

| AminoAc | 11 (WT = A) | 12 (WT = R) | 13 (WT = Y) | 14 (WT = Y) | 15 (WT = Y) | 16 (WT = Y) | 17 (WT = Y) | 18 (WT = M) | 19 (WT = D) | 20 (WT = V) |
|---|---|---|---|---|---|---|---|---|---|---|
| A | 73% | | | | | | | | 4% | 4% |
| C | | | 2% | | | | | | | |
| D | 2% | | | | | | | 2% | 77% | |
| E | | | | | | | | 2% | 4% | |
| F | | | 2% | 4% | | 5% | | | | 5% |
| G | 5% | 2% | | | | | | | 2% | 2% |
| H | | | 7% | | 7% | 2% | | | 4% | |
| I | | | | | | | | 5% | | 7% |
| K | | 4% | | | | | | | | |
| L | 2% | 2% | | | | | | 2% | | 9% |
| M | | | | | | | | 93% | | |
| N | | | 2% | 4% | 4% | | 4% | | 5% | |
| P | 4% | 2% | | | | | | | | 2% |
| Q | | 4% | | | | | | 5% | | |
| R | 2% | 83% | | | | | | | | |
| S | 5% | | | | 4% | | 5% | | 2% | |
| T | 5% | | | | | | | | | |
| V | 4% | | | | | | | | 2% | 71% |
| Y | | 4% | 88% | 92% | 85% | 93% | 82% | | 2% | |

TABLE 27

807B-M0079-D10 = 33 clones selected for Fab production

| AminoAc | 1(WT = G) | 2(WT = L) | 3(WT = Y) | 4(WT = R) |
|---|---|---|---|---|
| A | 11% | | 6% | |
| D | 3% | | | |
| F | | | 9% | |
| G | 69% | | | 3% |
| H | | | 11% | 9% |
| I | | 3% | | |
| K | | | | 3% |
| L | | 86% | 3% | 17% |
| M | | 6% | | |
| N | | | | 6% |
| P | | | | 3% |
| Q | | | 3% | 9% |
| R | | | | 43% |
| S | 14% | | 6% | 3% |
| T | 3% | | | |
| V | | | 3% | 3% |
| W | | | | 3% |
| Y | | | 57% | 6% |
| Stop | | | 2% | |

TABLE 28

807A-M0028-B02-CTD = 60 clones selected for Fab production

| AminoAc | 1 (WT = S) | 2 (WT = V) | 3 (WT = L) | 4 (WT = L) | 5 (WT = D) | 6 (WT = Y) |
|---|---|---|---|---|---|---|
| A | 18% | 2% | | | 2% | 2% |
| D | | 2% | | | 92% | |
| E | | | | | 2% | 2% |
| F | 2% | | | 19% | | 3% |
| G | 19% | 3% | | | | |
| H | | | 3% | 23% | 2% | 11% |
| I | | 23% | 2% | 2% | | 2% |
| K | | | | | | 16% |
| L | | 2% | 87% | 52% | | 2% |
| M | | | 3% | | | |
| N | | 2% | | | | 11% |
| P | 2% | | 2% | 3% | | 3% |
| Q | | | 2% | | | 3% |
| R | | | | 2% | | 3% |
| S | 57% | | | | | 8% |
| T | 2% | 2% | 2% | | | 3% |
| V | | 66.50% | | | | |
| Y | 2% | | | | 2% | 29% |

TABLE 29

807A-M0028-B02-fibrils = 12 clones selected for Fab production

| AminoAc | 1 (WT = S) | 2 (WT = V) | 3 (WT = L) | 4 (WT = L) | 5 (WT = D) | 6 (WT = Y) |
|---|---|---|---|---|---|---|
| A | 33% | | | | | |
| D | | | | | 100% | |
| F | | | | 25% | | |
| G | | | | | | |
| H | | | 8% | 17% | | 17% |
| I | | | | | | |
| K | | 8% | | | | |
| L | | | 92% | 58% | | |
| N | | | | | | 17% |
| Q | | | | | | 8% |
| R | | | | | | 8% |
| S | 67% | | | | | 17% |
| V | | 92% | | | | |
| Y | | | | | | 33% |

TABLE 30

807B-M0009-F06 = 24 clones selected for Fab production

| AminoAc | 1 (WT = V) | 2 (WT = G) | 3 (WT = M) | 4 (WT = S) | 5 (WT = T) | 6 (WT = Y) | 7 (WT = A) | 8 (WT = F) | 9 (WT = D) | 10 (WT = I) |
|---|---|---|---|---|---|---|---|---|---|---|
| A | | 8% | | 8% | | | 24% | | | |
| D | | | | | | | | | 96% | |
| E | | | | | | | | | 4% | |
| F | | | | 4% | | | | 96% | | 4% |
| G | | 92% | | | | | 60% | | | |
| H | | | | | | 4% | | | | |
| I | | | 20% | | | | | | | 56% |
| K | | | 4% | | | | | | | 14% |
| L | | | 12% | 4% | | | | 4% | | 16% |
| M | | | 60% | | | | | | | 4% |
| N | | | | | | 12% | | | | |
| P | | | | 8% | | | | | | |
| S | | | | 60% | 8% | | 16% | | | |
| T | | | 12% | | 76% | | | | | 8% |
| V | 100% | | 4% | | | | | | | 8% |
| Y | | | | 4% | | 100% | | | | |

TABLE 31

Biacore analysis of 807B-M0004-A03, original clone and variants

| Clone | HV-CDR3 | BC nM | koff 1/s | kon 1/Ms | KD nM | Ranking koff | Ranking KD |
|---|---|---|---|---|---|---|---|
| * 807B-M0004-A03/WT | SIAAAGTDY | 234 | 0.0294 | 3.18E+05 | 9.26E-08 | 27 | 13 |
| 807B-M0004-A03/WT | SIAAGTDY | 232 | 0.0275 | 2.54E+05 | 1.08E-07 | 23 | 16 |
| 807B-M0004-A03/M0117-A04 | SIAADGIDY | 181 | 0.0341 | ND | 3.07E+03 | 33 | 41 |
| 807B-M0004-A03/M0117-A12 | SIAATRTDY | 239 | 0.0215 | 1.47E+05 | 1.46E-07 | 10 | 28 |
| 807B-M0004-A03/M0117-B03 | SIAAARTEY | 192 | 0.0262 | 3.29E+04 | 7.97E-07 | 21 | 36 |
| 807B-M0004-A03/M0117-B04 | SIAPSGTDY | 210 | 0.132 | 6.22E-04 | 212 | 43 | 40 |
| 807B-M0004-A03/M0117-B05 | SIAPAGTDH | 224 | 0.0297 | 2.45E+05 | 1.21E-07 | 28 | 22 |

TABLE 31-continued

Biacore analysis of 807B-M0004-A03, original clone and variants

| Clone | HV-CDR3 | BC nM | koff 1/s | kon 1/Ms | KD nM | Ranking koff | Ranking KD |
|---|---|---|---|---|---|---|---|
| 807B-M0004-A03/M0117-B11 | SIAEAGTDY | 245 | 0.0464 | 3.02E+05 | 1.54E-07 | 35 | 29 |
| 807B-M0004-A03/M0117-C04 | SIAVAGTDY | 193 | 0.0902 | 1.25 | 0.072 | 41 | 38 |
| 807B-M0004-A03/M0117-C07 | SIAGAGNDY | 186 | 0.0306 | 2.40E+05 | 1.28E-07 | 30 | 23 |
| 807B-M0004-A03/M0117-C09 | SIAAAGTDH | 280 | 0.0188 | 2.53E+05 | 7.44E-08 | 6 | 10 |
| 807B-M0004-A03/M0117-C11 | SIGAAGTDY | 263 | 0.0767 | 0.0967 | 0.788 | 39 | 39 |
| 807B-M0004-A03/M0117-C12 | SIAASGTDY | 134 | 0.0284 | 3.95E+05 | 7.22E-08 | 26 | 8 |
| * 807B-M0004-A03/M0117-D03 | SIAAARTDY | 199 | 0.0128 | 9.45E+04 | 1.34E-07 | 3 | 25 |
| 807B-M0004-A03/M0117-E06 | SIQAAGTDH | 123 | 0.0247 | 1.96E-05 | 4.21E+03 | 15 | 42 |
| 807B-M0004-A03/M0117-E12 | SIASPGTDY | 228 | 0.0266 | 1.95E+05 | 1.37E-07 | 22 | 27 |
| * 807B-M0004-A03/M0117-F05 | SIASAGTDH | 290 | 0.0139 | 2.22E+05 | 6.13E-08 | 4 | 4 |
| 807B-M0004-A03/M0117-F11 | GISTSGTDD | 284 | 0.0243 | 2.08E+05 | 1.15E-07 | 14 | 19 |
| 807B-M0004-A03/M0117-F12 | SIAVAGTDY | 235 | 0.0906 | 1.82E-05 | 4.96E+03 | 42 | 43 |
| * 807B-M0004-A03/M0117-G01 | SIASARTDS | 256 | 0.0103 | 1.66E+05 | 6.07E-08 | 1 | 3 |
| 807B-M0004-A03/M0117-G03 | SIAAPGTDY | 220 | 0.011 | 1.92E+04 | 4.84E-07 | 2 | 35 |
| 807B-M0004-A03/M0117-G04 | RIAASGTDY | 92 | 0.049 | 4.42E+05 | 1.20E-07 | 36 | 21 |
| 807B-M0004-A03/M0117-G05 | SIAATGKDH | 280 | 0.0815 | 9.94E+04 | 8.24E-07 | 40 | 37 |
| 807B-M0004-A03/M0117-G07 | SIAAAGSDS | 471 | 0.0283 | 1.35E+05 | 2.23E-07 | 25 | 33 |
| 807B-M0004-A03/M0117-H06 | SIGASRTDY | 336 | 0.0502 | 3.42E+05 | 1.68E-07 | 37 | 31 |
| 807B-M0004-A03/M0117-H11 | SIASAGTDL | 217 | 0.0205 | 2.87E+05 | 6.97E-08 | 8 | 6 |
| 807B-M0004-A03/M0118-A03 | SIAAAGNDY | 167 | 0.0254 | 3.51E+05 | 7.12E-08 | 17 | 7 |
| * 807B-M0004-A03/M0118-B09 | SIAADRTDY | 252 | 0.0231 | 4.78E+05 | 4.70E-08 | 11 | 1 |
| 807B-M0004-A03/M0118-B11 | SIAESGTDY | 203 | 0.0298 | 3.34E+05 | 9.06E-08 | 29 | 12 |
| 807B-M0004-A03/M0118-C04 | SIASSGTDH | 213 | 0.0205 | 3.64E+05 | 5.47E-08 | 9 | 2 |
| 807B-M0004-A03/M0118-D02 | RMAAAGTDY | 225 | 0.0235 | 9.81E+04 | 2.42E-07 | 12 | 34 |

TABLE 31-continued

Biacore analysis of 807B-M0004-A03, original clone and variants

| Clone | HV-CDR3 | BC nM | koff 1/s | kon 1/Ms | KD nM | Ranking koff | Ranking KD |
|---|---|---|---|---|---|---|---|
| 807B-M0004-A03/M0118-D03 | SIAAAGKDY | 281 | 0.0306 | 2.90E+05 | 1.33E-07 | 31 | 24 |
| 807B-M0004-A03/M0118-D07 | SIAATGTDI | 263 | 0.028 | 2.54E+05 | 1.19E-07 | 24 | 20 |
| 807B-M0004-A03/M0118-E10 | SIAAAGNDH | 179 | 0.0236 | 3.19E+05 | 7.41E-08 | 13 | 9 |
| 807B-M0004-A03/M0118-E12 | SIASAGTDY | 267 | 0.0312 | 2.52E+05 | 1.55E-07 | 32 | 30 |
| * 807B-M0004-A03/M0118-F03 | SIAASRTDY | 230 | 0.0158 | 2.36E+05 | 6.56E-08 | 5 | 5 |
| 807B-M0004-A03/M0118-F06 | SIAAGTDH | 372 | 0.0194 | 2.38E+05 | 7.97E-08 | 7 | 11 |
| 807B-M0004-A03/M0118-F09 | SIAEAGTDY | 245 | 0.0456 | 2.92E+05 | 1.78E-07 | 34 | 32 |
| 807B-M0004-A03/M0118-F12 | SISAAGTDY | 278 | 0.0249 | 1.78E+05 | 1.37E-07 | 16 | 26 |
| 807B-M0004-A03/M0118-G03 | SIAADGTDY | 208 | 0.0669 | 6.16E+05 | 1.14E-07 | 38 | 18 |
| 807B-M0004-A03/M0118-G05 | TIAAAGTDY | 267 | 0.0259 | 2.42E+05 | 1.13E-07 | 20 | 17 |
| 807B-M0004-A03/M0118-G08 | SIAAAGHDH | 336 | 0.0256 | 2.70E+05 | 1.00E-07 | 18 | 14 |
| 807B-M0004-A03/M0118-H01 | SIAAAGNDY | 276 | 0.0258 | 2.69E+05 | 1.00E-07 | 19 | 15 |

* = selected clone
BC = Biacore

TABLE 32

Biacore analysis of 807B-M0004-H03, original clone and variants

| Clone | HV-CDR3 | BC nM | koff 1/s | kon 1/Ms | KD nM | Ranking koff | Ranking KD |
|---|---|---|---|---|---|---|---|
| * 807B-M0004-H03/WT | EGSAGVVKGPARYYYYYMDV | 703 | 1.18E-03 | 4.37E+03 | 2.56E-07 | 1 | 16 |
| 807B-M0004-H03/M0119-A07 | ERSAGVLKGPAWYYYYYMDV | 262 | 5.94E-03 | 1.48E+04 | 1.67E-07 | 36 | 7 |
| 807B-M0004-H03/M0119-A08 | EGSAAFVKGPARYYYYDMDI | 375 | 2.66E-01 | 1.24E+04 | 4.64E-07 | 55 | 30 |
| * 807B-M0004-H03/M0119-B05 | EGSSGVVKGPARYYYYYMDA | 371 | 1.53E-03 | 6.03E+03 | 1.59E-07 | 4 | 5 |
| 807B-M0004-H03/M0119-B06 | EGSVGAVKGRARYYYYYMNV | 729 | 2.62E-03 | 3.45E+03 | 4.00E-07 | 16 | 26 |
| 807B-M0004-H03/M0119-B07 | EGSAGVFKGPARYYYYYMDV | 486 | 7.20E-03 | 1.36E+04 | 3.98E-07 | 40 | 24 |
| * 807B-M0004-H03/M0119-C05 | ERSVAVFKARPRHYYYYMDV | 696 | 1.69E-03 | 1.09E+04 | 1.46E-07 | 5 | 3 |
| 807B-M0004-H03/M0119-C08 | EGSAGVDIGPARYYYYYMNV | 453 | 7.24E-03 | 1.46E+04 | 4.72E-07 | 41 | 32 |
| 807B-M0004-H03/M0119-C11 | EGSAAVYKAPAKYYYYYMEV | 347 | 7.39E-03 | 1.47E+04 | 4.70E-07 | 43 | 31 |
| 807B-M0004-H03/M0119-E01 | EGSVGVVKGPARYYHYQIDV | 541 | 3.03E-03 | 7.69E+03 | 3.29E-07 | 19 | 21 |
| 807B-M0004-H03/M0119-E04 | ESSARVVKGLARYYNYYMHV | 484 | 5.34E-03 | 5.43E+03 | 6.00E-07 | 31 | 38 |
| 807B-M0004-H03/M0119-E07 | ERPSRVVKGPTRYYYYYMDV | 577 | 5.51E-03 | 4.33E-03 | 7.70E-01 | 32 | 52 |

TABLE 32-continued

Biacore analysis of 807B-M0004-H03, original clone and variants

| Clone | HV-CDR3 | BC nM | koff 1/s | kon 1/Ms | KD nM | Ranking koff | Ranking KD |
|---|---|---|---|---|---|---|---|
| 807B-M0004-H03/M0119-E11 | EVSARVVKCPARYYYYMDV | 614 | 9.69E-03 | 7.74E-06 | 1.19E+03 | 45 | 54 |
| 807B-M0004-H03/M0119-F01 | EGSAGVIKGPARYYYFYMGV | 389 | 1.85E-01 | 1.38E+04 | 7.14E-07 | 54 | 41 |
| * 807B-M0004-H03/M0119-F04 | EGSARVTKGPARYYYYEMDV | 675 | 3.99E-03 | 2.68E+04 | 1.44E-07 | 29 | 2 |
| 807B-M0004-H03/M0119-F05 | ERSVGVVIGHARYFYYYMDV | 472 | 1.72E-03 | 8.05E+03 | 1.99E-07 | 6 | 8 |
| 807B-M0004-H03/M0119-F09 | EGPAGVVKGRARYYSYNMSV | 246 | 1.13E-01 | 8.96E+05 | 1.10E-07 | 52 | 1 |
| 807B-M0004-H03/M0119-F10 | ESSARVYNGPAWYYYYMDA | 261 | 5.71E-03 | 8.52E+03 | 6.47E-07 | 35 | 39 |
| 807B-M0004-H03/M0119-F11 | EGSSRAVKGAPRYYYYMDV | 1027 | 3.41E-03 | 1.52E+03 | 1.68E-06 | 24 | 45 |
| 807B-M0004-H03/M0119-F12 | EVSGGVVKGPARYYYYMAL | 862 | 2.57E-02 | 6.16E+03 | 3.93E-06 | 48 | 47 |
| 807B-M0004-H03/M0119-G08 | EGqARRVKGQARYYYYMDV | 270 | 3.33E-03 | 3.29E+03 | 6.81E-07 | 23 | 40 |
| 807B-M0004-H03/M0119-G10 | EGSAGLVKGPARYYYYMDV | 514 | 1.76E-03 | 4.94E+03 | 295E-07 | 7 | 19 |
| 807B-M0004-H03/M0119-G12 | ERSAGVVKGPSRNYYYYMDV | 728 | 3.73E-03 | 1.56E+04 | 2.36E-07 | 27 | 14 |
| 807B-M0004-H03/M0119-H01 | EGSARRVKRPGRYYYYQMDV | 912 | 1.06E-02 | 3.66E+04 | 2.84E-07 | 46 | 18 |
| 807B-M0004-H03/M0119-H03 | EGSARMLKGPARCYYYYMDV | 315 | 7.36E-03 | 1.55E+04 | 4.38E-07 | 42 | 28 |
| 807B-M0004-H03/M0119-H08 | EGMAGVVKFPARHNYHYMDV | 881 | 4.58E-02 | 8.86E+04 | 5.76E-07 | 49 | 37 |
| * 807B-M0004-H03/M0119-H09 | DGSARVVKGPRRYYYYIDV | 351 | 1.40E-03 | 7.92E+03 | 1.50E-07 | 2 | 4 |
| 807B-M0004-H03/M0119-H11 | ERPAGLVKGPARYYSYYMDV | 1205 | 2.21E-03 | 6.55E+03 | 3.11E-07 | 12 | 20 |
| 807B-M0004-H03/M0120-A03 | EGSARMVKGAARYYYYYMDV | 1109 | 1.62E-02 | 6.25E+04 | 2.50E-07 | 47 | 15 |
| 807B-M0004-H03/M0120-A07 | EGSAGTIKWLVRYYNFYMDV | 707 | 3.24E-03 | 6.77E+03 | 4.48E-07 | 21 | 29 |
| * 807B-M0004-H03/M0120-B05 | EGSARVVKGPARYFYYYMDL | 740 | 1.40E-03 | 4.70E+03 | 2.34E-07 | 3 | 13 |
| 807B-M0004-H03/M0120-B06 | EGSARVVKGPDRYYYYMAP | 309 | 5.62E-03 | 8.84E+03 | 4.82E-01 | 33 | 51 |
| 807B-M0004-H03/M0120-B09 | EGSAGKVIGPAPHYYYYMDV | 868 | 6.90E-03 | 2.05E+04 | 3.34E-07 | 39 | 22 |
| 807B-M0004-H03/M0120-B11 | EGRARVLKGLARYYHYYMDF | 1023 | 3.01E-03 | 3.50E+02 | 5.42E-06 | 18 | 49 |
| 807B-M0004-H03/M0120-C02 | EGSARFVKGPARYYYYMDI | 779 | 3.74E-03 | 5.68E+02 | 4.10E-06 | 28 | 48 |
| 807B-M0004-H03/M0120-C06 | EGSSRLVQWPARYYYSMDV | 747 | 3.67E-03 | 5.96E+03 | 5.18E-07 | 26 | 35 |
| 807B-M0004-H03/M0120-C07 | ERSAGVMKGPTLYYYYYMDV | 641 | 8.85E-03 | 6.51E+03 | 1.17E-06 | 44 | 44 |
| 807B-M0004-H03/M0120-C12 | EGSAGVVNRSSRYNYYYLDV | 959 | 4.94E-02 | ND | ND | 50 | — |
| 807B-M0004-H03/M0120-D04 | EGSSVEVKGPARYYHYYMDV | 652 | 1.85E-03 | 6.71E+03 | 2.07E-07 | 10 | 9 |
| 807B-M0004-H03/M0120-D05 | EGSAGVVKGPTRYYYYSMDV | 921 | 2.28E-03 | 3.84E+03 | 4.81E-07 | 15 | 33 |
| 807B-M0004-H03/M0120-E02 | EGSAVVKRSARYYYYYMNF | 827 | 6.72E-03 | 6.74E+03 | 8.20E-07 | 38 | 42 |
| 807B-M0004-H03/M0120-E04 | ERSARLLKGPLRYYYYMDV | 817 | 1.86E-03 | 2.35E+03 | 3.70E-07 | 11 | 23 |
| 807B-M0004-H03/M0120-E06 | ERAARAVKGPSRYYYYYMHV | 1110 | 1.15E-01 | 3.93E-03 | 3.76E+00 | 53 | 53 |
| 807B-M0004--H03/M0120-F03 | EGLAGVVKRPARFYYYYMDV | 873 | 3.26E-03 | 1.09E+04 | 2.80E-07 | 22 | 17 |
| 807B-M0004-H03/M0120-F04 | EGSARVVIWPAQYYYYMDF | 434 | 3.53E-03 | 5.48E+03 | 4.89E-07 | 25 | 34 |
| 807B-M0004-H03/M0120-F06 | EGSARVVKGPARYYYYSMVV | 850 | 2.94E-03 | 4.44E+03 | 4.17E-07 | 17 | 27 |
| 807B-M0004-H03/M0120-F07 | ERSAAVVKWPVRYYYYYMDL | 611 | 4.92E-03 | 1.26E+04 | 2.41E-06 | 30 | 46 |
| 807B-M0004-H03/M0120-G02 | EGWAALVKGPGRYYYQMYV | 749 | 3.19E-01 | 4.67E+02 | 2.80E-05 | 56 | 50 |
| 807B-M0004-H03/M0120-G03 | EGSAGVLKGPAKYYYYMDI | 755 | 1.77E-03 | 6.24E+03 | 2.33E-07 | 8 | 12 |

TABLE 32-continued

Biacore analysis of 807B-M0004-H03, original clone and variants

| Clone | HV-CDR3 | BC nM | koff 1/s | kon 1/Ms | KD nM | Ranking koff | Ranking KD |
|---|---|---|---|---|---|---|---|
| 807B-M0004-H03/M0120-G04 | EGSARVVKGPARYYYYYMDV | 956 | 1.81E-03 | 1.09E+04 | 1.64E-07 | 9 | 6 |
| 807B-M0004-H03/M0120-G10 | EGSAGVVKGPARHYYYYMDI | 755 | 2.28E-03 | 9.65E+03 | 2.30E-07 | 14 | 11 |
| 807B-M0004-H03/M0120-G12 | DGLAEEVKGPAQYYYYYIDG | 782 | 7.80E-02 | 7.72E+04 | 1.02E-06 | 51 | 43 |
| 807B-M0004-H03/M0120-H03 | EAAAGVVKGPARYYYFNMEV | 1114 | 2.27E-03 | 4.87E+03 | 3.99E-07 | 13 | 25 |
| 807B-M0004-H03/M0120-H04 | EGAAEAVRRPAGYYHYYMDL | 916 | 3.22E-03 | 1.46E+04 | 2.16E-07 | 20 | 10 |
| 807B-M0004-H03/M0120-H06 | QGWAGVVKWPARYYYYMDV | 3 | 5.71E-03 | ND | ND | 34 | — |
| 807B-M0004-H03/M0120-H10 | EGLAGVIPRAARYYYYYMDL | 800 | 6.12E-03 | 1.06E+04 | 5.45E-07 | 37 | 36 |

* = selected clones

TABLE 33

Biacore analysis of 807B-M0009-F06, original clone and variants

| Clone | HV-CDR3 | BC nM | koff 1/s | kon 1/Ms | KD nM | Ranking koff | Ranking KD |
|---|---|---|---|---|---|---|---|
| 807B-M0009-F06/WT | VGMSTYAFDI | 243 | 9.70E-02 | 0.043 | 2.26 | 23 | 25 |
| 807B-M0009-F06/M0127-A01 | VGMSTYGLEI | 471 | 2.79E-02 | 2.14E+04 | 1.26E-06 | 17 | 18 |
| *807B-M0009-F06/M0127-B07 | VGMSTYGFDK | 418 | 8.83E-03 | 5.62E+04 | 1.56E-07 | 2 | 8 |
| 807B-M0009-F06/M0127-B08 | VGMTTYAFDV | 390 | 8.59E-02 | 0.0434 | 1.85 | 20 | 22 |
| *807B-M0009-F06/M0127-C10 | VGISTYGFDL | 78 | 1.53E-02 | 1.74E+05 | 8.68E-08 | 10 | 2 |
| 807B-M0009-F06/M0127-D01 | VGISTYGFDI | 324 | 1.45E-02 | 5.56E+04 | 2.57E-07 | 7 | 15 |
| *807B-M0009-F06/M0127-D05 | VGMATYGFDI | 346 | 9.45E-03 | 6.97E+04 | 1.34E-07 | 3 | 5 |
| 807B-M0009-F06/M0127-E03 | VGISTYGFDV | 240 | 1.49E-02 | 1.09E+05 | 1.35E-07 | 9 | 6 |
| 807B-M0009-F06/M0127-E10 | VGMSTYGFDI | 289 | 1.05E-02 | 7.43E+04 | 1.40E-07 | 5 | 7 |
| 807B-M0009-F06/M0127-E11 | VGIPTYSFDI | 146 | 2.24E-02 | 2.61E+04 | 8.57E-07 | 14 | 17 |
| 807B-M0009-F06/M0127-F07 | VGLATYSFDL | 203 | 1.02E-01 | 0.0628 | 1.62 | 25 | 20 |
| *807B-M0009-F06/M0127-F09 | VGMYNYGFDI | 221 | 1.02E-02 | 1.09E+05 | 9.38E-08 | 4 | 3 |
| 807B-M0009-F06/M0127-F11 | VGMSTYSFDT | 271 | 1.01E-01 | 0.0453 | 2.23 | 24 | 24 |
| 807B-M0009-F06/M0127-G02 | VGVSTYGFDI | 39 | 1.59E-02 | 1.47E+05 | 1.08E-07 | 11 | 4 |
| 807B-M0009-F06/M0127-H04 | VGMFTYAFDT | 201 | 7.87E-02 | 0.0435 | 1.81 | 19 | 21 |
| 807B-M0009-F06/M0127-H05 | VGKSTYGFDI | 305 | 1.79E-02 | 8.37E+04 | 2.14E-07 | 12 | 13 |

TABLE 33-continued

Biacore analysis of 807B-M0009-F06, original clone and variants

| Clone | HV-CDR3 | BC nM | koff 1/s | kon 1/Ms | KD nM | Ranking koff | Ranking KD |
|---|---|---|---|---|---|---|---|
| 807B-M0009-F06/M0128-C01 | VAMTTYGFDL | 253 | 2.41E-02 | 3.70E+04 | 6.52E-07 | 16 | 16 |
| 807B-M0009-F06/M0128-D09 | VGISSYGFDI | 316 | 1.46E-02 | 7.76E+04 | 1.88E-07 | 8 | 11 |
| 807B-M0009-F06/M0128-D12 | VAMSNYGFDL | 159 | 2.38E-02 | 1.13E+05 | 2.10E-07 | 15 | 12 |
| 807B-M0009-F06/M0128-F02 | VGMTHYAFDI | 148 | 1.98E-02 | 7.91E+04 | 2.50E-07 | 13 | 14 |
| 807B-M0009-F06/M0128-F08 | VGMLTYAFDI | 120 | 7.71E-02 | 0.0765 | 1.01 | 18 | 19 |
| 807B-M0009-F06/M0128-G09 | VGLPSYSFDI | 115 | 8.98E-02 | 1.24E+05 | 1.72E-07 | 22 | 10 |
| *807B-M0009-F06/M0128-H01 | VGMSNYGFDF | 116 | 7.78E-03 | 1.62E+05 | 4.79E-08 | 1 | 1 |
| 807B-M0009-F06/M0128-H07 | VGMSTYAFDM | 211 | 8.98E-02 | 0.048 | 1.87 | 21 | 23 |
| 807B-M0009-F06/M0128-H11 | VGLSTYGFDI | 295 | 1.31E-02 | 8.09E+04 | 1.62E-07 | 6 | 9 |

* = selected clones

TABLE 34

Biacore screening of 807B-M0079-D10, original clone and variants

| Clone | HV-CDR3 | koff 1/s |
|---|---|---|
| * 807B-M0079-D10/WT | GLYR | 6.02E-03 |
| 807B-M0079-D10/M0121-A01 | GLHR | 1.29E-02 |
| 807B-M0079-D10/M0121-A02 | GLYG | 1.95E-02 |
| 807B-M0079-D10/M0121-A06 | GLYH | 1.47E-02 |
| 807B-M0079-D10/M0121-A08 | GLHL | 2.14E-02 |
| 807B-M0079-D10/M0121-A11 | GIYR | 1.43B-02 |
| 807B-M0079-D10/M0121-A12 | ALAR | 1.65E-02 |
| 807B-M0079-D10/M0121-B04 | GLFR | 1.07E-02 |
| 807B-M0079-D10/M0121-B05 | SLYQ | 2.31E-02 |
| 807B-M0079-D10/M0121-B12 | GLLL | 1.71E-02 |
| 807B-M0079-D10/M0121-C01 | GQYR | 1.93E-02 |
| 807B-M0079-D10/M0121-C03 | GLAR | 2.24E-02 |
| 807B-M0079-D10/M0121-D01 | GLYQ | 1.34E-02 |
| 807B-M0079-D10/M0121-D05 | GLYP | 5.93E-03 |
| 807B-M0079-D10/M0121-D06 | GMYR | 1.62E-02 |
| 807B-M0079-D10/M0121-E02 | ALYS | 5.34E-03 |
| 807B-M0079-D10/M0121-F02 | GLSR | 8.02E-03 |
| 807B-M0079-D10/M0121-F05 | SLYL | 1.84E-02 |
| 807B-M0079-D10/M0121-F06 | GLYL | 1.11E-02 |
| 807B-M0079-D10/M0121-F11 | GMYV | 5.92E-03 |
| 807B-M0079-D10/M0121-G03 | SLYR | 1.22E-02 |
| 807B-M0079-D10/M0121-G10 | ALYR | 1.03E-02 |
| 807B-M0079-D10/M0121-H04 | SLYH | 2.03E-02 |
| 807B-M0079-D10/M0121-H05 | GLYY | 1.70E-02 |
| 807B-M0079-D10/M0122-A01 | DLYR | 1.65E-02 |
| 807B-M0079-D10/M0122-B03 | TLHR | 2.58E-02 |
| 807B-M0079-D10/M0122-D01 | GLHH | 2.11E-02 |
| 807B-M0079-D10/M0122-D03 | GLNR | 1.29E-02 |
| 807B-M0079-D10/M0122-D05 | GLSQ | 1.43E-02 |
| 807B-M0079-D10/M0122-E06 | GLqR | 2.59E-02 |
| 807B-M0079-D10/M0122-F09 | GLFY | 8.76E-03 |

TABLE 34-continued

Biacore screening of 807B-M0079-D10, original clone and variants

| Clone | HV-CDR3 | koff 1/s |
|---|---|---|
| 807B-M0079-D10/M0122-F11 | GLNL | 1.21E-02 |
| 807B-M0079-D10/M0122-G07 | SLFK | 2.17E-02 |
| 807B-M0079-D10/M0122-G12 | ALYW | 6.11E-03 |
| 807B-M0079-D10/M0122-H11 | GVYL | 1.32E-02 |

\* = selected clones

TABLE 35

Biacore screening of 807A-M0028-B02, original clone and variants

| Clone | HV-CDR3 | BC nM | koff 1/s | kon 1/Ms | KD nM | Ranking koff | Ranking KD |
|---|---|---|---|---|---|---|---|
| * 807A-M0028-B02/WT | SVLLDY | 592 | 1.48E-02 | 1.73E+04 | 869 | 72 | 61 |
| 807A-M0028-B02/M0123-A04 | SVQLYP | 120 | 5.05E-02 | 0.0776 | 660000000 | 74 | 73 |
| 807A-M0028-B02/M0123-A05 | SVLHDK | 958 | 8.85E-03 | 1.16E+04 | 768 | 18 | 57 |
| 807A-M0028-202/M0123-A06 | FALLDY | 247 | 7.82E-03 | 2.20E+04 | 358 | 13 | 28 |
| 807A-M0028-B02/M0123-A07 | SVLFDK | 548 | 6.97E-03 | 1.96E+04 | 358 | 10 | 27 |
| 807A-M0028-B02/M0123-A09 | TLLLDs | 345 | 1.47E-02 | 5.85E-03 | 2530000000 | 71 | 74 |
| 807A-M0028-B02/M0123-A10 | GVLLDL | 385 | 9.74E-03 | 2.13E+04 | 462 | 27 | 40 |
| 807A-M0028-B02/M0123-A11 | SVLFDY | 398 | 1.30E-02 | 1.29E+04 | 1020 | 66 | 67 |
| 807A-M0028-B02/M0123-A12 | SILFDY | 449 | 1.02E-02 | 1.36E+04 | 757 | 33 | 56 |
| 807A-M0028-B02/M0123-B01 | SVLLDQ | 711 | 9.49E-03 | 8.59E+03 | 1110 | 25 | 70 |
| 807A-M0028-B02/M0123-B03 | SNLHDQ | 199 | 1.21E-02 | 1.12E+04 | 1080 | 55 | 69 |
| 807A-M0028-B02/M0123-B06 | AILLNY | 207 | 7.43E-03 | 2.89E+04 | 257 | 12 | 15 |
| 807A-M0028-B02/M0123-B08 | AVLLDH | 471 | 1.03E-02 | 1.38E+04 | 745 | 34 | 54 |
| 807A-M0028-B02/M0123-B10 | AVMHDK | 858 | 3.64E-03 | 1.80E+04 | 202 | 1 | 8 |
| 807A-M0028-202/M0123-C07 | SVLFDS | 706 | 1.25E-02 | 1.32E+04 | 945 | 61 | 63 |
| 807A-M0028-B02/M0123-C11 | GVLLDI | 345 | 9.78E-03 | 3.11E+04 | 315 | 29 | 20 |
| *807A-M0028-B02/M0123-D01 | GVLLDK | 578 | 5.62E-03 | 2.65E+04 | 212 | 6 | 9 |
| 807A-M0028-B02/M0123-D03 | SVLLDN | 710 | 1.12E-02 | 1.09E+04 | 1030 | 45 | 68 |
| 807A-M0028-B02/M0123-D04 | SVLHDY | 592 | 1.41E-02 | 1.22E+04 | 1160 | 70 | 71 |
| 807A-M0028-B02/M0123-D06 | SVLFDR | 510 | 9.07E-03 | 2.13E+04 | 427 | 20 | 35 |
| 807A-M0028-B02/M0123-D08 | SVLLDK | 1013 | 9.26E-03 | 1.08E+04 | 862 | 23 | 60 |
| 807A-M0028-B02/M0123-E05 | GGLLDY | 884 | 1.06E-02 | 1.10E+04 | 976 | 37 | 65 |
| 807A-M0028-B02/M0123-E12 | SVMFDY | 646 | 1.13E-02 | 1.14E+04 | 1000 | 46 | 66 |
| 807A-M0028-B02/M0123-F01 | SILHDY | 1049 | 1.21E-02 | 7.34E+03 | 1660 | 56 | 72 |
| *807A-M0028-B02/M0123-F04 | GILHDY | 718 | 4.82E-03 | 2.07E+04 | 233 | 5 | 13 |
| 807A-M0028-B02/M0123-F11 | SVIFDY | 522 | 1.26E-02 | 1.72E+04 | 739 | 62 | 53 |
| 807A-M0028-B02/M0123-F12 | SILFDN | 737 | 9.08~-03 | 1.45E+04 | 630 | 21 | 49 |
| 807A-M0028-B02/M0123-G02 | AILLDY | 190 | 1.55E-02 | 2.09E+04 | 747 | 73 | 55 |
| 807A-M0028-B02/M0123-G03 | AILLDH | 394 | 1.25E-02 | 1.76E+04 | 717 | 60 | 52 |

TABLE 35-continued

Biacore screening of 807A-M0028-B02, original clone and variants

| Clone | HV-CDR3 | BC nM | koff 1/s | kon 1/Ms | KD nM | Ranking koff | Ranking KD |
|---|---|---|---|---|---|---|---|
| 807A-M0028-B02/M0123-G12 | SILFDT | 628 | 8.17E-03 | 2.01E+04 | 409 | 15 | 34 |
| 807A-M0028-B02/M0123-H02 | AVLLDY | 276 | 1.11E-02 | 2.77E+04 | 404 | 42 | 33 |
| 807A-M0028-B02/M0123-H09 | SVLPDN | 685 | 8.78E-03 | 2.04E+04 | 434 | 16 | 36 |
| 807A-M0028-B02/M0123-H10 | GILLDK | 591 | 6.36E-03 | 2.85E+04 | 224 | 8 | 10 |
| 807A-M0028-B02/M0123-H11 | SVLFDN | 619 | 1.15E-02 | 1.95E+04 | 596 | 48 | 47 |
| 807A-M0028-B02/M0124-A01 | SVLLDS | 738 | 6.01E-03 | 1.75E+04 | 344 | 7 | 23 |
| 807A-M0028-B02/M0124-A10 | SDLRAE | 815 | 9.75E-03 | 1.15E+04 | 855 | 28 | 59 |
| 807A-M0028-B02/M0124-A11 | GVLLDY | 452 | 8.85E-03 | 3.47E+04 | 257 | 17 | 16 |
| *807A-M0028-B02/M0124-B02 | GVLHDY | 649 | 4.40E-03 | 2.66E+04 | 166 | 3 | 5 |
| 807A-M0028-202/M0124-B03 | SVLLDR | 201 | 1.25E-02 | 4.88E+04 | 258 | 59 | 17 |
| 807A-M0028-202/M0124-B08 | SILHDK | 590 | 6.37E-03 | 3.20E+04 | 200 | 9 | 7 |
| *807AM0028-B02/M0124-B11 | SILFDK | 389 | 4.49E-03 | 3.82E+04 | 118 | 4 | 2 |
| 807A-M0028-B02/M0124-C01 | SILLDH | 517 | 1.17E-02 | 2.00E+04 | 590 | 49 | 46 |
| 807A-M0028-B02/M0124-C02 | SVPIDH | 243 | 1.24E-02 | 3.63E+04 | 344 | 58 | 24 |
| 807A-M0028-B02/M0124-C03 | PVLLHF | 269 | 8.87E-03 | 3.87E+04 | 231 | 19 | 11 |
| 807A-M0028-B02/M0124-C04 | GVLLEP | 509 | 9.99E-03 | 2.05E+04 | 494 | 31 | 41 |
| *807A-M0028-B02/M0124-C05 | GVLFDN | 230 | 3.93E-03 | 7.01E+04 | 56 | 2 | 1 |
| 807A-M0028-B02/M0124-C06 | AILLDK | 272 | 8.08E-03 | 5.04E+04 | 162 | 14 | 4 |
| 807A-M0028-B02/M0124-D02 | STLLDH | 445 | 1.11E-02 | 2.07E+04 | 541 | 43 | 43 |
| 807A-M0028-B02/M0124-D06 | SIHLDY | 470 | 1.23E-02 | 1.40E+04 | 888 | 57 | 62 |
| 807A-M0028-B02/M0124-D08 | SVTLDA | 446 | 1.20E-02 | 2.23E-04 | 543 | 53 | 45 |
| 807A-M0028-B02/M0124-D09 | SVLHDF | 378 | 1.30E-02 | 2.87E+04 | 459 | 65 | 39 |
| 807A-M0028-B02/M0124-D10 | SVLHDS | 390 | 1.39E-02 | 2.22E+04 | 634 | 69 | 51 |
| 807A-M0028-B02/M0124-D12 | GGLLDK | 853 | 7.07E-03 | 2.16E+04 | 328 | 11 | 22 |
| 807A-M0028-B02/M0124-B02 | AVLLDT | 459 | 1.04E-02 | 2.74E+04 | 383 | 35 | 30 |
| 807A-M0028-B02/M0124-E03 | AVLHDY | 490 | 1.00E-02 | 2.21E+04 | 456 | 32 | 38 |
| 807A-M0028-B02/M0124-E04 | SVLHDQ | 272 | 1.21E-02 | 3.06E+04 | 399 | 54 | 32 |
| 807A-M0028-B02/M0124-E10 | GVLLDN | 493 | 9.68E-03 | 2.74E+04 | 357 | 26 | 26 |
| 807A-M0028-B02/M0124-F03 | SVLLDH | 513 | 9.24E-03 | 2.87E+04 | 325 | 22 | 21 |
| 807A-M0028-B02/M0124-F05 | AVLHDS | 211 | 1.19E-02 | 2.66E+04 | 451 | 52 | 37 |
| 807A-M0028-B02/M0124-G03 | YVHPDY | 655 | 1.32E-02 | 1.37E+04 | 971 | 68 | 64 |
| 807A-M0028-B02/M0124-G07 | SVLHDH | 516 | 9.81E-03 | 2.61E+04 | 380 | 30 | 29 |
| 807A-M0028-B02/M0124-G10 | AVLLDN | 316 | 1.08E-02 | 3.87E+04 | 282 | 38 | 18 |
| 807A-M0028-B02/M0125-C03 | SVLLDR | 473 | 1.18E-02 | 3.12E+04 | 385 | 50 | 31 |
| 807A-M0028-B02/M0125-D03 | SVLFDY | 295 | 1.11E-02 | 4.41E+04 | 254 | 40 | 14 |
| 807A-M0028-B02/M0125-D06 | SVHLDY | 161 | 1.12E-02 | 8.30E+04 | 136 | 44 | 3 |
| 807A-M0028-B02/M0125-D09 | AVLHDS | 639 | 1.06E-02 | 1.97E+04 | 542 | 36 | 44 |

TABLE 35-continued

Biacore screening of 807A-M0028-B02, original clone and variants

| Clone | HV-CDR3 | BC nM | koff 1/s | kon 1/Ms | KD nM | Ranking koff | Ranking KD |
|---|---|---|---|---|---|---|---|
| 807A-M0028-B02/M0125-F07 | SVLLDQ | 607 | 1.29E-02 | 2.06E+04 | 631 | 64 | 50 |
| 807A-M0028-B02/M0125-F11 | SVLFDS | 621 | 1.18E-02 | 2.39E+04 | 498 | 51 | 42 |
| 807A-M0028-B02/M0125-G02 | SVLLDH | 511 | 1.32E-02 | 2.21E+04 | 607 | 67 | 48 |
| 807A-M0028-B02/M0126-C09 | AVLLDY | 329 | 1.10E-02 | 3.18E+04 | 350 | 39 | 25 |
| 807A-M0028-B02/M0126-E03 | AVLLDN | 257 | 1.11E-02 | 3.86E+04 | 290 | 41 | 19 |
| 807A-M0028-B02/M0126-F08 | SILFDY | 335 | 9.35E-03 | 4.07E+04 | 232 | 24 | 12 |
| 807A-M0028-B02/M0126-G03 | SVLHDN | 627 | 1.28E-02 | 1.53E+04 | 846 | 63 | 58 |
| 807A-M0028-B02/M0126-G07 | AVLLDH | 221 | 1.15E-02 | 5.41E+04 | 194 | 47 | 6 |

\* = selected clones
BC = Biacore

TABLE 36

Detailed biacore analysis of 807B-M0004-A03, 807B-M0009-F06, 807A-M0028-B02 and variants

| Clone name | kon (1/Ms) | koff (1/s) | KD (nM) | CDR3 |
|---|---|---|---|---|
| 807B-M004-A03/WT | 1.82E+05 | 2.34E-02 | 128 | SIAAAGTDY |
| 807B-M004-A03/M0118-B09 | 3.12E+05 | 1.96E-02 | 63 | SIAADRTDY |
| 807B-M004-A03/M0117-G01 | 1.39E+05 | 7.72E-03 | 56 | SIAASARTDS |
| 807B-M004-A03/M0117-D03 | 2.75E+04 | 8.36E-03 | 304 | SIAAARTDY |
| 807B-M004-A03/M0117-F05 | 1.89E+05 | 1.05E-02 | 56 | SIASAGTDH |
| 807B-M004-A03/M0118-F03 | 1.35E+05 | 1.16E-02 | 86 | SIAASRTDY |
| 807B-M0009F06/WT | 1.31E+05 | 4.45E-02 | 340 | VGMSTYAFDI |
| 807B-M0009F06-M0128-H01 | 8.72E+04 | 7.99E-03 | 92 | VGMSNYGFDF |
| 807B-M0009F06-M0127-B07 | 1.00E+05 | 8.60E-03 | 86 | VGMSTYGFDK |
| 807B-M0009F06-M0127-D05 | 1.02E+05 | 9.39E-03 | 92 | VGMATYGFDI |
| 807B-M0009F06-M0127-F09 | 1.18E+05 | 1.10E-02 | 93 | VGMYNYGFDI |
| 807B-M0009F06-M0127-C10 | 1.13E+05 | 1.62E-02 | 144 | VGISTYGFDL |
| 807A-M0028-B02/WT | 9.31E+04 | 1.58E-02 | 169 | SVLLDY |
| 807A-M0028-B02/M0124-C05 | 2.76E+04 | 5.12E-03 | 185 | GVLFDN |
| 807A-M0028-B02/M0124-B02 | 6.07E+04 | 6.77E-03 | 112 | GVLHDY |
| 807A-M0028-B02/M0124-B11 | 5.23E+04 | 5.72E-03 | 109 | SILFDK |
| 807A-M0028-B02/M0123-F04 | 5.07E+04 | 7.56E-03 | 149 | GILHDY |
| 807A-M0028-B02/M0123-D01 | 9.25E+04 | 7.85E-03 | 85 | GVLLDK |
| 807B-M0004-H03/WT | — | — | 200 | EGSAGVVKGPARYYYYYMDV |
| 807B-M0004-H03/M0119-B05 | — | — | — | EGSSGVVKGPARYYYYYMDA |
| 807B-M0004-H03/M0119-C05 | — | — | — | ERSVAVFKARPRHYYYYMDV |
| 807B-M0004-H03/M0119-F04 | — | — | — | EGSARVIKGPARYYYYEMDV |
| 807B-M0004-H03/M0119-H09 | — | — | — | DGSARVVKGPRRYYYYYIDV |
| 807B-M0004-H03/M0120-B05 | — | — | — | EGSARVVKGPARYFYYYMDL |

TABLE 37

Immunohistochemistry of clones selected from Biacore screening

| | IHC |
|---|---|
| Clone 807B-M0004-A03 | |
| Original clone | +/− |
| 807B-M0004-A03/M0117-D03 | + |
| 807B-M0004-A03/M0117-F05 | + |
| 807B-M0004-A03/M0117-G01 | +/− |
| 807B-M0004-A03/M0118-B09 | +(+) |
| 807B-M0004-A03/M0118-F03 | +/− |
| Clone 807B-M0004-H03 | |
| Original clone | +/− |
| 807B-M0004-H03/M0119-B05 | ++(+) |
| 807B-M0004-H03/M0119-C05 | ++(+) |
| 807B-M0004-H03/M0119-F04 | ++(+) |
| 807B-M0004-H03/M0119-H09 | ++(+) |
| 807B-M0004-H03/M0120-B05 | ++ |
| Clone 807A-M0028-B02 | |
| Original clone | ++ |
| 807B-M0028-B02/M0123-D01 | ++ |
| 807B-M0028-B02/M0123-F04 | ++ |
| 807B-M0028-B02/M0124-B02 | ++ |
| 807B-M0028-B02/M0124-B11 | ++ |
| 807B-M0028-B02/M0124-C05 | ++ |
| Clone 807B-M0009-F06 | |
| Original clone | +/− |
| 807B-M0009-F06/M0127-B07 | +/− |
| 807B-M0009-F06/M0127-C10 | + |
| 807B-M0009-F06/M0127-D05 | − |
| 807B-M0009-F06/M0127-F09 | +/− |
| 807B-M0009-F06/M0128-H01 | + |

TABLE 38

Affinity matured clones of 807A-M0028-B02

| Initial Name | HV-CDR3 | LV-CDR1 | LV-CDR2 | LV-CDR3 | HV-CDR1 |
|---|---|---|---|---|---|
| 807A-M0028-B02/M0167-E01 | SEQ ID NO: 207 | SEQ ID NO: 211 | SEQ ID NO: 240 | SEQ ID NO: 262 | SEQ ID NO: 24 |
| 807A-M0028-B02/M0167-E07 | SEQ ID NO: 208 | SEQ ID NO: 212 | SEQ ID NO: 241 | SEQ ID NO: 263 | SEQ ID NO: 24 |
| 807A-M0028-B02/M0167-F07 | SEQ ID NO: 209 | SEQ ID NO: 213 | SEQ ID NO: 34 | SEQ ID NO: 35 | SEQ ID NO: 24 |
| 807A-M0028-B02/M0167-F09 | SEQ ID NO: 207 | SEQ ID NO: 214 | SEQ ID NO: 243 | SEQ ID NO: 265 | SEQ ID NO: 24 |
| 807A-M0028-B02/M0168-B11 | SEQ ID NO: 209 | SEQ ID NO: 215 | SEQ ID NO: 244 | SEQ ID NO: 266 | SEQ ID NO: 24 |
| 807A-M0028-B02/M0168-C08 | SEQ ID NO: 209 | SEQ ID NO: 216 | SEQ ID NO: 245 | SEQ ID NO: 267 | SEQ ID NO: 24 |
| 807A-M0028-B02/M0168-D10 | SEQ ID NO: 210 | SEQ ID NO: 33 | SEQ ID NO: 34 | SEQ ID NO: 35 | SEQ ID NO: 24 |
| 807A-M0028-B02/M0169-D08 | SEQ ID NO: 208 | SEQ ID NO: 218 | SEQ ID NO: 34 | SEQ ID NO: 268 | SEQ ID NO: 24 |
| 807A-M0028-B02/M0169-F03 | SEQ ID NO: 209 | SEQ ID NO: 219 | SEQ ID NO: 247 | SEQ ID NO: 269 | SEQ ID NO: 24 |
| 807A-M0028-B02/M0169-H04 | SEQ ID NO: 208 | SEQ ID NO: 220 | SEQ ID NO: 248 | SEQ ID NO: 270 | SEQ ID NO: 24 |
| 807A-M0028-B02/M0169-H05 | SEQ ID NO: 207 | SEQ ID NO: 221 | SEQ ID NO: 249 | SEQ ID NO: 271 | SEQ ID NO: 24 |
| 807A-M0028-B02/M0170-H08 | SEQ ID NO: 207 | SEQ ID NO: 222 | SEQ ID NO: 250 | SEQ ID NO: 272 | SEQ ID NO: 24 |
| 807A-M0028-B02/M0171-A08 | SEQ ID NO: 210 | SEQ ID NO: 223 | SEQ ID NO: 240 | SEQ ID NO: 273 | SEQ ID NO: 24 |
| 807A-M0028-B02/M0171-A09 | SEQ ID NO: 209 | SEQ ID NO: 224 | SEQ ID NO: 251 | SEQ ID NO: 274 | SEQ ID NO: 24 |
| 807A-M0028-B02/M0171-A10 | SEQ ID NO: 207 | SEQ ID NO: 33 | SEQ ID NO: 34 | SEQ ID NO: 35 | SEQ ID NO: 24 |
| 807A-M0028-B02/M0171-C12 | SEQ ID NO: 207 | SEQ ID NO: 226 | SEQ ID NO: 252 | SEQ ID NO: 275 | SEQ ID NO: 24 |
| 807A-M0028-B02/M0171-E03 | SEQ ID NO: 209 | SEQ ID NO: 218 | SEQ ID NO: 34 | SEQ ID NO: 268 | SEQ ID NO: 24 |
| 807A-M0028-B02/M0171-G02 | SEQ ID NO: 208 | SEQ ID NO: 228 | SEQ ID NO: 253 | SEQ ID NO: 276 | SEQ ID NO: 24 |
| 807A-M0028-B02/M0171-G09 | SEQ ID NO: 209 | SEQ ID NO: 229 | SEQ ID NO: 254 | SEQ ID NO: 277 | SEQ ID NO: 24 |
| 807A-M0028-B02/M0172-A05 | SEQ ID NO: 209 | SEQ ID NO: 230 | SEQ ID NO: 255 | SEQ ID NO: 278 | SEQ ID NO: 24 |
| 807A-M0028-B02/M0172-A08 | SEQ ID NO: 208 | SEQ ID NO: 231 | SEQ ID NO: 256 | SEQ ID NO: 279 | SEQ ID NO: 24 |
| 807A-M0028-B02/M0172-B09 | SEQ ID NO: 209 | SEQ ID NO: 232 | SEQ ID NO: 257 | SEQ ID NO: 280 | SEQ ID NO: 24 |
| 807A-M0028-B02/M0172-D05 | SEQ ID NO: 209 | SEQ ID NO: 233 | SEQ ID NO: 257 | SEQ ID NO: 281 | SEQ ID NO: 24 |
| 807A-M0028-B02/M0172-D09 | SEQ ID NO: 207 | SEQ ID NO: 234 | SEQ ID NO: 258 | SEQ ID NO: 282 | SEQ ID NO: 24 |
| 807A-M0028-B02/M0172-E06 | SEQ ID NO: 209 | SEQ ID NO: 235 | SEQ ID NO: 251 | SEQ ID NO: 283 | SEQ ID NO: 24 |
| 807A-M0028-B02/M0172-F02 | SEQ ID NO: 207 | SEQ ID NO: 236 | SEQ ID NO: 259 | SEQ ID NO: 284 | SEQ ID NO: 24 |
| 807A-M0028-B02/M0172-F07 | SEQ ID NO: 210 | SEQ ID NO: 213 | SEQ ID NO: 34 | SEQ ID NO: 35 | SEQ ID NO: 24 |
| 807A-M0028-B02/M0172-F12 | SEQ ID NO: 209 | SEQ ID NO: 238 | SEQ ID NO: 260 | SEQ ID NO: 285 | SEQ ID NO: 24 |
| 807A-M0028-B02/M0172-G08 | SEQ ID NO: 209 | SEQ ID NO: 239 | SEQ ID NO: 261 | SEQ ID NO: 286 | SEQ ID NO: 24 |

| Initial Name | HV-CDR2 | LV-WholeAA | HV-WholeAA |
|---|---|---|---|
| 807A-M0028-B02/M0167-E01 | SEQ ID NO: 25 | SEQ ID NO: 287 | SEQ ID NO: 316 |
| 807A-M0028-B02/M0167-E07 | SEQ ID NO: 25 | SEQ ID NO: 288 | SEQ ID NO: 317 |
| 807A-M0028-B02/M0167-F07 | SEQ ID NO: 25 | SEQ ID NO: 289 | SEQ ID NO: 318 |
| 807A-M0028-B02/M0167-F09 | SEQ ID NO: 25 | SEQ ID NO: 290 | SEQ ID NO: 316 |
| 807A-M0028-B02/M0168-B11 | SEQ ID NO: 25 | SEQ ID NO: 291 | SEQ ID NO: 318 |
| 807A-M0028-B02/M0168-C08 | SEQ ID NO: 25 | SEQ ID NO: 292 | SEQ ID NO: 318 |
| 807A-M0028-B02/M0168-D10 | SEQ ID NO: 25 | SEQ ID NO: 43 | SEQ ID NO: 319 |
| 807A-M0028-B02/M0169-D08 | SEQ ID NO: 25 | SEQ ID NO: 294 | SEQ ID NO: 317 |
| 807A-M0028-B02/M0169-F03 | SEQ ID NO: 25 | SEQ ID NO: 295 | SEQ ID NO: 318 |
| 807A-M0028-B02/M0169-H04 | SEQ ID NO: 25 | SEQ ID NO: 296 | SEQ ID NO: 317 |
| 807A-M0028-B02/M0169-H05 | SEQ ID NO: 25 | SEQ ID NO: 297 | SEQ ID NO: 316 |
| 807A-M0028-B02/M0170-H08 | SEQ ID NO: 25 | SEQ ID NO: 298 | SEQ ID NO: 316 |
| 807A-M0028-B02/M0171-A08 | SEQ ID NO: 25 | SEQ ID NO: 299 | SEQ ID NO: 319 |
| 807A-M0028-B02/M0171-A09 | SEQ ID NO: 25 | SEQ ID NO: 300 | SEQ ID NO: 318 |
| 807A-M0028-B02/M0171-A10 | SEQ ID NO: 25 | SEQ ID NO: 43 | SEQ ID NO: 316 |
| 807A-M0028-B02/M0171-C12 | SEQ ID NO: 25 | SEQ ID NO: 302 | SEQ ID NO: 316 |
| 807A-M0028-B02/M0171-E03 | SEQ ID NO: 25 | SEQ ID NO: 294 | SEQ ID NO: 318 |
| 807A-M0028-B02/M0171-G02 | SEQ ID NO: 25 | SEQ ID NO: 304 | SEQ ID NO: 317 |
| 807A-M0028-B02/M0171-G09 | SEQ ID NO: 25 | SEQ ID NO: 305 | SEQ ID NO: 318 |
| 807A-M0028-B02/M0172-A05 | SEQ ID NO: 25 | SEQ ID NO: 306 | SEQ ID NO: 318 |
| 807A-M0028-B02/M0172-A08 | SEQ ID NO: 25 | SEQ ID NO: 307 | SEQ ID NO: 317 |
| 807A-M0028-B02/M0172-B09 | SEQ ID NO: 25 | SEQ ID NO: 308 | SEQ ID NO: 318 |
| 807A-M0028-B02/M0172-D05 | SEQ ID NO: 25 | SEQ ID NO: 309 | SEQ ID NO: 318 |
| 807A-M0028-B02/M0172-D09 | SEQ ID NO: 25 | SEQ ID NO: 310 | SEQ ID NO: 316 |
| 807A-M0028-B02/M0172-E06 | SEQ ID NO: 25 | SEQ ID NO: 311 | SEQ ID NO: 318 |
| 807A-M0028-B02/M0172-F02 | SEQ ID NO: 25 | SEQ ID NO: 312 | SEQ ID NO: 316 |
| 807A-M0028-B02/M0172-F07 | SEQ ID NO: 25 | SEQ ID NO: 289 | SEQ ID NO: 319 |
| 807A-M0028-B02/M0172-F12 | SEQ ID NO: 25 | SEQ ID NO: 314 | SEQ ID NO: 318 |
| 807A-M0028-B02/M0172-G08 | SEQ ID NO: 25 | SEQ ID NO: 315 | SEQ ID NO: 318 |

TABLE 39

Affinity matured clones of 807B-M0004-A03

| Initial Name | HV-CDR3_1 | LV-CDR1 | LV-CDR2 | LV-CDR3 | HV-CDR1 |
|---|---|---|---|---|---|
| 807B-M0004-A03/M0148-E05 | SEQ ID NO: 320 | SEQ ID NO: 93 | SEQ ID NO: 333 | SEQ ID NO: 341 | SEQ ID NO: 48 |
| 807B-M0004-A03/M0148-E08 | SEQ ID NO: 320 | SEQ ID NO: 325 | SEQ ID NO: 333 | SEQ ID NO: 341 | SEQ ID NO: 48 |
| 807B-M0004-A03/M0149-D04 | SEQ ID NO: 322 | SEQ ID NO: 326 | SEQ ID NO: 334 | SEQ ID NO: 341 | SEQ ID NO: 48 |
| 807B-M0004-A03/M0149-F02 | SEQ ID NO: 322 | SEQ ID NO: 93 | SEQ ID NO: 333 | SEQ ID NO: 341 | SEQ ID NO: 48 |
| 807B-M0004-A03/M0149-G11 | SEQ ID NO: 323 | SEQ ID NO: 93 | SEQ ID NO: 333 | SEQ ID NO: 341 | SEQ ID NO: 48 |

TABLE 39-continued

Affinity matured clones of 807B-M0004-A03

| | | | | | |
|---|---|---|---|---|---|
| 807B-M0004-A03/M0149-H07 | SEQ ID NO: 322 | SEQ ID NO: 326 | SEQ ID NO: 334 | SEQ ID NO: 341 | SEQ ID NO: 48 |
| 807B-M0004-A03/M0149-H09 | SEQ ID NO: 320 | SEQ ID NO: 327 | SEQ ID NO: 333 | SEQ ID NO: 341 | SEQ ID NO: 48 |
| 807B-M0004-A03/M0150-A04 | SEQ ID NO: 320 | SEQ ID NO: 93 | SEQ ID NO: 333 | SEQ ID NO: 341 | SEQ ID NO: 48 |
| 807B-M0004-A03/M0150-A07 | SEQ ID NO: 321 | SEQ ID NO: 93 | SEQ ID NO: 333 | SEQ ID NO: 341 | SEQ ID NO: 48 |
| 807B-M0004-A03/M0150-A12 | SEQ ID NO: 320 | SEQ ID NO: 93 | SEQ ID NO: 333 | SEQ ID NO: 341 | SEQ ID NO: 48 |
| 807B-M0004-A03/M0150-D12 | SEQ ID NO: 320 | SEQ ID NO: 325 | SEQ ID NO: 333 | SEQ ID NO: 341 | SEQ ID NO: 48 |
| 807B-M0004-A03/M0150-E01 | SEQ ID NO: 320 | SEQ ID NO: 93 | SEQ ID NO: 335 | SEQ ID NO: 341 | SEQ ID NO: 48 |
| 807B-M0004-A03/M0150-E03 | SEQ ID NO: 320 | SEQ ID NO: 325 | SEQ ID NO: 333 | SEQ ID NO: 341 | SEQ ID NO: 48 |
| 807B-M0004-A03/M0150-E04 | SEQ ID NO: 320 | SEQ ID NO: 327 | SEQ ID NO: 333 | SEQ ID NO: 341 | SEQ ID NO: 48 |
| 807B-M0004-A03/M0150-E12 | SEQ ID NO: 320 | SEQ ID NO: 328 | SEQ ID NO: 336 | SEQ ID NO: 342 | SEQ ID NO: 48 |
| 807B-M0004-A03/M0150-G01 | SEQ ID NO: 320 | SEQ ID NO: 329 | SEQ ID NO: 337 | SEQ ID NO: 341 | SEQ ID NO: 48 |
| 807B-M0004-A03/M0151-A06 | SEQ ID NO: 320 | SEQ ID NO: 330 | SEQ ID NO: 338 | SEQ ID NO: 343 | SEQ ID NO: 48 |
| 807B-M0004-A03/M0151-B12 | SEQ ID NO: 320 | SEQ ID NO: 325 | SEQ ID NO: 333 | SEQ ID NO: 341 | SEQ ID NO: 48 |
| 807B-M0004-A03/M0151-C05 | SEQ ID NO: 320 | SEQ ID NO: 328 | SEQ ID NO: 336 | SEQ ID NO: 342 | SEQ ID NO: 48 |
| 807B-M0004-A03/M0151-D09 | SEQ ID NO: 322 | SEQ ID NO: 325 | SEQ ID NO: 333 | SEQ ID NO: 341 | SEQ ID NO: 48 |
| 807B-M0004-A03/M0151-F12 | SEQ ID NO: 320 | SEQ ID NO: 93 | SEQ ID NO: 333 | SEQ ID NO: 341 | SEQ ID NO: 48 |
| 807B-M0004-A03/M0151-H05 | SEQ ID NO: 320 | SEQ ID NO: 331 | SEQ ID NO: 339 | SEQ ID NO: 341 | SEQ ID NO: 48 |
| 807B-M0004-A03/M0153-D03 | SEQ ID NO: 320 | SEQ ID NO: 93 | SEQ ID NO: 94 | SEQ ID NO: 95 | SEQ ID NO: 48 |
| 807B-M0004-A03/M0153-F07 | SEQ ID NO: 320 | SEQ ID NO: 327 | SEQ ID NO: 333 | SEQ ID NO: 341 | SEQ ID NO: 48 |

| Initial Name | HV-CDR2 | LV-WholeAA | HV-WholeAA |
|---|---|---|---|
| 807B-M0004-A03/M0148-E05 | SEQ ID NO: 49 | SEQ ID NO: 345 | SEQ ID NO: 369 |
| 807B-M0004-A03/M0148-E08 | SEQ ID NO: 49 | SEQ ID NO: 346 | SEQ ID NO: 369 |
| 807B-M0004-A03/M0149-D04 | SEQ ID NO: 49 | SEQ ID NO: 347 | SEQ ID NO: 370 |
| 807B-M0004-A03/M0149-F02 | SEQ ID NO: 49 | SEQ ID NO: 348 | SEQ ID NO: 370 |
| 807B-M0004-A03/M0149-G11 | SEQ ID NO: 49 | SEQ ID NO: 348 | SEQ ID NO: 371 |
| 807B-M0004-A03/M0149-H07 | SEQ ID NO: 49 | SEQ ID NO: 350 | SEQ ID NO: 370 |
| 807B-M0004-A03/M0149-H09 | SEQ ID NO: 49 | SEQ ID NO: 351 | SEQ ID NO: 369 |
| 807B-M0004-A03/M0150-A04 | SEQ ID NO: 49 | SEQ ID NO: 352 | SEQ ID NO: 369 |
| 807B-M0004-A03/M0150-A07 | SEQ ID NO: 49 | SEQ ID NO: 348 | SEQ ID NO: 372 |
| 807B-M0004-A03/M0150-A12 | SEQ ID NO: 49 | SEQ ID NO: 354 | SEQ ID NO: 369 |
| 807B-M0004-A03/M0150-D12 | SEQ ID NO: 49 | SEQ ID NO: 355 | SEQ ID NO: 369 |
| 807B-M0004-A03/M0150-E01 | SEQ ID NO: 49 | SEQ ID NO: 356 | SEQ ID NO: 369 |
| 807B-M0004-A03/M0150-E03 | SEQ ID NO: 49 | SEQ ID NO: 357 | SEQ ID NO: 369 |
| 807B-M0004-A03/M0150-E04 | SEQ ID NO: 49 | SEQ ID NO: 358 | SEQ ID NO: 369 |
| 807B-M0004-A03/M0150-E12 | SEQ ID NO: 49 | SEQ ID NO: 359 | SEQ ID NO: 369 |
| 807B-M0004-A03/M0150-G01 | SEQ ID NO: 49 | SEQ ID NO: 360 | SEQ ID NO: 369 |
| 807B-M0004-A03/M0151-A06 | SEQ ID NO: 49 | SEQ ID NO: 361 | SEQ ID NO: 369 |
| 807B-M0004-A03/M0151-B12 | SEQ ID NO: 49 | SEQ ID NO: 362 | SEQ ID NO: 369 |
| 807B-M0004-A03/M0151-C05 | SEQ ID NO: 49 | SEQ ID NO: 363 | SEQ ID NO: 369 |
| 807B-M0004-A03/M0151-D09 | SEQ ID NO: 49 | SEQ ID NO: 362 | SEQ ID NO: 370 |
| 807B-M0004-A03/M0151-F12 | SEQ ID NO: 49 | SEQ ID NO: 348 | SEQ ID NO: 369 |
| 807B-M0004-A03/M0151-H05 | SEQ ID NO: 49 | SEQ ID NO: 366 | SEQ ID NO: 369 |
| 807B-M0004-A03/M0153-D03 | SEQ ID NO: 49 | SEQ ID NO: 151 | SEQ ID NO: 369 |
| 807B-M0004-A03/M0153-F07 | SEQ ID NO: 49 | SEQ ID NO: 368 | SEQ ID NO: 369 |

TABLE 40

Affinity matured clones of 807B-M0004-H03

| Initial Name | HV-CDR3 | LV-CDR1 | LV-CDR2 | LV-CDR3 | HV-CDR1 |
|---|---|---|---|---|---|
| 807B-M0004-H03/M0154-C07 | SEQ ID NO: 373 | SEQ ID NO: 388 | SEQ ID NO: 381 | SEQ ID NO: 377 | SEQ ID NO: 66 |
| 807B-M0004-H03/M0154-D08 | SEQ ID NO: 373 | SEQ ID NO: 389 | SEQ ID NO: 382 | SEQ ID NO: 378 | SEQ ID NO: 66 |
| 807B-M0004-H03/M0154-G05 | SEQ ID NO: 373 | SEQ ID NO: 390 | SEQ ID NO: 383 | SEQ ID NO: 379 | SEQ ID NO: 66 |
| 807B-M0004-H03/M0154-G08 | SEQ ID NO: 373 | SEQ ID NO: 389 | SEQ ID NO: 382 | SEQ ID NO: 378 | SEQ ID NO: 66 |
| 807B-M0004-H03/M0154-G11 | SEQ ID NO: 374 | SEQ ID NO: 389 | SEQ ID NO: 382 | SEQ ID NO: 378 | SEQ ID NO: 66 |
| 807B-M0004-H03/M0154-H03 | SEQ ID NO: 375 | SEQ ID NO: 389 | SEQ ID NO: 382 | SEQ ID NO: 378 | SEQ ID NO: 66 |
| 807B-M0004-H03/M0154-H06 | SEQ ID NO: 373 | SEQ ID NO: 391 | SEQ ID NO: 382 | SEQ ID NO: 378 | SEQ ID NO: 66 |
| 807B-M0004-H03/M0155-C08 | SEQ ID NO: 373 | SEQ ID NO: 389 | SEQ ID NO: 382 | SEQ ID NO: 378 | SEQ ID NO: 66 |
| 807B-M0004-H03/M0155-E10 | SEQ ID NO: 376 | SEQ ID NO: 392 | SEQ ID NO: 384 | SEQ ID NO: 380 | SEQ ID NO: 66 |
| 807B-M0004-H03/M0155-F08 | SEQ ID NO: 373 | SEQ ID NO: 389 | SEQ ID NO: 382 | SEQ ID NO: 378 | SEQ ID NO: 66 |
| 807B-M0004-H03/M0155-H06 | SEQ ID NO: 373 | SEQ ID NO: 389 | SEQ ID NO: 382 | SEQ ID NO: 378 | SEQ ID NO: 66 |
| 807B-M0004-H03/M0155-H08 | SEQ ID NO: 376 | SEQ ID NO: 389 | SEQ ID NO: 382 | SEQ ID NO: 378 | SEQ ID NO: 66 |
| 807B-M0004-H03/M0156-D01 | SEQ ID NO: 373 | SEQ ID NO: 389 | SEQ ID NO: 382 | SEQ ID NO: 378 | SEQ ID NO: 66 |
| 807B-M0004-H03/M0156-G08 | SEQ ID NO: 373 | SEQ ID NO: 389 | SEQ ID NO: 382 | SEQ ID NO: 378 | SEQ ID NO: 66 |
| 807B-M0004-H03/M0157-A08 | SEQ ID NO: 373 | SEQ ID NO: 389 | SEQ ID NO: 382 | SEQ ID NO: 378 | SEQ ID NO: 66 |
| 807B-M0004-H03/M0157-O10 | SEQ ID NO: 376 | SEQ ID NO: 389 | SEQ ID NO: 382 | SEQ ID NO: 378 | SEQ ID NO: 66 |
| 807B-M0004-H03/M0157-G08 | SEQ ID NO: 373 | SEQ ID NO: 389 | SEQ ID NO: 382 | SEQ ID NO: 378 | SEQ ID NO: 66 |
| 807B-M0004-H03/M0157-G11 | SEQ ID NO: 375 | SEQ ID NO: 393 | SEQ ID NO: 385 | SEQ ID NO: 378 | SEQ ID NO: 66 |
| 807B-M0004-H03/M0159-A09 | SEQ ID NO: 373 | SEQ ID NO: 394 | SEQ ID NO: 386 | SEQ ID NO: 378 | SEQ ID NO: 66 |
| 807B-M0004-H03/M0159-H03 | SEQ ID NO: 373 | SEQ ID NO: 389 | SEQ ID NO: 382 | SEQ ID NO: 378 | SEQ ID NO: 66 |

TABLE 40-continued

Affinity matured clones of 807B-M0004-H03

| 807B-M0004-H03/M0159-H07 | SEQ ID NO: 373 | SEQ ID NO: 395 | SEQ ID NO: 387 | SEQ ID NO: 380 | SEQ ID NO: 66 |
|---|---|---|---|---|---|
| 807B-M0004-H03/M0157-F04 | SEQ ID NO: 68 | SEQ ID NO: 396 | SEQ ID NO: 382 | SEQ ID NO: 378 | SEQ ID NO: 66 |

| | Initial Name | | HV-CDR2 | LV-WholeAA | HV-WholeAA |
|---|---|---|---|---|---|
| | 807B-M0004-H03/M0154-C07 | | SEQ ID NO: 67 | SEQ ID NO: 400 | SEQ ID NO: 397 |
| | 807B-M0004-H03/M0154-D08 | | SEQ ID NO: 67 | SEQ ID NO: 401 | SEQ ID NO: 397 |
| | 807B-M0004-H03/M0154-G05 | | SEQ ID NO: 67 | SEQ ID NO: 402 | SEQ ID NO: 397 |
| | 807B-M0004-H03/M0154-G08 | | SEQ ID NO: 67 | SEQ ID NO: 403 | SEQ ID NO: 397 |
| | 807B-M0004-H03/M0154-G11 | | SEQ ID NO: 67 | SEQ ID NO: 404 | SEQ ID NO: 217 |
| | 807B-M0004-H03/M0154-H03 | | SEQ ID NO: 67 | SEQ ID NO: 405 | SEQ ID NO: 398 |
| | 807B-M0004-H03/M0154-H06 | | SEQ ID NO: 67 | SEQ ID NO: 406 | SEQ ID NO: 397 |
| | 807B-M0004-H03/M0155-C08 | | SEQ ID NO: 67 | SEQ ID NO: 407 | SEQ ID NO: 397 |
| | 807B-M0004-H03/M0155-E10 | | SEQ ID NO: 67 | SEQ ID NO: 408 | SEQ ID NO: 399 |
| | 807B-M0004-H03/M0155-F08 | | SEQ ID NO: 67 | SEQ ID NO: 409 | SEQ ID NO: 397 |
| | 807B-M0004-H03/M0155-H06 | | SEQ ID NO: 67 | SEQ ID NO: 410 | SEQ ID NO: 397 |
| | 807B-M0004-H03/M0155-H08 | | SEQ ID NO: 67 | SEQ ID NO: 411 | SEQ ID NO: 399 |
| | 807B-M0004-H03/M0156-D01 | | SEQ ID NO: 67 | SEQ ID NO: 412 | SEQ ID NO: 397 |
| | 807B-M0004-H03/M0156-G08 | | SEQ ID NO: 67 | SEQ ID NO: 413 | SEQ ID NO: 397 |
| | 807B-M0004-H03/M0157-A08 | | SEQ ID NO: 67 | SEQ ID NO: 414 | SEQ ID NO: 397 |
| | 807B-M0004-H03/M0157-O10 | | SEQ ID NO: 67 | SEQ ID NO: 415 | SEQ ID NO: 399 |
| | 807B-M0004-H03/M0157-G08 | | SEQ ID NO: 67 | SEQ ID NO: 416 | SEQ ID NO: 397 |
| | 807B-M0004-H03/M0157-G11 | | SEQ ID NO: 67 | SEQ ID NO: 417 | SEQ ID NO: 398 |
| | 807B-M0004-H03/M0159-A09 | | SEQ ID NO: 67 | SEQ ID NO: 418 | SEQ ID NO: 397 |
| | 807B-M0004-H03/M0159-H03 | | SEQ ID NO: 67 | SEQ ID NO: 419 | SEQ ID NO: 397 |
| | 807B-M0004-H03/M0159-H07 | | SEQ ID NO: 67 | SEQ ID NO: 420 | SEQ ID NO: 397 |
| | 807B-M0004-H03/M0157-F04 | | SEQ ID NO: 67 | SEQ ID NO: 421 | SEQ ID NO: 142 |

TABLE 41

Affinity matured clones of 807B-M0009-F06

| Initial Name | HV-CDR3_1 | LV-CDR1 | LV-CDR2 | LV-CDR3 | HV-CDR1 |
|---|---|---|---|---|---|
| 807B-M0009-F06/M0173-F07 | SEQ ID NO: 485 | SEQ ID NO: 117 | SEQ ID NO: 118 | SEQ ID NO: 119 | SEQ ID NO: 72 |
| 807B-M0009-F06/M0174-B01 | SEQ ID NO: 486 | SEQ ID NO: 117 | SEQ ID NO: 118 | SEQ ID NO: 119 | SEQ ID NO: 72 |
| 807B-M0009-F06/M0174-B06 | SEQ ID NO: 487 | SEQ ID NO: 117 | SEQ ID NO: 118 | SEQ ID NO: 119 | SEQ ID NO: 72 |
| 807B-M0009-F06/M0174-B08 | SEQ ID NO: 488 | SEQ ID NO: 117 | SEQ ID NO: 118 | SEQ ID NO: 119 | SEQ ID NO: 72 |
| 807B-M0009-F06/M0175-A07 | SEQ ID NO: 488 | SEQ ID NO: 501 | SEQ ID NO: 118 | SEQ ID NO: 101 | SEQ ID NO: 72 |
| 807B-M0009-F06/M0175-B01 | SEQ ID NO: 485 | SEQ ID NO: 502 | SEQ ID NO: 497 | SEQ ID NO: 101 | SEQ ID NO: 72 |
| 807B-M0009-F06/M0175-B11 | SEQ ID NO: 485 | SEQ ID NO: 503 | SEQ ID NO: 498 | SEQ ID NO: 119 | SEQ ID NO: 72 |
| 807B-M0009-F06/M0175-C07 | SEQ ID NO: 488 | SEQ ID NO: 501 | SEQ ID NO: 118 | SEQ ID NO: 101 | SEQ ID NO: 72 |
| 807B-M0009-F06/M0175-D04 | SEQ ID NO: 485 | SEQ ID NO: 503 | SEQ ID NO: 498 | SEQ ID NO: 119 | SEQ ID NO: 72 |
| 807B-M0009-F06/M0175-E04 | SEQ ID NO: 485 | SEQ ID NO: 503 | SEQ ID NO: 118 | SEQ ID NO: 492 | SEQ ID NO: 72 |
| 807B-M0009-F06/M0175-E06 | SEQ ID NO: 486 | SEQ ID NO: 503 | SEQ ID NO: 118 | SEQ ID NO: 119 | SEQ ID NO: 72 |
| 807B-M0009-F06/M0176-A06 | SEQ ID NO: 485 | SEQ ID NO: 504 | SEQ ID NO: 118 | SEQ ID NO: 101 | SEQ ID NO: 72 |
| 807B-M0009-F06/M0176-C04 | SEQ ID NO: 485 | SEQ ID NO: 505 | SEQ ID NO: 499 | SEQ ID NO: 493 | SEQ ID NO: 72 |
| 807B-M0009-F06/M0176-G02 | SEQ ID NO: 485 | SEQ ID NO: 225 | SEQ ID NO: 118 | SEQ ID NO: 101 | SEQ ID NO: 72 |
| 807B-M0009-F06/M0177-E01 | SEQ ID NO: 489 | SEQ ID NO: 117 | SEQ ID NO: 118 | SEQ ID NO: 119 | SEQ ID NO: 72 |
| 807B-M0009-F06/M0177-E05 | SEQ ID NO: 486 | SEQ ID NO: 117 | SEQ ID NO: 118 | SEQ ID NO: 119 | SEQ ID NO: 72 |
| 807B-M0009-F06/M0177-E09 | SEQ ID NO: 488 | SEQ ID NO: 117 | SEQ ID NO: 118 | SEQ ID NO: 119 | SEQ ID NO: 72 |
| 807B-M0009-F06/M0177-F09 | SEQ ID NO: 488 | SEQ ID NO: 503 | SEQ ID NO: 118 | SEQ ID NO: 494 | SEQ ID NO: 72 |
| 807B-M0009-F06/M0177-H02 | SEQ ID NO: 488 | SEQ ID NO: 503 | SEQ ID NO: 118 | SEQ ID NO: 119 | SEQ ID NO: 72 |
| 807B-M0009-F06/M0177-H05 | SEQ ID NO: 489 | SEQ ID NO: 117 | SEQ ID NO: 118 | SEQ ID NO: 119 | SEQ ID NO: 72 |
| 807B-M0009-F06/M0177-H06 | SEQ ID NO: 488 | SEQ ID NO: 505 | SEQ ID NO: 499 | SEQ ID NO: 493 | SEQ ID NO: 72 |
| 807B-M0009-F06/M0177-H07 | SEQ ID NO: 488 | SEQ ID NO: 506 | SEQ ID NO: 118 | SEQ ID NO: 495 | SEQ ID NO: 72 |
| 807B-M0009-F06/M0178-A08 | SEQ ID NO: 488 | SEQ ID NO: 503 | SEQ ID NO: 118 | SEQ ID NO: 496 | SEQ ID NO: 72 |
| 807B-M0009-F06/M0178-E02 | SEQ ID NO: 486 | SEQ ID NO: 507 | SEQ ID NO: 118 | SEQ ID NO: 494 | SEQ ID NO: 72 |
| 807B-M0009-F06/M0178-H09 | SEQ ID NO: 488 | SEQ ID NO: 505 | SEQ ID NO: 499 | SEQ ID NO: 493 | SEQ ID NO: 72 |

| | Initial Name | | HV-CDR2 | LV-WholeAA | HV-WholeAA |
|---|---|---|---|---|---|
| | 807B-M0009-F06/M0173-F07 | | SEQ ID NO: 73 | SEQ ID NO: 508 | SEQ ID NO: 500 |
| | 807B-M0009-F06/M0174-B01 | | SEQ ID NO: 73 | SEQ ID NO: 508 | SEQ ID NO: 490 |
| | 807B-M0009-F06/M0174-B06 | | SEQ ID NO: 73 | SEQ ID NO: 508 | SEQ ID NO: 491 |
| | 807B-M0009-F06/M0174-B08 | | SEQ ID NO: 73 | SEQ ID NO: 508 | SEQ ID NO: 509 |
| | 807B-M0009-F06/M0175-A07 | | SEQ ID NO: 73 | SEQ ID NO: 227 | SEQ ID NO: 509 |
| | 807B-M0009-F06/M0175-B01 | | SEQ ID NO: 73 | SEQ ID NO: 237 | SEQ ID NO: 500 |
| | 807B-M0009-F06/M0175-B11 | | SEQ ID NO: 73 | SEQ ID NO: 242 | SEQ ID NO: 500 |
| | 807B-M0009-F06/M0175-C07 | | SEQ ID NO: 73 | SEQ ID NO: 246 | SEQ ID NO: 509 |
| | 807B-M0009-F06/M0175-D04 | | SEQ ID NO: 73 | SEQ ID NO: 264 | SEQ ID NO: 500 |
| | 807B-M0009-F06/M0175-E04 | | SEQ ID NO: 73 | SEQ ID NO: 293 | SEQ ID NO: 500 |
| | 807B-M0009-F06/M0175-E06 | | SEQ ID NO: 73 | SEQ ID NO: 301 | SEQ ID NO: 490 |
| | 807B-M0009-F06/M0176-A06 | | SEQ ID NO: 73 | SEQ ID NO: 303 | SEQ ID NO: 500 |
| | 807B-M0009-F06/M0176-C04 | | SEQ ID NO: 73 | SEQ ID NO: 313 | SEQ ID NO: 500 |

TABLE 41-continued

Affinity matured clones of 807B-M0009-F06

| | | | | |
|---|---|---|---|---|
| | 807B-M0009-F06/M0176-G02 | SEQ ID NO: 73 | SEQ ID NO: 324 | SEQ ID NO: 500 |
| | 807B-M0009-F06/M0177-E01 | SEQ ID NO: 73 | SEQ ID NO: 332 | SEQ ID NO: 510 |
| | 807B-M0009-F06/M0177-E05 | SEQ ID NO: 73 | SEQ ID NO: 340 | SEQ ID NO: 490 |
| | 807B-M0009-F06/M0177-E09 | SEQ ID NO: 73 | SEQ ID NO: 344 | SEQ ID NO: 509 |
| | 807B-M0009-F06/M0177-F09 | SEQ ID NO: 73 | SEQ ID NO: 349 | SEQ ID NO: 509 |
| | 807B-M0009-F06/M0177-H02 | SEQ ID NO: 73 | SEQ ID NO: 353 | SEQ ID NO: 509 |
| | 807B-M0009-F06/M0177-H05 | SEQ ID NO: 73 | SEQ ID NO: 508 | SEQ ID NO: 510 |
| | 807B-M0009-F06/M0177-H06 | SEQ ID NO: 73 | SEQ ID NO: 364 | SEQ ID NO: 509 |
| | 807B-M0009-F06/M0177-H07 | SEQ ID NO: 73 | SEQ ID NO: 365 | SEQ ID NO: 509 |
| | 807B-M0009-F06/M0178-A08 | SEQ ID NO: 73 | SEQ ID NO: 367 | SEQ ID NO: 509 |
| | 807B-M0009-F06/M0178-E02 | SEQ ID NO: 73 | SEQ ID NO: 439 | SEQ ID NO: 490 |
| | 807B-M0009-F06/M0178-H09 | SEQ ID NO: 73 | SEQ ID NO: 442 | SEQ ID NO: 509 |

TABLE 42

Affinity matured clones of 807B-M0079-D10

| Initial Name | LV-CDR1 | LV-CDR2 | LV-CDR3 | HV-CDR1 | HV-CDR2 |
|---|---|---|---|---|---|
| 807B-M0079-D10/M0160-F02 | SEQ ID NO: 422 | SEQ ID NO: 434 | SEQ ID NO: 444 | SEQ ID NO: 78 | SEQ ID NO: 453 |
| 807B-M0079-D10/M0160-F12 | SEQ ID NO: 423 | SEQ ID NO: 435 | SEQ ID NO: 445 | SEQ ID NO: 78 | SEQ ID NO: 453 |
| 807B-M0079-D10/M0161-B04 | SEQ ID NO: 424 | SEQ ID NO: 434 | SEQ ID NO: 446 | SEQ ID NO: 78 | SEQ ID NO: 453 |
| 807B-M0079-D10/M0161-G03 | SEQ ID NO: 423 | SEQ ID NO: 435 | SEQ ID NO: 445 | SEQ ID NO: 78 | SEQ ID NO: 453 |
| 807B-M0079-D10/M0162-A11 | SEQ ID NO: 425 | SEQ ID NO: 435 | SEQ ID NO: 447 | SEQ ID NO: 78 | SEQ ID NO: 453 |
| 807B-M0079-D10/M0162-D11 | SEQ ID NO: 424 | SEQ ID NO: 434 | SEQ ID NO: 445 | SEQ ID NO: 78 | SEQ ID NO: 453 |
| 807B-M0079-D10/M0162-F04 | SEQ ID NO: 426 | SEQ ID NO: 436 | SEQ ID NO: 448 | SEQ ID NO: 78 | SEQ ID NO: 453 |
| 807B-M0079-D10/M0164-B02 | SEQ ID NO: 423 | SEQ ID NO: 435 | SEQ ID NO: 445 | SEQ ID NO: 78 | SEQ ID NO: 453 |
| 807B-M0079-D10/M0164-B03 | SEQ ID NO: 425 | SEQ ID NO: 435 | SEQ ID NO: 447 | SEQ ID NO: 78 | SEQ ID NO: 453 |
| 807B-M0079-D10/M0164-C08 | SEQ ID NO: 425 | SEQ ID NO: 435 | SEQ ID NO: 447 | SEQ ID NO: 78 | SEQ ID NO: 453 |
| 807B-M0079-D10/M0164-C09 | SEQ ID NO: 427 | SEQ ID NO: 437 | SEQ ID NO: 449 | SEQ ID NO: 78 | SEQ ID NO: 453 |
| 807B-M0079-D10/M0164-C10 | SEQ ID NO: 428 | SEQ ID NO: 438 | SEQ ID NO: 450 | SEQ ID NO: 78 | SEQ ID NO: 453 |
| 807B-M0079-D10/M0164-E05 | SEQ ID NO: 424 | SEQ ID NO: 434 | SEQ ID NO: 446 | SEQ ID NO: 78 | SEQ ID NO: 453 |
| 807B-M0079-D10/M0165-A02 | SEQ ID NO: 429 | SEQ ID NO: 440 | SEQ ID NO: 451 | SEQ ID NO: 78 | SEQ ID NO: 453 |
| 807B-M0079-D10/M0165-A06 | SEQ ID NO: 430 | SEQ ID NO: 441 | SEQ ID NO: 452 | SEQ ID NO: 78 | SEQ ID NO: 453 |
| 807B-M0079-D10/M0165-B07 | SEQ ID NO: 423 | SEQ ID NO: 435 | SEQ ID NO: 445 | SEQ ID NO: 78 | SEQ ID NO: 453 |
| 807B-M0079-D10/M0165-B08 | SEQ ID NO: 428 | SEQ ID NO: 438 | SEQ ID NO: 450 | SEQ ID NO: 78 | SEQ ID NO: 453 |
| 807B-M0079-D10/M0165-D03 | SEQ ID NO: 431 | SEQ ID NO: 434 | SEQ ID NO: 445 | SEQ ID NO: 78 | SEQ ID NO: 453 |
| 807B-M0079-D10/M0165-D05 | SEQ ID NO: 428 | SEQ ID NO: 438 | SEQ ID NO: 450 | SEQ ID NO: 78 | SEQ ID NO: 453 |
| 807B-M0079-D10/M0165-D12 | SEQ ID NO: 428 | SEQ ID NO: 438 | SEQ ID NO: 450 | SEQ ID NO: 78 | SEQ ID NO: 453 |
| 807B-M0079-D10/M0165-E01 | SEQ ID NO: 426 | SEQ ID NO: 436 | SEQ ID NO: 448 | SEQ ID NO: 78 | SEQ ID NO: 453 |
| 807B-M0079-D10/M0166-A08 | SEQ ID NO: 429 | SEQ ID NO: 440 | SEQ ID NO: 451 | SEQ ID NO: 78 | SEQ ID NO: 453 |
| 807B-M0079-D10/M0165-A09 | SEQ ID NO: 424 | SEQ ID NO: 434 | SEQ ID NO: 446 | SEQ ID NO: 78 | SEQ ID NO: 453 |
| 807B-M0079-D10/M0166-B08 | SEQ ID NO: 423 | SEQ ID NO: 435 | SEQ ID NO: 445 | SEQ ID NO: 78 | SEQ ID NO: 453 |
| 807B-M0079-D10/M0166-C08 | SEQ ID NO: 430 | SEQ ID NO: 441 | SEQ ID NO: 452 | SEQ ID NO: 78 | SEQ ID NO: 453 |
| 807B-M0079-D10/M0166-D03 | SEQ ID NO: 432 | SEQ ID NO: 443 | SEQ ID NO: 454 | SEQ ID NO: 78 | SEQ ID NO: 453 |
| 807B-M0079-D10/M0166-F03 | SEQ ID NO: 423 | SEQ ID NO: 435 | SEQ ID NO: 445 | SEQ ID NO: 78 | SEQ ID NO: 453 |
| 807B-M0079-D10/M0166-F04 | SEQ ID NO: 425 | SEQ ID NO: 435 | SEQ ID NO: 447 | SEQ ID NO: 78 | SEQ ID NO: 453 |
| 807B-M0079-D10/M0166-F07 | SEQ ID NO: 433 | SEQ ID NO: 434 | SEQ ID NO: 445 | SEQ ID NO: 78 | SEQ ID NO: 453 |
| 807B-M0079-D10/M0166-F08 | SEQ ID NO: 424 | SEQ ID NO: 434 | SEQ ID NO: 446 | SEQ ID NO: 78 | SEQ ID NO: 453 |
| Initial Name | | | HV-CDR3 | LV-WholeAA | HV-WholeAA |
| 807B-M0079-D10/M0160-F02 | | | SEQ ID NO: 80 | SEQ ID NO: 455 | SEQ ID NO: 146 |
| 807B-M0079-D10/M0160-F12 | | | SEQ ID NO: 80 | SEQ ID NO: 456 | SEQ ID NO: 146 |
| 807B-M0079-D10/M0161-B04 | | | SEQ ID NO: 80 | SEQ ID NO: 457 | SEQ ID NO: 146 |
| 807B-M0079-D10/M0161-G03 | | | SEQ ID NO: 80 | SEQ ID NO: 458 | SEQ ID NO: 146 |
| 807B-M0079-D10/M0162-A11 | | | SEQ ID NO: 80 | SEQ ID NO: 459 | SEQ ID NO: 146 |
| 807B-M0079-D10/M0162-D11 | | | SEQ ID NO: 80 | SEQ ID NO: 460 | SEQ ID NO: 146 |
| 807B-M0079-D10/M0162-F04 | | | SEQ ID NO: 80 | SEQ ID NO: 461 | SEQ ID NO: 146 |
| 807B-M0079-D10/M0164-B02 | | | SEQ ID NO: 80 | SEQ ID NO: 462 | SEQ ID NO: 146 |
| 807B-M0079-D10/M0164-B03 | | | SEQ ID NO: 80 | SEQ ID NO: 463 | SEQ ID NO: 146 |
| 807B-M0079-D10/M0164-C08 | | | SEQ ID NO: 80 | SEQ ID NO: 464 | SEQ ID NO: 146 |
| 807B-M0079-D10/M0164-C09 | | | SEQ ID NO: 80 | SEQ ID NO: 465 | SEQ ID NO: 146 |
| 807B-M0079-D10/M0164-C10 | | | SEQ ID NO: 80 | SEQ ID NO: 466 | SEQ ID NO: 146 |
| 807B-M0079-D10/M0164-E05 | | | SEQ ID NO: 80 | SEQ ID NO: 467 | SEQ ID NO: 146 |
| 807B-M0079-D10/M0165-A02 | | | SEQ ID NO: 80 | SEQ ID NO: 468 | SEQ ID NO: 146 |
| 807B-M0079-D10/M0165-A06 | | | SEQ ID NO: 80 | SEQ ID NO: 469 | SEQ ID NO: 146 |
| 807B-M0079-D10/M0165-B07 | | | SEQ ID NO: 80 | SEQ ID NO: 470 | SEQ ID NO: 146 |
| 807B-M0079-D10/M0165-B08 | | | SEQ ID NO: 80 | SEQ ID NO: 471 | SEQ ID NO: 146 |
| 807B-M0079-D10/M0165-D03 | | | SEQ ID NO: 80 | SEQ ID NO: 472 | SEQ ID NO: 146 |
| 807B-M0079-D10/M0165-D05 | | | SEQ ID NO: 80 | SEQ ID NO: 473 | SEQ ID NO: 146 |
| 807B-M0079-D10/M0165-D12 | | | SEQ ID NO: 80 | SEQ ID NO: 474 | SEQ ID NO: 146 |
| 807B-M0079-D10/M0165-E01 | | | SEQ ID NO: 80 | SEQ ID NO: 475 | SEQ ID NO: 146 |
| 807B-M0079-D10/M0166-A08 | | | SEQ ID NO: 80 | SEQ ID NO: 476 | SEQ ID NO: 146 |
| 807B-M0079-D10/M0165-A09 | | | SEQ ID NO: 80 | SEQ ID NO: 477 | SEQ ID NO: 146 |

TABLE 42-continued

Affinity matured clones of 807B-M0079-D10

| | | | |
|---|---|---|---|
| 807B-M0079-D10/M0166-B08 | SEQ ID NO: 80 | SEQ ID NO: 478 | SEQ ID NO: 146 |
| 807B-M0079-D10/M0166-C08 | SEQ ID NO: 80 | SEQ ID NO: 479 | SEQ ID NO: 146 |
| 807B-M0079-D10/M0166-D03 | SEQ ID NO: 80 | SEQ ID NO: 480 | SEQ ID NO: 146 |
| 807B-M0079-D10/M0166-F03 | SEQ ID NO: 80 | SEQ ID NO: 481 | SEQ ID NO: 146 |
| 807B-M0079-D10/M0166-F04 | SEQ ID NO: 80 | SEQ ID NO: 482 | SEQ ID NO: 146 |
| 807B-M0079-D10/M0166-F07 | SEQ ID NO: 80 | SEQ ID NO: 483 | SEQ ID NO: 146 |
| 807B-M0079-D10/M0166-F08 | SEQ ID NO: 80 | SEQ ID NO: 484 | SEQ ID NO: 146 |

TABLE 43

Light chain sequences of antibodies selected by Vh-CDR3 spiking and light chain shuffling

| Initial Name | LV-FR1 | LV-CDR1 | LV-FR2 | LV-CDR2 | LV-FR3 | LV-CDR3 | LV-FR4 |
|---|---|---|---|---|---|---|---|
| 807B-M0004-A03/ M0149-D04 | QSVLTQSPS ASGTPGQRV TISC | SGSNSNVGTKTVN | WYQVLPGTAPKLLIY | SNTQRPS | GVPDRFSGSKSGTSAS LAISGLQSEDEADYYC | AAWDDSLNGPV | FGGGTRVTVL |
| 807B-M0004-A03/ M0149-F02 | QSALTQPPS ASGTPGQRV TISC | SGSSSNIGSNTVN | WYQQLPGTAPKLLIY | SNNQRPS | GVPDRFSGSKSGTSAS LAISGLQSEDEADYYC | AAWDDSLNGPV | FGGGTKLTVL |
| 807B-M0004-A03/ M0150-A07 | QSALTQPPS ASGTPGQRV TISC | SGSSSNIGSNTVN | WYQQLPGTAPKLLIY | SNNQRPS | GVPDRFSGSKSGTSAS LAISGLQSEDEADYYC | AAWDDSLNGPV | FGGGTKLTVL |
| 807B-M0004-A03/ M0150-E03 | QYELTQPPS ASGTPGQRV TISC | SGSSSNIGINTVN | WYQQLPGTAPKLLIY | SNNQRPS | GVPDRFSGSKSGTSAS LAISGLQSEDEADYYC | AAWDDSLNGPV | FGGGTKLTVL |
| 807B-M0004-A03/ M0151-D09 | QSALTQPPS ASGTPGQRV TISC | SGSSSNIGINTVN | WYQQLPGTAPKLLIY | SNNQRPS | GVPDRFSGSKSGTSAS LAISGLQSEDEADYYC | AAWDDSLNGPV | FGGGTKLTVL |
| 807A-M0028-B02/ M0169-F03 | QDIQMTQSP SSLSASVGD RVTITC | QASQDISNYLN | WYQQKPGKAPQRLIY | GASTVQS | GVPSRFSGSGSGTEFT LTISSLQPDDFATYYC | QQYKTYPFT | FGQGTRLDIK |
| 807A-M0028-B02/ M0171-E03 | QDIQMTQSP SSLSASVGD RVTITC | RTSQDIGNHLA | WYQQKPGKAPQRLIR | KASILQS | GVPSTFSGSGSGTEFT LTISSLQPEDFASYYC | QQYDAFPFT | FGQGTKLEIK |
| 807A-M0028-B02/ M0171-G02 | QDIQMTQSP SSLSASVGD TVTITC | RASQGITNYLA | WFQQKPGKAPKSLM | YGAYKLQY | GVPTKFSGSGSGTDFT LTIRSLQPEDFATYYC | LQYQTYPFT | FGPGTKVDLK |
| 807A-M0028-B02/ M0172-F07 | QDIQMTQSP SSLSASVGD TVTITC | RTSQGIRNHLG | WFQQKPGKAPQRLIR | EASILQS | GVPSTFSGSGSGTEFT LTISSLQPEDFATYYC | LQYDSFPYT | FGQGTKLEIK |
| 807B-M0004-H03/ M0154-H06 | QDIQMTQSP SSLSASVGD RVTITC | RASRGVSTSLN | WYQIKPEKAPKLLIY | AASSLQS | GVPSRFSGSGSGTDFT LAITSLQPEDFATYYC | QQSYSTPRT | FGPGTKVEIK |
| 807B-M0004-H03/ M0159-A09 | QDIQMTQSP SSLSASVGD RVTITC | RASQSIRSYLN | WFQQKPGKAPKLLIY | AASTLQS | GVPSRFSGSGSGTDFT LTISSLQPEDFATYYC | QQSYSTPRT | FGQGTKLEIK |
| 807A-M0028-B02/ M0168-D10 | QDIQMTQSP SSLSASVGD RVTITC | RTSQDIRNHLG | WFQQKPGKAPQRLIR | EASILQS | GVPSTFYGSGYGREFT LTISSLQPEDFATYYC | LQYDSFPYT | FGQGTKLEIK |
| 807B-M0004-A03/ M0149-G11 | QSALTQPPS ASGTPGQRV TISC | SGSSNIGSNTVN | WYQQLPGTAPKLLIY | SNNQRPS | GVPDRFSGSKSGTSAS LAISGLQSEDEADYYC | AAWDDSLNGPV | FGGGTKLTVL |

TABLE 44

Heavy chain sequences of antibodies selected by VH-CDR3 spiking and light chain shuffling

| Initial Name | HV-FR1 | HV-CDR1 | HV-FR2 | HV-CDR2 | HV-FR3 | HV-CDR3 | HV-FR4 |
|---|---|---|---|---|---|---|---|
| 807B-M0004-A03/ M0149-D04 | EVQLLESGGGLVQPG GSLRLSCAASGFTFS | RYLMM | WVRQAPGKGLEWVS | VISPSGGRTWYADS VKG | RFTISRDNSKNTLY LQMNSLRAEDTAVY YCVR | SIASAGTDH | WGQGTL VTVSS |
| 807B-M0004-A03/ M0149-F02 | EVQLLESGGGLVQPG GSLRLSCAASGFTFS | RYLMM | WVRQAPGKGLEWVS | VISPSGGRTWYADS VKG | RFTISRDNSKNTLY LQMNSLRAEDTAVY YCVR | SIASAGTDH | WGQGTL VTVSS |
| 807B-M0004-A03/ M0150-A07 | EVQLLESGGGLVQPG GSLRLSCAASGFTFS | RYLMM | WVRQAPGKGLEWVS | VISPSGGRTWYADS VKG | RFTISRDNSKNTLY LQMNSLRAEDTAVY YCVR | SIAASRTDY | WGQGTL VTVSS |
| 807B-M0004-A03/ M0150-E03 | EVQLLESGGGLVQPG GSLRLSCAASGFTFS | RYLMM | WVRQAPGKGLEWVS | VISPSGGRTWYADS VKG | RFTISRDNSKNTLY LQMNSLRAEDTAVY YCVR | SIAADRTDY | WGQGTL VTVSS |
| 807B-M0004-A03/ M0151-D09 | EVQLLESGGGLVQPG GSLRLSCAASGFTFS | RYLMM | WVRQAPGKGLEWVS | VISPSGGRTWYADS VKG | RFTISRDNSKNTLY LQMNSLRAEDTAVY YCAR | SIASAGTDH | WGQGTL VTVSS |
| 807A-M0028-B02/ M0169-F03 | EVQLLESGGGLVQPG GSLRLSCAASGFTFS | MYMMD | WVRQAPGKGLEWVS | SIWPSGGQTWYADS VKG | RFTISRDNSKNTLY LQMNSLRAEDTAVY YCAR | GVLLDK | WGQGTL VTVSS |
| 807A-M0028-B02/ M0171-E03 | EVQLLESGGGLVQPG GSLRLSCAASGFTFS | MYMMD | WVRQAPGKGLEWVS | SIWPSGGQTWYADS VKG | RFTISRDNSKNTLY LQMNSLRAEDTAVY YCAR | GVLLDK | WGQGTL VTVSS |
| 807A-M0028-B02- M0171-G02 | EVQLLESGGGLVQPG GSLRLSCAASGFTFS | MYMMD | WVRQAPGKGLEWVS | SIWPSGGQTWYADS VKG | RFTISRDNSKNTLY LQMNSLRAEDTAVY YCAR | GILHDY | WGQGTL VTVSS |
| 807A-M0028-B02/ M0127-F07 | EVQLLESGGGLVQPG GSLRLSCAASGFTFS | MYMMD | WVRQAPGKGLEWVS | SIWPSGGQTWYADS VKG | RFTISRDNSKNTLY LQMNSLRAEDTAVY YCAR | GVLFDN | WGQGTL VTVSS |
| 807B-M0004-H03/ M0154-H06 | EVQLLESGGGLVQPG GSLRLSCAASGFTFS | SYPMV | WVRQAPGKGLEMVS | GIWSSGGLTYYADS VKG | RFTISRDNSKNTLY LQMNSLRAEDTAVY YCAR | ERSVAVFKAR PRHYYYYMDV | WGKGTT VTVSS |
| 807B-M0004-H03/ M0159-A09 | EVQLLESGGGLVQPG GSLRLSCAASGFTFS | SYPMV | WVRQAPGKGLEWVS | GIWSSGGLTYYADS VKG | RFTISRDNSKNTLY LQMNSLRAEDTAVY YCAR | ERSVAVFKAR PRHYYYYMDV | WGKGTT VTVSS |
| 807A-M0028-B02/ M0168-D10 | EVQLLESGGGLVQPG GSLRLSCAASGFTFS | MYMMD | WVRQAPGKGLEWVS | SIWPSGGQTWYADS VKG | RFTISRDNSKNTLY LQMNSLRAEDTAVY YCAR | GVLFDN | WGQGTL VTVSS |
| 807B-M0004-A03/ M0149-G11 | EVQLLESGGGLVQPG GSLRLSCAASGFTFS | RYLMM | WVRQAPGKGLEWVS | VISPSGGRTWYADS VKG | RFTISRDNSKNTLY LQMNSLRAEDTAVY YCVR | SIASARTDS | WGQGTL VTVSS |

The invention claimed is:

1. A method of diagnosing an amyloid disorder in a subject comprising:
   (i) administering to said subject an antibody or antibody fragment, wherein said antibody or fragment: binds to a polypeptide having the amino acid sequence shown in SEQ ID NO: 1 of the C-terminal domain of Apolipoprotein E (ApoE-CTD) or the amino acid sequence of a part thereof; and
   (ii) determining whether or not said antibody or antibody fragment binds to plaques in said subject, wherein binding of said antibody or antibody fragment to plaques is indicative of an amyloid disorder,
thereby determining whether the subject has an amyloid disorder.

2. A method according to claim 1 wherein the amyloid disorder is selected from the group consisting of Alzheimer's disease, primary systemic amyloidosis, secondary systemic amyloidosis, senile systemic amyloidosis, familial amyloid polyneuropathy I, familial amyloid polyneuropathy III, familial non-neuropathic amyloidosis, hereditary cerebral amyloid angiopathy, Familial British Dementia (FBD), Haemodialysis-related amyloidosis, Familial amyloidosis (Finnish type), Familial subepithelial corneal amyloid, Type II diabetes, Hereditary renal amyloidosis, Pituitary-gland amyloidosis, injection localized amyloidosis, Medullary carcinoma of the thyroid, Atrial amyloidosis, Familial Danish Dementia (FDD), Downs syndrome, Spongiform encephalopathies, Sporadic Creutzfeldt-Jakob disease, Familial Creutzfeldt-Jakob disease, Iatropic prion disorders, Variant Creutzfeldt-Jakob disease, Gerstmann-Sträussler-Scheinker Disease (GSS), Kuru, Parkinson's disease, Huntington's disease, Familial amyotrophic lateral sclerosis (ALS) and Chronic obstructive pulmonary disease.

3. A method according to claim 1 wherein the antibody or antibody fragment comprises: (a) a heavy chain CDR3 region comprising the sequence shown in SEQ ID NO: 26, SEQ ID NO: 20, SEQ ID NO: 23, SEQ ID NO: 207, SEQ ID NO: 208, SEQ ID NO: 209, SEQ ID NO: 210, or SEQ ID NO: 512; (b) a heavy chain CDR2 region comprising the sequence shown in SEQ ID NO: 25; (c) a heavy chain CDR1 region comprising the sequence shown in SEQ ID NO: 24; (d) a light chain CDR3 region comprising the sequence shown in SEQ ID NO: 35; (e) a light chain CDR2 region comprising the sequence shown in SEQ ID NO: 34; and (f) a light chain CDR1 region comprising the sequence shown in SEQ ID NO: 33.

4. A method according to claim 1 wherein said antibody or antibody fragment binds to said plaques in the presence of VLDL.

5. A method according to claim 1 wherein said antibody or antibody fragment comprises: (a) the heavy chain sequence shown in SEQ ID NO: 40 and the light chain sequence shown in SEQ ID NO: 518 and/or 519 or (b) the heavy chain sequence shown in SEQ ID NO: 40 and the light chain sequence shown in SEQ ID NO: 520 and/or 521.

6. A method according to claim 1 wherein said antibody or antibody fragment comprises: (a) the heavy chain CDR1 sequence shown in SEQ ID NO: 24, the heavy chain CDR2 sequence shown in SEQ ID NO: 25 and the heavy chain CDR3 sequence shown in any one of SEQ ID NOS: 207, 209 and 210; and (b) the light chain CDR1, CDR2 and CDR3 sequences shown in SEQ ID NOS: 33, 34 and 35, SEQ ID NOS: 219, 247 and 269, SEQ ID NOS: 226, 252 and 275 or SEQ ID NOS: 218, 34 and 268.

7. A method according to claim 1 wherein said antibody is an IgG.

8. A method according to claim 1 wherein said antibody fragment is a Fab or a scFv.

9. A method according to claim 1 wherein said antibody or antibody fragment is a human antibody or antibody fragment.

10. A method according to claim 3 wherein said heavy chain CDR3 region of said antibody or antibody fragment comprises an affinity matured variant of SEQ ID NO: 26 having the sequence shown in SEQ ID NO: 512.

11. A method according to claim 3 wherein said heavy chain CDR3 region of said antibody or antibody fragment comprises an affinity matured variant of SEQ ID NO: 26 having the sequence shown in SEQ ID NO: 20.

12. A method according to claim 3 wherein said heavy chain CDR3 region of said antibody or antibody fragment comprises the sequence shown in SEQ ID NO: 23.

13. A method according to claim 3 wherein said heavy chain CDR3 region of said antibody or antibody fragment comprises an affinity matured variant of SEQ ID NO: 26 having the sequence shown in SEQ ID NO: 207, SEQ ID NO: 208, SEQ ID NO: 209 or SEQ ID NO: 210.

14. A method according to claim 13 wherein said heavy chain CDR3 region of said antibody or antibody fragment comprises an affinity matured variant of SEQ ID NO: 26 having the sequence shown in SEQ ID NO: 207, SEQ ID NO: 208 or SEQ ID NO: 209.

15. A method according to claim 4 wherein said VLDL is present in human plasma.

16. A method according to claim 15 wherein said antibody or antibody fragment binds to the plaques in the presence of from about 25% to 50% plasma.

17. A method according to claim 6 wherein the heavy chain CDR3 region of said antibody or antibody fragment comprises the sequence shown in SEQ ID NO: 210 and the light chain comprises the sequences shown in SEQ ID NOS: 33, 34 and 35, the heavy chain CDR3 region comprises the sequence shown in SEQ ID NO: 209 and the light chain comprises the sequences shown in SEQ ID NOS: 219, 247 and 269 or SEQ ID NOS: 218, 34 and 268, or the heavy chain CDR3 region comprises the sequence shown in SEQ ID NO: 207 and the light chain comprises the sequence shown in SEQ ID NOS: 226, 252 and 275.

18. A method according to claim 6 wherein the heavy chain of said antibody or antibody fragment comprises the sequence shown in any one of SEQ ID NO: 317, 318 or 319.

19. A method according to claim 6 wherein the light chain of said antibody or antibody fragment comprises the sequence shown in SEQ ID NO: 43, 295, 294 or 304.

* * * * *

SEQUENCE LISTING

<160> NUMBER OF SEQ ID NOS: 527

<210> SEQ ID NO 1
<211> LENGTH: 84
<212> TYPE: PRT
<213> ORGANISM: Homo sapiens

<400> SEQUENCE: 1

Ala Arg Met Glu Glu Met Gly Ser Arg Thr Arg Asp Arg Leu Asp Glu
1               5                   10                  15

Val Lys Glu Gln Val Ala Glu Val Arg Ala Lys Leu Glu Glu Gln Ala
            20                  25                  30

```
Gln Gln Ile Arg Leu Gln Ala Glu Ala Phe Gln Ala Arg Leu Lys Ser
        35                  40                  45

Trp Phe Glu Pro Leu Val Glu Asp Met Gln Arg Gln Trp Ala Gly Leu
     50                  55                  60

Val Glu Lys Val Gln Ala Ala Val Gly Thr Ser Ala Ala Pro Val Pro
 65                  70                  75                  80

Ser Asp Asn His

<210> SEQ ID NO 2
<211> LENGTH: 16
<212> TYPE: PRT
<213> ORGANISM: Homo sapiens

<400> SEQUENCE: 2

Ala Arg Met Glu Glu Met Gly Ser Arg Thr Arg Asp Arg Leu Asp Glu
 1               5                  10                  15

<210> SEQ ID NO 3
<211> LENGTH: 16
<212> TYPE: PRT
<213> ORGANISM: Homo sapiens

<400> SEQUENCE: 3

Val Lys Glu Gln Val Ala Glu Val Arg Ala Lys Leu Glu Glu Gln Ala
 1               5                  10                  15

<210> SEQ ID NO 4
<211> LENGTH: 16
<212> TYPE: PRT
<213> ORGANISM: Homo sapiens

<400> SEQUENCE: 4

Gln Gln Ile Arg Leu Gln Ala Glu Ala Phe Gln Ala Arg Leu Lys Ser
 1               5                  10                  15

<210> SEQ ID NO 5
<211> LENGTH: 16
<212> TYPE: PRT
<213> ORGANISM: Homo sapiens

<400> SEQUENCE: 5

Trp Phe Glu Pro Leu Val Glu Asp Met Gln Arg Gln Trp Ala Gly Leu
 1               5                  10                  15

<210> SEQ ID NO 6
<211> LENGTH: 16
<212> TYPE: PRT
<213> ORGANISM: Homo sapiens

<400> SEQUENCE: 6

Val Glu Lys Val Gln Ala Ala Val Gly Thr Ser Ala Ala Pro Val Pro
 1               5                  10                  15

<210> SEQ ID NO 7
<211> LENGTH: 16
<212> TYPE: PRT
<213> ORGANISM: Homo sapiens

<400> SEQUENCE: 7

Arg Thr Arg Asp Arg Leu Asp Glu Val Lys Glu Gln Val Ala Glu Val
 1               5                  10                  15

<210> SEQ ID NO 8
<211> LENGTH: 16
```

```
<212> TYPE: PRT
<213> ORGANISM: Homo sapiens

<400> SEQUENCE: 8

Arg Ala Lys Leu Glu Glu Gln Ala Gln Gln Ile Arg Leu Gln Ala Glu
1               5                   10                  15

<210> SEQ ID NO 9
<211> LENGTH: 16
<212> TYPE: PRT
<213> ORGANISM: Homo sapiens

<400> SEQUENCE: 9

Ala Phe Gln Ala Arg Leu Lys Ser Trp Phe Glu Pro Leu Val Glu Asp
1               5                   10                  15

<210> SEQ ID NO 10
<211> LENGTH: 16
<212> TYPE: PRT
<213> ORGANISM: Homo sapiens

<400> SEQUENCE: 10

Met Gln Arg Gln Trp Ala Gly Leu Val Glu Lys Val Gln Ala Ala Val
1               5                   10                  15

<210> SEQ ID NO 11
<211> LENGTH: 12
<212> TYPE: PRT
<213> ORGANISM: Homo sapiens

<400> SEQUENCE: 11

Gly Thr Ser Ala Ala Pro Val Pro Ser Asp Asn His
1               5                   10

<210> SEQ ID NO 12
<211> LENGTH: 8
<212> TYPE: PRT
<213> ORGANISM: Homo sapiens

<400> SEQUENCE: 12

Leu Val Glu Asp Met Gln Arg Gln
1               5

<210> SEQ ID NO 13
<211> LENGTH: 8
<212> TYPE: PRT
<213> ORGANISM: Homo sapiens

<400> SEQUENCE: 13

Met Gln Arg Gln Trp Ala Gly Leu
1               5

<210> SEQ ID NO 14
<211> LENGTH: 8
<212> TYPE: PRT
<213> ORGANISM: Homo sapiens

<400> SEQUENCE: 14

Trp Ala Gly Leu Val Glu Lys Val
1               5

<210> SEQ ID NO 15
<211> LENGTH: 8
<212> TYPE: PRT
<213> ORGANISM: Homo sapiens
```

```
<400> SEQUENCE: 15

Arg Thr Arg Asp Arg Leu Asp Glu
1               5

<210> SEQ ID NO 16
<211> LENGTH: 8
<212> TYPE: PRT
<213> ORGANISM: Homo sapiens

<400> SEQUENCE: 16

Trp Phe Glu Pro Leu Val Glu Asp
1               5

<210> SEQ ID NO 17
<211> LENGTH: 8
<212> TYPE: PRT
<213> ORGANISM: Homo sapiens

<400> SEQUENCE: 17

Ala Phe Gln Ala Arg Leu Lys Ser
1               5

<210> SEQ ID NO 18
<211> LENGTH: 24
<212> TYPE: PRT
<213> ORGANISM: Homo sapiens

<400> SEQUENCE: 18

Ala Arg Met Glu Glu Met Gly Ser Arg Thr Arg Asp Arg Leu Asp Glu
1               5                   10                  15

Val Lys Glu Gln Val Ala Glu Val
            20

<210> SEQ ID NO 19
<211> LENGTH: 32
<212> TYPE: PRT
<213> ORGANISM: Homo sapiens

<400> SEQUENCE: 19

Ala Phe Gln Ala Arg Leu Lys Ser Trp Phe Glu Pro Leu Val Glu Asp
1               5                   10                  15

Met Gln Arg Gln Trp Ala Gly Leu Val Glu Lys Val Gln Ala Ala Val
            20                  25                  30

<210> SEQ ID NO 20
<211> LENGTH: 6
<212> TYPE: PRT
<213> ORGANISM: Homo sapiens
<220> FEATURE:
<221> NAME/KEY: MISC_FEATURE
<222> LOCATION: (2)..(3)
<223> OTHER INFORMATION: Xaa = any amino acid

<400> SEQUENCE: 20

Ser Xaa Xaa Leu Asp Tyr
1               5

<210> SEQ ID NO 21
<211> LENGTH: 5
<212> TYPE: PRT
<213> ORGANISM: Homo sapiens

<400> SEQUENCE: 21

Lys Tyr Ser Met His
1               5
```

```
<210> SEQ ID NO 22
<211> LENGTH: 17
<212> TYPE: PRT
<213> ORGANISM: Homo sapiens

<400> SEQUENCE: 22

Gly Ile Tyr Ser Ser Gly Gly Lys Thr Ile Tyr Ala Asp Ser Val Lys
1               5                   10                  15

Gly

<210> SEQ ID NO 23
<211> LENGTH: 6
<212> TYPE: PRT
<213> ORGANISM: Homo sapiens

<400> SEQUENCE: 23

Ser Leu Asp Leu Asp Tyr
1               5

<210> SEQ ID NO 24
<211> LENGTH: 5
<212> TYPE: PRT
<213> ORGANISM: Homo sapiens

<400> SEQUENCE: 24

Met Tyr Met Met Asp
1               5

<210> SEQ ID NO 25
<211> LENGTH: 17
<212> TYPE: PRT
<213> ORGANISM: Homo sapiens

<400> SEQUENCE: 25

Ser Ile Trp Pro Ser Gly Gly Gln Thr Trp Tyr Ala Asp Ser Val Lys
1               5                   10                  15

Gly

<210> SEQ ID NO 26
<211> LENGTH: 6
<212> TYPE: PRT
<213> ORGANISM: Homo sapiens

<400> SEQUENCE: 26

Ser Val Leu Leu Asp Tyr
1               5

<210> SEQ ID NO 27
<211> LENGTH: 5
<212> TYPE: PRT
<213> ORGANISM: Homo sapiens

<400> SEQUENCE: 27

Tyr Tyr Ala Met Gln
1               5

<210> SEQ ID NO 28
<211> LENGTH: 17
<212> TYPE: PRT
<213> ORGANISM: Homo sapiens

<400> SEQUENCE: 28

Ser Leu Tyr Pro Ser Gly Gly Asn Thr Ser Tyr Ala Asp Ser Val Lys
```

-continued

```
                1               5                  10                 15

Gly

<210> SEQ ID NO 29
<211> LENGTH: 19
<212> TYPE: PRT
<213> ORGANISM: Homo sapiens

<400> SEQUENCE: 29

Gly Arg Gly Asn Tyr Asp Phe Trp Ser Ala Gly Tyr Tyr Tyr Tyr
1               5                  10                 15

Met Asp Val

<210> SEQ ID NO 30
<211> LENGTH: 11
<212> TYPE: PRT
<213> ORGANISM: Homo sapiens

<400> SEQUENCE: 30

Arg Ala Ser Gln Arg Ile Arg Lys Asn Leu His
1               5                  10

<210> SEQ ID NO 31
<211> LENGTH: 7
<212> TYPE: PRT
<213> ORGANISM: Homo sapiens

<400> SEQUENCE: 31

Asp Ala Ser Ser Asn Glu Arg
1               5

<210> SEQ ID NO 32
<211> LENGTH: 9
<212> TYPE: PRT
<213> ORGANISM: Homo sapiens

<400> SEQUENCE: 32

Gln Gln Ser Phe Ser Ser Pro Trp Thr
1               5

<210> SEQ ID NO 33
<211> LENGTH: 11
<212> TYPE: PRT
<213> ORGANISM: Homo sapiens

<400> SEQUENCE: 33

Arg Thr Ser Gln Asp Ile Arg Asn His Leu Gly
1               5                  10

<210> SEQ ID NO 34
<211> LENGTH: 7
<212> TYPE: PRT
<213> ORGANISM: Homo sapiens

<400> SEQUENCE: 34

Glu Ala Ser Ile Leu Gln Ser
1               5

<210> SEQ ID NO 35
<211> LENGTH: 9
<212> TYPE: PRT
<213> ORGANISM: Homo sapiens

<400> SEQUENCE: 35
```

```
Leu Gln Tyr Asp Ser Phe Pro Tyr Thr
1               5

<210> SEQ ID NO 36
<211> LENGTH: 12
<212> TYPE: PRT
<213> ORGANISM: Homo sapiens

<400> SEQUENCE: 36

Arg Ala Ser Gln Ser Ile Gly Ser Arg Tyr Leu Ala
1               5                   10

<210> SEQ ID NO 37
<211> LENGTH: 7
<212> TYPE: PRT
<213> ORGANISM: Homo sapiens

<400> SEQUENCE: 37

Asp Ala Ser Lys Arg Ala Thr
1               5

<210> SEQ ID NO 38
<211> LENGTH: 10
<212> TYPE: PRT
<213> ORGANISM: Homo sapiens

<400> SEQUENCE: 38

Gln Gln Gly Tyr Asn Trp Pro Pro Trp Thr
1               5                   10

<210> SEQ ID NO 39
<211> LENGTH: 115
<212> TYPE: PRT
<213> ORGANISM: Homo sapiens

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ser Met His Trp Val Arg Gln Ala Pro Gly Lys Gly Leu Glu Trp Val
        35                  40                  45

Ser Gly Ile Tyr Ser Ser Gly Gly Lys Thr Ile Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Asp Leu Asp Tyr Trp Gly Gln Gly Thr Leu Val Thr
            100                 105                 110

Val Ser Ser
        115

<210> SEQ ID NO 40
<211> LENGTH: 115
<212> TYPE: PRT
<213> ORGANISM: Homo sapiens

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
```

-continued

```
                    20                  25                  30
Met Met Asp Trp Val Arg Gln Ala Pro Gly Lys Gly Leu Glu Trp Val
            35                  40                  45
Ser Ser Ile Trp Pro Ser Gly Gly Gln Thr Trp Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Val Leu Leu Asp Tyr Trp Gly Gln Gly Thr Leu Val Thr
            100                 105                 110
Val Ser Ser
        115
```

<210> SEQ ID NO 41
<211> LENGTH: 128
<212> TYPE: PRT
<213> ORGANISM: Homo sapiens

<400> SEQUENCE: 41

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Tyr Tyr
            20                  25                  30
Ala Met Gln Trp Val Arg Gln Ala Pro Gly Lys Gly Leu Glu Trp Val
            35                  40                  45
Ser Ser Leu Tyr Pro Ser Gly Gly Asn Thr Ser Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Arg Gly Asn Tyr Asp Phe Trp Ser Ala Gly Tyr Tyr Tyr
            100                 105                 110
Tyr Tyr Met Asp Val Trp Gly Lys Gly Thr Thr Val Thr Val Ser Ser
        115                 120                 125
```

<210> SEQ ID NO 42
<211> LENGTH: 108
<212> TYPE: PRT
<213> ORGANISM: Homo sapiens

<400> SEQUENCE: 42

```
Gln Asp Ile Gln Met Thr Gln Ser Pro Ser Ser Leu Ser Ala Ser Val
1               5                   10                  15
Gly Asp Arg Val Thr Ile Thr Cys Arg Ala Ser Gln Arg Ile Arg Lys
            20                  25                  30
Asn Leu His Trp Tyr Gln Gln Lys Pro Gly Lys Ala Pro Asn Leu Leu
            35                  40                  45
Ile Tyr Asp Ala Ser Ser Asn Glu Arg Gly Val Pro Ser Arg Phe Ser
        50                  55                  60
Gly Arg Gly Ser Gly Thr Glu Phe Thr Leu Thr Ile Ser Ser Leu Gln
65                  70                  75                  80
Pro Glu Asp Leu Ala Thr Tyr Tyr Cys Gln Gln Ser Phe Ser Ser Pro
                85                  90                  95
Trp Thr Phe Gly Gln Gly Thr Lys Val Glu Ile Lys
            100                 105
```

```
<210> SEQ ID NO 43
<211> LENGTH: 108
<212> TYPE: PRT
<213> ORGANISM: Homo sapiens

<400> SEQUENCE: 43

Gln Asp Ile Gln Met Thr Gln Ser Pro Ser Ser Leu Ser Ala Ser Val
1               5                   10                  15

Gly Asp Arg Val Thr Ile Thr Cys Arg Thr Ser Gln Asp Ile Arg Asn
            20                  25                  30

His Leu Gly Trp Phe Gln Gln Lys Pro Gly Lys Ala Pro Gln Arg Leu
        35                  40                  45

Ile Arg Glu Ala Ser Ile Leu Gln Ser Gly Val Pro Ser Thr Phe Tyr
    50                  55                  60

Gly Ser Gly Tyr Gly Arg Glu Phe Thr Leu Thr Ile Ser Ser Leu Gln
65                  70                  75                  80

Pro Glu Asp Phe Ala Thr Tyr Tyr Cys Leu Gln Tyr Asp Ser Phe Pro
                85                  90                  95

Tyr Thr Phe Gly Gln Gly Thr Lys Val Glu Ile Lys
            100                 105

<210> SEQ ID NO 44
<211> LENGTH: 110
<212> TYPE: PRT
<213> ORGANISM: Homo sapiens

<400> SEQUENCE: 44

Gln Asp Ile Gln Met Thr Gln Ser Pro Gly Thr Leu Ser Leu Ser Pro
1               5                   10                  15

Gly Glu Arg Ala Thr Leu Ser Cys Arg Ala Ser Gln Ser Ile Gly Ser
            20                  25                  30

Arg Tyr Leu Ala Trp Tyr Gln Gln Lys Pro Gly Gln Ala Pro Arg Leu
        35                  40                  45

Leu Ile Tyr Asp Ala Ser Lys Arg Ala Thr Gly Val Pro Val Arg Phe
    50                  55                  60

Ser Gly Ser Gly Ser Gly Thr Asp Phe Thr Leu Thr Ile Ser Ser Leu
65                  70                  75                  80

Gly Pro Glu Asp Phe Ala Val Tyr Tyr Cys Gln Gln Tyr Asn Trp
                85                  90                  95

Pro Pro Trp Thr Phe Gly Gln Gly Thr Lys Val Glu Ile Lys
            100                 105                 110

<210> SEQ ID NO 45
<211> LENGTH: 5
<212> TYPE: PRT
<213> ORGANISM: Homo sapiens

<400> SEQUENCE: 45

Phe Tyr Gly Met Val
1               5

<210> SEQ ID NO 46
<211> LENGTH: 17
<212> TYPE: PRT
<213> ORGANISM: Homo sapiens

<400> SEQUENCE: 46

Ser Ile Ser Pro Ser Gly Gly Tyr Thr Leu Tyr Ala Asp Ser Val Lys
1               5                   10                  15
```

Gly

<210> SEQ ID NO 47
<211> LENGTH: 14
<212> TYPE: PRT
<213> ORGANISM: Homo sapiens

<400> SEQUENCE: 47

Asp Gly Arg Arg Pro His Tyr Gly Ser Gly Arg Trp Ala Tyr
1               5                   10

<210> SEQ ID NO 48
<211> LENGTH: 5
<212> TYPE: PRT
<213> ORGANISM: Homo sapiens

<400> SEQUENCE: 48

Arg Tyr Leu Met Met
1               5

<210> SEQ ID NO 49
<211> LENGTH: 17
<212> TYPE: PRT
<213> ORGANISM: Homo sapiens

<400> SEQUENCE: 49

Val Ile Ser Pro Ser Gly Gly Arg Thr Trp Tyr Ala Asp Ser Val Lys
1               5                   10                  15

Gly

<210> SEQ ID NO 50
<211> LENGTH: 9
<212> TYPE: PRT
<213> ORGANISM: Homo sapiens

<400> SEQUENCE: 50

Ser Ile Ala Ala Ala Gly Thr Asp Tyr
1               5

<210> SEQ ID NO 51
<211> LENGTH: 5
<212> TYPE: PRT
<213> ORGANISM: Homo sapiens

<400> SEQUENCE: 51

Asn Tyr Phe Met Ile
1               5

<210> SEQ ID NO 52
<211> LENGTH: 17
<212> TYPE: PRT
<213> ORGANISM: Homo sapiens

<400> SEQUENCE: 52

Trp Ile Ser Pro Ser Gly Gly Thr Thr Gln Tyr Ala Asp Ser Val Lys
1               5                   10                  15

Gly

<210> SEQ ID NO 53
<211> LENGTH: 4
<212> TYPE: PRT
<213> ORGANISM: Homo sapiens

<400> SEQUENCE: 53

```
Glu Ala Gly Tyr
1

<210> SEQ ID NO 54
<211> LENGTH: 5
<212> TYPE: PRT
<213> ORGANISM: Homo sapiens

<400> SEQUENCE: 54

Ala Tyr Tyr Met Gly
1               5

<210> SEQ ID NO 55
<211> LENGTH: 17
<212> TYPE: PRT
<213> ORGANISM: Homo sapiens

<400> SEQUENCE: 55

Val Ile Arg Pro Ser Gly Gly Lys Thr Lys Tyr Ala Asp Ser Val Lys
1               5                   10                  15

Gly

<210> SEQ ID NO 56
<211> LENGTH: 10
<212> TYPE: PRT
<213> ORGANISM: Homo sapiens

<400> SEQUENCE: 56

Gly Pro His Gly Gln Gly Gly Val Asp Ser
1               5                   10

<210> SEQ ID NO 57
<211> LENGTH: 5
<212> TYPE: PRT
<213> ORGANISM: Homo sapiens

<400> SEQUENCE: 57

Glu Tyr Phe Met Thr
1               5

<210> SEQ ID NO 58
<211> LENGTH: 17
<212> TYPE: PRT
<213> ORGANISM: Homo sapiens

<400> SEQUENCE: 58

Ser Ile Arg Pro Ser Gly Gly Lys Thr Arg Tyr Ala Asp Ser Val Lys
1               5                   10                  15

Gly

<210> SEQ ID NO 59
<211> LENGTH: 17
<212> TYPE: PRT
<213> ORGANISM: Homo sapiens

<400> SEQUENCE: 59

Val Ser Arg Tyr Tyr Asn Asn Gly Ala Tyr Arg Leu Asp Ala Phe Asp
1               5                   10                  15

Ile

<210> SEQ ID NO 60
<211> LENGTH: 5
<212> TYPE: PRT
```

<213> ORGANISM: Homo sapiens

<400> SEQUENCE: 60

Ala Tyr Arg Met Ala
1               5

<210> SEQ ID NO 61
<211> LENGTH: 17
<212> TYPE: PRT
<213> ORGANISM: Homo sapiens

<400> SEQUENCE: 61

Tyr Ile Ser Ser Ser Gly Gly Val Thr Ser Tyr Ala Asp Ser Val Lys
1               5                   10                  15

Gly

<210> SEQ ID NO 62
<211> LENGTH: 9
<212> TYPE: PRT
<213> ORGANISM: Homo sapiens

<400> SEQUENCE: 62

Gly Thr His Leu Pro Gly Val Asp Tyr
1               5

<210> SEQ ID NO 63
<211> LENGTH: 5
<212> TYPE: PRT
<213> ORGANISM: Homo sapiens

<400> SEQUENCE: 63

Gly Tyr Ile Met Ala
1               5

<210> SEQ ID NO 64
<211> LENGTH: 17
<212> TYPE: PRT
<213> ORGANISM: Homo sapiens

<400> SEQUENCE: 64

Gly Ile Gly Ser Ser Gly Gly Leu Thr Ala Tyr Ala Asp Ser Val Lys
1               5                   10                  15

Gly

<210> SEQ ID NO 65
<211> LENGTH: 4
<212> TYPE: PRT
<213> ORGANISM: Homo sapiens

<400> SEQUENCE: 65

Glu Ala Gly Tyr
1

<210> SEQ ID NO 66
<211> LENGTH: 5
<212> TYPE: PRT
<213> ORGANISM: Homo sapiens

<400> SEQUENCE: 66

Ser Tyr Pro Met Val
1               5

<210> SEQ ID NO 67
<211> LENGTH: 17

```
<212> TYPE: PRT
<213> ORGANISM: Homo sapiens

<400> SEQUENCE: 67

Gly Ile Trp Ser Ser Gly Gly Leu Thr Tyr Tyr Ala Asp Ser Val Lys
1               5                   10                  15

Gly

<210> SEQ ID NO 68
<211> LENGTH: 20
<212> TYPE: PRT
<213> ORGANISM: Homo sapiens

<400> SEQUENCE: 68

Glu Gly Ser Ala Gly Val Val Lys Gly Pro Ala Arg Tyr Tyr Tyr Tyr
1               5                   10                  15

Tyr Met Asp Val
            20

<210> SEQ ID NO 69
<211> LENGTH: 5
<212> TYPE: PRT
<213> ORGANISM: Homo sapiens

<400> SEQUENCE: 69

Lys Tyr Gln Met Thr
1               5

<210> SEQ ID NO 70
<211> LENGTH: 17
<212> TYPE: PRT
<213> ORGANISM: Homo sapiens

<400> SEQUENCE: 70

Val Ile Ser Ser Ser Gly Gly Asp Thr Ala Tyr Ala Asp Ser Val Lys
1               5                   10                  15

Gly

<210> SEQ ID NO 71
<211> LENGTH: 17
<212> TYPE: PRT
<213> ORGANISM: Homo sapiens

<400> SEQUENCE: 71

Asp Arg Gly Tyr Cys Ser Gly Asn Thr Cys Tyr Ile Asp Ala Phe Asp
1               5                   10                  15

Ile

<210> SEQ ID NO 72
<211> LENGTH: 5
<212> TYPE: PRT
<213> ORGANISM: Homo sapiens

<400> SEQUENCE: 72

Pro Tyr Trp Met Phe
1               5

<210> SEQ ID NO 73
<211> LENGTH: 17
<212> TYPE: PRT
<213> ORGANISM: Homo sapiens

<400> SEQUENCE: 73
```

```
Gly Ile Val Ser Ser Gly Gly Met Thr Gly Tyr Ala Asp Ser Val Lys
1               5                   10                  15

Gly

<210> SEQ ID NO 74
<211> LENGTH: 10
<212> TYPE: PRT
<213> ORGANISM: Homo sapiens

<400> SEQUENCE: 74

Val Gly Met Ser Thr Tyr Ala Phe Asp Ile
1               5                   10

<210> SEQ ID NO 75
<211> LENGTH: 5
<212> TYPE: PRT
<213> ORGANISM: Homo sapiens

<400> SEQUENCE: 75

His Tyr Gly Met Ser
1               5

<210> SEQ ID NO 76
<211> LENGTH: 17
<212> TYPE: PRT
<213> ORGANISM: Homo sapiens

<400> SEQUENCE: 76

Ser Ile Arg Ser Ser Gly Gly Arg Thr Trp Tyr Ala Asp Ser Val Lys
1               5                   10                  15

Gly

<210> SEQ ID NO 77
<211> LENGTH: 9
<212> TYPE: PRT
<213> ORGANISM: Homo sapiens

<400> SEQUENCE: 77

Gly Ser Leu Ser Ser Gly Trp Asp Tyr
1               5

<210> SEQ ID NO 78
<211> LENGTH: 5
<212> TYPE: PRT
<213> ORGANISM: Homo sapiens

<400> SEQUENCE: 78

Asn Tyr Arg Met Glu
1               5

<210> SEQ ID NO 79
<211> LENGTH: 17
<212> TYPE: PRT
<213> ORGANISM: Homo sapiens

<400> SEQUENCE: 79

Ser Ile Trp Ser Ser Gly Gly Leu Thr Lys Gln Ala Asp Ser Val Lys
1               5                   10                  15

Gly

<210> SEQ ID NO 80
<211> LENGTH: 4
<212> TYPE: PRT
<213> ORGANISM: Homo sapiens
```

<400> SEQUENCE: 80

Gly Leu Tyr Arg
1

<210> SEQ ID NO 81
<211> LENGTH: 5
<212> TYPE: PRT
<213> ORGANISM: Homo sapiens

<400> SEQUENCE: 81

Trp Tyr Leu Met His
1               5

<210> SEQ ID NO 82
<211> LENGTH: 17
<212> TYPE: PRT
<213> ORGANISM: Homo sapiens

<400> SEQUENCE: 82

Ser Ile Val Pro Ser Gly Gly Thr Thr Val Tyr Ala Asp Ser Val Lys
1               5                   10                  15

Gly

<210> SEQ ID NO 83
<211> LENGTH: 9
<212> TYPE: PRT
<213> ORGANISM: Homo sapiens

<400> SEQUENCE: 83

Asp Leu Trp Phe Gly Glu Trp Asp Tyr
1               5

<210> SEQ ID NO 84
<211> LENGTH: 5
<212> TYPE: PRT
<213> ORGANISM: Homo sapiens

<400> SEQUENCE: 84

Trp Tyr Ser Met Val
1               5

<210> SEQ ID NO 85
<211> LENGTH: 17
<212> TYPE: PRT
<213> ORGANISM: Homo sapiens

<400> SEQUENCE: 85

Ser Ile Gly Pro Ser Gly Gly Met Thr Arg Tyr Ala Asp Ser Val Lys
1               5                   10                  15

Gly

<210> SEQ ID NO 86
<211> LENGTH: 13
<212> TYPE: PRT
<213> ORGANISM: Homo sapiens

<400> SEQUENCE: 86

Asp Gln Gly Ile Thr Met Val Gln Gly Ala Met Gly Tyr
1               5                   10

<210> SEQ ID NO 87
<211> LENGTH: 5
<212> TYPE: PRT

<213> ORGANISM: Homo sapiens

<400> SEQUENCE: 87

Val Tyr Ser Met Ala
1               5

<210> SEQ ID NO 88
<211> LENGTH: 17
<212> TYPE: PRT
<213> ORGANISM: Homo sapiens

<400> SEQUENCE: 88

Gly Ile Trp Pro Ser Gly Gly Pro Thr Ala Tyr Ala Asp Ser Val Lys
1               5                   10                  15

Gly

<210> SEQ ID NO 89
<211> LENGTH: 10
<212> TYPE: PRT
<213> ORGANISM: Homo sapiens

<400> SEQUENCE: 89

Glu Asp Phe Trp Ser Gly Leu Glu Asp Val
1               5                   10

<210> SEQ ID NO 90
<211> LENGTH: 13
<212> TYPE: PRT
<213> ORGANISM: Homo sapiens

<400> SEQUENCE: 90

Ser Gly Ser Ser Ser Asn Ile Gly Ser Glu Tyr Val Tyr
1               5                   10

<210> SEQ ID NO 91
<211> LENGTH: 7
<212> TYPE: PRT
<213> ORGANISM: Homo sapiens

<400> SEQUENCE: 91

Arg Asn Asp Gln Arg Pro Ser
1               5

<210> SEQ ID NO 92
<211> LENGTH: 11
<212> TYPE: PRT
<213> ORGANISM: Homo sapiens

<400> SEQUENCE: 92

Ala Ala Trp Asp Asp Ser Leu Pro Gly Trp Cys
1               5                   10

<210> SEQ ID NO 93
<211> LENGTH: 13
<212> TYPE: PRT
<213> ORGANISM: Homo sapiens

<400> SEQUENCE: 93

Ser Gly Ser Ser Ser Asn Ile Gly Ser Asn Thr Val Asn
1               5                   10

<210> SEQ ID NO 94
<211> LENGTH: 7
<212> TYPE: PRT
<213> ORGANISM: Homo sapiens

<400> SEQUENCE: 94

Asn Asn Asn Gln Arg Pro Ser
1               5

<210> SEQ ID NO 95
<211> LENGTH: 11
<212> TYPE: PRT
<213> ORGANISM: Homo sapiens

<400> SEQUENCE: 95

Ala Ala Trp His Asp Gly Leu Asn Gly Pro Val
1               5                   10

<210> SEQ ID NO 96
<211> LENGTH: 11
<212> TYPE: PRT
<213> ORGANISM: Homo sapiens

<400> SEQUENCE: 96

Lys Ala Ser Gln Ser Val Arg Ala Phe Ile Ala
1               5                   10

<210> SEQ ID NO 97
<211> LENGTH: 7
<212> TYPE: PRT
<213> ORGANISM: Homo sapiens

<400> SEQUENCE: 97

Gly Ala Ser Asn Arg Ala Thr
1               5

<210> SEQ ID NO 98
<211> LENGTH: 9
<212> TYPE: PRT
<213> ORGANISM: Homo sapiens

<400> SEQUENCE: 98

Gln Gln Tyr Gly Ser Ser Arg Tyr Thr
1               5

<210> SEQ ID NO 99
<211> LENGTH: 16
<212> TYPE: PRT
<213> ORGANISM: Homo sapiens

<400> SEQUENCE: 99

Arg Ser Ser Gln Ser Leu Leu His Ser Ser Gly Tyr Asn Tyr Leu Asp
1               5                   10                  15

<210> SEQ ID NO 100
<211> LENGTH: 7
<212> TYPE: PRT
<213> ORGANISM: Homo sapiens

<400> SEQUENCE: 100

Leu Gly Ser Asn Arg Ala Ser
1               5

<210> SEQ ID NO 101
<211> LENGTH: 8
<212> TYPE: PRT
<213> ORGANISM: Homo sapiens

<400> SEQUENCE: 101

```
Met Gln Ala Leu Gln Thr Pro Thr
1               5

<210> SEQ ID NO 102
<211> LENGTH: 11
<212> TYPE: PRT
<213> ORGANISM: Homo sapiens

<400> SEQUENCE: 102

Arg Ala Ser Gln Ser Val Ser Ser Asn Leu Ala
1               5                   10

<210> SEQ ID NO 103
<211> LENGTH: 7
<212> TYPE: PRT
<213> ORGANISM: Homo sapiens

<400> SEQUENCE: 103

Gly Ala Ser Thr Arg Ala Thr
1               5

<210> SEQ ID NO 104
<211> LENGTH: 9
<212> TYPE: PRT
<213> ORGANISM: Homo sapiens

<400> SEQUENCE: 104

Gln Gln Tyr Ala Gly His Pro Ile Thr
1               5

<210> SEQ ID NO 105
<211> LENGTH: 8
<212> TYPE: PRT
<213> ORGANISM: Homo sapiens

<400> SEQUENCE: 105

Thr Gly Ala Thr Arg Asp Val Ser
1               5

<210> SEQ ID NO 106
<211> LENGTH: 8
<212> TYPE: PRT
<213> ORGANISM: Homo sapiens

<400> SEQUENCE: 106

Tyr Glu Val Ser Ser Arg Pro Ser
1               5

<210> SEQ ID NO 107
<211> LENGTH: 11
<212> TYPE: PRT
<213> ORGANISM: Homo sapiens

<400> SEQUENCE: 107

Ser Ser Thr Thr Ser Arg Ala Pro Arg Val Val
1               5                   10

<210> SEQ ID NO 108
<211> LENGTH: 16
<212> TYPE: PRT
<213> ORGANISM: Homo sapiens

<400> SEQUENCE: 108

Arg Ser Ser Gln Ser Leu Met His Arg Asn Gly His His Phe Phe Asp
1               5                   10                  15
```

```
<210> SEQ ID NO 109
<211> LENGTH: 7
<212> TYPE: PRT
<213> ORGANISM: Homo sapiens

<400> SEQUENCE: 109

Trp Ala Ser Asn Arg Ala Pro
1               5

<210> SEQ ID NO 110
<211> LENGTH: 9
<212> TYPE: PRT
<213> ORGANISM: Homo sapiens

<400> SEQUENCE: 110

Met Gln Ala Leu Gln Thr Pro Tyr Thr
1               5

<210> SEQ ID NO 111
<211> LENGTH: 11
<212> TYPE: PRT
<213> ORGANISM: Homo sapiens

<400> SEQUENCE: 111

Gln Ala Ser Gln Asn Ile Asp Asn Tyr Leu Asn
1               5                   10

<210> SEQ ID NO 112
<211> LENGTH: 7
<212> TYPE: PRT
<213> ORGANISM: Homo sapiens

<400> SEQUENCE: 112

Ala Ala Ser Ser Leu Gln Ser
1               5

<210> SEQ ID NO 113
<211> LENGTH: 9
<212> TYPE: PRT
<213> ORGANISM: Homo sapiens

<400> SEQUENCE: 113

Gln Gln Ser Tyr Ser Thr Pro Arg Thr
1               5

<210> SEQ ID NO 114
<211> LENGTH: 13
<212> TYPE: PRT
<213> ORGANISM: Homo sapiens

<400> SEQUENCE: 114

Ser Gly Ser Ser Ser Asn Ile Gly Ser Asn Tyr Val Tyr
1               5                   10

<210> SEQ ID NO 115
<211> LENGTH: 7
<212> TYPE: PRT
<213> ORGANISM: Homo sapiens

<400> SEQUENCE: 115

Arg Asn Asn Gln Arg Pro Ser
1               5

<210> SEQ ID NO 116
<211> LENGTH: 11
```

<212> TYPE: PRT
<213> ORGANISM: Homo sapiens

<400> SEQUENCE: 116

Ala Ala Trp Asp Asp Ser Leu Asn Ala Trp Val
1               5                   10

<210> SEQ ID NO 117
<211> LENGTH: 16
<212> TYPE: PRT
<213> ORGANISM: Homo sapiens

<400> SEQUENCE: 117

Lys Ser Ser Gln Ser Leu Leu His Ser Asn Gly Tyr Asn Tyr Leu Asp
1               5                   10                  15

<210> SEQ ID NO 118
<211> LENGTH: 7
<212> TYPE: PRT
<213> ORGANISM: Homo sapiens

<400> SEQUENCE: 118

Leu Gly Ser Asn Arg Ala Ser
1               5

<210> SEQ ID NO 119
<211> LENGTH: 8
<212> TYPE: PRT
<213> ORGANISM: Homo sapiens

<400> SEQUENCE: 119

Met Gln Ala Leu Gln Thr Ile Thr
1               5

<210> SEQ ID NO 120
<211> LENGTH: 11
<212> TYPE: PRT
<213> ORGANISM: Homo sapiens

<400> SEQUENCE: 120

Arg Ala Ser Gln Ser Ile Ser Arg Trp Leu Ala
1               5                   10

<210> SEQ ID NO 121
<211> LENGTH: 7
<212> TYPE: PRT
<213> ORGANISM: Homo sapiens

<400> SEQUENCE: 121

Ala Ala Ser Ser Leu Gln Ser
1               5

<210> SEQ ID NO 122
<211> LENGTH: 9
<212> TYPE: PRT
<213> ORGANISM: Homo sapiens

<400> SEQUENCE: 122

Gln Gln Ser Tyr Ser Thr Pro Leu Thr
1               5

<210> SEQ ID NO 123
<211> LENGTH: 11
<212> TYPE: PRT
<213> ORGANISM: Homo sapiens

```
<400> SEQUENCE: 123

Ala Gly Asp Glu Leu Gly Asn Lys Tyr Ala Ser
1               5                   10

<210> SEQ ID NO 124
<211> LENGTH: 7
<212> TYPE: PRT
<213> ORGANISM: Homo sapiens

<400> SEQUENCE: 124

Gln Asp Arg Lys Arg Pro Ser
1               5

<210> SEQ ID NO 125
<211> LENGTH: 9
<212> TYPE: PRT
<213> ORGANISM: Homo sapiens

<400> SEQUENCE: 125

Gln Ser Trp Asp Ser Ser Ser Val Ile
1               5

<210> SEQ ID NO 126
<211> LENGTH: 11
<212> TYPE: PRT
<213> ORGANISM: Homo sapiens

<400> SEQUENCE: 126

Arg Ala Ser Gln Ser Ile Ser Ser Tyr Leu Asn
1               5                   10

<210> SEQ ID NO 127
<211> LENGTH: 7
<212> TYPE: PRT
<213> ORGANISM: Homo sapiens

<400> SEQUENCE: 127

Ala Ala Ser Ser Leu Gln Ser
1               5

<210> SEQ ID NO 128
<211> LENGTH: 9
<212> TYPE: PRT
<213> ORGANISM: Homo sapiens

<400> SEQUENCE: 128

Gln Gln Ala Asn Ser Phe Pro Leu Thr
1               5

<210> SEQ ID NO 129
<211> LENGTH: 14
<212> TYPE: PRT
<213> ORGANISM: Homo sapiens

<400> SEQUENCE: 129

Thr Gly Thr Ser Ser Asp Val Gly Gly Tyr Asn Tyr Val Ser
1               5                   10

<210> SEQ ID NO 130
<211> LENGTH: 7
<212> TYPE: PRT
<213> ORGANISM: Homo sapiens

<400> SEQUENCE: 130

Glu Val Asn Lys Arg Pro Ser
```

```
<210> SEQ ID NO 131
<211> LENGTH: 10
<212> TYPE: PRT
<213> ORGANISM: Homo sapiens

<400> SEQUENCE: 131

Ser Ser Tyr Ala Gly Arg Asn Phe Val Val
1               5                   10

<210> SEQ ID NO 132
<211> LENGTH: 11
<212> TYPE: PRT
<213> ORGANISM: Homo sapiens

<400> SEQUENCE: 132

Gly Gly Asn Asn Ile Gly Thr Lys Ile Val Asn
1               5                   10

<210> SEQ ID NO 133
<211> LENGTH: 7
<212> TYPE: PRT
<213> ORGANISM: Homo sapiens

<400> SEQUENCE: 133

Asp Asn Ser Asp Arg Pro Ser
1               5

<210> SEQ ID NO 134
<211> LENGTH: 11
<212> TYPE: PRT
<213> ORGANISM: Homo sapiens

<400> SEQUENCE: 134

Gln Leu Trp Asp Ser Ser Ser Asp His Pro Ile
1               5                   10

<210> SEQ ID NO 135
<211> LENGTH: 123
<212> TYPE: PRT
<213> ORGANISM: Homo sapiens

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
                20                  25                  30

Gly Met Val Trp Val Arg Gln Ala Pro Gly Lys Gly Leu Glu Trp Val
            35                  40                  45

Ser Ser Ile Ser Pro Ser Gly Gly Tyr Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Arg Arg Pro His Tyr Gly Ser Gly Arg Trp Ala Tyr
                100                 105                 110

Trp Gly Gln Gly Thr Leu Val Thr Val Ser Ser
            115                 120

<210> SEQ ID NO 136
```

```
<211> LENGTH: 118
<212> TYPE: PRT
<213> ORGANISM: Homo sapiens

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Leu Met Met Trp Val Arg Gln Ala Pro Gly Lys Gly Leu Glu Trp Val
        35                  40                  45

Ser Val Ile Ser Pro Ser Gly Arg Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Ser Ile Ala Ala Ala Gly Thr Asp Tyr Trp Gly Gln Gly Thr
            100                 105                 110

Leu Val Thr Val Ser Ser
        115

<210> SEQ ID NO 137
<211> LENGTH: 113
<212> TYPE: PRT
<213> ORGANISM: Homo sapiens

<400> SEQUENCE: 137

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Phe Met Ile Trp Val Arg Gln Ala Pro Gly Lys Gly Leu Glu Trp Val
        35                  40                  45

Ser Trp Ile Ser Pro Ser Gly Gly Thr Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Gly Tyr Trp Gly Gln Gly Thr Leu Val Thr Val Ser
            100                 105                 110

Ser

<210> SEQ ID NO 138
<211> LENGTH: 119
<212> TYPE: PRT
<213> ORGANISM: Homo sapiens

<400> SEQUENCE: 138

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Tyr Met Gly Trp Val Arg Gln Ala Pro Gly Lys Gly Leu Glu Trp Val
        35                  40                  45

Ser Val Ile Arg Pro Ser Gly Gly Lys Thr Lys Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Pro His Gly Gln Gly Gly Val Asp Ser Trp Gly Gln Gly
            100                 105                 110

Thr Leu Val Thr Val Ser Ser
        115
```

<210> SEQ ID NO 139
<211> LENGTH: 126
<212> TYPE: PRT
<213> ORGANISM: Homo sapiens

<400> SEQUENCE: 139

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Phe Met Thr Trp Val Arg Gln Ala Pro Gly Lys Gly Leu Glu Trp Val
        35                  40                  45

Ser Ser Ile Arg Pro Ser Gly Gly Lys Thr Arg Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Ser Arg Tyr Tyr Asn Asn Gly Ala Tyr Arg Leu Asp Ala
            100                 105                 110

Phe Asp Ile Trp Gly Pro Gly Thr Val Val Thr Val Ser Ser
        115                 120                 125
```

<210> SEQ ID NO 140
<211> LENGTH: 118
<212> TYPE: PRT
<213> ORGANISM: Homo sapiens

<400> SEQUENCE: 140

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Arg Met Ala Trp Val Arg Gln Ala Pro Gly Lys Gly Leu Glu Trp Val
        35                  40                  45

Ser Tyr Ile Ser Ser Ser Gly Gly Val Thr Ser Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
                 85                  90                  95

Ala Arg Gly Thr His Leu Pro Gly Val Asp Tyr Trp Gly Gln Gly Thr
            100                 105                 110

Leu Val Thr Val Ser Ser
        115
```

<210> SEQ ID NO 141
<211> LENGTH: 113

```
<212> TYPE: PRT
<213> ORGANISM: Homo sapiens

<400> SEQUENCE: 141

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ile Met Ala Trp Val Arg Gln Ala Pro Gly Lys Gly Leu Glu Trp Val
        35                  40                  45

Ser Gly Ile Gly Ser Ser Gly Gly Leu Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Gly Tyr Trp Gly Gln Gly Thr Leu Val Thr Val Ser
            100                 105                 110

Ser

<210> SEQ ID NO 142
<211> LENGTH: 129
<212> TYPE: PRT
<213> ORGANISM: Homo sapiens

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Val Trp Val Arg Gln Ala Pro Gly Lys Gly Leu Glu Trp Val
        35                  40                  45

Ser Gly Ile Trp Ser Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ser Ala Gly Val Val Lys Gly Pro Ala Arg Tyr Tyr
            100                 105                 110

Tyr Tyr Tyr Met Asp Val Trp Gly Lys Gly Thr Thr Val Thr Val Ser
        115                 120                 125

Ser

<210> SEQ ID NO 143
<211> LENGTH: 126
<212> TYPE: PRT
<213> ORGANISM: Homo sapiens

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Gln Met Thr Trp Val Arg Gln Ala Pro Gly Lys Gly Leu Glu Trp Val
        35                  40                  45

Ser Val Ile Ser Ser Ser Gly Gly Asp Thr Ala Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Asp Arg Gly Tyr Cys Ser Gly Asn Thr Cys Tyr Ile Asp Ala
                100                 105                 110

Phe Asp Ile Trp Gly Gln Gly Thr Met Val Thr Val Ser Ser
                115                 120                 125

<210> SEQ ID NO 144
<211> LENGTH: 119
<212> TYPE: PRT
<213> ORGANISM: Homo sapiens

<400> SEQUENCE: 144

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Pro Tyr
                20                  25                  30

Trp Met Phe Trp Val Arg Gln Ala Pro Gly Lys Gly Leu Glu Trp Val
            35                  40                  45

Ser Gly Ile Val Ser Ser Gly Gly Met Thr Gly Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Val Gly Met Ser Thr Tyr Ala Phe Asp Ile Trp Gly Gln Gly
                100                 105                 110

Thr Met Val Thr Val Ser Ser
            115

<210> SEQ ID NO 145
<211> LENGTH: 118
<212> TYPE: PRT
<213> ORGANISM: Homo sapiens

<400> SEQUENCE: 145

Glu Val Gln Leu Leu Glu Ser Gly Gly Gly Leu Val Gln Leu Gly Gly
 1               5                  10                  15

Ser Leu Arg Leu Ser Cys Ala Ala Ser Gly Phe Thr Phe Ser His Tyr
                20                  25                  30

Gly Met Ser Trp Val Arg Gln Ala Pro Gly Lys Gly Leu Glu Trp Val
            35                  40                  45

Ser Ser Ile Arg Ser Ser Gly Gly Arg Thr Trp Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Gly Ser Leu Ser Ser Gly Trp Asp Tyr Trp Gly Gln Gly Thr
                100                 105                 110

Leu Val Thr Val Ser Ser
            115

<210> SEQ ID NO 146
```

```
<211> LENGTH: 113
<212> TYPE: PRT
<213> ORGANISM: Homo sapiens

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Arg Met Glu Trp Val Arg Gln Ala Pro Gly Lys Gly Leu Glu Trp Val
        35                  40                  45

Ser Ser Ile Trp Ser Ser Gly Leu Thr Lys Glu Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Tyr Arg Trp Gly Gln Gly Thr Leu Val Thr Val Ser
            100                 105                 110

Ser

<210> SEQ ID NO 147
<211> LENGTH: 118
<212> TYPE: PRT
<213> ORGANISM: Homo sapiens

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Leu Met His Trp Val Arg Gln Ala Pro Gly Lys Gly Leu Glu Trp Val
        35                  40                  45

Ser Ser Ile Val Pro Ser Gly Gly Thr Thr Val Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Phe Gly Glu Trp Asp Tyr Trp Gly Gln Gly Thr
            100                 105                 110

Leu Val Thr Val Ser Ser
        115

<210> SEQ ID NO 148
<211> LENGTH: 122
<212> TYPE: PRT
<213> ORGANISM: Homo sapiens

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Val Trp Val Arg Gln Ala Pro Gly Lys Gly Leu Glu Trp Val
        35                  40                  45

Ser Ser Ile Gly Pro Ser Gly Gly Met Thr Arg Tyr Ala Asp Ser Val
50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Gly Ile Thr Met Val Gln Gly Ala Met Gly Tyr Trp
            100                 105                 110

Gly Gln Gly Thr Leu Val Thr Val Ser Ser
        115                 120

<210> SEQ ID NO 149
<211> LENGTH: 119
<212> TYPE: PRT
<213> ORGANISM: Homo sapiens

<400> SEQUENCE: 149

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Val Tyr
                20                  25                  30

Ser Met Ala Trp Val Arg Gln Ala Pro Gly Lys Gly Leu Glu Trp Val
            35                  40                  45

Ser Gly Ile Trp Pro Ser Gly Gly Pro Thr Ala Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asp Phe Trp Ser Gly Leu Glu Asp Val Trp Gly Lys Gly
            100                 105                 110

Thr Thr Val Thr Val Ser Ser
        115

<210> SEQ ID NO 150
<211> LENGTH: 110
<212> TYPE: PRT
<213> ORGANISM: Homo sapiens

<400> SEQUENCE: 150

Gln Tyr Glu Leu Thr Gln Pro Pro Ser Val Ser Gly Thr Pro Gly Gln
 1               5                  10                  15

Arg Val Thr Ile Ser Cys Ser Gly Ser Ser Ser Asn Ile Gly Ser Glu
                20                  25                  30

Tyr Val Tyr Trp Phe Gln Gln Leu Pro Gly Thr Ala Pro Arg Leu Leu
            35                  40                  45

Ile Tyr Arg Asn Asp Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Pro Gly Trp Cys Phe Gly Gly Gly Thr Lys Leu Thr Val Leu
            100                 105                 110

<210> SEQ ID NO 151
<211> LENGTH: 110
<212> TYPE: PRT
<213> ORGANISM: Homo sapiens
```

```
<400> SEQUENCE: 151

Gln Ser Glu Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Asn Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp His Asp Gly Leu
                85                  90                  95

Asn Gly Pro Val Phe Gly Gly Gly Thr Lys Leu Thr Val Leu
            100                 105                 110

<210> SEQ ID NO 152
<211> LENGTH: 108
<212> TYPE: PRT
<213> ORGANISM: Homo sapiens

<400> SEQUENCE: 152

Gln Asp Ile Gln Met Thr Gln Ser Pro Ala Thr Leu Ser Leu Ser Pro
 1               5                  10                  15

Gly Glu Arg Ala Thr Leu Ser Cys Lys Ala Ser Gln Ser Val Arg Ala
            20                  25                  30

Phe Ile Ala Trp Tyr Gln Gln Lys Pro Gly Gln Ala Pro Arg Leu Leu
            35                  40                  45

Ile Ser Gly Ala Ser Asn Arg Ala Thr Gly Ile Pro Asp Arg Phe Ser
 50                  55                  60

Gly Gly Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Arg
                85                  90                  95

Tyr Thr Phe Gly Gln Gly Thr Lys Leu Glu Ile Lys
            100                 105

<210> SEQ ID NO 153
<211> LENGTH: 112
<212> TYPE: PRT
<213> ORGANISM: Homo sapiens

<400> SEQUENCE: 153

Gln Asp Ile Gln Met Thr Gln Ser Pro Ser Ser Leu Pro Val Thr Pro
 1               5                  10                  15

Gly Glu Pro Ala Ser Ile Ser Cys Arg Ser Ser Gln Ser Leu Leu His
            20                  25                  30

Ser Ser Gly Tyr Asn Tyr Leu Asp Trp Tyr Leu Gln Lys Pro Gly Gln
            35                  40                  45

Ser Pro Gln Leu Leu Ile Tyr Leu Gly Ser Asn Arg Ala Ser Gly Val
 50                  55                  60

Pro Asp Arg Phe Thr Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                85                  90                  95

Ala Leu Gln Thr Pro Thr Phe Gly Gly Gly Thr Lys Val Asp Ile Lys
            100                 105                 110
```

<210> SEQ ID NO 154
<211> LENGTH: 108
<212> TYPE: PRT
<213> ORGANISM: Homo sapiens

<400> SEQUENCE: 154

Gln Asp Ile Gln Met Thr Gln Ser Pro Ala Thr Leu Ser Val Ser Pro
1               5                   10                  15

Gly Glu Arg Ala Thr Leu Ser Cys Arg Ala Ser Gln Ser Val Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Thr Arg Ala Thr Gly Val Pro Ala Arg Phe Ser
50                  55                  60

Gly Ser Gly Ser Gly Thr Asp Phe Thr Leu Ser Ile Ser Ser Leu Gln
65                  70                  75                  80

Pro Glu Asp Phe Ala Thr Tyr Tyr Cys Gln Gln Tyr Ala Gly His Pro
                85                  90                  95

Ile Thr Phe Gly Gln Gly Thr Arg Leu Glu Ile Lys
            100                 105

<210> SEQ ID NO 155
<211> LENGTH: 105
<212> TYPE: PRT
<213> ORGANISM: Homo sapiens

<400> SEQUENCE: 155

Gln Ser Glu Leu Thr Gln Ala Ala Ser Val Ser Gly Ser Pro Gly Gln
1               5                   10                  15

Ser Ile Thr Leu Ser Cys Thr Gly Ala Thr Arg Asp Val Ser Trp Tyr
            20                  25                  30

Gln Gln His Pro Gly Lys Ala Pro Lys Leu Val Leu Tyr Glu Val Ser
        35                  40                  45

Ser Arg Pro Ser Gly Val Ser Asp Arg Phe Ser Gly Ser Met Ser Gly
50                  55                  60

Asn Thr Ala Ser Leu Thr Ile Ser Gly Leu Gln Ala Glu Asp Glu Ala
65                  70                  75                  80

Asp Tyr Tyr Cys Ser Ser Thr Ser Arg Ala Pro Arg Val Val Phe
                85                  90                  95

Gly Gly Gly Thr Lys Leu Thr Val Leu
            100                 105

<210> SEQ ID NO 156
<211> LENGTH: 113
<212> TYPE: PRT
<213> ORGANISM: Homo sapiens

<400> SEQUENCE: 156

Gln Asp Ile Gln Met Thr Gln Ser Pro Leu Ser Leu Pro Val Thr Pro
1               5                   10                  15

Gly Glu Pro Ala Ser Ile Ser Cys Arg Ser Ser Gln Ser Leu Met His
            20                  25                  30

Arg Asn Gly His His Phe Phe Asp Trp Tyr Leu Gln Lys Pro Gly Gln
        35                  40                  45

Ser Pro Gln Leu Leu Ile Tyr Trp Ala Ser Asn Arg Ala Pro Gly Val
50                  55                  60

Pro Asp Arg Phe Ser Gly Ser Gly Ser Gly Thr Asp Phe Thr Leu Lys

```
                65                  70                  75                  80
Ile Ser Arg Val Glu Ala Glu Asp Val Gly Ile Tyr Tyr Cys Met Gln
                    85                  90                  95
Ala Leu Gln Thr Pro Tyr Thr Phe Gly Gln Gly Thr Lys Leu Glu Ile
                    100                 105                 110
Lys

<210> SEQ ID NO 157
<211> LENGTH: 108
<212> TYPE: PRT
<213> ORGANISM: Homo sapiens

<400> SEQUENCE: 157

Gln Asp Ile Gln Met Thr Gln Ser Pro Ser Ser Leu Ser Ala Ser Ile
1               5                   10                  15

Gly Asp Arg Val Thr Ile Ser Cys Gln Ala Ser Gln Asn Ile Asp Asn
                20                  25                  30

Tyr Leu Asn Trp Tyr Gln Gln Lys Pro Gly Lys Ala Pro Lys Leu Leu
            35                  40                  45

Ile Tyr Ala Ala Ser Ser Leu Gln Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Arg Thr Phe Gly Gln Gly Thr Lys Val Glu Ile Lys
                100                 105

<210> SEQ ID NO 158
<211> LENGTH: 110
<212> TYPE: PRT
<213> ORGANISM: Homo sapiens

<400> SEQUENCE: 158

Gln Ser Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Ala Trp Val Phe Gly Gly Gly Thr Lys Leu Thr Val Leu
                100                 105                 110

<210> SEQ ID NO 159
<211> LENGTH: 112
<212> TYPE: PRT
<213> ORGANISM: Homo sapiens

<400> SEQUENCE: 159

Gln Asp Ile Gln Met Thr Gln Ser Pro Leu Ser Leu Pro Val Thr Pro
1               5                   10                  15

Gly Glu Pro Ala Ser Ile Ser Cys Lys Ser Ser Gln Ser Leu Leu His
```

-continued

```
                20                  25                  30
Ser Asn Gly Tyr Asn Tyr Leu Asp Trp Tyr Leu Gln Lys Pro Gly Gln
        35                  40                  45
Ser Pro Gln Leu Leu Ile Ser Leu Gly Ser Asn Arg Ala Ser Gly Val
    50                  55                  60
Pro Ala Arg Phe Ser Gly Ser Gly Ser Gly Thr Asp Phe Thr Leu Lys
65                  70                  75                  80
Ile Ser Arg Val Glu Ala Glu Asp Val Gly Val Tyr Tyr Cys Met Gln
                85                  90                  95
Ala Leu Gln Thr Ile Thr Phe Gly Gln Gly Thr Arg Leu Glu Ile Lys
            100                 105                 110

<210> SEQ ID NO 160
<211> LENGTH: 108
<212> TYPE: PRT
<213> ORGANISM: Homo sapiens

<400> SEQUENCE: 160

Gln Asp Ile Gln Met Thr Gln Ser Pro Ser Thr Leu Ser Ala Ser Val
1               5                   10                  15
Gly Asp Arg Val Thr Ile Thr Cys Arg Ala Ser Gln Ser Ile Ser Arg
            20                  25                  30
Trp Leu Ala Trp Tyr Gln Gln Lys Pro Gly Lys Ala Pro Lys Leu Leu
        35                  40                  45
Ile Tyr Ala Ala Ser Ser Leu Gln Ser Gly Val Pro Ser Arg Phe Ser
    50                  55                  60
Gly Ser Gly Ser Gly Thr Asp Phe Thr Leu Thr Ile Ser Ser Leu Gln
65                  70                  75                  80
Pro Glu Asp Phe Ala Thr Tyr Tyr Cys Gln Gln Ser Tyr Ser Thr Pro
                85                  90                  95
Leu Thr Phe Gly Gly Gly Thr Lys Val Glu Ile Lys
            100                 105

<210> SEQ ID NO 161
<211> LENGTH: 106
<212> TYPE: PRT
<213> ORGANISM: Homo sapiens

<400> SEQUENCE: 161

Gln Ser Ala Leu Thr Gln Pro Pro Ser Val Ser Val Ser Pro Gly Gln
1               5                   10                  15
Thr Ala Ser Ile Thr Cys Ala Gly Asp Glu Leu Gly Asn Lys Tyr Ala
            20                  25                  30
Ser Trp Tyr Gln Gln Lys Pro Gly Gln Ser Pro Val Leu Val Ile Tyr
        35                  40                  45
Gln Asp Arg Lys Arg Pro Ser Gly Ile Pro Glu Arg Phe Ser Gly Ser
    50                  55                  60
His Ser Gly Asn Thr Ala Thr Leu Thr Ile Ser Gly Thr Gln Ala Leu
65                  70                  75                  80
Asp Glu Ala Asp Tyr Tyr Cys Gln Ser Trp Asp Ser Ser Ser Val Ile
                85                  90                  95
Phe Gly Gly Gly Thr Lys Val Thr Val Leu
            100                 105

<210> SEQ ID NO 162
<211> LENGTH: 108
<212> TYPE: PRT
<213> ORGANISM: Homo sapiens
```

```
<400> SEQUENCE: 162

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Glu Phe Ser Leu Ser Ile Ser Ser Leu Gln
65                  70                  75                  80

Pro Glu Asp Phe Ala Thr Tyr Tyr Cys Gln Gln Ala Asn Ser Phe Pro
            85                  90                  95

Leu Thr Phe Gly Gly Gly Thr Lys Val Glu Ile Lys
            100                 105

<210> SEQ ID NO 163
<211> LENGTH: 110
<212> TYPE: PRT
<213> ORGANISM: Homo sapiens

<400> SEQUENCE: 163

Gln Tyr Glu Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Phe
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Arg
            85                  90                  95

Asn Phe Val Val Phe Gly Gly Gly Thr Lys Leu Thr Val Leu
            100                 105                 110

<210> SEQ ID NO 164
<211> LENGTH: 108
<212> TYPE: PRT
<213> ORGANISM: Homo sapiens

<400> SEQUENCE: 164

Gln Ser Ala Leu Thr Gln Pro Pro Ser Val Ser Val Ala Pro Gly Gln
1               5                   10                  15

Thr Ala Arg Ile Thr Cys Gly Gly Asn Asn Ile Gly Thr Lys Ile Val
            20                  25                  30

Asn Trp Tyr Gln Gln Arg Pro Gly Gln Ala Pro Val Val Val Val Tyr
        35                  40                  45

Asp Asn Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Leu Trp Asp Ser Ser Ser Asp His
            85                  90                  95

Pro Ile Phe Gly Thr Gly Thr Lys Val Thr Val Leu
```

```
                    100                 105

<210> SEQ ID NO 165
<211> LENGTH: 317
<212> TYPE: PRT
<213> ORGANISM: Homo sapiens

<400> SEQUENCE: 165

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Arg Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315

<210> SEQ ID NO 166
<211> LENGTH: 317
<212> TYPE: PRT
<213> ORGANISM: Homo sapiens

<400> SEQUENCE: 166

Met Lys Val Leu Trp Ala Ala Leu Leu Val Thr Phe Leu Ala Gly Cys
1               5                   10                  15
```

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315

<210> SEQ ID NO 167
<211> LENGTH: 317
<212> TYPE: PRT
<213> ORGANISM: Homo sapiens

<400> SEQUENCE: 167

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

```
Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Cys
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315

<210> SEQ ID NO 168
<211> LENGTH: 299
<212> TYPE: PRT
<213> ORGANISM: Homo sapiens

<400> SEQUENCE: 168

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
    50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Arg
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
    130                 135                 140
```

```
Arg Lys Arg Leu Leu Arg Asp Ala Asp Leu Gln Lys Arg Leu Ala
145                 150                 155                 160

Val Tyr Gln Ala Gly Ala Arg Glu Gly Ala Glu Arg Gly Leu Ser Ala
            165                 170                 175

Ile Arg Glu Arg Leu Gly Pro Leu Val Glu Gln Gly Arg Val Arg Ala
                180                 185                 190

Ala Thr Val Gly Ser Leu Ala Gly Gln Pro Leu Gln Glu Arg Ala Gln
            195                 200                 205

Ala Trp Gly Glu Arg Leu Arg Ala Arg Met Glu Glu Met Gly Ser Arg
            210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
                260                 265                 270

Gln Arg Gln Trp Ala Gly Leu Val Glu Lys Val Gln Ala Ala Val Gly
            275                 280                 285

Thr Ser Ala Ala Pro Val Pro Ser Asp Asn His
    290                 295
```

<210> SEQ ID NO 169
<211> LENGTH: 299
<212> TYPE: PRT
<213> ORGANISM: Homo sapiens

<400> SEQUENCE: 169

```
Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
            35                  40                  45

Glu Glu Leu Leu Ser Ser Gln Val Thr Gln Glu Leu Arg Ala Leu Met
50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
            115                 120                 125

Ser Thr Glu Glu Leu Arg Val Arg Leu Ala Ser His Leu Arg Lys Leu
130                 135                 140

Arg Lys Arg Leu Leu Arg Asp Ala Asp Leu Gln Lys Arg Leu Ala
145                 150                 155                 160

Val Tyr Gln Ala Gly Ala Arg Glu Gly Ala Glu Arg Gly Leu Ser Ala
            165                 170                 175

Ile Arg Glu Arg Leu Gly Pro Leu Val Glu Gln Gly Arg Val Arg Ala
                180                 185                 190

Ala Thr Val Gly Ser Leu Ala Gly Gln Pro Leu Gln Glu Arg Ala Gln
            195                 200                 205

Ala Trp Gly Glu Arg Leu Arg Ala Arg Met Glu Glu Met Gly Ser Arg
            210                 215                 220
```

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
            245                 250                 255

Phe Gln Ala Arg Leu Lys Ser Trp Phe Glu Pro Leu Val Glu Asp Met
        260                 265                 270

Gln Arg Gln Trp Ala Gly Leu Val Glu Lys Val Gln Ala Ala Val Gly
    275                 280                 285

Thr Ser Ala Ala Pro Val Pro Ser Asp Asn His
290                 295

<210> SEQ ID NO 170
<211> LENGTH: 299
<212> TYPE: PRT
<213> ORGANISM: Homo sapiens

<400> SEQUENCE: 170

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
    50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
            85                  90                  95

Leu Gln Ala Ala Gln Ala Arg Leu Gly Ala Asp Met Glu Asp Val Cys
        100                 105                 110

Gly Arg Leu Val Gln Tyr Arg Gly Glu Val Gln Ala Met Leu Gly Gln
    115                 120                 125

Ser Thr Glu Glu Leu Arg Val Arg Leu Ala Ser His Leu Arg Lys Leu
130                 135                 140

Arg Lys Arg Leu Leu Arg Asp Ala Asp Asp Leu Gln Lys Cys Leu Ala
145                 150                 155                 160

Val Tyr Gln Ala Gly Ala Arg Glu Gly Ala Glu Arg Gly Leu Ser Ala
            165                 170                 175

Ile Arg Glu Arg Leu Gly Pro Leu Val Glu Gln Gly Arg Val Arg Ala
        180                 185                 190

Ala Thr Val Gly Ser Leu Ala Gly Gln Pro Leu Gln Glu Arg Ala Gln
    195                 200                 205

Ala Trp Gly Glu Arg Leu Arg Ala Arg Met Glu Glu Met Gly Ser Arg
210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
            245                 250                 255

Phe Gln Ala Arg Leu Lys Ser Trp Phe Glu Pro Leu Val Glu Asp Met
        260                 265                 270

Gln Arg Gln Trp Ala Gly Leu Val Glu Lys Val Gln Ala Ala Val Gly
    275                 280                 285

Thr Ser Ala Ala Pro Val Pro Ser Asp Asn His
290                 295

<210> SEQ ID NO 171
<211> LENGTH: 330
<212> TYPE: DNA
<213> ORGANISM: Homo sapiens

<400> SEQUENCE: 171

| | | | | | |
|---|---|---|---|---|---|
| caagacatcc | agatgaccca | gtctccaggc | accctgtctt | tgtctccagg | ggaaagagcc | 60 |
| accctctcct | gcagggccag | tcagagtatt | ggcagccgct | acttagcctg | gtaccagcag | 120 |
| aaacctggcc | aggctcccag | gctcctcatc | tatgatgcat | ccaagagggc | cactggcgtc | 180 |
| ccagtcaggt | tcagcggcag | tggatctggg | acagacttca | ctctcaccat | cagcagcctg | 240 |
| gggcctgaag | attttgcagt | ttattactgc | caacagggct | acaactggcc | tccgtggacg | 300 |
| ttcggccaag | ggaccaaggt | ggaaatcaaa | | | | 330 |

<210> SEQ ID NO 172
<211> LENGTH: 384
<212> TYPE: DNA
<213> ORGANISM: Homo sapiens

<400> SEQUENCE: 172

| | | | | | |
|---|---|---|---|---|---|
| gaagttcaat | tgttagagtc | tggtggcggt | cttgttcagc | ctggtggttc | tttacgtctt | 60 |
| tcttgcgctg | cttccggatt | cactttctct | tattacgcta | tgcagtgggt | tcgccaagct | 120 |
| cctggtaaag | gtttggagtg | ggtttcttct | ctctatcctt | ctggtggcaa | tacttcttat | 180 |
| gctgactccg | ttaaaggtcg | cttcactatc | tctagagaca | actctaagaa | tactctctac | 240 |
| ttgcagatga | acagcttaag | ggctgaggac | actgcagtct | actattgtgc | gagaggtcgc | 300 |
| gggaattacg | atttttggag | tgcgggctac | tactactact | acatggacgt | ctggggcaaa | 360 |
| gggaccacgg | tcaccgtctc | aagc | | | | 384 |

<210> SEQ ID NO 173
<211> LENGTH: 324
<212> TYPE: DNA
<213> ORGANISM: Homo sapiens

<400> SEQUENCE: 173

| | | | | | |
|---|---|---|---|---|---|
| caagacatcc | agatgaccca | gtctccatcc | tccctgtctg | catctgtagg | agacagagtc | 60 |
| accatcactt | gccgggcaag | tcagcgcata | agaaagaatt | tacattggta | tcagcagaaa | 120 |
| ccagggaaag | cccctaacct | cctgatctat | gatgcatcca | gtaacgaacg | tggggtccca | 180 |
| tcaaggttca | gtggcagagg | atctgggaca | gagttcactc | tcaccatcag | cagtctacaa | 240 |
| cctgaagatc | ttgcaactta | ctactgtcaa | cagagtttca | gtagcccctg | gacgttcggc | 300 |
| caagggacca | aggtggaaat | caaa | | | | 324 |

<210> SEQ ID NO 174
<211> LENGTH: 345
<212> TYPE: DNA
<213> ORGANISM: Homo sapiens

<400> SEQUENCE: 174

| | | | | | |
|---|---|---|---|---|---|
| gaagttcaat | tgttagagtc | tggtggcggt | cttgttcagc | ctggtggttc | tttacgtctt | 60 |
| tcttgcgctg | cttccggatt | cactttctct | aagtactcta | tgcattgggt | tcgccaagct | 120 |
| cctggtaaag | gtttggagtg | ggtttctggt | atctattctt | ctggtggcaa | gactatttat | 180 |
| gctgactccg | ttaaaggtcg | cttcactatc | tctagagaca | accctaagaa | tactctctac | 240 |
| ttgcagatga | acagcttaag | ggctgaggac | actgcagtct | actattgtgc | gagatcgctt | 300 |

```
gatcttgact actggggcca gggaaccctg gtcaccgtct caagc            345
```

<210> SEQ ID NO 175
<211> LENGTH: 324
<212> TYPE: DNA
<213> ORGANISM: Homo sapiens

<400> SEQUENCE: 175

```
caagacatcc agatgaccca gtctccatcc tccctgtctg catctgtagg agacagagtc    60
accatcactt gccggacaag tcaggacatt agaaatcatt taggctggtt tcagcagaaa   120
ccagggaaag cccctcagcg cctgattcgt gaagcatcca ttttacaaag tggggtccca   180
tcaacatttt acggcagtgg atatgggaga gaattcactc tcacaatcag cagcctgcag   240
cctgaggatt ttgcaaccta ttattgtcta caatatgatt ctttcccata cacctttggc   300
caggggacca agctggagat caaa                                          324
```

<210> SEQ ID NO 176
<211> LENGTH: 345
<212> TYPE: DNA
<213> ORGANISM: Homo sapiens

<400> SEQUENCE: 176

```
gaagttcaat tgttagagtc tggtggcggt cttgttcagc ctggtggttc tttacgtctt    60
tcttgcgctg cttccggatt cactttctct atgtacatga tggattgggt tcgccaagct   120
cctggtaaag gtttggagtg gtttcttcct atctggcctt ctggtggcca gacttggtat   180
gctgactccg ttaaaggtcg cttcactatc tctagagaca actctaagaa tactctctac   240
ttgcagatga acagcttaag ggctgaggac actgcagtct actattgtgc gagatccgtc   300
ctccttgact actggggcca gggaaccctg gtcaccgtct caagc                   345
```

<210> SEQ ID NO 177
<211> LENGTH: 330
<212> TYPE: DNA
<213> ORGANISM: Homo sapiens

<400> SEQUENCE: 177

```
cagtacgaat tgactcagcc accctcagtg tctgggaccc ccgggcagag ggtcaccatc    60
tcttgttctg gaagcagttc caacatcgga agtgagtatg tgtactggtt ccagcagctc   120
ccaggaacgg cccccagact cctcatctat aggaatgatc agcggccctc aggggtccct   180
gaccgattct ctggctccaa gtctggcacc tcagcctccc tggccatcag tggcctccag   240
tctgaggatg aggctgatta ttactgtgca gcatgggatg acagcctgcc tggttggtgt   300
tccggcggcg ggaccaagct gaccgtccta                                    330
```

<210> SEQ ID NO 178
<211> LENGTH: 369
<212> TYPE: DNA
<213> ORGANISM: Homo sapiens

<400> SEQUENCE: 178

```
gaagttcaat tgttagagtc tggtggcggt cttgttcagc ctggtggttc tttacgtctt    60
tcttgcgctg cttccggatt cactttctct ttttacggta tggtttgggt tcgccaagct   120
cctggtaaag gtttggagtg gtttcttcct atctctcctt ctggtggcta tactctttat   180
gctgactccg ttaaaggtcg cttcactatc tctagagaca actctaagaa tactctctac   240
ttgcagatga acagcttaag ggctgaggac actgcagtct actattgtgc gaaagatggg   300
```

```
agacggcccc actatggttc ggggaggtgg gcctactggg gccagggaac cctggtcacc    360
gtctcaagc                                                            369

<210> SEQ ID NO 179
<211> LENGTH: 330
<212> TYPE: DNA
<213> ORGANISM: Homo sapiens

<400> SEQUENCE: 179
cagagcgaat tgactcagcc accctcagcg tctgggaccc ccgggcagag ggtcaccatc     60
tcttgttctg gaagcagctc caacatcgga agtaatactg taaactggta ccagcagctc    120
ccaggaacgg cccccaaact cctcatctat aataataatc agcggccctc aggggtccct    180
gaccgattct ctggctccaa gtctggcacc tcagcctccc tggccatcag tgggctccag    240
tctgaggatg aggctgatta ttactgtgca gcatggcatg acggcctgaa tggtccggtg    300
ttcggcggag ggaccaagct gaccgtccta                                     330

<210> SEQ ID NO 180
<211> LENGTH: 354
<212> TYPE: DNA
<213> ORGANISM: Homo sapiens

<400> SEQUENCE: 180
gaagttcaat tgttagagtc tggtggcggt cttgttcagc ctggtggttc tttacgtctt     60
tcttgcgctg cttccggatt cactttctct cgttacctta tgatgtgggt tcgccaagct    120
cctggtaaag gtttggagtg ggtttctgtt atctctcctt ctggtggccg tacttggtat    180
gctgactccg ttaaaggtcg cttcactatc tctagagaca actctaagaa tactctctac    240
ttgcagatga acagcttaag ggctgaggac actgcagtct actattgtgt gaggagtata    300
gcagcagctg gaactgacta ctggggccag ggaaccctgg tcaccgtctc aagc          354

<210> SEQ ID NO 181
<211> LENGTH: 321
<212> TYPE: DNA
<213> ORGANISM: Homo sapiens

<400> SEQUENCE: 181
gacatccaga tgacccagtc tccagccacc ctgtctttgt ctccagggga aagagccacc     60
ctctcttgta aggccagtca gagtgttcgc gccttcatag cctggtacca gcagaaacct    120
ggccaggctc ccaggctcct catctctggt gcatccaaca gggccactgg catcccagac    180
aggttcagtg gcggtgggtc tgggacagac ttcactctca ccatcagcag actggagcct    240
gaagattttg cagtgtatta ctgtcagcag tacggtagtt cacggtacac ttttggccag    300
gggaccaagc tggagatcaa a                                              321

<210> SEQ ID NO 182
<211> LENGTH: 339
<212> TYPE: DNA
<213> ORGANISM: Homo sapiens

<400> SEQUENCE: 182
gaagttcaat tgttagagtc tggtggcggt cttgttcagc ctggtggttc tttacgtctt     60
tcttgcgctg cttccggatt cactttctct aattacttta tgatttgggt tcgccaagct    120
cctggtaaag gtttggagtg ggtttcttgg atctctcctt ctggtggcac tactcagtat    180
gctgactccg ttaaaggtcg cttcactatc tctagagaca actctaagaa tactctctac    240
```

```
ttgcagatga acagcttaag ggctgaggac actgcagtct actattgtgc gagagaagcc    300
ggctactggg gccagggaac cctggtcacc gtctcaagc                           339

<210> SEQ ID NO 183
<211> LENGTH: 333
<212> TYPE: DNA
<213> ORGANISM: Homo sapiens

<400> SEQUENCE: 183
gacatccaga tgacccagtc tccatcctcc ctgcccgtca cccctggaga gccggcctcc    60
atctcctgca ggtctagtca gagcctccta catagtagtg gatacaacta tttggattgg    120
tacctgcaga agccaggaca gtctccacaa ctcctgattt atttgggttc taatcgggcc    180
tccggggtcc ctgacaggtt cactggcagt ggatcaggca cagattttac actgaaaatc    240
agcagagtgg aggctgagga tgttggggtt tattactgca tgcaagctct acaaaccccc    300
actttcggcg agggaccaa ggtggacatc aaa                                  333

<210> SEQ ID NO 184
<211> LENGTH: 357
<212> TYPE: DNA
<213> ORGANISM: Homo sapiens

<400> SEQUENCE: 184
gaagttcaat tgttagagtc tggtggcggt cttgttcagc ctggtggttc tttacgtctt    60
tcttgcgctg cttccggatt cactttctct gcttactata tgggttgggt tcgccaagct    120
cctggtaaag gtttggagtg gtttctgtt atccgtcctt ctggtggcaa gactaagtat    180
gctgactccg ttaaaggtcg cttcactatc tctagagaca actctaagaa tactctctac    240
ttgcagatga acagcttaag ggctgaggac actgcagtct actattgtgc gagaggcccg    300
catggtcagg gggtgttga ctcgtggggc cagggaaccc tggtcaccgt ctcaagc       357

<210> SEQ ID NO 185
<211> LENGTH: 321
<212> TYPE: DNA
<213> ORGANISM: Homo sapiens

<400> SEQUENCE: 185
gacatccaga tgacccagtc tccagccacc ctgtctgtgt ctccagggga aagagccacc    60
ctctcctgta gggccagtca gagtgttagc agcaacttag cctggtacca gcagaaacct    120
ggccaggctc ccaggctcct catctatggt gcatccacca gggccactgg cgtcccagcc    180
aggttcagtg gcagtgggtc tgggacagac ttcactctct ccatcagcag cctgcagcct    240
gaagactttg caacttatta ctgtcaacag tatgctggtc accccatcac cttcggccaa    300
gggacccgac tggagattaa a                                              321

<210> SEQ ID NO 186
<211> LENGTH: 378
<212> TYPE: DNA
<213> ORGANISM: Homo sapiens

<400> SEQUENCE: 186
gaagttcaat tgttagagtc tggtggcggt cttgttcagc ctggtggttc tttacgtctt    60
tcttgcgctg cttccggatt cactttctct gagtacttta tgacttgggt tcgccaagct    120
cctggtaaag gtttggagtg gtttcttct atccgtcctt ctggtggcaa gactcgttat    180
gctgactccg ttaaaggtcg cttcactatc tctagagaca actctaagaa tactctctac    240
```

```
ttgcagatga acagcttaag ggctgaggac actgcagtct actattgtgc gagagttagt    300
cgctactata ataatggtgc ttatcgcctt gatgcatttg atatctgggg cccagggaca    360
gtggtcaccg tctcaagc                                                  378

<210> SEQ ID NO 187
<211> LENGTH: 315
<212> TYPE: DNA
<213> ORGANISM: Homo sapiens

<400> SEQUENCE: 187
cagagcgaat tgactcaggc tgcctccgtg tctgggtctc ctggacagtc gatcaccctc     60
tcctgcactg gagccaccag ggacgtctcc tggtaccagc aacacccagg caaggccccc    120
aaactcgtcc tttatgaagt cagtagtcgc ccctcaggcg tttccgatcg cttctctggc    180
tccatgtctg gcaacacggc ctccctgacc atctctggac tccaggctga ggacgaggct    240
gattattact gctcctcaac cacaagtcgc gcccctcgcg tggttttcgg cggagggacc    300
aaactgaccg tccta                                                    315

<210> SEQ ID NO 188
<211> LENGTH: 354
<212> TYPE: DNA
<213> ORGANISM: Homo sapiens

<400> SEQUENCE: 188
gaagttcaat tgttagagtc tggtggcggt cttgttcagc ctggtggttc tttacgtctt     60
tcttgcgctg cttccggatt cactttctct gcttaccgta tggcttgggt tcgccaagct    120
cctggtaaag gtttggagtg ggtttcttat atctcttctt ctggtggcgt tacttcttat    180
gctgactccg ttaaaggtcg cttcactatc tctagagaca actctaagaa tactctctac    240
ttgcagatga agagcttaag ggctgaggac actgcagtct actattgtgc gagaggcacg    300 cacctccgg ggggttgacta ctggggccag ggaaccctgg tcaccgtctc aagc          354

<210> SEQ ID NO 189
<211> LENGTH: 336
<212> TYPE: DNA
<213> ORGANISM: Homo sapiens

<400> SEQUENCE: 189
gacatccaga tgacccagtc tccactctcc ctgcccgtca cccctggaga gccggcctcc     60
atctcctgca gatctagtca gagcctcatg cataggaatg gacaccactt cttcgattgg    120
tacctgcaga agccagggca gtctccacag ctcctgatct attgggcttc taatcgggcc    180
cccggggtcc ctgacaggtt cagtggcagt ggatcaggca cagactttac actaaaaatc    240
agcagagtgg aggctgagga tgttgggatt tattactgca tgcaagctct acaaaccccg    300 tacactttg gccaggggac caagctggag atcaaa                              336

<210> SEQ ID NO 190
<211> LENGTH: 339
<212> TYPE: DNA
<213> ORGANISM: Homo sapiens

<400> SEQUENCE: 190
gaagttcaat tgttagagtc tggtggcggt cttgttcagc ctggtggttc tttacgtctt     60
tcttgcgctg cttccggatt cactttctct ggttacatta tggcttgggt tcgccaagct    120
cctggtaaag gtttggagtg ggtttctggt atcggttctt ctggtggcct tactgcttat    180
```

```
gctgactccg ttaaaggtcg cttcactatc tctagagaca actctaagaa tactctctac    240
ttgcagatga acagcttaag ggctgaggac actgcagtct actattgtgc gagagaagcc    300
ggctactggg gccagggaac cctggtcacc gtctcaagc                           339
```

<210> SEQ ID NO 191
<211> LENGTH: 321
<212> TYPE: DNA
<213> ORGANISM: Homo sapiens

<400> SEQUENCE: 191

```
gacatccaga tgacccagtc tccatcctcc ctgtctgcat ctataggaga cagagtcacc     60
atctcttgcc aggcgagtca aaacattgac aactatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctcgaac gttcggccaa    300
gggaccaagg tggaaatcaa a                                              321
```

<210> SEQ ID NO 192
<211> LENGTH: 387
<212> TYPE: DNA
<213> ORGANISM: Homo sapiens

<400> SEQUENCE: 192

```
gaagttcaat tgttagagtc tggtggcggt cttgttcagc ctggtggttc tttacgtctt     60
tcttgcgctg cttccggatt cactttctct tcttacccta tggtttgggt tcgccaagct    120
cctggtaaag gtttggagtg gtttctggt atctggtctt ctggtggcct tacttattat    180
gctgactccg ttaaaggtcg cttcactatc tctagagaca actctaagaa tactctctac    240
ttgcagatga acagcttaag ggctgaggac actgcagtct actattgtgc gagagagggc    300
tcggccggag tggttaaagg gccggcccgg tactactact actacatgga cgtctggggc    360
aaagggacca cggtcaccgt ctcaagc                                        387
```

<210> SEQ ID NO 193
<211> LENGTH: 330
<212> TYPE: DNA
<213> ORGANISM: Homo sapiens

<400> SEQUENCE: 193

```
cagagcgaat tgactcagcc accctcagcg tctgggaccc ccgggcagag ggtcaccatc     60
tcttgttctg gaagcagctc caacatcgga agtaattatg tatactggta ccagcagctc    120
ccaggaacgg cccccaaact cctcatctat aggaataatc agcggccctc aggggtccct    180
gaccgattct ctggctccaa gtctggcacc tcagcctccc tggccatcag tgggctccag    240
tctgaggatg aggctgatta ttactgtgca gcatgggatg acagcctgaa tgcctgggtg    300
ttcggcggag ggaccaagct gaccgtccta                                     330
```

<210> SEQ ID NO 194
<211> LENGTH: 378
<212> TYPE: DNA
<213> ORGANISM: Homo sapiens

<400> SEQUENCE: 194

```
gaagttcaat tgttagagtc tggtggcggt cttgttcagc ctggtggttc tttacgtctt     60
tcttgcgctg cttccggatt cactttctct aagtaccaga tgacttgggt tcgccaagct    120
```

```
cctggtaaag gtttggagtg ggtttctgtt atctcttctt ctggtggcga tactgcttat    180
gctgactccg ttaaaggtcg cttcactatc tctagagaca actctaagaa tactctctac    240
ttgcagatga acagcttaag ggctgaggac actgcagtct actattgtgc gagagatcgg    300
ggttattgta gtggtaatac ttgctatatt gatgcttttg atatctgggg ccaagggaca    360
atggtcaccg tctcaagc                                                  378

<210> SEQ ID NO 195
<211> LENGTH: 333
<212> TYPE: DNA
<213> ORGANISM: Homo sapiens

<400> SEQUENCE: 195
gacatccaga tgacccagtc tccactctcc ctgcccgtca cccctggaga gccggcctcc     60
atctcctgca gtctagtcag agcctcctg catagtaatg gatacaacta tttagattgg    120
tacctgcaga accagggca gtctccacag ctcctgatct ctttgggttc taatcgggcc    180
tccggggtcc ctgccaggtt cagtggcagt ggctcaggca cagattttac actgaaaatc    240
agcagagtgg aggctgagga tgttggagtt tactactgca tgcaagctct acaaactatc    300
accttcggcc aagggacacg actggagatt aaa                                333

<210> SEQ ID NO 196
<211> LENGTH: 357
<212> TYPE: DNA
<213> ORGANISM: Homo sapiens

<400> SEQUENCE: 196
gaagttcaat tgttagagtc tggtggcggt cttgttcagc ctggtggttc tttacgtctt     60
tcttgcgctg cttccggatt cactttctct ccttactgga tgttttgggt tcgccaagct    120
cctggtaaag gtttggagtg ggtttctggt atcgtttctt ctggtggcat gactggttat    180
gctgactccg ttaaaggtcg cttcactatc tctagagaca actctaagaa tactctctac    240
ttgcagatga acagcttaag ggctgaggac actgcagtct actattgtgc gagagtgggg    300
atgtccacct atgcttttga tatctggggc caagggacaa tggtcaccgt ctcaagc       357

<210> SEQ ID NO 197
<211> LENGTH: 321
<212> TYPE: DNA
<213> ORGANISM: Homo sapiens

<400> SEQUENCE: 197
gacatccaga tgacccagtc tccttccacc ctgtctgcat ctgtaggaga cagagtcacc     60
atcacttgcc gggccagtca gagtattagt aggtggttgg cctggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccgctcac tttcggcgga    300
gggaccaagg tggagatcaa a                                              321

<210> SEQ ID NO 198
<211> LENGTH: 354
<212> TYPE: DNA
<213> ORGANISM: Homo sapiens

<400> SEQUENCE: 198
gaagttcaat tgttagagtc tggtggcggt cttgttcagc ttggtggttc tttacgtctt     60
```

```
tcttgcgctg cttccggatt cactttctct cattacggta tgtcttgggt tcgccaagct    120
cctggtaaag gtttggagtg ggtttcttct atccgttctt ctggtggccg tacttggtat    180
gctgactccg ttaaaggtcg cttcactatc tctagagaca actctaagaa tactctctac    240
ttgcagatga acagcttaag ggctgaggac actgcagttt actattgtgc gaaaggctcc    300
cttagcagtg gctgggacta ctggggccag ggaaccctgg tcaccgtctc aagc          354
```

<210> SEQ ID NO 199
<211> LENGTH: 318
<212> TYPE: DNA
<213> ORGANISM: Homo sapiens

<400> SEQUENCE: 199

```
cagagcgctt tgactcagcc accctcagtg tccgtgtccc ctggacagac agccagcatc     60
acctgcgctg gagatgaatt gggtaataaa tatgcttcct ggtatcagca gaagccaggc    120
cagtcccctg tgctggtcat ctatcaagat aggaagcggc cctcagggat ccctgagcga    180
ttctctggct cccactctgg gaacacagcc actctgacca tcagcgggac ccaggctctc    240
gatgaggctg actattactg tcagtcgtgg gacagcagct ctgtgatatt cggcggcggg    300
accaaggtga ccgtccta                                                  318
```

<210> SEQ ID NO 200
<211> LENGTH: 339
<212> TYPE: DNA
<213> ORGANISM: Homo sapiens

<400> SEQUENCE: 200

```
gaagttcaat tgttagagtc tggtggcggt cttgttcagc ctggtggttc tttacgtctt     60
tcttgcgctg cttccggatt cactttctct aattaccgta tggagtgggt tcgccaagct    120
cctggtaaag gtttggagtg ggtttcttct atctggtctt ctggtggcct tactaaggag    180
gctgactccg ttaaaggtcg cttcactatc tctagagaca actctaagaa tactctctac    240
ttgcagatga acagcttaag ggctgaggac actgcagtct actattgtgc gagaggcctg    300
taccggtggg gccagggaac cctggtcacc gtctcaagc                           339
```

<210> SEQ ID NO 201
<211> LENGTH: 330
<212> TYPE: DNA
<213> ORGANISM: Homo sapiens

<400> SEQUENCE: 201

```
cagtacgaat tgactcagcc tccctccgcg tccgggtctc ctggacagtc agtcaccatc     60
tcctgcactg gaaccagcag tgacgttggt ggttataact atgtctcctg gtaccaacag    120
catccaggca aagcccccaa attcatgatt tatgaggtca ataagcggcc ctcaggggtc    180
cctgatcgct tctctggctc caagtctggc aacacggcct ccctgaccgt ctctgggctc    240
caggctgagg atgaggctga ttattactgc agctcatatg caggcaggaa ctttgtggta    300
ttcggcggag ggaccaagct gaccgtccta                                     330
```

<210> SEQ ID NO 202
<211> LENGTH: 366
<212> TYPE: DNA
<213> ORGANISM: Homo sapiens

<400> SEQUENCE: 202

```
gaagttcaat tgttagagtc tggtggcggt cttgttcagc ctggtggttc tttacgtctt     60
```

```
tcttgcgctg cttccggatt cactttctct tggtactcta tggtttgggt tcgccaagct    120
cctggtaaag gtttggagtg ggtttcttct atcggtcctt ctggtggcat gactcgttat    180
gctgactccg ttaaaggtcg cttcactatc tctagagaca actctaagaa tactctctac    240
ttgcagatga acagcttaag ggctgaggac actgcagtct actattgtgc gagagatcaa    300
gggattacta tggttcaggg agctatgggc tactggggcc agggaaccct ggtcaccgtc    360
tcaagc                                                               366

<210> SEQ ID NO 203
<211> LENGTH: 324
<212> TYPE: DNA
<213> ORGANISM: Homo sapiens

<400> SEQUENCE: 203
cagagcgctt tgactcagcc accctcggtg tcagtggccc caggacagac ggccaggatt     60
acctgtgggg gaaacaacat tggtactaaa attgtaaact ggtaccagca gaggccaggc    120
caggcccctg tggtggtcgt ctatgataat agcgaccggc cctcagggat ccctgagcga    180
ttctctggct ccaactctgg gaacacggcc accctgacca tcagcagggt cgaagccggg    240
gatgaggccg actattactg tcagctgtgg gatagtagta gtgaccatcc gatcttcgga    300
actgggacca aggtcaccgt ccta                                           324

<210> SEQ ID NO 204
<211> LENGTH: 357
<212> TYPE: DNA
<213> ORGANISM: Homo sapiens

<400> SEQUENCE: 204
gaagttcaat tgttagagtc tggtggcggt cttgttcagc ctggtggttc tttacgtctt     60
tcttgcgctg cttccggatt cactttctct gtttactcta tggcttgggt tcgccaagct    120
cctggtaaag gtttggagtg ggtttctggt atctggcctt ctggtggccc tactgcttat    180
gctgactccg ttaaaggtcg cttcactatc tctagagaca actctaagaa tactctctac    240
ttgcagatga acagcttaag ggctgaggac actgcagtct actattgtgc gagagaagat    300
ttttggagtg gtttggagga cgtctggggc aaagggacca cggtcaccgt ctcaagc       357

<210> SEQ ID NO 205
<211> LENGTH: 321
<212> TYPE: DNA
<213> ORGANISM: Homo sapiens

<400> SEQUENCE: 205
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagaa ttctctctct ccatcagcag cctgcagcct    240
gaagattttg caacttacta ttgtcaacag gctaacagtt ccctctcac tttcggcgga    300 gggaccaagg tggagatcaa a                                              321

<210> SEQ ID NO 206
<211> LENGTH: 354
<212> TYPE: DNA
<213> ORGANISM: Homo sapiens

<400> SEQUENCE: 206
```

```
gaagttcaat tgttagagtc tggtggcggt cttgttcagc ctggtggttc tttacgtctt      60
tcttgcgctg cttccggatt cactttctct tggtaccttc tgcattgggt tcgccaagct     120
cctggtaaag gtttggagtg ggtttcttct atcgttcctt ctggtggcac tactgtttat     180
gctgactccg ttaaaggtcg cttcactatc tctagagaca actctaagaa tactctctac     240
ttgcagatga acagcttaag ggctgaggac actgcagtct actattgtgc gagagaccta     300
tggttcgggg agtgggacta ctggggccag ggaaccctgg tcaccgtctc aagc           354
```

<210> SEQ ID NO 207
<211> LENGTH: 6
<212> TYPE: PRT
<213> ORGANISM: Homo sapiens

<400> SEQUENCE: 207

Gly Val Leu Asp His Tyr
1               5

<210> SEQ ID NO 208
<211> LENGTH: 6
<212> TYPE: PRT
<213> ORGANISM: Homo sapiens

<400> SEQUENCE: 208

Gly Ile Leu His Asp Tyr
1               5

<210> SEQ ID NO 209
<211> LENGTH: 6
<212> TYPE: PRT
<213> ORGANISM: Homo sapiens

<400> SEQUENCE: 209

Gly Val Leu Leu Asp Lys
1               5

<210> SEQ ID NO 210
<211> LENGTH: 6
<212> TYPE: PRT
<213> ORGANISM: Homo sapiens

<400> SEQUENCE: 210

Gly Val Leu Phe Asp Asn
1               5

<210> SEQ ID NO 211
<211> LENGTH: 11
<212> TYPE: PRT
<213> ORGANISM: Homo sapiens

<400> SEQUENCE: 211

Arg Ala Ser Gln Asn Ile His Thr Trp Leu Ala
1               5                   10

<210> SEQ ID NO 212
<211> LENGTH: 16
<212> TYPE: PRT
<213> ORGANISM: Homo sapiens

<400> SEQUENCE: 212

Arg Ser Ser Gln Ser Leu Ala Ser Ser Asp Gly Asn Met Tyr Leu Asn
1               5                   10                  15

```
<210> SEQ ID NO 213
<211> LENGTH: 11
<212> TYPE: PRT
<213> ORGANISM: Homo sapiens

<400> SEQUENCE: 213

Arg Thr Ser Gln Gly Ile Arg Asn His Leu Gly
1               5                   10

<210> SEQ ID NO 214
<211> LENGTH: 11
<212> TYPE: PRT
<213> ORGANISM: Homo sapiens

<400> SEQUENCE: 214

Arg Ala Ser Gln Thr Ile Ser Arg Tyr Leu Asn
1               5                   10

<210> SEQ ID NO 215
<211> LENGTH: 16
<212> TYPE: PRT
<213> ORGANISM: Homo sapiens

<400> SEQUENCE: 215

Arg Ser Ser Arg Asn Leu Leu His Arg Asn Gly Asn Asn Tyr Leu Asp
1               5                   10                  15

<210> SEQ ID NO 216
<211> LENGTH: 11
<212> TYPE: PRT
<213> ORGANISM: Homo sapiens

<400> SEQUENCE: 216

Arg Ala Ser His Gly Ile Asn Gly Tyr Leu Ala
1               5                   10

<210> SEQ ID NO 217
<211> LENGTH: 142
<212> TYPE: PRT
<213> ORGANISM: Homo sapiens

<400> SEQUENCE: 217

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Val Trp Val Arg Gln Ala Pro Gly Lys Gly Leu Glu Trp Val
        35                  40                  45

Ser Gly Ile Trp Ser Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ala Arg Val Val Lys Gly Pro Arg Tyr Tyr
            100                 105                 110

Tyr Tyr Tyr Ile Asp Val Trp Gly Lys Gly Thr Thr Val Thr Val Ser
        115                 120                 125

Ser Ala Ser Thr Lys Gly Pro Ser Val Phe Pro Leu Ala Pro
    130                 135                 140

<210> SEQ ID NO 218
```

```
<211> LENGTH: 11
<212> TYPE: PRT
<213> ORGANISM: Homo sapiens

<400> SEQUENCE: 218

Arg Thr Ser Gln Asp Ile Gly Asn His Leu Ala
1               5                   10

<210> SEQ ID NO 219
<211> LENGTH: 11
<212> TYPE: PRT
<213> ORGANISM: Homo sapiens

<400> SEQUENCE: 219

Gln Ala Ser Gln Asp Ile Ser Asn Tyr Leu Asn
1               5                   10

<210> SEQ ID NO 220
<211> LENGTH: 11
<212> TYPE: PRT
<213> ORGANISM: Homo sapiens

<400> SEQUENCE: 220

Arg Ala Ser Gln Asp Ile Tyr Arg Trp Leu Val
1               5                   10

<210> SEQ ID NO 221
<211> LENGTH: 11
<212> TYPE: PRT
<213> ORGANISM: Homo sapiens

<400> SEQUENCE: 221

Arg Ala Ser Gln Ser Ile Ser Ser Tyr Leu Asn
1               5                   10

<210> SEQ ID NO 222
<211> LENGTH: 11
<212> TYPE: PRT
<213> ORGANISM: Homo sapiens

<400> SEQUENCE: 222

Arg Ala Ser Gln Asp Ile Arg Ser Tyr Leu Ala
1               5                   10

<210> SEQ ID NO 223
<211> LENGTH: 11
<212> TYPE: PRT
<213> ORGANISM: Homo sapiens

<400> SEQUENCE: 223

Arg Ala Ser Gln Asp Ile Ser Ile His Leu Ala
1               5                   10

<210> SEQ ID NO 224
<211> LENGTH: 11
<212> TYPE: PRT
<213> ORGANISM: Homo sapiens

<400> SEQUENCE: 224

Arg Ala Ser Lys Ser Val Ala Ser Tyr Val Ala
1               5                   10

<210> SEQ ID NO 225
<211> LENGTH: 16
<212> TYPE: PRT
<213> ORGANISM: Homo sapiens
```

<400> SEQUENCE: 225

Arg Ser Ser Gln Ser Leu Leu His Ser Asn Gly Asn Thr Tyr Leu Asp
1               5                   10                  15

<210> SEQ ID NO 226
<211> LENGTH: 11
<212> TYPE: PRT
<213> ORGANISM: Homo sapiens

<400> SEQUENCE: 226

Arg Ala Ser Arg Gly Ile Arg Asn Asn Leu Ala
1               5                   10

<210> SEQ ID NO 227
<211> LENGTH: 112
<212> TYPE: PRT
<213> ORGANISM: Homo sapiens

<400> SEQUENCE: 227

Gln Asp Ile Gln Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Thr Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

Ala Leu Gln Thr Pro Thr Phe Gly Gln Gly Thr Lys Leu Glu Ile Lys
            100                 105                 110

<210> SEQ ID NO 228
<211> LENGTH: 11
<212> TYPE: PRT
<213> ORGANISM: Homo sapiens

<400> SEQUENCE: 228

Arg Ala Ser Gln Gly Ile Thr Asn Tyr Leu Ala
1               5                   10

<210> SEQ ID NO 229
<211> LENGTH: 11
<212> TYPE: PRT
<213> ORGANISM: Homo sapiens

<400> SEQUENCE: 229

Arg Ala Ser Gln Val Ile Gly Asn Tyr Leu Ala
1               5                   10

<210> SEQ ID NO 230
<211> LENGTH: 11
<212> TYPE: PRT
<213> ORGANISM: Homo sapiens

<400> SEQUENCE: 230

Arg Ala Ser Gln Ser Val Lys Met Asn Leu Ala
1               5                   10

```
<210> SEQ ID NO 231
<211> LENGTH: 11
<212> TYPE: PRT
<213> ORGANISM: Homo sapiens

<400> SEQUENCE: 231

Arg Ala Ser Gln Thr Ile Asn Asn Trp Leu Ala
1               5                   10

<210> SEQ ID NO 232
<211> LENGTH: 11
<212> TYPE: PRT
<213> ORGANISM: Homo sapiens

<400> SEQUENCE: 232

Arg Ala Ser Gln Asp Ile Glu Asn Tyr Leu Ala
1               5                   10

<210> SEQ ID NO 233
<211> LENGTH: 11
<212> TYPE: PRT
<213> ORGANISM: Homo sapiens

<400> SEQUENCE: 233

Arg Ala Ser Gln Asp Ile His Thr Trp Leu Ala
1               5                   10

<210> SEQ ID NO 234
<211> LENGTH: 11
<212> TYPE: PRT
<213> ORGANISM: Homo sapiens

<400> SEQUENCE: 234

Arg Ala Ser Gln Gly Ile Ser Ser Trp Leu Ala
1               5                   10

<210> SEQ ID NO 235
<211> LENGTH: 11
<212> TYPE: PRT
<213> ORGANISM: Homo sapiens

<400> SEQUENCE: 235

Arg Ala Ser Gln Ser Ile Ser Arg Tyr Leu Ala
1               5                   10

<210> SEQ ID NO 236
<211> LENGTH: 11
<212> TYPE: PRT
<213> ORGANISM: Homo sapiens

<400> SEQUENCE: 236

Arg Ala Ser Gln Asp Ile Arg Asn Ala Leu Gly
1               5                   10

<210> SEQ ID NO 237
<211> LENGTH: 112
<212> TYPE: PRT
<213> ORGANISM: Homo sapiens

<400> SEQUENCE: 237

Gln Asp Ile Gln Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Gly Asn Gly Asn Asn Tyr Leu Asp Trp Tyr Leu Gln Lys Pro Gly Gln
```

```
                35                  40                  45
Ser Pro Gln Leu Leu Ile Tyr Met Gly Ser Asn Arg Ala Ser Gly Val
         50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Ala Leu Gln Thr Pro Thr Phe Gly Gly Gly Thr Lys Val Glu Ile Lys
            100                 105                 110
```

<210> SEQ ID NO 238
<211> LENGTH: 11
<212> TYPE: PRT
<213> ORGANISM: Homo sapiens

<400> SEQUENCE: 238

```
Arg Ala Ser Gln Asp Ile Arg Asn Asp Leu Gly
 1               5                  10
```

<210> SEQ ID NO 239
<211> LENGTH: 11
<212> TYPE: PRT
<213> ORGANISM: Homo sapiens

<400> SEQUENCE: 239

```
Arg Ala Ser Gln Ser Val Asp Ser Trp Leu Ala
 1               5                  10
```

<210> SEQ ID NO 240
<211> LENGTH: 7
<212> TYPE: PRT
<213> ORGANISM: Homo sapiens

<400> SEQUENCE: 240

```
Gly Ala Ser Ser Leu Gln Ser
 1               5
```

<210> SEQ ID NO 241
<211> LENGTH: 7
<212> TYPE: PRT
<213> ORGANISM: Homo sapiens

<400> SEQUENCE: 241

```
Lys Val Ser Asp Arg Asp Ser
 1               5
```

<210> SEQ ID NO 242
<211> LENGTH: 112
<212> TYPE: PRT
<213> ORGANISM: Homo sapiens

<400> SEQUENCE: 242

```
Gln Asp Ile Gln Met Thr Gln Ser Pro Leu Ser Leu Pro Val Thr Pro
 1               5                  10                  15

Gly Glu Pro Ala Ser Ile Ser Cys Arg Ser Ser Gln Ser Leu Leu His
             20                  25                  30

Ser Asn Gly Tyr Asn Tyr Leu Asp Trp Tyr Leu Gln Lys Pro Gly Gln
         35                  40                  45

Ser Pro Gln Leu Leu Ile Tyr Leu Gly Ser His Arg Ala Ser Gly Val
     50                  55                  60

Pro Asp Arg Phe Ser Gly Ser Gly Ser Gly Thr Asp Phe Thr Leu Lys
 65                  70                  75                  80
```

Ile Ser Arg Val Glu Ala Glu Asp Val Gly Val Tyr Tyr Cys Met Gln
            85                  90                  95

Ala Leu Gln Thr Ile Thr Phe Gly Gln Gly Thr Arg Leu Glu Ile Lys
            100                 105                 110

<210> SEQ ID NO 243
<211> LENGTH: 7
<212> TYPE: PRT
<213> ORGANISM: Homo sapiens

<400> SEQUENCE: 243

Ala Thr Ser Thr Leu His Ser
1               5

<210> SEQ ID NO 244
<211> LENGTH: 7
<212> TYPE: PRT
<213> ORGANISM: Homo sapiens

<400> SEQUENCE: 244

Met Gly Ser Asn Arg Ala Ser
1               5

<210> SEQ ID NO 245
<211> LENGTH: 7
<212> TYPE: PRT
<213> ORGANISM: Homo sapiens

<400> SEQUENCE: 245

Ala Ala Ser Lys Leu Gln Ser
1               5

<210> SEQ ID NO 246
<211> LENGTH: 112
<212> TYPE: PRT
<213> ORGANISM: Homo sapiens

<400> SEQUENCE: 246

Gln Asp Ile Val Met Thr Gln Thr Pro Pro Ser Leu Pro Val Asn Pro
1               5                   10                  15

Gly Glu Pro Ala Ser Ile Ser Cys Arg Ser Ser Gln Ser Leu Leu His
            20                  25                  30

Ser Thr Gly Tyr Asn Tyr Leu Asp Trp Tyr Leu Gln Lys Pro Gly Gln
            35                  40                  45

Ser Pro Gln Leu Leu Ile Tyr Leu Gly Ser Asn Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
            85                  90                  95

Ala Leu Gln Thr Pro Thr Phe Gly Gln Gly Thr Lys Leu Glu Ile Lys
            100                 105                 110

<210> SEQ ID NO 247
<211> LENGTH: 7
<212> TYPE: PRT
<213> ORGANISM: Homo sapiens

<400> SEQUENCE: 247

Gly Ala Ser Thr Val Gln Ser
1               5

<210> SEQ ID NO 248
<211> LENGTH: 7
<212> TYPE: PRT
<213> ORGANISM: Homo sapiens

<400> SEQUENCE: 248

Ala Ala Ser Ser Leu Gln Asn
1               5

<210> SEQ ID NO 249
<211> LENGTH: 7
<212> TYPE: PRT
<213> ORGANISM: Homo sapiens

<400> SEQUENCE: 249

Ala Ala Phe Asn Leu Gln Ser
1               5

<210> SEQ ID NO 250
<211> LENGTH: 7
<212> TYPE: PRT
<213> ORGANISM: Homo sapiens

<400> SEQUENCE: 250

Ala Ala Ser Thr Leu Gln Thr
1               5

<210> SEQ ID NO 251
<211> LENGTH: 7
<212> TYPE: PRT
<213> ORGANISM: Homo sapiens

<400> SEQUENCE: 251

Asp Ala Ser Asn Arg Ala Thr
1               5

<210> SEQ ID NO 252
<211> LENGTH: 7
<212> TYPE: PRT
<213> ORGANISM: Homo sapiens

<400> SEQUENCE: 252

His Ala Ser Thr Leu Gln Ser
1               5

<210> SEQ ID NO 253
<211> LENGTH: 7
<212> TYPE: PRT
<213> ORGANISM: Homo sapiens

<400> SEQUENCE: 253

Gly Ala Tyr Lys Leu Gln Tyr
1               5

<210> SEQ ID NO 254
<211> LENGTH: 7
<212> TYPE: PRT
<213> ORGANISM: Homo sapiens

<400> SEQUENCE: 254

Gly Ala Ser His Leu Gln Ser
1               5

<210> SEQ ID NO 255
<211> LENGTH: 7

```
<212> TYPE: PRT
<213> ORGANISM: Homo sapiens

<400> SEQUENCE: 255

Gly Ala Ser Ser Arg Ala Thr
1               5

<210> SEQ ID NO 256
<211> LENGTH: 7
<212> TYPE: PRT
<213> ORGANISM: Homo sapiens

<400> SEQUENCE: 256

Lys Thr Ser Asn Leu Gln Ser
1               5

<210> SEQ ID NO 257
<211> LENGTH: 7
<212> TYPE: PRT
<213> ORGANISM: Homo sapiens

<400> SEQUENCE: 257

Ala Ala Ser Ser Leu Gln Ser
1               5

<210> SEQ ID NO 258
<211> LENGTH: 7
<212> TYPE: PRT
<213> ORGANISM: Homo sapiens

<400> SEQUENCE: 258

Val Ala Ser Ser Leu Gln Asp
1               5

<210> SEQ ID NO 259
<211> LENGTH: 7
<212> TYPE: PRT
<213> ORGANISM: Homo sapiens

<400> SEQUENCE: 259

Ala Ala Ser Asn Leu Gln Ser
1               5

<210> SEQ ID NO 260
<211> LENGTH: 7
<212> TYPE: PRT
<213> ORGANISM: Homo sapiens

<400> SEQUENCE: 260

Thr Ala Ser Arg Leu Gln Ser
1               5

<210> SEQ ID NO 261
<211> LENGTH: 7
<212> TYPE: PRT
<213> ORGANISM: Homo sapiens

<400> SEQUENCE: 261

Lys Ala Ser Ser Leu Gln Ser
1               5

<210> SEQ ID NO 262
<211> LENGTH: 9
<212> TYPE: PRT
<213> ORGANISM: Homo sapiens
```

<400> SEQUENCE: 262

Gln Gln Ala Asn Ser Phe Pro Phe Ala
1               5

<210> SEQ ID NO 263
<211> LENGTH: 9
<212> TYPE: PRT
<213> ORGANISM: Homo sapiens

<400> SEQUENCE: 263

Met Gln Gly Thr His Trp Pro Pro Thr
1               5

<210> SEQ ID NO 264
<211> LENGTH: 112
<212> TYPE: PRT
<213> ORGANISM: Homo sapiens

<400> SEQUENCE: 264

Gln Asp Ile Val Met Thr Gln Thr Pro Pro Ser Leu Pro Val Asn Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser His Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Thr Ile Thr Phe Gly Gln Gly Thr Arg Leu Glu Ile Lys
            100                 105                 110

<210> SEQ ID NO 265
<211> LENGTH: 9
<212> TYPE: PRT
<213> ORGANISM: Homo sapiens

<400> SEQUENCE: 265

Leu Gln Tyr Asn Asn Tyr Pro Phe Thr
1               5

<210> SEQ ID NO 266
<211> LENGTH: 8
<212> TYPE: PRT
<213> ORGANISM: Homo sapiens

<400> SEQUENCE: 266

Met Gln Ala Leu Gln Ala Trp Thr
1               5

<210> SEQ ID NO 267
<211> LENGTH: 9
<212> TYPE: PRT
<213> ORGANISM: Homo sapiens

<400> SEQUENCE: 267

Gln Gln Tyr Asp Ser Tyr Pro Phe Thr
1               5

<210> SEQ ID NO 268

```
<211> LENGTH: 9
<212> TYPE: PRT
<213> ORGANISM: Homo sapiens

<400> SEQUENCE: 268

Gln Gln Tyr Asp Ala Phe Pro Phe Thr
1               5

<210> SEQ ID NO 269
<211> LENGTH: 9
<212> TYPE: PRT
<213> ORGANISM: Homo sapiens

<400> SEQUENCE: 269

Gln Gln Tyr Lys Thr Tyr Pro Phe Thr
1               5

<210> SEQ ID NO 270
<211> LENGTH: 9
<212> TYPE: PRT
<213> ORGANISM: Homo sapiens

<400> SEQUENCE: 270

Gln Gln Ala Asn Ser Phe Pro Trp Thr
1               5

<210> SEQ ID NO 271
<211> LENGTH: 9
<212> TYPE: PRT
<213> ORGANISM: Homo sapiens

<400> SEQUENCE: 271

Leu Gln Phe Asn Thr Tyr Pro Phe Thr
1               5

<210> SEQ ID NO 272
<211> LENGTH: 9
<212> TYPE: PRT
<213> ORGANISM: Homo sapiens

<400> SEQUENCE: 272

Leu Gln His Asp Ser Tyr Pro Phe Thr
1               5

<210> SEQ ID NO 273
<211> LENGTH: 9
<212> TYPE: PRT
<213> ORGANISM: Homo sapiens

<400> SEQUENCE: 273

Gln Gln Tyr Glu Ser Tyr Pro Phe Thr
1               5

<210> SEQ ID NO 274
<211> LENGTH: 8
<212> TYPE: PRT
<213> ORGANISM: Homo sapiens

<400> SEQUENCE: 274

Gln Gln Tyr Tyr Asn Pro Tyr Thr
1               5

<210> SEQ ID NO 275
<211> LENGTH: 9
<212> TYPE: PRT
<213> ORGANISM: Homo sapiens
```

```
<400> SEQUENCE: 275

Leu Gln Pro Glu Thr Tyr Pro Trp Thr
1               5

<210> SEQ ID NO 276
<211> LENGTH: 9
<212> TYPE: PRT
<213> ORGANISM: Homo sapiens

<400> SEQUENCE: 276

Leu Gln Tyr Gln Thr Tyr Pro Phe Thr
1               5

<210> SEQ ID NO 277
<211> LENGTH: 9
<212> TYPE: PRT
<213> ORGANISM: Homo sapiens

<400> SEQUENCE: 277

Gln Gln Ser Ser Ser Ile Pro Tyr Thr
1               5

<210> SEQ ID NO 278
<211> LENGTH: 9
<212> TYPE: PRT
<213> ORGANISM: Homo sapiens

<400> SEQUENCE: 278

Gln Gln Tyr Ala Asn Trp Pro Phe His
1               5

<210> SEQ ID NO 279
<211> LENGTH: 9
<212> TYPE: PRT
<213> ORGANISM: Homo sapiens

<400> SEQUENCE: 279

Gln Gln Tyr Lys Ala Phe Pro Trp Thr
1               5

<210> SEQ ID NO 280
<211> LENGTH: 9
<212> TYPE: PRT
<213> ORGANISM: Homo sapiens

<400> SEQUENCE: 280

Gln Gln Tyr Ser Ser Tyr Pro Phe Thr
1               5

<210> SEQ ID NO 281
<211> LENGTH: 9
<212> TYPE: PRT
<213> ORGANISM: Homo sapiens

<400> SEQUENCE: 281

Leu Gln His Asn Thr Tyr Pro Leu Thr
1               5

<210> SEQ ID NO 282
<211> LENGTH: 9
<212> TYPE: PRT
<213> ORGANISM: Homo sapiens

<400> SEQUENCE: 282
```

```
Leu Gln His Asn Ser Tyr Pro Leu Thr
1               5

<210> SEQ ID NO 283
<211> LENGTH: 9
<212> TYPE: PRT
<213> ORGANISM: Homo sapiens

<400> SEQUENCE: 283

Gln Gln Tyr Ala Thr Leu Pro Arg Thr
1               5

<210> SEQ ID NO 284
<211> LENGTH: 9
<212> TYPE: PRT
<213> ORGANISM: Homo sapiens

<400> SEQUENCE: 284

Leu Gln Tyr Asn Ser Tyr Pro Phe Thr
1               5

<210> SEQ ID NO 285
<211> LENGTH: 9
<212> TYPE: PRT
<213> ORGANISM: Homo sapiens

<400> SEQUENCE: 285

Leu Gln Gln Lys Asn Tyr Pro Leu Thr
1               5

<210> SEQ ID NO 286
<211> LENGTH: 9
<212> TYPE: PRT
<213> ORGANISM: Homo sapiens

<400> SEQUENCE: 286

Gln Gln Tyr Lys Ser Phe Pro Phe Thr
1               5

<210> SEQ ID NO 287
<211> LENGTH: 108
<212> TYPE: PRT
<213> ORGANISM: Homo sapiens

<400> SEQUENCE: 287

Gln Asp Ile Gln Met Thr Gln Ser Pro Ser Ser Val Ser Ala Ser Val
1               5                   10                  15

Gly Asp Arg Val Thr Ile Ser Cys Arg Ala Ser Gln Asn Ile His Thr
            20                  25                  30

Trp Leu Ala Trp Phe Gln Gln Lys Pro Gly Glu Ala Pro Lys Leu Leu
        35                  40                  45

Ile Tyr Gly Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ala Asn Ser Phe Pro
                85                  90                  95

Phe Ala Phe Gly Gln Gly Thr Arg Leu Glu Ile Lys
            100                 105

<210> SEQ ID NO 288
<211> LENGTH: 113
<212> TYPE: PRT
```

```
<213> ORGANISM: Homo sapiens

<400> SEQUENCE: 288

Gln Asp Ile Val Met Thr Gln Thr Pro Pro Ser Leu Pro Val Asn Pro
1               5                   10                  15

Gly Glu Pro Ala Ser Ile Ser Cys Arg Ser Ser Gln Ser Leu Ala Ser
            20                  25                  30

Ser Asp Gly Asn Met Tyr Leu Asn Trp Phe His Gln Arg Pro Gly Gln
        35                  40                  45

Ser Pro Arg Arg Leu Ile Tyr Lys Val Ser Asp Arg Asp Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Thr His Trp Pro Pro Thr Phe Gly Pro Gly Thr Lys Val Asp Ile
            100                 105                 110

Lys

<210> SEQ ID NO 289
<211> LENGTH: 108
<212> TYPE: PRT
<213> ORGANISM: Homo sapiens

<400> SEQUENCE: 289

Gln Asp Ile Gln Met Thr Gln Ser Pro Ser Ser Leu Ser Ala Ser Val
1               5                   10                  15

Gly Asp Arg Val Thr Ile Thr Cys Arg Thr Ser Gln Gly Ile Arg Asn
            20                  25                  30

His Leu Gly Trp Phe Gln Gln Lys Pro Gly Lys Ala Pro Gln Arg Leu
        35                  40                  45

Ile Arg Glu Ala Ser Ile Leu Gln Ser Gly Val Pro Ser Thr Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln Tyr Asp Ser Phe Pro
                85                  90                  95

Tyr Thr Phe Gly Gln Gly Thr Lys Leu Glu Ile Lys
            100                 105

<210> SEQ ID NO 290
<211> LENGTH: 108
<212> TYPE: PRT
<213> ORGANISM: Homo sapiens

<400> SEQUENCE: 290

Gln Asp Ile Gln Met Thr Gln Ser Pro Ser Ser Leu Ser Ala Ser Val
1               5                   10                  15

Gly Asp Arg Val Thr Ile Ser Cys Arg Ala Ser Gln Thr Ile Ser Arg
            20                  25                  30

Tyr Leu Asn Trp Tyr Gln Gln Lys Pro Gly Lys Ala Pro Lys Leu Leu
        35                  40                  45

Ile Tyr Ala Thr Ser Thr Leu His Ser Gly Val Pro Ser Arg Phe Ser
    50                  55                  60

Gly Ser Gly Ser Gly Thr Asp Phe Thr Leu Thr Ile Ser Gly Leu Gln
65                  70                  75                  80

Pro Glu Asp Ser Ala Thr Tyr Tyr Cys Leu Gln Tyr Asn Asn Tyr Pro
```

```
                85                  90                  95

Phe Thr Phe Gly Gly Gly Thr Lys Val Glu Ile Lys
            100                 105

<210> SEQ ID NO 291
<211> LENGTH: 112
<212> TYPE: PRT
<213> ORGANISM: Homo sapiens

<400> SEQUENCE: 291

Gln Asp Ile Gln Met Thr Gln Ser Pro Leu Ser Leu Pro Val Thr Pro
1               5                   10                  15

Gly Glu Pro Ala Ser Ile Ser Cys Arg Ser Ser Arg Asn Leu Leu His
            20                  25                  30

Arg Asn Gly Asn Asn Tyr Leu Asp Trp Tyr Leu Gln Lys Pro Gly Gln
        35                  40                  45

Ser Pro Gln Leu Leu Ile Tyr Met Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Ala Trp Thr Phe Gly Pro Gly Thr Arg Leu Asp Ile Lys
            100                 105                 110

<210> SEQ ID NO 292
<211> LENGTH: 108
<212> TYPE: PRT
<213> ORGANISM: Homo sapiens

<400> SEQUENCE: 292

Gln Asp Ile Gln Met Thr Gln Ser Pro Ala Thr Leu Ser Ala Ser Val
1               5                   10                  15

Gly Asp Arg Val Thr Ile Thr Cys Arg Ala Ser His Gly Ile Asn Gly
            20                  25                  30

Tyr Leu Ala Trp Phe Gln Gln Lys Pro Gly Arg Ala Pro Lys Ser Leu
        35                  40                  45

Ile Tyr Ala Ala Ser Lys Leu Gln Ser Gly Val Pro Ser Lys Phe Ser
    50                  55                  60

Gly Ser Gly Ser Gly Thr Glu Phe Thr Leu Thr Ile Asn Ser Leu Gln
65                  70                  75                  80

Pro Glu Asp Phe Ala Thr Tyr Tyr Cys Gln Gln Tyr Asp Ser Tyr Pro
                85                  90                  95

Phe Thr Phe Gly Pro Gly Thr Lys Val Asp Ile Lys
            100                 105

<210> SEQ ID NO 293
<211> LENGTH: 112
<212> TYPE: PRT
<213> ORGANISM: Homo sapiens

<400> SEQUENCE: 293

Gln Asp Ile Gln Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45
```

Ser Pro Gln Leu Leu Ile Tyr Leu Gly Ser Asn Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Ala Leu Gln Thr Leu Thr Phe Gly Gly Gly Thr Lys Val Glu Ile Lys
            100                 105                 110

<210> SEQ ID NO 294
<211> LENGTH: 108
<212> TYPE: PRT
<213> ORGANISM: Homo sapiens

<400> SEQUENCE: 294

Gln Asp Ile Gln Met Thr Gln Ser Pro Ser Ser Leu Ser Ala Ser Val
 1               5                  10                  15

Gly Asp Arg Val Thr Ile Thr Cys Arg Thr Ser Gln Asp Ile Gly Asn
             20                  25                  30

His Leu Ala Trp Tyr Gln Gln Lys Pro Gly Lys Ala Pro Gln Arg Leu
         35                  40                  45

Ile Arg Glu Ala Ser Ile Leu Gln Ser Gly Val Pro Ser Thr Phe Ser
 50                  55                  60

Gly Ser Gly Ser Gly Thr Glu Phe Thr Leu Thr Ile Ser Ser Leu Gln
 65                  70                  75                  80

Pro Glu Asp Phe Ala Ser Tyr Tyr Cys Gln Gln Tyr Asp Ala Phe Pro
                 85                  90                  95

Phe Thr Phe Gly Gln Gly Thr Lys Leu Glu Ile Lys
            100                 105

<210> SEQ ID NO 295
<211> LENGTH: 108
<212> TYPE: PRT
<213> ORGANISM: Homo sapiens

<400> SEQUENCE: 295

Gln Asp Ile Gln Met Thr Gln Ser Pro Ser Ser Leu Ser Ala Ser Val
 1               5                  10                  15

Gly Asp Arg Val Thr Ile Thr Cys Gln Ala Ser Gln Asp Ile Ser Asn
             20                  25                  30

Tyr Leu Asn Trp Tyr Gln Gln Lys Pro Gly Lys Ala Pro Gln Arg Leu
         35                  40                  45

Ile Tyr Gly Ala Ser Thr Val Gln Ser Gly Val Pro Ser Arg Phe Ser
 50                  55                  60

Gly Ser Gly Ser Gly Thr Glu Phe Thr Leu Thr Ile Ser Ser Leu Gln
 65                  70                  75                  80

Pro Asp Asp Phe Ala Thr Tyr Tyr Cys Gln Gln Tyr Lys Thr Tyr Pro
                 85                  90                  95

Phe Thr Phe Gly Gln Gly Thr Arg Leu Asp Ile Lys
            100                 105

<210> SEQ ID NO 296
<211> LENGTH: 108
<212> TYPE: PRT
<213> ORGANISM: Homo sapiens

<400> SEQUENCE: 296

Gln Asp Ile Gln Met Thr Gln Ser Pro Ser Ser Val Ser Ala Ser Val
 1               5                  10                  15

Gly Asp Arg Val Thr Ile Ser Cys Arg Ala Ser Gln Asp Ile Tyr Arg
            20                  25                  30

Trp Leu Val Trp Tyr Gln Gln Lys Pro Gly Lys Thr Pro Glu Leu Leu
        35                  40                  45

Ile Tyr Ala Ala Ser Ser Leu Gln Asn Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ala Asn Ser Phe Pro
                85                  90                  95

Trp Thr Phe Gly Gln Gly Thr Lys Val Glu Ile Lys
            100                 105

<210> SEQ ID NO 297
<211> LENGTH: 108
<212> TYPE: PRT
<213> ORGANISM: Homo sapiens

<400> SEQUENCE: 297

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Phe Asn Leu Gln Ser Gly Val Pro Ser Arg Phe Ser
    50                  55                  60

Gly Gly Arg Ser Glu Ala Asp Phe Thr Leu Ala Ile Thr Ser Leu Gln
65                  70                  75                  80

Pro Glu Asp Phe Ala Thr Tyr Tyr Cys Leu Gln Phe Asn Thr Tyr Pro
                85                  90                  95

Phe Thr Phe Gly Gly Gly Thr Lys Val Glu Leu Lys
            100                 105

<210> SEQ ID NO 298
<211> LENGTH: 108
<212> TYPE: PRT
<213> ORGANISM: Homo sapiens

<400> SEQUENCE: 298

Gln Asp Ile Gln Met Thr Gln Ser Pro Ser Ser Val Ser Ala Ser Thr
1               5                   10                  15

Gly Asp Arg Val Thr Ile Thr Cys Arg Ala Ser Gln Asp Ile Arg Ser
            20                  25                  30

Tyr Leu Ala Trp Tyr Gln Gln Lys Pro Gly Lys Ala Pro Asp Leu Leu
        35                  40                  45

Ile Tyr Ala Ala Ser Thr Leu Gln Thr Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln His Asp Ser Tyr Pro
                85                  90                  95

Phe Thr Phe Gly Pro Gly Ser Lys Val Asp Ile Lys
            100                 105

<210> SEQ ID NO 299
<211> LENGTH: 108

```
<212> TYPE: PRT
<213> ORGANISM: Homo sapiens

<400> SEQUENCE: 299

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Ile Ser Ile
            20                  25                  30

His Leu Ala Trp Phe Gln Lys Lys Pro Gly Lys Ala Pro Lys Ser Leu
        35                  40                  45

Ile Tyr Gly Ala Ser Ser Leu Gln Ser Gly Val Pro Ser Lys Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Glu Ser Tyr Pro
                85                  90                  95

Phe Thr Phe Gly Pro Gly Thr Lys Val Asp Ile Lys
            100                 105

<210> SEQ ID NO 300
<211> LENGTH: 107
<212> TYPE: PRT
<213> ORGANISM: Homo sapiens

<400> SEQUENCE: 300

Gln Asn Ile Gln Met Thr Gln Ser Pro Gly Thr Leu Ser Leu Ser Pro
1               5                   10                  15

Gly Glu Arg Ala Thr Leu Ser Cys Arg Ala Ser Lys Ser Val Ala Ser
            20                  25                  30

Tyr Val Ala Trp Tyr Gln Gln Arg Pro Gly Gln Ser Pro Arg Leu Leu
        35                  40                  45

Met Tyr Asp Ala Ser Asn Arg Ala Thr Gly Ile Pro Ala Arg Phe Ser
    50                  55                  60

Gly Ser Gly Ser Gly Ala Asp Phe Thr Leu Thr Ile Ser Ser Leu Glu
65                  70                  75                  80

Pro Glu Asp Phe Ala Val Tyr Tyr Cys Gln Gln Tyr Tyr Asn Pro Tyr
                85                  90                  95

Thr Phe Gly Gln Gly Thr Lys Leu Glu Ile Lys
            100                 105

<210> SEQ ID NO 301
<211> LENGTH: 112
<212> TYPE: PRT
<213> ORGANISM: Homo sapiens

<400> SEQUENCE: 301

Gln Asp Ile Gln Met Thr Gln Ser Pro Asp Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95
```

```
Ala Leu Gln Thr Ile Thr Phe Gly Gln Gly Thr Arg Leu Glu Ile Lys
            100                 105                 110
```

<210> SEQ ID NO 302
<211> LENGTH: 108
<212> TYPE: PRT
<213> ORGANISM: Homo sapiens

<400> SEQUENCE: 302

```
Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Arg Gly Ile Arg Asn
            20                  25                  30

Asn Leu Ala Trp Tyr Gln His His Pro Gly Lys Ala Pro Lys Arg Leu
        35                  40                  45

Ile Tyr His Ala Ser Thr Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln Pro Glu Thr Tyr Pro
                85                  90                  95

Trp Thr Phe Gly Gln Gly Thr Lys Leu Glu Ile Lys
            100                 105
```

<210> SEQ ID NO 303
<211> LENGTH: 112
<212> TYPE: PRT
<213> ORGANISM: Homo sapiens

<400> SEQUENCE: 303

```
Gln Asp Ile Gln Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Ser Gly Tyr His Tyr Leu Asp Trp Tyr Val Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

Ala Leu Gln Thr Pro Thr Phe Gly Gly Gly Thr Lys Val Glu Ile Lys
            100                 105                 110
```

<210> SEQ ID NO 304
<211> LENGTH: 108
<212> TYPE: PRT
<213> ORGANISM: Homo sapiens

<400> SEQUENCE: 304

```
Gln Asp Ile Gln Met Thr Gln Ser Pro Ser Ser Leu Ser Ala Ser Val
1               5                   10                  15

Gly Asp Thr Val Thr Ile Thr Cys Arg Ala Ser Gln Gly Ile Thr Asn
            20                  25                  30

Tyr Leu Ala Trp Phe Gln Gln Lys Pro Gly Lys Ala Pro Lys Ser Leu
        35                  40                  45

Met Tyr Gly Ala Tyr Lys Leu Gln Tyr Gly Val Pro Thr Lys Phe Ser
```

```
                50                  55                  60
Gly Ser Gly Ser Gly Thr Asp Phe Thr Leu Thr Ile Arg Ser Leu Gln
 65                  70                  75                  80

Pro Glu Asp Phe Ala Thr Tyr Tyr Cys Leu Gln Tyr Gln Thr Tyr Pro
                 85                  90                  95

Phe Thr Phe Gly Pro Gly Thr Lys Val Asp Leu Lys
                100                 105

<210> SEQ ID NO 305
<211> LENGTH: 108
<212> TYPE: PRT
<213> ORGANISM: Homo sapiens

<400> SEQUENCE: 305

Gln Asp Ile Gln Met Thr Gln Ser Pro Leu Ser Leu Ser Ala Ser Val
  1               5                  10                  15

Gly Asp Arg Val Ser Ile Thr Cys Arg Ala Ser Gln Val Ile Gly Asn
                 20                  25                  30

Tyr Leu Ala Trp Phe Gln Gln Lys Pro Gly Gln Ala Pro Lys Arg Leu
                 35                  40                  45

Ile Tyr Gly Ala Ser His Leu Gln Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Ser Ser Ser Ile Pro
                 85                  90                  95

Tyr Thr Phe Gly Gln Gly Thr Lys Leu Glu Ile Lys
                100                 105

<210> SEQ ID NO 306
<211> LENGTH: 108
<212> TYPE: PRT
<213> ORGANISM: Homo sapiens

<400> SEQUENCE: 306

Gln Asp Ile Gln Met Thr Gln Ser Pro Ala Thr Leu Ser Met Ser Pro
  1               5                  10                  15

Gly Glu Arg Ala Thr Leu Ser Cys Arg Ala Ser Gln Ser Val Lys Met
                 20                  25                  30

Asn Leu Ala Trp Tyr Gln His Lys Leu Gly Gln Ala Pro Arg Leu Leu
                 35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ala Asn Trp Pro
                 85                  90                  95

Phe His Phe Gly Pro Gly Thr Val Asp Ile Lys
                100                 105

<210> SEQ ID NO 307
<211> LENGTH: 108
<212> TYPE: PRT
<213> ORGANISM: Homo sapiens

<400> SEQUENCE: 307

Gln Asp Ile Gln Met Thr Gln Ser Pro Ser Thr Leu Ser Ala Ser Ile
  1               5                  10                  15
```

Gly Asp Arg Val Thr Ile Thr Cys Arg Ala Ser Gln Thr Ile Asn Asn
            20                  25                  30

Trp Leu Ala Trp Tyr Gln Gln Lys Pro Gly Gln Ala Pro Gln Leu Leu
        35                  40                  45

Ile Tyr Lys Thr Ser Asn Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Val Asp Asp Phe Ala Thr Tyr His Cys Gln Gln Tyr Lys Ala Phe Pro
                85                  90                  95

Trp Thr Phe Gly Gln Gly Thr Lys Val Glu Ser Lys
            100                 105

<210> SEQ ID NO 308
<211> LENGTH: 108
<212> TYPE: PRT
<213> ORGANISM: Homo sapiens

<400> SEQUENCE: 308

Gln Asp Ile Gln Met Thr Gln Ser Pro Ser Ala Leu Ser Ala Ser Val
1               5                   10                  15

Gly Asp Arg Val Thr Val Thr Cys Arg Ala Ser Gln Asp Ile Glu Asn
            20                  25                  30

Tyr Leu Ala Trp Phe Gln Gln Lys Pro Gly Lys Ala Pro Lys Ser Leu
        35                  40                  45

Ile Tyr Ala Ala Ser Ser Leu Gln Ser Gly Val Pro Pro Lys Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Ser Ser Tyr Pro
                85                  90                  95

Phe Thr Phe Gly Gln Gly Thr Arg Leu Glu Ile Lys
            100                 105

<210> SEQ ID NO 309
<211> LENGTH: 108
<212> TYPE: PRT
<213> ORGANISM: Homo sapiens

<400> SEQUENCE: 309

Gln Asp Ile Gln Met Thr Gln Ser Pro Ser Val Ser Ala Ser Val
1               5                   10                  15

Gly Asp Arg Val Thr Ile Ile Cys Arg Ala Ser Gln Asp Ile His Thr
            20                  25                  30

Trp Leu Ala Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gln His Asn Thr Tyr Pro
                85                  90                  95

Leu Thr Phe Gly Gln Gly Thr Arg Leu Glu Ile Lys
            100                 105

<210> SEQ ID NO 310
<211> LENGTH: 108
<212> TYPE: PRT

<213> ORGANISM: Homo sapiens

<400> SEQUENCE: 310

Gln Asp Ile Gln Met Thr Gln Ser Pro Ser Ser Val Ser Ala Ser Val
1               5                   10                  15

Gly Asp Arg Val Thr Ile Thr Cys Arg Ala Ser Gln Gly Ile Ser Ser
                20                  25                  30

Trp Leu Ala Trp Tyr Gln Gln Lys Pro Gly Lys Ala Pro Lys Arg Leu
            35                  40                  45

Ile Tyr Val Ala Ser Ser Leu Gln Asp Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln His Asn Ser Tyr Pro
                85                  90                  95

Leu Thr Phe Gly Gly Gly Thr Lys Val Glu Ile Lys
            100                 105

<210> SEQ ID NO 311
<211> LENGTH: 108
<212> TYPE: PRT
<213> ORGANISM: Homo sapiens

<400> SEQUENCE: 311

Gln Asp Ile Gln Met Thr Gln Ser Pro Ala Thr Leu Ser Leu Ser Pro
1               5                   10                  15

Gly Glu Arg Ala Thr Leu Ser Cys Arg Ala Ser Gln Ser Ile Ser Arg
                20                  25                  30

Tyr Leu Ala Trp Tyr Gln Gln Lys Pro Gly Gln Ala Pro Arg Leu Phe
            35                  40                  45

Ile Tyr Asp Ala Ser Asn Arg Ala Thr Gly Ile Pro Ala Arg Phe Ser
    50                  55                  60

Gly Ser Gly Ser Gly Thr Asp Phe Thr Leu Thr Leu Arg Gly Leu Glu
65                  70                  75                  80

Pro Glu Asp Ser Ala Val Tyr Phe Cys Gln Gln Tyr Ala Thr Leu Pro
                85                  90                  95

Arg Thr Phe Gly Gln Gly Thr Arg Leu Glu Ile Lys
            100                 105

<210> SEQ ID NO 312
<211> LENGTH: 108
<212> TYPE: PRT
<213> ORGANISM: Homo sapiens

<400> SEQUENCE: 312

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Ile Arg Asn
                20                  25                  30

Ala Leu Gly Trp Tyr Gln Gln Lys Pro Gly Lys Ala Pro Lys Arg Leu
            35                  40                  45

Ile Tyr Ala Ala Ser Asn Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln Tyr Asn Ser Tyr Pro
                85                  90                  95

```
Phe Thr Phe Gly Pro Gly Thr Val Asp Ile Lys
            100                 105
```

<210> SEQ ID NO 313
<211> LENGTH: 112
<212> TYPE: PRT
<213> ORGANISM: Homo sapiens

<400> SEQUENCE: 313

```
Gln Asp Ile Gln Met Thr Gln Ser Pro Leu Ser Leu Pro Val Thr Pro
1               5                   10                  15

Gly Gln Pro Ala Ser Ile Ser Cys Arg Ser Ser Gln Ser Leu Leu Asn
            20                  25                  30

Ile Asp Gly Tyr Asn Tyr Leu Asp Trp Tyr Leu Gln Lys Pro Gly Gln
        35                  40                  45

Ser Pro Gln Leu Leu Ile Tyr Phe Gly Ser Asn Arg Ala Ser Gly Val
    50                  55                  60

Pro Asp Arg Phe Ser Gly Ser Gly Ser Gly Thr Glu Phe Thr Leu Lys
65                  70                  75                  80

Ile Ser Arg Val Glu Ala Glu Asp Val Gly Val Tyr Tyr Cys Met Gln
                85                  90                  95

Ala Leu Arg Ala Ile Thr Phe Gly Gln Gly Thr Arg Leu Glu Ile Lys
            100                 105                 110
```

<210> SEQ ID NO 314
<211> LENGTH: 108
<212> TYPE: PRT
<213> ORGANISM: Homo sapiens

<400> SEQUENCE: 314

```
Gln Asp Ile Gln Met Thr Gln Ser Pro Ser Ser Leu Ser Ala Ser Val
1               5                   10                  15

Gly Asp Arg Val Thr Met Thr Cys Arg Ala Ser Gln Asp Ile Arg Asn
            20                  25                  30

Asp Leu Gly Trp Tyr Gln Gln Lys Pro Gly Gln Ala Pro Lys Arg Leu
        35                  40                  45

Ile Tyr Thr Ala Ser Arg Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln Gln Lys Asn Tyr Pro
                85                  90                  95

Leu Thr Phe Gly Gly Gly Thr Lys Val Glu Ile Lys
            100                 105
```

<210> SEQ ID NO 315
<211> LENGTH: 108
<212> TYPE: PRT
<213> ORGANISM: Homo sapiens

<400> SEQUENCE: 315

```
Gln Asp Ile Gln Met Thr Gln Ser Pro Ser Thr Leu Ser Ala Tyr Val
1               5                   10                  15

Gly Asp Arg Val Asn Ile Pro Cys Arg Ala Ser Gln Ser Val Asp Ser
            20                  25                  30

Trp Leu Ala Trp Tyr Gln Gln Lys Pro Gly Lys Ala Pro Lys Leu Leu
        35                  40                  45

Ile Tyr Lys Ala Ser Ser Leu Gln Ser Gly Val Pro Ser Arg Phe Ser
    50                  55                  60
```

Gly Ser Gly Ser Gly Thr Glu Phe Thr Leu Ser Val Ser Ser Leu Gln
65                  70                  75                  80

Pro Asp Asp Phe Val Thr Tyr Tyr Cys Gln Gln Tyr Lys Ser Phe Pro
                85                  90                  95

Phe Thr Phe Gly Gln Gly Thr Lys Leu Glu Ile Lys
            100                 105

<210> SEQ ID NO 316
<211> LENGTH: 128
<212> TYPE: PRT
<213> ORGANISM: Homo sapiens

<400> SEQUENCE: 316

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Met Met Asp Trp Val Arg Gln Ala Pro Gly Lys Gly Leu Glu Trp Val
        35                  40                  45

Ser Ser Ile Trp Pro Ser Gly Gly Gln Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Leu His Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

<210> SEQ ID NO 317
<211> LENGTH: 115
<212> TYPE: PRT
<213> ORGANISM: Homo sapiens

<400> SEQUENCE: 317

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Met Met Asp Trp Val Arg Gln Ala Pro Gly Lys Gly Leu Glu Trp Val
        35                  40                  45

Ser Ser Ile Trp Pro Ser Gly Gly Gln Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Leu His Asp Tyr Trp Gly Gln Gly Thr Leu Val Thr
            100                 105                 110

Val Ser Ser
        115

<210> SEQ ID NO 318
<211> LENGTH: 115
<212> TYPE: PRT
<213> ORGANISM: Homo sapiens

<400> SEQUENCE: 318

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Met Met Asp Trp Val Arg Gln Ala Pro Gly Lys Gly Leu Glu Trp Val
        35                  40                  45

Ser Ser Ile Trp Pro Ser Gly Gln Thr Trp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Val Leu Leu Asp Lys Trp Gly Gln Gly Thr Leu Val Thr
            100                 105                 110

Val Ser Ser
        115

<210> SEQ ID NO 319
<211> LENGTH: 115
<212> TYPE: PRT
<213> ORGANISM: Homo sapiens

<400> SEQUENCE: 319

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Met Met Asp Trp Val Arg Gln Ala Pro Gly Lys Gly Leu Glu Trp Val
        35                  40                  45

Ser Ser Ile Trp Pro Ser Gly Gln Thr Trp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Val Leu Phe Asp Asn Trp Gly Gln Gly Thr Leu Val Thr
            100                 105                 110

Val Ser Ser
        115

<210> SEQ ID NO 320
<211> LENGTH: 9
<212> TYPE: PRT
<213> ORGANISM: Homo sapiens

<400> SEQUENCE: 320

Ser Ile Ala Ala Asp Arg Thr Asp Tyr
1               5

<210> SEQ ID NO 321
<211> LENGTH: 9
<212> TYPE: PRT
<213> ORGANISM: Homo sapiens

<400> SEQUENCE: 321

Ser Ile Ala Ala Ser Arg Thr Asp Tyr
1               5

```
<210> SEQ ID NO 322
<211> LENGTH: 9
<212> TYPE: PRT
<213> ORGANISM: Homo sapiens

<400> SEQUENCE: 322

Ser Ile Ala Ser Ala Gly Thr Asp His
1               5

<210> SEQ ID NO 323
<211> LENGTH: 9
<212> TYPE: PRT
<213> ORGANISM: Homo sapiens

<400> SEQUENCE: 323

Ser Ile Ala Ser Ala Arg Thr Asp Ser
1               5

<210> SEQ ID NO 324
<211> LENGTH: 112
<212> TYPE: PRT
<213> ORGANISM: Homo sapiens

<400> SEQUENCE: 324

Gln Asp Ile Gln Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
                20                  25                  30

Ser Asn Gly Asn Thr Tyr Leu Asp Trp Tyr Leu Gln Lys Pro Gly Gln
            35                  40                  45

Ser Pro Gln Leu Leu Ile Tyr Leu Gly Ser Asn Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Gly Asp Val Gly Val Tyr Tyr Cys Met Gln
                85                  90                  95

Ala Leu Gln Thr Pro Thr Phe Gly Gln Gly Thr Lys Leu Glu Ile Lys
            100                 105                 110

<210> SEQ ID NO 325
<211> LENGTH: 13
<212> TYPE: PRT
<213> ORGANISM: Homo sapiens

<400> SEQUENCE: 325

Ser Gly Ser Ser Ser Asn Ile Gly Ile Asn Thr Val Asn
1               5                   10

<210> SEQ ID NO 326
<211> LENGTH: 13
<212> TYPE: PRT
<213> ORGANISM: Homo sapiens

<400> SEQUENCE: 326

Ser Gly Ser Asn Ser Asn Val Gly Thr Lys Thr Val Asn
1               5                   10

<210> SEQ ID NO 327
<211> LENGTH: 13
<212> TYPE: PRT
<213> ORGANISM: Homo sapiens

<400> SEQUENCE: 327
```

Ser Gly Ser Ser Ser Asn Ile Glu Thr Asn Thr Val Asn
1               5                   10

<210> SEQ ID NO 328
<211> LENGTH: 13
<212> TYPE: PRT
<213> ORGANISM: Homo sapiens

<400> SEQUENCE: 328

Ser Gly Gly Ser Ser Asn Ile Gly Ser Asn Thr Val Asn
1               5                   10

<210> SEQ ID NO 329
<211> LENGTH: 13
<212> TYPE: PRT
<213> ORGANISM: Homo sapiens

<400> SEQUENCE: 329

Ser Gly Ser Ser Ser Asn Ile Gly Ser Lys Thr Val Asn
1               5                   10

<210> SEQ ID NO 330
<211> LENGTH: 13
<212> TYPE: PRT
<213> ORGANISM: Homo sapiens

<400> SEQUENCE: 330

Ser Gly Ser Asn Ser Asn Ile Gly Ser Lys Thr Val Asn
1               5                   10

<210> SEQ ID NO 331
<211> LENGTH: 13
<212> TYPE: PRT
<213> ORGANISM: Homo sapiens

<400> SEQUENCE: 331

Ser Gly Ser Ser Ser Asn Ile Gly Thr Asn Asn Val Asn
1               5                   10

<210> SEQ ID NO 332
<211> LENGTH: 112
<212> TYPE: PRT
<213> ORGANISM: Homo sapiens

<400> SEQUENCE: 332

Gln Asp Ile Val Met Thr Gln Thr Pro Pro Ser Leu Pro Val Asn Pro
1               5                   10                  15

Gly Glu Pro Ala Ser Ile Ser Cys Lys Ser Ser Gln Ser Leu Leu His
                20                  25                  30

Ser Asn Gly Tyr Asn Tyr Leu Asp Trp Tyr Leu Gln Lys Pro Gly Gln
            35                  40                  45

Ser Pro Gln Leu Leu Ile Ser Leu Gly Ser Asn Arg Ala Ser Gly Val
        50                  55                  60

Pro Ala Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Thr Ile Thr Phe Gly Gln Gly Thr Arg Leu Glu Ile Lys
            100                 105                 110

<210> SEQ ID NO 333
<211> LENGTH: 7

```
<212> TYPE: PRT
<213> ORGANISM: Homo sapiens

<400> SEQUENCE: 333

Ser Asn Asn Gln Arg Pro Ser
1               5

<210> SEQ ID NO 334
<211> LENGTH: 7
<212> TYPE: PRT
<213> ORGANISM: Homo sapiens

<400> SEQUENCE: 334

Ser Asn Thr Gln Arg Pro Ser
1               5

<210> SEQ ID NO 335
<211> LENGTH: 7
<212> TYPE: PRT
<213> ORGANISM: Homo sapiens

<400> SEQUENCE: 335

Ser Asp Asp Gln Arg Pro Ser
1               5

<210> SEQ ID NO 336
<211> LENGTH: 7
<212> TYPE: PRT
<213> ORGANISM: Homo sapiens

<400> SEQUENCE: 336

Asn Ser Ser Gln Arg Pro Ser
1               5

<210> SEQ ID NO 337
<211> LENGTH: 7
<212> TYPE: PRT
<213> ORGANISM: Homo sapiens

<400> SEQUENCE: 337

Asn Asn Ile Gln Arg Pro Ser
1               5

<210> SEQ ID NO 338
<211> LENGTH: 7
<212> TYPE: PRT
<213> ORGANISM: Homo sapiens

<400> SEQUENCE: 338

Met Asn Tyr Glu Arg Pro Ser
1               5

<210> SEQ ID NO 339
<211> LENGTH: 7
<212> TYPE: PRT
<213> ORGANISM: Homo sapiens

<400> SEQUENCE: 339

Ser His His Arg Arg Pro Ser
1               5

<210> SEQ ID NO 340
<211> LENGTH: 112
<212> TYPE: PRT
<213> ORGANISM: Homo sapiens
```

<400> SEQUENCE: 340

```
Gln Asp Ile Val Met Thr Gln Thr Pro Pro Ser Leu Pro Val Asn Pro
1               5                   10                  15

Gly Glu Pro Ala Ser Ile Ser Cys Lys Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Ser Leu Gly Ser Asn Arg Ala Ser Gly Val
    50                  55                  60

Pro Ala Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Thr Ile Thr Phe Gly Gln Gly Thr Arg Leu Glu Ile Lys
            100                 105                 110
```

<210> SEQ ID NO 341
<211> LENGTH: 11
<212> TYPE: PRT
<213> ORGANISM: Homo sapiens

<400> SEQUENCE: 341

```
Ala Ala Trp Asp Asp Ser Leu Asn Gly Pro Val
1               5                   10
```

<210> SEQ ID NO 342
<211> LENGTH: 11
<212> TYPE: PRT
<213> ORGANISM: Homo sapiens

<400> SEQUENCE: 342

```
Ala Ala Trp Asp Asp Ser Leu Asn Gly Pro Leu
1               5                   10
```

<210> SEQ ID NO 343
<211> LENGTH: 11
<212> TYPE: PRT
<213> ORGANISM: Homo sapiens

<400> SEQUENCE: 343

```
Ala Ala Trp Asp Asp Ser Leu Ser Gly Pro Val
1               5                   10
```

<210> SEQ ID NO 344
<211> LENGTH: 112
<212> TYPE: PRT
<213> ORGANISM: Homo sapiens

<400> SEQUENCE: 344

```
Gln Asp Ile Val Met Thr Gln Thr Pro Pro Ser Leu Pro Val Asn Pro
1               5                   10                  15

Gly Glu Pro Ala Ser Ile Ser Cys Lys Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Ser Leu Gly Ser Asn Arg Ala Ser Gly Val
    50                  55                  60

Pro Ala Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
```

```
                    85                  90                  95

Ala Leu Gln Thr Ile Thr Phe Gly Gln Gly Thr Arg Leu Glu Ile Lys
                100                 105                 110

<210> SEQ ID NO 345
<211> LENGTH: 110
<212> TYPE: PRT
<213> ORGANISM: Homo sapiens

<400> SEQUENCE: 345

Gln Ser Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
                100                 105                 110

<210> SEQ ID NO 346
<211> LENGTH: 110
<212> TYPE: PRT
<213> ORGANISM: Homo sapiens

<400> SEQUENCE: 346

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ile Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
                100                 105                 110

<210> SEQ ID NO 347
<211> LENGTH: 110
<212> TYPE: PRT
<213> ORGANISM: Homo sapiens

<400> SEQUENCE: 347

Gln Ser Val Leu Thr Gln Ser Pro Ser Ala Ser Gly Thr Pro Gly Gln
1               5                   10                  15

Arg Val Thr Ile Ser Cys Ser Gly Ser Asn Ser Asn Val Gly Thr Lys
            20                  25                  30

Thr Val Asn Trp Tyr Gln Val Leu Pro Gly Thr Ala Pro Lys Leu Leu
        35                  40                  45
```

Ile Tyr Ser Asn Thr Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Arg Val Thr Val Leu
            100                 105                 110

<210> SEQ ID NO 348
<211> LENGTH: 110
<212> TYPE: PRT
<213> ORGANISM: Homo sapiens

<400> SEQUENCE: 348

Gln Ser Ala Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Lys Leu Thr Val Leu
            100                 105                 110

<210> SEQ ID NO 349
<211> LENGTH: 112
<212> TYPE: PRT
<213> ORGANISM: Homo sapiens

<400> SEQUENCE: 349

Gln Asp Ile Gln Met Thr Gln Ser Pro Leu Ser Leu Pro Val Thr Pro
 1               5                  10                  15

Gly Glu Pro Ala Ser Ile Ser Cys Arg Ser Ser Gln Ser Leu Leu His
             20                  25                  30

Ser Asn Gly Tyr Asn Tyr Leu Asp Trp Tyr Leu Gln Lys Pro Gly Gln
         35                  40                  45

Ser Pro Gln Leu Leu Ile Tyr Leu Gly Ser Asn Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Ala Leu Gln Ala Ile Thr Phe Gly Gln Gly Thr Arg Leu Glu Ile Lys
            100                 105                 110

<210> SEQ ID NO 350
<211> LENGTH: 110
<212> TYPE: PRT
<213> ORGANISM: Homo sapiens

<400> SEQUENCE: 350

Gln Ser Ala Leu Thr Gln Ser Pro Ser Ala Ser Gly Thr Pro Gly Gln
 1               5                  10                  15

```
Arg Val Thr Ile Ser Cys Ser Gly Ser Asn Ser Asn Val Gly Thr Lys
            20                  25                  30

Thr Val Asn Trp Tyr Gln Val Leu Pro Gly Thr Ala Pro Lys Leu Leu
        35                  40                  45

Ile Tyr Ser Asn Thr Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Arg Val Thr Val Leu
                100                 105                 110
```

<210> SEQ ID NO 351
<211> LENGTH: 110
<212> TYPE: PRT
<213> ORGANISM: Homo sapiens

<400> SEQUENCE: 351

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Glu Thr Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
                100                 105                 110
```

<210> SEQ ID NO 352
<211> LENGTH: 110
<212> TYPE: PRT
<213> ORGANISM: Homo sapiens

<400> SEQUENCE: 352

```
Gln Tyr Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
                100                 105                 110
```

<210> SEQ ID NO 353
<211> LENGTH: 112

```
<212> TYPE: PRT
<213> ORGANISM: Homo sapiens

<400> SEQUENCE: 353

Gln Asp Ile Gln Met Thr Gln Ser Pro Leu Ser Leu Pro Val Thr Pro
1               5                   10                  15
Gly Glu Pro Ala Ser Ile Ser Cys Arg Ser Ser Gln Ser Leu Leu His
            20                  25                  30
Ser Asn Gly Tyr Asn Tyr Leu Asp Trp Tyr Leu Gln Lys Pro Gly Gln
        35                  40                  45
Ser Pro Gln Leu Leu Ile Tyr Leu Gly Ser Asn Arg Ala Ser Gly Val
    50                  55                  60
Pro Asp Arg Phe Ser Gly Ser Gly Ser Gly Thr Asp Phe Thr Leu Lys
65                  70                  75                  80
Ile Ser Arg Val Glu Ala Glu Asp Val Gly Val Tyr Tyr Cys Met Gln
                85                  90                  95
Ala Leu Gln Thr Ile Thr Phe Gly Gln Gly Thr Arg Leu Glu Ile Lys
            100                 105                 110

<210> SEQ ID NO 354
<211> LENGTH: 110
<212> TYPE: PRT
<213> ORGANISM: Homo sapiens

<400> SEQUENCE: 354

Gln Ser Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Ser Asn
            20                  25                  30
Thr Val Asn Trp Tyr Gln Gln Leu Pro Gly Thr Ala Pro Lys Leu Leu
        35                  40                  45
Ile Tyr Ser Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
Asn Gly Pro Val Phe Gly Gly Gly Thr Lys Leu Thr Val Leu
            100                 105                 110

<210> SEQ ID NO 355
<211> LENGTH: 110
<212> TYPE: PRT
<213> ORGANISM: Homo sapiens

<400> SEQUENCE: 355

Gln Ser Glu Leu Thr Gln Pro Pro Ser Ala Ser Gly Thr Pro Gly Gln
1               5                   10                  15
Arg Val Thr Ile Ser Cys Ser Gly Ser Ser Asn Ile Gly Ile Asn
            20                  25                  30
Thr Val Asn Trp Tyr Gln Gln Leu Pro Gly Thr Ala Pro Lys Leu Leu
        35                  40                  45
Ile Tyr Ser Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
```

Asn Gly Pro Val Phe Gly Gly Gly Thr Lys Leu Thr Val Leu
            100                 105                 110

<210> SEQ ID NO 356
<211> LENGTH: 117
<212> TYPE: PRT
<213> ORGANISM: Homo sapiens

<400> SEQUENCE: 356

Gln Tyr Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asp Asp Gln Arg Pro Ser Gly Val Pro Asp Arg Pro Ser
    50                  55                  60

Gly Val Pro Asp Arg Phe Ser Gly Ser Lys Ser Gly Thr Ser Ala Ser
65                  70                  75                  80

Leu Ala Ile Ser Gly Leu Gln Ser Glu Asp Glu Ala Asp Tyr Tyr Cys
                85                  90                  95

Ala Ala Trp Asp Asp Ser Leu Asn Gly Pro Val Phe Gly Gly Gly Thr
            100                 105                 110

Lys Leu Thr Val Leu
        115

<210> SEQ ID NO 357
<211> LENGTH: 110
<212> TYPE: PRT
<213> ORGANISM: Homo sapiens

<400> SEQUENCE: 357

Gln Tyr Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ile Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 358
<211> LENGTH: 110
<212> TYPE: PRT
<213> ORGANISM: Homo sapiens

<400> SEQUENCE: 358

Gln Ser Ala Leu Thr Gln Pro Pro Ser Ala Ser Gly Thr Pro Gly Gln
1               5                   10                  15

Arg Val Thr Ile Ser Cys Ser Gly Ser Ser Ser Asn Ile Glu Thr Asn
            20                  25                  30

Thr Val Asn Trp Tyr Gln Gln Leu Pro Gly Thr Ala Pro Lys Leu Leu

```
                    35                  40                  45
Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Lys Leu Thr Val Leu
            100                 105                 110

<210> SEQ ID NO 359
<211> LENGTH: 123
<212> TYPE: PRT
<213> ORGANISM: Homo sapiens

<400> SEQUENCE: 359

Phe Tyr Ser His Ser Ala Gln Tyr Glu Leu Thr Gln Pro Pro Ser Ala
 1               5                  10                  15

Ala Gly Thr Pro Gly Gln Arg Val Thr Ile Ser Cys Ser Gly Gly Ser
            20                  25                  30

Ser Asn Ile Gly Ser Asn Thr Val Asn Trp Tyr Gln Gln Leu Pro Gly
        35                  40                  45

Thr Ala Pro Lys Leu Leu Ile Tyr Asn Ser Ser Gln Arg Pro Ser Gly
 50                  55                  60

Val Pro Asp Arg Phe Ser Gly Ser Arg Ser Gly Thr Ser Ala Ser Leu
 65                  70                  75                  80

Ala Ile Ser Gly Leu Gln Ser Gln Asp Glu Ala Asp Tyr Tyr Cys Ala
                 85                  90                  95

Ala Trp Asp Asp Ser Leu Asn Gly Pro Leu Phe Gly Gly Gly Thr Lys
            100                 105                 110

Leu Thr Val Leu Gly Gln Pro Lys Ala Ala Pro
        115                 120

<210> SEQ ID NO 360
<211> LENGTH: 110
<212> TYPE: PRT
<213> ORGANISM: Homo sapiens

<400> SEQUENCE: 360

Gln Ser Val Leu Thr Gln Pro Pro Ser Ala Ser Gly Thr Pro Gly Gln
 1               5                  10                  15

Ser Val Thr Ile Ser Cys Ser Gly Ser Ser Asn Ile Gly Ser Lys
            20                  25                  30

Thr Val Asn Trp Tyr Gln Gln Phe Pro Arg Ala Ala Pro Lys Leu Leu
        35                  40                  45

Ile His Asn Asn Ile Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Asp Asp Glu Gly Asp Tyr Tyr Cys Ala Ala Trp Asp Asp Ser Leu
                 85                  90                  95

Asn Gly Pro Val Phe Gly Gly Gly Thr Lys Leu Thr Val Leu
            100                 105                 110

<210> SEQ ID NO 361
<211> LENGTH: 110
<212> TYPE: PRT
<213> ORGANISM: Homo sapiens
```

<400> SEQUENCE: 361

Gln Ser Ala Leu Thr Gln Pro Pro Ser Thr Ser Gly Thr Pro Gly Gln
1               5                   10                  15

Arg Val Thr Ile Ser Cys Ser Gly Ser Asn Ser Asn Ile Gly Ser Lys
            20                  25                  30

Thr Val Asn Trp Tyr Gln Gln Leu Pro Gly Thr Ala Pro Lys Leu Leu
        35                  40                  45

Ile Tyr Met Asn Tyr Glu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Gly Pro Val Phe Gly Gly Gly Thr Lys Leu Thr Val Leu
            100                 105                 110

<210> SEQ ID NO 362
<211> LENGTH: 110
<212> TYPE: PRT
<213> ORGANISM: Homo sapiens

<400> SEQUENCE: 362

Gln Ser Ala Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ile Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 363
<211> LENGTH: 110
<212> TYPE: PRT
<213> ORGANISM: Homo sapiens

<400> SEQUENCE: 363

Gln Ser Ala Leu Thr Gln Pro Pro Ser Ala Ala Gly Thr Pro Gly Gln
1               5                   10                  15

Arg Val Thr Ile Ser Cys Ser Gly Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Asn Ser Ser Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Gln Asp Glu Ala Asp Tyr Tyr Cys Ala Ala Trp Asp Asp Ser Leu
                85                  90                  95

Asn Gly Pro Leu Phe Gly Gly Gly Thr Lys Leu Thr Val Leu

-continued

```
            100                 105                 110
```

<210> SEQ ID NO 364
<211> LENGTH: 112
<212> TYPE: PRT
<213> ORGANISM: Homo sapiens

<400> SEQUENCE: 364

```
Gln Asp Ile Gln Met Thr Gln Ser Pro Leu Ser Leu Pro Val Thr Pro
1               5                   10                  15

Gly Gln Pro Ala Ser Ile Ser Cys Arg Ser Ser Gln Ser Leu Leu Asn
            20                  25                  30

Ile Asp Gly Tyr Asn Tyr Leu Asp Trp Tyr Leu Gln Lys Pro Gly Gln
        35                  40                  45

Ser Pro Gln Leu Leu Ile Tyr Phe Gly Ser Asn Arg Ala Ser Gly Val
    50                  55                  60

Pro Asp Arg Phe Ser Gly Ser Gly Ser Gly Thr Glu Phe Thr Leu Lys
65                  70                  75                  80

Ile Ser Arg Val Glu Ala Glu Asp Val Gly Val Tyr Tyr Cys Met Gln
                85                  90                  95

Ala Leu Arg Ala Ile Thr Phe Gly Gln Gly Thr Arg Leu Glu Ile Lys
            100                 105                 110
```

<210> SEQ ID NO 365
<211> LENGTH: 112
<212> TYPE: PRT
<213> ORGANISM: Homo sapiens

<400> SEQUENCE: 365

```
Gln Asp Ile Gln Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Arg Asn Gly Tyr Asn Phe Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Ser Pro Thr Phe Gly Gln Gly Thr Lys Val Glu Ile Lys
            100                 105                 110
```

<210> SEQ ID NO 366
<211> LENGTH: 110
<212> TYPE: PRT
<213> ORGANISM: Homo sapiens

<400> SEQUENCE: 366

```
Gln Ser Ala Leu Thr Gln Pro Pro Ser Ala Ser Gln Thr Pro Gly Gln
1               5                   10                  15

Thr Val Thr Ile Ser Cys Ser Gly Ser Ser Ser Asn Ile Gly Thr Asn
            20                  25                  30

Asn Val Asn Trp Tyr Gln Gln Leu Pro Gly Thr Ala Pro Lys Leu Leu
        35                  40                  45

Ile Ser Ser His His Arg Arg Pro Ser Gly Val Pro Asp Arg Phe Ser
    50                  55                  60
```

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 367
<211> LENGTH: 112
<212> TYPE: PRT
<213> ORGANISM: Homo sapiens

<400> SEQUENCE: 367

Gln Asp Ile Gln Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
                20                  25                  30

Ser Asn Gly Tyr Asn Tyr Leu Asp Trp Tyr Leu Gln Lys Pro Gly Gln
            35                  40                  45

Ser Pro Gln Leu Leu Ile Tyr Leu Gly Ser Asn Arg Ala Ser Gly Val
50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Ser Ile Thr Phe Gly Gln Gly Thr Arg Leu Glu Ile Lys
            100                 105                 110

<210> SEQ ID NO 368
<211> LENGTH: 110
<212> TYPE: PRT
<213> ORGANISM: Homo sapiens

<400> SEQUENCE: 368

Gln Ser Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Glu Thr Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 369
<211> LENGTH: 131
<212> TYPE: PRT
<213> ORGANISM: Homo sapiens

<400> SEQUENCE: 369

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
                20                  25                  30

```
Leu Met Met Trp Val Arg Gln Ala Pro Gly Lys Gly Leu Glu Trp Val
            35                  40                  45

Ser Val Ile Ser Pro Ser Gly Gly Arg Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Ser Ile Ala Ala Asp Arg Thr Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro
        130

<210> SEQ ID NO 370
<211> LENGTH: 131
<212> TYPE: PRT
<213> ORGANISM: Homo sapiens

<400> SEQUENCE: 370

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Leu Met Met Trp Val Arg Gln Ala Pro Gly Lys Gly Leu Glu Trp Val
            35                  40                  45

Ser Val Ile Ser Pro Ser Gly Gly Arg Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Ser Ile Ala Ser Ala Gly Thr Asp His Trp Gly Gln Gly Thr
            100                 105                 110

Leu Val Thr Val Ser Ser Ala Ser Thr Lys Gly Pro Ser Val Phe Pro
            115                 120                 125

Leu Ala Pro
        130

<210> SEQ ID NO 371
<211> LENGTH: 131
<212> TYPE: PRT
<213> ORGANISM: Homo sapiens

<400> SEQUENCE: 371

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Leu Met Met Trp Val Arg Gln Ala Pro Gly Lys Gly Leu Glu Trp Val
            35                  40                  45

Ser Val Ile Ser Pro Ser Gly Gly Arg Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Val Arg Ser Ile Ala Ser Ala Arg Thr Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro
    130

<210> SEQ ID NO 372
<211> LENGTH: 131
<212> TYPE: PRT
<213> ORGANISM: Homo sapiens

<400> SEQUENCE: 372

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Leu Met Met Trp Val Arg Gln Ala Pro Gly Lys Gly Leu Glu Trp Val
        35                  40                  45

Ser Val Ile Ser Pro Ser Gly Gly Arg Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Ser Ile Ala Ala Ser Arg Thr Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro
    130

<210> SEQ ID NO 373
<211> LENGTH: 20
<212> TYPE: PRT
<213> ORGANISM: Homo sapiens

<400> SEQUENCE: 373

Glu Arg Ser Val Ala Val Phe Lys Ala Arg Pro Arg His Tyr Tyr Tyr
1               5                   10                  15

Tyr Met Asp Val
            20

<210> SEQ ID NO 374
<211> LENGTH: 20
<212> TYPE: PRT
<213> ORGANISM: Homo sapiens

<400> SEQUENCE: 374

Asp Gly Ser Ala Arg Val Val Lys Gly Pro Arg Tyr Tyr Tyr Tyr
1               5                   10                  15

Tyr Ile Asp Val
            20

<210> SEQ ID NO 375
<211> LENGTH: 20
<212> TYPE: PRT
<213> ORGANISM: Homo sapiens

<400> SEQUENCE: 375

Glu Gly Ser Ala Arg Val Val Lys Gly Pro Ala Arg Tyr Phe Tyr Tyr
1               5                   10                  15

Tyr Met Asp Leu
            20

<210> SEQ ID NO 376
<211> LENGTH: 20
<212> TYPE: PRT
<213> ORGANISM: Homo sapiens

<400> SEQUENCE: 376

Glu Gly Ser Ser Gly Val Val Lys Gly Pro Ala Arg Tyr Tyr Tyr Tyr
1               5                   10                  15

Tyr Met Asp Ala
            20

<210> SEQ ID NO 377
<211> LENGTH: 9
<212> TYPE: PRT
<213> ORGANISM: Homo sapiens

<400> SEQUENCE: 377

Gln Gln Thr Tyr Ser Thr Pro Arg Thr
1               5

<210> SEQ ID NO 378
<211> LENGTH: 9
<212> TYPE: PRT
<213> ORGANISM: Homo sapiens

<400> SEQUENCE: 378

Gln Gln Ser Tyr Ser Thr Pro Arg Thr
1               5

<210> SEQ ID NO 379
<211> LENGTH: 9
<212> TYPE: PRT
<213> ORGANISM: Homo sapiens

<400> SEQUENCE: 379

Gln Gln Ser Asn Ser Ile Pro Arg Thr
1               5

<210> SEQ ID NO 380
<211> LENGTH: 9
<212> TYPE: PRT
<213> ORGANISM: Homo sapiens

<400> SEQUENCE: 380

Gln Gln Ser Tyr Thr Thr Pro Arg Thr
1               5

<210> SEQ ID NO 381
<211> LENGTH: 7
<212> TYPE: PRT
<213> ORGANISM: Homo sapiens

<400> SEQUENCE: 381

Ala Ala Ser Asn Leu Gln Ser
1               5

<210> SEQ ID NO 382

```
<211> LENGTH: 7
<212> TYPE: PRT
<213> ORGANISM: Homo sapiens

<400> SEQUENCE: 382

Ala Ala Ser Ser Leu Gln Ser
1               5

<210> SEQ ID NO 383
<211> LENGTH: 7
<212> TYPE: PRT
<213> ORGANISM: Homo sapiens

<400> SEQUENCE: 383

Ala Ala Tyr Thr Leu Gln Ser
1               5

<210> SEQ ID NO 384
<211> LENGTH: 7
<212> TYPE: PRT
<213> ORGANISM: Homo sapiens

<400> SEQUENCE: 384

Ser Ala Ser Ser Leu Gln Ser
1               5

<210> SEQ ID NO 385
<211> LENGTH: 7
<212> TYPE: PRT
<213> ORGANISM: Homo sapiens

<400> SEQUENCE: 385

Asp Ala Ser Thr Leu Gln Asn
1               5

<210> SEQ ID NO 386
<211> LENGTH: 7
<212> TYPE: PRT
<213> ORGANISM: Homo sapiens

<400> SEQUENCE: 386

Ala Ala Ser Thr Leu Gln Ser
1               5

<210> SEQ ID NO 387
<211> LENGTH: 7
<212> TYPE: PRT
<213> ORGANISM: Homo sapiens

<400> SEQUENCE: 387

Gly Ala Ser Ser Leu Gln Ser
1               5

<210> SEQ ID NO 388
<211> LENGTH: 11
<212> TYPE: PRT
<213> ORGANISM: Homo sapiens

<400> SEQUENCE: 388

Arg Ala Ser Gln Thr Ile Lys Asn Tyr Leu Asn
1               5                   10

<210> SEQ ID NO 389
<211> LENGTH: 11
<212> TYPE: PRT
<213> ORGANISM: Homo sapiens
```

<400> SEQUENCE: 389

Arg Ala Ser Gln Ser Ile Ser Ser Tyr Leu Asn
1               5                   10

<210> SEQ ID NO 390
<211> LENGTH: 11
<212> TYPE: PRT
<213> ORGANISM: Homo sapiens

<400> SEQUENCE: 390

Arg Ala Ser Gln Ser Ile Ser Arg Tyr Leu Asn
1               5                   10

<210> SEQ ID NO 391
<211> LENGTH: 11
<212> TYPE: PRT
<213> ORGANISM: Homo sapiens

<400> SEQUENCE: 391

Arg Ala Ser Arg Gly Val Ser Thr Ser Leu Asn
1               5                   10

<210> SEQ ID NO 392
<211> LENGTH: 11
<212> TYPE: PRT
<213> ORGANISM: Homo sapiens

<400> SEQUENCE: 392

Arg Ala Ser Gln Thr Ile Ser Lys Asn Leu Asn
1               5                   10

<210> SEQ ID NO 393
<211> LENGTH: 11
<212> TYPE: PRT
<213> ORGANISM: Homo sapiens

<400> SEQUENCE: 393

Arg Ala Ser Arg Arg Ile Gly Thr Tyr Leu Asn
1               5                   10

<210> SEQ ID NO 394
<211> LENGTH: 11
<212> TYPE: PRT
<213> ORGANISM: Homo sapiens

<400> SEQUENCE: 394

Arg Ala Ser Gln Ser Ile Arg Ser Tyr Leu Asn
1               5                   10

<210> SEQ ID NO 395
<211> LENGTH: 11
<212> TYPE: PRT
<213> ORGANISM: Homo sapiens

<400> SEQUENCE: 395

Arg Ala Ser Gln Thr Ile Asn Ser Tyr Leu Asn
1               5                   10

<210> SEQ ID NO 396
<211> LENGTH: 11
<212> TYPE: PRT
<213> ORGANISM: Homo sapiens

<400> SEQUENCE: 396

```
Arg Ala Ser Gln Ser Ile Asn Arg Trp Leu Ala
1               5                   10
```

<210> SEQ ID NO 397
<211> LENGTH: 142
<212> TYPE: PRT
<213> ORGANISM: Homo sapiens

<400> SEQUENCE: 397

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Val Trp Val Arg Gln Ala Pro Gly Lys Gly Leu Glu Trp Val
        35                  40                  45

Ser Gly Ile Trp Ser Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ser Val Ala Val Phe Lys Ala Arg Pro Arg His Tyr
            100                 105                 110

Tyr Tyr Tyr Met Asp Val Trp Gly Lys Gly Thr Thr Val Thr Val Ser
        115                 120                 125

Ser Ala Ser Thr Lys Gly Pro Ser Val Phe Pro Leu Ala Pro
    130                 135                 140
```

<210> SEQ ID NO 398
<211> LENGTH: 142
<212> TYPE: PRT
<213> ORGANISM: Homo sapiens

<400> SEQUENCE: 398

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Val Trp Val Arg Gln Ala Pro Gly Lys Gly Leu Glu Trp Val
        35                  40                  45

Ser Gly Ile Trp Ser Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ala Arg Val Val Lys Gly Pro Arg Arg Tyr Tyr
            100                 105                 110

Tyr Tyr Tyr Ile Asp Val Trp Gly Lys Gly Thr Thr Val Thr Val Ser
        115                 120                 125

Ser Ala Ser Thr Lys Gly Pro Ser Val Phe Pro Leu Ala Pro
    130                 135                 140
```

<210> SEQ ID NO 399
<211> LENGTH: 142
<212> TYPE: PRT
<213> ORGANISM: Homo sapiens

<400> SEQUENCE: 399

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Val Trp Val Arg Gln Ala Pro Gly Lys Gly Leu Glu Trp Val
        35                  40                  45

Ser Gly Ile Trp Ser Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ser Ser Gly Val Val Lys Gly Pro Ala Arg Tyr Tyr
            100                 105                 110

Tyr Tyr Tyr Met Asp Ala Trp Gly Lys Gly Thr Thr Val Thr Val Ser
            115                 120                 125

Ser Ala Ser Thr Lys Gly Pro Ser Val Phe Pro Leu Ala Pro
    130                 135                 140
```

<210> SEQ ID NO 400
<211> LENGTH: 108
<212> TYPE: PRT
<213> ORGANISM: Homo sapiens

<400> SEQUENCE: 400

```
Gln Asp Ile Gln Met Thr Gln Ser Pro Ser Ser Leu Ser Val Ser Val
1               5                   10                  15

Gly Asp Arg Val Ile Ile Thr Cys Arg Ala Ser Gln Thr Ile Lys Asn
            20                  25                  30

Tyr Leu Asn Trp Tyr Gln Gln Lys Pro Gly Lys Ala Pro Lys Leu Leu
            35                  40                  45

Ile Tyr Ala Ala Ser Asn Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Thr Tyr Ser Thr Pro
                85                  90                  95

Arg Thr Phe Gly Gln Gly Thr Lys Leu Glu Ile Lys
            100                 105
```

<210> SEQ ID NO 401
<211> LENGTH: 108
<212> TYPE: PRT
<213> ORGANISM: Homo sapiens

<400> SEQUENCE: 401

```
Gln Asp Ile Gln Met Thr Gln Ser Pro Leu Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
            35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80
```

```
Pro Glu Asp Phe Ala Thr Tyr Tyr Cys Gln Gln Ser Tyr Ser Thr Pro
                85                  90                  95

Arg Thr Phe Gly Gln Gly Thr Lys Val Glu Ile Lys
            100                 105

<210> SEQ ID NO 402
<211> LENGTH: 108
<212> TYPE: PRT
<213> ORGANISM: Homo sapiens

<400> SEQUENCE: 402

Gln Asp Ile Gln Met Thr Gln Ser Pro Ala Ser Leu Ser Ala Ser Val
1               5                   10                  15

Gly Asp Arg Val Thr Ile Thr Cys Arg Ala Ser Gln Ser Ile Ser Arg
            20                  25                  30

Tyr Leu Asn Trp Tyr Gln Gln Lys Pro Gly Lys Ala Pro Lys Leu Leu
        35                  40                  45

Ile Tyr Ala Ala Tyr Thr Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Arg Glu Asp Phe Ala Thr Tyr Tyr Cys Gln Gln Ser Asn Ser Ile Pro
                85                  90                  95

Arg Thr Phe Gly Gln Gly Thr Val Glu Ile Arg
            100                 105

<210> SEQ ID NO 403
<211> LENGTH: 108
<212> TYPE: PRT
<213> ORGANISM: Homo sapiens

<400> SEQUENCE: 403

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Arg Thr Phe Gly Gln Gly Thr Lys Val Glu Ile Lys
            100                 105

<210> SEQ ID NO 404
<211> LENGTH: 108
<212> TYPE: PRT
<213> ORGANISM: Homo sapiens

<400> SEQUENCE: 404

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45
```

```
Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Ser Tyr Ser Thr Pro
                 85                  90                  95

Arg Thr Phe Gly Gln Gly Thr Lys Val Glu Ile Lys
            100                 105
```

<210> SEQ ID NO 405
<211> LENGTH: 108
<212> TYPE: PRT
<213> ORGANISM: Homo sapiens

<400> SEQUENCE: 405

```
Gln Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser Ser
                20                  25                  30

Tyr Leu Asn Trp Tyr Gln Gln Lys Pro Gly Lys Ala Pro Lys Leu Leu
            35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gln Gln Ser Tyr Ser Thr Pro
                 85                  90                  95

Arg Thr Phe Gly Gln Gly Thr Lys Val Glu Ile Lys
            100                 105
```

<210> SEQ ID NO 406
<211> LENGTH: 108
<212> TYPE: PRT
<213> ORGANISM: Homo sapiens

<400> SEQUENCE: 406

```
Gln Asp Ile Gln Met Thr Gln Ser Pro Ser Ser Leu Ser Ala Ser Val
 1               5                  10                  15

Gly Asp Arg Val Thr Ile Thr Cys Arg Ala Ser Arg Gly Val Ser Thr
                20                  25                  30

Ser Leu Asn Trp Tyr Gln Ile Lys Pro Glu Lys Ala Pro Lys Leu Leu
            35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Ala Ile Thr Ser Leu Gln
 65                  70                  75                  80

Pro Glu Asp Phe Ala Thr Tyr Tyr Cys Gln Gln Ser Tyr Ser Thr Pro
                 85                  90                  95

Arg Thr Phe Gly Pro Gly Thr Lys Val Glu Ile Lys
            100                 105
```

<210> SEQ ID NO 407
<211> LENGTH: 108
<212> TYPE: PRT
<213> ORGANISM: Homo sapiens

<400> SEQUENCE: 407

Gln Asp Ile Gln Met Thr Gln Ser Pro Ser Ser Leu Ser Ala Ser Val

```
                1               5                   10                  15
Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
            35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Arg Thr Phe Gly Gln Gly Thr Lys Val Glu Ile Lys
                100                 105
```

<210> SEQ ID NO 408
<211> LENGTH: 108
<212> TYPE: PRT
<213> ORGANISM: Homo sapiens

<400> SEQUENCE: 408

```
Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Thr Ile Ser Lys
            20                  25                  30

Asn Leu Asn Trp Tyr Gln Gln Lys Pro Gly Ser Ala Pro Lys Leu Leu
            35                  40                  45

Ile Tyr Ser Ala Ser Ser Leu Gln Ser Gly Val Pro Ser Arg Phe Ser
    50                  55                  60

Gly Ser Gly Ser Gly Thr Asp Phe Thr Leu Ser Ile Asn Gly Leu Gln
65                  70                  75                  80

Pro Glu Asp Phe Ala Thr Tyr Tyr Cys Gln Gln Ser Tyr Thr Thr Pro
                85                  90                  95

Arg Thr Phe Gly Gln Gly Thr Lys Val Glu Ile Glu
                100                 105
```

<210> SEQ ID NO 409
<211> LENGTH: 108
<212> TYPE: PRT
<213> ORGANISM: Homo sapiens

<400> SEQUENCE: 409

```
Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
            35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Arg Thr Phe Gly Gln Gly Thr Lys Leu Glu Ile Lys
                100                 105
```

<210> SEQ ID NO 410

<211> LENGTH: 108
<212> TYPE: PRT
<213> ORGANISM: Homo sapiens

<400> SEQUENCE: 410

Gln Asp Ile Gln Met Thr Gln Ser Pro Asp Ser Leu Ser Ala Ser Val
1               5                   10                  15

Gly Asp Arg Val Thr Ile Thr Cys Arg Ala Ser Gln Ser Ile Ser Ser
                20                  25                  30

Tyr Leu Asn Trp Tyr Gln Gln Lys Pro Gly Lys Ala Pro Lys Leu Leu
            35                  40                  45

Ile Tyr Ala Ala Ser Ser Leu Gln Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Arg Thr Phe Gly Gln Gly Thr Lys Val Glu Ile Lys
            100                 105

<210> SEQ ID NO 411
<211> LENGTH: 108
<212> TYPE: PRT
<213> ORGANISM: Homo sapiens

<400> SEQUENCE: 411

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
                20                  25                  30

Tyr Leu Asn Trp Tyr Gln Gln Lys Pro Gly Lys Ala Pro Lys Leu Leu
            35                  40                  45

Ile Tyr Ala Ala Ser Ser Leu Gln Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Arg Thr Phe Gly Gln Gly Thr Lys Val Glu Ile Lys
            100                 105

<210> SEQ ID NO 412
<211> LENGTH: 108
<212> TYPE: PRT
<213> ORGANISM: Homo sapiens

<400> SEQUENCE: 412

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
                20                  25                  30

Tyr Leu Asn Trp Tyr Gln Gln Lys Pro Gly Lys Ala Pro Lys Leu Leu
            35                  40                  45

Ile Tyr Ala Ala Ser Ser Leu Gln Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro

-continued

```
                85                  90                  95
Arg Thr Phe Gly Gln Gly Thr Lys Val Glu Ile Lys
            100                 105

<210> SEQ ID NO 413
<211> LENGTH: 108
<212> TYPE: PRT
<213> ORGANISM: Homo sapiens

<400> SEQUENCE: 413

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Arg Thr Phe Gly Gln Gly Thr Lys Val Glu Ile Lys
            100                 105

<210> SEQ ID NO 414
<211> LENGTH: 108
<212> TYPE: PRT
<213> ORGANISM: Homo sapiens

<400> SEQUENCE: 414

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Arg Thr Phe Gly Gln Gly Thr Lys Val Glu Ile Lys
            100                 105

<210> SEQ ID NO 415
<211> LENGTH: 108
<212> TYPE: PRT
<213> ORGANISM: Homo sapiens

<400> SEQUENCE: 415

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45
```

Ile Tyr Ala Ala Ser Ser Leu Gln Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Arg Thr Phe Gly Gln Gly Thr Lys Leu Glu Ile Lys
                100                 105

<210> SEQ ID NO 416
<211> LENGTH: 108
<212> TYPE: PRT
<213> ORGANISM: Homo sapiens

<400> SEQUENCE: 416

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
                20                  25                  30

Tyr Leu Asn Trp Tyr Gln Gln Lys Pro Gly Lys Ala Pro Lys Leu Leu
            35                  40                  45

Ile Tyr Ala Ala Ser Ser Leu Gln Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Arg Thr Phe Gly Gln Gly Thr Lys Leu Glu Ile Lys
                100                 105

<210> SEQ ID NO 417
<211> LENGTH: 108
<212> TYPE: PRT
<213> ORGANISM: Homo sapiens

<400> SEQUENCE: 417

Gln Asp Ile Gln Met Thr Gln Ser Pro Ser Ser Leu Ser Ala Thr Val
1               5                   10                  15

Gly Asp Arg Val Thr Ile Thr Cys Arg Ala Ser Arg Arg Ile Gly Thr
                20                  25                  30

Tyr Leu Asn Trp Tyr Gln Gln Lys Ala Gly Lys Ala Pro Lys Leu Leu
            35                  40                  45

Ile Tyr Asp Ala Ser Thr Leu Gln Asn Gly Val Pro Ser Arg Phe Ser
50                  55                  60

Gly Thr Glu Ser Gly Thr Asp Phe Thr Leu Thr Ile Ser Ser Leu Gln
65                  70                  75                  80

Pro Glu Asp Val Ala Thr Tyr Phe Cys Gln Gln Ser Tyr Ser Thr Pro
                85                  90                  95

Arg Thr Phe Gly Gln Gly Thr Lys Val Glu Ile Lys
                100                 105

<210> SEQ ID NO 418
<211> LENGTH: 108
<212> TYPE: PRT
<213> ORGANISM: Homo sapiens

<400> SEQUENCE: 418

Gln Asp Ile Gln Met Thr Gln Ser Pro Ser Ser Leu Ser Ala Ser Val
1               5                   10                  15

```
Gly Asp Arg Val Thr Ile Thr Cys Arg Ala Ser Gln Ser Ile Arg Ser
            20                  25                  30

Tyr Leu Asn Trp Phe Gln Gln Lys Pro Gly Lys Ala Pro Lys Leu Leu
        35                  40                  45

Ile Tyr Ala Ala Ser Thr Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Arg Thr Phe Gly Gln Gly Thr Lys Leu Glu Ile Lys
                100                 105

<210> SEQ ID NO 419
<211> LENGTH: 108
<212> TYPE: PRT
<213> ORGANISM: Homo sapiens

<400> SEQUENCE: 419

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Arg Thr Phe Gly Gln Gly Thr Lys Val Glu Ile Lys
                100                 105

<210> SEQ ID NO 420
<211> LENGTH: 108
<212> TYPE: PRT
<213> ORGANISM: Homo sapiens

<400> SEQUENCE: 420

Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Thr Ile Asn Ser
            20                  25                  30

Tyr Leu Asn Trp Tyr Gln Gln Lys Pro Gly Lys Ala Pro Asp Leu Leu
        35                  40                  45

Ile Phe Gly Ala Ser Ser Leu Gln Ser Gly Val Pro Ser Arg Phe Ser
    50                  55                  60

Gly Ser Gly Ser Gly Thr Asp Phe Thr Leu Thr Ile Thr Ser Leu Gln
65                  70                  75                  80

Pro Glu Asp Phe Ala Thr Tyr Tyr Cys Gln Gln Ser Tyr Thr Thr Pro
                85                  90                  95

Arg Thr Phe Gly Gln Gly Thr Lys Leu Glu Ile Lys
                100                 105

<210> SEQ ID NO 421
<211> LENGTH: 108
```

```
<212> TYPE: PRT
<213> ORGANISM: Homo sapiens

<400> SEQUENCE: 421

Gln Asp Ile Gln Met Thr Gln Ser Pro Ser Thr Leu Ser Ala Ser Val
1               5                   10                  15

Gly Asp Arg Val Thr Ile Thr Cys Arg Ala Ser Gln Ser Ile Asn Arg
            20                  25                  30

Trp Leu Ala Trp Tyr Gln Gln Lys Pro Gly Lys Ala Pro Asn Leu Leu
        35                  40                  45

Ile Tyr Ala Ala Ser Ser Leu Gln Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Ser Thr Pro
                85                  90                  95

Arg Thr Phe Gly Gln Gly Thr Lys Val Glu Ile Lys
            100                 105

<210> SEQ ID NO 422
<211> LENGTH: 11
<212> TYPE: PRT
<213> ORGANISM: Homo sapiens

<400> SEQUENCE: 422

Ala Gly Asp Glu Leu Gly Asn Lys Tyr Ala Ser
1               5                   10

<210> SEQ ID NO 423
<211> LENGTH: 11
<212> TYPE: PRT
<213> ORGANISM: Homo sapiens

<400> SEQUENCE: 423

Ser Gly Asp Ile Leu Gly Asn Lys Tyr Ser Ser
1               5                   10

<210> SEQ ID NO 424
<211> LENGTH: 11
<212> TYPE: PRT
<213> ORGANISM: Homo sapiens

<400> SEQUENCE: 424

Ser Gly Asp Lys Leu Arg Asn Lys Tyr Ala Ser
1               5                   10

<210> SEQ ID NO 425
<211> LENGTH: 11
<212> TYPE: PRT
<213> ORGANISM: Homo sapiens

<400> SEQUENCE: 425

Ser Gly Asn Lys Leu Gly Asn Thr Tyr Ile Ser
1               5                   10

<210> SEQ ID NO 426
<211> LENGTH: 14
<212> TYPE: PRT
<213> ORGANISM: Homo sapiens

<400> SEQUENCE: 426

Thr Gly Thr Gly Ser Asp Val Gly Arg Tyr Ser His Val Ser
1               5                   10
```

```
<210> SEQ ID NO 427
<211> LENGTH: 13
<212> TYPE: PRT
<213> ORGANISM: Homo sapiens

<400> SEQUENCE: 427

Ser Gly Gly Ser Ser Asn Ile Gly Leu Asn Pro Val Asn
1               5                   10

<210> SEQ ID NO 428
<211> LENGTH: 11
<212> TYPE: PRT
<213> ORGANISM: Homo sapiens

<400> SEQUENCE: 428

Ser Gly Asp Lys Leu Gly Ser Lys Tyr Thr Ser
1               5                   10

<210> SEQ ID NO 429
<211> LENGTH: 11
<212> TYPE: PRT
<213> ORGANISM: Homo sapiens

<400> SEQUENCE: 429

Ser Gly Gln Ile Leu Gly Glu Arg Ser Ala Ser
1               5                   10

<210> SEQ ID NO 430
<211> LENGTH: 14
<212> TYPE: PRT
<213> ORGANISM: Homo sapiens

<400> SEQUENCE: 430

Thr Gly Thr Ser Ser Asp Val Gly Arg Tyr Asn Arg Val Ser
1               5                   10

<210> SEQ ID NO 431
<211> LENGTH: 11
<212> TYPE: PRT
<213> ORGANISM: Homo sapiens

<400> SEQUENCE: 431

Ser Gly Asp Thr Leu Arg Asn Lys Tyr Ala Ser
1               5                   10

<210> SEQ ID NO 432
<211> LENGTH: 13
<212> TYPE: PRT
<213> ORGANISM: Homo sapiens

<400> SEQUENCE: 432

Ser Gly Ser Ser Ser Asn Ile Gly Gly Asn Thr Val Asn
1               5                   10

<210> SEQ ID NO 433
<211> LENGTH: 11
<212> TYPE: PRT
<213> ORGANISM: Homo sapiens

<400> SEQUENCE: 433

Ser Gly Asp Lys Leu Arg Asn Lys Tyr Gly Ser
1               5                   10

<210> SEQ ID NO 434
```

```
<211> LENGTH: 7
<212> TYPE: PRT
<213> ORGANISM: Homo sapiens

<400> SEQUENCE: 434

Gln Asp Arg Lys Arg Pro Ser
1               5

<210> SEQ ID NO 435
<211> LENGTH: 7
<212> TYPE: PRT
<213> ORGANISM: Homo sapiens

<400> SEQUENCE: 435

Gln Asp Lys Lys Arg Pro Ser
1               5

<210> SEQ ID NO 436
<211> LENGTH: 7
<212> TYPE: PRT
<213> ORGANISM: Homo sapiens

<400> SEQUENCE: 436

Ala Val Thr Asn Arg Pro Ser
1               5

<210> SEQ ID NO 437
<211> LENGTH: 7
<212> TYPE: PRT
<213> ORGANISM: Homo sapiens

<400> SEQUENCE: 437

Ser Asn Asn Gln Arg Pro Ser
1               5

<210> SEQ ID NO 438
<211> LENGTH: 7
<212> TYPE: PRT
<213> ORGANISM: Homo sapiens

<400> SEQUENCE: 438

Gln Asn Arg Lys Arg Pro Ser
1               5

<210> SEQ ID NO 439
<211> LENGTH: 112
<212> TYPE: PRT
<213> ORGANISM: Homo sapiens

<400> SEQUENCE: 439

Gln Asp Ile Val Met Thr Gln Thr Pro Pro Ser Leu Pro Val Asn Pro
1               5                   10                  15

Gly Glu Pro Ala Ser Ile Ser Cys Arg Ser Ser Gln Ser Leu Arg His
                20                  25                  30

Asn Asn Gly Tyr Asn Tyr Leu Asp Trp Tyr Leu Gln Lys Pro Gly Gln
            35                  40                  45

Ser Pro Gln Leu Leu Ile Tyr Leu Gly Ser Asn Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Ala Ile Thr Phe Gly Gln Gly Thr Arg Leu Glu Ile Lys
```

<210> SEQ ID NO 440
<211> LENGTH: 7
<212> TYPE: PRT
<213> ORGANISM: Homo sapiens

<400> SEQUENCE: 440

Gln Ser Ser Gln Arg Pro Ser
1               5

<210> SEQ ID NO 441
<211> LENGTH: 7
<212> TYPE: PRT
<213> ORGANISM: Homo sapiens

<400> SEQUENCE: 441

Glu Val Ser Asn Arg Pro Ser
1               5

<210> SEQ ID NO 442
<211> LENGTH: 112
<212> TYPE: PRT
<213> ORGANISM: Homo sapiens

<400> SEQUENCE: 442

Gln Asp Ile Val Met Thr Gln Thr Pro Pro Ser Leu Pro Val Asn Pro
1               5                   10                  15

Gly Glu Pro Ala Ser Ile Ser Cys Arg Ser Ser Gln Ser Leu Leu Asn
            20                  25                  30

Ile Asp Gly Tyr Asn Tyr Leu Asp Trp Tyr Leu Gln Lys Pro Gly Gln
        35                  40                  45

Ser Pro Gln Leu Leu Ile Tyr Phe Gly Ser Asn Arg Ala Ser Gly Val
    50                  55                  60

Pro Asp Arg Phe Ser Gly Ser Gly Ser Gly Thr Glu Phe Thr Leu Lys
65                  70                  75                  80

Ile Ser Arg Val Glu Ala Glu Asp Val Gly Val Tyr Tyr Cys Met Gln
                85                  90                  95

Ala Leu Arg Ala Ile Thr Phe Gly Gln Gly Thr Arg Leu Glu Ile Lys
            100                 105                 110

<210> SEQ ID NO 443
<211> LENGTH: 7
<212> TYPE: PRT
<213> ORGANISM: Homo sapiens

<400> SEQUENCE: 443

Arg Asn Asn Gln Arg Pro Ser
1               5

<210> SEQ ID NO 444
<211> LENGTH: 9
<212> TYPE: PRT
<213> ORGANISM: Homo sapiens

<400> SEQUENCE: 444

Gln Ser Trp Asp Ser Ser Ser Val Ile
1               5

<210> SEQ ID NO 445
<211> LENGTH: 9
<212> TYPE: PRT
<213> ORGANISM: Homo sapiens

```
<400> SEQUENCE: 445

Gln Ala Trp Asp Ser Ser Ser Val Ile
1               5

<210> SEQ ID NO 446
<211> LENGTH: 9
<212> TYPE: PRT
<213> ORGANISM: Homo sapiens

<400> SEQUENCE: 446

Gln Thr Trp Asp Ser Ser Ser Val Ile
1               5

<210> SEQ ID NO 447
<211> LENGTH: 9
<212> TYPE: PRT
<213> ORGANISM: Homo sapiens

<400> SEQUENCE: 447

Gln Thr Trp Asp Arg Ser Ser Val Val
1               5

<210> SEQ ID NO 448
<211> LENGTH: 10
<212> TYPE: PRT
<213> ORGANISM: Homo sapiens

<400> SEQUENCE: 448

Gln Ser Tyr Thr Thr Thr Gly Thr Leu Ile
1               5                   10

<210> SEQ ID NO 449
<211> LENGTH: 9
<212> TYPE: PRT
<213> ORGANISM: Homo sapiens

<400> SEQUENCE: 449

Ser Ser Tyr Thr Asn Ser Ser Val Ile
1               5

<210> SEQ ID NO 450
<211> LENGTH: 9
<212> TYPE: PRT
<213> ORGANISM: Homo sapiens

<400> SEQUENCE: 450

Gln Ala Trp Asp Asn Ser Ala Val Ile
1               5

<210> SEQ ID NO 451
<211> LENGTH: 8
<212> TYPE: PRT
<213> ORGANISM: Homo sapiens

<400> SEQUENCE: 451

Gln Thr Trp Asp Thr Ser Ile Leu
1               5

<210> SEQ ID NO 452
<211> LENGTH: 9
<212> TYPE: PRT
<213> ORGANISM: Homo sapiens

<400> SEQUENCE: 452
```

```
Ser Ser Tyr Arg Asn Thr Gly Pro Leu
1               5
```

<210> SEQ ID NO 453
<211> LENGTH: 17
<212> TYPE: PRT
<213> ORGANISM: Homo sapiens

<400> SEQUENCE: 453

```
Ser Ile Trp Ser Ser Gly Gly Leu Thr Lys Glu Ala Asp Ser Val Lys
1               5                   10                  15

Gly
```

<210> SEQ ID NO 454
<211> LENGTH: 10
<212> TYPE: PRT
<213> ORGANISM: Homo sapiens

<400> SEQUENCE: 454

```
Asn Ser Tyr Thr Asn Ser Ala Thr Leu Val
1               5                   10
```

<210> SEQ ID NO 455
<211> LENGTH: 119
<212> TYPE: PRT
<213> ORGANISM: Homo sapiens

<400> SEQUENCE: 455

```
Phe Tyr Ser His Ser Ala Gln Ser Ala Leu Thr Gln Pro Pro Ser Val
1               5                   10                  15

Ser Val Ser Pro Gly Gln Thr Ala Ser Ile Thr Cys Ala Gly Asp Glu
                20                  25                  30

Leu Gly Asn Lys Tyr Ala Ser Trp Tyr Gln Gln Lys Pro Gly Gln Ser
            35                  40                  45

Pro Val Leu Val Ile Tyr Gln Asp Arg Lys Arg Pro Ser Gly Ile Pro
        50                  55                  60

Glu Arg Phe Ser Gly Ser His Ser Gly Asn Thr Ala Thr Leu Thr Ile
65                  70                  75                  80

Ser Gly Thr Gln Ala Leu Asp Glu Ala Asp Tyr Tyr Cys Gln Ser Trp
                85                  90                  95

Asp Ser Ser Val Ile Phe Gly Gly Thr Lys Val Thr Val Leu
                100                 105                 110

Ser Gln Pro Lys Ala Ala Pro
        115
```

<210> SEQ ID NO 456
<211> LENGTH: 106
<212> TYPE: PRT
<213> ORGANISM: Homo sapiens

<400> SEQUENCE: 456

```
Gln Ser Ala Leu Thr Gln Pro Pro Ser Val Ser Val Ser Pro Gly Gln
1               5                   10                  15

Thr Ala Ser Ile Thr Cys Ser Gly Asp Ile Leu Gly Asn Lys Tyr Ser
                20                  25                  30

Ser Trp Tyr Gln Gln Arg Pro Gly Gln Ser Pro Val Leu Val Ile Tyr
            35                  40                  45

Gln Asp Lys Lys Arg Pro Ser Gly Ile Pro Glu Arg Phe Ser Gly Ser
        50                  55                  60

His Ser Gly Asn Thr Ala Thr Leu Thr Ile Ser Gly Thr Gln Ala Met
```

```
                 65                  70                  75                  80
Asp Glu Ala Asp Tyr Tyr Cys Gln Ala Trp Asp Ser Ser Val Ile
                85                  90                  95

Phe Gly Gly Gly Thr Lys Val Thr Val Leu
            100                 105

<210> SEQ ID NO 457
<211> LENGTH: 106
<212> TYPE: PRT
<213> ORGANISM: Homo sapiens

<400> SEQUENCE: 457

Gln Ser Glu Leu Thr Gln Pro Pro Ser Val Ser Val Ser Pro Gly Gln
1               5                   10                  15

Thr Ala Ser Ile Thr Cys Ser Gly Asp Lys Leu Arg Asn Lys Tyr Ala
            20                  25                  30

Ser Trp Tyr Gln Gln Lys Pro Gly Gln Ala Pro Val Leu Val Ile Tyr
        35                  40                  45

Gln Asp Arg Lys Arg Pro Ser Glu Ile Pro Glu Arg Phe Ser Gly Ser
    50                  55                  60

His Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Ser Ser Val Ile
                85                  90                  95

Phe Gly Gly Gly Thr Lys Val Thr Val Leu
            100                 105

<210> SEQ ID NO 458
<211> LENGTH: 106
<212> TYPE: PRT
<213> ORGANISM: Homo sapiens

<400> SEQUENCE: 458

Gln Ser Val Leu Thr Gln Pro Pro Ser Val Ser Val Ser Pro Gly Gln
1               5                   10                  15

Thr Ala Ser Ile Thr Cys Ser Gly Asp Ile Leu Gly Asn Lys Tyr Ser
            20                  25                  30

Ser Trp Tyr Gln Gln Arg Pro Gly Gln Ser Pro Val Leu Val Ile Tyr
        35                  40                  45

Gln Asp Lys Lys Arg Pro Ser Gly Ile Pro Glu Arg Phe Ser Gly Ser
    50                  55                  60

His Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Val Ile
                85                  90                  95

Phe Gly Gly Gly Thr Lys Val Thr Val Leu
            100                 105

<210> SEQ ID NO 459
<211> LENGTH: 106
<212> TYPE: PRT
<213> ORGANISM: Homo sapiens

<400> SEQUENCE: 459

Gln Ser Val Leu Thr Gln Pro Pro Ser Val Ser Val Ser Pro Gly Gln
1               5                   10                  15

Thr Ala Thr Ile Thr Cys Ser Gly Asn Lys Leu Gly Asn Thr Tyr Ile
            20                  25                  30
```

```
Ser Trp Tyr Gln Lys Lys Pro Gly Gln Ser Pro Val Leu Val Ile Tyr
         35                  40                  45

Gln Asp Lys Lys Arg Pro Ser Gly Ile Pro Glu Arg Phe Ser Gly Ser
 50                  55                  60

Asn Ser Gly Asn Thr Ala Thr Leu Thr Ile Thr Gly Thr Gln Ser Leu
 65                  70                  75                  80

Asp Glu Ser Asp Tyr Tyr Cys Gln Thr Trp Asp Arg Ser Ser Val Val
                 85                  90                  95

Phe Gly Gly Gly Thr Lys Leu Thr Val Leu
                100                 105

<210> SEQ ID NO 460
<211> LENGTH: 119
<212> TYPE: PRT
<213> ORGANISM: Homo sapiens

<400> SEQUENCE: 460

Phe Tyr Ser His Ser Ala Gln Ser Glu Leu Thr Gln Pro Pro Ser Val
 1               5                  10                  15

Ser Val Ser Pro Gly Gln Thr Ala Ser Ile Thr Cys Ser Gly Asp Lys
                 20                  25                  30

Leu Arg Asn Lys Tyr Ala Ser Trp Tyr Gln Gln Lys Pro Gly Gln Ser
         35                  40                  45

Pro Val Leu Val Ile Tyr Gln Asp Arg Lys Arg Pro Ser Glu Ile Pro
 50                  55                  60

Glu Arg Phe Ser Gly Ser His Ser Gly Asn Thr Ala Thr Leu Thr Ile
 65                  70                  75                  80

Ser Gly Thr Gln Ala Met Asp Glu Ala Asp Tyr Tyr Cys Gln Ala Trp
                 85                  90                  95

Asp Ser Ser Ser Val Ile Phe Gly Gly Gly Thr Lys Val Thr Val Leu
                100                 105                 110

Gly Gln Pro Lys Ala Ala Pro
        115

<210> SEQ ID NO 461
<211> LENGTH: 109
<212> TYPE: PRT
<213> ORGANISM: Homo sapiens

<400> SEQUENCE: 461

Gln Ser Glu Leu Thr Gln Pro Ala Ser Val Ser Gly Ser Pro Gly Gln
 1               5                  10                  15

Ser Ile Thr Ile Ser Cys Thr Gly Thr Gly Ser Asp Val Gly Arg Tyr
                 20                  25                  30

Ser His Val Ser Trp Tyr Gln Gln His Pro Gly Lys Ala Pro Lys Leu
         35                  40                  45

Ile Ile Tyr Ala Val Thr Asn Arg Pro Ser Gly Val Ser Ala Arg Phe
 50                  55                  60

Ser Gly Ser Arg Ser Gly Asn Thr Ala Ser Leu Thr Ile Ser Gly Leu
 65                  70                  75                  80

Gln Ser Glu Asp Glu Ala Thr Tyr His Cys Gln Ser Tyr Thr Thr Thr
                 85                  90                  95

Gly Thr Leu Ile Phe Gly Gly Gly Thr Asn Leu Thr Val
                100                 105

<210> SEQ ID NO 462
<211> LENGTH: 106
<212> TYPE: PRT
```

<213> ORGANISM: Homo sapiens

<400> SEQUENCE: 462

Gln Ser Val Leu Thr Gln Pro Pro Ser Val Ser Val Ser Pro Gly Gln
1               5                   10                  15

Thr Ala Ile Ile Thr Cys Ser Gly Asp Ile Leu Gly Asn Lys Tyr Ser
            20                  25                  30

Ser Trp Tyr Gln Gln Arg Pro Gly Gln Ser Pro Val Leu Val Ile Phe
        35                  40                  45

Gln Asp Lys Lys Arg Pro Ser Gly Ile Pro Glu Arg Phe Ser Gly Ser
    50                  55                  60

His Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Ser Val Ile
                85                  90                  95

Phe Gly Gly Gly Thr Lys Val Thr Val Leu
            100                 105

<210> SEQ ID NO 463
<211> LENGTH: 106
<212> TYPE: PRT
<213> ORGANISM: Homo sapiens

<400> SEQUENCE: 463

Gln Ser Glu Leu Thr Gln Pro Pro Ser Val Ser Val Ser Pro Gly Gln
1               5                   10                  15

Thr Ala Thr Ile Thr Cys Ser Gly Asn Lys Leu Gly Asn Thr Tyr Ile
            20                  25                  30

Ser Trp Tyr Gln Lys Lys Pro Gly Gln Ser Pro Val Leu Val Ile Tyr
        35                  40                  45

Gln Asp Lys Lys Arg Pro Ser Gly Ile Pro Glu Arg Phe Ser Gly Ser
    50                  55                  60

Asn Ser Gly Asn Thr Ala Thr Leu Thr Ile Thr Gly Thr Gln Ser Leu
65                  70                  75                  80

Asp Glu Ser Asp Tyr Tyr Cys Gln Thr Trp Asp Arg Ser Ser Val Val
                85                  90                  95

Phe Gly Gly Gly Thr Lys Leu Thr Val Leu
            100                 105

<210> SEQ ID NO 464
<211> LENGTH: 106
<212> TYPE: PRT
<213> ORGANISM: Homo sapiens

<400> SEQUENCE: 464

Gln Tyr Glu Leu Thr Gln Pro Pro Ser Val Ser Val Ser Pro Gly Gln
1               5                   10                  15

Thr Ala Thr Ile Thr Cys Ser Gly Asn Lys Leu Gly Asn Thr Tyr Ile
            20                  25                  30

Ser Trp Tyr Gln Lys Lys Pro Gly Gln Ser Pro Val Leu Val Ile Tyr
        35                  40                  45

Gln Asp Lys Lys Arg Pro Ser Gly Ile Pro Glu Arg Phe Ser Gly Ser
    50                  55                  60

Asn Ser Gly Asn Thr Ala Thr Leu Thr Ile Thr Gly Thr Gln Ser Leu
65                  70                  75                  80

Asp Glu Ser Asp Tyr Tyr Cys Gln Thr Trp Asp Arg Ser Ser Val Val
                85                  90                  95

```
Phe Gly Gly Gly Thr Lys Leu Thr Val Leu
            100                 105

<210> SEQ ID NO 465
<211> LENGTH: 107
<212> TYPE: PRT
<213> ORGANISM: Homo sapiens

<400> SEQUENCE: 465

Gln Ser Leu Thr Gln Pro Pro Ser Ala Ser Gly Thr Pro Gly Gln Arg
1               5                   10                  15

Val Thr Ile Ser Cys Ser Gly Gly Ser Ser Asn Ile Gly Leu Asn Pro
            20                  25                  30

Val Asn Trp Tyr Gln Gln Leu Pro Gly Thr Ala Pro Lys Leu Leu Ile
        35                  40                  45

Tyr Ser Asn Asn Gln Arg Pro Ser Gly Val Pro Asp Arg Phe Ser Gly
    50                  55                  60

Ser Lys Ser Gly Thr Ser Ala Ser Leu Ala Ile Ser Gly Leu Gln Ala
65                  70                  75                  80

Glu Asp Glu Ala Asp Tyr Tyr Cys Ser Ser Tyr Thr Asn Ser Ser Val
                85                  90                  95

Ile Phe Gly Gly Gly Thr Lys Leu Thr Val Leu
            100                 105

<210> SEQ ID NO 466
<211> LENGTH: 106
<212> TYPE: PRT
<213> ORGANISM: Homo sapiens

<400> SEQUENCE: 466

Gln Tyr Glu Leu Thr Gln Pro Pro Ser Val Ser Val Ser Pro Gly Gln
1               5                   10                  15

Thr Ala Thr Ile Thr Cys Ser Gly Asp Lys Leu Gly Ser Lys Tyr Thr
            20                  25                  30

Ser Trp Tyr Gln Gln Lys Pro Gly Gln Ser Pro Val Leu Val Val Tyr
        35                  40                  45

Gln Asn Arg Lys Arg Pro Ser Gly Ile Pro Glu Arg Phe Ser Gly Ser
    50                  55                  60

Asn Ser Gly Asn Thr Ala Thr Leu Thr Val Ser Gly Thr Gln Ala Ile
65                  70                  75                  80

Asp Glu Ala Asp Tyr Tyr Cys Gln Ala Trp Asp Asn Ser Ala Val Ile
                85                  90                  95

Phe Gly Gly Gly Thr Lys Leu Thr Val Leu
            100                 105

<210> SEQ ID NO 467
<211> LENGTH: 106
<212> TYPE: PRT
<213> ORGANISM: Homo sapiens

<400> SEQUENCE: 467

Gln Ser Val Leu Thr Gln Pro Pro Ser Val Ser Val Ser Pro Gly Gln
1               5                   10                  15

Thr Ala Ser Ile Thr Cys Ser Gly Asp Lys Leu Arg Asn Lys Tyr Ala
            20                  25                  30

Ser Trp Tyr Gln Gln Lys Pro Gly Gln Ala Pro Val Leu Val Ile Tyr
        35                  40                  45

Gln Asp Arg Lys Arg Pro Ser Glu Ile Pro Glu Arg Phe Ser Gly Ser
    50                  55                  60
```

```
His Ser Gly Asn Thr Ala Thr Leu Thr Ile Ser Gly Thr Gln Ala Met
 65                  70                  75                  80

Asp Glu Ala Asp Tyr Tyr Cys Gln Thr Trp Asp Ser Ser Val Ile
                 85                  90                  95

Phe Gly Gly Gly Thr Lys Val Thr Val Leu
            100                 105

<210> SEQ ID NO 468
<211> LENGTH: 105
<212> TYPE: PRT
<213> ORGANISM: Homo sapiens

<400> SEQUENCE: 468

Gln Ser Ala Leu Thr Gln Pro Pro Ser Val Ser Val Ser Pro Gly His
1               5                   10                  15

Thr Ala Thr Ile Thr Cys Ser Gly Gln Ile Leu Gly Glu Arg Ser Ala
            20                  25                  30

Ser Trp Tyr Gln Gln Arg Pro Gly Gln Ala Pro Val Leu Val Leu Tyr
        35                  40                  45

Gln Ser Ser Gln Arg Pro Ser Gly Ile Pro Glu Arg Phe Ser Gly Ser
    50                  55                  60

Ile Ser Gly Asn Thr Ala Thr Leu Thr Ile Ser Gly Ala Gln Ser Ile
65                  70                  75                  80

Asp Glu Ala Asp Tyr Tyr Cys Gln Thr Trp Asp Thr Ser Ile Leu Phe
                85                  90                  95

Gly Gly Gly Thr Lys Leu Thr Val Leu
            100                 105

<210> SEQ ID NO 469
<211> LENGTH: 109
<212> TYPE: PRT
<213> ORGANISM: Homo sapiens

<400> SEQUENCE: 469

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Arg Tyr
            20                  25                  30

Asn Arg Val Ser Trp Tyr Gln Gln Ser Pro Gly Thr Ala Pro Lys Leu
        35                  40                  45

Ile Ile Phe Glu Val Ser Asn Arg Pro Ser Gly Val Pro Asp Arg Phe
    50                  55                  60

Ser Gly Ser Arg Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Asn Thr
                85                  90                  95

Gly Pro Leu Phe Gly Gly Gly Thr Lys Leu Thr Val Leu
            100                 105

<210> SEQ ID NO 470
<211> LENGTH: 106
<212> TYPE: PRT
<213> ORGANISM: Homo sapiens

<400> SEQUENCE: 470

Gln Ser Glu Leu Thr Gln Pro Pro Ser Val Ser Val Ser Pro Gly Gln
1               5                   10                  15

Thr Ala Ser Ile Thr Cys Ser Gly Asp Ile Leu Gly Asn Lys Tyr Ser
```

```
                20                  25                  30
Ser Trp Tyr Gln Gln Arg Pro Gly Gln Ser Pro Val Leu Val Ile Tyr
            35                  40                  45

Gln Asp Lys Lys Arg Pro Ser Gly Ile Pro Glu Arg Phe Ser Gly Ser
        50                  55                  60

His Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Val Ile
                85                  90                  95

Phe Gly Gly Gly Thr Lys Val Thr Val Leu
            100                 105

<210> SEQ ID NO 471
<211> LENGTH: 106
<212> TYPE: PRT
<213> ORGANISM: Homo sapiens

<400> SEQUENCE: 471

Gln Ser Glu Leu Thr Gln Pro Pro Ser Val Ser Val Ser Pro Gly Gln
1               5                   10                  15

Thr Ala Thr Ile Thr Cys Ser Gly Asp Lys Leu Gly Ser Lys Tyr Thr
            20                  25                  30

Ser Trp Tyr Gln Gln Lys Pro Gly Gln Ser Pro Val Leu Val Val Tyr
            35                  40                  45

Gln Asn Arg Lys Arg Pro Ser Gly Ile Pro Glu Arg Phe Ser Gly Ser
        50                  55                  60

Asn Ser Gly Asn Thr Ala Thr Leu Thr Val Ser Gly Thr Gln Ala Ile
65                  70                  75                  80

Asp Glu Ala Asp Tyr Tyr Cys Gln Ala Trp Asp Asn Ser Ala Val Ile
                85                  90                  95

Phe Gly Gly Gly Thr Lys Leu Thr Val Leu
            100                 105

<210> SEQ ID NO 472
<211> LENGTH: 106
<212> TYPE: PRT
<213> ORGANISM: Homo sapiens

<400> SEQUENCE: 472

Gln Ser Val Leu Thr Gln Pro Pro Ser Val Ser Val Ser Pro Gly Gln
1               5                   10                  15

Thr Ala Ser Ile Thr Cys Ser Gly Asp Thr Leu Arg Asn Lys Tyr Ala
            20                  25                  30

Ser Trp Tyr Gln Gln Lys Pro Gly Gln Ser Pro Val Leu Val Ile Tyr
            35                  40                  45

Gln Asp Arg Lys Arg Pro Ser Asn Ile Pro Glu Arg Phe Ser Gly Ser
        50                  55                  60

His Ser Gly Asn Thr Ala Thr Leu Thr Ile Ser Gly Thr Gln Val Met
65                  70                  75                  80

Asp Glu Ala Asp Tyr Tyr Cys Gln Ala Trp Asp Ser Ser Val Ile
                85                  90                  95

Phe Gly Gly Gly Thr Lys Val Thr Val Leu
            100                 105

<210> SEQ ID NO 473
<211> LENGTH: 106
<212> TYPE: PRT
<213> ORGANISM: Homo sapiens
```

<400> SEQUENCE: 473

Gln Ser Ala Leu Thr Gln Pro Pro Ser Val Ser Val Ser Pro Gly Gln
1               5                   10                  15

Thr Ala Thr Ile Thr Cys Ser Gly Asp Lys Leu Gly Ser Lys Tyr Thr
            20                  25                  30

Ser Trp Tyr Gln Gln Lys Pro Gly Gln Ser Pro Val Leu Val Val Tyr
        35                  40                  45

Gln Asn Arg Lys Arg Pro Ser Gly Ile Pro Glu Arg Phe Ser Gly Ser
    50                  55                  60

Asn Ser Gly Asn Thr Ala Thr Leu Thr Val Ser Gly Thr Gln Ala Ile
65                  70                  75                  80

Asp Glu Ala Asp Tyr Tyr Cys Gln Ala Trp Asp Asn Ser Ala Val Ile
                85                  90                  95

Phe Gly Gly Gly Thr Lys Leu Thr Val Leu
            100                 105

<210> SEQ ID NO 474
<211> LENGTH: 106
<212> TYPE: PRT
<213> ORGANISM: Homo sapiens

<400> SEQUENCE: 474

Gln Ser Val Leu Thr Gln Pro Pro Ser Val Ser Val Ser Pro Gly Gln
1               5                   10                  15

Thr Ala Thr Ile Thr Cys Ser Gly Asp Lys Leu Gly Ser Lys Tyr Thr
            20                  25                  30

Ser Trp Tyr Gln Gln Lys Pro Gly Gln Ser Pro Val Leu Val Val Tyr
        35                  40                  45

Gln Asn Arg Lys Arg Pro Ser Gly Ile Pro Glu Arg Phe Ser Gly Ser
    50                  55                  60

Asn Ser Gly Asn Thr Ala Thr Leu Thr Val Ser Gly Thr Gln Ala Ile
65                  70                  75                  80

Asp Glu Ala Asp Tyr Tyr Cys Gln Ala Trp Asp Asn Ser Ala Val Ile
                85                  90                  95

Phe Gly Gly Gly Thr Lys Leu Thr Val Leu
            100                 105

<210> SEQ ID NO 475
<211> LENGTH: 110
<212> TYPE: PRT
<213> ORGANISM: Homo sapiens

<400> SEQUENCE: 475

Gln Tyr Glu Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Arg Tyr
            20                  25                  30

Ser His Val Ser Trp Tyr Gln Gln His Pro Gly Lys Ala Pro Lys Leu
        35                  40                  45

Ile Ile Tyr Ala Val Thr Asn Arg Pro Ser Gly Val Ser Ala Arg Phe
    50                  55                  60

Ser Gly Ser Arg Ser Gly Asn Thr Ala Ser Leu Thr Ile Ser Gly Leu
65                  70                  75                  80

Gln Ser Glu Asp Glu Ala Thr Tyr His Cys Gln Ser Tyr Thr Thr Thr
                85                  90                  95

Gly Thr Leu Ile Phe Gly Gly Gly Thr Asn Leu Thr Val Leu

```
                        100                 105                 110

<210> SEQ ID NO 476
<211> LENGTH: 105
<212> TYPE: PRT
<213> ORGANISM: Homo sapiens

<400> SEQUENCE: 476

Gln Ser Glu Leu Thr Gln Pro Pro Ser Val Ser Val Ser Pro Gly His
1               5                   10                  15

Thr Ala Thr Ile Thr Cys Ser Gly Gln Ile Leu Gly Glu Arg Ser Ala
            20                  25                  30

Ser Trp Tyr Gln Gln Arg Pro Gly Gln Ala Pro Val Leu Val Leu Tyr
        35                  40                  45

Gln Ser Ser Gln Arg Pro Ser Gly Ile Pro Glu Arg Phe Ser Gly Ser
    50                  55                  60

Ile Ser Gly Asn Thr Ala Thr Leu Thr Ile Ser Gly Ala Gln Ser Ile
65                  70                  75                  80

Asp Glu Ala Asp Tyr Tyr Cys Gln Thr Trp Asp Thr Ser Ile Leu Phe
                85                  90                  95

Gly Gly Gly Thr Lys Leu Thr Val Leu
            100                 105

<210> SEQ ID NO 477
<211> LENGTH: 106
<212> TYPE: PRT
<213> ORGANISM: Homo sapiens

<400> SEQUENCE: 477

Gln Ser Ala Leu Thr Gln Pro Pro Ser Val Ser Val Ser Pro Gly Gln
1               5                   10                  15

Thr Ala Ser Ile Thr Cys Ser Gly Asp Lys Leu Arg Asn Lys Tyr Ala
            20                  25                  30

Ser Trp Tyr Gln Gln Lys Pro Gly Gln Ala Pro Val Leu Val Ile Tyr
        35                  40                  45

Gln Asp Arg Lys Arg Pro Ser Glu Ile Pro Glu Arg Phe Ser Gly Ser
    50                  55                  60

His Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Ser Ser Ser Val Ile
                85                  90                  95

Phe Gly Gly Gly Thr Lys Val Thr Val Leu
            100                 105

<210> SEQ ID NO 478
<211> LENGTH: 106
<212> TYPE: PRT
<213> ORGANISM: Homo sapiens

<400> SEQUENCE: 478

Gln Ser Ala Leu Thr Gln Pro Pro Ser Val Ser Val Ser Pro Gly Gln
1               5                   10                  15

Thr Ala Ser Ile Thr Cys Ser Gly Asp Ile Leu Gly Asn Lys Tyr Ser
            20                  25                  30

Ser Trp Tyr Gln Gln Arg Pro Gly Gln Ser Pro Val Leu Val Ile Tyr
        35                  40                  45

Gln Asp Lys Lys Arg Pro Ser Gly Ile Pro Glu Arg Phe Ser Gly Ser
    50                  55                  60
```

His Ser Gly Asn Thr Ala Thr Leu Thr Ile Ser Thr Gln Ala Met
 65                  70                  75                  80

Asp Glu Ala Asp Tyr Tyr Cys Gln Ala Trp Asp Ser Ser Val Ile
                 85                  90                  95

Phe Gly Gly Gly Thr Lys Val Thr Val Leu
            100                 105

<210> SEQ ID NO 479
<211> LENGTH: 109
<212> TYPE: PRT
<213> ORGANISM: Homo sapiens

<400> SEQUENCE: 479

Gln Ser Glu Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Arg Tyr
            20                  25                  30

Asn Arg Val Ser Trp Tyr Gln Gln Ser Pro Gly Thr Ala Pro Lys Leu
        35                  40                  45

Ile Ile Phe Glu Val Ser Asn Arg Pro Ser Gly Val Pro Asp Arg Phe
    50                  55                  60

Ser Gly Ser Arg Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Asn Thr
                85                  90                  95

Gly Pro Leu Phe Gly Gly Gly Thr Lys Leu Thr Val Leu
            100                 105

<210> SEQ ID NO 480
<211> LENGTH: 109
<212> TYPE: PRT
<213> ORGANISM: Homo sapiens

<400> SEQUENCE: 480

Gln Ser Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Gly Asn
            20                  25                  30

Thr Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Asn Ser Tyr Thr Asn Ser Ala
                85                  90                  95

Thr Leu Val Phe Gly Gly Gly Thr Lys Leu Thr Val Leu
            100                 105

<210> SEQ ID NO 481
<211> LENGTH: 106
<212> TYPE: PRT
<213> ORGANISM: Homo sapiens

<400> SEQUENCE: 481

Gln Ser Ala Leu Thr Gln Pro Ser Val Ser Val Ser Pro Gly Gln
1               5                   10                  15

Thr Ala Ser Ile Thr Cys Ser Gly Asp Ile Leu Gly Asn Lys Tyr Ser
            20                  25                  30

Ser Trp Tyr Gln Gln Arg Pro Gly Gln Ser Pro Leu Leu Val Ile Tyr
        35                  40                  45

Gln Asp Lys Lys Arg Pro Ser Gly Ile Pro Glu Arg Phe Ser Gly Ser
    50                  55                  60

His Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Ser Val Ile
                85                  90                  95

Phe Gly Gly Gly Thr Lys Val Thr Val Leu
            100                 105

<210> SEQ ID NO 482
<211> LENGTH: 106
<212> TYPE: PRT
<213> ORGANISM: Homo sapiens

<400> SEQUENCE: 482

Gln Ser Ala Leu Thr Gln Pro Pro Ser Val Ser Val Ser Pro Gly Gln
1               5                   10                  15

Thr Ala Thr Ile Thr Cys Ser Gly Asn Lys Leu Gly Asn Thr Tyr Ile
            20                  25                  30

Ser Trp Tyr Gln Lys Lys Pro Gly Gln Ser Pro Val Leu Val Ile Tyr
        35                  40                  45

Gln Asp Lys Lys Arg Pro Ser Gly Ile Pro Glu Arg Phe Ser Gly Ser
    50                  55                  60

Asn Ser Gly Asn Thr Ala Thr Leu Thr Ile Thr Gly Thr Gln Ser Leu
65                  70                  75                  80

Asp Glu Ser Asp Tyr Tyr Cys Gln Thr Trp Asp Arg Ser Ser Val Val
                85                  90                  95

Phe Gly Gly Gly Thr Lys Leu Thr Val Leu
            100                 105

<210> SEQ ID NO 483
<211> LENGTH: 106
<212> TYPE: PRT
<213> ORGANISM: Homo sapiens

<400> SEQUENCE: 483

Gln Ser Ala Leu Thr Gln Pro Pro Ser Val Ser Val Ser Pro Gly Gln
1               5                   10                  15

Thr Ala Ser Ile Thr Cys Ser Gly Asp Lys Leu Arg Asn Lys Tyr Gly
            20                  25                  30

Ser Trp Tyr Gln Gln Lys Pro Gly Gln Ser Pro Val Leu Val Ile Tyr
        35                  40                  45

Gln Asp Arg Lys Arg Pro Ser Glu Ile Pro Glu Arg Phe Ser Gly Ser
    50                  55                  60

His Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Ser Val Ile
                85                  90                  95

Phe Gly Gly Gly Thr Lys Leu Thr Val Leu
            100                 105

<210> SEQ ID NO 484
<211> LENGTH: 106
<212> TYPE: PRT
<213> ORGANISM: Homo sapiens

<400> SEQUENCE: 484

Gln Ser Ala Leu Thr Gln Pro Pro Ser Val Ser Val Ser Pro Gly Gln
1               5                   10                  15
Thr Ala Ser Ile Thr Cys Ser Gly Asp Lys Leu Arg Asn Lys Tyr Ala
            20                  25                  30
Ser Trp Tyr Gln Gln Lys Pro Gly Gln Ala Pro Val Leu Val Ile Tyr
        35                  40                  45
Gln Asp Arg Lys Arg Pro Ser Glu Ile Pro Glu Arg Phe Ser Gly Ser
    50                  55                  60
His Ser Gly Asn Thr Ala Thr Leu Thr Ile Ser Gly Thr Gln Thr Met
65                  70                  75                  80
Asp Glu Ala Asp Tyr Tyr Cys Gln Thr Trp Asp Ser Ser Ser Val Ile
                85                  90                  95
Phe Gly Gly Gly Thr Lys Val Thr Val Leu
            100                 105

<210> SEQ ID NO 485
<211> LENGTH: 10
<212> TYPE: PRT
<213> ORGANISM: Homo sapiens

<400> SEQUENCE: 485

Val Gly Ile Ser Thr Tyr Gly Phe Asp Leu
1               5                   10

<210> SEQ ID NO 486
<211> LENGTH: 10
<212> TYPE: PRT
<213> ORGANISM: Homo sapiens

<400> SEQUENCE: 486

Val Gly Met Ala Thr Tyr Gly Phe Asp Ile
1               5                   10

<210> SEQ ID NO 487
<211> LENGTH: 10
<212> TYPE: PRT
<213> ORGANISM: Homo sapiens

<400> SEQUENCE: 487

Val Gly Met Ser Asn Tyr Gly Phe Asp Phe
1               5                   10

<210> SEQ ID NO 488
<211> LENGTH: 10
<212> TYPE: PRT
<213> ORGANISM: Homo sapiens

<400> SEQUENCE: 488

Val Gly Met Ser Thr Tyr Gly Phe Asp Lys
1               5                   10

<210> SEQ ID NO 489
<211> LENGTH: 10
<212> TYPE: PRT
<213> ORGANISM: Homo sapiens

<400> SEQUENCE: 489

Val Gly Met Tyr Asn Tyr Gly Phe Asp Ile
1               5                   10

<210> SEQ ID NO 490

```
<211> LENGTH: 132
<212> TYPE: PRT
<213> ORGANISM: Homo sapiens

<400> SEQUENCE: 490

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Trp Met Phe Trp Val Arg Gln Ala Pro Gly Lys Gly Leu Glu Trp Val
        35                  40                  45

Ser Gly Ile Val Ser Ser Gly Gly Met Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Met Ala Thr Tyr Gly Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro
    130

<210> SEQ ID NO 491
<211> LENGTH: 132
<212> TYPE: PRT
<213> ORGANISM: Homo sapiens

<400> SEQUENCE: 491

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Trp Met Phe Trp Val Arg Gln Ala Pro Gly Lys Gly Leu Glu Trp Val
        35                  40                  45

Ser Gly Ile Val Ser Ser Gly Gly Met Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Met Ser Asn Tyr Gly Phe Asp Phe Trp Gly Gln Gly
            100                 105                 110

Thr Met Val Thr Val Ser Ser Ala Ser Thr Lys Gly Pro Ser Val Phe
        115                 120                 125

Pro Leu Ala Pro
    130

<210> SEQ ID NO 492
<211> LENGTH: 8
<212> TYPE: PRT
<213> ORGANISM: Homo sapiens

<400> SEQUENCE: 492

Met Gln Ala Leu Gln Thr Leu Thr
1               5
```

<210> SEQ ID NO 493
<211> LENGTH: 8
<212> TYPE: PRT
<213> ORGANISM: Homo sapiens

<400> SEQUENCE: 493

Met Gln Ala Leu Arg Ala Ile Thr
1               5

<210> SEQ ID NO 494
<211> LENGTH: 8
<212> TYPE: PRT
<213> ORGANISM: Homo sapiens

<400> SEQUENCE: 494

Met Gln Ala Leu Gln Ala Ile Thr
1               5

<210> SEQ ID NO 495
<211> LENGTH: 8
<212> TYPE: PRT
<213> ORGANISM: Homo sapiens

<400> SEQUENCE: 495

Met Gln Ala Leu Gln Ser Pro Thr
1               5

<210> SEQ ID NO 496
<211> LENGTH: 8
<212> TYPE: PRT
<213> ORGANISM: Homo sapiens

<400> SEQUENCE: 496

Met Gln Ala Leu Gln Ser Ile Thr
1               5

<210> SEQ ID NO 497
<211> LENGTH: 7
<212> TYPE: PRT
<213> ORGANISM: Homo sapiens

<400> SEQUENCE: 497

Met Gly Ser Asn Arg Ala Ser
1               5

<210> SEQ ID NO 498
<211> LENGTH: 7
<212> TYPE: PRT
<213> ORGANISM: Homo sapiens

<400> SEQUENCE: 498

Leu Gly Ser His Arg Ala Ser
1               5

<210> SEQ ID NO 499
<211> LENGTH: 7
<212> TYPE: PRT
<213> ORGANISM: Homo sapiens

<400> SEQUENCE: 499

Phe Gly Ser Asn Arg Ala Ser
1               5

<210> SEQ ID NO 500
<211> LENGTH: 132
<212> TYPE: PRT

<213> ORGANISM: Homo sapiens

<400> SEQUENCE: 500

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Trp Met Phe Trp Val Arg Gln Ala Pro Gly Lys Gly Leu Glu Trp Val
        35                  40                  45

Ser Gly Ile Val Ser Gly Gly Met Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ile Ser Thr Tyr Gly Phe Asp Leu Trp Gly Gln Gly
            100                 105                 110

Thr Met Val Thr Val Ser Ser Ala Ser Thr Lys Gly Pro Ser Val Phe
        115                 120                 125

Pro Leu Ala Pro
    130
```

<210> SEQ ID NO 501
<211> LENGTH: 16
<212> TYPE: PRT
<213> ORGANISM: Homo sapiens

<400> SEQUENCE: 501

```
Arg Ser Ser Gln Ser Leu Leu His Ser Thr Gly Tyr Asn Tyr Leu Asp
1               5                   10                  15
```

<210> SEQ ID NO 502
<211> LENGTH: 16
<212> TYPE: PRT
<213> ORGANISM: Homo sapiens

<400> SEQUENCE: 502

```
Arg Ser Ser Gln Ser Leu Leu His Gly Asn Gly Asn Asn Tyr Leu Asp
1               5                   10                  15
```

<210> SEQ ID NO 503
<211> LENGTH: 16
<212> TYPE: PRT
<213> ORGANISM: Homo sapiens

<400> SEQUENCE: 503

```
Arg Ser Ser Gln Ser Leu Leu His Ser Asn Gly Tyr Asn Tyr Leu Asp
1               5                   10                  15
```

<210> SEQ ID NO 504
<211> LENGTH: 16
<212> TYPE: PRT
<213> ORGANISM: Homo sapiens

<400> SEQUENCE: 504

```
Arg Ser Ser Gln Ser Leu Leu His Ser Ser Gly Tyr His Tyr Leu Asp
1               5                   10                  15
```

<210> SEQ ID NO 505
<211> LENGTH: 16
<212> TYPE: PRT

<400> SEQUENCE: 505

Arg Ser Ser Gln Ser Leu Leu Asn Ile Asp Gly Tyr Asn Tyr Leu Asp
1               5                   10                  15

<210> SEQ ID NO 506
<211> LENGTH: 16
<212> TYPE: PRT
<213> ORGANISM: Homo sapiens

<400> SEQUENCE: 506

Arg Ser Ser Gln Ser Leu Leu His Arg Asn Gly Tyr Asn Phe Leu Asp
1               5                   10                  15

<210> SEQ ID NO 507
<211> LENGTH: 16
<212> TYPE: PRT
<213> ORGANISM: Homo sapiens

<400> SEQUENCE: 507

Arg Ser Ser Gln Ser Leu Arg His Asn Asn Gly Tyr Asn Tyr Leu Asp
1               5                   10                  15

<210> SEQ ID NO 508
<211> LENGTH: 112
<212> TYPE: PRT
<213> ORGANISM: Homo sapiens

<400> SEQUENCE: 508

Gln Asp Ile Gln Met Thr Gln Ser Pro Leu Ser Leu Pro Val Thr Pro
1               5                   10                  15

Gly Glu Pro Ala Ser Ile Ser Cys Lys Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Ser Leu Gly Ser Asn Arg Ala Ser Gly Val
    50                  55                  60

Pro Ala Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Thr Ile Thr Phe Gly Gln Gly Thr Arg Leu Glu Ile Lys
            100                 105                 110

<210> SEQ ID NO 509
<211> LENGTH: 132
<212> TYPE: PRT
<213> ORGANISM: Homo sapiens

<400> SEQUENCE: 509

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Trp Met Phe Trp Val Arg Gln Ala Pro Gly Lys Gly Leu Glu Trp Val
        35                  40                  45

Ser Gly Ile Val Ser Ser Gly Gly Met Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Val Gly Met Ser Thr Tyr Gly Phe Asp Lys Trp Gly Gln Gly
            100                 105                 110

Thr Met Val Thr Val Ser Ser Ala Ser Thr Lys Gly Pro Ser Val Phe
        115                 120                 125

Pro Leu Ala Pro
    130

<210> SEQ ID NO 510
<211> LENGTH: 132
<212> TYPE: PRT
<213> ORGANISM: Homo sapiens

<400> SEQUENCE: 510

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Trp Met Phe Trp Val Arg Gln Ala Pro Gly Lys Gly Leu Glu Trp Val
        35                  40                  45

Ser Gly Ile Val Ser Ser Gly Gly Met Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Met Tyr Asn Tyr Gly Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro
    130

<210> SEQ ID NO 511
<211> LENGTH: 112
<212> TYPE: PRT
<213> ORGANISM: Homo sapiens

<400> SEQUENCE: 511

Gln Asp Ile Gln Met Thr Gln Ser Pro Leu Ser Leu Pro Val Thr Pro
1               5                   10                  15

Gly Glu Pro Ala Ser Ile Ser Cys Lys Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Ser Leu Gly Ser Asn Arg Ala Ser Gly Val
    50                  55                  60

Pro Ala Arg Phe Ser Gly Ser Gly Ser Gly Thr Asp Phe Thr Leu Lys
65                  70                  75                  80

Ile Ser Arg Val Glu Ala Asp Val Gly Val Tyr Tyr Cys Met Gln
                85                  90                  95

Ala Leu Gln Thr Ile Thr Phe Gly Gln Gly Thr Arg Leu Glu Ile Lys
            100                 105                 110

<210> SEQ ID NO 512
<211> LENGTH: 6
<212> TYPE: PRT
```

-continued

```
<213> ORGANISM: Artificial Sequence
<220> FEATURE:
<223> OTHER INFORMATION: Consensus amino acid sequence of the CDR3
      regions of affinity matured clones of 807A-M0028-B02
<220> FEATURE:
<221> NAME/KEY: MISC_FEATURE
<222> LOCATION: (1)..(1)
<223> OTHER INFORMATION: Xaa = S or G
<220> FEATURE:
<221> NAME/KEY: MISC_FEATURE
<222> LOCATION: (2)..(2)
<223> OTHER INFORMATION: Xaa = V or I
<220> FEATURE:
<221> NAME/KEY: MISC_FEATURE
<222> LOCATION: (4)..(4)
<223> OTHER INFORMATION: Xaa = L, H or F
<220> FEATURE:
<221> NAME/KEY: MISC_FEATURE
<222> LOCATION: (6)..(6)
<223> OTHER INFORMATION: Xaa = Y, N or K

<400> SEQUENCE: 512

Xaa Xaa Leu Xaa Asp Xaa
1               5

<210> SEQ ID NO 513
<211> LENGTH: 9
<212> TYPE: PRT
<213> ORGANISM: Artificial Sequence
<220> FEATURE:
<223> OTHER INFORMATION: Consensus amino acid sequence of the CDR3
      regions of affinity matured clones of 807B-M0004-A03
<220> FEATURE:
<221> NAME/KEY: MISC_FEATURE
<222> LOCATION: (4)..(4)
<223> OTHER INFORMATION: Xaa =  A or S
<220> FEATURE:
<221> NAME/KEY: MISC_FEATURE
<222> LOCATION: (5)..(5)
<223> OTHER INFORMATION: Xaa =  D, S or A
<220> FEATURE:
<221> NAME/KEY: MISC_FEATURE
<222> LOCATION: (6)..(6)
<223> OTHER INFORMATION: Xaa =  R or G
<220> FEATURE:
<221> NAME/KEY: MISC_FEATURE
<222> LOCATION: (9)..(9)
<223> OTHER INFORMATION: Xaa =  Y, H or S

<400> SEQUENCE: 513

Ser Ile Ala Xaa Xaa Xaa Thr Asp Xaa
1               5

<210> SEQ ID NO 514
<211> LENGTH: 20
<212> TYPE: PRT
<213> ORGANISM: Artificial Sequence
<220> FEATURE:
<223> OTHER INFORMATION: Consensus amino acid sequence of the CDR3
      regions of affinity matured clones of 807B-M0004-H03
<220> FEATURE:
<221> NAME/KEY: MISC_FEATURE
<222> LOCATION: (1)..(1)
<223> OTHER INFORMATION: Xaa = E or D
<220> FEATURE:
<221> NAME/KEY: MISC_FEATURE
<222> LOCATION: (2)..(2)
<223> OTHER INFORMATION: Xaa = G or R
<220> FEATURE:
<221> NAME/KEY: MISC_FEATURE
<222> LOCATION: (4)..(4)
<223> OTHER INFORMATION: Xaa = A, S or V
<220> FEATURE:
<221> NAME/KEY: MISC_FEATURE
<222> LOCATION: (5)..(5)
<223> OTHER INFORMATION: Xaa = G, R or A
```

```
<220> FEATURE:
<221> NAME/KEY: MISC_FEATURE
<222> LOCATION: (7)..(7)
<223> OTHER INFORMATION: Xaa = V or F
<220> FEATURE:
<221> NAME/KEY: MISC_FEATURE
<222> LOCATION: (9)..(9)
<223> OTHER INFORMATION: Xaa = G or A
<220> FEATURE:
<221> NAME/KEY: MISC_FEATURE
<222> LOCATION: (10)..(10)
<223> OTHER INFORMATION: Xaa = P or R
<220> FEATURE:
<221> NAME/KEY: MISC_FEATURE
<222> LOCATION: (11)..(11)
<223> OTHER INFORMATION: Xaa = A, P or R
<220> FEATURE:
<221> NAME/KEY: MISC_FEATURE
<222> LOCATION: (13)..(13)
<223> OTHER INFORMATION: Xaa = Y or H
<220> FEATURE:
<221> NAME/KEY: MISC_FEATURE
<222> LOCATION: (14)..(14)
<223> OTHER INFORMATION: Xaa = Y or F
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: Xaa = V, L or A

<400> SEQUENCE: 514

Xaa Xaa Ser Xaa Xaa Val Xaa Lys Xaa Xaa Xaa Arg Xaa Xaa Tyr Tyr
1               5                   10                  15

Tyr Xaa Asp Xaa
            20

<210> SEQ ID NO 515
<211> LENGTH: 10
<212> TYPE: PRT
<213> ORGANISM: Artificial Sequence
<220> FEATURE:
<223> OTHER INFORMATION: Consensus amino acid sequence of the CDR3
      regions of affinity matured clones of 807B-M0009-F06
<220> FEATURE:
<221> NAME/KEY: MISC_FEATURE
<222> LOCATION: (3)..(3)
<223> OTHER INFORMATION: Xaa = M or I
<220> FEATURE:
<221> NAME/KEY: MISC_FEATURE
<222> LOCATION: (4)..(4)
<223> OTHER INFORMATION: Xaa = S or A
<220> FEATURE:
<221> NAME/KEY: MISC_FEATURE
<222> LOCATION: (5)..(5)
<223> OTHER INFORMATION: Xaa = T or N
<220> FEATURE:
<221> NAME/KEY: MISC_FEATURE
<222> LOCATION: (7)..(7)
<223> OTHER INFORMATION: Xaa = A or G
<220> FEATURE:
<221> NAME/KEY: MISC_FEATURE
<222> LOCATION: (10)..(10)
<223> OTHER INFORMATION: Xaa = I, L, F or K

<400> SEQUENCE: 515

Val Gly Xaa Xaa Xaa Tyr Xaa Phe Asp Xaa
1               5                   10

<210> SEQ ID NO 516
<211> LENGTH: 6
<212> TYPE: PRT
<213> ORGANISM: Artificial Sequence
```

```
<220> FEATURE:
<223> OTHER INFORMATION: Consensus amino acid sequence of the CDR3
      regions of affinity matured clones of 807B-M0009-F06
<220> FEATURE:
<221> NAME/KEY: MISC_FEATURE
<222> LOCATION: (2)..(2)
<223> OTHER INFORMATION: Xaa = V or I
<220> FEATURE:
<221> NAME/KEY: MISC_FEATURE
<222> LOCATION: (4)..(4)
<223> OTHER INFORMATION: Xaa = L, H or F
<220> FEATURE:
<221> NAME/KEY: MISC_FEATURE
<222> LOCATION: (6)..(6)
<223> OTHER INFORMATION: Xaa = K, Y or N

<400> SEQUENCE: 516

Gly Xaa Leu Xaa Asp Xaa
1               5

<210> SEQ ID NO 517
<211> LENGTH: 9
<212> TYPE: PRT
<213> ORGANISM: Artificial Sequence
<220> FEATURE:
<223> OTHER INFORMATION: Consensus amino acid sequence of the CDR3
      regions of affinity matured clones of 807A-M0004-A03
<220> FEATURE:
<221> NAME/KEY: MISC_FEATURE
<222> LOCATION: (4)..(4)
<223> OTHER INFORMATION: Xaa = S or A
<220> FEATURE:
<221> NAME/KEY: MISC_FEATURE
<222> LOCATION: (5)..(5)
<223> OTHER INFORMATION: Xaa = S or A
<220> FEATURE:
<221> NAME/KEY: MISC_FEATURE
<222> LOCATION: (6)..(6)
<223> OTHER INFORMATION: Xaa = R or G
<220> FEATURE:
<221> NAME/KEY: MISC_FEATURE
<222> LOCATION: (9)..(9)
<223> OTHER INFORMATION: Xaa = H or Y

<400> SEQUENCE: 517

Ser Ile Ala Xaa Xaa Xaa Thr Asp Xaa
1               5

<210> SEQ ID NO 518
<211> LENGTH: 107
<212> TYPE: PRT
<213> ORGANISM: Artificial Sequence
<220> FEATURE:
<223> OTHER INFORMATION: Amino acid sequence of the VL chains of the
      Germline-corrected antibodies

<400> SEQUENCE: 518

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Arg Asn His
                20                  25                  30

Leu Gly Trp Phe Gln Gln Lys Pro Gly Lys Ala Pro Gln Arg Leu Ile
            35                  40                  45

Arg Glu Ala Ser Ile Leu Gln Ser Gly Val Pro Ser Thr Phe Tyr Gly
        50                  55                  60

Ser Gly Tyr Gly Arg Glu Phe Thr Leu Thr Ile Ser Ser Leu Gln Pro
65                  70                  75                  80

Glu Asp Phe Ala Thr Tyr Tyr Cys Leu Gln Tyr Asp Ser Phe Pro Tyr
                85                  90                  95
```

Thr Phe Gly Gln Gly Thr Lys Leu Glu Ile Lys
            100                 105

<210> SEQ ID NO 519
<211> LENGTH: 107
<212> TYPE: PRT
<213> ORGANISM: Artificial Sequence
<220> FEATURE:
<223> OTHER INFORMATION: Amino acid sequence of the CL chains of the
      Germline-corrected antibodies

<400> SEQUENCE: 519

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 520
<211> LENGTH: 107
<212> TYPE: PRT
<213> ORGANISM: Artificial Sequence
<220> FEATURE:
<223> OTHER INFORMATION: Amino acid sequence of the VL chains of the
      Germline-corrected antibodies

<400> SEQUENCE: 520

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Arg Asn His
            20                  25                  30

Leu Gly Trp Tyr Gln Gln Lys Pro Gly Lys Ala Pro Lys Arg Leu Ile
        35                  40                  45

Tyr Glu Ala Ser Ile Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Ser Phe Pro Tyr
                85                  90                  95

Thr Phe Gly Gln Gly Thr Lys Leu Glu Ile Lys
            100                 105

<210> SEQ ID NO 521
<211> LENGTH: 107
<212> TYPE: PRT
<213> ORGANISM: Artificial Sequence
<220> FEATURE:
<223> OTHER INFORMATION: Amino acid sequence of the CL chains of the
      Germline-corrected antibodies

<400> SEQUENCE: 521

Arg Thr Val Ala Ala Pro Ser Val Phe Ile Phe Pro Pro Ser Asp Glu
1               5                   10                  15

Gln Leu Lys Ser Gly Thr Ala Ser Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 522
<211> LENGTH: 110
<212> TYPE: PRT
<213> ORGANISM: Artificial Sequence
<220> FEATURE:
<223> OTHER INFORMATION: Amino acid sequence of the VL chains of the
      Germline-corrected antibodies

<400> SEQUENCE: 522

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Asn Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp His Asp Gly Leu
                85                  90                  95

Asn Gly Pro Val Phe Gly Gly Gly Thr Lys Leu Thr Val Leu
            100                 105                 110

<210> SEQ ID NO 523
<211> LENGTH: 106
<212> TYPE: PRT
<213> ORGANISM: Artificial Sequence
<220> FEATURE:
<223> OTHER INFORMATION: Amino acid sequence of the CL chains of the
      Germline-corrected antibodies

<400> SEQUENCE: 523

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

```
Glu Lys Thr Val Ala Pro Thr Glu Cys Ser
            100                 105
```

<210> SEQ ID NO 524
<211> LENGTH: 107
<212> TYPE: PRT
<213> ORGANISM: Artificial Sequence
<220> FEATURE:
<223> OTHER INFORMATION: Amino acid sequence of the VL chains of the
      Germline-corrected antibodies

<400> SEQUENCE: 524

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Asp Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys
            100                 105
```

<210> SEQ ID NO 525
<211> LENGTH: 111
<212> TYPE: PRT
<213> ORGANISM: Artificial Sequence
<220> FEATURE:
<223> OTHER INFORMATION: Amino acid sequence of the VL chains of the
      Germline-corrected antibodies

<400> SEQUENCE: 525

```
Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Ile Thr Phe Gly Gln Gly Thr Arg Leu Glu Ile Lys
            100                 105                 110
```

<210> SEQ ID NO 526
<211> LENGTH: 106
<212> TYPE: PRT
<213> ORGANISM: Artificial Sequence
<220> FEATURE:
<223> OTHER INFORMATION: Amino acid sequence of the VL chains of the
      Germline-corrected antibodies

<400> SEQUENCE: 526

```
Ser Tyr Glu Leu Thr Gln Pro Pro Ser Val Ser Val Ser Pro Gly Gln
1               5                   10                  15
```

```
Thr Ala Ser Ile Thr Cys Ala Gly Asp Glu Leu Gly Asn Lys Tyr Ala
            20                  25                  30

Ser Trp Tyr Gln Gln Lys Pro Gly Gln Ser Pro Val Leu Val Ile Tyr
        35                  40                  45

Gln Asp Arg Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ser Trp Asp Ser Ser Val Ile
                85                  90                  95

Phe Gly Gly Gly Thr Lys Leu Thr Val Leu
            100                 105

<210> SEQ ID NO 527
<211> LENGTH: 106
<212> TYPE: PRT
<213> ORGANISM: Artificial Sequence
<220> FEATURE:
<223> OTHER INFORMATION: Amino acid sequence of the CL chains of the
      Germline-corrected antibodies

<400> SEQUENCE: 527

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```